United States Patent
Hussa et al.

(10) Patent No.: US 7,943,294 B2
(45) Date of Patent: May 17, 2011

(54) METHODS FOR DETECTING ONCOFETAL FIBRONECTIN

(75) Inventors: Robert Hussa, Sunnyvale, CA (US); Mark Fischer-Colbrie, Cupertino, CA (US); Jerome P. LaPointe, Oakland, CA (US); Simon Shorter, Campbell, CA (US); Andrew Senyei, La Jolla, CA (US)

(73) Assignee: Hologic, Inc., Bedford, MA (US)

( * ) Notice: Subject to any disclaimer, the term of this patent is extended or adjusted under 35 U.S.C. 154(b) by 1036 days.

(21) Appl. No.: 11/193,789

(22) Filed: Jul. 29, 2005

(65) Prior Publication Data

US 2006/0024723 A1    Feb. 2, 2006

Related U.S. Application Data

(60) Provisional application No. 60/592,823, filed on Jul. 30, 2004, provisional application No. 60/592,803, filed on Jul. 30, 2004, provisional application No. 60/592,825, filed on Jul. 30, 2004, provisional application No. 60/592,804, filed on Jul. 30, 2004, provisional application No. 60/592,824, filed on Jul. 30, 2004.

(51) Int. Cl.
*C12Q 1/00* (2006.01)
*G01N 33/53* (2006.01)

(52) U.S. Cl. .............. 435/4; 435/6; 435/7.23; 435/7.1

(58) Field of Classification Search .................. None
See application file for complete search history.

(56) References Cited

U.S. PATENT DOCUMENTS

| | | | |
|---|---|---|---|
| 4,595,011 A | 6/1986 | Phillips | 600/362 |
| 4,628,027 A | 12/1986 | Gay | 435/7.23 |
| 4,663,290 A | 5/1987 | Weis et al. | 435/252.33 |
| 4,683,195 A | 7/1987 | Mullis et al. | 435/6 |
| 4,683,202 A | 7/1987 | Mullis | 435/91.2 |
| 4,700,713 A | 10/1987 | Kist | 600/569 |
| 4,746,508 A | 5/1988 | Carey et al. | 424/278.1 |
| 4,759,376 A | 7/1988 | Stormby | 600/569 |
| 4,762,133 A | 8/1988 | Bayne et al. | 600/569 |
| 4,777,128 A | 10/1988 | Lippa | 435/5 |
| 4,889,818 A | 12/1989 | Gelfand et al. | 435/194 |
| 4,894,326 A * | 1/1990 | Matsuura et al. | 435/7.21 |
| 4,919,889 A | 4/1990 | Jones et al. | 422/40 |
| 4,927,923 A | 5/1990 | Mathis | 540/456 |
| 4,956,302 A | 9/1990 | Gordon et al. | 436/161 |
| 4,960,467 A | 10/1990 | Peck | 252/408.1 |
| 4,960,691 A | 10/1990 | Gordon et al. | 435/6 |
| 4,965,188 A | 10/1990 | Mullis et al. | 435/6 |
| 5,073,484 A | 12/1991 | Swanson et al. | 435/7.92 |
| 5,079,171 A | 1/1992 | Senyei et al. | 436/510 |
| 5,096,830 A | 3/1992 | Senyei et al. | 436/65 |
| 5,108,898 A | 4/1992 | Peters et al. | 435/7.9 |
| 5,118,937 A | 6/1992 | Hillenkamp et al. | 250/282 |
| 5,120,643 A | 6/1992 | Ching et al. | 435/7.92 |
| 5,132,097 A | 7/1992 | Van Deusen et al. | 422/82.09 |
| 5,139,023 A | 8/1992 | Stanley et al. | 600/368 |
| 5,149,622 A | 9/1992 | Brown et al. | 435/5 |
| 5,162,508 A | 11/1992 | Lehn et al. | 534/15 |
| 5,185,270 A | 2/1993 | Senyei et al. | 436/510 |
| 5,198,340 A | 3/1993 | Mukku | 435/7.8 |
| 5,209,904 A | 5/1993 | Forney et al. | 422/73 |
| 5,223,440 A | 6/1993 | Teng et al. | 436/510 |
| 5,236,846 A | 8/1993 | Senyei et al. | 436/65 |
| 5,243,029 A | 9/1993 | Matsuura et al. | 530/395 |
| 5,244,797 A | 9/1993 | Kotewicz et al. | 435/194 |
| 5,252,459 A | 10/1993 | Tarcha et al. | 435/6 |
| 5,270,166 A | 12/1993 | Parsons et al. | 435/7.4 |
| 5,279,943 A | 1/1994 | Mathis et al. | 435/7.32 |
| 5,281,522 A | 1/1994 | Senyei et al. | 435/7.9 |
| 5,362,307 A | 11/1994 | Guy et al. | 604/20 |
| 5,374,553 A | 12/1994 | Gelfand et al. | 435/252.3 |
| 5,380,411 A | 1/1995 | Schlief | 204/157.15 |
| 5,413,573 A | 5/1995 | Koivukangas | 606/1 |
| 5,438,984 A | 8/1995 | Schoendorfer | 600/573 |
| 5,455,170 A | 10/1995 | Abramson et al. | 435/252.3 |
| 5,466,591 A | 11/1995 | Abramson | 435/194 |
| 5,468,619 A | 11/1995 | Senyei et al. | 435/7.94 |
| 5,480,776 A | 1/1996 | Dullien | 435/7.9 |
| 5,491,130 A | 2/1996 | Roberts et al. | 514/13 |
| 5,500,375 A | 3/1996 | Lee-Own et al. | 436/514 |
| 5,512,493 A | 4/1996 | Mathis et al. | 436/537 |
| 5,516,702 A | 5/1996 | Senyei et al. | 436/510 |

(Continued)

FOREIGN PATENT DOCUMENTS

EP    0 316 919    6/1995

(Continued)

OTHER PUBLICATIONS

Matsuura et al., PNAS, vol. 82, p. 6517-6521, 1985.* Mandel et al., APMIS, vol. 102 p. 695-702, 1994.*
Menzin et al., Cancer, vol. 82, p. 152-8, 1998.*
Achilefu, S. and R.B. Dorshow, "Dynamic and continuous monitoring of renal and hepatic functions with exogenous markers," Topics in Current Chemistry, 222:31-72 (2002).
Adeza Directional Inserts "fFN Fetal Fibronectin Membrane Immunoassay" Catalog Nos. 00095 and 00290, 4 pages, (Feb. 2003).
Adeza Directional Inserts "fFN RAPID fFN Cassette Kit" Catalog No. 01200, 5 pages, (Dec. 2003).
Ahner et al. "Fetal fibronectin as a selection criterion for induction of term labor" Am. J. Obstet Gynecol. 173:1513-1517 (1995).
Akins et al., "Mitochondrial plasmids of neurospora integration into mitochondrial DNA and evidence for reverse transcription in mitochondria," Cell 47:505-516 (1986).

(Continued)

*Primary Examiner* — Misook Yu
*Assistant Examiner* — Lei Yao
(74) *Attorney, Agent, or Firm* — Theodore R. Allen

(57) ABSTRACT

Methods and products for the detection of oncofetal fibronectin indicating molecules in samples are provided. Methods for imaging of oncofetal fibronectin are provided. In some methods provided herein, the sample is treated with a reagent and/or contacted with a non-specific binder. Provided are methods for testing subjects to ascertain health and disease status and to assess the risk of developing a disease or condition. Methods for detecting the presence of oncofetal fibronectin indicating molecules by a variety of methods such as immunoassays and mass spectrometry also are provided. Methods and products for detection of oncofetal fibronection for selection of concepti are provided.

1 Claim, 5 Drawing Sheets

U.S. PATENT DOCUMENTS

| | | | |
|---|---|---|---|
| 5,523,229 A * | 6/1996 | Feinberg et al. | 435/337 |
| 5,538,897 A | 7/1996 | Yates, III et al. | 436/89 |
| 5,554,504 A | 9/1996 | Rutanen | 435/7.8 |
| 5,578,577 A | 11/1996 | Ching et al. | 514/21 |
| 5,582,184 A | 12/1996 | Erickson et al. | 600/576 |
| 5,586,981 A | 12/1996 | Hu | 606/9 |
| 5,591,595 A | 1/1997 | Van Aken et al. | 435/7.23 |
| 5,591,645 A | 1/1997 | Rosenstein | 436/514 |
| 5,597,700 A | 1/1997 | Konstantinov et al. | 435/7.92 |
| 5,622,871 A | 4/1997 | May et al. | 436/514 |
| 5,645,537 A | 7/1997 | Powles et al. | 604/240 |
| 5,654,162 A | 8/1997 | Guire et al. | 435/7.92 |
| 5,656,502 A | 8/1997 | MacKay et al. | 436/180 |
| 5,656,503 A | 8/1997 | May et al. | 436/514 |
| 5,658,801 A | 8/1997 | Poissant et al. | 436/518 |
| 5,691,151 A | 11/1997 | Braun et al. | 435/7.2 |
| 5,693,479 A | 12/1997 | Feinberg et al. | 435/7.21 |
| 5,719,060 A | 2/1998 | Hutchens et al. | 436/174 |
| 5,770,367 A | 6/1998 | Southern et al. | 435/6 |
| 5,804,452 A | 9/1998 | Pronovost et al. | 436/514 |
| 5,808,300 A | 9/1998 | Caprioli | 250/288 |
| 5,823,973 A | 10/1998 | Racchini et al. | 600/573 |
| 5,876,978 A | 3/1999 | Willey et al. | 435/91.2 |
| 5,894,063 A | 4/1999 | Hutchens et al. | 436/155 |
| 5,897,840 A | 4/1999 | Owens, Jr. et al. | 422/102 |
| 5,939,301 A | 8/1999 | Hughes et al. | 435/194 |
| 5,948,614 A | 9/1999 | Chatterjee | 435/6 |
| 5,955,729 A | 9/1999 | Nelson et al. | 250/282 |
| 5,964,735 A | 10/1999 | Alexander | 604/195 |
| 5,989,409 A | 11/1999 | Kurnik et al. | 205/792 |
| 6,004,770 A | 12/1999 | Nelson | 435/23 |
| 6,005,113 A | 12/1999 | Wu et al. | 548/110 |
| 6,015,668 A | 1/2000 | Hughes et al. | 435/6 |
| 6,017,693 A | 1/2000 | Yates, III et al. | 435/5 |
| 6,017,703 A | 1/2000 | Kinders et al. | 435/6 |
| 6,023,629 A | 2/2000 | Tamada | 600/347 |
| 6,024,939 A | 2/2000 | Unger | 424/9.5 |
| 6,093,541 A | 7/2000 | Nelson | 435/6 |
| 6,124,137 A | 9/2000 | Hutchens et al. | 436/155 |
| 6,146,657 A | 11/2000 | Unger et al. | 424/450 |
| 6,156,546 A | 12/2000 | Konkel et al. | 435/91.2 |
| 6,168,779 B1 | 1/2001 | Barsky et al. | 424/9.2 |
| 6,174,287 B1 | 1/2001 | Resnick et al. | 600/458 |
| 6,190,315 B1 | 2/2001 | Kost et al. | 600/309 |
| 6,225,047 B1 | 5/2001 | Hutchens et al. | 435/5 |
| 6,265,715 B1 | 7/2001 | Perreault et al. | 250/288 |
| 6,267,722 B1 | 7/2001 | Anderson et al. | 600/300 |
| 6,287,872 B1 | 9/2001 | Schurenberg et al. | 436/181 |
| 6,312,612 B1 | 11/2001 | Sherman et al. | 216/2 |
| 6,316,266 B1 | 11/2001 | Nelson | 436/86 |
| 6,323,186 B1 | 11/2001 | Klaubert et al. | 514/47 |
| 6,334,851 B1 | 1/2002 | Hayes et al. | 600/573 |
| 6,338,848 B1 | 1/2002 | Leonard et al. | 424/130.1 |
| 6,368,873 B1 | 4/2002 | Chang et al. | 436/573 |
| 6,387,059 B1 | 5/2002 | Marchitto et al. | 600/573 |
| 6,394,952 B1 | 5/2002 | Anderson et al. | 600/300 |
| 6,409,679 B2 | 6/2002 | Pyo | 600/573 |
| 6,416,758 B1 | 7/2002 | Thorpe et al. | 424/145.1 |
| 6,436,721 B1 | 8/2002 | Kuo et al. | 436/514 |
| 6,465,778 B1 | 10/2002 | Koster et al. | 250/288 |
| 6,482,604 B2 | 11/2002 | Kwon | 435/14 |
| 6,489,121 B1 | 12/2002 | Skilling | 435/7.1 |
| 6,492,180 B2 | 12/2002 | Brown et al. | 436/77 |
| 6,496,728 B2 | 12/2002 | Li et al. | 604/20 |
| 6,498,039 B2 | 12/2002 | Nelson | 436/86 |
| 6,503,198 B1 | 1/2003 | Aronowtiz et al. | 600/365 |
| 6,508,785 B1 | 1/2003 | Eppstein | 604/113 |
| 6,556,977 B1 | 4/2003 | Lapointe et al. | 706/15 |
| 6,558,902 B1 | 5/2003 | Hillenkamp | 435/6 |
| 6,562,014 B2 | 5/2003 | Lin et al. | 604/317 |
| 6,589,173 B1 | 7/2003 | Mitragotri | 600/437 |
| 6,596,853 B1 | 7/2003 | Theze et al. | 536/23.5 |
| 6,620,123 B1 | 9/2003 | Mitragotri et al. | 604/22 |
| 6,624,882 B2 | 9/2003 | Sopp et al. | 356/39 |
| 6,632,976 B1 | 10/2003 | Tomizuka et al. | 800/18 |
| 6,657,191 B2 | 12/2003 | Park | 250/288 |
| 6,663,612 B2 | 12/2003 | Shingu et al. | 604/391 |
| 6,670,194 B1 | 12/2003 | Aebersold et al. | 436/173 |
| 6,685,699 B1 | 2/2004 | Eppstein et al. | 606/2 |
| 6,692,456 B1 | 2/2004 | Eppstein et al. | 604/22 |
| 6,702,791 B1 | 3/2004 | Hilgers et al. | 604/274 |
| 6,706,032 B2 | 3/2004 | Weaver et al. | 604/500 |
| 6,713,610 B1 | 3/2004 | Kucherlapati et al. | 530/388.23 |
| 6,716,636 B1 | 4/2004 | Schneider et al. | 436/89 |
| 6,788,128 B2 | 9/2004 | Tsuchida | 327/427 |
| 2001/0019829 A1 | 9/2001 | Nelson et al. | 435/7.1 |
| 2001/0021535 A1 | 9/2001 | Nelson et al. | 436/518 |
| 2001/0034038 A1 | 10/2001 | Hung | 435/7.23 |
| 2002/0013539 A1 | 1/2002 | Hung | 600/573 |
| 2002/0019017 A1 | 2/2002 | Love et al. | 435/7.23 |
| 2002/0037265 A1 | 3/2002 | Hung | 424/70.1 |
| 2002/0039557 A1 | 4/2002 | White | 424/1.49 |
| 2002/0042075 A1 | 4/2002 | Nelson | 435/6 |
| 2002/0045162 A1 | 4/2002 | Hung | 435/5 |
| 2002/0058887 A1 | 5/2002 | Soito et al. | 600/573 |
| 2002/0094566 A1 | 7/2002 | Tubbs et al. | 435/287.2 |
| 2002/0110904 A1 | 8/2002 | Nelson et al. | 435/287.2 |
| 2002/0164818 A1 | 11/2002 | Gruber et al. | 436/173 |
| 2002/0193849 A1 | 12/2002 | Fenn et al. | 607/89 |
| 2003/0017454 A1 | 1/2003 | Sukamar et al. | 435/6 |
| 2003/0021787 A1 | 1/2003 | Hung et al. | 424/155.1 |
| 2003/0022161 A1 | 1/2003 | Love et al. | 435/6 |
| 2003/0027216 A1 | 2/2003 | Kiernan et al. | 435/7.1 |
| 2003/0029461 A1 | 2/2003 | Hermonat et al. | 128/898 |
| 2003/0045681 A1 | 3/2003 | Neri et al. | 530/350 |
| 2003/0049658 A1 | 3/2003 | Smart et al. | 436/5 |
| 2003/0087235 A1 | 5/2003 | Dairkee et al. | 435/6 |
| 2003/0104483 A1 | 6/2003 | Davidson et al. | 435/7.1 |
| 2003/0113712 A1 | 6/2003 | Lee et al. | 435/5 |
| 2003/0114434 A1 | 6/2003 | Chen et al. | 514/185 |
| 2003/0138783 A1 | 7/2003 | Sukamar et al. | 435/6 |
| 2003/0138823 A1 | 7/2003 | Brock et al. | 435/6 |
| 2003/0157550 A1 | 8/2003 | Mitsuhashi | 435/6 |
| 2003/0176663 A1 | 9/2003 | Neri et al. | 530/388.22 |
| 2003/0190602 A1 | 10/2003 | Pressman et al. | 435/5 |
| 2003/0194717 A1 | 10/2003 | Schmidt et al. | 435/6 |
| 2003/0232010 A2 | 12/2003 | Goldenburg et al. | 424/1.49 |
| 2003/0232399 A1 | 12/2003 | Robertson et al. | 435/7.23 |
| 2004/0009551 A1 | 1/2004 | Borgford | 435/69.1 |
| 2004/0019032 A1 | 1/2004 | North et al. | 514/185 |
| 2004/0048320 A1 | 3/2004 | Hanash et al. | 435/7.23 |
| 2004/0054014 A1 | 3/2004 | Margalit et al. | 514/651 |
| 2004/0059519 A1 | 3/2004 | Chandler et al. | 702/19 |
| 2004/0266025 A1 | 12/2004 | Hickok et al. | 436/518 |
| 2006/0024722 A1 | 2/2006 | Fischer-Colbrie et al. | |
| 2006/0024724 A1 | 2/2006 | Hussa et al. | |
| 2006/0024725 A1 | 2/2006 | Hussa et al. | |
| 2006/0024757 A1 | 2/2006 | Hussa et al. | |

FOREIGN PATENT DOCUMENTS

| | | |
|---|---|---|
| EP | 1 293 926 | 3/2003 |
| EP | 1293926 A2 | 3/2003 |
| JP | 63163167 | 7/1988 |
| JP | 01-195848 | 8/1989 |
| WO | 89/10724 | 11/1989 |
| WO | 91/16633 | 10/1991 |
| WO | 91/16855 | 11/1991 |
| WO | 92/01225 | 1/1992 |
| WO | 92/06200 | 4/1992 |
| WO | 92/10585 | 6/1992 |
| WO | 92/10585 A | 6/1992 |
| WO | 92/12426 | 7/1992 |
| WO | 93/09432 | 5/1993 |
| WO | 93/09438 | 5/1993 |
| WO | 93/24836 | 12/1993 |
| WO | 93/24838 | 12/1993 |
| WO | 94/00765 | 1/1994 |
| WO | 94/17405 | 8/1994 |
| WO | 97/27327 | 7/1997 |
| WO | 97/45544 | 12/1997 |
| WO | 98/26095 | 6/1998 |
| WO | 98/31830 | 7/1998 |
| WO | 99/09507 | 2/1999 |
| WO | 99/57318 | 11/1999 |
| WO | 01/83816 | 11/2001 |
| WO | 02/46455 | 6/2002 |
| WO | 02/057786 | 7/2002 |

| WO | 02/101075 A2 | 12/2002 |
| WO | 03/020115 | 3/2003 |
| WO | 03/036300 | 5/2003 |
| WO | 03/083051 | 10/2003 |
| WO | 2004/003555 | 1/2004 |
| WO | 2004/071427 | 8/2004 |
| WO | 2006/026020 | 3/2006 |

OTHER PUBLICATIONS

Alary et al., "Evaluation of a modified sanitary napkin as a sample self-collection device for the detection of genial chlamydial infection in women," J. Clin. Microbiol. 39:2508-2512 (2001).

Albrecht et al., "Fibronectin in human prostatic cells in vivo and in vitro: expression, distribution, and pathological significance," Histochem. Cell. Biol. 112:51-61 (1999).

Alessandri et al. "Isolation and characterization of human tumor-derived capillary endothelial cells: role of oncofetal fibronectin" Lab Invest 78:(1)127-8 (1998).

Allen, J.E. and T.H. Maugh II, "Drug found to prevent many premature births," Los Angeles Times, Feb. 7, 2003 (3 pages).

Amexis et al., "Quantitative mutant analysis of viral quasispecies by chip-based matrix-assisted laser desorption/ionization time-of-flight mass spectrometry," Proc. Natl. Acad. Sci. USA 98:12097-12102 (2001).

Andersen, H.F. and I.R. Merkatz, "Preterm Labor," Chapter 17 in *Danforth's Obstetrics & Gynecology*, 6$^{th}$ ed., L. McAllister et al.(Eds.), Philadelphia: J.P. Lippincott Company, pp. 335-351 (1990).

Arndt et al., "Helix-stabilized Fv, (hsFv) Antibody Fragments: Substituting the Constant Domains of a Fab Fragment for a Heterdimric Coiled-coil Domain," J. Mol. Biol. 7:312:221-228 (2001).

ATCC No. CRL-1605 (accessed on Sep. 22, 2005).
ATCC No. CRL-1606 (accessed on Sep. 22, 2005).
ATCC No. HB 9018 (accessed on Sep. 22, 2005).
ATCC No. HB-91 (accessed on Sep. 22, 2005).

Avrameas, S., "Coupling of enzymes to proteins with glutaraldehyde. Use of the conjugates for the detection of antigens and antibodies," Immunochem. 6:43-52 (1969).

Bailit et al., "Reducing the caesarean delivery risk in elective inductions of labour: a decision analysis," Paediatric and Perinatal Epidemiology 16:90-96 (2002).

Bej, A. K. and M.H. Mahbubani, "Thermostable DNA polymerases for in vitro DNA amplifications," Chapter 25 in *PCR Technology: Current Innovations*, Griffin, H. G. and A.M. Griffin, (Eds.), Boca Raton, Florida: CRC Press, Inc. pp. 219-237 (1994).

Berndt et al., "Evidence of ED-B$^+$ fibronectin synthesis in human tissues by non-radioactive RNA in situ hybridization. Investigations on carcinoma (oral squamous cell and breast carcinoma), chronic inflammation (rheumatoid synovitis) and fibromatosis (Morbus Dupuyten)," Histochem. Cell Biol. 109:249-255 (1998).

Birchler et al., "Infrared photodetection for the in vivo localisation of phage-derived antibodies directed against angiogenic markers," J. Immun Meth 231:239-248 (1999).

Bird et al., "Single-chain antigen-binding proteins," Science, 242:423-426 (1988).

Bittar et al., "Cervical fetal fibronectin in patients at increased risk for preterm delivery," American Journal of Obstetrics and Gynecology 175(1):178-181 (1996).

Blanch et al., "The presence of fetal fibronectin in the cervicovaginal secretons of women in term—Its role in the assessment of women before labor induction and in the investigation of the physiologic mechanisms of labor," Am. J. Obstet. Gyn. 174:262-266 (1996).

Borsi et al., "Structural differences in the cell binding region of human fibronectin molecules isolated from cultured normal and tumor-derived human cells," FEBS Lett. 192:71-74 (1985).

Borsi et al., "Selective targeting of tumoral vasculature: comparison of different formats of an antibody (L19) to the ED-B domain of fibronectin," Int. J. Cancer 102:75-85 (2002).

Bourhis et al., "Analysis of p53 serum antibodies in patients with head and neck squamos cell carcinoma," J. Natl Cancer Inst 88:1228-1233 (1996).

Brichory et al., "Proteomic-based identification of protein gene product 9.5 as a tumor antigen that induces a humoral immune response in lung cancer," Cancer Res. 61:7908-12 (2001).

Bucknall et al., "Practical quantitative biomedical applications of MALDI-TOF Mass Spectrometry," J. Am. Soc. Mass Spectrom. 13:1015-1027 (2002).

Bustin, S.A., "Quantification of mRNA using real-time reverse transcription PCR (RT-PCR): trends and problems," J. Mol. Endocrinology 29:23-39 (2002).

Cardullo et al., "Detection of nucleic acid hybridization by nonradiative fluorescence resonance energy transfer," Proc. Natl. Acad. Sci. U.S.A. 85:8790-8794 (1988).

Carnemolla et al., "The inclusion of the type III repeat ED-B in the fibronectin molecule generates conformational modifications that unmask a cryptic sequence," J. Biol. Chem. 267:24689-24692 (1992).

Carnemolla et al., "Localization of the cellular-fibronectin-specific epitope recognized by the monoclonal antibody IST-9 using fusion proteins expressed in *E. coli*," FEBS Lett., 215:269-273 (1987).

Carnemolla et al., "A tumor-associated fibronectin isoform generated by alternative splicing of messenger RNA precursors," J. Cell. Biol., 108:1139-1148 (1989).

Castellani et al., "The Angiogenesis Marker ED-B+ Fibronectin Isoform in Intracranial Meningiomas," Acta Neurochir 142:277-282 (2000).

Castellani et al., "The fibronectin isoform containing the ED-B oncofetal domain: a marker of angiogenesis," Int. J. Cancer 59:612-618 (1994).

Chandra et al., "Transvaginal ultrasound and digital examination in predicting successful labor induction," Obstet Gynecol 98:2-6 (2001).

Chapman et al., "Comparison of Mono- and Dichlorinated Tyrosines with Carbonyls for Detection of Hypochlorous Acid Modified Proteins," Arch. Biochem. Biophys. 377:95-100 (2000).

Da Fonseca et al., "Prophylactic administration of progesterone by vaginal suppository to reduce the incidence of spontaneous preterm birth in women at increased risk: a randomized placebo-controlled double-blind study," American Journal of Obstetrics and Gynecology 188(2):419-424 (2003).

Dalifard et al., "Cytosolic p53 protein and serum p53 autoantibody evaluation in breast cancer. Comparison with prognostic factors," Anticancer Research 19:5015-5022 (1999).

Dame et al., "Increased saliva oestriol to progesterone ratio before idiopathic preterm delivery: a possible predictor for preterm labour?", British Medical Journal, 294:270-272 (1987).

Decsi et al., "Inverse association between *trans* isomeric and long-chain polyunsaturated fatty acids in cord blood lipid of full-term infants," Am J. Clin Nutr 74:364-368 (2001).

Derwent English abstract for Japanese Patent Application JP 63163167, published Jul. 6, 1988, entitled: "Detecting human cancer—by determining amt. of human fibronectin in living body sample and comparing with normal value".

Doi et al., "Reverse transcription-polymerase chain reaction and immunohistochemical study of the expression of fibronectin mRNA in human submandibular salivary gland," Arch Oral Biol 43:589-596 (1998).

Dole et al., "Molecular beams of macroions," J. Chem. Phys. 49:2240-2249 (1968).

Drop et al., "Isolation of a somatomedin-binding protein from preterm amniotic fluid. Development of a radioimmunoassay," J. Clin. Endocrinology and Metabolism, 59:899-907 (1984).

Edwards, R.K. and D.S. Richards, "Preinduction Cervical Assessment [Cervical Ripening and Labor Induction," Clin. Obstet Gynecol. 43:440-446 (2000).

Engvall, E. and E. Ruoslahti, "Binding of soluble form of fibroblast surface protein, fibronectin, to collagen," Int. J. Cancer, 20:1-5 (1977).

Evans, J.J., "Two radioimmunoassay methods for measuring plasma oestriol," N.Z.J. Med. Lab. Tech. 33:86 (1979).

Fant, M., "Insulin-like growth factor binding proteins (BP) from human placenta are immunologically related to the growth hormone dependent binding protein in adult human serum (BP-$_{53}$)," Placenta, 11:123-133 (1990).

Fattorusso et al., "NMR structure of the human oncofetal fibronectin ED-B domain, a specific marker for agiogenesis," Structure with Folding & Design 7:381-390 (1999).
Fawcett et al., "Transposable elements controlling I-R hybrid dysgenesis in D. melanogaster are similar to mammalian LINEs," Cell 47:1007-1015 (1986).
Feinberg et al., "Monoclonal antibody FDC-6 exhibits binding to human plasma fibronectin: A caveat for cervicovaginal oncofetal fibronectin testing?" Am. J. Obstet Gynecol 171:1302-1308 (1994).
Feinberg et al., "Monoclonal antibody X18A4 identifies an oncofetal fibronectin epitope distinct from the FDC-6 binding site," Am. J. Obstet. Gynecol. 172:1526-1536 (1995).
Feinberg et al., "Transforming growth factor-β stimulates trophoblast oncofetal fibronectin synthesis in vitro: implications for trophoblast implantation in vivo," J. Clin. Endocrin Metabl 78:1241-8 (1994).
Feinberg et al., "Tropho-uteronectin (TUN): A unique oncofetal fibronectin deposited in the extracellular matrix of the tropho-uterine junction and regulated in vitro by cultured human trophoblast cells," Trophoblast Res. 7:167-179 (1993).
Feinberg et al., "Is oncofetal fibronectin a trophoblast glue for human implantation?", Am. J. Pathol. 138:537-543 (1991).
Flaman, et al., "A rapid PCR fidelity assay," Nucleic Acids Research 22(15):3259-3260 (1994).
French-Constant, C., "Alternative splicing of fibronectin—many different proteins but few different functions," Exp. Cell Res. 221:261-271 (1995).
Friedman et al., "Circulating concentrations of fetal fibronectin do not reflect reduced trophoblastic invasion in preeclampic pregnancies," Am J Obst Gynecol 167:496-7 (1992).
Gabler et al., "Matrix remodeling in dilated cardiomyopathy entails the occurrence of oncofetal fibronectin molecular variants," Heart 75:358-62 (1996).
Gaits, F. and K. Hahn, "Shedding Light on Cell Signaling: Interpretation of FRET Biosensors," Science STKE 165:PE3, (5 pages) (2003).
Galfre, G. and C. Milstein, "Preparation of Monoclonal Antibodies: Strategies and Procedure," Meth. Enzymol., 73(Pt.B):3-46 (1981).
Garite et al., "Fetal fibronectin: A new tool for the prediction of successful induction of labor," Am. J. Obstet. Gyn. 175:1516-1521 (1996).
George et al., "Defects in mesoderm, neural tube and vascular development in mouse embryos lacking fibronectin," Development 119:1079-1091 (1993).
Gerard et al., "Influence on Stability in *Escherichia coil* of the Carboxy-Terminal Structure of Cloned Moloney Murine Leukemia Virus Reverse Transcriptase," DNA 5(4):271-279 (1986).
Giovannoni et al., "Isolation of anti-angiogenesis antibodies from a large combinatorial repertoire by colony filter screening," Nucleic Acids Res. 29:e27 (6 pages) (2001).
Gottschlich et al., "A new prognostic indicator for head and neck cancer—p53 serum antibodies?," Anticancer Research 19:2703-2705 (1999).
Gown, A.M. and A.M. Vogel, "Monoclonal antibodies to human intermediate filament proteins. II. Distribution of Filament Proteins in Normal Human Tissues," Am. J. Pathol., 114:309-321 (1984).
Grady, D., "Hormone Cuts Risk of Premature Birth," The New York Times, Feb. 7, 2003, (2 pages).
Griffin et al., "Quantitative proteomic analysis using a MALDI quadrupole time-of-flight mass spectrometer," Anal. Chem. 73:978-986 (2001).
Guo et al., "Structural alterations of sugar chains in urine fibronectin from bladder cancer patients and its enzymatic mechanism," J. Cancer Res. Clin. Oncol. 127:512-519 (2001).
Halin et al., "Enhancement of the antitumor activity of interleukin-12 by targeted delivery to neovascularature," Nature Biotech 20:264-269 (2002).
Hammel et al., "Detection and monitoring of serum p53 antibodies in patients with colorectal cancer," Gut 40:356-361 (1997).
Hammel, P. and T. Soussi, "Le dosage sérique des anticorps anti-p53: application au cancer colorectal," Rev. Méd. Interne 21:167-73 (2000) [Article in French with an English Summary on the first page of the article].

Hazen, S.L. and J.W. Helnecke, "3-Chlorotyrosine, a specific marker of myeloperoxidase-catalyzed oxidation is markedly elevated in low density lipoprotein isolated from human atherosclerotic intima," J. Clin. Invest. 99:2075-2081 (1997).
Helland et al., "Similar effects on infants of n-3 and n-6 fatty acids supplementation to pregnant and lactating women," Pediatrics 108:e82 (10 pages) (2001).
Helland et al., "Maternal supplementation with very-long-chain n-3 fatty acids during pregnancy and lactation augments children's IQ at 4 years of age," Pediatrics 111:e39-e44 (2003).
Higashiyama et al., "Measurement of the Expression of Oncofetal Fibronectin mRNA in Thyroid Carcinomas by Competitive Reverse Transcription-Polymerasde Chain Reaction," Thyroid 9:235-240 (1999).
Hillenkamp et al., "Matrix Assisted UV-Laser Desorption/Ionization: A New Approach to Mass Spectrometry of Large Biomolecules," *Biological Mass Spectrometry*, (Burlingame and McCloskey, Eds.), Amsterdam: Elsevier Science Publishers, pp. 49-60 (1990).
Holliger et al., "'Diabodies': Small bivalent and bispecifif antibody fragments," Proc. Natl. Acad Sci. USA 90:6444-6448 (1993).
Howard et al., "Wound healing-associated proteins Hsp47 and fibronectin are elevated in Dupuytren's Contracture," J. Surg. Res. 117:232-238 (2004).
Huober et al., "Prognostic significance of circulating p53 autoantibodies in patients with breast cancer," Zentralbl Gynakol 188:560-564 (1996) [Article in German with an English language abstract on the first page of the article].
Hussa, R.O., *The clinical marker hCG*, New York: Praeger Publishers, pp. 38-40 (1987).
Husslein, P. and R. Ahner, "Term labor and post-term pregnancy can be predicted using fetal fibronectin (fFN) and IL-lb concentrations in cervicovaginal secretions of pregnant women," J. Obstet. Gynecol. Rep. Biol. 104(2):186 (2002).
Huston et al., "Protein engineering of antibody binding sites: recovery of specific activity in an anti-digoxin single-chain Fv analogue produced in *Escherichia coli*," Proc. Natl. Acad. Sci. USA 85:5879-5883 (1988).
Imai et al., "Significance of fetal fibronectin and cytokine measurement in the cervicovaginal secretions of women at term in predicting term labor and post-term pregnancy," European Journal of Obstetics & Gynecology and Reproductive Biology 97:53-58 (2001).
Innis et al., "Intakes of essential n-6 and n-3 polyunsaturated fatty acids among pregnant Canadian women," Am J Clin Nutr 77:473-478 (2003).
Innis et al., "Docosahexaenoic acid and arachidonic acid enhance growth with no adverse effects in preterm infants fed formula," J. Pedatr. 140:547-554 (2002).
Islami et al., "Is cellular fibronectin a biological marker for preeclampsia," Eur. J. Obstet. Gynecol. Reprod. Biol. 97:40-45 (2001).
Jacobs et al. "Radial scars of the breast and breast carcinomas have similar alterations in expression of factors involved in vascular stroma formation," Human Pathology 33:29-38 (2002).
Jalbout et al., "Autoantibodies to tubulin are specifically associated with the young age onset of the nasopharyngeal carcinoma," Int J. Cancer 101: 101:146-50 (2002).
Jameson, D.M. and W.H. Sawyer, "Fluorescence Anisotropy Applied to Biomolecular Interactions," Methods Enzymol. 246:283-300 (1995).
Jassem et al., "Serum p53 antibodies in small cell lung cancer: the lack of prognostic relevance," Lung Cancer 31:17-23 (2001).
Jensen, C.L. and W.C. Heird, "Lipids with an emphasis in long-chain polyunsaturated fatty acids," Clin Perinatol 29:261-281 (2002).
Johnson, J.P., "Cell adhesion molecules of the immunoglobulin supergene family and their role in malignant transformation and progression to metastatic disease," Cancer Metastasis Rev., 10:11-22 (1991).
Kaczmarek et al., "Distribution of oncofetal fibronectin isoforms in normal hyperplastic and neoplastic human breast tissues," Int. J. Cancer 59:11-16 (1994).
Kanayama et al., "The relationship between granulocyte elastase-like activity of cervical mucus and cervical maturation," Acta Obstet. Gynecol. Scand. 70:29-34 (1991).

Karas et al., "Laser Desorption Ionization of Proteins with Molecular Masses Exceeding 10 000 Daltons," Anal. Chem. 60:2299-2301 (1988).

Karelina, T.V. and A.Z. Eisen, "Interstitial collagenase and the ED-B oncofetal domain of fibronectin are markers of angiogenesis in human skin tumors," Cancer Detection & Prevention 22:438-444 (1998).

Keirse, M.J.N.C., "Progestogen administration in pregnancy may prevent preterm delivery," British Journal of Obstetrics and Gynaecology 97(2):149-154 (1990).

Kettle, A.J., "Detection of 3-Chlorotyrosine in Proteins Exposed to Neutrophil Oxidants," Methods Enzymol. 300:111-120 (1999).

Khan et al., "Oncofetal fibronectin in diabetic retinopathy," Investigative Ophthalmology & Visual Science 45(1):287-295 (2004).

Kiss et al., "Fetal fibronectin as a predictor of term labor," Acta Obstet Gynecol Scand 79:3 7 (2000).

Köhler et al., "Derivation of specific antibody-producing tissue culture and tumor lines by cell fusion," Eur. J. Immunol. 6:511-519 (1976).

Köhler, G. and C. Milstein, "Continuous cultures of fused cells secreting antibody of predefined specificity," Nature 256:495-497 (1975).

Kornblihtt et al., "Primary structure of human fibronectin: differential splicing may generate at least 10 polypeptides from a single gene," EMBO J. 4(7): 1755-1759 (1985).

Kosmehl et al., "Molecular variants of fibronectin and laminin: structure, physiological occurrence and histopathological aspects," Virchows Arch, 429:311-322, (1996).

Kosmehl et al., "Distribution of laminin and fibronectin isoforms in oral mucosa and oral squamous cell carcinoma," Br. J. Cancer 81:1071-1079 (1999).

Kotewicz et al., "Cloning and overexpression of Moloney murine leukemia virus transcriptase in *Escherichia coli*," Gene 35:249-258 (1985).

Kriegsman et al., "Expression of fibronectin splice variants and oncofetal glycosylated fibronectin in the synovial membranes of patients with rheumatoid arthritis and osteoarthritis," Rhematol Int. 24:25-33 (2004).

Kupferminc et al., "Fetal fibronectin levels are elevated in maternal plasma and amniotic fluid of patients with severe preeclampsia," 41st Annual Meeting of the Society for Gynecological Investigation, Chicago, Illinois, Mar. 22-26, 1994, Abstract # O150, p. 161, (1994)2.

Kupferminc et al., "Fetal fibronectin levels are elevated in maternal plasma and amniotic fluid of patients with severe preeclampsia," Am. J. Obstet. Gynecol. 172:649-652 (1995).

Lange et al., "A double antibody solid phase assay for DNA autoantibodies for clinical use," Clin. Exp. Immunol. 25(2):191-198 (1976).

Larque et al. "Perinatal supply and metabolism of long-chain polyunsaturated fatty acids: importance for the early development of the nervous system" Ann N Y Acad Sci. 967:299-310 (2002).

Larque et al., "In vivo investigation of the placental transfer of $^{13}$C-labeled fatty acids in humans," J. Lipid Research 44:49-55 (2003).

Lavieille et al. "Analysis of p53 Antibody Response in Patients with Squamous Cell Carcinoma of the Head and Neck," 16:2385-2388 (1996).

Lenner et al., "Serum antibodies against p53 in relation to cancer risk and prognosis in breast cancer: a population-based epidemiological study," British Journal of Cancer 79:927-932 (1999).

Lewis et al., "Mass Spectrometric Methods for Evaluating Point Mutations," Biotechniques 24:102-110 (1998).

Li et al., "Mammalian cell expression of dimeric small immune proteins," Protein Engineering 10:731-736 (1997).

Liao et al., "Identification of Two Amino Acids within the EIIIA (ED-A) Segment of Fibronectin Constituting the Epitope for Two Function-blocking Monoclonal Antibodies," Journal of Biological Chemistry 274:17876-17884 (1999).

Liao et al., "The EIIIA segment of fibronectin is a ligand for integrins $\alpha_9\beta_1$ and $\alpha_4\beta_1$ providing a novel mechanism for regulating cell adhesion by alternative splicing," J. Biol. Chem., 277:14467-14474, (2002).

Lockwood et al., "Fetal fibronectin in cervical and vaginal secretions as a predictor of preterm delivery," New England J. Medicine 325:669-671 (1991).

Lockwood et al., "Cervico-vaginal oncofetal fibronectin in preterm labor patients: a result of chorion extracellular matrix degradation," Am. J. Obstet. Gynecol., 164:374, Abstract # 467 (1991).

Loridon-Rosa et al., "Distribution of Oncofetal Fibronectin in Human Mammary Tumors: Immunofluorescence Study of Histological Sections," Cancer Research 50:1608-1612 (1990).

Lubin et al., "Serum p53 antibodies as early markers of lung cancer," Nat Med 1:701-702 (1995).

Luton et al.. "Fetal fibronectin in the cervical secretion predicts accurately the onset of labor at term," Eur. J. Obstet Gynecol. Rep Biol. 74:161-164 (1997).

Lyons et al., "Oncofetal fibronectin and oral squamous cell carcinoma," Br. J. Oral Maxillofac. Surg. 39:471-477 (2001).

Mack et al., "Serum anti-p53 antibodies in patients with lung cancer," Oncology Reports 7:669-674 (2000).

Makrides, A. and R.A. Gibson, "The role of fats in the lifecycle stages: pregnancy and the first year of life," Med J. Aust 176 (Supplement): S111-S112 (2002).

Manabe et al., "Modulation of Cell-adhesive Activity of Fibronectin by the Alternatively Spliced EDA Segment," J. Cell. Biol. 139:295-307 (1997).

Mandel et al., "Oncofetal fibronectins in oral carcinomas: Correlation of two different types," APMIS 102:695-702 (1994).

Mandel et al., "Cancer-associated changes in glycosylation of fibronectin," APMIS, 100:817-826 (1992).

Mardon et al., "Regulation of alternative splicing in the IIICS region of human fibronectin pre-mRNA encoding cell binding sites CS and CS5," J. Cell Science 103:423-433 (1992).

Mardon et al., "Fibronectin splice variants are differentially incorporated into the extracellular matrix of tumorigenic and non-tumorigenic hybrids between normal fibroblasts and sarcoma cells," J. Cell Sci. 104: 783-792 (1993).

Mariani "Tumor targeting potential of the monoclonal antibody BC-1 against oncofetal fibronectin in nude mice bearing human tumor implants," Cancer 80: 2378-2384 (1997).

Mariani et al., "A pilot pharmacokinetic and immunoscintigraphic study with the technetium-99m-labeled monoclonal antibody BC-1 directed against oncofetal fibronectin in patients with brain tumors," Cancer 80:2484-2489 (1997).

Marty et al., "Cytotoxic targeting of F9 teratocarcinoma tumours with anti-ED-B fibronectin scFv antibody modified liposomes," Br. J. Cancer 87:106-112 (2002).

Matsumoto et al., "Expression of Fibronectin Isoforms in Human Breast Tissue: Production of Extra Domain A$^+$/Extra Domain B$^+$ by Cancer Cells and Extra Domain A$^+$ By Stromal Cells," Jpn. J. Cancer Res. 90:320-325 (1999).

Matsuura et al "The Oncofetal Structure of Human Fibronectin Defined by Monoclonal Antibody FDC-6," The Journal of Biological Chemistry 263:3314-22 (1988).

Matsuura et. al., "The oncofetal domain of fibronectin defined by monoclonal antibody FDC-6: Its presence in fibronectin from fetal and tumor tissues and it absence in those normal adult tissues and plasma," Proc. Natl. Acad. Sci. USA, 82:6517-6521 (1985).

McFayden et al., "Maternal and umbilical cord erythrocyte omega-3 and omega-6 fatty acids and haemorrheaology in singleton and twin pregnancies," Arch. Dis. Child Fetal Neonatal Ed. 88(2):F134-F138 (2003).

Meis, Paul J., "171 Alpha hydroxyprogesterone caproate prevents recurrent preterm birth," American Journal of Obstetrics and Gynecology 187(6 Suppl):S54 (2002).

Menzin et al., "Identification of Oncofetal Fibronectin in Patients with Advanced Epithelial Ovarian Cancer," Cancer 82:152-158 (1998).

Merchant, M. and S.R. Weinberger, "Recent advancements in surface-enhanced laser desorption/ionization-time of flight-mass spectrometry," Electrophoresis 21:1164-1177 (2000).

Michel, F. and B. Franz Lang, "Mitochondrial class II introns encode proteins related to the reverse transcriptases of retroviruses," Nature 316:641-643 (1985).

Midulla et al., "Source of Oncofetal ED-B-containing Fibronectin: Implications of Production by both Tumor and Endothelial Cells," Cancer Res. 60:164-169 (2000).

Mighell et al., "RT-PCR Investigation of Fibronectin mRNA Isoforms in Malignant, Normal and Reactive Oral Mucosa," Oral Oncol 33:155-162 (1997).

Mintz et al., "Fingerprinting the circulating repertoire of antibodies from cancer patients," Nature Biotechnology 21:57-63 (2003).

Mishell, B.B. and S.M. Shiigi (Ed.), *Selected Methods in Cellular Immunology*, San Francisco, California: W.H. Freeman & Co. pp. 368-370 (1980).

Miyawaki et al., "Fluorescent indicators for $Ca^{2+}$ based on green fluorescent proteins and calmodulin," Nature 388:882-887 (1997).

Moll et al., "The Catalog of Human Cytokeratins: Patterns of Expression in Normal Epithelia, Tumors and Cultured Cells," Cell 30:11-24 (1982).

Mouillesseaux et al., "Improvement in the specificity and sensitivity of detection for the Taura syndrome virus and yellow head virus of penaeid shrimp by increasing the amplicon size in SYBR Green real-time RT-PCR," J. Virol. Methods 111(2):121-127 (2003).

Mudenda et al., "The relationship between serum p53 autoantibodies and characteristics of human breast cancer," Br. J. Cancer 69:1115-1119 (1994).

Murray et al., "Serum p53 antibodies: predictors of survival in small-cell lung cancer," Br. J Cancer 83:1418-24 (2000).

Nageotte et al, "Fetal fibronectin in patients at increased risk for premature birth," Am J Obstet Gynecol. 170:20-25 (1994).

Nanki et al., "Expression of Oncofetal Fibronectin and Syndecan-1 MRNA in 18 human lung cancer cell lines," Tumor Biology 22:390-396 (2001).

NCBI Nucleotide GenBank No. AJ297960 (accessed on Sep. 23, 2005).

NCBI Protein GenBank No. CAA63371 (accessed on Sep. 23, 2005).

NCBI Nucleotide GenBank No. X92689 (accessed on Sep. 23, 2005).

NCBI Nucleotide GenBank No. Y10345 (accessed on Sep. 23, 2005).

Nelson, R.W., "The use of bioreactive probes in protein characterization," Mass Spectrometry Reviews 16:353-376 (1997).

Nilsson et al., "Targeted Delivery of Tissue Factor to the ED-B Domain of Fibronectin, a Marker of Angiogenesis, Mediates the Infarction of Solid Tumors in Mice," Cancer Research 61:711-716 (2001).

Noblot et al., "The use of micronized progesterone in the treatment of menace of preterm delivery," European Journal of Obstetrics and Gynecology and Reproductive Biology 40(3):203-209 (1991).

Old, R. W. et al. (Eds.), *Principals of Gene Manipulation: An Introduction to Genetic Engineering*, $2^{nd}$ edition, Studies in Microbiology, vol. 2, Berkeley, California: University of California Press, p. 26 (1981).

Olthoff et al., "Modification of Wiley-McLAren TOF Analyzers for Laser Desorption," Anal. Instrument. 16:93-115 (1987).

Oyama et al., "Oncodevelopmental Regulation of the Alternative Splicing of Fibronectin Pre-Messenger RNA in Human Lung Tissues," Cancer Research 50:1075-1078 (1990).

Oyama et al., "Coordinate Oncodevelopental Modulation of Alternative Splicing of Fibronectin Pre-Messenger RNA at ED-A, ED-B, and CS1 Regions in Human Liver Tumors," Cancer Res. 53:2005-2011 (1993).

Paidas et al., "Third Trimester Fetal Fibronectin (FFN) levels are associated with the development of pre-eclampsia (PE)," 41st Annual Meeting of the Society for Gynecological Investigation, Chicago, Illinois, Mar. 22-26, 1994, Abstract # P392, p. 390, (1994).

Pankov, R. and K.M. Yamada, "Fibronectin at a glance," J. Cell Science 115:3861-3863 (2002).

Pau et al., "Oncofetal matrix glycoproteins in cerebral arteriovenous malformations and neighbouring vessels," J. Neurol. Neurosurg. Psych. 68(1):101-102 (2000).

Peerce et al., "Distance between substrate sites on the Na-glucose cotransporter by fluorescence energy transfer," Proc. Natl. Acad. Sci. U.S.A. 83:8092-8096 (1986).

Pekonen et al., "A monoclonal antibody-based immunoradiometric assay for low molecular weight isulin-like growth factor binding protein/placental protein 12," J. Immunoassay 10(4):325-337 (1989).

Pini et al., "Design and Use of a Phage Display Library," J. Biol Chem 273:21769-21776 (1998).

Pisetsky et al., "A simple enzyme-linked immunosorbent assay for antibodies to native DNA," J. Immun. Meth. 41(2):187-200 (1981).

Plow et al., "Ligand binding to integrins," J. Biol. Chem. 275:21785-21788 (2000).

Poljak et al., "Production and structure of diabodies," Structure 2:1121-1123 (1994).

Preudomme et al., "Very low incidence pf p53 antibodies in adult non-Hodgkin's lymphoma and multiple myeloma," British Journal of Haematology 100:184-186 (1998).

Pujuguet et al., "Expression of Fibronectin ED-$A^+$ and ED-$B^+$ Isoforms by Human and Experimental Colorectal Cancer," American Journal of Pathology 148:579-592 (1996).

Reese et al., "Global Gene Expression Analysis to Identify Molecular Markers of Uterine Receptivity and Embryo Implantation," J. Biol. Chem. 276:44137-44145 (2001).

Reis et al., "Prediction of successful induction of labor at term: Role of clinical history, digital examination, ultrasound, assessment of the cervix, and fetal fibronectin assay," Am. J. Obstet. Gyn 189:1361-1367 (2003).

Rhodes et al., "Large-scale meta-analysis of cancer microarray data identifies common transcriptional profiles of neoplastic transformation and progression," Proc. Natl. Acad. Sci. USA 101: 9309-9314 (2004).

Roman et al., "Does ultrasound examination when the cervix is unfavorable improve the prediction of failed labor induction?," Ultrasound in obstetrics & gynecology 23:357-362 (2004).

Ross et al., "Quantitative Approach to Single-Nucleotide Polymorphism Analysis Using MALDI-TOF Mass Spectrometry," Biotechniques 29(3):620-629 (2000).

Roth et al., "Purification and Characterization of Murine Retroviral Reverse Transcriptase Expressed in *Escherichia coli*," J. Biol. Chem. 260:9326-9335 (1985).

Rozenberg et al., "Comparison of the Bishop score, ultrasonographically measured cervical length, and fetal fibronectin assay in predicting time until delivery and type of delivery of term," Am. J. Obstet Gynecol. 182:108-113 (2000).

Rutanen et al., "Measurement of insulin-like growth factor binding protein-1 in cervical/vaginal secretions: comparison with the ROM-check Membrane Immunoassay in the diagnosis of ruptured fetal membranes," Clinica Chimica Acta, 214:73-81 (1993).

Rutanen et al., "Diagnosis of Premature Rupture of Fetal Membranes by the Measurement of Insulin-like Growth Factor Binding Protein-1 in Cervical Secretion," Am. J. Obstet. Gynecol., 164:258 (1991).

Saad et al., "Cancer Cell-associated Fibronectin Induces Release of Matrix Metalloproteinase-2 from Normal Fibroblasts," Cancer Research 62:283-289 (2002).

Sabir et al., "Can magnetic resonance imaging predict the success of parturition in oxytocin-induced pregnant women?" Eur Radiol 10:768-71 (2000).

Sangrajrang et al., "Serum p53 antibodies in correlation to other biological parameters of breast cancer," Cancer Detection & Prevention 27:182-6 (2003).

Sangrajrang et al., "Serum p53 antibodies in patients with lung cancer: correlation with clinicopathologic features and smoking," Lung Cancer 39:297-301 (2003).

Santimaria et al., "Immunoscintigraphic Detection of the ED-B Domain of Fibronectin, a Marker of Angiogenesis, in Patients with Cancer," Clin. Cancer Res. 9:571-579 (2003).

Scarpino et al., "Expression of EDA/EDB Isoforms of Fibronectin in Papillary Carcinoma of the Thyroid," J. Pathol. 188:163-167 (1999).

Scheuermann, Jörg, "Isolation of binding molecules to the EDB domain of fibronectin, a marker of angiogenesis," A dissertation submitted to the Swiss Federal Institute of Technology Zurich for the degree of Doctor of Natural Sciences, 143 pages. (Zürich, Dec. 2002).

Schoen RC, et al. "Monoclonal antibody against human fibronectin which inhibits cell attachment." Hybridoma 1: 99-108 (1982).

Schor et al., "Migration-Stimulating Factor: A Genetically Truncated Onco-Fetal Fibronectin Isoform Expressed by Carcinoma and Tumor-Associated Stromal Cells," Cancer Research 63:8827-8836 (2003).

Sekiguchi et al., "Differences in domain structure between human fibronectins isolated from plasma and from culture supernatants of normal and transformed fibroblasts," J. Biol. Chem. 260:5105-5114 (1985).

Senyei, A.E. and E.R. Wassman, "Fetal cells in the maternal circulation. Technical considerations for practical application to prenatal diagnosis," Obstet Gynecol Clin North Am. 20(3):583-98 (1993).

Shimoya et al., "Cervical fluid oncofetal fibronectin as a predictor of early ectopic pregnancy. Is it affected by blood contamination," J. Reprod Med 47:640-644 (2002).

Shulman et al., "A better cell line for making hybridomas secreting specific antibodies," Nature, 276:269-270 (1978).

Smuts et al., "A Randomized Trial of Docosahexaenoic Acid Supplementation During the Third Trimester of Pregnancy," Obstet Gynecol 101(3):469-479 (2003).

Soussi et al., "Les anticorps anti-p53: une nouvelle méthode d'analyse des alterations du gene p53: application au cancer du sein," Pathol Biol 44:232-234 (1996) [Article in French with an English language summary on the first page].

Stollar, B.D., "The Experimental Induction of Antibodies to Nucleic Acids," Meth. Enzymol., 70(A):70-85 (1980).

Tabet et al., "Laser Desorption Time-of-Flight Mass Spectrometry of High Mass Molecules," Anal. Chem. 56:1662-1667 (1984).

Takano et al., "Accurate and Objective Preoperative Diagnosis of Thyroid Papillary Carcinomas by Reverse Transcription-PCR Detection of Oncofetal Fibronectin Messenger RNA in Fine-Needle Aspiration Biopsies," Cancer Research 58:4913-4917 (1998).

Takano et al, "Preoperative Diagnosis of Thyroid and Anaplastic Carcinomas by Real-Time Quantitative Reserve Transcription-Polymerase Chain Reaction of Oncofetal Fibronectin Messenger RNA," Cancer Research 59:4542-4545 (1999).

Takano et al., "Rapid Detection of Specific Messenger RNAs in Thyroid Carcinomas by Reserve Transcription-PCR with Degenerative Primers: Specific Expression of Oncofetal Fibronectin Messenger RNA in Papillary Carcinoma," Cancer Res. 57:3792-3797 (1997).

Takano et al., "Self-Examination of Thyroid Nodules," Endocrin J. 47(5):591-3 (2000).

Takano et al., "Preoperative Diagnosis of Thyroid Carcinomas by Aspiration Biopsy-Reserve Transcription-Polymerase Chain Reaction," Endocrin J. 47:271-275 (2000).

Takano et al., "Expression of Oncofetal Fibronectin Messenger Ribonucleic Acid in Fibroblasts in the Thyroid: A Possible Cause of False Positive Results in Molecular-Based Diagnosis of Thyroid Carcinomas," J. Clin. Endo Met 85:765-768 (2000).

Takano et al., "[Molecular-based diagnosis of thyroid carcinomas by detecting cancer specific mRNAs," Rinsho Byori 48:149-54 (2000) [Article in Japanese with an English summary on the first page of the article].

Takano et al., "[Aspiration biopsy-RT-PCR(ABRP): lessons from its success]," Rinsho Byori 49:1248-1254 (2001) [Article in Japanese with an English summary on the first page of the article].

Takano et al., "[Aspiration biopsy RNA diagnosis]," Rinsho Byori 51(2):152-157 (2003) [Article in Japanese with an English summary on the first page of the article].

Takano et al., "[Aspiration biopsy RNA diagnosis]," Rinsho Byori Suppl. 123:156-162 (2002) [Article in Japanese with an English summary on the first page of the article].

Takano et al., "Restricted expression of oncofetal fibronectin mRNA in thyroid papillary and anaplastic carcinoma: an in situ hydridization study," Br. J. Cancer 78:221-224 (1998).

Takano et al., "Analysis of splice variants of the fibronectin gene in thyroid carcinomas by reverse transcription-polymerase chain reaction: Increased expression of oncofetal fibronectin mRNA in papillary carcinomas is not caused by the alternation in splicing," J. Endocrinol. Invest. 22:18-22 (1999).

Tam et al., "Prediction of cervical response to prostaglandin $E_2$ using fetal fibronectin," Acta Obstet Gynecol Scand. 78:861-865 (1999).

Tanaka et al., "Protein and Polymer Analyses up to $m/z$ 100 000 by laser ionization time-of-flight mass spectrometry," Rapid Commun. Mass Spectrom. 2:151-153 (1988).

Tanese, N. et al., "Expression of enzymatically active reverse transcriptase in Escherichia coli," Proc. Natl. Acad. Sci. USA 82(15):4944-4948 (1985).

Tang et al., "Humoral response to p53 in humans colorectal tumors: a prospective study of 1,209 patients," Int Cancer 94(6):859-863 (2001).

Tavassoli et al., "p53 antibodies in the saliva of patients with squamous cell carcinoma of the oral cavity," Int J Cancer 78:390-391 (1998).

Tavian et al., "RT-PCR detection of fibronectin $EDA^+$ and $EDB^+$ mRNA isoforms: molecular markers for hepatocellular carcinoma," Int. J. Cancer 56: 820-825 (1994).

Thelwell et al., "Mode of action and application of Scorpion primers to mutation detection," Nucleic Acids Res. 28:3752-3761 (2000).

Tijssen, P., Laboratory Techniques in Biochemistry and Molecular Biology: Practice and Theory of Enzyme Immunoassays, Amsterdam: Elsevier Science Publishers, pp. 105-107 (1985).

Ting et al., "Overexpression of the Oncofetal Fn variant containing the EDA Splice-in Segment in the Dermal-Epidermal Junction of Psoriatic Uninvolved Skin," J. Invent Dermatolo 114:706-711 (2000).

Toh et al., "Close structural resemblance between putative polymerase of a Drosophila transposable genetic element 17.6 and pol gene product of Moloney murine leukaemia virus," EMBO J. 4:1267-1272 (1985).

Tominaga et al., "Detection of p73 antibodies in patients with various types of cancer: immunological characterization," Br. J Cancer 84:57-63 (2001).

Tomkiel et al., "Autoimmunity to the $M_r$ 32,000 Subunit of Replication Protein A in Breast Cancer," Clin Canc Res 8:752-758 (2002).

Toyoshima et al., "High-molecular-weight fibronectin synthesized by adenoid cystic carcinoma cells of salivary gland origin," Jpn J Canc Res 90:308-319 (1999).

Van Breeman et al., "Time-resolved laser desorption mass spectrometry. I. Desorption of Preformed Ions," Int. J. Mass Spectrom. Ion Phys. 49:35-50 (1983).

Van Vliet et al., "Distribution of fibronectin isoforms in human renal disease," J Path 193:256-262 (2001).

Vartio et al., "Differential expression of the ED sequence-containing form of cellular fibronectin in embryonic and adult human tissues," J. Cell Sci. 88:419-430 (1987).

Viti et al., "Increased binding affinity and valence of recombinant antibody fragments lead to improved targeting of tumoral angiogenesis," Cancer Research 59:347-352 (1999).

Vogl et al., "p53 Autoantibodies in patients with primary ovarian cancer are associated with higher age, advanced stage and higher proportion of p53 positive tumor cells," Oncology 57(4): 324-329 (1999).

Vojtesek et al., "Absence of p53 autoantibodies in a significant proportion of breast cancer patients," Br. J. Cancer 71:1253-1256 (1995).

Volk et al., "Monoclonal Antibodies to the Glycoprotein of Vesicular Stomatitis Virus: Comparative Neutralizing Activity," J. Virol., 42:220-227 (1982).

Volkmann et al., "Anti-p53 in Breast Cancer: Concordance of Different Assay Procedures and Association with p53 Antigen Expression," Oncology 63:297-305 (2002).

Waites et al., "Immunohistological localization of the human endometrial secretory protein pregnancy-associated endometrial $\alpha_1$-globulin, an insulin-like growth factor-binding protein, during the menstrual cycle," J. Clinical and Metabolism, 67:1100-1104 (1988).

Wandall et al., "Substrate Specificities of Three Members of the Human UDP-N-Acetyl-α-D-galactosamine: Polypeptide N-Acetylgalactosaminyltransferase Family, GalNAc-T1, -T2, and -T3," J. Biol. Chem. 272: 23503-23514 (1997).

Wang et al., "Identification of a Mutated Fibronectin As a Tumor Antigen Recognized by $CD4^+$ T Cells: Its Role in Extracellular Matrix Formation and Tumor Metastasis," J. Exp. Med. 195: 1397-1406 (2002).

Warnakulasuriya et al., "Expression of p53 in oral squamous cell carcinoma is associated with the presence of IgG and IgA p53 autoantibodies in sera and saliva of the patients," J. Pathol. 192(1): 52-57 (2000).

Watson et al. (Eds.), *Molecular Biology of the Gene*, 4th Edition, Menlo Park, California: The Benjamin/Cummings Publishing Company, Inc., p. 224 (1987).

Weiner et al., "The therapeutic efficacy and cost-effectiveness of aggressive tocolysis for premature labor associated with premature rupture of the membranes," Am. J. Obstet. Gynecol., 159:216-222 (1988).

Willsher et al., "The significance of p53 autoantibodies in the serum of patients with breast cancer," Anticancer Res 16:927-930 (1996).

Wilm et al., "Electrospray and Taylor-Cone theory, Dole's beam of macromolecules at last?," Int. J. Mass Spectrom. Ion Processes 136: 167-180 (1994).

Wing et al., "Factors affecting the likelihood of successful induction after intravaginal misoprostol application for cervical ripening and labor induction," Am. J. Obstet Gynecol. 186:1237-40 (2002).

Winterbourn et al., "Biomarkers of myeloperoxidase-derived hypochlorous acid," Free Radical Biology & Medicine 29:403-409 (2000).

Wunderlich et al., "Fetal fibronectin: A new screening-marker for bladder cancer," Oncol. Rep. 8:669-672 (2001).

Wurl et al., "Detection of p53 Autoantibodies in Sera of Gastric Cancer Patients and Their Prognostic Relevance," Scand J. Gastroenterol 32:1147-51 (1997).

Yamada, K.M. and R.A.F. Clark, "Provisional Matrix," Chapter 2 in *The Molecular and Cellular Biology of Wound Repair*, $2^{nd}$ edition R.A.F. Clark (Ed.), New York: Plenum Press, pp. 51-93, (1996).

Yamaguchi et al., "Circulating antibodies to $P40^{AIS}$ in the sera of respiratory tract cancer patients," Int. J. Cancer 89:524-8 (2000).

Yeast et al., "Fetal anemia as a response to prophylactic platelet transfusion in the management of alloimmune thrombocytopenia," Am. J. Obstet Gynecol 189(6): 874-876 (2003).

Yeast et al., "A positive fetal fibronectin test is associated with more favorable induction of labor outcomes," Am. J. Obstet Gynecol 189:S199 (2003).

Yi et al., "A fibronectin fragment inhibits tumor growth, angiogenesis, and metastasis," Proc. Natl. Acad. Sci. USA 98:620-624 (2001).

Yoshida et al., "Co-expression of tenascin and fibronectin in epithelial and stromal cells of benign lesions and ductal carcinomas in the human breast," J Pathol. 182:421-8 (1997).

Yoshioka et al., "Determination of Genes Involved in the Process of Implantation: Application of GeneChip to Scan 6500 Genes," Biochem. Biophys. Res. Commun. 272:531-538 (2000).

Zalcman et al., "Monitoring of p53 Autoantibodies in Lung Cancer during Therapy: Relationship to Reponse to Treatment," Clin Canc Res 4:1359-1366 (1998).

Zalcman et al., "Prognostic significance of serum p53 antibodies in patients with limited-stage small cell lung cancer," Int. J Cancer 89:81-6 (2000).

Zardi et al., "Transformed human cells produce a new fibronectin isoform by preferential alternative splicing of a previously unobserved exon," EMBO J 6(8):2337-2342 (1987).

Zijlstra, A. and M.E. Schelling, "Detection of multiple fibronectin isoforms in fetal fibroblast monolayer culture: a novel method for the qualitative and quantitative detection of multiple antigens," Hist Cell Biol. 111:163-169 (1999).

Feinburg, et al., "Human Trophoblasts and Tropho-uteronectin (TUN): A Model for Studying Early Implantation Events," Ass Reprod Reviews, 3(1):19-25 (1993).

Iams, et al., "Fetal fibronectin improves the accuracy of diagnosis of preterm labor," Am. J Obs Gyn., 173(1):141-145(1995).

Lu, George, et al., "Vaginal fetal fibronectin levels and spontaneous preterm birth in symptomatic women," Onc Gyn. 97(2):225-227 (2001).

Luton, et al., "Fetal fibronectin in the cervical secretion predicts accurately the onset of labor at term," Eur J Obs Gyn Reprod Biol., 74, 167-164 (1997).

Mouw, et al., "High cervical fetal-fibronectin concentrations and birth within 3 days in pregnancies of 41 weeks or more," NEJM, 332(16):1105 (1995).

Peaceman, et al., "Fetal fibronectin as a predictor of preterm birth in patients with symptoms: a multicenter trial," Am J Obstet Gynecol., 177(1):13-17 (1997).

Takeuchi, et al., "Localization and significance of fibronectin in peri-implantation mouse embryos," Asia-Oceania J Obs Gyn., 15(2):191-197 (1989).

Turpeeinniemi-Hujanen, et al., "Extracellular matrix interactions in early human embryos: implications for normal implantation events," Fertil. Steril., 64(1):132-138 (1995).

Wunderlich, et al., "Fetal fibronectin: a new screening-marker for bladder cancer?" Oncology reports, 8,669-672 (2001).

\* cited by examiner

METHODS FOR DETECTING ONCOFETAL FIBRONECTIN

RELATED APPLICATIONS

Benefit of priority under 35 U.S.C. §119(e) is claimed to U.S. Provisional Application Ser. No. 60/592,823, filed Jul. 30, 2004, to Robert Hussa, Mark Fischer-Colbrie, Jerome Lapointe, Simon Shorter and Andrew Senyei entitled "Methods for Detecting Oncofetal Fibronectin;" to U.S. Provisional Application Ser. No. 60/592,803 to Robert Hussa, Mark Fischer-Colbrie, Jerome Lapointe, and Durlin Hickok, filed Jul. 30, 2004, entitled "Oncofetal Fibronectin as a Marker for Pregnancy-Related Indications;" to U.S. Provisional Application Ser. No. 60/592,825, filed Jul. 30, 2004, to Mark Fischer-Colbrie, Jerome Lapointe, and Durlin Hickok, entitled "Samples for Detection of Oncofetal Fibronectin and Uses Thereof;" to U.S. Provisional Application Ser. No. 60/592,804, filed Jul. 30, 2004, to Robert Hussa, Mark Fischer-Colbrie, Jerome Lapointe, and Simon Shorter, entitled "Oncofetal Fibronectin as a Marker for Health and Disease;" and to U.S. Provisional Application Ser. No. 60/592,824, filed Jul. 30, 2004, to Robert Hussa and Simon Shorter, entitled "Detection of Oncofetal Fibronectin for Selection of Concepti. This application also is related to International PCT Serial No. PCT/US05/027183, filed Jul. 29, 2005; and to each of U.S. application Ser. No. 11/193,857; 11/193,806; 11/193,771; and 11/193,561, each filed the same day herewith.

The subject matter of each of the above noted provisional applications, applications and international application is incorporated by reference in its entirety by reference thereto.

FIELD OF THE INVENTION

Methods and products for the detection of oncofetal fibronectin protein and nucleic acid molecule encoding oncofetal fibronectin in samples are provided. In particular, methods and products for the detection of oncofetal fibronectin proteins or nucleic acids, and/or autoantibodies therefor, in body tissue and fluid samples, such as lavage samples, cervicovaginal and urine samples are provided. The methods permit screening or indicating of risk for diseases including cancers, inflammatory diseases and pregnancy-related conditions.

BACKGROUND

Fibronectins constitute a family of proteins expressed from a single gene. Various isoforms of fibronectin are present in plasma and adult tissue, including connective tissue, skin, colon, liver, spleen and kidney (Matsuura and Hakomori, Proc. Natl. Acad. Sci. USA 82:6517-6521 (1985)). Fetal tissues and some tumor cells and other cells contain or express fibronectin isoforms collectively called "fetal" or "oncofetal" fibronectins. For example, oncofetal fibronectin (onfFN) is present in placenta, amniotic fluid, fetal tissue and cell lines from hepatomas and sarcomas (Matsuura and Hakomori, Proc. Natl. Acad. Sci. USA, 82:6517-6521 (1985)). Oncofetal fibronectin has been used as a marker for pre-term delivery by a pregnant woman and also as a marker for some cancers.

Because early detection of cancer and other diseases and prediction of risk factors associated with pregnancy-related conditions are important to developing effective treatment strategies, and oncofetal fibronectin is associated with some of these conditions, a need exists for improved tests to detect oncofetal fibronectin, for improved sampling methods and oncofetal fibronectin detection methods in order to exploit its use as a marker. Therefore, among the objects herein, it is an object herein to provide methods and products for detection of oncofetal fibronectin proteins and nucleic acids encoding the proteins, and to provide sampling methods and to provide diagnostic tests and products therefor.

SUMMARY

Provided are methods for detection of an oncofetal fibronectin indicating molecule and methods for obtaining samples for use in methods of detection. Also provided are products for use in methods of detection of oncofetal fibronectin or of molecules indicative thereof in samples.

Provided are methods that include detection of oncofetal fibronectin for any of a variety of indications and uses related to pregnancy or delivery, including, but not limited to, risk of preterm, impending and/or imminent delivery, prediction of delivery date, prediction of maintenance of pregnancy, use in methods of preventing preterm delivery and use in inducing delivery.

Among the methods provided herein, are methods for assessing whether a subject has an increased likelihood of imminent or preterm delivery, by detecting an oncofetal fibronectin indicating molecule in a sample from a pregnant subject, wherein presence of the oncofetal fibronectin indicating molecule in the sample indicates that the subject has an increased likelihood of imminent or preterm delivery. In such methods, presence of an amount of oncofetal fibronectin indicating molecule at or above a threshold level can indicate that the subject has an increased likelihood of imminent or preterm delivery. The threshold level for such methods can be 1 ng/ml or about 1 ng/ml, 2 ng/ml or about 2 ng/ml, 3 ng/ml or about 3 ng/ml, 4 ng/ml or about 4 ng/ml, 5 ng/ml or about 5 ng/ml, for a buffer-treated sample, or 1 ng/ml or about 1 ng/ml, 3 ng/ml or about 3 ng/ml, 5 ng/ml or about 5 ng/ml, 7 ng/ml or about 7 ng/ml, 10 ng/ml or about 10 ng/ml, for an untreated sample.

In other embodiments, provided herein are methods for determining whether to administer oxytocin for induction of delivery, by determining the amount of an oncofetal fibronectin indicating molecule in a sample of a pregnant subject, and if the amount of oncofetal fibronectin indicating molecule is equal to or above threshold level, identifying the subject as one for whom oxytocin induction is likely to result in vaginal delivery. Such methods can be used to identify a subject as one for whom oxytocin induction of delivery is favorable, and to administer to the subject a dose of oxytocin effective to induce delivery. According to such methods when the sample is positive for an oncofetal fibronectin indicating molecule, the subject is likely to vaginally deliver within 24 or 48 hours and/or is likely to vaginally deliver after a single induction procedure. In such methods, the induction procedure can be vaginal ripening, administration of a pre-induction agent, or administration of an induction agent. In some instances, subject can be likely to deliver after a single administration of a pre-induction agent. Also provided are methods for evaluating the effectiveness of induction, by determining the amount of an oncofetal fibronectin indicating molecule in a sample from a pregnant subject who has undergone an induction procedure, and if the amount of oncofetal fibronectin indicating molecule is equal to or above threshold level, identifying the subject as one who is likely to vaginally deliver. In such methods, the subject can be likely to vaginally deliver within 48 hours or 24 hours, after a single induction procedure, or after a single administration of a pre-induction agent. Induction procedures can be selected from vaginal ripening, administration of a pre-induction agent and administration of an induction agent.

Also provided herein are methods for identifying a subject for induction of delivery, by determining the amount of an oncofetal fibronectin indicating molecule in a sample from a pregnant subject, determining a second indicator of induction outcome for the subject, and if the amount of oncofetal fibronectin indicating molecule is above threshold level and the second indicator indicates favorable induction outcome, identifying the subject as one for whom induction is likely to be successful. Such methods can be used to identify a subject as one for whom induction of delivery is likely to be successful, and to administer to the subject an induction procedure. Likelihood of successful induction can indicated by any of the following: increased likelihood of vaginal delivery upon induction relative to subjects negative for oncofetal fibronectin and/or having a negative result for the second indicator of induction outcome, likely decreased time interval between initiating induction and delivery relative to subjects negative for oncofetal fibronectin and/or having a negative result for the second indicator of induction outcome, likely decreased time interval between administering a parturifacient and delivery relative to subjects negative for oncofetal fibronectin and/or having a negative result for the second indicator of induction outcome, likely decreased time interval between administering oxytocin and delivery relative to subjects negative for oncofetal fibronectin and/or having a negative result for the second indicator of induction outcome, increased likelihood of delivering within 24 hours of induction relative to subjects negative for oncofetal fibronectin and/or having a negative result for the second indicator of induction outcome, increased likelihood of delivering within 48 hours of induction relative to subjects negative for oncofetal fibronectin and/or having a negative result for the second indicator of induction outcome and decreased likelihood of more than one administration of pre-induction agent to the subject relative to subjects negative for oncofetal fibronectin and/or having a negative result for the second indicators of induction outcome, and combinations thereof. The second indicator of induction outcome can be any of a measurement or observation of the pregnant subject, a measurement or observation of the fetus(es), and medical history of the pregnant subject. Such indicators include, but are not limited to, cervical length, Bishop score, effacement, parity, cervical dilation, gestational age, body mass index, station, consistency, transvaginal ultrasound, and digital examination, or a combination thereof.

Also provided are methods for determining the likelihood of successful induction of a subject, by determining the amount of an oncofetal fibronectin indicating molecule in a sample of a pregnant subject, determining the highest of multi-tiered threshold levels equal to or less than the amount of oncofetal fibronectin indicating molecule in the sample, where each higher threshold indicates an increased likelihood of successful induction relative to each lower threshold, and identifying the likelihood of successful induction for the subject according to likelihood indicated by the highest threshold. Also provided are methods for identifying a subject for whom induction of delivery is unfavorable, by determining the amount of an oncofetal fibronectin indicating molecule in a sample of a pregnant subject, and if the amount of oncofetal fibronectin indicating molecule is below threshold level, identifying the subject as one for whom oxytocin induction is unlikely to result in vaginal delivery.

In the methods provided, successful induction can be indicated by each increasing amount in the multi-tiered thresholds indicating, relative to lower thresholds: increased likelihood of vaginal delivery upon induction relative to subjects negative for oncofetal fibronectin and/or having a negative result for the second indicator of induction outcome, likely decreased time interval between initiating induction and delivery relative to subjects negative for oncofetal fibronectin and/or having a negative result for the second indicator of induction outcome, likely decreased time interval between administering a parturifacient and delivery relative to subjects negative for oncofetal fibronectin and/or having a negative result for the second indicator of induction outcome, likely decreased time interval between administering oxytocin and delivery relative to subjects negative for oncofetal fibronectin and/or having a negative result for the second indicator of induction outcome, increased likelihood of delivering within 24 hours of induction relative to subjects negative for oncofetal fibronectin and/or having a negative result for the second indicator of induction outcome, increased likelihood of delivering within 48 hours of induction relative to subjects negative for oncofetal fibronectin and/or having a negative result for the second indicator of induction outcome and decreased likelihood of more than one administration of pre-induction agent to the subject relative to subjects negative for oncofetal fibronectin and/or having a negative result for the second indicators of induction outcome, or combinations thereof.

In such methods, the sample can be any one of a swab of the point of a possible cervicovaginal lesion, urine, blood, plasma, serum, a body tissue, lavage and cervical vaginal fluid, sampled from among the cervical canal, cervical os, ectocervix, transition zone on the cervix between squamous and columnar cells, posterior fornix, a portion of the vagina below the posterior fornix, lower third of the vagina, labia, cervical interstitial fluid and combinations thereof. In a particular embodiment, the sample is any one of a swab of the cervical canal, a swab of the cervical os, a swab of the ectocervix, a swab of the transition zone on the cervix between squamous and columnar cells, a swab of the vagina, a swab of the posterior fornix, a swab of the portion of the vagina below the posterior fornix, a swab of the lower third of the vagina, a swab of the labia, and combinations thereof. A sample can be collected with a polyester swab, a cotton swab or a rayon swab. When the sample is a cotton swab, the method can be conducted on the swab. When the sample is tested by vertical flow, the sample essentially does not contain blood, or contain 5% or about 5% or less, 1% or about 1% or less, 0.5% or about 0.5% or less, 0.1% or about 0.1% or less blood.

Further in such methods testing for the presence of oncofetal fibronectin indicating molecule can include testing for the presence of an oncofetal fibronectin protein, or a fragment thereof, testing for the presence of a nucleic acid molecule encoding oncofetal fibronectin, a nucleic acid molecule complementary to a nucleic acid molecule encoding oncofetal fibronectin, or a fragment thereof, or testing for the presence of an autoantibody for oncofetal fibronectin protein or an autoantibody for a nucleic acid molecule encoding oncofetal fibronectin and fragments thereof. When the indicating molecule is a nucleic acid molecule, the methods can further include treating the sample under nucleic acid synthesis conditions such as reverse transcriptase polymerase chain reaction.

Such methods can further include contacting the sample with a fibronectin or oncofetal fibronectin binding partner, and detecting complexes of the binding partner and oncofetal fibronectin, whereby detection of a complex is indicative of the amount of oncofetal fibronectin indicating molecule in the sample. The method can further include contacting the sample with a first fibronectin or oncofetal fibronectin binding partner, contacting the sample with a second fibronectin or oncofetal fibronectin binding partner, wherein the second fibronectin or oncofetal fibronectin binding partner is conjugated to a detectable or bindable moiety, or the second fibronectin or oncofetal fibronectin binding partner is immobilized to a solid support, and detecting complexes of the first binding partner, oncofetal fibronectin indicating molecule, and the second binding partner, whereby detection of a complex is indicative of the amount of oncofetal fibronectin indicating molecule in the sample. The methods further can include contacting a sample from the subject with a non-specific binding compound, contacting the sample with a second fibronectin or oncofetal fibronectin binding partner, such as a conjugate or immobilized binding partner. In one aspect, the first binding partner is conjugated to a moiety such as, for example, colloidal metal, photodetectable latex microsphere, chromophore, fluorescent moiety, quantum dot, and detectable enzyme. The method can further include contacting the sample with a detectable compound that specifically binds the first binding partner, wherein the detectable compound is an antibody conjugate or a nucleic acid conjugate. The first binding partner or second binding partner can be an anti-fibronectin antibody or an antigen-binding fragment thereof.

The methods provided herein can be performed in any of numerous manners. For example, complexes can be detected by determining if any first binding partner is in spatial proximity to the second binding partner, whereby detection of any first and second binding partners in spatial proximity indicates presence of an oncofetal fibronectin indicating molecule in a sample, where spatial proximity can be determined by a non-radioactive energy transfer reaction, such as fluorescence energy transfer (FET), fluorescence resonance energy transfer (FRET), and homogeneous time-resolved fluorescence (HTRF). In other methods, oncofetal fibronectin indicating molecule or fragment thereof or binding partner can be detected by mass spectrometry or gel electrophoresis. In some methods, the amount of oncofetal fibronectin indicating molecule detected can be compared to one or more thresholds, wherein the sample is classified according to the highest threshold that is less than or equal to the detected amount of oncofetal fibronectin indicating molecule. In some methods, the sample is contacted with a non-specific binding compound or with a non-specific binding surface of a solid support. In the methods described herein, the complex can be detected by measuring the oncofetal fibronectin indicating molecule that bound to the fibronectin or oncofetal fibronectin binding partner, or to a fragment of the oncofetal fibronectin indicating molecule that bound to the fibronectin or oncofetal fibronectin binding partner. In the methods described herein, the complex can be detected by detecting the weight of a compound bound to the fibronectin or oncofetal fibronectin binding partner, wherein a detected weight that corresponds to oncofetal fibronectin indicating molecule indicates the presence of oncofetal fibronectin in the sample. In the methods described herein, the complex can be measured by detecting the fibronectin or oncofetal fibronectin binding partner. The fibronectin or oncofetal fibronectin binding partner can measured by detecting fluorescence, reflectance, absorption, bioluminescence, enzyme-linked detectable signal, or radioactive decay. In particular methods provided herein, at least one fibronectin or oncofetal fibronectin binding partner is immobilized to a test strip.

The fibronectin or oncofetal fibronectin binding partner can bind to the EDA-specific portion of an oncofetal fibronectin indicating molecule and the EDA-specific portion of an oncofetal fibronectin indicating molecule is any of an EDA portion of an oncofetal fibronectin protein, an EDA-encoding portion of a nucleic acid molecule encoding oncofetal fibronectin, a portion of an autoantibody that binds to EDA of oncofetal fibronectin protein, and a portion of an autoantibody that binds to the EDA-encoding portion of a nucleic acid molecule encoding oncofetal fibronectin.

The fibronectin or oncofetal fibronectin binding partner can bind to the EDB-specific portion of an oncofetal fibronectin indicating molecule and the EDB-specific portion of an oncofetal fibronectin indicating molecule is any of an EDB portion of an oncofetal fibronectin protein, an EDB-encoding portion of a nucleic acid molecule encoding oncofetal fibronectin, a portion of an autoantibody that binds to EDB of oncofetal fibronectin protein, and a portion of an autoantibody that binds to the EDB-encoding portion of a nucleic acid molecule encoding oncofetal fibronectin.

The fibronectin or oncofetal fibronectin binding partner can bind to the IIICS-specific portion of an oncofetal fibronectin indicating molecule and the IIICS-specific portion of an oncofetal fibronectin indicating molecule is any of a IIICS portion of an oncofetal fibronectin protein, a IIICS-encoding portion of a nucleic acid molecule encoding oncofetal fibronectin, a portion of an autoantibody that binds to IIICS of oncofetal fibronectin protein, and a portion of an autoantibody that binds to the IIICS-encoding portion of a nucleic acid molecule encoding oncofetal fibronectin. The IIICS portion can be any one of V64, V89, V95 and V120. When the oncofetal fibronectin indicating molecule is a IIICS portion of oncofetal fibronectin protein, the fibronectin or oncofetal fibronectin binding partner can recognize a post-translational modification of oncofetal fibronectin protein. In one aspect, the post-translational modification can be O-glycosylation of threonine 33 of IIICS.

In one aspect the oncofetal fibronectin indicating molecule is identified as lacking EDA, EDB or IIICS. If the oncofetal fibronectin indicating molecule is identified as lacking, the portion of IIICS can be amino acids 1-25 of IIICS, amino acids 90-120 of IIICS or both.

Also provided are methods that include contacting the sample with a test strip containing a mobilizable oncofetal fibronectin binding partner conjugated to a detectable moiety and a fibronectin or oncofetal fibronectin binding partner immobilized to the test strip, and detecting complexes of the first binding partner, oncofetal fibronectin indicating molecule, and the second binding partner, whereby detection of a complex is indicative of the amount of oncofetal fibronectin indicating molecule in the sample. The oncofetal fibronectin binding partner specifically binds a oncofetal fibronectin indicating molecule in preference to a non-oncofetal fibronectin indicating molecule.

Also provided are methods that include contacting the sample with a test strip containing a mobilizable fibronectin or oncofetal fibronectin binding partner conjugated to a detectable moiety and an oncofetal fibronectin binding partner immobilized to the test strip, and detecting complexes of the first binding partner, oncofetal fibronectin indicating molecule, and the second binding partner, whereby detection of a complex is indicative of the amount of oncofetal fibronectin indicating molecule in the sample. The oncofetal fibronectin binding partner specifically binds an oncofetal fibronectin indicating molecule in preference to a non-oncofetal fibronectin indicating molecule.

Also provided herein are methods for increasing the accuracy of delivery date prediction, by measuring an oncofetal fibronectin indicating molecule in a sample from a pregnant subject, wherein an amount of oncofetal fibronectin indicating molecule in the sample at or above a threshold level indicates an increased likelihood that the subject will deliver within a particular time period, relative to a pregnant subject having a sample with an amount of oncofetal fibronectin indicating molecule below the threshold level. Also provided are methods for increasing the accuracy of pregnancy maintenance prediction, by measuring an oncofetal fibronectin indicating molecule in a sample from a pregnant subject, wherein an amount of oncofetal fibronectin indicating molecule in the sample below a threshold level indicates an increased likelihood that the subject will maintain her pregnancy for a particular time period, relative to a pregnant subject having a sample with an amount of oncofetal fibronectin indicating molecule amount at or above the threshold level. The particular time period can be any one of 3 weeks or less, 2 weeks or less, 10 days or less, 1 week or less, 6 days or less, 5 days or less, 4 days or less, 3 days or less, 2 days or less, and 1 day or less. The subject can be at least 50% more likely to deliver within the particular time period, relative to a pregnant subject having a sample with an amount of oncofetal fibronectin indicating molecule amount below the threshold level.

Also provided are combinations and kits, including combinations and kits for performing the methods provided herein. In one embodiment, a combination is provided, containing a fibronectin or oncofetal fibronectin binding partner, a parturifacient, and optionally instructions for use of the combination. Combinations also can include a non-specific binding compound. The kits provided herein can include the combinations provided herein and also a system for classifying the sample according to one or more threshold levels, and/or instructions for use.

Provided herein is the use of any of the products provided herein for use in the preparation of a medicament for any of the methods provided herein, including, but not limited to, diagnosis, imaging, and/or treatment of a health disorder characterized by the presence of, or elevated levels of oncofetal fibronectin.

Provided are methods for detection of an oncofetal fibronectin indicating molecule and methods for obtaining samples for use in methods of detection. Also provided are products for use in methods of detection of oncofetal fibronectin or of molecules indicative thereof in samples.

Provided are methods for detecting the presence of an oncofetal fibronectin indicating molecule in a variety of samples. In some methods provided herein, the sample is treated with a reagent and/or contacted with a non-specific binder.

Provided herein are methods for detecting the presence of an oncofetal fibronectin indicating molecule in a sample, by contacting a sample with a substance that reduces non-specific binding of background material to a fibronectin or oncofetal fibronectin binding partner, contacting the sample with a fibronectin or oncofetal fibronectin binding partner, and detecting any complex formed between an oncofetal fibronectin indicating molecule and the fibronectin or oncofetal fibronectin binding partner, whereby detection of complex is indicative of the presence of oncofetal fibronectin indicating molecule in the sample. Also provided are methods for detecting the presence of an oncofetal fibronectin protein or fragment thereof in a sample, by contacting a sample with a substance that reduces non-specific binding of background material to a fibronectin or oncofetal fibronectin binding partner, wherein the fibronectin or oncofetal fibronectin binding partner is a fibronectin or oncofetal fibronectin binding protein, contacting the sample with a fibronectin or oncofetal fibronectin binding protein, and detecting any complex formed between an oncofetal fibronectin indicating molecule and the fibronectin or oncofetal fibronectin binding protein, wherein the oncofetal fibronectin indicating molecule is an oncofetal fibronectin protein or fragment thereof, whereby detection of complex is indicative of the presence of oncofetal fibronectin protein or fragment thereof in the sample. Also provided are methods for detecting the presence of an oncofetal fibronectin indicating molecule in a sample, by contacting a sample with solution that reduces the ionic strength of a sample, whereby specific binding of an oncofetal fibronectin indicating molecule to a fibronectin or oncofetal fibronectin binding partner is increased, contacting the solution-contacted sample with a fibronectin or oncofetal fibronectin binding partner, and detecting any complex formed between the oncofetal fibronectin indicating molecule and the fibronectin or oncofetal fibronectin binding partner, whereby detection of complex is indicative of the presence of oncofetal fibronectin indicating molecule in the sample.

In such methods, the substance can be a solid support, and can contain a non-specific binder to which oncofetal fibronectin indicating molecule in the sample does not specifically bind. In some methods, the non-specific binding compound can be a non-specific binding protein or a non-specific binding nucleic acid molecule. In some methods, the ionic strength of the sample after contacting with the substance is at least 150µ or about 150µ, or is less than or equal to 500µ or about 500µ. For example, the ionic strength can range from 50µ to 350µ, or from about 50µ to about 350µ, or from 150µ to 250µ, or ranging from about 150µ to about 250µ. In such methods, the amount of background material in the sample can be decreased relative to the amount of oncofetal fibronectin indicating molecule in the sample, or the amount of oncofetal fibronectin indicating molecule in the sample can be increased relative to the amount of background material in the sample. In some methods, the sample is a liquid sample, and the solute concentration of oncofetal fibronectin indicating molecule in the sample is unchanged. In some such methods, background material binds no more than 10% of the fibronectin or oncofetal fibronectin binding partner. These methods can further include contacting the sample with a second fibronectin or oncofetal fibronectin binding partner, wherein the second fibronectin or oncofetal fibronectin binding partner is conjugated to a detectable or bindable moiety, or the second fibronectin or oncofetal fibronectin binding partner is immobilized on a solid support; and the detecting step includes detecting complexes of the first binding partner, the second binding partner, and the oncofetal fibronectin indicating molecule.

Samples used in the methods provided herein can be any of urine, lymph, blood, plasma, serum, saliva, seminal fluid, lavages, cervical fluid, cervicovaginal fluid, vaginal fluid, breast fluid, breast milk, synovial fluid, semen, seminal fluid, stool, sputum, cerebral spinal fluid, tears, mucus, interstitial fluid, follicular fluid, amniotic fluid, aqueous humor, vitreous humor, peritoneal fluid, ascites, sweat, lymphatic fluid, lung sputum, lavage, or fractions or components thereof. The sample can be any of urine, lavage, breast milk, cervicovaginal swab, saliva, serum, plasma, blood, and interstitial fluid. In a particular embodiment, the sample is a urine sample. Exemplary urine samples are a neat (as obtained, i.e., unmodified or untreated) urine sample, and a frozen urine sample. In some methods, at least 30 minutes or about 30 minutes, or at least 12 hours or about 12 hours, prior the contacting or detecting steps, the urine sample is collected from a subject.

In the methods provided herein, the non-specific binding compound is any of albumin, casein, fetal calf serum, gelatin, or an antibody that does not specifically bind an oncofetal fibronectin indicating molecule; and can be, for example, bovine serum albumin (BSA). In some of the methods provided herein, the second binding partner is immobilized to the solid support of a test strip. The second binding partner can be immobilized to a first region of the test strip, and a non-specific binding compound can be immobilized to a second region of the test strip, wherein the first region is downstream of the sample fluid flow pathway relative to the second region.

In some embodiments, the methods include normalizing the amount of oncofetal fibronectin indicating molecule in the sample according to the concentration of one or more normalization analytes in the sample; an exemplary normalization analyte is creatinine. The methods provided herein can further include contacting a sample with a non-specific binding compound, and separating the sample from the non-specific binding compound; and additionally further include, after separating the sample from the non-specific binding compound, contacting the sample with a solid support whereby protein and/or nucleic acid components of the sample are immobilized on the solid support, and contacting the solid support with a fibronectin or oncofetal fibronectin binding partner. In some cases, background material is removed from the sample. The non-specific binding compound can be immobilized on a solid support.

In some methods, a sample positive for oncofetal fibronectin can identify the subject from whom the sample was collected as having cancer (e.g., malignant neoplastic or metastatic) cells; and in some instances, the cancer cells can originate from bladder, kidney, prostate, cervix or ovary. In a particular aspect, the cancerous cells originate from bladder.

In other methods, a sample positive for oncofetal fibronectin identifies the subject from whom the sample was collected as having an increased risk of imminent or preterm delivery. For example, a sample positive for oncofetal fibronectin identifies the subject from whom the sample was collected as one for whom induction is likely to be successful. In the methods provided, successful induction can be indicated by each increasing amount relative to lower thresholds: increased likelihood of vaginal delivery upon induction relative to subjects negative for oncofetal fibronectin and/or having a negative result for the second indicator of induction outcome, likely decreased time interval between initiating induction and delivery relative to subjects negative for oncofetal fibronectin and/or having a negative result for the second indicator of induction outcome, likely decreased time interval between administering a parturifacient and delivery relative to subjects negative for oncofetal fibronectin and/or having a negative result for the second indicator of induction outcome, likely decreased time interval between administering oxytocin and delivery relative to subjects negative for oncofetal fibronectin and/or having a negative result for the second indicator of induction outcome, increased likelihood of delivering within 24 hours of induction relative to subjects negative for oncofetal fibronectin and/or having a negative result for the second indicator of induction outcome, increased likelihood of delivering within 48 hours of induction relative to subjects negative for oncofetal fibronectin and/or having a negative result for the second indicator of induction outcome and decreased likelihood of more than one administration of pre-induction agent to the subject relative to subjects negative for oncofetal fibronectin and/or having a negative result for the second indicators of induction outcome, or combinations thereof.

Also provided herein are methods for detecting the presence of an oncofetal fibronectin indicating molecule in a urine sample, by determining the amount of oncofetal fibronectin indicating molecule present in a buffer-treated urine sample, whereby 60 ng/ml or more, or about 60 ng/ml or more oncofetal fibronectin indicating molecule present in the buffer-treated sample identifies the sample as positive for oncofetal fibronectin. Also provided herein are methods for detecting the presence of an oncofetal fibronectin indicating molecule in a urine sample, by thawing a frozen urine sample, and determining the amount of oncofetal fibronectin indicating molecule present in the thawed urine sample. In some such methods, the determining step can include contacting the sample with a first fibronectin or oncofetal fibronectin binding partner, contacting the sample with a second fibronectin or oncofetal fibronectin binding partner, wherein: the second fibronectin or oncofetal fibronectin binding partner is conjugated to a detectable or bindable moiety, or the second fibronectin or oncofetal fibronectin binding partner is immobilized to a solid support, and detecting complexes of the first binding partner, oncofetal fibronectin indicating molecule and the second binding partner.

In these embodiments, the methods also can include contacting the sample with a non-specific binding compound. Such methods can be used to identify the subject from whom the sample was collected as having cancerous (e.g., neoplastic, malignant or metastatic) cells; for example the cancerous cells can originate from bladder, kidney, prostate, cervix or ovary. In a particular aspect, the cancerous cells originate from bladder.

In another embodiment, provided herein are methods for detecting the presence of an oncofetal fibronectin indicating molecule in an interstitial fluid sample, by detecting any oncofetal fibronectin indicating molecule in an interstitial fluid sample.

In yet another embodiment, provided herein are methods for detecting the presence of an oncofetal fibronectin indicating molecule in a lavage sample, by detecting any oncofetal fibronectin indicating molecule in a lavage sample.

In such embodiments, the methods can further include contacting the sample with a fibronectin or oncofetal fibronectin binding partner, and detecting any complex formed between an oncofetal fibronectin indicating molecule and the fibronectin or oncofetal fibronectin binding partner, whereby detection of complex is indicative of the presence of oncofetal fibronectin indicating molecule in the sample. A lavage sample can be a ductal lavage sample. In such methods, a sample positive for oncofetal fibronectin can identify the subject from whom the sample was collected as having cancerous (e.g., neoplastic, malignant or metastatic) cells, and in some cases the cells can be from breast.

In the methods provided herein, complexes can be detected by determining if any first binding partner is in spatial proximity to the second binding partner, whereby detection of any first and second binding partners in spatial proximity indicates presence of an oncofetal fibronectin indicating molecule in a sample. In such methods, spatial proximity can be detected as a result of a non-radioactive energy transfer reaction, where the non-radioactive energy transfer reaction can be any one of fluorescence energy transfer (FET), fluorescence resonance energy transfer (FRET), homogeneous time-resolved fluorescence (HTRF).

Also in such methods, the oncofetal fibronectin indicating molecule can be any of an oncofetal fibronectin protein, a nucleic acid molecule encoding oncofetal fibronectin, a nucleic acid molecule complementary to a nucleic acid molecule encoding oncofetal fibronectin, an autoantibody for oncofetal fibronectin protein, an autoantibody for a nucleic acid molecule encoding oncofetal fibronectin, and fragments thereof. In the methods provided herein, the binding partner can be an anti-fibronectin antibody, or a nucleic acid molecule, or a fragment thereof. In any of the methods provided herein, the oncofetal fibronectin indicating molecule can be any of an oncofetal fibronectin protein or a fragment thereof, a nucleic acid molecule encoding oncofetal fibronectin or a fragment thereof, a nucleic acid molecule complementary to a nucleic acid molecule encoding oncofetal fibronectin or a fragment thereof, an autoantibody for oncofetal fibronectin protein or a fragment thereof, or an autoantibody for a nucleic acid molecule encoding oncofetal fibronectin or a fragment thereof.

Also in the methods provided herein, presence of an oncofetal fibronectin indicating molecule below a threshold amount can classify the sample as oncofetal fibronectin negative; and presence of an oncofetal fibronectin indicating molecule equal to or above a threshold amount can classify the sample as oncofetal fibronectin positive. A threshold amount of oncofetal fibronectin protein can be 50 ng/mL or about 50 ng/mL. In some such methods, the amount of oncofetal fibronectin detected is compared to two or more thresholds, wherein the sample can be classified according to the highest threshold that is less than or equal to the detected amount of oncofetal fibronectin indicating molecule. For example, a first threshold is 50 ng/mL and a second threshold is 150 ng/mL. In methods where the subject from whom the sample is collected is pregnant, the two or more threshold amounts can be a function of pregnancy gestational duration. In the methods provided herein, the complex can be detected by measuring the oncofetal fibronectin indicating molecule that bound to the fibronectin or oncofetal fibronectin binding partner, or a fragment of the oncofetal fibronectin indicating molecule that bound to the fibronectin or oncofetal fibronectin binding partner.

The methods provided herein can be used to detect oncofetal fibronectin by mass spectrometry or gel electrophoresis, by measuring the fibronectin or oncofetal fibronectin binding partner bound to the oncofetal fibronectin indicating molecule, and/or by detecting fluorescence, reflectance, absorption, bioluminescence, enzyme-linked detectable signal, or radioactive decay. In one aspect, at least one fibronectin or oncofetal fibronectin binding partner is immobilized to a test strip. The fibronectin or oncofetal fibronectin binding partner can bind to the EDA-specific portion of an oncofetal fibronectin indicating molecule and the EDA-specific portion of an oncofetal fibronectin indicating molecule is any of an EDA portion of an oncofetal fibronectin protein, an EDA-encoding portion of a nucleic acid molecule encoding oncofetal fibronectin, a portion of an autoantibody that binds to EDA of oncofetal fibronectin protein, and a portion of an autoantibody that binds to the EDA-encoding portion of a nucleic acid molecule encoding oncofetal fibronectin.

The fibronectin or oncofetal fibronectin binding partner can bind to the EDB-specific portion of an oncofetal fibronectin indicating molecule and the EDB-specific portion of an oncofetal fibronectin indicating molecule is any of an EDB portion of an oncofetal fibronectin protein, an EDB-encoding portion of a nucleic acid molecule encoding oncofetal fibronectin, a portion of an autoantibody that binds to EDB of oncofetal fibronectin protein, and a portion of an autoantibody that binds to the EDB-encoding portion of a nucleic acid molecule encoding oncofetal fibronectin.

The fibronectin or oncofetal fibronectin binding partner can bind to the IIICS-specific portion of an oncofetal fibronectin indicating molecule and the IIICS-specific portion of an oncofetal fibronectin indicating molecule is any of a IIICS portion of an oncofetal fibronectin protein, a IIICS-encoding portion of a nucleic acid molecule encoding oncofetal fibronectin, a portion of an autoantibody that binds to mcs of oncofetal fibronectin protein, and a portion of an autoantibody that binds to the IIICS-encoding portion of a nucleic acid molecule encoding oncofetal fibronectin. The ICS portion can be any one of V64, V89, V95 and V120. When the oncofetal fibronectin indicating molecule is a IIICS portion of oncofetal fibronectin protein, the fibronectin or oncofetal fibronectin binding partner can recognize a post-translational modification of oncofetal fibronectin protein. In one aspect, the post-translational modification can be O-glycosylation of threonine 33 of IIICS.

In one aspect the oncofetal fibronectin indicating molecule is identified as lacking EDA, EDB or IIICS. If the oncofetal fibronectin indicating molecule is identified as lacking, the portion of IIICS can be amino acids 1-25 of IIICS, amino acids 90-120 of IIICS or both.

In another embodiment, provided herein are test strips, containing a non-specific binding region, and an analyte binding region containing a first fibronectin or oncofetal fibronectin binding partner immobilized thereon, wherein the analyte binding region is downstream of the sample fluid flow pathway relative to the non-specific binding region. In yet another embodiment, provided herein are test strips for detecting the presence of an oncofetal fibronectin indicating molecule in a sample, containing a non-specific binding region, and an analyte binding region containing a first fibronectin or oncofetal fibronectin binding partner immobilized thereon, wherein the analyte binding region is downstream of the sample fluid flow pathway relative to the non-specific binding region.

The test strips provided herein can also contain a conjugate pad, which serves as a sample application component, an absorbent pad, which serves to draw liquid continuously through the device, wherein the materials of the membrane system form a single fluid flow pathway, and a porous or bibulous member in fluid communication with the absorbent pad and conjugate pad, which porous or bibulous member accommodates a liquid sample, wherein the porous or bibulous member contains the analyte binding region. The test strips provided herein also can contain a mobilization region containing a second fibronectin or oncofetal fibronectin binding partner, wherein the second fibronectin or oncofetal fibronectin binding partner is mobilized upon contact with the sample, and the mobilization region is upstream of the analyte binding region. The test strips also can contain a control region containing a biomolecule that specifically binds the second fibronectin or oncofetal fibronectin binding partner, wherein the control region is downstream of the analyte binding region.

In some of the test strips provided herein the first fibronectin or oncofetal fibronectin binding partner binds oncofetal fibronectin in preference to fibronectin. In some of the test strips provided herein, the non-specific binding region contains a non-specific binding protein immobilized thereon, wherein the non-specific binding protein can be, for example, BSA, methylated BSA, W632 or mouse IgG.

Also provided herein are combinations containing a fibronectin or oncofetal fibronectin binding partner and a non-specific binding compound. The combinations provided herein can be used for performing the methods provided herein. In such combinations, the non-specific binder can be a non-specific binding compound. Also in such combinations, the non-specific binder can be a non-specific binding surface of a solid support. The combinations can further contain a fibronectin or oncofetal fibronectin binding partner and a solid support containing a non-specific binding surface. The combinations can contain a test strip with a non-specific binding compound immobilized thereto. The combinations can contain a sample collection device.

Also provided herein are kits containing the combinations provided herein, and also containing instructions for use, and/or a system for classifying the subject with respect to multiple thresholds.

Also provided herein are methods for indicating oncofetal fibronectin in a subject, by collecting a lower vaginal sample from a subject, and testing for the presence of an oncofetal fibronectin indicating molecule in the sample, wherein the presence of oncofetal fibronectin indicating molecule in the sample indicates the presence of oncofetal fibronectin in the subject. In such methods, the lower vaginal sample can include a sample collected from any portion of the vagina below the posterior fornix. In some methods, the lower vaginal sample can be collected from the lower third of the vagina, and can be collected with a swab. In some methods, the sample can include a labial sample. In some methods, the sample is collected by an individual unskilled in the medical profession, including, in some instances, the subject.

Also provided herein are methods for indicating oncofetal fibronectin in a subject, by collecting a labial sample from a subject, and testing for the presence of an oncofetal fibronectin indicating molecule in the sample, wherein the presence of oncofetal fibronectin indicating molecule in the sample indicates the presence of oncofetal fibronectin in the subject. In such methods, the sample can further include a lower vaginal sample. In some methods, the labial sample can be collected from the lower third of the vagina, and can be collected with a swab. In some methods, the sample is collected by an individual unskilled in the medical profession, including, in some instances, the subject.

Also provided herein are methods for indicating oncofetal fibronectin in a subject, by passively collecting a cervicovaginal sample from a subject, and testing for the presence of an oncofetal fibronectin indicating molecule in the sample, wherein the presence of oncofetal fibronectin indicating molecule in the sample indicates the presence of oncofetal fibronectin in the subject. In such methods, the step of passively collecting a cervicovaginal sample can further comprise inserting a sample collection device into the vagina. In such methods, the sample collection device can be maintained in the vagina for at least 5 minutes or about 5 minutes, at least 15 minutes or about 15 minutes, at least 1 hour or about 1 hour, or at least 2 hours or about 2 hours. In such methods, the sample collection device can be inserted into the lower third of the vagina. In such methods, the sample collection device can be inserted into the vagina in the same manner as a tampon is inserted. The sample collection device can be absorptive, and/or can be a tampon-like device or a sanitary napkin-like device. In such methods, the step of passively collecting a cervicovaginal sample can further include placing a sample collection device outside of and below the vagina. In some methods, the sample collection device can contact the labia. In some methods, the sample collection device can be placed between the labia or vaginal orifice and the subject's undergarment. In some methods, the sample collection device can be maintained in place for 5 minutes or more, 10 minutes or more, 15 minutes or more, 1 hour or more, or 2 hours or more.

In such methods, the presence of oncofetal fibronectin indicating molecule above a threshold level can indicate that the sample is positive for oncofetal fibronectin. A threshold level can be 1 ng/ml, 2 ng/ml, 3 ng/ml, 5 ng/ml, 7 ng/ml, 10 ng/ml, 15 ng/ml, or 20 ng/ml for a buffer-treated sample. A threshold level can be 1 ng/ml, 3 ng/ml, 5 ng/ml, 10 ng/ml, 25 ng/ml, 35 ng/ml, or 50 ng/ml for an untreated sample.

In the methods provided herein, presence of oncofetal fibronectin in the sample can indicate a risk of imminent or preterm delivery, the likelihood of successful induction, the presence of cancerous cells in a subject, the risk of a subject developing cancerous cells, the aggressiveness of cancerous cells in a subject, or the effectiveness of treating cancerous cells in a subject.

Also provided herein are combinations containing a sample collection device and a fibronectin or oncofetal fibronectin binding partner. In such combinations, the sample collection device includes, but is not limited to, a urine collection device, a dipstick, a swab and a passive cervicovaginal fluid collection device. In one combination, the passive cervicovaginal sample collection device is insertable into the vagina. In another combination the passive cervicovaginal sample collection device is placed between the labia or vaginal orifice and the undergarment of a subject. The combination also can include a swab long enough to insert into the vagina, but not long enough to contact the cervix, which can be a swab 10 cm or shorter. In another combination, the fibronectin or oncofetal fibronectin binding partner can be immobilized onto the sample collection device.

Combinations provided herein also can include a second fibronectin or oncofetal fibronectin binding partner. In such combinations, the second fibronectin or oncofetal fibronectin binding partner can be conjugated to a detectable label.

The combinations provided herein can be configured to indicate a positive result when the amount of oncofetal fibronectin indicating molecule in the sample is above a threshold level. The combinations provided herein also can contain a test strip reader configured to indicate a positive result when the amount of oncofetal fibronectin indicating molecule in the sample is above a threshold level. In some such combinations, the threshold level is about or is 1 ng/ml, is about or is 2 ng/ml, is about or is 3 ng/ml, is about or is 5 ng/ml, is about or is 7 ng/ml, is about or is 10 ng/ml, is about or is 15 ng/ml, or is about or is 20 ng/ml for a buffer-treated sample. In some such combinations, the threshold level is about or is 1 ng/ml, is about or is 3 ng/ml, is about or is 5 ng/ml, is about or is 10 ng/ml, is about or is 15 ng/ml, is about or is 25 ng/ml, is about or is 35 ng/ml, or is about or is 50 ng/ml for an untreated sample. Also provided herein are kits containing the combinations provided herein, and optionally one or more of instructions for collecting and/or measuring the oncofetal fibronectin indicating molecule, and reagents therefor.

Also provided herein are methods for indicating oncofetal fibronectin in a subject, comprising collecting the sample and testing the sample for the presence of an oncofetal fibronectin indicating molecule with the combinations provided herein. In some such methods, the sample is collected from the portion of the vagina below the posterior fornix. In some such methods, the sample is collected from the lower third of the vagina. In some such methods, the sample is collected from the labia. In the methods provided herein, the sample can be collected with a passive sample collection device. In some methods provided herein, the sample is urine. In such methods, the sample can be collected by an individual not skilled in medical practice. In such methods, the sample can be collected by the subject. Provided herein are any of the methods where the step of testing the sample for the presence of oncofetal fibronectin indicating molecule is performed by an individual not skilled in medical practice or by the subject.

Also provided are methods for determining the presence and/or amount of an oncofetal fibronectin indicating molecule in a sample, by treating a urine sample under conditions for fragmentation of an oncofetal fibronectin indicating molecule, and detecting any fragments of oncofetal fibronectin in the sample, whereby detected oncofetal fibronectin fragments indicate the presence and/or amount of oncofetal fibronectin indicating molecule in a sample.

Also provided are methods for determining the presence and/or amount of an oncofetal fibronectin indicating molecule in a sample, by contacting a body surface or cavity with a lavage fluid, and detecting any oncofetal fibronectin indicating molecule in the lavage fluid.

Provided herein is the use of any of the products provided herein for use in the preparation of a medicament for any of the methods provided herein, including, but not limited to, diagnosis, imaging, and/or treatment of a health disorder characterized by the presence of, or elevated levels of oncofetal fibronectin.

Provided are methods for detection of an oncofetal fibronectin indicating molecule and methods for obtaining samples for use in methods of detection. Also provided are products for use in methods of detection of oncofetal fibronectin or of molecules indicative thereof in samples. Provided are methods for testing subjects to ascertain health and disease status and to assess the risk of developing a disease or condition.

Provided herein are methods for identifying the presence of cervical cancer in a subject by testing for an oncofetal fibronectin indicating molecule in a sample from a subject, wherein an oncofetal fibronectin positive sample identifies the presence of cervical cancer in the subject. Also provide herein are methods of detecting the presence of cancerous (e.g., neoplastic, malignant or metastatic) cervical cells in a subject, by testing for an oncofetal fibronectin indicating molecule in a sample from a subject, wherein an oncofetal fibronectin positive sample indicates the presence of cancerous (e.g., malignant neoplastic or metastatic) cervical cells in the subject.

In the methods provided herein, the sample can be, for example, a swab of the point of a possible cervicovaginal lesion, a swab of the cervical canal, a swab of the cervical os, a swab of the ectocervix, a swab of the transition zone on the cervix between squamous and columnar cells, a swab of the vagina, a swab of the posterior fornix, a swab of the portion of the vagina below the posterior fornix, a swab of the lower third of the vagina, a swab of the labia, cervical interstitial fluid, urine, blood, plasma, serum and combinations thereof. In one aspect, the sample is a cervicovaginal sample, and the sample is one or more of the following: a swab of cervical os, a swab of cervical lesion, a swab of ectocervix, a swab of transition zone between squamous and columnar cells of cervix, or a combination thereof. In another aspect, the sample is a swab of the portion of the vagina below the posterior fornix. In some methods, the sample is collected with a polyester swab, cotton swab or rayon swab. When the sample is a cotton swab, the method can be conducted on the swab.

In some methods provided herein, presence of oncofetal fibronectin indicating molecule in the sample identifies the sample as oncofetal fibronectin positive. In some methods, absence of oncofetal fibronectin indicating molecule in the sample identifies the sample as oncofetal fibronectin negative. In other of the methods provided herein, an amount of oncofetal fibronectin indicating molecule in the sample at or above a threshold identifies the sample as oncofetal fibronectin positive. In some methods, an amount of oncofetal fibronectin indicating molecule in the sample below a threshold identifies the sample as oncofetal fibronectin negative. In some methods, the threshold amount is 40 ng/ml or about 40 ng/ml, 10 ng/ml or about 10 ng/ml, or 5 ng/ml or about 5 ng/ml.

When the sample is assayed using vertical flow, the sample essentially does not contain blood. In such methods, the sample can contain 1% or about 1% or less blood, 0.5% or about 0.5% or less blood, or 0.1% or about 0.1% or less blood.

The methods provided herein also include methods in which the step of testing for the oncofetal fibronectin indicating molecule further includes testing for an oncofetal fibronectin protein, or a fragment thereof, testing for a nucleic acid molecule encoding oncofetal fibronectin, a nucleic acid molecule complementary to a nucleic acid molecule encoding oncofetal fibronectin, or a fragment thereof, or testing for an autoantibody for oncofetal fibronectin protein, an autoantibody for a nucleic acid molecule encoding oncofetal fibronectin, and fragments thereof. In some methods, the step of testing further includes contacting the sample with an fibronectin or oncofetal fibronectin binding partner, and detecting complexes of the binding partner and oncofetal fibronectin indicating molecule. In some methods, the step of testing further includes contacting the sample with a second fibronectin or oncofetal fibronectin binding partner, wherein the second fibronectin or oncofetal fibronectin binding partner is conjugated to a detectable or bindable moiety, or the second fibronectin or oncofetal fibronectin binding partner is immobilized to a solid support. The methods provided herein also can include, prior to detecting complexes, contacting the sample with a non-specific binding compound.

In the methods provided herein, a binding partner can be conjugated to a moiety such as, for example, colloidal metal, photodetectable latex bead, chromophore, fluorescent moiety, quantum dot and detectable enzyme. The methods provided herein can further include, after contacting the first binding partner and sample, contacting the sample with a detectable compound that specifically binds the first binder. In such methods, the detectable compound is an antibody conjugate or a nucleic acid conjugate. In some methods provided herein, a binding partner can be an anti-fibronectin antibody, or a fragment thereof.

In the methods provided herein, complexes can be detected by determining if any first binding partner is in spatial proximity to the second binding partner, whereby detection of any first and second binding partners in spatial proximity indicates presence of an oncofetal fibronectin indicating molecule in a sample. In some such methods, spatial proximity is detected as a result of a non-radioactive energy transfer reaction. In such methods, the non-radioactive energy transfer reaction can be, for example, fluorescence energy transfer (FET), fluorescence resonance energy transfer (FRET), or homogeneous time-resolved fluorescence (HTRF).

In some methods provided herein, the sample is contacted with a non-specific binding compound. In some methods, the sample is contacted with a non-specific binding surface of a solid support.

The methods provided herein include methods in which the amount of oncofetal fibronectin indicating molecule detected is compared to two or more thresholds, wherein the sample is classified according to the highest threshold that is less than or equal to the detected amount of oncofetal fibronectin indicating molecule.

In some methods provided herein, the complex is detected by measuring the oncofetal fibronectin indicating molecule that bound to the fibronectin or oncofetal fibronectin binding partner, or a fragment of the oncofetal fibronectin indicating molecule that bound to the fibronectin or oncofetal fibronectin binding partner. In some methods, complex is detected by detecting the molecular weight of compounds bound to the fibronectin or oncofetal fibronectin binding partner; wherein a molecular weight that corresponds to an oncofetal fibronectin indicating molecule indicates the presence of the oncofetal fibronectin indicating molecule in the sample. In some methods, the oncofetal fibronectin indicating molecule is detected by mass spectrometry or gel electrophoresis. In some methods, the complex is detected by detecting the fibronectin or oncofetal fibronectin binding partner bound to the oncofetal fibronectin indicating molecule. In some such methods, the fibronectin or oncofetal fibronectin binding partner is detected by detecting fluorescence, reflectance, absorption, bioluminescence, enzyme-linked detectable signal, or radioactive decay. In some methods, at least one fibronectin or oncofetal fibronectin binding partner is immobilized to a test strip.

The fibronectin or oncofetal fibronectin binding partner can bind to the EDA-specific portion of an oncofetal fibronectin indicating molecule and the EDA-specific portion of an oncofetal fibronectin indicating molecule is any of an EDA portion of an oncofetal fibronectin protein, an EDA-encoding portion of a nucleic acid molecule encoding oncofetal fibronectin, a portion of an autoantibody that binds to EDA of oncofetal fibronectin protein, and a portion of an autoantibody that binds to the EDA-encoding portion of a nucleic acid molecule encoding oncofetal fibronectin.

The fibronectin or oncofetal fibronectin binding partner can bind to the EDB-specific portion of an oncofetal fibronectin indicating molecule and the EDB-specific portion of an oncofetal fibronectin indicating molecule is any of an EDB portion of an oncofetal fibronectin protein, an EDB-encoding portion of a nucleic acid molecule encoding oncofetal fibronectin, a portion of an autoantibody that binds to EDB of oncofetal fibronectin protein, and a portion of an autoantibody that binds to the EDB-encoding portion of a nucleic acid molecule encoding oncofetal fibronectin.

The fibronectin or oncofetal fibronectin binding partner can bind to the IIICS-specific portion of an oncofetal fibronectin indicating molecule and the IIICS-specific portion of an oncofetal fibronectin indicating molecule is any of a IIICS portion of an oncofetal fibronectin protein, a IIICS-encoding portion of a nucleic acid molecule encoding oncofetal fibronectin, a portion of an autoantibody that binds to IIICS of oncofetal fibronectin protein, and a portion of an autoantibody that binds to the IIICS-encoding portion of a nucleic acid molecule encoding oncofetal fibronectin. The IIICS portion can be any one of V64, V89, V95 and V120. When the oncofetal fibronectin indicating molecule is a IIICS portion of oncofetal fibronectin protein, the fibronectin or oncofetal fibronectin binding partner can recognize a post-translational modification of oncofetal fibronectin protein. In one aspect, the post-translational modification can be O-glycosylation of threonine 33 of IIICS.

In one aspect the oncofetal fibronectin indicating molecule is identified as lacking EDA, EDB or IIICS. If the oncofetal fibronectin indicating molecule is identified as lacking, the portion of IIICS can be amino acids 1-25 of IIICS, amino acids 90-120 of IIICS or both.

Also provided herein are methods of detecting the location in a subject of cervical cancer or cancerous cervical cells, by identifying the presence of cancer in a subject, or the presence of cancerous cells in a subject, according to the methods provided herein, administering to a subject a fibronectin or oncofetal fibronectin binding partner conjugated to an imaging moiety, whereby the conjugate localizes to tissue or cells in the subject containing an oncofetal fibronectin indicating molecule, and detecting the localization of the conjugate within the subject, thereby detecting the oncofetal fibronectin indicating molecule in tissue or cells of the subject, wherein detection is indicative of cancer or a disease state characterized by the presence of oncofetal fibronectin. In one embodiment, the tissues or cells are cervical tissues or cells. Such methods can further include detecting the location in a subject of cervical cancer or cancerous cervical cells, and administering to a subject a treatment fibronectin or oncofetal fibronectin binding partner, whereby the treatment binding partner localizes to regions in the subject containing an oncofetal fibronectin indicating molecule, whereby the localized treatment binding partner causes cell death or inhibits cell growth of cervical cancer or cancerous cervical cells.

Also provided herein are methods of treating a subject having cervical cancer or cancerous cervical cells, by identifying the presence of cervical cancer in a subject, or the presence of cancerous cervical cells in a subject, according to the methods provided herein, and administering to a subject a treatment fibronectin or oncofetal fibronectin binding partner, whereby the treatment binding partner localizes to regions in the subject containing an oncofetal fibronectin indicating molecule, whereby the localized binding partner causes cell death or inhibits cell growth of cervical cancer or cancerous cervical cells. In such methods, the treatment binding partner can be conjugated to a therapeutic moiety.

In some methods, the imaging binding partner conjugate or treatment binding partner can be, for example, a nucleic acid molecule, a binding partner that binds the IIICS region of an oncofetal fibronectin protein, and a binding partner that binds the EDA region of an oncofetal fibronectin protein. In some methods, the imaging conjugate or treatment binding partner is administered topically.

Also provided herein are test strips for performing the methods provided herein. Also provided herein are test strips containing an analyte binding region containing a first fibronectin or oncofetal fibronectin binding partner immobilized to a solid support. The test strips provided herein can further contain a non-specific binding region, wherein the analyte binding region is downstream of the sample fluid flow pathway relative to the non-specific binding region. The test strips provided herein can further contain a conjugate pad, which serves as a sample application component, an absorbent pad, which serves to draw liquid continuously through the device, wherein the materials of the membrane system form a single fluid flow pathway, and a porous or bibulous member in fluid communication with the absorbent pad and conjugate pad, which porous or bibulous member accommodates a liquid sample and serves as the solid support upon which biomolecule interactions occur, wherein the porous or bibulous member contains the analyte binding region.

Some test strips provided herein can further contain an immobilization region containing a second fibronectin or oncofetal fibronectin binding partner, wherein the second fibronectin or oncofetal fibronectin binding partner is mobilized upon contact with the sample, and the immobilization region is upstream of the analyte binding region. Some test strips can further contain a control region containing a biomolecule that specifically binds the second fibronectin or oncofetal fibronectin binding partner, wherein the control region is downstream of the analyte binding region. In some test strips, the first fibronectin or oncofetal fibronectin binding partner binds oncofetal fibronectin in preference to fibronectin. In some test strips, the non-specific binding region contains a non-specific binding protein immobilized to the solid support, wherein the non-specific binding protein can be, for example, BSA, methylated BSA, W632 or mouse IgG.

Also provided herein are combinations for performing the methods provided herein. Also provided herein are combinations containing an fibronectin or oncofetal fibronectin binding partner and a non-specific binding compound. Some combinations further contain a test strip containing the non-specific binding partner. Also provided herein are combinations containing an fibronectin or oncofetal fibronectin binding partner and a solid support containing a non-specific binding surface. Such combinations can also contain a test strip containing the solid support. Also provided herein are combinations containing a fibronectin or oncofetal fibronectin binding partner and a sample collection device. The combinations provided herein also can contain a sample collection device.

Also provided herein are kits that contain the combinations provided herein, and optionally further comprising instructions for use. Also provided herein are kits that contain the combinations provided herein, and also a system for classifying the subject with respect to multiple thresholds.

Also provided herein are methods of detecting an oncofetal fibronectin indicating molecule in a subject, by administering to a subject a fibronectin or oncofetal fibronectin binding partner conjugated to an imaging moiety, whereby the conjugate localizes to regions in the subject containing an oncofetal fibronectin indicating molecule, and detecting the localization of the conjugate within the subject, thereby detecting the oncofetal fibronectin indicating molecule in the subject, wherein the oncofetal fibronectin binding partner is, for example, a nucleic acid molecule, a binding partner that binds the IIICS region of an oncofetal fibronectin protein and a binding partner that binds the EDA region of an oncofetal fibronectin protein. Also provided are methods of imaging tumorous tissue in a subject, by detecting an oncofetal fibronectin indicating molecule in a subject, thereby imaging tumorous tissue in the subject. Also provided herein are methods of imaging cancerous cells in a subject, by detecting an oncofetal fibronectin indicating molecule in a subject, thereby imaging tumorous or cancerous cells in the subject.

Also provided herein are methods of detecting an oncofetal fibronectin indicating molecule in cervical tissue or cells of a subject, by administering to a subject a fibronectin or oncofetal fibronectin binding partner conjugated to an imaging moiety, whereby the conjugate localizes to cervical tissue or cells in the subject containing an oncofetal fibronectin indicating molecule, and detecting the localization of the conjugate within the subject, thereby detecting the oncofetal fibronectin indicating molecule in cervical tissue or cells of the subject. Also provided herein are methods of indicating the presence of cancerous (e.g., hyperplastic or malignant neoplastic) cervical cells in a subject, by detecting an oncofetal fibronectin indicating molecule in cervical tissue or cells of a subject, thereby indicating the presence of cancerous cervical cells in the subject. Also provided are methods of imaging tumorous cervical tissue or cancerous cervical cells in a subject comprising detecting an oncofetal fibronectin indicating molecule in cervical tissue or cells of a subject, thereby imaging tumorous cervical tissue or cancerous cervical cells in the subject.

In the methods provided herein, the fibronectin or oncofetal fibronectin binding partner can specifically bind the EDA, EDB or IIICS region of an oncofetal fibronectin protein or oncofetal fibronectin-encoding nucleic acid molecule as described above. In the methods provided herein, the fibronectin or oncofetal fibronectin binding partner can be an antibody, or fragment thereof, or a nucleic acid molecule.

In the methods provided herein the tumorous tissue or cells can include, for example, lung, breast, ovary, stomach, pancreas, larynx, esophagus, testes, liver, parotid, biliary tract, colon, rectum, cervix, uterus, endometrium, kidney, bladder, prostate, thyroid, pituitary, eye, brain, oral, skin, head and neck cancer, lymphoma, leukemia, squamous cell carcinoma, adenocarcinoma, small cell carcinoma, melanoma, glioma, sarcoma and neuroblastoma.

In the methods provided herein, the conjugate can be administered intravenously, topically, or orally. In some methods, the imaging method can be, for example, magnetic resonance imaging, ultrasonic imaging, fluorescence imaging, scintigraphy, computed tomography, computerized axial tomography, positron emission tomography, single photon emission computed tomography, ultrasound tomography and x-ray tomography. In some methods, the imaging moiety can be, for example, fluorescent moieties, radionuclides, magnetically detectable isotopes or compounds, sonographic imaging agents, chromophores, latex microspheres, or quantum dots.

Also provided herein are methods of detecting an oncofetal fibronectin indicating molecule in a subject, by topically administering to a subject a fibronectin or oncofetal fibronectin binding partner conjugated to an imaging moiety, whereby the conjugate localizes to surfaces on the subject containing an oncofetal fibronectin indicating molecule, and detecting the localization of the conjugate on the subject, thereby detecting the oncofetal fibronectin indicating molecule on the subject. Also provided herein are methods of indicating the presence of cancerous cells in a subject, by detecting an oncofetal fibronectin indicating molecule in a subject, wherein the detected oncofetal fibronectin indicating molecule indicates the presence of cancerous cells on the subject. In some methods, cancerous cells on the surface of the cervix are indicated.

The methods of treating a subject provided herein can also include indicating the location in a subject of cancer cells, and administering to a subject a treatment fibronectin or oncofetal fibronectin binding partner, whereby the treatment binding partner localizes to regions in the subject containing oncofetal fibronectin, whereby the localized treatment binding partner causes cell death or inhibits cell growth of cancer cells. In some such methods, the cancer is cervical cancer and the cancerous cells are cervical malignant, neoplastic or hyperplastic cells.

Also provided herein are methods of treating a health problem associated with oncofetal fibronectin in a subject, by administering to a subject a fibronectin or oncofetal fibronectin binding partner, whereby the binding partner localizes to regions in the subject containing an oncofetal fibronectin indicating molecule, whereby the localized binding partner causes cell death or inhibits cell growth, whereby the cell death or cell growth inhibition caused by the binding partner treats the health problem associated with oncofetal fibronectin, wherein the fibronectin or oncofetal fibronectin binding partner is not conjugated to a therapeutic moiety. Also provided herein are methods of treating a health problem associated with oncofetal fibronectin in a subject, by administering to a subject a fibronectin or oncofetal fibronectin binding partner, whereby the binding partner localizes to regions in the subject containing an oncofetal fibronectin indicating molecule, whereby the localized binding partner causes cell death or inhibits cell growth, whereby the cell death or cell growth inhibition caused by the binding partner treats the health problem associated with oncofetal fibronectin, wherein the fibronectin or oncofetal fibronectin binding partner is, for example, a fibronectin or oncofetal fibronectin binding partner nucleic acid molecule, a binding partner that binds the IIICS region of a fibronectin or oncofetal fibronectin protein and a binding partner that binds the EDA region of a fibronectin or oncofetal fibronectin protein. In some methods, tumorous tissue or malignant, hyperplastic or neoplastic cells of a subject no longer proliferate.

Also provided herein are methods of treating a cervical cancer subject, by administering to a subject a fibronectin or oncofetal fibronectin binding partner, whereby the binding partner localizes to regions in the subject containing an oncofetal fibronectin indicating molecule, whereby the localized binding partner causes cervical cell death or inhibits cell growth, whereby the cell death or cell growth inhibition caused by the binding partner stops the proliferation of cancerous cervical cells in the subject. Also provided herein are methods of treating tumorous cervical tissue in a subject, by stopping the proliferation of cancerous cervical cells in the subject, thereby treating tumorous cervical tissue in the subject.

In some methods, the fibronectin or oncofetal fibronectin binding partner specifically binds the EDA region, the EDB region, or the mcs region of an oncofetal fibronectin protein or oncofetal fibronectin-encoding nucleic acid molecule as described above. In some methods, the fibronectin or oncofetal fibronectin binding partner is an antibody, or fragment thereof, or a nucleic acid molecule.

In some methods provided herein, the tumorous tissue or cells are from, for example, lung, breast, ovary, stomach, pancreas, larynx, esophagus, testes, liver, parotid, biliary tract, colon, rectum, cervix, uterus, endometrium, kidney, bladder, prostate, thyroid, pituitary, eye, brain, oral, skin, head and neck cancer, lymphoma, leukemia, squamous cell carcinoma, adenocarcinoma, small cell carcinoma, melanoma, glioma, sarcoma and neuroblastoma.

In some methods, the binding partner is administered intravenously, topically or orally. In some methods, the binding partner is conjugated to a therapeutic moiety. In some such methods, the therapeutic moiety is, for example, a biological toxin, a cytokine, a photosensitizing agent, a toxin, an anticancer antibiotic, a chemotherapeutic compound, a radionuclide, a binding partner and a bioluminescent compound.

Also provided herein are methods of indicating the presence of cancerous cells in a subject, by topically administering to a subject a fibronectin or oncofetal fibronectin binding partner, whereby the binding partner localizes to surfaces on the subject containing an oncofetal fibronectin indicating molecule, and detecting the localization of the conjugate on the subject, thereby indicating presence of cancerous cells in the subject. Also provided herein are methods of treating tumorous tissue in a subject, by topically administering to a subject a fibronectin or oncofetal fibronectin binding partner, whereby the binding partner localizes to surfaces on the subject containing an oncofetal fibronectin indicating molecule, whereby the localized binding partner causes cell death or inhibits cell growth, whereby the cell death or cell growth inhibition caused by the binding partner inhibits tumor proliferation in the subject. In some such methods, cancerous cells on the surface of the cervix are treated.

Also provided herein are methods of testing for an oncofetal fibronectin indicating molecule in a sample, thereby detecting oncofetal fibronectin indicating molecule, if present, in the sample. As provided herein, such methods can be used for a variety of applications, examples of which are included in the following paragraph.

Some oncofetal fibronectin indicating molecule testing methods can be used in methods of indicating cancerous cells in a subject, by testing for the presence of an oncofetal fibronectin indicating molecule in a sample from a subject, whereby presence of oncofetal fibronectin indicating molecule in the sample identifies the presence of cancerous cells in the subject. Some oncofetal fibronectin indicating molecule testing methods can be used in methods of determining the risk of a subject developing cancer, by testing for the presence of an oncofetal fibronectin indicating molecule in a sample from a subject, whereby presence of oncofetal fibronectin indicating molecule in the sample identifies a risk of the subject developing neoplastic, malignant or metastatic cells. Some oncofetal fibronectin indicating molecule testing methods can be used in methods of predicting the development of cancerous cells in a subject, by testing for the presence of an oncofetal fibronectin indicating molecule in a sample from a subject, whereby presence of oncofetal fibronectin indicating molecule in the sample identifies the likelihood of a subject developing cancerous cells. Some oncofetal fibronectin indicating molecule testing methods can be used in methods of assessing the aggressiveness of cancerous cells in a subject, by testing for the presence of an oncofetal fibronectin indicating molecule in a sample from a subject, whereby presence of oncofetal fibronectin indicating molecule in the sample identifies the cancerous cells as aggressive. Some oncofetal fibronectin indicating molecule testing methods can be used in methods of predicting the outcome of a treatment of a cancerous disease in a subject, by testing for the presence of an oncofetal fibronectin indicating molecule in a sample from a subject, whereby presence of oncofetal fibronectin indicating molecule in the sample indicates that a treatment of a cancerous disease is predicted to be successful. Some oncofetal fibronectin indicating molecule testing methods can be used in methods of predicting the outcome of a treatment of a cancerous disease in a subject, by testing for the presence of an oncofetal fibronectin indicating molecule in a sample from a subject, whereby presence of oncofetal fibronectin indicating molecule in the sample indicates that a treatment of a cancerous is predicted to be unsuccessful. Some oncofetal fibronectin indicating molecule testing methods can be used in methods of monitoring a treatment of a cancerous disease in a subject, by testing for the presence of an oncofetal fibronectin indicating molecule in a sample from a subject, whereby presence of oncofetal fibronectin indicating molecule in the sample indicates that a treatment of a cancerous disease is effective. Some oncofetal fibronectin indicating molecule testing methods can be used in methods of monitoring a treatment of a cancerous disease in a subject, by testing for the presence of an oncofetal fibronectin indicating molecule in a sample from a subject, whereby presence of oncofetal fibronectin indicating molecule in the sample indicates that a treatment of a cancerous disease is ineffective.

Some oncofetal fibronectin indicating molecule testing methods can be used in methods for determining the risk of cells becoming cancerous, by detecting the presence of the oncofetal fibronectin indicating molecule in a sample from cells, wherein the presence of oncofetal fibronectin indicating molecule in the sample identifies a risk of the cells becoming cancerous. In some methods, the cells have an abnormal morphology. In some methods, the cells are dysplastic cells.

Also provided herein are methods for inhibiting the development of cancer in a subject, by treating a subject for cancer, and administering to the treated subject a fibronectin or oncofetal fibronectin binding partner, whereby development of cancer is inhibited. Also provided herein are methods for inhibiting the recurrence of cancer in a subject, by treating a subject for cancer, and administering to the treated subject a fibronectin or oncofetal fibronectin binding partner, whereby recurrence of cancer is inhibited.

In some methods, the cancer cells are, for example, lung, breast, ovary, stomach, pancreas, larynx, esophagus, testes, liver, parotid, biliary tract, colon, rectum, cervix, uterus, endometrium, kidney, bladder, prostate, thyroid, pituitary, eye, brain, oral, skin, head and neck cancer, lymphoma, leukemia, squamous cell carcinoma, adenocarcinoma, small cell carcinoma, melanoma, glioma, sarcoma and neuroblastoma cells.

Also provided herein are methods of testing for an oncofetal fibronectin indicating molecule in a sample, thereby detecting oncofetal fibronectin indicating molecule, if present, in the sample. As provided herein, such methods can be used for a variety of applications, examples of which are included in the following paragraph.

Some oncofetal fibronectin indicating molecule testing methods can be used in methods of determining the overall health state of a subject, by testing for the presence of an oncofetal fibronectin indicating molecule in a sample from a subject, whereby presence of oncofetal fibronectin indicating molecule in the sample indicates that the subject is not free of disease. Some oncofetal fibronectin indicating molecule testing methods can be used in methods of determining that a subject is disease free, by testing a sample for the presence or absence of an oncofetal fibronectin indicating molecule, wherein absence of oncofetal fibronectin indicating molecule indicates that the subject is free of disease. Some oncofetal fibronectin indicating molecule testing methods can be used in methods of screening a subject for a health problem associated with oncofetal fibronectin, comprising testing a sample from a subject for the presence or absence of an oncofetal fibronectin indicating molecule, wherein presence of oncofetal fibronectin indicating molecule indicates that the subject has a health problem associated with oncofetal fibronectin. In some methods, the disease is, for example, cancer, pregnancy-related disorder, arthritis, diabetic retinopathy and Dupuytren's contracture. In some methods, prior to testing for the presence or absence of oncofetal fibronectin indicating molecule, the subject has not been diagnosed with a disease. Some methods further include performing one or more additional tests to identify the disease. Some oncofetal fibronectin indicating molecule testing methods can be used in methods of indicating arthritis in a subject, by testing for the presence of an oncofetal fibronectin indicating molecule in a sample from a subject, whereby presence of oncofetal fibronectin indicating molecule in the sample identifies the presence of arthritis in the subject. Some oncofetal fibronectin indicating molecule testing methods can be used in methods of indicating diabetic retinopathy in a subject, by testing for the presence of an oncofetal fibronectin indicating molecule in a sample from a subject, whereby presence of oncofetal fibronectin indicating molecule in the sample identifies the presence of diabetic retinopathy in the subject. Some oncofetal fibronectin indicating molecule testing methods can be used in methods of indicating Dupuytren's contracture in a subject, by testing for the presence of an oncofetal fibronectin indicating molecule in a sample from a subject, whereby presence of oncofetal fibronectin indicating molecule in the sample identifies the presence of Dupuytren's contracture in the subject.

In some methods the sample is, for example, urine, lymph, lymphatic fluid, blood, plasma, serum, saliva, cervical fluid, cervicovaginal fluid, vaginal fluid, breast fluid, synovial fluid, semen, seminal fluid, stool, sputum, cerebral spinal fluid, tears, mucus, interstitial fluid, follicular fluid, amniotic fluid, aqueous humor, vitreous humor, lavage, tissue, peritoneal fluid, ascites and sweat. In some methods the oncofetal fibronectin indicating molecule is detected by a method such as, for example, mass spectrometry, sandwich assay, Western blot, dot blot, FRET, fluorescence polarization, fluorimetry, flow cytometry, RT-PCR, Southern blot, Northern blot, fluorescence in situ and in vivo imaging. In some methods, the oncofetal fibronectin indicating molecule is, for example, an oncofetal fibronectin protein, an oncofetal fibronectin-encoding nucleic acid and an autoantibody that preferentially binds oncofetal fibronectin.

Provided herein is the use of any of the products provided herein for use in the preparation of a medicament for any of the methods provided herein, including, but not limited to, diagnosis, imaging, and/or treatment of a health disorder characterized by the presence of, or elevated levels of oncofetal fibronectin.

Provided are methods for detection of an oncofetal fibronectin indicating molecule and methods for obtaining samples for use in methods of detection. Also provided are products for use in methods of detection of oncofetal fibronectin or of molecules indicative thereof in samples.

Provided herein are methods for detecting an oncofetal fibronectin indicating molecule in a sample, by treating a sample under conditions that separate one or more first sample components from one or more second sample components, wherein an oncofetal fibronectin indicating molecule, if present, is among the one or more first sample components, and detecting the oncofetal fibronectin indicating molecule or fragment thereof by its molecular weight.

In such methods, the treating step can further comprise contacting the sample with a fibronectin or oncofetal fibronectin binding partner immobilized on a solid support to form a complex thereof and then treating the solid support to release oncofetal fibronectin indicating molecule or a fragment thereof from the complex, and the detecting step can further comprise detecting the released oncofetal fibronectin indicating molecule or fragment thereof. In some methods, the detecting step can further comprise calculating the molecular weight of the detected oncofetal fibronectin indicating molecule or fragment thereof. In the methods provided herein, the detecting step can further comprise comparing detected first sample components to one or more references, wherein a reference that matches a detected first sample component corresponds to a fibronectin indicating molecule or fragment thereof. The methods provided herein also can include, prior to treating the solid support to release oncofetal fibronectin indicating molecule from the binding partner, treating the solid support under conditions that separate the solid support from sample components not specifically bound to the binding partner. In some of the methods provided herein, prior to detecting and subsequent to contacting the sample with a fibronectin or oncofetal fibronectin binding partner, the method further comprises a step of contacting the sample with a fragmentation reagent. In such methods, the fragmentation reagent can be a protease or a nuclease. In some methods, the fragmentation reagent is immobilized onto a second solid support and the step of contacting the sample with a fragmentation reagent further comprises contacting the sample with the second solid support. In some methods, prior to detecting and subsequent to contacting the sample with a fragmentation reagent, the method further comprises a step of treating the sample under conditions whereby the oncofetal fibronectin indicating molecule or fragment thereof is released from the second solid support. In some methods, release of the oncofetal fibronectin indicating molecule or fragment thereof from the second solid support is accomplished by matrix-assisted laser desorption or electrospray desorption.

Also provided herein are methods where the mass corresponding to the mass of a fragment of an oncofetal fibronectin indicting molecule can be, for example, 14 kDa, 35 kDa, 55 kDa, 65 kDa, 85 kDa, 110 kDa, 120 kDa, 160 kDa, 200 kDa or 235 kDa. In some methods, the oncofetal fibronectin binding partner binds IIICS, the sample is contacted with trypsin, and the mass corresponding to the mass of a fragment of an oncofetal fibronectin indicating molecule can be, for example, 55 kDa, 65 kDa, 120 kDa, 160 kDa, 200 kDa or 235 kDa. In some other methods, the oncofetal fibronectin binding partner binds IIICS, the sample is contacted with cathepsin D, and the mass corresponding to the mass of a fragment of an oncofetal fibronectin indicating molecule can be, for example, 85 kDa or 110 kDa. In some other methods, the oncofetal fibronectin binding partner binds EDB, the sample is contacted with thermolysin, and the mass corresponding to the mass of a fragment of an oncofetal fibronectin indicating molecule can be, for example, 35 kDa, 85 kDa or 120 kDa. In some other methods, the oncofetal fibronectin binding partner binds IIICS, wherein the sample is contacted with *Achromobacter* protease I and wherein the mass corresponding to the mass of a fragment of an oncofetal fibronectin indicating molecule is 14 kDa.

Some of the methods provided herein further include separating DNA from RNA in a sample. Such methods further include contacting the sample with a primer complementary to an oncofetal fibronectin-encoding nucleotide sequence, which primer contacts RNA in the sample, and treating the sample with one or more nucleic acid synthesis steps. In some methods, the primer is complementary to mRNA encoding oncofetal fibronectin. In some methods, a first nucleic acid synthesis step includes nucleic acid synthesis by reverse transcriptase. In some such methods, the binding partner specifically binds to a nucleotide sequence encoding oncofetal fibronectin, a nucleotide sequence complementary to a nucleotide sequence encoding oncofetal fibronectin, or a fragment thereof.

The methods provided herein also can be directed to methods wherein the binding partner specifically binds to a nucleotide sequence encoding the EDA region of oncofetal fibronectin, a nucleotide sequence complementary to a nucleotide sequence encoding the EDA region of oncofetal fibronectin, a nucleotide sequence encoding the EDB region of oncofetal fibronectin, a nucleotide sequence complementary to a nucleotide sequence encoding the EDB region of oncofetal fibronectin, a nucleotide sequence encoding the IIICS region of oncofetal fibronectin, a nucleotide sequence complementary to a nucleotide sequence encoding the mcs region of oncofetal fibronectin, or a fragment thereof.

In another embodiment, provided herein are methods of detecting an oncofetal fibronectin indicating molecule in a sample, by contacting the sample with a first fibronectin or oncofetal fibronectin binding partner immobilized to a solid support, contacting the solid support with a second fibronectin or oncofetal fibronectin binding partner, contacting the solid support with a third fibronectin or oncofetal fibronectin binding partner, and detecting any complex formed between an oncofetal fibronectin indicating molecule in the sample and the first fibronectin or oncofetal fibronectin binding partner, and either the second fibronectin or oncofetal fibronectin binding partner or the third fibronectin or oncofetal fibronectin binding partner, or both, whereby detection of complex is indicative of the presence of the oncofetal fibronectin indicating molecule in the sample, and wherein at least one of the first fibronectin or oncofetal fibronectin binding partner, the second fibronectin or oncofetal fibronectin binding partner, and the third fibronectin or oncofetal fibronectin binding partner is an oncofetal fibronectin binding partner. In some methods, the first oncofetal fibronectin binding partner binds a region of an oncofetal fibronectin indicating molecule and can be, for example, EDA, EDB, IIICS, or a combination thereof. In some methods, the first oncofetal fibronectin binding partner binds a region of an oncofetal fibronectin indicating molecule other than EDA, EDB or IIICS. In some methods, the second oncofetal fibronectin binding partner binds a region of an oncofetal fibronectin indicating molecule such as, for example, EDA, EDB, IIICS or a combination thereof. In some methods, third oncofetal fibronectin binding partner binds a region of an oncofetal fibronectin indicating molecule such as, for example, EDA, EDB, IIICS or a combination thereof. In some methods, the second and third oncofetal fibronectin binding partners bind to a region of an oncofetal fibronectin indicating molecule such as, for example, EDA, EDB, IIICS or a combination thereof, wherein the second and third oncofetal fibronectin binding partners do not bind to the same oncofetal fibronectin indicating molecule region. Some methods further include contacting the sample with a fourth fibronectin or oncofetal fibronectin binding partner. In some such methods, the fourth fetal or oncofetal fibronectin binding partner binds a region of an oncofetal fibronectin indicating molecule such as, for example, EDA, EDB, IIICS or a combination thereof. In some methods, the second, third and fourth fetal or oncofetal fibronectin binding partners bind to a region of an oncofetal fibronectin indicating molecule such as, for example, EDA, EDB, IIICS or a combination thereof, wherein the second, third and fourth fetal or oncofetal fibronectin binding partners do not bind to the same oncofetal fibronectin indicating molecule region.

The IIICS portion can be any one of V64, V89, V95 and V120. When the oncofetal fibronectin indicating molecule is a IIICS portion of oncofetal fibronectin protein, the fibronectin or oncofetal fibronectin binding partner can recognize a post-translational modification of oncofetal fibronectin protein. In one aspect, the post-translational modification can be O-glycosylation of threonine 33 of IIICS.

In one aspect the oncofetal fibronectin indicating molecule is identified as lacking EDA, EDB or IIICS. If the oncofetal fibronectin indicating molecule is identified as lacking, the portion of IIICS can be amino acids 1-25 of IIICS, amino acids 90-120 of IIICS or both.

In some methods, the complex is detected by measuring products of a nucleic acid synthesis reaction. In some methods, the first binding partner is immobilized to a test strip.

In another embodiment, provided herein are methods of detecting an oncofetal fibronectin indicating molecule in a sample, by contacting the sample with a first fibronectin or oncofetal fibronectin binding partner, contacting the sample with a second oncofetal fibronectin binding partner, and detecting by flow cytometry any complex formed between an oncofetal fibronectin indicating molecule in the sample, the first fetal or oncofetal fibronectin binding partner, and the second oncofetal fibronectin binding partner, whereby detection of complex is indicative of the presence of the oncofetal fibronectin indicating molecule in the sample. In some methods, complexes are detected by detecting spatial proximity between the first binding partner and the second binding partner. In some methods, complexes are detected by detecting two spatially proximal signals, wherein the first detected signal arises from the first binding partner and the second detected signal arises from the second binding partner. In some methods, the first binding partner and the second binding partner are bound to the same or different oncofetal fibronectin indicating molecules on the surface of a cell.

In the methods provided herein, the sample can be, for example a tissue or cell sample, or a liquid sample. A tissue or cell sample can be any of the following: lung, breast, ovary, stomach, pancreas, larynx, esophagus, testes, liver, parotid, biliary tract, colon, rectum, cervix, uterus, endometrium, kidney, bladder, prostate, thyroid, pituitary, eye, brain, oral, skin, head and neck cancer, lymphoma, leukemia, squamous cell carcinoma, adenocarcinoma, small cell carcinoma, melanoma, glioma, sarcoma neuroblastoma, semen, stool and a fraction or component thereof. A liquid sample can be a body fluid or tissue such as, for example, urine, blood, plasma, serum, saliva, lavage, cervical fluid, cervicovaginal fluid, vaginal fluid, breast fluid, breast milk, synovial fluid, seminal fluid, sputum, cerebral spinal fluid, tears, interstitial fluid, follicular fluid, amniotic fluid, aqueous humor, vitreous humor, peritoneal fluid, ascites, sweat, lymphatic fluid, and a fraction or component thereof. In some methods, the sample is treated with one or more reagents prior to the detecting step. Some methods further include removing sample components not bound to the binding partner prior to the step of removing oncofetal fibronectin indicating molecule or fragment thereof from the complex.

In the methods provided herein, the binding partner can contain an energy absorbing moiety. In some methods, the step of removing is accomplished by ultraviolet Matrix-Assisted Laser Desorption/Ionization, infrared Matrix-Assisted Laser Desorption/Ionization, or electrospray ionization. In some methods, the oncofetal fibronectin indicating molecule or fragment thereof is detected by a mass spectrometry method such as, but not limited to, time-of-flight, Fourier transform, or magnetic sector/magnetic deflection. Some methods provided herein can further include the step of enhancing a signal from the oncofetal fibronectin indicating molecule bound to the binding partner. The methods provided herein can further include quantitating the amount of oncofetal fibronectin indicating molecule in the sample.

In some of the methods provided herein, presence of the oncofetal fibronectin indicating molecule in a sample determines a risk or identifies a health problem associated with oncofetal fibronectin, or indicates an increased risk of imminent or preterm delivery.

In some embodiments, methods are provided for indicating oncofetal fibronectin in a subject by detecting the presence of autoantibodies specific for oncofetal fibronectin in a sample from a subject, wherein the presence of anti-oncofetal fibronectin autoantibodies in the sample indicates the presence oncofetal fibronectin in the subject. Some methods can include indicating an oncofetal fibronectin associated health problem in a subject by detecting the presence of autoantibodies specific for oncofetal fibronectin in a sample from a subject according to the methods provided herein, wherein the presence of anti-oncofetal fibronectin autoantibodies in the sample indicates the presence of an oncofetal fibronectin associated health problem in the subject. Some methods can include indicating oncofetal fibronectin in a subject by detecting the presence of autoantibodies specific for oncofetal fibronectin in a sample from a subject according to the methods provided herein, wherein the presence of anti-oncofetal fibronectin autoantibodies in the sample indicates the presence oncofetal fibronectin in the subject. Such methods can further include contacting the sample with an anti-oncofetal fibronectin autoantibody binding partner, and detecting complexes formed between the binding partner and an anti-oncofetal fibronectin autoantibody.

Also provided herein are methods for indicating an oncofetal fibronectin associated health problem in a subject by indicating the presence of autoantibodies specific for oncofetal fibronectin in a subject according to the methods provided herein, wherein the presence of anti-oncofetal fibronectin autoantibodies in the subject indicates the presence of an oncofetal fibronectin associated health problem in the subject. In some such methods, the binding partner is oncofetal fibronectin protein or a fragment thereof, or an antibody that specifically binds human antibodies, or a fragment thereof. Some methods further include a second binding partner, wherein the second binding partner is oncofetal fibronectin protein or a fragment thereof, or an antibody that specifically binds human antibodies, or a fragment thereof.

The methods provided herein can include methods in which the sample is contacted with a non-specific binding compound under conditions in which substantially no oncofetal fibronectin indicating molecule in the sample binds to the non-specific binding compound. In some methods, the sample is contacted with a non-specific binding surface of a solid support under conditions in which substantially no oncofetal fibronectin indicating molecule in the sample binds to the non-specific binding surface. In some methods, the non-specific binding surface contains a non-specific binding compound immobilized thereto. In some methods, 10% or less of the oncofetal fibronectin indicating molecule in the sample binds to the non-specific binding compound or surface. Some methods can further include contacting a sample with a solution that reduces non-specific binding of background material to a fibronectin or oncofetal fibronectin binding partner. In some methods, the ionic strength of the sample when contacted by the binding partner ranges from 50μ to 350μ or from about 50μ to about 350μ. Some methods can further include contacting a sample with solution that increases specific binding of oncofetal fibronectin indicating molecule in the sample to a fibronectin or oncofetal fibronectin binding partner. Some methods can further include a step of increasing the relative amount of oncofetal fibronectin indicating molecule in a sample. Some methods can further include decreasing the amount of background material in a sample that non-specifically binds to oncofetal fibronectin binding partner.

In some methods provided herein, the sample is, for example, urine, lavage, breast milk, cervicovaginal swab, saliva, serum, plasma, blood and interstitial fluid. In some methods, prior to the detecting step, one or more reagents are added to a urine sample. In some methods, the non-specific binding compound can be, for example, albumin, casein, fetal calf serum, gelatin and an antibody that does not specifically bind to an oncofetal fibronectin indicating molecule, for example, a non-specific binding compound can be methylated bovine serum albumin.

In some of the methods provided herein, a sample positive for oncofetal fibronectin identifies the subject from whom the sample was collected as having cancerous (e.g., neoplastic, malignant or metastatic) cells. In some such methods, the cancerous (e.g., neoplastic, malignant or metastatic) cells originate from bladder, kidney, prostate, cervix or ovary. In a particular method, the cancerous cells originate from bladder.

In other methods provided herein, a sample positive for oncofetal fibronectin identifies the subject from whom the sample was collected as having an increased risk of imminent or preterm delivery. In some such methods, a sample positive for oncofetal fibronectin identifies the subjected from whom the sample was collected as one for whom induction is likely to be successful. Such methods can be used to identify a subject as one for whom induction of delivery is likely to be successful, and to administer to the subject an induction procedure. Likelihood of successful induction can indicated by any of the following: increased likelihood of vaginal delivery upon induction relative to subjects negative for oncofetal fibronectin and/or having a negative result for the second indicator of induction outcome, likely decreased time interval between initiating induction and delivery relative to subjects negative for oncofetal fibronectin and/or having a negative result for the second indicator of induction outcome, likely decreased time interval between administering a parturifacient and delivery relative to subjects negative for oncofetal fibronectin and/or having a negative result for the second indicator of induction outcome, likely decreased time interval between administering oxytocin and delivery relative to subjects negative for oncofetal fibronectin and/or having a negative result for the second indicator of induction outcome, increased likelihood of delivering within 24 hours of induction relative to subjects negative for oncofetal fibronectin and/or having a negative result for the second indicator of induction outcome, increased likelihood of delivering within 48 hours of induction relative to subjects negative for oncofetal fibronectin and/or having a negative result for the second indicator of induction outcome and decreased likelihood of more than one administration of pre-induction agent to the subject relative to subjects negative for oncofetal fibronectin and/or having a negative result for the second indicators of induction outcome, and combinations thereof. The second indicator of induction outcome can be any of a measurement or observation of the pregnant subject, a measurement or observation of the fetus(es), and medical history of the pregnant subject. Such indicators include, but are not limited to, cervical length, Bishop score, effacement, parity, cervical dilation, gestational age, body mass index, station, consistency, transvaginal ultrasound, and digital examination, or a combination thereof.

In some methods, the first binding partner is conjugated to a moiety such as, but not limited to, colloidal metal, photodetectable latex microsphere, chromophore, fluorescent moiety, quantum dot and detectable enzyme. Some methods further include contacting the sample with a binding partner that specifically binds the first fibronectin or oncofetal fibronectin binding partner. In some such methods, the binding partner that specifically binds the first fibronectin or oncofetal fibronectin binding partner is an antibody or a nucleic acid molecule.

In some methods provided herein, the first fibronectin or oncofetal fibronectin binding partner is an anti-fibronectin antibody, or a fragment thereof. In some methods, the second fibronectin or oncofetal fibronectin binding partner is an anti-fibronectin antibody, or a fragment thereof.

In some of the methods provided herein, complexes are detected by determining if any first binding partner is in spatial proximity to the second binding partner, whereby detection of any first and second binding partners in spatial proximity indicates presence of an oncofetal fibronectin molecule in a sample. In some such methods, spatial proximity is detected as a result of a non-radioactive energy transfer reaction. In some such methods, the non-radioactive energy transfer reaction is, for example, fluorescence energy transfer (FET), fluorescence resonance energy transfer (FRET), or homogeneous time-resolved fluorescence (HTRF).

In the methods provided herein, the oncofetal fibronectin indicating molecule can be, for example, an oncofetal fibronectin protein, a nucleic acid molecule encoding oncofetal fibronectin, a nucleic acid molecule complementary to a nucleic acid molecule encoding oncofetal fibronectin, an autoantibody for oncofetal fibronectin protein, an autoantibody for a nucleic acid molecule encoding oncofetal fibronectin and a fragment thereof.

In some methods, presence of an oncofetal fibronectin indicating molecule below a threshold level classifies the sample as oncofetal fibronectin negative. In some methods, presence of an oncofetal fibronectin indicating molecule equal to or above a threshold level classifies the sample as oncofetal fibronectin positive. In some such methods, the oncofetal fibronectin indicating molecule is an oncofetal fibronectin protein and the threshold level of oncofetal fibronectin protein is 50 ng/mL.

In some methods provided herein, the amount of oncofetal fibronectin indicating molecule detected is compared to one or more thresholds, wherein the sample is classified according to the highest threshold that is less than or equal to the detected amount of oncofetal fibronectin indicating molecule. In some such methods, a first threshold is 50 ng/mL and a second threshold is 150 ng/mL. In some methods, the subject from whom the sample is collected is pregnant and the one or more threshold levels correspond to increasing likelihood of imminent pregnancy termination.

In some methods, the complex between the oncofetal fibronectin indicating molecule and the fibronectin or oncofetal fibronectin binding partner is measured by detecting the oncofetal fibronectin indicating molecule or a fragment thereof. In some methods, the oncofetal fibronectin indicating molecule is detected by mass spectrometry or gel electrophoresis. In some methods, the complex between the oncofetal fibronectin indicating molecule and the fibronectin or oncofetal fibronectin binding partner is measured by detecting the fibronectin or oncofetal fibronectin binding partner. In such methods, the fibronectin or oncofetal fibronectin binding partner is detected by detecting fluorescence, reflectance, absorption, bioluminescence, enzyme-linked detectable signal, or radioactive decay. In some methods, the fibronectin or oncofetal fibronectin binding partner is immobilized to a test strip.

The methods provided herein can include methods in which the fibronectin or oncofetal fibronectin binding partner binds to the EDA-specific portion, EDB-specific portion, or IIICS-specific portion of an oncofetal fibronectin indicating molecule as described above.

Also provided herein are test strips. Exemplary test strips include an analyte binding region containing a first fibronectin or oncofetal fibronectin binding partner immobilized on a solid support. Such test strip can contain a non-specific binding region, wherein the analyte binding region is downstream of the sample fluid flow pathway relative to the non-specific binding region. Some test strips can further contain a conjugate pad, which serves as a sample application component, an absorbent pad, which serves to draw liquid continuously through the device, wherein the materials of the membrane system form a single fluid flow pathway, and a porous or bibulous member in fluid communication with the absorbent pad and conjugate pad, which porous or bibulous member accommodates a liquid sample and serves as the solid support upon which molecule interactions occur, wherein the porous or bibulous member contains the analyte binding region. Some test strips can further contain a mobilization region containing a second fibronectin or oncofetal fibronectin binding partner, wherein the second fibronectin or oncofetal fibronectin binding partner is mobilized upon contact with the sample and the mobilization region is upstream of the analyte binding region. Some test strips can further contain a control region containing a molecule that specifically binds the second fibronectin or oncofetal fibronectin binding partner, wherein the control region is downstream of the analyte binding region. In some test strips, the first fibronectin or oncofetal fibronectin binding partner binds oncofetal fibronectin in preference to fibronectin. In some test strips, the non-specific binding region contains a non-specific binding protein immobilized to the solid support, wherein the non-specific binding protein is, for example, BSA, methylated BSA, W632 or mouse IgG.

Also provided herein are combinations containing a first binding partner and a sample collection device. Combinations provided herein can contain a first binding partner and a solid support. Combinations provided herein can contain a first binding partner and a second binding partner. Combinations provided herein can contain a first binding partner and a non-specific binding compound. Combinations provided herein can contain a first binding partner and a parturifacient. The combinations provided herein also can contain a non-specific binding compound. Also provided herein are kits containing the combinations provided herein and further containing instructions for use and/or a system for classifying the sample according to one or more threshold levels.

In another embodiment, provided herein are probes for detecting an oncofetal fibronectin indicating molecule, containing a mass spectrometry substrate, and a fibronectin or oncofetal fibronectin binding partner immobilized on the substrate. In some probes, the substrate contains a substance such as, but not limited to, glass, metal, ceramic, Teflon coated magnetic material, organic polymer, biopolymer and inorganic polymer.

Also provided herein are methods of characterizing oncofetal fibronectin protein in a sample, by contacting a sample with a first oncofetal fibronectin binding partner that binds oncofetal fibronectin protein in preference to non-oncofetal fibronectin protein, contacting a sample with a second oncofetal fibronectin binding partner that binds oncofetal fibronectin protein in preference to non-oncofetal fibronectin protein, and detecting complexes between oncofetal fibronectin protein and either the first oncofetal fibronectin binding partner, the second oncofetal fibronectin binding partner, or both binding partners, whereby the presence or absence of two domains of oncofetal fibronectin protein in the sample is determined. In such methods, the presence or absence of two domains of individual oncofetal fibronectin proteins in the sample is determined.

Also provided herein are methods of characterizing oncofetal fibronectin protein in a sample, by contacting a sample with a first oncofetal fibronectin binding partner that binds oncofetal fibronectin protein in preference to non-oncofetal fibronectin protein, contacting a sample with a second oncofetal fibronectin binding partner that binds oncofetal fibronectin protein in preference to non-oncofetal fibronectin protein, contacting a sample with a third oncofetal fibronectin binding partner that binds oncofetal fibronectin protein in preference to non-oncofetal fibronectin protein, and detecting complexes between oncofetal fibronectin and any combination of the first oncofetal fibronectin binding partner, the second oncofetal fibronectin binding partner and the third oncofetal fibronectin binding partner, whereby the presence or absence of three domains of oncofetal fibronectin protein in the sample is determined. In such methods, the presence or absence of three domains of individual oncofetal fibronectin proteins in the sample can be determined. In some methods, the first oncofetal fibronectin binding partner preferentially binds oncofetal fibronectin protein containing an EDA domain, an EDB domain, a IIICS domain, or a combination thereof. In some such methods, the second oncofetal fibronectin binding partner preferentially binds oncofetal fibronectin protein containing an EDA domain, an EDB domain, a IIICS domain, or a combination thereof and wherein the first and the second binding partners do not bind to the same region of oncofetal fibronectin protein. In some such methods, the third oncofetal fibronectin binding partner preferentially binds oncofetal fibronectin protein containing an EDA domain, an EDB domain, a mcs domain, or a combination thereof and wherein the first, the second and the third binding partners do not bind to the same region of oncofetal fibronectin protein. In some methods, complexes are detected by measuring oncofetal fibronectin protein, or a fragment thereof. In some such methods, oncofetal fibronectin is dissociated from one or more of the fibronectin or oncofetal fibronectin binding partners and a mass of oncofetal fibronectin protein, or a fragment thereof, is measured. In some methods, complexes are measured by detecting one or more of the fibronectin or oncofetal fibronectin binding partners. In some such methods, the first, second and/or third oncofetal fibronectin binding partners are measured by detecting fluorescence, reflectance, absorption, bioluminescence, enzyme-linked detectable signal or radioactive decay. In some methods, at least one oncofetal fibronectin binding partner is immobilized to a solid support.

Also provided herein are methods for classifying the level of oncofetal fibronectin in a sample, by measuring the amount of an oncofetal fibronectin indicating molecule in a sample, comparing the amount of oncofetal fibronectin indicating molecule in a sample to two or more threshold levels, and classifying the amount of oncofetal fibronectin indicating molecule in a sample according to the highest threshold level that is less than or equal to the amount of oncofetal fibronectin indicating molecule in the sample. In some such methods, each threshold level is correlated with a higher risk of preterm, impending and/or imminent delivery, increased ability to predict delivery date, decreased likelihood of maintaining pregnancy, increased benefit from using methods of preventing preterm delivery, increased likelihood of success in inducing delivery, increased likelihood of delivery within a predetermined time, presence of cancerous (e.g., malignant neoplastic) disease, an increased risk of developing cancerous disease or recurrence of cancerous disease, a faster progression of the cancerous disease, or a more aggressive cancerous disease, or a decreased efficacy of cancerous disease therapy for the subject that provided the sample. In some methods, one threshold level is about or is 50 ng/mL, or is about or is 150 ng/mL.

Also provided herein are methods for classifying a sample as oncofetal fibronectin positive or negative, by measuring the amount of an oncofetal fibronectin indicating molecule in a sample, comparing the measured sample oncofetal fibronectin indicating molecule amount to a threshold level of 150 ng/ml, and classifying the sample as oncofetal fibronectin positive if the amount of oncofetal fibronectin indicating molecule is equal to or greater than the threshold level, otherwise classifying the sample as oncofetal fibronectin negative. Also provided herein are methods for detecting the presence of an oncofetal fibronectin indicating molecule in a sample, by contacting a sample with a first fibronectin or oncofetal fibronectin binding partner and a second fibronectin or oncofetal fibronectin binding partner, and measuring formation of a complex of oncofetal fibronectin, the first binding partner and the second binding partner by detecting fluorescence from non-radioactive energy transfer. In some methods, the non-radioactive energy transfer occurs by fluorescence energy transfer (FET), fluorescence resonance energy transfer (FRET), or homogeneous time-resolved fluorescence (HTRF). In some methods, a binding partner is conjugated to a fluorescent dye or quantum dot.

Also provided herein are methods for detecting the presence of an oncofetal fibronectin indicating molecule in a sample, by contacting a sample with a fibronectin or oncofetal fibronectin binding partner, measuring formation of a complex of an oncofetal fibronectin indicating molecule and the binding partner by detecting fluorescence polarization indicative of complex formation. In some methods, the fluorescence polarization measurement indicates the quantity of oncofetal fibronectin indicating molecule in the sample. In some methods, the fluorescence polarization measurement indicates the mass of the complex. In some methods, the binding partner is conjugated to a fluorescent dye or quantum dot.

Some methods provided herein can further include, prior to contacting the sample, contacting the fibronectin or oncofetal fibronectin binding partner with an oncofetal fibronectin indicating molecule or analog thereof conjugated to a fluorescent dye or quantum dot, wherein signal dissipation or change indicates complex formation of a sample oncofetal fibronectin indicating molecule and the binding partner.

Also provided herein are conjugates that contain a fibronectin or oncofetal fibronectin binding partner linked to a leukocyte binding partner. In some such conjugates, the leukocyte binding partner is a natural killer cell binding partner. In some conjugates the leukocyte binding partner is an antibody. In some conjugates, the fibronectin or oncofetal fibronectin binding partner is FDC-6.

Also provided herein are methods for detecting an oncofetal fibronectin indicating molecule in a sample, by detecting the molecular weight of an oncofetal fibronectin indicating molecule or fragment thereof, by mass spectrometry to thereby detect the presence of an oncofetal fibronectin indicating molecule. The oncofetal fibronectin indicating molecule can be, for example, an oncofetal fibronectin protein or fragment thereof or an oncofetal fibronectin nucleic acid or fragment thereof.

Provided herein is the use of any of the products provided herein for use in the preparation of a medicament for any of the methods provided herein, including, but not limited to, diagnosis, imaging, and/or treatment of a health disorder characterized by the presence of, or elevated levels of oncofetal fibronectin.

Provided are methods for detection of an oncofetal fibronectin indicating molecule and methods for obtaining samples for use in methods of detection. Also provided are products for use in methods of detection of oncofetal fibronectin and/or of molecules indicative thereof in samples.

Provided are methods for assessing the suitability of concepti for implantation and selecting concepti for implantation. Concepti that produce oncofetal fibronectin can be used in implantation methods with greater success than concepti that do not produce oncofetal fibronectin.

Provided herein are methods for assessing a conceptus for implantation. These methods include testing a conceptus sample to detect an oncofetal fibronectin indicating molecule, wherein a conceptus for which a sample is oncofetal fibronectin positive is suitable for implantation. Also provided herein are methods for selecting concepti for implantation, by testing one or more conceptus samples to detect oncofetal fibronectin indicating molecule, and selecting a conceptus or concepti for implantation that yielded an oncofetal fibronectin positive sample.

In some such methods, a conceptus for which a sample is oncofetal fibronectin negative is not suitable for implantation. In some methods, presence of any oncofetal fibronectin indicating molecule in the sample identifies the sample as oncofetal fibronectin positive. In other methods, an amount of oncofetal fibronectin indicating molecule in the sample equal to or greater than a predetermined threshold level identifies the sample as oncofetal fibronectin positive. The threshold level can be a level predetermined to indicate that the conceptus will implant. Provided herein, the oncofetal fibronectin indicating molecule comprises a fibronectin III connecting segment (IIICS), an EDA or EDB segment or an autoantibody that specifically binds to IIICS, EDA or EDB.

In some embodiments of the methods provided herein, samples from two or more concepti are assayed, and a first conceptus for which a sample contains a higher amount of oncofetal fibronectin indicating molecule is identified as more suitable for implantation than a second conceptus for which a sample contains a lower amount of oncofetal fibronectin indicating molecule. In other embodiments of the methods provided herein, subsequent to testing the first conceptus sample, testing a second conceptus sample from the same conceptus to detect an oncofetal fibronectin indicating molecule, wherein a conceptus for which the second sample contains more oncofetal fibronectin indicating molecule than the first sample is suitable for implantation. In such embodiments, two or more samples from each of two or more concepti are assayed, and a first conceptus for which a sample contains a higher rate of increasing amount of oncofetal fibronectin indicating molecule is identified as more suitable for implantation than a second conceptus for which a sample contains a lower rate of increasing amount or a decreasing amount of oncofetal fibronectin indicating molecule. Suitability for implantation of a conceptus can increase with increasing amounts of oncofetal fibronectin indicating molecule or increasing rate of increase of oncofetal fibronectin indicating molecule can indicate suitability of a conceptus for implantation.

In the methods provided herein, the conceptus sample can be selected from among conceptus extract, sample from outside of the conceptus, and an extract of a cell from the conceptus. In some methods the sample can be treated with a reagent and/or fractionated prior to the step of testing for an oncofetal fibronectin indicating molecule in a conceptus sample. In one exemplary sample, from outside the conceptus, the sample is an extract of culture medium in which a single conceptus has been cultured.

The methods provided herein can further include determining an additional maternal or conceptus marker, wherein an oncofetal fibronectin positive conceptus having a favorable additional markers is identified as a conceptus favorable for implantation. In such methods the additional marker can be detected in a conceptus sample, can be determined by visual inspection of the conceptus, or can be detected in a maternal sample. Exemplary additional markers can be selected from among genetic composition of the conceptus, gene expression of the conceptus, and morphology of the conceptus. In methods in which the additional marker is morphology of the conceptus, the morphology of the conceptus can be graded according to factors, such as cell number, degree of fragmentation, cell regularity, symmetry, pronuclear morphology, follicle size, follicular fluid volume, multi-nucleation, presence of vacuoles, granularity and combinations thereof.

Provided herein is the use of any of the products provided herein for use in the preparation of a medicament for any of the methods provided herein, including, but not limited to, diagnosis, imaging, and/or treatment of a health disorder characterized by the presence of, or elevated levels of oncofetal fibronectin.

DETAILED DESCRIPTION

Figure 1A:
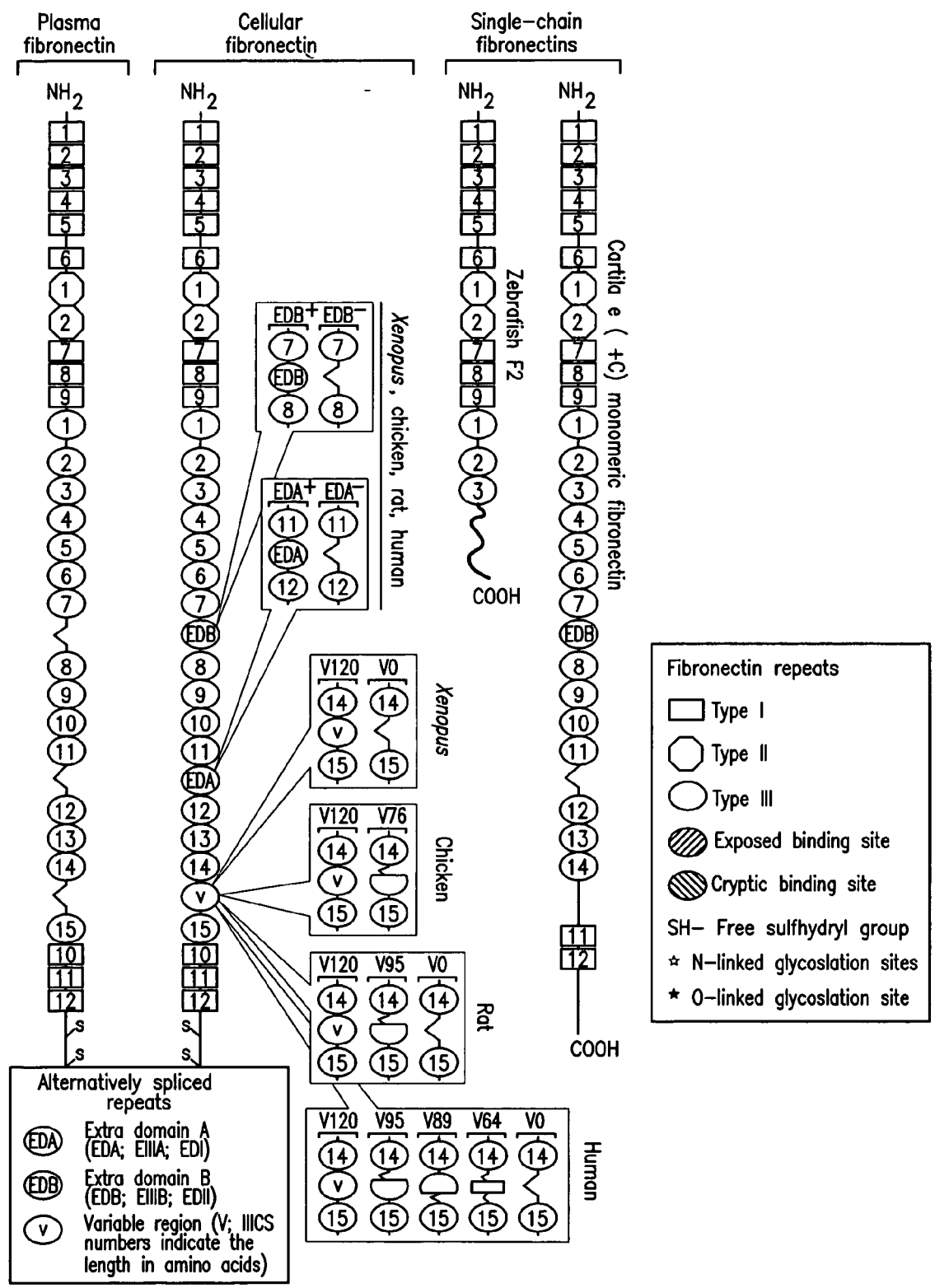
FIGS. 1A, 1B, and 1C depict schematics of fibronectin, including domain organization, protein interaction sites, proteolysis sites and ligand interaction sites. These figures were adapted from the publication by Pankov et al., *J. Cell Science* 2002 115:3861-3863.

Outline
A. Definitions
B. Detection of Oncofetal Fibronectin
C. Structure and Properties of Fibronectin
 1. Structural Characteristics of Fibronectin
 2. Binding Properties and Proteolysis of Fibronectin
 3. Oncofetal Fibronectin
  a. Structural Features of Oncofetal Fibronectin
  b. Molecules that Bind to Oncofetal Fibronectin
  c. Proteolysis of Oncofetal Fibronectin
D. Use of Oncofetal Fibronectin as a Biological Marker
 1. Pregnancy Indications
  a. Likelihood of Pre-term delivery
  b. Preventing Pre-term delivery
  c. Predictor of Delivery Date
  d. Use with Inducing Delivery
   i. Induction Methods and Compounds
   ii. Post-Induction Measurements
  e. Conceptus Indications
   i. Detection of Oncofetal Fibronectin Production by a Conceptus
   ii. Assisted Reproduction Technology Related Uses
   iii. Post-Measurement Steps
    a. Increasing Oncofetal Fibronectin Production
    b. Identify Conceptus Based on Oncofetal Fibronectin Production
     i. Selection of a Conceptus
     ii. Criteria for Selection
    c. Other Markers Used in Conjunction with Oncofetal Fibronectin
     i. Conceptus Markers
     ii. Maternal Markers
   iv. Stem Cell Related Uses
 2. Indicator of Cancer
  a. Bladder Cancer
  b. Breast Cancer
  c. Cervical Cancer
  d. Ovarian Cancer
  e. Prostate Cancer
  f. Lung Cancer
  g. Colorectal Cancer
  h. Additional Cancers
 3. Health State Assessment
 4. Other Health Problems
  a. Arthritis
  b. Diabetic Retinopathy
  c. Dupuytren's Contracture
E. Collection of Samples
 1. Swab and Cervicovaginal Samples
 2. Lavage Samples
  a. Sample Collection
  b. Lavage Fluid
  c. Applying a Label with Lavage
  d. Ductal Lavage
   i. Sample Collection
   ii. Applying a Label to a Duct
   iii. Lavage Fluid
 3. Collection of Urine Samples
  a. Sample Handling
  b. Sample Condition Modification
   i. Ionic Strength
   ii. Ionic Strength Testing
   iii. Normalization
  c. Sample Treatment
   i. Non-specific Binding
   ii. Filtration
 4. Interstitial Fluid
F. Methods of Detecting Oncofetal Fibronectin
 1. Compounds and Compositions in Detecting Oncofetal Fibronectin
  a. Molecules that Indicate the Presence of Oncofetal Fibronectin
  b. Fibronectin Portions Indicative of Oncofetal Fibronectin
  c. Autoantibody to Oncofetal Fibronectin or to a Nucleic Acid Molecule Encoding Oncofetal Fibronectin
  d. Binding Partner
   i. Antibodies
    a. Antibodies for Oncofetal Fibronectin
    b. Conjugation of the Antibody to a Label
   ii. Nucleic Acid Molecules
   iii. Binding Partners to Autoantibodies
   iv. Additional Binding Partners
   v. Binding Partners That Bind a Region of Oncofetal Fibronectin
  e. Non-Specific Binder
 2. Assays for Detecting Oncofetal Fibronectin Complexed with a Binding Partner
  a. Solution Detection
   i. Signal Indicative of Complex Formation
   ii. Molecular Weight Corresponding to Complex
  b. Immobilized Sample
   i. Dot Blot Analysis
   ii. Western Blot Analysis
   iii. Southern and Northern Blot Analyses
   iv. In Situ Analysis
    a. Tissue or Organ Samples
    b. Detection in a Subject
    c. Treatment in a Subject
  c. Immobilized Binding Partner
   i. Sandwich Assay
   ii. Test Device
    a. Test strip
    b. Test Strip Housing
    c. Analysis with a Test Device
   iii. Quantitation
   iv. Affinity-Based Isolation of Oncofetal Fibronectin
  d. Detection of Regions of Oncofetal Fibronectin
 3. Detection of Oncofetal Fibronectin by Mass Spectrometry
  a. Sample Manipulation
   i. Contact with Binding Partner
   ii. Contact with Fragmentation Compound
    a. Trypsin Proteolysis
    b. Cathepsin D Proteolysis
    c. Thermolysin Proteolysis
    d. *Achromobacter* Protease I Proteolysis
   iii. Solid Support
   iv. Conditioning
   v. Combinations of Sample Manipulation Steps
  b. Substrate for Mass Spectrometry
  c. Mass Spectrometric Analysis
   i. Formation of Ions in the Gas Phase
   ii. Detection
   iii. Use of Mass Spectrometry for Detecting Oncofetal Fibronectin in a Sample a. Direct Measurement
        b. With Signal Enhancement
      iv. Detection of Regions of Oncofetal Fibronectin
      v. Quantitation of Oncofetal Fibronectin
  4. Detecting Nucleic Acid Molecules
    a. Detection Methods
    b. Detection of RNA
      i. Reverse Transcription
      ii. cDNA Amplification
      iii. Additional Components
      iv. Nucleic Acid Synthesis Steps
      v. Detection
        a. DNA Detection Methods
        b. Quantitation
    c. Detection of Regions of Oncofetal Fibronectin
  5. Detection of Autoantibodies to Oncofetal Fibronectin
  6. Measurement of Other Analytes
    a. Normalization
    b. Combination with Other Markers
      i. Indicators of membrane rupture
        a. Insulin-Like Growth Factor Binding Protein
        b. Hypochlorous Acid
          ii. Estriol
          iii. Other Tumor Indicators
G. Analysis of Detection Measurements
  1. Quantitation
  2. Thresholds
  3. Identification of Tissue Source
H. Combinations, Probes, Conjugates and Kits
I. Examples

A. DEFINITIONS

Unless defined otherwise, all technical and scientific terms used herein have the same meaning as is commonly understood by one of skill in the art to which the invention(s) belong. All patents, patent applications, published applications and publications, Genbank sequences, websites and other published materials referred to throughout the entire disclosure herein, unless noted otherwise, are incorporated by reference in their entirety. In the event that there are a plurality of definitions for terms herein, those in this section prevail. Where reference is made to a URL or other such identifier or address, it is understood that such identifiers can change and particular information on the internet can come and go, but equivalent information is known and can be readily accessed, such as by searching the internet and/or appropriate databases. Reference thereto evidences the availability and public dissemination of such information.

As used herein, fibronectins refer to a family of high molecular weight glycoproteins encoded by a single gene. They occur in soluble forms in plasma and other body fluids and in cellular forms in the extracellular matrices. The family of fibronectins includes at least twenty isoforms. These arise from alternative splicing in regions of the primary transcript of a single gene (see, e.g., SEQ ID NO: 37) and from post-translational modifications, generally in the EDA, EDB and IIICS regions. The amino acid sequence of an exemplary fibronectin protein containing EDA, EDB and IIICS (V64 splice variant) regions is set forth in SEQ ID NO: 38. SEQ ID NO: 15 sets forth the amino acid sequence of a fibronectin containing the complete EDA, EDB and IIICS (V120 splice variant) domains.

Cellular and plasma fibronectins often occur as heterodimers containing similar polypeptides. Alternative splicing occurs in at least two regions of the pre-mRNA, causing variability in internal primary sequences. This results in differences between the fibronectin subunits (Kornblihtt et al. EMBO J. 4(7): 1755-1759 (1985)). Plasma fibronectins generally lack extradomain A (EDA) and extradomain B ((EDB) regions of fibronectin. Cellular fibronectins can have EDA and/or EDB included or excluded, depending on the cellular and extracellular contents. Another variable region, the fibronectin III connecting segment (IIICS) region occurs in certain fibronectins and in variant forms by virtue of alternative splicing. The encoding nucleic acid contains multiple splice sites leading to variants in humans that include those designated V0, V120, V95, V89 and V64 (see, e.g., Khan et al. Investigative Ophthalmology & Visual Science 45(1): 287-295 (2004)).

Fibronectins designated oncofetal fibronectins, constitute a subset of cellular fibronectins. The oncofetal fibronectins include one or more of an EDA, EDB and/or IIICS region or are determined to be oncofetal fibronectin by virtue of expression or altered expression, such as by alternative splicing of the encoding gene to produce a truncated fibronectin (see, e.g. Schor et al. (2003) Cancer Research 63:8827-883; see, e.g., SEQ ID Nos. 26 and 27). Oncofetal fibronectins can be expressed at higher levels in tumor cells than normal cells and tissues and also in fetal cells and tissues (Kaczmarek et al. Int. J. Cancer 58: 11-16 (1994); Castellani et al., Int. J. Cancer 59: 612-618 (1994); and Tavian et al. Int. J. Cancer 56: 820-825 (1994)) or can be produced by virtue of alternative splicing in tumor cells or other cells and tissues in subjects with particular diseases. Fibronectins also can be associated with tumors and acquire metastatic potential by virtue of mutations. For example, tumor cells containing a fibronectin containing a single point mutation were found to have reduced fibronectin matrix formation and an increase in metastatic potential relative to tumor cells expressing wild-type fibronectin (Wang et al., J. Exp. Med., 195: 1397-1406 (2002)).

As used herein, oncofetal fibronectin refers to this heterogeneous subset of fibronectin proteins that share characteristic domains and/or expression patterns. Oncofetal fibronectins generally are cellular fibronectins. In tumor cells and tissues the extracellular domain portion can be shed (see, e.g., Mardon et al., J. Cell Sci. 104: 783-792 (1993)) or splicing of the encoding nucleic acid can be altered. Oncofetal fibronectins include fibronectins that are expressed in or shed by tumors, by tissues or cells involved in other disease states and also in fetal cells or tissues (also referred to as fetal fibronectins). Hence oncofetal fibronectins, while typically cellular fibronectins, can be detected in connection with disease states and pregnancy-related conditions by virtue of expression of particular splice variants, increased expression and/or shedding from such tissues and cells by virtue of overexpression or proteolytic cleavage or other mechanism.

For purposes herein, oncofetal fibronectin proteins contain extra-domain A (EDA), extra-domain B (EDB), or fibronectin III connecting segment (IIICS), or any combination thereof or are produced as a result of alternative splicing or post-translation events in tumor cells and tissues to produce for example truncated fibronectins. The group of oncofetal fibronectins includes fibronectins that result from alternative splicing of these three regions (EDA, EDB and IIICS) in fibronectin and also from post-translational modifications and other variations in splicing of the encoding nucleic acid. The splicing and expression of oncofetal fibronectin is differently regulated in cells and tissues and at different developmental stages. In fetal tissues and in some abnormal cells and tissues, expression of fibronectin is altered to produce what is designated an oncofetal fibronectin or the expression of an oncofetal fibronectin is increased relative to the corresponding normal adult cells and tissues. In some normal adult cells, tissues and sample types, oncofetal fibronectin is not present in amounts detectable by antibody assay. Accordingly, for purposes of detection of oncofetal fibronectin, abnormal levels of oncofetal fibronectin can be determined by comparing the detected amount to a control or to a predetermined amount. The amino acid sequence of human fibronectins including EDA, EDB and IIICS regions (SEQ ID NOS: 4, 6 and 8, respectively) and encoding nucleic acid molecules (SEQ ID NOS: 3, 5 and 7, respectively) are known in the art and are available in public databases. An exemplary sequence of a human EDA region also is set forth as amino acid residues 1432-1621 of SEQ ID NO: 2. An exemplary sequence of a human EDB region also is set forth as amino acid residues 963-1109 of SEQ ID NO: 2. An exemplary sequence of a human IIICS region also is set forth as amino acid residues 1830-1949 of SEQ ID NO: 2.

The amino acid sequences of exemplary oncofetal fibronectins and the sequences of encoding nucleic acid molecules are set forth in SEQ ID NO. 1, 14, 16, 18, 20, 22, 24 and 26 and the encoded amino acid molecules are set forth in SEQ ID NOS: 2, 15, 17, 19, 21, 23, 25 and 27. Examples of oncofetal fibronectin variants that generally are absent in normal tissues and cells as detected by antibody-based assays include oncofetal fibronectins generated by O-glycosylation in the IIICS splicing region and oncofetal ED-B containing fibronectin such as, for example, the amino acid sequence and the sequence of encoding nucleic acid molecule set forth in SEQ ID NOS: 25 and 24, respectively (see, e.g., Kaczmarek et al. *Int. J. Cancer* 58: 11-16 (1994); Castellani et al., *Int. J. Cancer* 59: 612-618 (1994); Midulla et al., *Cancer Res.* 60:164-169 (2000)).

The nucleic acid sequence for the entire human fn1 gene is set forth in SEQ ID NO: 37. The protein and encoding nucleic acid molecules for a variety of species including, for example, rat, mouse, chicken, cow and *Xenopus laevis* also are known and readily available in public databases. Oncofetal fibronectins include fibronectins that bind specifically to the FDC-6 monoclonal antibody (see, e.g., Matsuura and S. Hakomori, *Proc. Natl. Acad. Sci. USA*, 82:6517-6521 (1985)), which is produced by the hybridoma (deposited at the American Type Culture Collection under accession number ATCC HB 9018; see also in U.S. Pat. No. 4,894,326, issued Jan. 16, 1990, to Matsuura et al.)

The fibronectin III connecting segment (IIICS) contains three separate splice regions that can be expressed in particular combinations, resulting in a variety of different sizes and sequences of a IIICS region present in oncofetal fibronectin. The three segments encode an N-terminal segment of 25 amino acids, a middle segment encoding 64 amino acids and a C-terminal segment encoding 31 amino acids, resulting in IIICS regions that, when present can contain 64 amino acids, 89 amino acids, 95 amino acids, or 120 amino acids. Exemplary sequences are set forth in SEQ ID Nos. 35, 33, 31 and 29, respectively, which are encoded by nucleic acid sequences set forth in SEQ ID Nos. 34, 32, 30 and 28, respectively.

An oncofetal fibronectin can be identified by specific binding of one or more anti-oncofetal fibronectin antibodies. Such antibodies bind with less affinity or do not bind to non-oncofetal fibronectin. A variety of anti-oncofetal fibronectin antibodies are known in the art, including, for example, IST-9 (Carnemolla et al., *FEBS Lett.* 215:269-273 (1987); available at Accurate Chemical & Sci. Corp., Westbury, N.Y.), DH1 (Vartio et al., *J. Cell Sci.* 88:419-430 (1987)), BC-1 (Carnemolla et al., *J. Cell Biol.* 108:1139-1148 (1989)), L19 (U.S. patent application No. 20030176663), ME4C (Giovannoni et al., *Nucleic Acids Res.* 29:e27 (2001); the nucleic acid encoding sequence and the amino acid sequence for ME4C scFv recombinant antibody are provided as SEQ ID Nos:9 and 10, respectively; the sequences also are available at GenBank accession no. AJ297960), A134 (Islami et al., *Eur. J. Obstet. Gynecol. Reprod. Biol.*, 97:40-45 (2001)) FDC-6 (U.S. Pat. No. 4,894,326; ATCC HB 9018), 5C10 (Mandel et al., *APMIS* 100:817-826 (1992)) and X18A4, X20C4 and X8E3 (U.S. Pat. No. 5,523,229; ATCC Nos. HB-11587, HB-11589 and HB-11588, respectively). Antibodies that bind specifically and preferentially to oncofetal fibronectin also can be prepared. Methods for preparing such anti-oncofetal fibronectin antibodies are known in the art as exemplified in U.S. Pat. No. 4,894,326 and WO 02/46455.

Oncofetal fibronectin can be captured with a fibronectin binding partner that binds to most or all fibronectins, such as an integrin, heparin or an anti-fibronectin antibody, or oncofetal fibronectin can be captured with an oncofetal fibronectin binding partner, such as an anti-oncofetal fibronectin antibody.

As used herein, use of oncofetal fibronectin as a marker refers to detection of oncofetal fibronectin. This refers to detection of any oncofetal fibronectin indicating molecule, including an oncofetal fibronectin protein, a nucleic acid molecule encoding oncofetal fibronectin or a complement thereto, or an autoantibody that specifically binds oncofetal fibronectin protein or a nucleic acid molecule encoding oncofetal fibronectin, and fragments thereof indicative of oncofetal fibronectin.

As used herein, a fetal-restricted antigen refers to an antigen present in pregnant women uniquely, or in substantially elevated amounts compared to non-pregnant women. The fetal restricted antigen can be present in maternal serum, plasma, urine, saliva, sweat, tears and other bodily fluids. Oncofetal fibronectin can contain a fetal restricted antigen and can be found in placenta, amniotic fluid and fetal connective tissue.

As used herein, a binding partner is a compound that specifically binds to a particular molecule or class of molecules. Binding partners can include proteins, nucleic acid molecules, carbohydrates, lipids, ligands, drugs, ions and any other compound that can specifically bind to a particular molecule. A fibronectin binding partner specifically binds to any fibronectin indicating molecule, including a fibronectin protein, an oncofetal fibronectin protein, an autoantibody to a fibronectin protein or fibronectin-encoding nucleic acid or a complement thereto, an autoantibody to an oncofetal fibronectin protein or oncofetal fibronectin-encoding nucleic acid, a nucleic acid encoding fibronectin or a complement thereto, a nucleic acid encoding oncofetal fibronectin or a complement thereto, and fragments of any of these.

As used herein, an oncofetal fibronectin binding partner is a molecule that specifically binds to an oncofetal fibronectin protein, an autoantibody to an oncofetal fibronectin protein or oncofetal fibronectin-encoding nucleic acid, a nucleic acid encoding oncofetal fibronectin or a complement thereto, and fragments of any of these. In particular, an oncofetal fibronectin binding partner binds to portions of an oncofetal fibronectin indicating molecule that are unique to oncofetal fibronectin, such as EDA, EDB or IIICS and also can bind to portions of oncofetal fibronectin that are present in non-oncofetal fibronectin protein and nucleic acid molecules, such as an $FNIII_9$ region, where binding of such a region occurs by virtue of the presence of EDA, EDB or IIICS in the molecule (see, e.g., Carnemolla et al. *J. Biol. Chem.* 267:24689-24692 (1992)).

As used herein, selective binding of a binding partner to the binding of a binding partner to a particular molecule with at least about 2-fold and typically at least about 5-fold, 10-fold, 50-fold, 100-fold, or more, greater affinity (Ka or Keq) than for another molecule, or at least 2-fold and typically at least 5-fold, 10-fold, 50-fold, 100-fold, or more, greater affinity (Ka or Keq) than for another molecule. Typical conditions for detecting and determining binding affinity constants or for determining the selectivity of binding include physiological conditions, such as PBS (137 mM NaCl, 2.7 mM KCl, 10 mM phosphate buffer pH 7.4). Binding partners that specifically bind, bind with a binding affinity Ka of typically at least about 107 l/mol, 108 l/mol or more. Generally, it refers to binding partners that selectively and specifically bind.

As used herein, a compound that binds preferentially to an oncofetal fibronectin indicating molecule, is a compound that binds to an oncofetal fibronectin indicating molecule in preference to binding to a non-oncofetal fibronectin molecule, where the preference can be manifested as at least about 2-fold higher affinity and typically at least about 5-fold, 10-fold, 50-fold, 100-fold, or more, higher affinity, or at least 2-fold higher affinity and typically at least 5-fold, 10-fold, 50-fold, 100-fold, or more, higher affinity. Preferential binding is selective and also, typically is specific, and demonstrates less than about 25% or 10% and typically less than about 5%, or less than 25% or 10% and typically less than 5%, cross-reactive nonspecific binding. For example, an antibody such as FDC-6 preferentially binds to oncofetal fibronectin protein rather than non-oncofetal fibronectin protein because FDC-6 can bind to a IIICS-containing oncofetal fibronectin protein with much higher affinity than FDC-6 binds to fibronectin protein not containing the IIICS region. Typical conditions for performing such binding or for determining preferential binding include physiological conditions, such as PBS (137 mM NaCl, 2.7 mM KCl, 10 mM phosphate buffer pH 7.4).

As used herein, non-oncofetal fibronectin refers to a fibronectin protein or nucleic acid molecule that does not contain or encode an EDA, EDB and IIICS domain as detected by methods herein.

As used herein, an oncofetal fibronectin indicating molecule refers to any molecule associated with the expression or presence of oncofetal fibronectin. For example, an oncofetal fibronectin indicating molecule includes an oncofetal fibronectin protein or a fragment thereof, a nucleic acid encoding oncofetal fibronectin such as RNA or cDNA or a complement thereto, or an autoantibody to an oncofetal fibronectin protein or oncofetal fibronectin encoding nucleic acid molecule or an antibody fragment thereof and a fragment or fragments thereof.

As used herein, cancer refers to the growth of abnormal cells in the body in an uncontrolled manner; unlike benign tumors, these tend to invade surrounding tissues, and spread to distant sites of the body via the blood stream and lymphatic system. Cancer also refers to any of various malignant neoplasms characterized by the proliferation of anaplastic cells that tend to invade surrounding tissue and metastasize to new body sites. A cancer can be a solid tumor or a blood born cancer. As used herein, a tumor refers to an abnormal growth of tissue resulting from uncontrolled, progressive multiplication of cells and serving no physiological function or a neoplasm. A cancer cell, as used herein, refers to malignant neoplastic, anaplastic, metastatic, hyperplastic, dysplastic, neoplastic, malignant tumor (solid or blood-borne) cells that display abnormal growth in the body in an uncontrolled manner. Cancer can be of lung, prostate, bladder, cervical, kidney or ovarian tissue.

As used herein, neoplasm refers to new and abnormal growth of tissue, which can be cancerous, such as a malignant tumor.

As used herein, neoplastic disease, means a disease brought about by the existence of a neoplasm in the body.

As used herein, metastasis refers to the migration of cancerous cells to other parts of the body. As used herein, hyperplasia refers to an abnormal increase in the number of cells in an organ or a tissue with consequent enlargement. As used herein, neoplasm and dysplasia refer to abnormal growth of tissues, organs or cells. As used herein, malignant means cancerous or tending to metastasize. As used herein, anaplastic means cells that have become less differentiated.

As used herein, leukemia refers to a cancer of blood cells. Any of various acute or chronic neoplastic diseases of the bone marrow in which unrestrained proliferation of white blood cells occurs, are usually accompanied by anemia, impaired blood clotting, and enlargement of the lymph nodes, liver and spleen. Leukemia occurs when bone marrow cells multiply abnormally caused by mutations in the DNA of stem cells. Bone marrow stem cells, as used herein, refer to undifferentiated stem cells that differentiate into red blood cells and white blood cells. Leukemia is characterized by an excessive production of abnormal white blood cells, overcrowding the bone marrow and spilling into peripheral blood. Various types of leukemias spread to lymph nodes, spleen, liver, the central nervous system and other organs and tissues.

As used herein, lymphoma generally refers to a malignant tumor that arises in the lymph nodes or other lymphoid tissue.

As used herein, detection of oncofetal fibronectin refers to detection of an oncofetal fibronectin indicating molecule, where a fragment can be formed using the methods described herein or known in the art, such as, but not limited to, proteolysis or PCR. Further in regard to this phrase, one skilled in the art recognizes that, even if not explicitly provided for herein, methods for detecting oncofetal fibronectin proteins or fragments also can be used for detecting other oncofetal fibronectin indicating molecules such as oncofetal fibronectin-encoding nucleic acid molecules or complements thereto, or fragments thereof, or autoantibodies to oncofetal fibronectin proteins or nucleic acids or antibody fragments thereof. Selection of any particular method for detecting an oncofetal fibronectin indicating molecule can be a matter of design choice, where one skilled in the art will know which method or methods (e.g., PCR, mass spectrometry, sandwich assay) to select according to the nature (e.g., protein, nucleic acid) of the oncofetal fibronectin indicating molecule detected.

As used herein, a subject includes any animal for whom diagnosis, screening, monitoring or treatment is contemplated. Animals include mammals such as primates and domesticated animals. An exemplary primate is human. A patient refers to a subject such as a mammal, primate, human or livestock subject afflicted with a disease condition or for which a disease condition is to be determined or risk of a disease condition is to be determined.

As used herein, sample generally refers to anything that contains an analyte for which an analyte assay is to be performed. For example, a sample can be a specimen from a subject, where presence or absence of an oncofetal fibronectin indicating molecule in the specimen is to be determined using, for example, the oncofetal fibronectin indicating molecule detection methods provided herein. A sample can be used in neat form (e.g., unmodified) or can be modified by adding one or more reagents such as a buffer and/or by one or more fractionation or separation steps. The sample can be a biological sample, such as a biological or body fluid sample or a biological tissue sample. Examples of biological or body fluid samples include urine, lymph, blood, plasma, serum, saliva, cervical fluid, cervicovaginal fluid, vaginal fluid, breast fluid, breast milk, synovial fluid, semen, seminal fluid, stool, sputum, cerebral spinal fluid, tears, mucus, interstitial fluid, follicular fluid, amniotic fluid, aqueous humor, vitreous humor, peritoneal fluid, ascites, sweat, lymphatic fluid, lung sputum and lavage or samples derived therefrom (e.g., reagent-modified and/or fractionated samples). Urine samples can be neat or frozen. A fluid sample can be analyzed as it is being provided (e.g., a urine stream dipstick), can be collected in a container, or can be collected with a swab. Exemplary swab samples include cervicovaginal swab samples, including, but not limited to swab of the point of a possible cervicovaginal lesion, the cervical canal, the cervical os, the ectocervix, the transition zone on the cervix between squamous and columnar cells (i.e., the squamocolumnar junction), the vagina, the posterior fornix, the portion of the vagina below the posterior fornix such as the lower third of the vagina, the labia, or combinations thereof. Biological tissue samples are samples containing an aggregate of cells, usually of a particular kind, together with intercellular substances that form one of the structural materials of a human, animal, plant, bacterial, fungal or viral structure, including connective, epithelium, muscle and nerve tissues. Examples of biological tissue samples also include organs (e.g., breasts), tumors, lymph nodes, arteries and individual cell(s). For example, the sample can be a tissue sample suspected of being cancerous. Reference herein to any of the above fluid types or any tissue or cell sample also includes reagent-modified and fractionated samples. Thus, reference to a cervicovaginal sample also includes a buffer-treated cervicovaginal sample, and reference to a tissue sample includes the supernatant from a homogenate of that tissue.

As used herein, a normalizing analyte refers to an analyte used to normalizing the amount of oncofetal fibronectin indicating molecule in the sample according to the concentration of one or more normalization analytes in the sample. A normalizing agent is, for example, creatinine. For a vaginal swab sample, for example, the sample can be a swab of any portion of the vagina, including the posterior fornix or the portion of the vagina below the posterior fornix, such as, for example, the lower third of the vagina.

As used herein, below the posterior fornix refers to the portion of the vagina that includes the vaginal vestibule and regions of the vagina superior to the vaginal vestibule but inferior to the posterior fornix, which can include the vaginal vault, the lower third of the vagina, and the vaginal sphincter. Thus, a vaginal swab below the posterior fornix refers to a swab of the vaginal vestibule and regions of the vagina superior to the vaginal vestibule, but inferior to the posterior fornix, which can include the vaginal vault, the lower third of the vagina, and the vaginal sphincter. In the case of a labial swab, the swab can be from the labia minora or labia majora and typically includes a swab of the labia minora.

As used herein, cervicovaginal fluid can contain cervical fluid, vaginal fluid, or combinations thereof.

As used herein, an in vivo method refers to a method performed within the living body of a subject.

As used herein, a conjugate or a binding partner conjugated to a moiety refers to a complex that includes a binding partner bound to a moiety, where the binding between the binding partner and the moiety can arise from one or more covalent bonds or non-covalent interactions such as hydrogen bonds, or electrostatic interactions. A conjugate also can include a linker that connects the binding partner to the moiety. Included within the scope of conjugates are binding partners immobilized on a support such as a solid support. Exemplary conjugates include binding partners conjugated to a detectable moiety such as a detectable label, or a bindable moiety such as a bindable compound.

As used herein, a detectable moiety or an imaging moiety refer to moieties used to image an oncofetal fibronectin indicating molecule in any of the methods provided herein. Imaging moieties include, for example, fluorescent moieties, radionuclides, magnetically detectable isotopes or compounds, sonographic imaging agents, chromophores, latex microspheres, or quantum dots.

As used herein, a binding partner immobilized on a support such as a solid support refers to a binding partner bound to a support by covalent or non-covalent interactions. Binding to a support can be accomplished by a linker connected to the binding partner and the support, or the binding partner can be bound directly to the support.

As used herein, a detectable label or detectable moiety refers to an atom, molecule or composition, wherein the presence of the atom, molecule or composition can be directly or indirectly measured. Such a label can be detected, for example, by visual inspection, by fluorescence spectroscopy, by reflectance measurement, by flow cytometry, or by mass spectrometry. Direct detection of a detectable label refers to measurement of a physical phenomenon, such as energy or particle emission or absorption, of the moiety itself. Indirect detection refers to measurement of a physical phenomenon, such as energy or particle emission or absorption, of an atom, molecule or composition that binds directly or indirectly to the detectable moiety. In an example of indirect detection, a detectable label can be biotin, which can be detected by binding to avidin and avidin can be detected by, for example, binding avidin with a second biotin molecule linked to fluorescein. Thus, included within the scope of a detectable label or detectable moiety is a bindable label or bindable moiety, which refers to an atom, molecule or composition, wherein the presence of the atom, molecule or composition can be detected as a result of the label or moiety binding to another atom, molecule or composition.

A detectable label can be conjugated to a fibronectin or oncofetal fibronectin binding partner, or can specifically bind to a fibronectin or oncofetal fibronectin binding partner. For example, a detectable label such as colloidal gold or a dye in a latex microsphere can be conjugated to an anti-oncofetal fibronectin antibody. In another example, a detectable label such as a goat anti-mouse IgG antibody conjugated to horseradish peroxidase can specifically bind to a mouse IgG antibody fibronectin or oncofetal fibronectin binding partner.

As used herein, bind, bound and binding refer to the binding between atoms or molecules with a $K_d$ in the range of $10^{-2}$ to $10^{-15}$ mole/L, generally, $10^{-6}$ to $10^{-15}$, $10^{-7}$ to $10^{-15}$ and typically $10^{-8}$ to $10^{-15}$ (and/or a $K_a$ of $10^{-5}$-$10^{12}$, $10^7$-$10^{12}$, $10^8$-$10^{12}$ L/mole).

As used herein, complex refers generally to an association between two or more species regardless of the nature of the interaction between the species (i.e., ionic, covalent, or electrostatic).

As used herein, mass spectrometry encompasses any mass spectrometric format known to those of skill in the art. In particular, the phrases mass spectrometry include time-of-flight, Fourier transform, inductively coupled plasma, ion trap, magnetic sector/magnetic deflection instruments in single or triple quadrupole mode (MS/MS) and also can include combinations thereof. SELDI and MALDI mass spectrometry can be particularly attractive when a time-of-flight (TOF) configuration is used as a mass analyzer. The MALDI-TOF mass spectrometry was introduced by Hillenkamp et al., "Matrix Assisted UV-Laser Desorption/Ionization: A New Approach to Mass Spectrometry of Large Biomolecules," *Biological Mass Spectrometry*, (Burlingame and McCloskey, editors), Elsevier Science Publishers, Amsterdam, pp. 49-60 (1990)). SELDI-TOF methods are summarized in Merchant et al., *Electrophoresis* 21:1164-1177 (2000).

As used herein, desorb, desorbed and desorbing refer to the departure of a species from a surface and/or entry of the species into the gaseous phase. In particular, analytes can be desorbed from substrates using any of a variety of techniques, such as, for example, ultraviolet (UV) and infrared (IR) Matrix-Assisted Laser Desorption/Ionization (MALDI; see, e.g., published International PCT Application No. WO 99/57318 and U.S. Pat. No. 5,118,937), field desorption (FD) or fast atom bombardment (FAB). For the MALDI desorption/ionization process, numerous matrix/laser combinations can be used. Additional desorption methods include surface-enhanced neat desorption (SEND; see, e.g., U.S. Pat. No. 5,894,063) and surface-enhanced photolabile attachment and release (SEPAR; see, e.g., U.S. Pat. No. 6,124,137).

As used herein, ionization in the context of mass spectrometry refers to methods of creating charged particles in the gaseous phase. Ionization methods include desorption methods provided above such as SELDI, MALDI, FD and FAB. Ionization methods also include non-desorption methods such as electrospray (ES), electron impact (EI) and chemical ionization (CI). For ES, the samples, dissolved in water or in a volatile buffer, are injected either continuously or discontinuously into an atmospheric pressure ionization interface (API). Such ions can be mass analyzed by a quadrupole. The generation of multiple ion peaks which can be obtained using ES mass spectrometry can increase the accuracy of the mass determination.

As used herein, matrix material refers to any one of several small, photon absorbing compounds that can be mixed in solution with an analyte (e.g., an oncofetal fibronectin indicating molecule) in such a manner so that, upon drying on the mass spectrometry substrate, the matrix-embedded analyte molecules are successfully desorbed and ionized from the solid phase (e.g., crystals) into the gaseous or vapor phase and accelerated as intact molecular ions. For MALDI, sample can be mixed with a prepared solution of the chemical matrix (e.g., at a matrix-to-sample molar ratio of about 10,000:1, or 10,000:1) and placed on the mass spectrometry substrate and dried. Alternatively, a sample can be placed on a mass spectrometry substrate containing matrix and then dried. The large fold excess of matrix, present at concentrations near saturation, facilitates crystal formation and entrapment of analyte.

As used herein, energy absorbing molecule refers to any one of several small, photon absorbing compounds that, when presented on the surface of a mass spectrometry substrate, facilitate the neat desorption of molecules from the solid phase (i.e., the surface of the probe) into the gaseous or vapor phase for subsequent detection.

As used herein, substrate when used in the context of mass spectrometry, refers to an insoluble support that can serve as a surface from which a sample is desorbed and ionized in the process of mass measurement of sample components.

As used herein, a combination refers to any association between two or among more items.

As used herein, detect, detected and detecting refer generally to any manner of discovering or determining the presence of a signal, such as fluorescence or absorption, or a substance such as an oncofetal fibronectin indicating molecule or a binding partner.

As used herein, lavage refers generally to a method for obtaining a sample from a biological region or surface by contacting the region or surface with a fluid.

As used herein, ductal lavage refers generally to a method for obtaining a sample from a biological passageway through which excretions or secretions can pass (e.g., a sample from a milk duct of a breast).

As used herein, fine needle aspiration refers to a technique whereby a lumen-containing needle is used to obtain a sample. The needle is typically passed through the skin into the tissue to be sampled (e.g., a suspected tumor). A negative pressure in the needle can be formed to draw a small amount of tissue fluid, typically together with loose cells, into the needle. The needle then is removed from the tissue. Fine needle aspiration is described, for example, in U.S. Pat. No. 5,964,735 (Oct. 12, 1999) and U.S. Pat. No. 5,645,537 (Jul. 8, 1997).

As used herein, a fragmentation compound refers to a compound that can be used to fragment a molecule such as a protein or a nucleic acid molecule. For example a fragmentation compound can be used to fragment an oncofetal fibronectin protein or nucleic acid encoding oncofetal fibronectin or complement thereto. A fragmentation compound can be a protein, peptide, oligonucleotide, or other compound that can fragment molecules, particularly biomolecules, including macromolecules. For example, a fragmentation compound can be a protease or other compound that can be used to fragment an oncofetal fibronectin protein. Exemplary compounds for fragmenting oncofetal fibronectin protein include cathepsin D, trypsin, thermolysin, 2-nitro-5-thiocyanobenzoic acid (for S-cyanylation), *Achromobacter* protease 1, *S. aureus* V8 protease and hydroxylamine. In another example, a fragmentation compound can be nuclease, ribozyme, DNAzyme, or other compound that can be used to fragment an oncofetal fibronectin nucleic acid molecule or complement thereto. Exemplary compounds for fragmenting nucleic acid molecules include restriction endonucleases, exonucleases, hammerhead ribozymes and RNases.

As used herein, fragment refers to a derivative of a species that is less than the full species. For example, a fragment of an oncofetal fibronectin protein is typically a polypeptide containing fewer than the total amount of amino acids present in a translated fibronectin protein. In another example, a fragment of an oncofetal fibronectin-encoding nucleic acid molecule or complement thereto is typically an oligonucleotide containing fewer nucleic acids than the total amount of nucleic acids present in a transcribed oncofetal fibronectin-encoding nucleic acid molecule.

As used herein, an immunoassay is defined as any method using a specific or preferential binding of an antigen with a second material (i.e., a binding partner, usually an antibody, antibody fragment or another substance having an antigen binding site) that specifically or preferentially binds to an epitope of the antigen. The immunoassay methods provided herein include any known to those of skill in the art, including, but not limited to, sandwich, competition, agglutination, or precipitation assays.

As used herein, antibody refers to an immunoglobulin, whether natural or partially or wholly recombinantly or synthetically produced, including any derivative thereof that retains the specific binding ability of the antibody. Hence, antibody includes any protein having an immunoglobulin binding domain or a binding domain that is homologous or substantially homologous to an immunoglobulin binding domain. For purposes herein, antibody includes antibody fragments, such as Fab fragments, which are composed of a light chain and the variable region of a heavy chain. Antibodies include members of any immunoglobulin class, including IgG, IgM, IgA, IgD and IgE.

As used herein, a monoclonal antibody refers to an antibody secreted by a transfected or cloned cell such as a hybridoma clone. Each such hybridoma clone is derived from a single B cell and, therefore, all of the antibody molecules are identical. Monoclonal antibodies can be prepared using standard methods known to those with skill in the art (see, e.g., Kohler et al., Nature 256:495-497 (1975), Kohler et al., Eur. J. Immunol. 6:511-519 (1976) and WO 02/46455). For example, an animal is immunized by standard methods to produce antibody-secreting somatic cells. These cells then are removed from the immunized animal for fusion to myeloma cells.

Somatic cells with the potential to produce antibodies, particularly B cells, can be used for fusion with a myeloma cell line. These somatic cells can be derived from the lymph nodes, spleens and peripheral blood of primed animals. Specialized myeloma cell lines have been developed from lymphocytic tumors for use in hybridoma-producing fusion procedures (Kohler and Milstein, Eur. J. Immunol. 6:511-519 (1976); Shulman et al., Nature, 276:269-282 (1978); Volk et al., J. Virol., 42:220-227 (1982)). These cell lines have three useful properties. The first is they facilitate the selection of fused hybridomas from unfused and similarly indefinitely self-propagating myeloma cells by having enzyme deficiencies that render them incapable of growing in selective medium that support the growth of hybridomas. The second is they have the ability to produce antibodies and are incapable of producing endogenous light or heavy immunoglobulin chains. A third property is they efficiently fuse with other cells. Other methods for producing hybridomas and monoclonal antibodies are well known to those of skill in the art.

As used herein, an antibody fragment refers to any derivative of an antibody that is less than a full length antibody, retaining at least a portion of the full-length antibody's specific binding ability. Examples of antibody fragments include, but are not limited to, Fab, Fab', F(ab)$_2$, single-chain Fvs (scFv), small immune proteins, Fv, dsFv diabody and Fd fragments. The fragment can include multiple chains linked together, such as by disulfide bridges. An antibody fragment generally contains at least about 50 amino acids and typically at least about 200 amino acids, or at least 50 amino acids and typically at least 200 amino acids.

As used herein, a Fv antibody fragment is composed of one variable heavy domain ($V_H$) and one variable light ($V_L$) domain linked by non-covalent interactions.

As used herein, a dsFv refers to a Fv with an engineered intermolecular disulfide bond, which stabilizes the $V_H$-$V_L$ pair.

As used herein, scFvs refer to antibody fragments that contain a variable light chain domain ($V_L$) and variable heavy chain domain ($V_H$) covalently connected by a polypeptide linker in any order. The linker is of a length such that the two variable domains are bridged without substantial interference. Exemplary linkers are (Gly-Ser)$_n$ residues with some Glu or Lys residues dispersed throughout to increase solubility.

As used herein, diabodies are dimeric scFv; diabodies typically have shorter peptide linkers than scFvs and they preferentially dimerize.

As used herein, small immune proteins (SIP) are scFv fragments connected to a dimerization domain of an antibody, such as an IgG CH$_3$ domain. For example an SIP can be formed by connecting scFvs through a short linker to the CH3 domain of the human immunoglobin 1γ H-chain, or a similar domain such as the CH4 domain of human IgE (see, e.g., Li et al., Protein Engineering 10:731-736 (1997) and Borsi et al., Int. J. Cancer 102:75-85 (2002)).

As used herein, a Fab fragment is an antigen-binding antibody fragment containing one variable heavy domain ($V_H$), one variable light ($V_L$) domain, one constant heavy domain 1 ($C_H1$) and one constant light ($C_L$) domain. An Fab fragment can be produced by digestion of an immunoglobulin with papain; a Fab fragment also can be recombinantly produced.

As used herein, hsFv refers to antibody fragments in which the constant domains normally present in an Fab fragment have been substituted with a heterodimeric coiled-coil domain (see, e.g., Arndt et al. J. Mol. Biol. 7:312:221-228 (2001)).

As used herein, an F(ab)$_2$ fragment is an antibody fragment containing two variable heavy domains ($V_H$), two variable light ($V_L$) domains, two constant heavy domains 1 ($C_H1$) and two constant light ($C_L$) domains. An F(ab)$_2$ can be produced by digestion of an immunoglobulin with pepsin at pH 4.0-4.5; an F(ab)$_2$ fragment also can be recombinantly produced.

As used herein, humanized antibodies refer to antibodies that are modified to include "human" sequences of amino acids so that administration to a human does not provoke an immune response. Methods for preparation of such antibodies are known. For example, a hybridoma that expresses a monoclonal antibody is altered by recombinant DNA techniques to express an antibody in which the amino acid composition of the non-variable regions is based on human antibodies. Computer programs that identify such regions are known in the art.

As used herein, autoantibody refers to an antibody produced by a subject that binds to an endogenous antigen of the subject. For example, an autoantibody can be produced in response to presence of a tumor, cancer, or cancerous condition with the subject. Autoantibodies, although produced by the subject in response to an endogenous antigen, can be detected or measured by reaction of the autoantibody with a binding partner, such as a test antigen produced or obtained from a variety of sources including by recombinant techniques. An anti-fibronectin autoantibody refers to an antibody that specifically binds fibronectin. An anti-oncofetal fibronectin autoantibody refers to an antibody that specifically and preferentially binds to oncofetal fibronectin protein or nucleic acid molecule; that is, the autoantibody specifically binds an oncofetal fibronectin molecule in preference to a non-oncofetal fibronectin molecule.

As used herein in regard to nucleic acid molecules, amplify, amplified and amplifying refer to methods for increasing the number of copies of a specific nucleic acid molecule, such as a DNA fragment. In particular, amplify, amplified and amplifying include processes wherein a nucleic acid molecule is increased in copy number using techniques such as, for example, cloning, transcription, the polymerase chain reaction (PCR), the ligase chain reaction (LCR) and strand displacement.

As used herein, an amplified nucleic acid molecule corresponding to an oncofetal fibronectin encoding nucleic acid molecule refers to an amplified nucleic acid molecule formed using any amplification method and using an oncofetal fibronectin encoding nucleic acid molecule as the template nucleic acid molecule. Such an amplified nucleic acid molecule can contain all or a portion of the nucleic acid molecule of an oncofetal fibronectin encoding nucleic acid molecule or all or a portion of the nucleotide molecule complementary to an oncofetal fibronectin encoding nucleic acid molecule. For example, an amplified nucleic acid molecule can contain all or a portion of the nucleic acid molecule encoding the EDA, EDB or IIICS regions of fibronectin. In another example, a complement to an oncofetal fibronectin encoding nucleic acid molecule can contain all or a portion of the nucleic acid molecule complementary to the nucleic acid molecule encoding the EDA, EDB or IIICS regions of fibronectin.

As used herein, the terms convert, converted and converting refer to processes wherein species are converted using, for example, chemical, physical and/or biological reactions.

As used herein, risk refers to a predictive process in which the probability of a particular outcome is assessed.

As used herein, the phrases impending delivery and imminent delivery refer to delivery within a predetermined time frame, such as within about 7, 14, 21, or 28 days, or within 7, 14, 21, or 28 days.

As used herein, the phrase pre-term delivery refers to delivery that occurs from about 20 weeks gestation to about 37 weeks gestation, or from 20 weeks gestation to 37 weeks gestation. The number of weeks gestation (i.e., gestational age) can be determined using any of a number of conventional methods. For example, the gestational age can be calculated from the first day of the last menstruation.

As used herein, a support refers to any solid or semisolid or insoluble support to which a molecule of interest, typically a biological molecule or organic molecule or biospecific ligand, is linked or contacted. Typically, a support contains immobilized thereto one or more fibronectin or oncofetal fibronectin binding partners. Support materials include any material that can be used as affinity matrices or supports for chemical and biological molecule syntheses and analyses, such as, but are not limited to: organic or inorganic polymers, biopolymers, natural and synthetic polymers, including, but not limited to, agarose, cellulose, nitrocellulose, cellulose acetate, other cellulose derivatives, dextran, dextran-derivatives and dextran co-polymers, other polysaccharides, gelatin, polyvinyl pyrrolidone, rayon, nylon, polyethylene, polypropylene, polybutlyene, polycarbonate, polyesters, polyamides, vinyl polymers, polyvinylalcohols, polyvinylidenedifluoride (PVDF), polystyrene and polystyrene copolymers, polystyrene cross-linked with divinylbenzene or the like, acrylic resins, acrylates and acrylic acids, acrylamides, polyacrylamides, polyacrylamide blends, co-polymers of vinyl and acrylamide, methacrylates, methacrylate derivatives and co-polymers, other polymers and co-polymers with various functional groups, rubber, latex, butyl rubber and other synthetic rubbers, silicon, glass (e.g. controlled-pore glass (CPG)), silica gels, ceramics, paper, natural sponges, insoluble protein, surfactants, red blood cells, metals (including metal ions; e.g., steel, gold, silver, aluminum and copper), metalloids, magnetic materials (including Teflon® coated magnetic materials and magnetic beads), Wang resin, Merrifield resin, Sephadex®, Sepharose®, nylon, dextran, chitin, sand, pumice, dendrimers, buckyballs, or other commercially available medium. Exemplary supports include, but are not limited to flat supports such as glass fiber filters, silicon surfaces, glass surfaces, magnetic beads, metal surfaces (steel, gold, silver, aluminum and copper) and plastic materials.

The support can take any of a variety of forms. For example, the substrate can be formed as plates; whiskers; single crystals; ceramics; self-assembling monolayers; beads or microbeads (e.g., silica gel, controlled pore glass, magnetic, Sephadex/Sepharose, cellulose); flat surfaces or chips (e.g., glass fiber filters, glass surfaces, glass slides, metal surfaces (steel, gold, silver, aluminum, copper and silicon)); capillaries; membranes or microtiter plates (e.g., nylon, polyethylene, polypropylene, polyvinylidenedifluoride, or nitrocellulose membranes or microtiter plates); pins or combs; wafers (e.g., silicon wafers); and combinations thereof (e.g., beads placed into pits in flat surfaces).

When particulate, typically the supports have at least one dimension in the 5-100 µm range or smaller. Such supports, referred collectively herein as beads, are often, but not necessarily, spherical. Such reference, however, does not constrain the geometry of the support, which can be any shape, including random shapes, needles, fibers and elongated. Roughly spherical beads, particularly microspheres that can be used in the liquid phase, can be employed. Beads can include additional components, such as magnetic or paramagnetic particles (e.g., Dynabeads® (Dynal, Oslo, Norway)) for separation using magnets, as long as the additional components do not interfere with the methods and analyses herein.

As used herein, support particles refer to support materials that are in the form of discrete particles. The particles can have any shape and dimensions, but typically have at least one dimension that is 100 mm or less, 50 mm or less, 10 mm or less, 5 mm or less, 4 mm or less, 3 mm or less, 2 mm or less, 1 mm or less, 900 Am or less, 800 µm or less, 700 µm or less, 600 µm or less, 500 µm or less, 400 µm or less, 300 µm or less, 200 µm or less, 100 µm or less, 50 µm or less, 40 µm or less, 30 µm or less, 20 µm or less, 10 µm or less, 5 µm or less, 4 µm or less, 3 µm or less, 2 µm or less, 1 µm or less, 900 nm or less, 800 nm or less, 700 nm or less, 600 nm or less, 500 nm or less, 400 nm or less, 300 nm or less, 200 nm or less, 100 nm or less, 50 nm or less, 40 nm or less, 30 nm or less, 20 nm or less and 10 nm or less. The particles typically have a size that is 100 $mm^3$ or less, 50 $mm^3$ or less, 10 $mm^3$ or less and 5 $mm^3$ or less, 4 $mm^3$ or less, 3 $mm^3$ or less, 2 $mm^3$ or less and 1 $mm^3$ or less, 900 $µm^3$ or less, 800 $µm^3$ or less, 700 $µm^3$ or less, 600 $µm^3$ or less, 500 $µm^3$ or less, 400 $µm^3$ or less, 300 $µm^3$ or less, 200 $µm^3$ or less, 100 $µm^3$ or less, 50 $µm^3$ or less, 40 $µm^3$ or less, 30 $µm^3$ or less, 20 $µm^3$ or less, 10 $µm^3$ or less, 5 $µm^3$ or less, 4 $µm^3$ or less, 3 $µm^3$ or less, 2 $µm^3$ or less, 1 $µm^3$ or less, 900 $nm^3$ or less, 800 $nm^3$ or less, 700 $nm^3$ or less, 600 $nm^3$ or less, 500 $nm^3$ or less, 400 $nm^3$ or less, 300 $nm^3$ or less, 200 $nm^3$ or less, 100 $nm^3$ or less, 50 $nm^3$ or less, 40 $nm^3$ or less, 30 $nm^3$ or less, 20 $nm^3$ or less, 10 $nm^3$ or less, 5 $nm^3$ and can be on the order of cubic nanometers; typically the particles have a diameter of about 1.5 microns and less than about 15 microns, such as about 4-6 microns, or 1.5 microns and less than 15 microns, such as 4-6 microns. Such particles are collectively called beads.

As used herein in the context of a test strip, upstream describes a relationship between at least two regions, where a first region that is upstream of a second region is a first region that is contacted by the sample prior to sample contact with the second region. Similarly, downstream describes the relationship between two or more regions where a first region that is downstream of a second region is a first region that is contacted by the sample subsequent to sample contact with the second region.

As used herein, an epitope present in fibronectin refers to any region present in fibronectin that binds to an antibody or fragment thereof. For example, an epitope present in fibronectin can include an epitope that is present in a non-oncofetal fibronectin, for example, an epitope in the $FNIII_7$ repeat. A large number of antibodies that bind to epitopes present on fibronectins are known in the art, including antibodies HFN 36.3 and HFN 7.1 (Schoen R C, et al. "Monoclonal antibody against human fibronectin which inhibits cell attachment." *Hybridoma* 1: 99-108, 1982; ATCC Nos. CRL-1605 and CRL-1606, respectively), P3NP/PFn (ATCC No. HB-91), 3E3 (Borsi et al., *FEBS Lett.* 192:71-74 (1985)) and IST-4 (Sekiguchi et al., *J. Biol. Chem.* 260:5105-5114 (1985)); Accurate Chemical and Scientific Corp., Westbury, N.Y.).

As used herein, an epitope present in oncofetal fibronectin refers to any region present in oncofetal fibronectin that binds to an anti-oncofetal fibronectin antibody or fragment thereof. For example, an epitope present in oncofetal fibronectin can include a splice region specific to an oncofetal fibronectin indicating molecule, for example, an epitope in EDA, EDB or IIICS and also can include other regions in an oncofetal fibronectin indicating molecule to which an anti-oncofetal fibronectin antibody binds by virtue of the presence of one or more of EDA, EDB or IIICS, for example the $FNIII_9$ repeat when EDB is present. A large number of antibodies that bind specifically to oncofetal fibronectin are known in the art, including IST-9 (Carnemolla et al., *FEBS Lett.* 215:269-273 (1987)); available at Accurate Chemical & Sci. Corp., Westbury, N.Y.), DH1 (Vartio et al., *J. Cell Sci.* 88:419-430 (1987)), BC-1 (Carnemolla et al., *J. Cell Biol.* 108:1139-1148 (1989)), L19 (U.S. Pat. App. No. 20030176663), ME4C (SEQ ID NO: 9) (Giovannoni et al., *Nucleic Acids Res.* 29:e27 (2001)); the ME4C scFv recombinant antibody sequence is provided as SEQ ID No:10 (see, also GenBank accession no. AJ297960), A134 (U.S. Pat. App. No. 20030176663), A134 (Islami et al., *Eur. J. Obstet. Gynecol. Reprod. Biol.,* 97:40-45 (2001)) FDC-6 (U.S. Pat. No. 4,894,326; ATCC HB 9018), 5C10 (Mandel et al., *APMIS* 100:817-826 (1992)) and X18A4, X20C4 and X8E3 (U.S. Pat. No. 5,523,229; ATCC Nos. HB-11587, HB-11589 and HB-11588, respectively).

As used herein, non-radioactive energy transfer reactions, such as FET (fluorescence energy transfer) assays, FRET (fluorescence resonance energy transfer) assays, fluorescence polarization assays and HTRF (homogeneous time-resolved fluorescence), are homogeneous luminescence assays based on energy transfer between a donor luminescent label and an acceptor label (see, e.g., Cardullo et al. *Proc. Natl. Acad. Sci. U.S.A.* 85:8790-8794 (1988); Peerce et al. *Proc. Natl. Acad. Sci. U.S.A.* 83:8092-8096 (1986); U.S. Pat. No. 4,777,128; U.S. Pat. No. 5,162,508; U.S. Pat. No. 4,927,923; U.S. Pat. No. 5,279,943; and International PCT Application No. WO 92/01225).

As used herein, Fluorescence Resonance Energy Transfer (FRET) refers to non-radioactive energy transfer between chemical and/or protein fluors. Fluorescent resonance energy transfer (FRET) is an art-recognized process in which one fluorophore (the acceptor) can be promoted to an excited electronic state through quantum mechanical coupling with and receipt of energy from an electronically excited second fluorophore (the donor). This transfer of energy results in a decrease in visible fluorescence emission by the donor and an increase in fluorescent energy emission by the acceptor.

For FRET to occur efficiently, the absorption and emission spectra between the donor and acceptor have to overlap. Dye pairs are characterized by their spectral overlap properties. Emission spectrum of donor must overlap acceptor absorption spectrum. Extent of overlap determines the efficiency of energy transfer. Extent of overlap also determines the optimal distance for which the assay is sensitive. Where the overlap of spectra is large, the transfer is efficient, so it is sensitive to longer distances. The selection of donor/acceptor depends upon the distances considered.

Significant energy transfer can only occur when the donor and acceptor are sufficiently closely positioned since the efficiency of energy transfer is highly dependent upon the distance between donor and acceptor fluorophores. The fluorophores can be chemical fluors and/or protein fluors. For example, FRET energy transfer between two fluorescent proteins as a physiological reporter has been reported (Miyawaki et al. *Nature* 388:882-887 (1997)), in which two different fluorescent proteins were fused to the carboxyl and amino termini of calmodulin. Changes in calcium ion concentration caused a sufficient conformational change in calmodulin to alter the level of energy transfer between the fluorescent protein moieties.

As used herein, fluorescence polarization or fluorescence polarization anisotropy (see, e.g., Jameson et al. *Methods Enzymol.* 246:283-300 (1995)) refers to procedures in which fluorescently labeled molecules are illuminated in solution with plane-polarized light. When fluorescently labeled molecules in solution are so-illuminated, the emitted fluorescence is in the same plane provided the molecules remain stationary. Since all molecules in solution tumble as a result of collisional motion, depolarization phenomenon is proportional to the rotational relaxation time of the molecule, which is defined by the expression $3\eta V/RT$. At constant viscosity ($\eta$) and temperature (T) of the solution, polarization is directly proportional to the molecular volume (V) (R is the universal gas constant). Hence, changes in molecular volume or molecular weight due to binding interactions can be detected as a change in polarization. For example, the binding of a fluorescently labeled ligand to its receptor results in significant changes in measured fluorescence polarization values for the ligand. Measurements can be made in a "mix and measure" mode without physical separation of the bound and free ligands. The polarization measurements are relatively insensitive to fluctuations in fluorescence intensity when working in solutions with moderate optical intensity.

As used herein, luminescence refers to the detectable EM radiation, generally, UV, IR or visible EM radiation that is produced when the excited product of an exergic chemical process reverts to its ground state with the emission of light. Chemiluminescence is luminescence that results from a chemical reaction. Bioluminescence is chemiluminescence that results from a chemical reaction using biological molecules (or synthetic versions or analogs thereof) as substrates and/or enzymes.

As used herein, chemiluminescence refers to a chemical reaction in which energy is specifically channeled to a molecule causing it to become electronically excited and subsequently to release a photon thereby emitting visible light. Temperature does not contribute to this channeled energy. Thus, chemiluminescence involves the direct conversion of chemical energy to light energy.

As used herein, bioluminescence, which is a type of chemiluminescence, refers to the emission of light by biological molecules, particularly proteins. The essential condition for bioluminescence is molecular oxygen, either bound or free in the presence of an oxygenase, a luciferase, which acts on a substrate, a luciferin. Bioluminescence is generated by an enzyme or other protein (luciferase) that is an oxygenase that acts on a substrate luciferin (a bioluminescence substrate) in the presence of molecular oxygen and transforms the substrate to an excited state, which, upon return to a lower energy level releases the energy in the form of light.

As used herein, the substrates and enzymes for producing bioluminescence are generically referred to as luciferin and luciferase, respectively. When reference is made to a particular species thereof, for clarity, each generic term is used with the name of the organism from which it derives, for example, bacterial luciferin or firefly luciferase.

As used herein, luciferase refers to oxygenases that catalyze a light emitting reaction. For instance, bacterial luciferases catalyze the oxidation of flavin mononucleotide (FMN) and aliphatic aldehydes, which reaction produces light. Another class of luciferases, found among marine arthropods, catalyzes the oxidation of *Cypridina* (*Vargula*) luciferin and another class of luciferases catalyzes the oxidation of Coleoptera luciferin.

Thus, luciferase refers to an enzyme or photoprotein that catalyzes a bioluminescent reaction (a reaction that produces bioluminescence). The luciferases, such as firefly and *Gaussia* and *Renilla* luciferases, are enzymes which act catalytically and are unchanged during the bioluminescence generating reaction. The luciferase photoproteins, such as the aequorin photoprotein to which luciferin is non-catalytically bound, are changed, such as by release of the luciferin, during bioluminescence generating reaction. The luciferase is a protein that occurs naturally in an organism or a variant or mutant thereof, such as a variant produced by mutagenesis that has one or more properties, such as thermal stability, that differ from the naturally-occurring protein. Luciferases and modified mutant or variant forms thereof are well known. For purposes herein, reference to luciferase refers to either the photoproteins or luciferases.

Thus, reference, for example, to *Renilla* luciferase refers to an enzyme isolated from member of the genus *Renilla* or an equivalent molecule obtained from any other source, such as from another related copepod, or that has been prepared synthetically. It is intended to encompass Renilla luciferases with conservative amino acid substitutions that do not substantially alter activity. Conservative substitutions of amino acids are known to those of skill in this art and can be made generally without altering the biological activity of the resulting molecule. Those of skill in this art recognize that, in general, single amino acid substitutions in non-essential regions of a polypeptide do not substantially alter biological activity (see, e.g., Watson et al. *Molecular Biology of the Gene,* 4th Edition, 1987, The Benjamin/Cummings Pub. co., p. 224).

As used herein, bioluminescence substrate refers to the compound that is oxidized in the presence of a luciferase and any necessary activators and generates light. These substrates are referred to as luciferins herein, are substrates that undergo oxidation in a bioluminescence reaction. These bioluminescence substrates include any luciferin or analog thereof or any synthetic compound with which a luciferase interacts to generate light. Typical substrates include those that are oxidized in the presence of a luciferase or protein in a light-generating reaction. Bioluminescence substrates, thus, include those compounds that those of skill in the art recognize as luciferins. Luciferins, for example, include firefly luciferin, *Cypridina* (also known as *Vargula*) luciferin (coelenterazine), bacterial luciferin, as well as synthetic analogs of these substrates or other compounds that are oxidized in the presence of a luciferase in a reaction the produces bioluminescence.

As used herein, capable of conversion into a bioluminescence substrate refers to being susceptible to chemical reaction, such as oxidation or reduction, that yields a bioluminescence substrate. For example, the luminescence producing reaction of bioluminescent bacteria involves the reduction of a flavin mononucleotide group (FMN) to reduced flavin mononucleotide (FMNH2) by a flavin reductase enzyme. The reduced flavin mononucleotide (substrate) then reacts with oxygen (an activator) and bacterial luciferase to form an intermediate peroxy flavin that undergoes further reaction, in the presence of a long-chain aldehyde, to generate light. With respect to this reaction, the reduced flavin and the long chain aldehyde are substrates.

As used herein, a bioluminescence generating system refers to the set of reagents required to conduct a bioluminescent reaction. Thus, the specific luciferase, luciferin and other substrates, solvents and other reagents that can be required to complete a bioluminescent reaction form a bioluminescence system. Thus a bioluminescence generating system refers to any set of reagents that, under appropriate reaction conditions, yield bioluminescence. Appropriate reaction conditions refers to the conditions necessary for a bioluminescence reaction to occur, such as pH, salt concentrations and temperature. In general, bioluminescence systems include a bioluminescence substrate, luciferin, a luciferase, which includes enzymes luciferases and photoproteins and one or more activators. A specific bioluminescence system can be identified by reference to the specific organism from which the luciferase derives; for example, the *Renilla* bioluminescence system includes a *Renilla* luciferase, such as a luciferase isolated from the *Renilla* or produced using recombinant methods or modifications of these luciferases. This system also includes the particular activators necessary to complete the bioluminescence reaction, such as oxygen and a substrate with which the luciferase reacts in the presence of the oxygen to produce light.

As used herein, a fluorescent protein (FP) refers to a protein that possesses the ability to fluoresce (i.e., to absorb energy at one wavelength and emit it at another wavelength). For example, a green fluorescent protein (GFP) refers to a polypeptide that has a peak in the emission spectrum at 510 nm or about 510 nm. A variety of FPs that emit at various wavelengths are known in the art.

As used herein, *Aequora* GFP refers to GFPs from the genus *Aequora* and to mutants or variants thereof. Such variants and GFPs from other species are well known and are available and known to those of skill in the art.

As used herein, quantitation of an oncofetal fibronectin indicating molecule refers to the calculation of the concentration, mass, or molar quantity of an oncofetal fibronectin indicating molecule in a sample.

As used herein, a threshold level of an oncofetal fibronectin indicating molecule refers to a level of an oncofetal fibronectin indicating molecule that is compared to a measured amount of an oncofetal fibronectin indicating molecule, where a measured amount above or equal to the threshold level is categorized differently than a measured amount below a threshold level. For example, a measured amount above or equal to a threshold level can be categorized as oncofetal fibronectin positive and a measured amount below the threshold level can be categorized as oncofetal fibronectin negative. In the case of multiple thresholds, the measured amount can be categorized according to the highest level that is less than or equal to the measured amount. One or more thresholds as used herein, refers to 1, 2, 3, 4, 5, 6, 7, 8, 9, 10 or more thresholds. A level of an oncofetal fibronectin indicating molecule, such as a threshold level, can be a reference amount represented as a raw concentration (i.e., not normalized), normalized concentration, mass quantity, molar quantity, or other quantitative amount. For example, the threshold level can be the level of an oncofetal fibronectin indicating molecule that is present in a sample from a population of normal individuals or from the subject at different time points. For example, a subject that is negative for oncofetal fibronectin, as used herein, refers to a subject that does not exhibit oncofetal fibronectin indicating molecule levels significantly above normal oncofetal fibronectin indicating molecule levels. As is understood by one skilled in the art, the threshold level can vary depending on the tissue or fluid sampled, depending on the sample type, depending on the detection method, depending on the age, gender or biological state (e.g., pregnant or not pregnant) of a subject. In some instances, the threshold level for an oncofetal fibronectin indicating molecule is zero (i.e., when any oncofetal fibronectin indicating molecule is present, the sample is positive for oncofetal fibronectin).

As used herein, a primer refers to an oligonucleotide to which can be enzymatically added one or more additional nucleotides. Typically a primer contains a free 3' hydroxy moiety.

As used herein, an amplifiable signaling nucleic acid refers to a nucleic acid that can be amplified using known amplification methods such as polymerase chain reaction (PCR) and the presence of which indicates complex formation between an oncofetal fibronectin indicating molecule and a fibronectin or oncofetal fibronectin binding partner.

As used herein, a health problem associated with oncofetal fibronectin refers to an adverse health condition, such as a disease or pregnancy trouble, that is more common in subjects having the presence of an oncofetal fibronectin indicating molecule or an amount at or over a threshold relative to subjects having absence of an oncofetal fibronectin indicating molecule or an amount below a threshold, or that is less common in subjects having an absence of an oncofetal fibronectin indicating molecule or an amount below a threshold relative to subjects having the presence of an oncofetal fibronectin indicating molecule or an amount at or over a threshold. An oncofetal fibronectin-associated health problem is characterized by the presence of, or elevated levels of, an oncofetal fibronectin indicating molecule in a body tissue or fluid sample. The presence of, or elevated levels of, an oncofetal fibronectin indicating molecule does not necessarily indicate that the health problem is caused by an oncofetal fibronectin indicating molecule, but that elevated levels of an oncofetal fibronectin indicating molecule are observed in tissue and/or fluid samples. For example, an oncofetal fibronectin indicating molecule can serve as an indicator of cancer, can serve as an indicator of pre-term or imminent delivery and also can serve as an indicator of a condition such as, but not limited to, arthritis, diabetic retinopathy, renal disease and Dupuytren's contracture. Detection of an oncofetal fibronectin indicating molecule in a body tissue or fluid sample at or above one or more thresholds or at a level above a baseline for a particular individual can be an indicator of a variety of health problems or risk therefor. Similarly, its absence or presence below one or more thresholds can be indicative of the absence of any of these variety of diseases and disorders (i.e., health problems).

As used herein, progestational therapy refers to one or more therapeutic methods that favor, or is conducive to, gestation, or inhibit premature labor, or increase the viability of an infant after birth, particularly the viability of a pre-term infant. Progestational therapy can include methods such as bedrest for the pregnant subject and also can include administration of one or more agents that reduce or inhibit uterine contractions, that prolong the pregnancy, or that increase the viability of an infant delivered pre-term. For example, progestational therapy can include administration of a tocolytic agent.

As used herein, a tocolytic agent refers to a compound or composition that, upon administration to a subject, reduces or inhibits uterine contractions, or otherwise inhibits premature labor.

As used herein, conceptus refers to any cells, cell masses, and tissues resulting from fertilization of an ovum by a sperm from the moment of fertilization through birth. These include, but not limited to, zygotes, embryos, blastocysts, and fetuses.

As used herein, concepti is the plural of conceptus.

As used herein, a conceptus sample refers to a sample that contains compounds produced by a conceptus. Conceptus samples include conceptus extracts, samples from outside of the conceptus, such as culture medium, cell and tissue extracts, and cells, where one or more cells is removed from a conceptus, leaving the remainder of the conceptus competent for subsequent culture, implantation and/or development. A conceptus sample can be analyzed neat, or can be reagent-treated and/or fractionated prior to detection of an oncofetal fibronectin indicating molecule.

As used herein, an additional maternal or conceptus marker refers to a marker that is predetermined to be marker for successful implantation. The additional marker can be detected in a conceptus sample, is determined by visual inspection of the conceptus or is detected in a maternal sample. Any such marker can be employed. Exemplary markers include, but are not limited to, genetic composition of the conceptus, gene expression of the conceptus and morphology of the conceptus. One additional marker can also be, for example morphology of the conceptus, and the morphology of the conceptus is graded according to factors such as cell number, degree of fragmentation, cell regularity, symmetry, pronuclear morphology, follicle size, follicular fluid volume, multi-nucleation, presence of vacuoles, granularity, and combinations thereof.

As used herein, gametes refer to ova and sperm.

As used herein, fertilization refers to the fusion of a sperm cell with an ovum.

As used herein, implantation with reference to the uterus, uterine wall, or endometrial layer, refers to the penetration and/or attachment of a conceptus (or concepti) and/or cells of a conceptus (or concepti) into or onto such cells and/or tissues.

As used herein, trophoblast refers to the outer layer of epithelial cells surrounding the inner cell mass of a blastocyst. The trophoblast also is referred to as the outer cell mass. Trophoblast cells can develop into extra-embryonic cells and tissues including placenta, amnion and umbilical cord.

As used herein a non-specific binder, or a substance that reduces non-specific binding, is a substance that binds to at least a portion of background material in a sample without binding more than a small amount, typically less than or less than about 1%, 2%, 5% or 10% depending upon the assay or application, of oncofetal fibronectin indicating molecule in the sample. A non-specific binder can include, for example, a non-specific binding compound, or a solid support containing a non-specific binding surface.

As used herein, a non-specific binding compound can bind to at least a portion of background material in a sample without binding more than a small amount (e.g., less than 10%) of oncofetal fibronectin indicating molecule in the sample. A non-specific binding compound can be in any of a variety of forms, including, but not limited to, soluble in solution, mobile in a solvent, present in an emulsion, present in a gel, present on a solid support (including, e.g., immobilized on a solid support). Exemplary, non-limiting, non-specific binding compounds that can be used include non-specific binding proteins, including albumins such as bovine serum albumin (BSA), human, rabbit, goat, sheep and horse serum albumins; and other proteins such as ovalbumin, fibrinogen, thrombin, transferrin, glycoproteins, casein, antibodies not specific for an oncofetal fibronectin indicating molecule and other proteins. Non-specific binding proteins also can include water-soluble polyamino acids such as, for example, polymers of one or more amino acids such as lysine, glutamic acid, alanine, histidine, methionine and proline. Non-specific binding compounds also can be protein-containing compositions including serum such as fetal calf serum, gelatin and dried milk.

Non-specific binders can include non-specific binding surfaces, which are solid structures that can contain one or more components, where the non-specific binding surface binds to at least a portion of background material in a sample while not binding more than a small amount (e.g., less than 10%) of oncofetal fibronectin indicating molecule in the sample. Exemplary solid supports for non-specific binding surfaces include paper and cellulose derivatives, such as cellulose esters and ethers, natural and synthetic polymeric materials, such as latex, vinyl polymers, polypropylene, polyethylene and partially hydrolyzed derivatives, polycondensates, copolymers and inorganic materials. For example, a non-specific binding surface is a porous or bibulous member capable of transporting a liquid sample along a test strip. Non-specific binding surfaces can have immobilized thereon one or more non-specific binding compounds such as, but not limited to, albumin (including bovine serum albumin, or BSA), antibodies not specific for an oncofetal fibronectin indicating molecule and others provided herein or known in the art.

As used herein, therapeutic agents are agents that ameliorate the symptoms of a disease or disorder or ameliorate the disease or disorder. Therapeutic agents include, but are not limited to, moieties that inhibit cell growth or promote cell death, that can be activated to inhibit cell growth or promote cell death, or that activate another agent to inhibit cell growth or promote cell death. Optionally, the therapeutic agent can exhibit or manifest additional properties, such as, properties that permit its use as an imaging agent, as described elsewhere herein. Therapeutic agents include, but are not limited to, for example, cytokines and growth factors, photosensitizing agents toxins, anticancer antibiotics, a chemotherapeutic compound, a radionuclide, an angiogenesis inhibitor, a signaling modulator, a bioluminescent compound or a combination thereof.

Cytokines and growth factors include, but are not limited to, interleukins, such as, for example, interleukin-1, interleukin-2, interleukin-6 and interleukin-12, tumor necrosis factors, such as tumor necrosis factor alpha (TNF-α), interferons such as interferon gamma (IFN-γ), granulocyte macrophage colony stimulating factors (GM-CSF), angiogenins, and tissue factors.

Exemplary photosensitizing agents include, but are not limited to, for example, indocyanine green, toluidine blue, aminolevulinic acid, texaphyrins, benzoporphyrins, phenothiazines, phthalocyanines, porphyrins such as sodium porfimer, chlorins such as tetra(m-hydroxyphenyl)chlorin or tin(IV) chlorin e6, purpurins such as tin ethyl etiopurpurin, purpurinimides, bacteriochlorins, pheophorbides, pyropheophorbides or cationic dyes.

Anti-cancer agents, include, but are not limited to, for example, porfiromycin, doxorubicin, dactinomycin, plicamycin, mitomycin, bleomycin, actinomycin, or daunorubicin and chemotherapeutic compounds.

Radionuclides, which depending up the radionuclide, amount and appliatien-application can be used for diagnosis and/or for treatment. They include, but are not limited to, for example, a compound or molecule containing $^{32}$Phosphate, $^{60}$Cobalt, $^{90}$Yttirum, $^{99}$Technicium, $^{103}$Palladium, $^{106}$Ruthenium, $^{111}$Indium, $^{117}$Lutetium, $^{125}$Iodine, $^{131}$Iodine, $^{137}$Cesium, $^{153}$Samarium, $^{186}$Rhenium, $^{188}$Rhenium, $^{192}$Iridium, $^{198}$Gold, $^{211}$Astatine, $^{212}$Bismuth or $^{213}$Bismuth. Toxins include, but are not limited to, chemotherapeutic compounds such as, but not limited to, 5-fluorouridine, calicheamicin and maytansine. Signaling modulators include, but are not limited to, for example, inhibitors of macrophage inhibitory factor, toll-like receptor agonists and stat 3 inhibitors.

Chemotherapeutic compounds include, but are not limited to, alkylating agents such as thiotepa and cyclosphosphamide; alkyl sulfonates such as busulfan, improsulfan and piposulfan; aziridines such as benzodopa, carboquone, meturedopa and uredopa; ethylenimines and methylamelamines including altretamine, triethylenemelamine, trietylenephosphoramide, triethylenethiophosphaoramide and trimethylolomelamime nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; polysaccharide-K; razoxane; sizofuran; spirogermanium; tenuazonic acid; triaziquone; 2, 2',2"-trichlorotriethylamine; urethan; vindesine; dacarbazine; mannomustine; mitobronitol; mitolactol; pipobroman; gacytosine; cytosine arabinoside; cyclophosphamide; thiotepa; taxoids, e.g. paclitaxel and doxetaxel; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitor RFS 2000; difluoromethylomithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone and toremifene (Fareston); and antiandrogens such as flutamide, nilutamide, bicalutamide, leuprolide and goserelin; and pharmaceutically acceptable salts, acids or derivatives of any of the above. Such chemotherapeutic compounds that can be used herein include compounds whose toxicities preclude use of the compound in general systemic chemotherapeutic methods.

As used herein, a pre-induction agent or procedure refers to an agent or process, such as cervical and vaginal ripening, prostaglandin, a foley catheter, or dinoprostone agents such as Prepidil and Cervidil used to prepare a pregnant subject for induction of labor.

As used herein, an induction agent refers to an agent in is administered to causes labor to begin.

As used herein, an induction procedure refers any procedure that is used to induce labor. The procedures include, but are not limited to, balloon catheterization such as foley balloon catheterization or Atad balloon catheterization, amniotic membrane stripping, extra-amniotic saline infusion, amniotomy and/or nipple stimulation, and administration of an induction agent.

As used herein, an induction agent, refers to an agent that induces labor, and includes, for example, oxytocin. Oxytocin plays a role in the initiation of labor, stimulates the contraction of smooth muscle of the uterus during labor and facilitates ejection of milk from the breast during nursing.

As used herein, a parturifacient refers to any of a variety of compounds or compositions known in the art for pre-inducement, cervical ripening, or inducement. Exemplary parturifacients include, but are not limited to, prostaglandins such as PGE1 (misoprostol) and PGE2 (dinoprostone), oxytocic hormones such as oxytocin and steroids such as RU486 (mifepristone).

As used herein, successful induction is an induction that, for example, results in vaginal delivery, or a shorter time to delivery, or fewer administrations of induction or pre-induction agents compared to in the absence of induction. The likelihood of a successful induction refers to a subject who has been induced and the likelihood that induction will be successful. In this context, a positive test for oncofetal fibronectin is correlated with successful induction, which can be manifested by exhibiting a mean time interval between a first dose of pre-induction agent and delivery that is shorter than the mean time interval between first dose of parturifacient and delivery. A positive test can be measured can be relative to a threshold amount or compared to similar subjects. A negative test for oncofetal fibronectin is correlated with an observation of a mean time interval between first dose of pre-induction agent and delivery that is longer than the mean time interval between first dose of parturifaceient and delivery for subjects testing positive for oncofetal fibronectin or a sample having an amount of oncofetal fibronectin indicating molecule above a threshold.

As used herein, a second indicator of induction outcome refers to measurements or observations of the pregnant subject, a measurement or observation of the fetus(es), and/or a medical history of the pregnant subject. Second indicators include, but are not limited to, for example, cervical length, Bishop score, effacement, parity, cervical dilation, gestational age, body mass index, station, consistency, transvaginal ultrasound, and/or digital examination.

As used herein, the stage and grading of bladder cancer is in accordance with the Union Internationale Centre le Cancer (UICC) staging from 1997. Tis: carcinoma in situ (CIS), Ta: papillary, Stage 1 (T1) occurs when papillary invade lamina propria, stage 2 (T2a) occurs when the papillary invade superficial muscle, stage 3 (T2b) occurs when the papillary invade deep muscle, stage 3 occurs when there is microscopic invasion of perivesical tissue (T3a) or gross invasions of perivesical tissue (T3b), and stage 4 occurs when there is invasion pelvic organs (prostate, uterus, vagina; T4a) or the pelvic wall or abdominal wall (T4b). The N stage (status of lymph nodes) and M stage (metastatic sites) also are described. Transitional cell carcinoma can be divided into grade 1 (well-differentiated), grade 2 (moderately differentiated) and grade 3 (poorly differentiated).

For clarity of disclosure and not by way of limitation, the detailed description is divided into the subsections that follow.

B. DETECTION OF ONCOFETAL FIBRONECTIN

Provided herein are methods of detecting oncofetal fibronectin indicating molecules. Oncofetal fibronectin indicating molecules can serve as a marker for health state such as general health, cancer, pregnancy and delivery. Detection of an oncofetal fibronectin indicating molecule by the methods provided herein can improve the accuracy, speed and/or convenience of oncofetal fibronectin indicating molecule detection. The detection methods herein also can provide further information, such as the amount or level of an oncofetal fibronectin indicating molecule present in the sample, the domains present in the detected oncofetal fibronectin indicating molecule and post-translational modifications of a detected oncofetal fibronectin protein.

In some embodiments, detection methods can be performed by contacting an oncofetal fibronectin indicating molecule with one or more binding partners and detecting complex formation between the oncofetal fibronectin indicating molecule and one or more binding partners. The detection methods can be performed in any of a variety of ways, for example either the sample components or a fibronectin or oncofetal fibronectin binding partner can be immobilized on a solid support; or neither can be immobilized. In another example, detection can be performed in vivo, for example, in an in vivo diagnostic method. In vivo methods also can be used in treatment of a health problem associated with oncofetal fibronectin.

Presence of oncofetal fibronectin can be determined by detecting an oncofetal fibronectin indicating molecule, such as oncofetal fibronectin protein, nucleic acid molecules encoding oncofetal fibronectin or complements thereto, or autoantibodies specific for oncofetal fibronectin protein or nucleic acid molecules encoding onco fetal fibronectin, or a fragment thereof. Any of a variety of protein, nucleic acid molecule and antibody detection methods can be used to detect an oncofetal fibronectin indicating molecule. Exemplary detection methods include RT-PCR for detecting mRNA encoding oncofetal fibronectin or fragments thereof and mass spectrometry for detecting oncofetal fibronectin proteins or fragments thereof. In addition, methods such as immunoassays are provided herein for the detection of autoantibodies to oncofetal fibronectin.

In some embodiments, an oncofetal fibronectin indicating molecule can be detected such that the presence or absence of portions of the oncofetal fibronectin indicating molecule can be identified. As described herein, an oncofetal fibronectin indicating molecule can contain one or more of the domains EDA, EDB and IIICS. The methods provided herein can be used to determine the presence or absence of EDA, EDB and/or mcs in an oncofetal fibronectin indicating molecule. Such an identification can be used, for example, to identify the tissue source of the oncofetal fibronectin indicating molecule.

Detection of an oncofetal fibronectin indicating molecule can be used to determine whether or not an oncofetal fibronectin indicating molecule is present in a sample, or can be used to measure the amount of an oncofetal fibronectin indicating molecule present in a sample. When the amount is measured, the measured amount can be compared to one or more threshold levels. When a single threshold level is used, an measured amount of an oncofetal fibronectin indicating molecule above the threshold can indicate, for example, overall health state, imminent or pre-term delivery, delivery date, or a health problem such as a cancerous condition or arthritis. When two or more threshold levels are used, the amount of oncofetal fibronectin indicating molecule measured can be used to classify the subject that provided the sample according to the highest threshold value less than or equal to the measured oncofetal fibronectin indicating molecule amount, where such classification can indicate, for example, different overall health state, different expected outcomes of pregnancy and delivery, different accuracies of delivery date prediction, or different severities of a health problem such as a cancerous condition or arthritis.

C. STRUCTURE AND PROPERTIES OF FIBRONECTINS

Methods are provided herein that include detection of oncofetal fibronectin proteins, oncofetal fibronectin-encoding nucleic acids or complements thereto, autoantibodies to oncofetal fibronectin and fragments thereof. Hence, knowledge of the structure and properties and identity of oncofetal fibronectin proteins or nucleic acids encoding the proteins can aid in practice of the methods herein. For example, knowledge of proteolytic fragments of the molecule can aid in mass spectrometric detection as can knowledge of glycosylation patterns. Knowledge of the sequences of nucleic acid encoding oncofetal fibronectin molecules and/or domains thereof can aid in methods requiring specific amplification. Knowledge of oncofetal fibronectin domains and molecules that specifically and preferentially bind to oncofetal fibronectin domains can aid in design of apparatuses for detecting oncofetal fibronectin, in methods such as reflectance methods for detecting oncofetal fibronectin and in methods for characterizing oncofetal fibronectin.

Fibronectin (FN) is one of a largest multi-domain proteins (Pankov et al., *Journal of Cell Science,* 115:3861-3863, (2002)). Fibronectin (FN) mediates a variety of cellular interactions with the extracellular matrix (ECM) and is important for cell adhesion, migration, growth and differentiation (Mosher, D. F., "Fibronectin," San Diego: Academic Press, Inc., (1989); Carsons, S. E., "Fibronectin in Health and Disease," Florida: CRC Press, Inc., (1989); Hynes, R. O., "Fibronectins," New York: Springer-Verlag, (1990); Yamada and Clark, "The Molecular and Cellular Biology of Wound Repair," (ed. R. A. F. Clark) pp 51-93, New York: Plenum Press, (1996). FN is expressed by multiple cell types and is important in vertebrate development, as demonstrated by the early embryonic lethality of mice with targeted inactivation of the FN gene (George et al., "Defects in mesoderm, neural tube and vascular development in mouse embryos lacking fibronectin," *Development,* 119:1079-1091, (1993).

1. Structural Characteristics of Fibronectin

A variety of features of the fibronectin structure are known; a summary of such features is available at (Pankov et al., *Journal of Cell Science,* 115:3861-3863, (2002)) and summarized herein. Fibronectin usually exists as a dimer containing two nearly identical approximately 250 kDa subunits linked covalently near their C-termini by a pair of disulfide bonds. Each monomer includes three types of repeating units (termed FN repeats): type I, type II and type III. Fibronectin contains 12 type I repeats, two type II repeats and 15-17 type III repeats, which together account for approximately 90% of the fibronectin sequence. Type I repeats are about 40 amino-acid residues in length and contain two disulfide bonds; type II repeats contain a stretch of approximately 60 amino acids and two intra-chain disulfide bonds; and type III repeats are about 90 residues long without any disulfide bonds.

Fibronectin is encoded by a single gene, the product of which can exist in multiple forms resulting from alternative splicing of a single pre-mRNA that can generate as many as 20 variants in human fibronectin (see, e.g., French-Constant, C., "Alternative splicing of fibronectin—many different proteins but few different functions," *Exp. Cell Res.,* 221:261-271, (1995); Kosmehl et al., "Molecular variants of fibronectin and laminin: structure, physiological occurrence and histopathological aspects," *Virchows Arch,* 429:311-322, (1996)). Splicing occurs within the central set of type III repeats, FN III7 to FNIII15. Exon usage or skipping leads to inclusion or exclusion of two type III repeats—EDB (also termed EIIIB or EDII and located between FN repeats III7 and III8) and EDA (also called EIIIA or EDI and located between FN repeats III11 and III2), or both. This splicing of fibronectin ED domains is found in many vertebrates, including *Xenopus,* chickens, rats and humans.

A third region of alternative splicing is localized to a portion of fibronectin not homologous to FNIII repeats, called the V (variable in length) or IIICS (type III connecting segment) region. The structural variations in this region can include splice variants and are species dependent. In most species, this region can be either partially or completely included or excluded; for example, in human fibronectin, there can be five different V region variants. In chicken, the whole 120 amino acid residues of the V region can be included or a 44 amino acid segment from the 5' end can be excluded (creating V76), but the whole V region of chicken fibronectin is never missing. Splicing in rat leads to exclusion of a 25 amino acid fragment, generating V95 that can be detected, as can be the V0 and V120 forms. Splicing of the V region in human can include combinations of three different regions, the first containing 25 amino acids, the second containing 64 amino acids and the third containing 31 amino acids. Differential splicing in humans leads to at least five variants where segments from the 5' (25aa) and 3' (31 aa) ends can be omitted independently (creating V95 and V89 correspondingly) or together (V64), or can both be present (V120), or all three regions can be absent (V0), producing five different V splice variants.

FNs are glycoproteins that contain 4-9% carbohydrate, depending on the cell source. N-linked and O-linked glycosylation sites are located mainly in type m repeats and the collagen-binding domain.

Some forms of fibronectin are abundant and soluble in plasma (300 µg/ml) and other body fluids and also part of the insoluble extracellular matrix.

2. Binding Properties and Proteolysis of Fibronectin

FN can be a ligand for numerous members of the integrin receptor family (see, e.g., Plow et al., "Ligand binding to integrins," *J. Biol. Chem.,* 275:21785-21788, (2000)). Integrins are structurally and functionally related cell-surface heterodimeric receptors that link the ECM with the intracellular cytoskeleton. A number of different integrins bind to FN, including the FN receptor $\alpha_5\beta_1$. Several integrin-recognition sequences are known. For example, integrin $\alpha_5\beta_1$ is recognized by the RGD sequence located in FN repeat III10. The recognition of this simple tripeptide sequence can be influenced by flanking residues, the tripeptide's three-dimensional presentation and individual features of the integrin-binding pockets. A second site, in FN repeat III9 (the 'synergy site' PHSRN), promotes specific $\alpha_5\beta_1$ integrin binding to FN via interactions with the $\alpha_5$ subunit. The FN receptor $\alpha_5\beta_1$ also can interact with an N-terminal fragment containing repeats I1-9 and II1,2, which also promotes $\alpha_5\beta_1$-integrin-mediated cell adhesion. Interaction with this N-terminal region triggers integrin-mediated intracellular signals that are distinct from those generated in response to ligation with the RGD sequence.

A second set of fibronectin sequences, which are bound by the $\alpha_4\beta_1$ integrin, also are known. Two such cell-recognition sequences (LDV and REDV) are present in the alternatively spliced V region. Both are recognized by $\alpha_4\beta_1$ and $\alpha_4\beta_7$. Additional sites recognized by the $\alpha_4,\beta_1$ integrin—IDAPS and KLDAPT—also are present in repeats III14 and III15, respectively (KLDAPT also binds to the $\alpha_4\beta_7$ integrin). The EDGIHEL sequence of EDA can bind to $\alpha_4,\beta_1$ as well as $\alpha_9\beta_1$ (Liao et al., "The EIIIA segment of fibronectin is a ligand for integrins $\alpha_9\beta_1$ and $\alpha_4,\beta_1$ providing a novel mechanism for regulating cell adhesion by alternative splicing," *J. Biol. Chem.*, 277:14467-14474, (2002)).

Figure 1B:
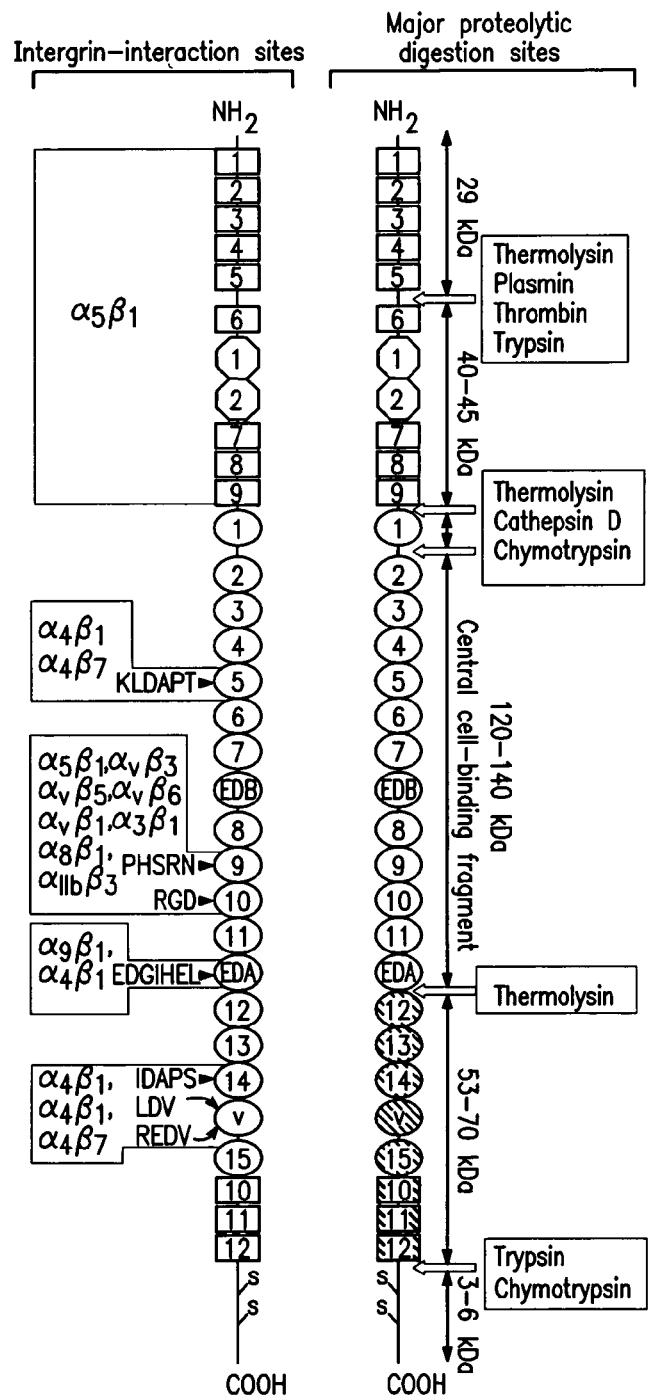

Fibronectins can be cleaved at known locations when subjected to limited proteolytic digestion (reviewed by Mosher, D. F., "Fibronectin,"San Diego: Academic Press, Inc.,(1989); Hynes, R. O., "Fibronectin," New York: Springer-Verlag, (1990)). Even a protease capable of cleaving proteins at many sites (such as pronase) initially cleaves FN at highly specific locations. A simplified scheme of major proteolytic cleavage sites is shown in FIG. 1B. The binding activities of FN can be preserved after such proteolysis and identified within particular fragments.

Fibronectin has a variety of functional activities besides binding to cell surfaces through integrins. It also can bind to biologically important molecules such as heparin, collagen/gelatin and fibrin. These interactions are mediated by several distinct structural and functional domains, which have been defined by proteolytic fragmentation or recombinant DNA analyses (see FIG. 1C and Mosher, D. F., "Fibronectin," San Diego: Academic Press, Inc., (1989); Hynes, R. O., "Fibronectins," New York: Springer-Verlag, (1990); and Yamada and Clark, "The Molecular and Cellular Biology of Wound Repair," (ed. R. A. F. Clark), pp. 51-93, New York: Plenum Press, (1996)).

Fibronectin contains two major heparin-binding domains that interact with heparin sulfate proteoglycans. A strong heparin-binding site is located in the C-terminal part (Heparin II) and a weaker binding domain is situated at the N-terminal end of the protein (Heparin I). The high-affinity heparin II domain also can bind to a widely distributed glycosaminoglycan, chondroitin sulfate; the weaker heparin-binding domain contains a *Staphylococcus aureus*-binding site that mediates FN interactions with bacteria. A glycosaminoglycan-binding site is located within the V region of fibronectin (Mostafavi-Pour et al., 2001) (marked as Heparin at the V domain). In at least some cell types, the heparin-binding domains of fibronectin mediate cell adhesion.

The collagen-binding domain includes repeats I6-9 and II1,2 and these repeats bind more effectively to denatured collagen (gelatin) than to native collagen. This fibronectin domain also can interact with native collagen in vivo.

Fibronectin also contains two major fibrin-binding sites (Fibrin I and Fibrin II). The Fibrin I binding site is in the N-terminal domain and is formed by type I repeats 4 and 5. The interaction of fibronectin with fibrin is involved in cell adhesion or cell migration into fibrin clots. In both instances, cross-linking between fibronectin and fibrin is mediated by factor XIII transglutaminase (the cross-linking site on the fibronectin molecule of FIG. 1C is marked by factor XIIIa and an arrow).

Figure 1C:
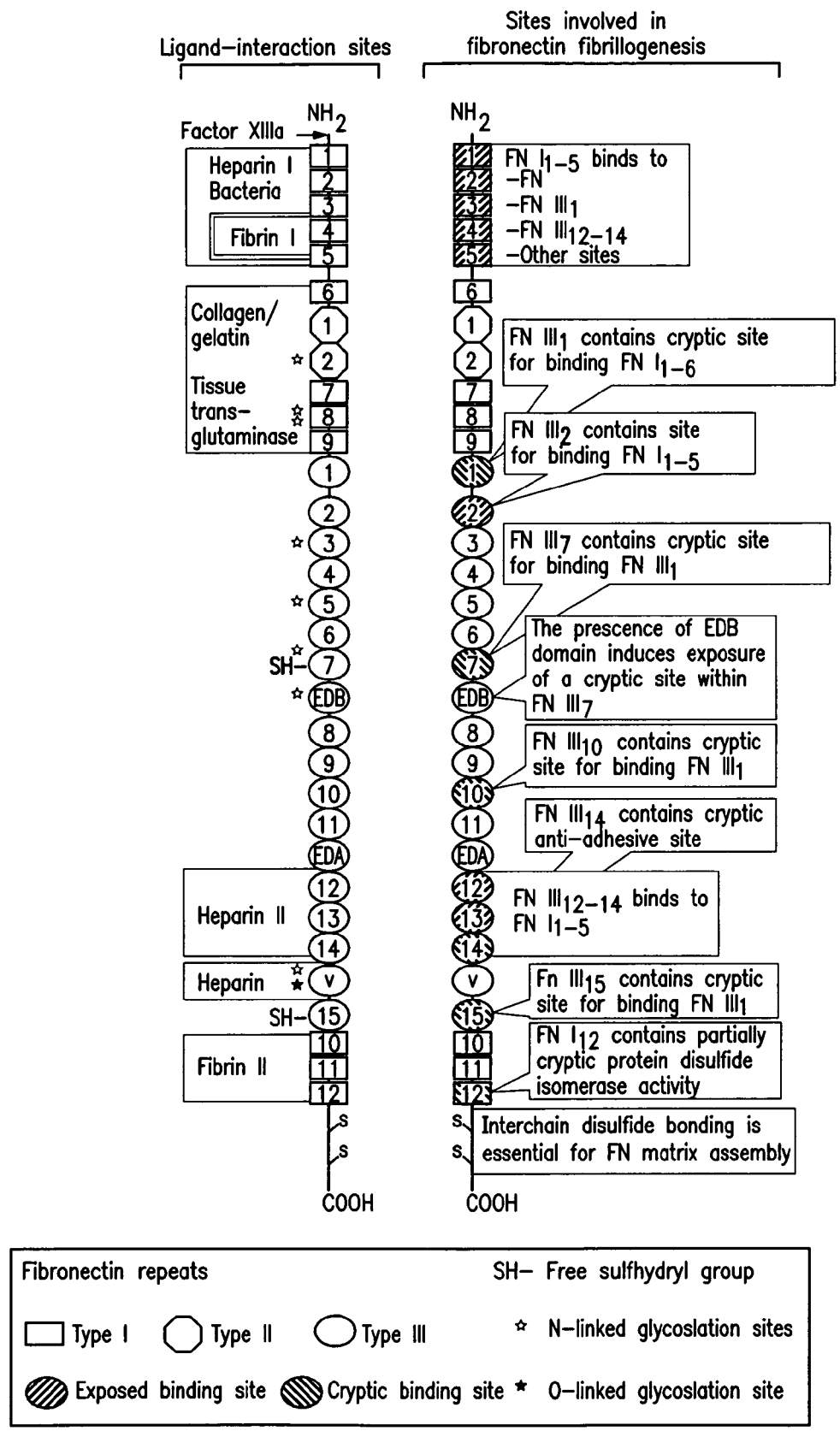

Fibronectin also can self-associate into aggregates and fibrils, at multiple binding sites that have been identified along the molecule (FIG. 1C). Some of these self-interaction sites are exposed and available for binding, while others are cryptic and become accessible only after conformational changes, for example, mechanical stretching of the fibronectin molecule.

3. Oncofetal Fibronectins

Oncofetal fibronectins constitute a heterogeneous group of fibronectin proteins that share certain characteristics. As noted oncofetal fibronectin proteins contain extra-domain A (EDA), extra-domain B (EDB), or fibronectin III connecting segment (IIICS), or any combination thereof. They also are expressed in or shed from certain cells or tissues, and their pattern of expression or shedding or level of expression can vary in tissues. The group of oncofetal fibronectins results from alternative splicing of these three regions (EDA, EDB and IIICS) in fibronectin and also from post-translational modifications. The splicing and expression of oncofetal fibronectin is differently regulated in cells and tissues and at different developmental stages. In fetal tissues and in some abnormal cells and tissues, expression of oncofetal fibronectin is increased relative to the corresponding normal adult cells and tissues. In some normal adult cells, tissues and sample types, oncofetal fibronectin is not present in amounts detectable by antibody assay. Accordingly, for purposes of detection of oncofetal fibronectin, abnormal levels of oncofetal fibronectin can be determined by comparing the detected amount to a control or to a predetermined amount. The amino acid sequence of human fibronectin including EDA, EDB and IIICS and the fibronectin encoding nucleic acid molecule are known in the art and are available in public databases. Exemplary sequences of human oncofetal fibronectins, and EDA, EDB and IIICS regions are set forth in SEQ ID Nos. 4, 6 and 8. Exemplary sequences of human oncofetal fibronectin IIICS regions V120, V95, V89 and V64 are set forth in SEQ ID Nos. 29, 31, 33 and 35, respectively. The protein and encoding nucleic acid molecules from a variety of additional species including, for example, rat, mouse, chicken, cow and *Xenopus laevis* also are known and readily available in public databases. An example of oncofetal fibronectin is a protein that binds specifically to the FDC-6 monoclonal antibody (see, Matsuura and S. Hakomori, Proc. Natl. Acad. Sci. USA, 82:6517-6521 (1985). Production of the hybridoma (deposited at the American Type Culture Collection as accession number ATCC HB 9018) which produces FDC-6 antibody is described in detail in U.S. Pat. No. 4,894,326, issued Jan. 16, 1990, to Matsuura et al. Another example of oncofetal fibronectin is a protein that binds preferentially with the BC-1 monoclonal antibody described by Carnemolla et al., J. Cell. Biol., 108:1139-1148 (1989). Another example of oncofetal fibronectin is a protein that binds preferentially with the IST-9 monoclonal antibody described by Carnemolla et al., FEBS Lett., 215:269-273 (1987).

a. Structural Features of Oncofetal Fibronectin

Oncofetal fibronectin contains extra-domain A (EDA), extra-domain B (EDB), or fibronectin III connecting segment (IIICS), or any combination thereof. The amino acid sequence of human fibronectin including EDA, EDB and IIICS and the fibronectin encoding nucleic acid molecule are known in the art and are available in public databases and the nucleotide and amino acid sequences also are provided herein as SEQ ID NOS: 1 and 2, 14 and 15, 16 and 17, 18 and 19, 20 and 21, 22 and 23, and 24 and 25, respectively. Nucleic acid molecules encoding a variety of oncofetal fibronectins from other species including, but not limited to, rat, mouse, chicken, cow and *Xenopus laevis* also are known and readily available in public databases.

Human fibronectin is encoded by the nucleotide and amino acid sequences of SEQ ID NOS: 1 and 2, respectively. EDA is encoded by nucleotides 4405 to 4674 of SEQ ID NO: 1 (SEQ ID NO: 3) and amino acids 1432 to 1621 of SEQ ID NO: 2 (SEQ ID NO: 4). EDB is encoded by nucleotides 3037 to 3309 of SEQ ID NO: 1 (SEQ ID NO: 5) and amino acid 963 to 1109 of SEQ ID NO: 2 (SEQ ID NO: 6). Full length IIICS is encoded by nucleotides 5488 to 5847 of SEQ ID NO: 1 (SEQ ID NO: 7) and amino acid 1830 to 1949 of SEQ ID NO: 2 (SEQ ID NO: 8).

IIICS can contain various combinations of splice regions resulting in five different splice variants (see Table 1). Amino acid positions 1-25 of IIICS make up splice region A (A). Amino acid positions 26-89 of IIICS make up splice region B (B). Amino acid positions 90-120 of IIICS make up splice region C (C). IIICS, which also is termed the variable or V domain, can be any of at least five different splice variants, including V0 which contains 0 amino acids of IIICS, V64 which contains amino acids 26-89 of IIICS (D; SEQ ID NO: 35), V89 which contains amino acids 1-89 of IIICS (E; SEQ ID NO: 33), V95 which contains amino acids 26-120 of IIICS (F; SEQ ID NO: 31) or V120 which contains amino acids 1-120 of IIICS (G; SEQ ID NO:29), (see, e.g., Pankov et al., *J. Cell Science* 115:3861-3863 (2002)).

Portions of IIICS also can be represented as CS1 which contains amino acids 1-25 of IIICS (H), CS2 which contains amino acids 23-47 of IIICS (II), CS3 which contains amino acids 45-68 (J), CS4 which contains amino acids 66-92 of IIICS (K), CS5 which contains amino acids 90-109 of IIICS (L) and CS6 which contains amino acids 107-120 of IIICS (M) (see Table 1).

IIICS can be glycosylated at one or more sites. One site for glycosylation is threonine 33 of IIICS, which is O-glycosylated (see Table 1, N). The enzyme that glycosylates threonine 33 is N-acetylgalactosaminyltransferase-T2. The genomic, mRNA, and predicted amino acid sequences of N-acetylgalactosaminyltransferase-T2 are provided in SEQ ID NOS: 11, 12 and 13, respectively, and also are available at GenBank Accession Numbers Y10345 (genomic sequence), X92689 (mRNA sequence), or CAA63371 (amino acid sequence predicted from mRNA sequence); see Wandall et al., J. Biol. Chem. 272: 23503-23514 (1997)).

TABLE 1

Splice regions and variable domains of IIICS

| Reference letter | Region of IIICS | Nucleotides (See Seq ID NO: 7) | Amino Acids (See Seq ID NO: 8) |
|---|---|---|---|
| A | Splice region A | 1-75 | 1-25 |
| B | Splice region B | 76-267 | 26-89 |
| C | Splice region C | 268-360 | 90-120 |
| D | V64 | 76-360 | 26-89 |
| E | V89 | 1-267 | 1-89 |
| F | V95 | 76-360 | 26-120 |
| G | V120 | 1-360 | 1-120 |
| H | CS1 | 1-75 | 1-25 |
| I | CS2 | 67-141 | 23-47 |
| J | CS3 | 133-204 | 45-68 |
| K | CS4 | 196-276 | 66-92 |
| L | CS5 | 268-327 | 90-109 |
| M | CS6 | 319-360 | 107-120 |
| N | O-glycosylation | 97-99 | 33 | b. Molecules that Bind to Oncofetal Fibronectin

Oncofetal fibronectin can be specifically bound by one or more anti-oncofetal fibronectin antibodies. A variety of anti-oncofetal fibronectin antibodies are known in the art, including IST-9 (Carnemolla et al., *FEBS Lett.* 215:269-273 (1987)); available at Accurate Chemical & Sci. Corp., Westbury, N.Y.), DH1 (Vartio et al., *J. Cell Sci.* 88:419-430 (1987)), BC-1 (Carnemolla et al., *J. Cell Biol.* 108:1139-1148 (1989)), L19 (U.S. patent application No. 20030176663), ME4C (Giovannoni et al., *Nucleic Acids Res.* 29:e27 (2001)); the ME4C scFv recombinant antibody sequence is available at GenBank accession no. AJ297960), H10 (U.S. patent application No. 20030176663), FDC-6 (U.S. Pat. No. 4,894, 326), 5C10 (Mandel et al., *APMIS,* 100:817-826 (1992)) and X18A4, X20C4 and X8E3 (U.S. Pat. No. 5,523,229, ATCC Nos. HB-1 1587, HB-20 11589 and HB-1 1588, respectively).

IST-9 and DH1 can bind to oncofetal fibronectin when EDA is present. IST-9 and DH1 can bind to at least amino acids Ile-43 and His-44 of EDA. IST-9 and DH1 can bind to the region in EDA containing amino acids 31-44.

BC-1, L19, ME4C, H10, C6 and A134 can bind to oncofetal fibronectin when EDB is present. BC-1 can bind to oncofetal fibronectin when fibronectin repeat III-7 (FNIII-7) and EDB are present. C6 can bind to oncofetal fibronectin when EDB and fibronectin repeat III-8 (FNIII-8) are present. L19 can bind to EDB.

FDC-6 can bind to IIICS. FDC-6 can bind to the hexapeptide VTHPGY of mCs (IIICS amino acids 32-37; SEQ ID NO: 39) when the hexapeptide is O-glycosylated at Thr-33. Typically, the glycosylation of Thr-33 contains an α-N-acetylgalactosamine bonded to the oxygen atom of the threonine side chain. The Thr-33 glycosyl moiety can be NeuAcα2→3Galβ1→3GalNac, or 3Galβ1→3GalNac. 5C10 can bind to a IIICS sequence that overlaps with the FDC-6 hexapeptide. X18A4 can bind to a IIICS sequence different than the hexapeptide bound by FDC-6.

EDB can contain one or more N-linked glycosylation sites. IIICS can contain one or more O-linked glycosylation sites and from 1 to 6 or about 6 N-linked glycosylation sites.

EDA can bind to $\alpha_4\beta_1$ integrin and $\alpha_9\beta_1$ integrin. The amino acid sequence EDGIHEL of EDA (EDA amino acids 40-46) can bind to $\alpha_4\beta_1$ integrin and $\alpha_9\beta_1$ integrin. IIICS can bind to $\alpha_4\beta_1$ integrin, $\alpha_4\beta_7$ integrin and heparin. The V95 splice variant of IIICS can bind to heparin. CS1 and CS5 of IIICS can bind to $\alpha_4\beta_1$ integrin and $\alpha_4\beta_7$ integrin. The IIICS amino acid sequence LDV (IIICS amino acids 20-22) can bind to $\alpha_4\beta_1$ integrin and $\alpha_4\beta_7$ integrin. The IIICS amino acid sequence REDV (IIICS amino acids 100-103) can bind to $\alpha_4\beta_1$ integrin and $\alpha_4\beta_7$ integrin.

c. Proteolysis of Oncofetal Fibronectin

Oncofetal fibronectin can be detected according to a variety of properties of oncofetal fibronectin. One method for identifying oncofetal fibronectin is by characteristic proteolysis patterns, including protein fragments with characteristic masses and/or binding properties. Masses of fragments can be measured by any of a variety of methods known in the art or provided elsewhere herein; an exemplary mass measurement method is mass spectrometry.

One exemplary proteolysis pattern can be generated using trypsin. Trypsin digest of oncofetal fibronectin can yield trypsin fragments that are 235 kDa, 200 kDa, 160 kDa, 120 kDa, 65 kDa and/or 55 kDa. Typically, each of these six trypsin fragments binds to the antibody FDC-6. In one example, trypsin fragments from oncofetal fibronectin can be 200 kDa, 120 kDa or 55 kDa, where each smaller fragment represents a product of further trypsin cleavage of a larger fragment. In another example, trypsin fragments from an oncofetal fibronectin can be 235 kDa, 160 kDa or 65 kDa, where each smaller fragment represents a product of further trypsin cleavage of a larger fragment.

Another exemplary proteolysis pattern can be generated using cathepsin D. Cathepsin D digest of oncofetal fibronectin can yield fragments of 110 kDa and/or 85 kDa. Typically these two cathepsin D fragments can bind to the antibody FDC-6.

Another exemplary proteolysis pattern can be generated using thermolysin. Thermolysin digest of oncofetal fibronectin can yield fragments of 120 kDa, 85 kDa and/or 35 kDa. Typically the 120 kDa and 85 kDa can bind to the antibody BC-1 and the 85 kDa fragment represents a product of further thermolysin cleavage of the 120 kDa fragment.

Another exemplary proteolysis pattern can be generated using Achromobacter protease I. *Achromobacter* protease I digest of oncofetal fibronectin can yield a 14 kDa fragment, where this fragment typically can bind to the antibody FDC-6.

D. USE OF ONCOFETAL FIBRONECTIN AS A BIOLOGICAL MARKER

Detection of an oncofetal fibronectin indicating molecule serves as a biological marker for a variety of current or future health conditions such as general health state, cancer, pregnancy and delivery. Any of the uses of oncofetal fibronectin as a biological marker provided herein can be performed using any of sample types provided herein or known in the art and in conjunction with any of the oncofetal fibronectin indicating molecule detection methods provided herein or known in the art. For example, any of a variety of samples can be measured for the presence of an oncofetal fibronectin indicating molecule, including, but not limited to tissue samples, organ samples, urine, lymph, blood, plasma, serum, saliva, cervical fluid, cervicovaginal fluid, vaginal fluid, breast fluid, breast milk, synovial fluid, semen, seminal fluid, stool, sputum, cerebral spinal fluid, tears, mucus, interstitial fluid, follicular fluid, amniotic fluid, aqueous humor, vitreous humor, peritoneal fluid, ascites, sweat, lymphatic fluid, lung sputum and lavage. Further, any of a variety of methods provided herein or otherwise known in the art for detecting an oncofetal fibronectin indicating molecule in a sample can be used, including, but not limited to, dot blot analysis, western blot analysis, northern blot analysis, southern blot analysis, RT-PCR methods, mass spectrometric methods, sandwich assays such as test strip-based sandwich assays, ELISA methods, fluorescence polarization methods, FRET methods and flow cytometry methods. Selection of any particular any particular method for detecting an oncofetal fibronectin indicating molecule is a matter of design choice, where one skilled in the art can select an appropriate assay or detection (e.g., PCR, mass spectrometry, sandwich assay) based upon the nature (e.g., protein, nucleic acid) of the oncofetal fibronectin indicating molecule to be detected. Similarly, selection of a particular sample type can be a matter of choice to one skilled in the art, and can be based on any of a variety of criteria, for example, based on the relevance of the sample type to the diagnostic purpose, on the ease of sample collection or handling or on the detection method to be used.

A sample or subject can be categorized according to the presence and/or amount of an oncofetal fibronectin indicating molecule measured. Categorization of an oncofetal fibronectin indicating molecule measurement can vary according to a variety of factors known to one skilled in the art, including the tissue or fluid sampled, the sample type, the detection method, the age, gender or biological state (e.g., pregnant or not pregnant) of a subject.

In some cases a measurement is considered positive for oncofetal fibronectin when any oncofetal fibronectin indicating molecule is detected in a sample. In other cases, a measurement is considered positive for oncofetal fibronectin when the presence of an oncofetal fibronectin indicating molecule in a sample is equal to or above one or more threshold levels. In one example, a threshold level of oncofetal fibronectin protein in a buffer-treated cervicovaginal sample assayed using a test strip can be 50 ng/mL. In another example, a threshold level for oncofetal fibronectin protein in a buffer-treated cervicovaginal sample assayed using a test strip can be 150 ng/mL.

In embodiments that compare the amount of an oncofetal fibronectin indicating molecule in a sample to a threshold level, the threshold level can be the amount of oncofetal fibronectin indicating molecule present in an unmodified sample, or the threshold level can be the amount of oncofetal fibronectin indicating molecule present in a modified sample (e.g., the concentration of an oncofetal fibronectin indicating molecule of a cervicovaginal swab sample after mixture with a buffer solution). Reference herein to the level of an oncofetal fibronectin indicating molecule in a sample or the threshold level of an oncofetal fibronectin indicating molecule typically refers to the level of an oncofetal fibronectin indicating molecule in a modified sample. For example, some oncofetal fibronectin indicating molecule measurements, such as measurement of an oncofetal fibronectin indicating molecule in a cervicovaginal swab sample, are known in the art according to the sample-modified form; thus, oncofetal fibronectin indicating molecule levels and threshold levels for a cervicovaginal swab sample typically refer to the sample modified level.

In some embodiments, the measured amount of an oncofetal fibronectin indicating molecule can be compared to one or more thresholds. Typically, an oncofetal fibronectin indicating molecule concentration in the sample equal to or above a threshold level indicates that the sample is oncofetal fibronectin positive. In one embodiment, an oncofetal fibronectin indicating molecule, such as oncofetal fibronectin protein, concentration in a buffer-treated cervicovaginal swab sample of 50 ng/ml or more (or 500 ng/ml untreated swab sample or more), or about 50 ng/ml or more (or about 500 ng/ml untreated swab sample or more) indicates that the sample is oncofetal fibronectin positive. Typically, an oncofetal fibronectin indicating molecule concentration in the sample below a threshold level indicates that the sample is oncofetal fibronectin negative. In one embodiment, an oncofetal fibronectin indicating molecule concentration in a buffer-treated cervicovaginal swab sample of less than 50 ng/ml (or less than 500 ng/ml untreated swab sample), or about 50 ng/ml (or less than about 500 ng/ml untreated swab sample) indicates that the sample is oncofetal fibronectin negative.

Different sample types can have different threshold levels. Provided herein, different sample types also can have related threshold levels. For example, the amount of an oncofetal fibronectin indicating molecule in a cervicovaginal swab sample collected from the portion of the vagina below the posterior fornix, such as the lower third of the vagina, can be one-third or about one-third the amount of an oncofetal fibronectin indicating molecule in a cervicovaginal swab of the posterior fornix collected from the same subject. Accordingly, in methods provided herein in which the level of an oncofetal fibronectin indicating molecule in a sample is compared to a threshold level, the threshold level for a swab of the lower portion of the vagina, such as the lower third of the vagina, can be one-third or about one-third of the threshold level for a swab of the posterior fornix. For example, when the threshold level for a buffer-treated swab of the posterior fornix is 60 ng/ml (or 600 ng/ml for an untreated sample), or about 60 ng/ml (or about 600 ng/ml for an untreated sample), the threshold level of a buffer-treated swab of the lower portion of the vagina such as the lower third of the vagina can be 20 ng/ml (or 200 ng/ml for an untreated sample), or about 20 ng/ml (or about 200 ng/ml for an untreated sample). Similarly, when the threshold level for a buffer-treated swab of the posterior fornix is 300 ng/ml (or 3000 ng/ml for an untreated sample), 200 ng/ml (or 2000 ng/ml for an untreated sample), 150 ng/ml (or 1500 ng/ml for an untreated sample), 100 ng/ml (or 1000 ng/ml for an untreated sample), 50 ng/ml (or 500 ng/ml for an untreated sample), 30 ng/ml (or 300 ng/ml for an untreated sample), 15 ng/ml (or 150 ng/ml for an untreated sample) or 10 ng/ml (or 100 ng/ml for an untreated sample), the threshold level of a buffer-treated swab of the lower portion of the vagina such as the lower third of the vagina can respectively be 100 ng/ml (or 1000 ng/ml for an untreated sample), 60-70 ng/ml (or 600-700 ng/ml for an untreated sample), 50 ng/ml (or 500 ng/ml for an untreated sample), 30-40 ng/ml (or 300-400 ng/ml for an untreated sample), 15-20 ng/ml (or 150-200 ng/ml for an untreated sample), 10 ng/ml (or 100 ng/ml for an untreated sample), 5 ng/ml (or 50 ng/ml for an untreated sample) or 3-4 ng/ml (or 30-40 ng/ml for an untreated sample). Similarly, when the threshold level for a buffer-treated swab of the posterior fornix is about 300 ng/ml (or about 3000 ng/ml for an untreated sample), about 200 ng/ml (or about 2000 ng/ml for an untreated sample), about 150 ng/ml (or about 1500 ng/ml for an untreated sample), about 100 ng/ml (or about 1000 ng/ml for an untreated sample), about 50 ng/ml (or about 500 ng/ml for an untreated sample), about 30 ng/ml (or about 300 ng/ml for an untreated sample), about 15 ng/ml (or about 150 ng/ml for an untreated sample) or about 10 ng/ml (or about 100 ng/ml for an untreated sample), the threshold level of a buffer-treated swab of the lower portion of the vagina such as the lower third of the vagina can respectively be about 100 ng/ml (or about 1000 ng/ml for an untreated sample), about 60-70 ng/ml (or about 600-700 ng/ml for an untreated sample), about 50 ng/ml (or about 500 ng/ml for an untreated sample), about 30-40 ng/ml (or about 300-400 ng/ml for an untreated sample), about 15-20 ng/ml (or about 150-200 ng/ml for an untreated sample), about 10 ng/ml (or about 100 ng/ml for an untreated sample), about 5 ng/ml (or about 50 ng/ml for an untreated sample) or about 3-4 ng/ml (or about 30-40 ng/ml for an untreated sample).

In another example, the amount of an oncofetal fibronectin indicating molecule in a urine sample can be one-tenth or about one-tenth the amount of an oncofetal fibronectin indicating molecule in a cervicovaginal swab of the posterior fornix collected from the same subject. Accordingly, in methods provided herein in which the level of an oncofetal fibronectin indicating molecule in a sample is compared to a threshold level, the threshold level for a urine sample can be one-tenth or about one-tenth of the threshold level for a swab of the posterior fornix. For example, when the threshold level for a buffer-treated swab of the posterior fornix is 60 ng/ml (or 600 ng/ml for an untreated sample) or about 60 ng/ml (or about 600 ng/ml for an untreated sample), the threshold level of a buffer-treated swab of the lower portion of the vagina such as the lower third of the vagina can be 6 ng/ml (or 60 ng/ml for an untreated sample) or about 6 ng/ml (or about 60 ng/ml for an untreated sample). Similarly, when the threshold level for a buffer-treated swab of the posterior fornix is 300 ng/ml (or 3000 ng/ml for an untreated sample), 200 ng/ml (or 2000 ng/ml for an untreated sample), 150 ng/ml (or 1500 ng/ml for an untreated sample), 100 ng/ml (or 1000 ng/ml for an untreated sample), 50 ng/ml (or 500 ng/ml for an untreated sample), 30 ng/ml (or 300 ng/ml for an untreated sample), 15 ng/ml (or 150 ng/ml for an untreated sample) or 10 ng/ml (or 100 ng/ml for an untreated sample), the threshold level of a urine sample can respectively be 30 ng/ml (or 300 ng/ml for an untreated sample), 20 ng/ml (or 200 ng/ml for an untreated sample), 15 ng/ml (or 150 ng/ml for an untreated sample), 10 ng/ml (or 100 ng/ml for an untreated sample), 5 ng/ml (or 50 ng/ml for an untreated sample), 3 ng/ml (or 30 ng/ml for an untreated sample), 1.5 ng/ml (or 15 ng/ml for an untreated sample) or 1 ng/ml (or 10 ng/ml for an untreated sample). Similarly, when the threshold level for a buffer-treated swab of the posterior fornix is about 300 ng/ml (or about 3000 ng/ml for an untreated sample), about 200 ng/ml (or about 2000 ng/ml for an untreated sample), about 150 ng/ml (or about 1500 ng/ml for an untreated sample), about 100 ng/ml (or about 1000 ng/ml for an untreated sample), about 50 ng/ml (or about 500 ng/ml for an untreated sample), about 30 ng/ml (or about 300 ng/ml for an untreated sample), about 15 ng/ml (or about 150 ng/ml for an untreated sample) or about 10 ng/ml (or about 100 ng/ml for an untreated sample), the threshold level of a urine sample can respectively be about 30 ng/ml (or about 300 ng/ml for an untreated sample), about 20 ng/ml (or about 200 ng/ml for an untreated sample), about 15 ng/ml (or about 150 ng/ml for an untreated sample), about 10 ng/ml (or about 100 ng/ml for an untreated sample), about 5 ng/ml (or about 50 ng/ml for an untreated sample), about 3 ng/ml (or about 30 ng/ml for an untreated sample), about 1.5 ng/ml (or about 15 ng/ml for an untreated sample) or about 1 ng/ml (or about 10 ng/ml for an untreated sample).

In another embodiment, a threshold oncofetal fibronectin indicating molecule, such as oncofetal fibronectin protein, concentration in a buffer-treated cervicovaginal swab sample is 150 ng/ml (or 1500 ng/ml untreated swab sample) or about 150 ng/ml (or about 1500 ng/ml untreated swab sample), where a measured amount in a subject's sample at or above the 150 ng/ml threshold indicates that the sample is oncofetal fibronectin positive and a measured amount in a subject's sample below the 150 ng/ml threshold indicates that the sample is oncofetal fibronectin negative.

Exemplary threshold values for buffer-treated samples that can indicate different likelihoods of imminent or pre-term delivery include 50 ng/ml, 150 ng/ml, 200 ng/ml, 300 ng/ml, 500 ng/ml, 750 ng/ml and 1000 ng/ml, or about 50 ng/ml, about 150 ng/ml, about 200 ng/ml, about 300 ng/ml, about 500 ng/ml, about 750 ng/ml and about 1000 ng/ml. Exemplary threshold values for untreated samples that can indicate different likelihoods of imminent or pre-term delivery include 500 ng/ml, 1500 ng/ml, 2000 ng/ml, 3000 ng/ml, 5000 ng/ml, 7500 ng/ml and 10000 ng/ml, or about 500 ng/ml, about 1500 ng/ml, about 2000 ng/ml, about 3000 ng/ml, about 5000 ng/ml, about 7500 ng/ml and about 10000 ng/ml.

In other cases, multi-tiered thresholds can be applied to the oncofetal fibronectin indicating molecule measurement, where multi-tiered thresholds include two or more threshold levels, where each larger threshold level indicates a separate health state categorization; for example each larger threshold level can indicate a more severe health problem, an increased likelihood of imminent delivery, increased certainty of delivery date, or increased aggressiveness of a tumor. An exemplary multi-tiered threshold is a two-tiered threshold for oncofetal fibronectin protein, where the lower threshold is 50 ng/mL and the higher threshold is 150 ng/mL for buffer-treated samples. Another exemplary multi-tiered threshold contains two threshold levels where the lower threshold level is 500 ng/mL and the higher threshold level is 1500 ng/mL for untreated samples. Another exemplary multi-tiered threshold contains two threshold levels where the lower threshold level is 50 ng/mL and the higher threshold level is 200 ng/mL for buffer-treated samples. An exemplary multitiered threshold contains two threshold levels where the lower threshold level is 500 ng/mL and the higher threshold level is 2000 ng/mL for untreated samples. Another exemplary multi-tiered threshold contains two threshold levels where the lower threshold level is 50 ng/mL and the higher threshold level is 300 ng/mL for buffer-treated samples. An exemplary multi-tiered threshold contains two threshold levels where the lower threshold level is 500 ng/mL and the higher threshold level is 3000 ng/mL for untreated samples.

In some embodiments, the threshold level can vary over time, for example, as a function of the gestation period of pregnancy, the progression of disease, or the age of the subject. The varying threshold level can be expressed as a threshold curve where the threshold level of an oncofetal fibronectin indicating molecule varies as a function of time (e.g., week of pregnancy term). In some cases, a threshold level can decrease with increasing time, such as, for example, in weeks 12 to 20 of a pregnancy. In other cases, a threshold level can increase with increasing time, such as for example, over the progression of a cancerous condition. Thus, in one example, a measured amount of an oncofetal fibronectin indicating molecule can be classified as greater than a threshold level or less than a threshold level, depending on the point along a defined time period that the sample was collected. Similarly two or more threshold levels can vary over time, resulting in two or more threshold curves that each separate different health categories. The two or more threshold levels can increase with increasing time or can decrease with increasing time. Thus, in one example, a measured amount of an oncofetal fibronectin indicating molecule can be differently categorized depending on the point along a defined time period that the sample was collected.

Thus, provided herein are methods for categorizing the health state of a subject, by measuring the amount of an oncofetal fibronectin indicating molecule in a sample and comparing the amount to two or more threshold levels or curves, where a measured amount below the lowest threshold indicates a more favorable health state and a measured amount higher than respectively higher threshold levels indicates increasingly less favorable health state, or increasingly unfavorable health problems.

In some embodiments, one or more threshold levels or one or more threshold curves applied to a measured amount in a subject's sample can be determined according to any of a variety of subject-specific factors. In one example, a subject-specific factor can be the measured amount of one or more samples from a subject. In some instances, a single sample measurement can be used to define one or more subject-specific threshold levels or one or more subject-specific threshold curves. A single sample measurement can be used, for example, to modify one or more pre-defined threshold levels or one or more threshold curves. For example, a measured sample amount can be compared to the mean or median normal amount and the ratio of the sample amount:normal amount can be applied to one or more pre-defined threshold levels or one or more threshold curves to either increase or decrease the levels or curves (e.g., a sample amount that is twice the normal amount can be applied to double one or more standard threshold levels or curves).

In some instances, the rate of change of the amount of an oncofetal fibronectin indicating molecule in a particular sample type (e.g., cervicovaginal swab) from a subject can be used to identify a sample as oncofetal fibronectin positive or negative, or to categorize the sample into two or more populations. The rate of change of the amount of an oncofetal fibronectin indicating molecule in a type of sample can indicate a stable, increasing or decreasing amount of oncofetal fibronectin indicating molecule in a sample. In some cases, when the rate of change is equal to or greater than one or more threshold rates, the rate of change can be categorized according to the highest threshold rate less than or equal to the rate of change measured in the samples. Exemplary rates of change include an increase of 10% or more per week, an increase of 20% or more per week, an increase of 30% or more per week, an increase of 40% or more per week, an increase of 50% or more per week, an increase of 60% or more per week, an increase of 70% or more per week, an increase of 80% or more per week, an increase of 90% or more per week, or an increase of 100% or more per week. In other cases, the measured rate of change can be compared to one or more threshold curves or one or more threshold rates of change and a measured rate of change can be categorized according to the highest slope of a threshold curve or the highest rate equal to or less than the measured rate of change over the same time period.

Additional factors also can be applied to increase or decrease one or more pre-defined threshold levels, one or more threshold curves, or one or more threshold rates of change. Such additional factors can include other health state markers, for example, overall health markers, cancer markers, pregnancy or delivery markers, or genetic markers, as are exemplified herein or otherwise known in the art.

Also provided herein, methods for indicating health state of a subject can include measurement of an oncofetal fibronectin indicating molecule in a sample and also can include consideration of one or more other health markers. Health markers can include any of a variety of known markers, including markers related to overall health, pregnancy or delivery markers, or cancer or tumor markers. Any of a variety of markers related to overall health are known in the art or are provided elsewhere herein, exemplary markers include, but are not limited to, blood pressure, pulse, body weight, health history, family history or sample tests. A variety of detectable tumor markers are known in the art or are provided elsewhere herein, exemplary markers include, but are not limited to, AE1/AE3, BCA-225, Cathepsin D, E-Cadherin, Epidermal Growth Factor Receptor (EGFR), Estrogen receptor (ER), Gross Cystic Disease Fluid Protein 15 (GCDFP-15), HOX-B3, Ki-67, p65, Progesterone Receptor (PR), Retinoblastoma (Rb) and Transglutaminase K (TGK), p21, DCC, NF-1, NF-2, BRCA-3, p16, FHIT, WT-1, MEN-I, MEN-IIa, MEN-IIb, VHL, FCC, MCC, raf, erb, src, fms, jun, trk, ret, gsp, hst, bcr/abl, p53, c-erbB2, c-myc, MUC1, BRCA1, BRCA2, Her-2/neu, bcl-2, bax, PSA, CYFRA 21-1, PTH-RP, CA125, CEA gene family members, pro-gastrin, gastrin G17, gastrin G34, CA 19-9, CA 15-3, CA 27-29, CA 72-4, APC, SCC, HPV subtypes, TK, alphaFP, p62, Kallikrein, ras, vasopressin, gastrin releasing peptide, annexin I, annexin II, Hu and KOC. A variety of markers associated with pregnancy or delivery are known in the art or are provided elsewhere herein, exemplary markers include, but are not limited to, multiple fetus gestations, incompetent cervix, uterine anomalies, polyhydramnios, previous pre-term rupture of membranes or pre-term labor, pre-eclampsia, first trimester vaginal bleeding, little or no antenatal care, cervical length, Bishop score, effacement, parity (i.e., previous vaginal delivery by the subject), cervical dilation, gestational age, body mass index (BMI), station, consistency, transvaginal ultrasound, digital examination, maternal obesity, fetus size, maternal age, previous post date delivery, gender of fetus, particular genetic disorders, fetal anomalies, abnormal placental formation, maternal infectious disease, endocrine disorder, cardiovascular renal hypertension, autoimmune and other immunologic disease, malnutrition and symptoms such as abdominal pain, low backache, passage of cervical mucus and contractions. Methods of indicating health state of a subject that include measurement of an oncofetal fibronectin indicating molecule in a sample and also consideration of one or more other health markers are known in the art, including decision support systems. In one example, a decision support system, such as a neural network can analyze patient data or information, typically patient history or clinical data, to guide further testing or treatment of a subject. (see, U.S. Pat. Nos. 6,678,669 and 6,267,722).

1. Pregnancy Indications

The present methods and probes can be used to determine whether a pregnant woman is at risk of pre-term, impending and/or imminent delivery, to predict delivery date, to predict maintenance of pregnancy, for use in methods of preventing pre-term delivery, or for use in inducing delivery.

Oncofetal fibronectin (onfFN) can contain a fetal restricted antigen and can be found in placenta, amniotic fluid and fetal connective tissue. The presence of an oncofetal fibronectin indicating molecule, for example, in cervicovaginal fluid samples in subjects after week 12 of pregnancy, is associated with a risk of impending delivery, including spontaneous abortions (12-20 weeks), pre-term delivery (20-37 weeks), term (37-42 weeks) and post-date delivery (after 42 weeks), in pregnant women. In addition, the presence of an oncofetal fibronectin indicating molecule, for example, in a cervicovaginal sample, provides a method for determining increased risk of labor and fetal membrane rupture after week 20 of pregnancy. Indication of rupture of the amniotic membrane is important in distinguishing true and false labor and when the rupture is small and the volume of amniotic liquid escaping is small, the rupture is often undetermined. The methods and systems herein provide a manner to reliably assess the risk of pregnancy and delivery-related conditions.

Any of a variety of samples can be used for pregnancy-related indications, where exemplary samples include blood, plasma, serum, interstitial fluid, urine, cervicovaginal lavage, cervicovaginal swab, swab of the lower portion of the vagina, swab of the lower third of the vagina, swab of the labia, passive cervicovaginal fluid collection, or other collection of cervical fluid and/or vaginal fluid. For example, the sample can be a cervicovaginal swab. For pregnancy-related indications, any of a variety of methods provided herein or otherwise known in the art for detecting an oncofetal fibronectin indicating molecule in a sample can be used, including, but not limited to, dot blot analysis, western blot analysis, northern blot analysis, southern blot analysis, RT-PCR methods, mass spectrometric methods, sandwich assays such as test strip-based sandwich assays and ELISA methods. For example, a test strip containing mobilizable mouse anti-oncofetal fibronectin antibody conjugated to a blue latex particle and polyclonal anti-human fibronectin antibody immobilized to the test strip, can be used to detect oncofetal fibronectin protein in conjunction with pregnancy-related indications.

Low or undetectable amounts of an oncofetal fibronectin indicating molecule indicate decreased risk of pre-term, impending and/or imminent delivery, decrease the ability to predict delivery date, predict increased likelihood of maintaining pregnancy, indicate decreased benefit from using methods of preventing pre-term delivery, or indicate decreased likelihood of success in inducing delivery. The methods provided herein can be sensitive and specific and have a high negative predictive value. For example, a large percentage of subjects who do not deliver early, who have a less certain predicted delivery date, who maintain pregnancy, who do not require methods of preventing pre-term delivery, or with less successful induction outcomes, have low oncofetal fibronectin indicating molecule values. As such, the test is an effective screening procedure for pregnant women.

In one embodiment, an elevated amount of an oncofetal fibronectin indicating molecule detected in the sample from a pregnant woman indicates that the woman has an increased risk of pre-term, impending and/or imminent delivery, increased accuracy in predicted delivery date, decreased likelihood of maintaining pregnancy, increased benefit from using methods of preventing pre-term delivery, or increased likelihood of success in inducing delivery, relative to women with a lower level. For example, an amount of an oncofetal fibronectin indicating molecule detected in the sample from a pregnant woman at or near a full 39-week term who will soon deliver is elevated over the level for pregnant women at or near a full 39-week term who will not soon deliver. In another example an amount of an oncofetal fibronectin indicating molecule detected in the sample from a pregnant woman beyond full term who will soon deliver is elevated over the level for pregnant women beyond a full term who will not soon deliver. In another example, an amount of an oncofetal fibronectin indicating molecule detected in the sample from a pregnant woman with an increased risk of pre-term delivery is elevated over the level for pregnant women at the same stage of gestation with a decreased risk of pre-term delivery. In another example, an amount of an oncofetal fibronectin indicating molecule in the sample from a pregnant woman whose delivery date can be more accurately predicted is elevated over the level for pregnant women whose delivery date is less accurately predicted. In another example, an amount of an oncofetal fibronectin indicating molecule in the sample from a pregnant woman with an increased likelihood of maintaining her pregnancy is lower than the level for pregnant women with a decreased likelihood of maintaining their pregnancy. In another example, an amount of an oncofetal fibronectin indicating molecule in the sample from a pregnant woman with a decreased benefit from methods of preventing pre-term delivery is lower than the level for pregnant women with an increased benefit from methods of preventing pre-term delivery. In another example, the amount of an oncofetal fibronectin indicating molecule in the sample from a pregnant woman with an increased likelihood of successful induction is elevated over the level for pregnant women with a decreased likelihood of successful induction.

In some embodiments, the measured amount of an oncofetal fibronectin indicating molecule can be compared to one or more thresholds. Typically, an oncofetal fibronectin indicating molecule concentration in the sample equal to or above a threshold level indicates that the sample is oncofetal fibronectin positive. In one embodiment, an oncofetal fibronectin indicating molecule, such as oncofetal fibronectin protein, concentration in a buffer-treated cervicovaginal swab sample of 50 ng/ml or more (or 500 ng/ml untreated swab sample or more) or about 50 ng/ml or more (or about 500 ng/ml untreated swab sample or more) indicates a pregnant woman has an increased risk of pre-term, impending and/or imminent delivery, has an increased accuracy of delivery date, has an increased likelihood of maintaining her pregnancy, has a decreased benefit from methods of preventing pre-term delivery, or has an increased likelihood of success in inducing delivery.

In another embodiment, a lower amount of an oncofetal fibronectin indicating molecule detected in the sample from a pregnant woman indicates that the woman has a decreased risk of pre-term, impending and/or imminent delivery, decreased accuracy in predicted delivery date, increased likelihood of maintaining pregnancy, decreased benefit from using methods of preventing pre-term delivery, or decreased likelihood of success in inducing delivery, relative to women with an elevated level. For example, an amount of an oncofetal fibronectin indicating molecule detected in the sample from a pregnant woman at or near a full 39-week term who will not soon deliver is lower than the level for pregnant women at or near a full 39-week term who will soon deliver. In another example an amount of an oncofetal fibronectin indicating molecule detected in the sample from a pregnant woman beyond full term who will not soon deliver is lower than the level for pregnant women beyond a full term who will soon deliver. In another example, an amount of an oncofetal fibronectin indicating molecule detected in the sample from a pregnant woman with a decreased risk of pre-term delivery is lower than the level for pregnant women at the same stage of gestation with an increased risk of pre-term delivery. In another example, an amount of an oncofetal fibronectin indicating molecule in the sample from a pregnant woman whose delivery date can be less accurately predicted is lower than the level for pregnant women whose delivery date is more accurately predicted. In another example, an amount of an oncofetal fibronectin indicating molecule in the sample from a pregnant woman with a decreased likelihood of maintaining her pregnancy is elevated over the level for pregnant women with an increased likelihood of maintaining their pregnancy. In another example, an amount of an oncofetal fibronectin indicating molecule in the sample from a pregnant woman with an increased benefit from methods of preventing pre-term delivery is elevated over the level for pregnant women with a decreased benefit from methods of preventing pre-term delivery. In another example, the amount of an oncofetal fibronectin indicating molecule in the sample from a pregnant woman with a decreased likelihood of successful induction is lower than the level for pregnant women with an increased likelihood of successful induction.

Typically, an oncofetal fibronectin indicating molecule concentration in the sample below a threshold level indicates that the sample is oncofetal fibronectin negative. In one embodiment, an oncofetal fibronectin indicating molecule, such as oncofetal fibronectin protein, concentration in a buffer-treated cervicovaginal swab sample of less than 50 ng/ml (or less than 500 ng/ml untreated swab sample) or about 50 ng/ml (or less than about 500 ng/ml untreated swab sample) indicates a pregnant woman has a decreased risk of pre-term, impending and/or imminent delivery, has a decreased accuracy of delivery date, has a decreased likelihood of maintaining her pregnancy, has an increased benefit from methods of preventing pre-term delivery, or has a decreased likelihood of success in inducing delivery.

In another embodiment, multi-tiered thresholds can be applied to the oncofetal fibronectin indicating molecule measurement, where multi-tiered thresholds can include two or more thresholds, where each larger threshold indicates a further increased risk of pre-term, impending and/or imminent delivery, increased accuracy in predicted delivery date, decreased likelihood of maintaining pregnancy, increased benefit from using methods of preventing pre-term delivery, or increased likelihood of success in inducing delivery, relative to each lower threshold. An exemplary multi-tiered threshold contains two threshold levels where the lower threshold level is 50 ng/mL and the higher threshold level is 150 ng/mL for buffer-treated samples. An exemplary multi-tiered threshold contains two threshold levels where the lower threshold level is 500 ng/mL and the higher threshold level is 1500 ng/mL for untreated samples. Another exemplary multi-tiered threshold contains two threshold levels where the lower threshold level is 50 ng/mL and the higher threshold level is 200 ng/mL for buffer-treated samples. An exemplary multi-tiered threshold contains two threshold levels where the lower threshold level is 500 ng/mL and the higher threshold level is 2000 ng/mL for untreated samples. Another exemplary multi-tiered threshold contains two threshold levels where the lower threshold level is 50 ng/mL and the higher threshold level is 300 ng/mL for buffer-treated samples. An exemplary multi-tiered threshold contains two threshold levels where the lower threshold level is 500 ng/mL and the higher threshold level is 3000 ng/mL for untreated samples.

In accordance with the methods that include multi-tiered thresholds, methods are provided herein for classifying a sample, by measuring the amount of an oncofetal fibronectin indicating molecule in a sample and comparing the sample to two or more thresholds, where classification in each larger threshold indicates a further increased risk of pre-term, impending and/or imminent delivery, increased accuracy in predicted delivery date, decreased likelihood of maintaining pregnancy, increased benefit from using methods of preventing pre-term delivery, or increased likelihood of success in inducing delivery, relative to each lower threshold.

Also provided herein, methods for pregnancy and delivery-related indications can include measurement of an oncofetal fibronectin indicating molecule in a sample and also can include consideration of one or more other pregnancy or delivery markers. A variety of markers associated with pregnancy or delivery are known in the art or are provided elsewhere herein, exemplary markers include, but are not limited to, multiple fetus gestations, incompetent cervix, uterine anomalies, polyhydramnios, previous pre-term rupture of membranes or pre-term labor, pre-eclampsia, first trimester vaginal bleeding, little or no antenatal care, cervical length, Bishop score, effacement, parity (i.e., previous vaginal delivery by the subject), cervical dilation, gestational age, body mass index (BMI), station, consistency, transvaginal ultrasound, digital examination, maternal obesity, fetus size, maternal age, previous post-date delivery, gender of fetus, particular genetic disorders, fetal anomalies, abnormal placental formation, maternal infectious disease, endocrine disorder, cardiovascular renal hypertension, autoimmune and other immunologic disease, malnutrition and symptoms such as abdominal pain, low backache, passage of cervical mucus and contractions. Thus, provided herein are methods of determining risk of pre-term, impending and/or imminent delivery, accuracy in predicted delivery date, likelihood of maintaining pregnancy, benefit from using methods of preventing pre-term delivery, or likelihood of success in inducing delivery, where the methods include detecting an oncofetal fibronectin indicating molecule in a sample and determining one or more additional pregnancy or delivery-related markers, where presence or higher amount of an oncofetal fibronectin indicating molecule and one or more pregnancy or delivery-related markers can indicate, relative to absence or lower amount of an oncofetal fibronectin indicating molecule and/or a positive result for one or more additional pregnancy or delivery-related markers, increased risk of pre-term, impending and/or imminent delivery, increased accuracy in predicted delivery date, decreased likelihood of maintaining pregnancy, increased benefit from using methods of preventing pre-term delivery, or increased likelihood of success in inducing delivery. Also provided herein are methods of determining risk of pre-term, impending and/or imminent delivery, accuracy in predicted delivery date, likelihood of maintaining pregnancy, benefit from using methods of preventing pre-term delivery, or likelihood of success in inducing delivery, where the methods include detecting an oncofetal fibronectin indicating molecule in a sample and determining one or more additional pregnancy or delivery-related markers, where absence or lower amount of an oncofetal fibronectin indicating molecule and one or more pregnancy or delivery-related markers can indicate, relative to presence or higher amount of an oncofetal fibronectin indicating molecule and/or a positive result for one or more additional pregnancy or delivery-related markers, decreased risk of pre-term, impending and/or imminent delivery, decreased accuracy in predicted delivery date, increased likelihood of maintaining pregnancy, decreased benefit from using methods of preventing pre-term delivery, or decreased likelihood of success in inducing delivery.

Methods of indicating health state of a subject that include measurement of an oncofetal fibronectin indicating molecule in a sample and also consideration of one or more other pregnancy or delivery-related markers are known in the art, including decision support systems. In one example, a decision support system, such as a neural network can analyze patient data or information, typically patient history or clinical data, to guide further testing or treatment of a subject. (see, U.S. Pat. Nos. 6,678,669 and 6,267,722).

The methods can be performed for all pregnant women following 12 weeks or about 12 weeks gestation until delivery. The present methods can be used for any pregnant woman after about 12 weeks, after about 13 weeks, after about 14 weeks, after about 15 weeks, after about 16 weeks, after about 17 weeks, after about 18 weeks, after about 19 weeks, after about 20 weeks, after about 21 weeks, after about 22 weeks, after about 23 weeks, after about 24 weeks, after about 25 weeks, after about 26 weeks, after about 27 weeks, after about 28 weeks, after about 29 weeks, after about 30 weeks, after about 31 weeks, after about 32 weeks, after about 33 weeks, after about 34 weeks, after about 35 weeks, after about 36 weeks, after about 37 weeks, after about 38 weeks, after about 39 weeks, after about 40 weeks, after about 41 weeks, after about 42 weeks, after about 43 weeks, after about 44 weeks, or after about 45 weeks.

For example, the present methods can be used for any pregnant woman after about day 80, after about day 81, after about day 82, after about day 83, after about day 84, after about day 85, after about day 86, after about day 87, after about day 88, after about day 89, after about day 90, after about day 91, after about day 92, after about day 93, after about day 94, after about day 95, after about day 96, after about day 97, after about day 98, after about day 99, after about day 100, after about day 101, after about day 102, after about day 103, after about day 104, after about day 105, after about day 106, after about day 107, after about day 108, after about day 109, after about day 110, after about day 111, after about day 112, after about day 113, after about day 114, after about day 115, after about day 116, after about day 117, after about day 118, after about day 119, after about day 120, after about day 121, after about day 122, after about day 123, after about day 124, after about day 125, after about day 126, after about day 127, after about day 128, after about day 129, after about day 130, after about day 131, after about day 132, after about day 133, after about day 134, after about day 135, after about day 136, after about day 137, after about day 138, after about day 139, after about day 140, after about day 141, after about day 142, after about day 143, after about day 144, after about day 145, after about day 146, after about day 147, after about day 148, after about day 149, after about day 150, after about day 151, after about day 152, after about day 153, after about day 154, after about day 155, after about day 156, after about day 157, after about day 158, after about day 159, after about day 160, after about day 161, after about day 162, after about day 163, after about day 164, after about day 165, after about day 166, after about day 167, after about day 168, after about day 169, after about day 170, after about day 171, after about day 172, after about day 173, after about day 174, after about day 175, after about day 176, after about day 177, after about day 178, after about day 179, after about day 180, after about day 181, after about day 182, after about day 183, after about day 184, after about day 185, after about day 186, after about day 187, after about day 188, after about day 189, after about day 190, after about day 191, after about day 192, after about day 193, after about day 194, after about day 195, after about day 196, after about day 197, after about day 198, after about day 199, after about day 200, after about day 201, after about day 202, after about day 203, after about day 204, after about day 205, after about day 206, after about day 207, after about day 208, after about day 209, after about day 210, after about day 211, after about day 212, after about day 213, after about day 214, after about day 215, after about day 216, after about day 217, after about day 218, after about day 219, after about day 220, after about day 221, after about day 222, after about day 223, after about day 224, after about day 225, after about day 226, after about day 227, after about day 228, after about day 229, after about day 230, after about day 231, after about day 232, after about day 233, after about day 234, after about day 235, after about day 236, after about day 237, after about day 238, after about day 239, after about day 240, after about day 241, after about day 242, after about day 243, after about day 244, after about day 245, after about day 246, after about day 247, after about day 248, after about day 249, after about day 250, after about day 251, after about day 252, after about day 253, after about day 254, after about day 255, after about day 256, after about day 257, after about day 258, after about day 259, after about day 260, after about day 261, after about day 262, after about day 263, after about day 264, after about day 265, after about day 266, after about day 267, after about day 268, after about day 269, after about day 270, after about day 271, after about day 272, after about day 273, after about day 274, after about day 275, after about day 276, after about day 277, after about day 278, after about day 279, after about day 280, after about day 182, after about day 282, after about day 283, after about day 284, after about day 285, after about day 286, after about day 287, after about day 288, after about day 289, after about day 290, after about day 291, after about day 292, after about day 293, after about day 294, after about day 295, after about day 296, after about day 297, after about day 298, after about day 299, after about day 300, after about day 301, after about day 302, after about day 303, after about day 304, after about day 305, after about day 306, after about day 307, after about day 308, after about day 309, after about day 310, after about day 311, after about day 312, after about day 313, after about day 314, or after about day 315 of pregnancy.

a. Likelihood of Pre-term Delivery

The methods provided herein can be used to determine the likelihood of pre-term delivery for a pregnant subject. For example, a large percentage of subjects who do not deliver pre-term have low oncofetal fibronectin indicating molecule values. Thus, the methods provided herein can be sensitive and specific and have a high negative predictive value. The methods provided herein can indicate an increased or decreased likelihood of imminent or pre-term delivery, according to the amount of an oncofetal fibronectin indicating molecule measured in a sample. For example, a subject with a decreased likelihood of imminent or pre-term delivery can have measured amounts of an oncofetal fibronectin indicating molecule lower than levels in women with an increased likelihood of imminent or pre-term delivery and a subject with an increased likelihood of imminent or pre-term delivery can have measured amounts of an oncofetal fibronectin indicating molecule higher than levels in women with a decreased likelihood of imminent or pre-term delivery. A measured amount of an oncofetal fibronectin indicating molecule also can be compared to one or more thresholds, where the likelihood of imminent or pre-term delivery increases for each increasing threshold level. A measured amount of an oncofetal fibronectin indicating molecule also can be considered along with one or more other pregnancy or delivery-related markers in determining the likelihood of imminent or pre-term delivery.

Elevated levels of an oncofetal fibronectin indicating molecule can indicate increased risk of pre-term delivery. In one embodiment, an amount of an oncofetal fibronectin indicating molecule detected in the sample from a pregnant woman who will soon deliver is elevated over the level for pregnant women who will not soon deliver. For example, an amount of an oncofetal fibronectin indicating molecule detected in the sample from a pregnant woman at increased risk of pre-term delivery is elevated over the level for pregnant women at the same stage of gestation with a decreased risk of pre-term delivery.

Typically, an oncofetal fibronectin indicating molecule concentration in the sample above or equal to a threshold indicates an increased likelihood of imminent or pre-term delivery relative to an oncofetal fibronectin indicating molecule concentration in the sample below the threshold. For example, an oncofetal fibronectin indicating molecule, such as oncofetal fibronectin protein, concentration in a buffer-treated cervicovaginal swab sample of 50 ng/ml or more (or 500 ng/ml untreated swab sample or more) or about 50 ng/ml or more (or about 500 ng/ml untreated swab sample or more) indicates an increased likelihood of imminent or pre-term delivery relative to an oncofetal fibronectin indicating molecule concentration in a sample below 50 ng/ml or about 50 ng/ml.

In another embodiment, an amount of an oncofetal fibronectin indicating molecule detected in the sample from a pregnant woman who will not soon deliver is below the level for pregnant women who will soon deliver. For example, an amount of an oncofetal fibronectin indicating molecule detected in the sample from a pregnant woman with a decreased risk of pre-term delivery is below the level for pregnant women at the same stage of gestation with an increased risk of pre-term delivery.

Typically, an oncofetal fibronectin indicating molecule concentration in the sample below a threshold value indicates a decreased likelihood of imminent or pre-term delivery relative to an oncofetal fibronectin indicating molecule concentration in the sample at or above the threshold. For example, an oncofetal fibronectin indicating molecule, such as oncofetal fibronectin protein, concentration in a buffer-treated cervicovaginal swab sample less than 50 ng/ml (or 500 ng/ml untreated swab sample) or about 50 ng/ml (or about 500 ng/ml untreated swab sample) indicates a decreased likelihood of imminent or pre-term delivery relative to an oncofetal fibronectin indicating molecule concentration in the sample at or above 50 ng/ml or about 50 ng/ml.

In another embodiment, a threshold oncofetal fibronectin indicating molecule, such as oncofetal fibronectin protein, concentration in a buffer-treated cervicovaginal swab sample is 150 ng/ml (or 1500 ng/ml untreated swab sample) or about 150 ng/ml (or about 1500 ng/ml untreated swab sample), where a measured amount in a subject's sample at or above the 150 ng/ml threshold indicates a higher risk of imminent or pre-term delivery and a measured amount in a subject's sample below the 150 ng/ml threshold indicates a lower risk of imminent or pre-term delivery. For example, an oncofetal fibronectin indicating molecule, such as oncofetal fibronectin protein, concentration in a buffer-treated cervicovaginal swab sample of 150 ng/ml or more (or 1500 ng/ml untreated swab sample or more) or about 150 ng/ml or more (or about 1500 ng/ml untreated swab sample or more) can indicate a 5%, 10%, 15%, 20% or greater likelihood of imminent or pre-term delivery. In one example, an oncofetal fibronectin indicating molecule, such as oncofetal fibronectin protein, concentration in a buffer-treated cervicovaginal swab sample of 150 ng/ml or more (or 1500 ng/ml untreated swab sample or more) or about 150 ng/ml or more (or about 1500 ng/ml untreated swab sample or more) can indicate a 5% or greater likelihood of delivery within six weeks or about six weeks, a 5% or greater likelihood of delivery within four weeks or about four weeks, a 5% or greater likelihood of delivery within two weeks or about two weeks, or a 5% or greater likelihood of delivery within a week or about a week. In another example, an oncofetal fibronectin indicating molecule, such as oncofetal fibronectin protein concentration in a buffer-treated cervicovaginal swab sample of 150 ng/ml or more (or 1500 ng/ml untreated swab sample or more) or about 150 ng/ml or more (or about 1500 ng/ml untreated swab sample or more) can indicate a 10% or greater likelihood of delivery within six weeks or about six weeks, a 10% or greater likelihood of delivery within four weeks or about four weeks, or a 10% or greater likelihood of delivery within two weeks or about two weeks. In another example, an oncofetal fibronectin indicating molecule, such as oncofetal fibronectin protein, concentration in a buffer-treated cervicovaginal swab sample of 150 ng/ml or more (or 1500 ng/ml untreated swab sample or more) or about 150 ng/ml or more (or about 1500 ng/ml untreated swab sample or more) can indicate a 20% or greater likelihood of delivery within eight weeks or about eight weeks, a 20% or greater likelihood of delivery within six weeks or about six weeks, or a 20% or greater likelihood of delivery within four weeks or about four weeks. In another example, an oncofetal fibronectin indicating molecule, such as oncofetal fibronectin protein, concentration in a buffer-treated cervicovaginal swab sample of 150 ng/ml or more (or 1500 ng/ml untreated swab sample or more) or about 150 ng/ml or more (or about 1500 ng/ml untreated swab sample or more) can indicate a 25% or greater likelihood of delivery within ten weeks or about ten weeks, a 25% or greater likelihood of delivery within eight weeks or about eight weeks, or a 25% or greater likelihood of delivery within six weeks or about six weeks. In another example, an oncofetal fibronectin indicating molecule, such as oncofetal fibronectin protein, concentration in a buffer-treated cervicovaginal swab sample of 150 ng/ml or more (or 1500 ng/ml untreated swab sample or more) or about 150 ng/ml or more (or about 1500 ng/ml untreated swab sample or more) can indicate a 30% or greater likelihood of delivery within ten weeks or about ten weeks, or a 30% or greater likelihood of delivery within eight weeks or about eight weeks. In another example, an oncofetal fibronectin indicating molecule, such as oncofetal fibronectin protein, concentration in a buffer-treated cervicovaginal swab sample of 150 ng/ml or more (or 1500 ng/ml untreated swab sample or more) or about 150 ng/ml or more (or about 1500 ng/ml untreated swab sample or more) can indicate a 35% or greater likelihood of delivery within ten weeks or about ten weeks. In another example, an oncofetal fibronectin indicating molecule, such as oncofetal fibronectin protein, concentration in a buffer-treated cervicovaginal swab sample of 150 ng/ml or more (or 1500 ng/ml untreated swab sample or more) or about 150 ng/ml or more (or about 1500 ng/ml untreated swab sample or more) can indicate a 40% or greater likelihood of delivery within twelve weeks or about twelve weeks.

In another embodiment, a threshold oncofetal fibronectin indicating molecule, such as oncofetal fibronectin protein, concentration in a buffer-treated cervicovaginal swab sample is 200 ng/ml (or 2000 ng/ml untreated swab sample) or about 200 ng/ml (or about 2000 ng/ml untreated swab sample), where a measured amount in a subject's sample at or above the 200 ng/ml threshold indicates a higher risk of imminent or pre-term delivery and a measured amount in a subject's sample below the 200 ng/ml threshold indicates a lower risk of imminent or pre-term delivery. For example, an oncofetal fibronectin indicating molecule, such as oncofetal fibronectin protein, concentration in buffer-treated cervicovaginal swab sample of 200 ng/ml (or 2000 ng/ml untreated swab sample) or about 200 ng/ml (or about 2000 ng/ml untreated swab sample) can indicate a 5%, 10%, 15%, 20% or greater likelihood of imminent or pre-term delivery. In one example, an oncofetal fibronectin indicating molecule, such as oncofetal fibronectin protein, concentration in a buffer-treated cervicovaginal swab sample of 200 ng/ml (or 2000 ng/ml untreated swab sample) or about 200 ng/ml (or about 2000 ng/ml untreated swab sample) can indicate a 5% or greater likelihood of delivery within six weeks or about six weeks, a 5% or greater likelihood of delivery within four weeks or about four weeks, a 5% or greater likelihood of delivery within two weeks or about two weeks, or a 5% or greater likelihood of delivery within a week or about a week. In another example, an oncofetal fibronectin indicating molecule, such as oncofetal fibronectin protein, concentration in a buffer-treated cervicovaginal swab sample of 200 ng/ml (or 2000 ng/ml untreated swab sample) or about 200 ng/ml (or about 2000 ng/ml untreated swab sample) can indicate a 10% or greater likelihood of delivery within six weeks or about six weeks, a 10% or greater likelihood of delivery within four weeks or about four weeks, or a 10% or greater likelihood of delivery within two weeks or about two weeks. In another example, an oncofetal fibronectin indicating molecule, such as oncofetal fibronectin protein, concentration in a buffer-treated cervicovaginal swab sample of 200 ng/ml (or 2000 ng/ml untreated swab sample) or about 200 ng/ml (or about 2000 ng/ml untreated swab sample) can indicate a 20% or greater likelihood of delivery within eight weeks or about eight weeks, a 20% or greater likelihood of delivery within six weeks or about six weeks, or a 20% or greater likelihood of delivery within four weeks or about four weeks. In another example, an oncofetal fibronectin indicating molecule, such as oncofetal fibronectin protein, concentration in a buffer-treated cervicovaginal swab sample of 200 ng/ml (or 2000 ng/ml untreated swab sample) or about 200 ng/ml (or about 2000 ng/ml untreated swab sample) can indicate a 25% or greater likelihood of delivery within ten weeks or about ten weeks, a 25% or greater likelihood of delivery within eight weeks or about eight weeks, or a 25% or greater likelihood of delivery within about six weeks. In another example, an oncofetal fibronectin indicating molecule, such as oncofetal fibronectin protein, concentration in a buffer-treated cervicovaginal swab sample of 200 ng/ml (or 2000 ng/ml untreated swab sample) or about 200 ng/ml (or about 2000 ng/ml untreated swab sample) can indicate a 30% or greater likelihood of delivery within ten weeks or about ten weeks, or a 30% or greater likelihood of delivery within eight weeks or about eight weeks. In another example, an oncofetal fibronectin indicating molecule, such as oncofetal fibronectin protein, concentration in a buffer-treated cervicovaginal swab sample of 200 ng/ml (or 2000 ng/ml untreated swab sample) or about 200 ng/ml (or about 2000 ng/ml untreated swab sample) can indicate a 35% or greater likelihood of delivery within ten weeks or about ten weeks. In another example, an oncofetal fibronectin indicating molecule, such as oncofetal fibronectin protein, concentration in a buffer-treated cervicovaginal swab sample of 200 ng/ml (or 2000 ng/ml untreated swab sample) or about 200 ng/ml (or about 2000 ng/ml untreated swab sample) can indicate a 40% or greater likelihood of delivery within twelve weeks or about twelve weeks.

Exemplary subjects for pre-term delivery screening are those subjects with a gestational age of 80 days or about 80 days gestation or later, or 12 weeks or about 12 weeks gestation or later, until delivery, or at least until the risk of premature delivery (i.e., until week 37 or about week 37) ceases. Typically, the subjects have intact membranes.

In some instances, a subject can be tested on multiple occasions. For example, if the oncofetal fibronectin indicating molecule amount is above a threshold value, the subject can be subsequently tested again for the presence of oncofetal fibronectin indicating molecule in her cervicovaginal secretions. For subjects that are oncofetal fibronectin positive, testing can be performed more frequently than performed for subjects testing negative for oncofetal fibronectin. In addition, for oncofetal fibronectin positive subjects, measures to determine or enhance fetal lung maturity, or to prolong the pregnancy, can be undertaken. If the oncofetal fibronectin indicating molecule assay is negative, the subject can be monitored and repeated evaluations of the subject's oncofetal fibronectin indicating molecule levels can be performed on subsequent visits. In general, subjects can be examined every two weeks from 12 to 36 or about 12 to 36 weeks and weekly from week 36 or about week 36. If the oncofetal fibronectin indicating molecule test is negative, the test can be repeated on each subsequent antenatal visit until either the test is positive or the subject has delivered her baby.

b. Preventing Pre-Term Delivery

The methods of detecting the presence of an oncofetal fibronectin indicating molecule also can be used to prevent pre-term delivery of a pregnant woman. As with other pregnancy or delivery-related methods, a sample from a pregnant woman that is oncofetal fibronectin positive can indicate that the woman has an increased likelihood of imminent or pre-term delivery relative to pregnant women with samples that are oncofetal fibronectin negative. For such women with an increased likelihood of imminent or pre-term delivery, methods can be performed that can favor or extend pregnancy, or increase the viability of an infant delivered pre-term. For example, by monitoring the amount of an oncofetal fibronectin indicating molecule in a subject, when an elevated level of an oncofetal fibronectin indicating molecule indicative of increased likelihood of pre-term or imminent delivery is measured, progestational therapy such as a tocolytic agent can be administered to the subject. A measured amount of an oncofetal fibronectin indicating molecule also can be compared to one or more thresholds, where the benefit from using methods of preventing pre-term delivery increases for each increasing threshold level. A measured amount of an oncofetal fibronectin indicating molecule also can be considered along with one or more other pregnancy or delivery-related markers in determining the likelihood of imminent or pre-term delivery.

Thus, provided herein is a method of screening and, if appropriate, treating a pregnant subject, by obtaining a sample from the subject, measuring the amount of an oncofetal fibronectin indicating molecule in the sample and assessing whether the level of an oncofetal fibronectin indicating molecule is equal to or above a threshold level that is indicative of an increased risk of pre-term or imminent delivery and if the amount of an oncofetal fibronectin indicating molecule is equal to or above the threshold level, administering progestational therapy, such as a therapeutically effective amount of a progestational agent to the subject. Methods provided herein for screening a pregnant subject at risk of pre-term delivery and treating the subject with progestational therapy such as a tocolytic agent also can be used in conjunction with the methods provided in copending application U.S. patent application Ser. No. 10/774,144, which is incorporated by reference herein in its entirety.

Progestational therapy such as administration of a tocolytic agent, favors, or is conducive to, gestation, or inhibits premature labor by, for example, inhibiting uterine contractions, or increases the viability of an infant born pre-term. Progestational therapy that can be administered in accordance with the methods provided herein can include any of a variety of techniques for prolonging gestation, inhibiting premature labor, or increasing the viability of an infant born pre-term. Progestational therapy can include methods such as bedrest for the pregnant subject and also can include administration of one or more agents that reduce or inhibit uterine contractions, that prolong the pregnancy, or that increase the viability of an infant delivered pre-term. For example, progestational therapy can include administration of a tocolytic agent.

Tocolytic agents include any of a group of agents known to inhibit pre-term labor. Any such agent can be employed. Exemplary tocolytic agents for use in accord with the methods herein include, but are not limited to, any of the following: magnesium salts such as magnesium sulfate; prostaglandin synthesis inhibitors, including non-steroidal anti-inflammatory compounds such as indomethacin, sulindac, naproxen, aspirin and fenoprofen; β-adrenergic agonists such as ritodrine, terbutaline, albuterol, fenoterol, hexoprenaline, isoxuprine, metaproterenol, nylidrin, orciprenaline and salbutamol, or other epinephrin or norepinephrine analogs or derivatives; calcium channel blockers such as nifedipine and nicardipine; oxytocin antagonists such as atosiban; nitric oxide donors such as glyceryl trinitrate; hormones secreted by the corpus luteum, placenta and adrenal cortex and derivatives thereof, including dydrogesterone, ethynodiol diacetate, hydroxyprogesterone caproate, medroxyprogesterone acetate, norethindrone, norethindrone acetate, norethynodrel, norgestrel, megesterol acetate, gestodene, desogestrel, cingestol, lynestrenol, quingestanol acetate, levonorgestrel, 3-ketodesogestrel, norgestimate, osaterone, cyproterone acetate, trimegestone, dienogest, drospirenone, nomegestrol, (17-deacetyl)norgestimnate, 19-norprogesterone, melengestrol, ethisterone, medroxyprogesterone acetate, 17-α-hydroxyprogesterone, dimethisterone, ethinylestrenol, demegestone, promegestone, chlormadinone, pregn-4-ene-3, 20-dione (progesterone), 19-nor-pregn-4-ene-3,20-dione, 17-hydroxy-19-nor-17α-pregn-5(10)-ene-20-yn-3-one, dl-11α-ethyl-17-ethinyl-17-α-hydroxygon-4-ene-3-one, 17-ethynyl-17-hydroxy-5 (10)-estren-3-one, 17α-ethynyl-19-norestosterone, 6-chloro-17-hydroxypregna-4,6-diene-3, 20-dione, 17α-hydroxy-6α-methyl-17(-1-propynl-)androst-4-ene-3-one, 9α,10α-pregna-4,6-diene-3,20-dione, 17-hydroxy-17α-pregn-4-en-20-yne-3-one, 19-nor-17α-preg-4-en-20-yen-3,17-diol, 17-hydroxy-pregn-4-ene-3,20-dione, 1-7-hydroxy-6α-methylpregn-4-ene-3,20-dione and derivatives and mixtures thereof (see, e.g., U.S. Pat. No. 5,211,952). Tocolytic agents also include omega-3 fatty acids, whether naturally or synthetically produced and derivatives thereof. Exemplary omega-3 fatty acids include, for example, docosahexaenoic acid (DHA).

Tocolytic agents can be administered by any of a variety of methods known in the art. For example, the tocolytic agent can be administered orally, parenterally by injection (e.g., by bolus injection or continuous infusion), transdermally, intranasally, or by inhalation. The therapeutically effective amount of tocolytic agent will vary according to, for example, the particular agent and/or pharmaceutical composition being used, the mode of administration and the course of treatment. Optimal dosages for a given set of conditions can be ascertained using conventional dosage-determination tests. Further, administration of the tocolytic agent can be repeated at appropriate intervals (e.g., daily, weekly, etc.). In one embodiment, the dose is determined by measuring the concentration of tocolytic agent in the circulating blood and adjusting the mode of administration and/or course of treatment accordingly.

c. Predictor of Delivery Date

In another embodiment, the methods of detecting the presence of an oncofetal fibronectin indicating molecule can be used to predict the delivery date of a pregnant woman. As with the methods provided for prediction of pre-term or imminent delivery provided herein, an amount of an oncofetal fibronectin indicating molecule detected in the sample from a pregnant woman who will soon deliver is elevated over the level for pregnant women who will not soon deliver. The methods provided herein can be used to indicate a subject with an increased likelihood of imminent delivery, as well as an increased likelihood of delivery within a particular time frame. The methods provided herein also can be used to indicate the likelihood in which a subject will soon deliver or will deliver within a particular time frame. The methods provided herein also can include comparing a measured amount of an oncofetal fibronectin indicating molecule to one or more thresholds, where the likelihood of imminent delivery increases for each increasing threshold level, or where the likelihood of delivery within a particular time frame increases with each increasing threshold level. A measured amount of an oncofetal fibronectin indicating molecule also can be considered along with one or more other pregnancy or delivery-related markers in determining the likelihood of imminent delivery or the likelihood of delivery within a particular time frame.

Additionally, provided herein are methods in which an amount of an oncofetal fibronectin indicating molecule detected in the sample from a pregnant woman who will maintain her pregnancy is lower than the level for pregnant women who will soon deliver. The methods provided herein can be used to indicate a subject with an increased likelihood of maintaining her pregnancy until full term, as well as an increased likelihood of maintaining pregnancy for a particular time frame. The methods provided herein also can be used to indicate the likelihood in which a subject will maintain her pregnancy until full term or will maintain her pregnancy for a particular time frame. The methods provided herein also can include comparing a measured amount of an oncofetal fibronectin indicating molecule to one or more thresholds, where the likelihood of maintaining pregnancy increases for each decreasing threshold level, or where the likelihood of maintaining pregnancy for a particular time frame increases with each decreasing threshold level. A measured amount of an oncofetal fibronectin indicating molecule also can be considered along with one or more other pregnancy or delivery-related markers in determining the likelihood of maintaining a pregnancy to full term or the likelihood of maintaining a pregnancy for a particular time frame.

In one embodiment, an amount of an oncofetal fibronectin indicating molecule detected in the sample from a pregnant woman who will soon deliver is elevated over the level for pregnant women who will not soon deliver. For example, an amount of an oncofetal fibronectin indicating molecule detected in the sample from a pregnant woman at or near a 24-week gestation who will soon deliver is elevated over the level for pregnant women at or near a 24-week gestation who will not soon deliver. For example, an amount of an oncofetal fibronectin indicating molecule detected in the sample from a pregnant woman at or near a 35-week gestation who will soon deliver is elevated over the level for pregnant women at or near a 35-week gestation who will not soon deliver. In another example, an amount of an oncofetal fibronectin indicating molecule detected in the sample from a pregnant woman at or near a 37-week gestation who will soon deliver is elevated over the level for pregnant women at or near a 37-week gestation who will not soon deliver. In another example, an amount of an oncofetal fibronectin indicating molecule detected in the sample from a pregnant woman at or near a 39-week gestation who will soon deliver is elevated over the level for pregnant women at or near a 39-week gestation who will not soon deliver. In another example an amount of an oncofetal fibronectin indicating molecule detected in the sample from a pregnant woman beyond full term who will soon deliver is elevated over the level for pregnant women beyond a full term who will not soon deliver. In such examples, a threshold level can be defined, where an oncofetal fibronectin indicating molecule amount in a sample that is equal to or above the threshold level indicates an increased likelihood that the subject will soon deliver and an oncofetal fibronectin indicating molecule amount in a sample that is below the threshold level indicates an increased likelihood that the subject will not soon deliver.

In one embodiment, an amount of an oncofetal fibronectin indicating molecule detected in the sample from a pregnant woman who will maintain her pregnancy is lower than the level for pregnant women who will not maintain her pregnancy. For example, an amount of an oncofetal fibronectin indicating molecule detected in the sample from a pregnant woman at or near a 24-week gestation who will maintain her pregnancy is lower than the level for pregnant women at or near a 24-week gestation who will not maintain her pregnancy. For example, an amount of an oncofetal fibronectin indicating molecule detected in the sample from a pregnant woman at or near a 35-week gestation who will maintain her pregnancy is lower than the level for pregnant women at or near a 35-week gestation who will not maintain her pregnancy. In another example, an amount of an oncofetal fibronectin indicating molecule detected in the sample from a pregnant woman at or near a 37-week gestation who will maintain her pregnancy is lower than the level for pregnant women at or near a 37-week gestation who maintain her pregnancy. In another example, an amount of an oncofetal fibronectin indicating molecule detected in the sample from a pregnant woman at or near a 39-week gestation who will maintain her pregnancy is lower than the level for pregnant women at or near a 39-week gestation who will not maintain her pregnancy. In another example an amount of an oncofetal fibronectin indicating molecule detected in the sample from a pregnant woman beyond full term who will maintain her pregnancy is lower than the level for pregnant women beyond a full term who will not maintain her pregnancy. In such examples, a threshold level can be defined, where an oncofetal fibronectin indicating molecule amount in a sample that is below the threshold level indicates an increased likelihood that the subject will maintain her pregnancy and an oncofetal fibronectin indicating molecule amount in a sample that is equal to or above the threshold level indicates an increased likelihood that the subject will not maintain her pregnancy.

Typically, an amount of an oncofetal fibronectin indicating molecule detected in the sample from a pregnant woman who will deliver within a particular time period is elevated over the level for pregnant women who will not deliver within that time period. For example, an amount of an oncofetal fibronectin indicating molecule detected in the sample from a pregnant woman at or near a 24 week, 35 week, 37 week, 39 week, or beyond full-term pregnancy who will deliver within a particular time period is elevated over the level for pregnant women at or near a 24 week, 35 week, 37 week, 39 week, or beyond full-term pregnancy who will not soon deliver. In such examples, a threshold level can be defined, where an oncofetal fibronectin indicating molecule amount in a sample that is equal to or above the threshold level indicates an increased likelihood that the subject will deliver within a particular time period and an oncofetal fibronectin indicating molecule amount in a sample that is below the threshold level indicates an increased likelihood that the subject will not deliver within that time period. Exemplary time periods for which a likelihood of delivery can be indicated include 5 months or less, 4 months or less, 14 weeks or less, 3 months or less, 12 weeks or less, 11 weeks or less, 10 weeks or less, 9 weeks or less, 2 months or less, 8 weeks or less, 7 weeks or less, 6 weeks or less, 5 weeks or less, 1 month or less, 4 weeks or less, 3 weeks or less, 2 weeks or less, 10 days or less, 1 week or less, 6 days or less, 5 days or less, 4 days or less, 3 days or less, 2 days or less, or 1 day or less.

In related methods, an amount of an oncofetal fibronectin indicating molecule detected in the sample from a pregnant woman who will maintain pregnancy for a particular time period is lower than the level for pregnant women who will not maintain pregnancy over that time period. For example, an amount of an oncofetal fibronectin indicating molecule detected in the sample from a pregnant woman at or near a 24 week, 35 week, 37 week, 39 week, or beyond full-term pregnancy who will maintain pregnancy for a particular time period is lower than the level for pregnant women at or near a 24 week, 35 week, 37 week, 39 week, or beyond full-term pregnancy who will not maintain pregnancy over this time period. In such examples, a threshold level can be defined, where an oncofetal fibronectin indicating molecule amount in a sample that is below the threshold level indicates an increased likelihood that the subject will maintain pregnancy for a particular time period and an oncofetal fibronectin indicating molecule amount in a sample that is equal to or greater than the threshold level indicates an increased likelihood that the subject will not maintain pregnancy over that time period. Exemplary time periods for which a likelihood of delivery can be indicated include at least 1 day, at least 2 days, at least 3 days, at least 4 days, at least 5 days, at least 6 days, at least 1 week, at least 10 days, at least 2 weeks, at least 3 weeks, at least 4 weeks, at least 1 month, at least 5 weeks, at least 6 weeks, at least 7 weeks, at least 8 weeks, at least 2 months, at least 9 weeks, at least 10 weeks, at least 11 weeks, at least 12 weeks, at least 3 months, at least 14 weeks, at least 4 months, or at least 5 months.

In some instances, the degree of likelihood of delivering can be indicated according to the amount of an oncofetal fibronectin indicating molecule present in the sample of a subject. For example, a sample from a pregnant woman with an elevated amount of an oncofetal fibronectin indicating molecule indicates a higher likelihood of imminent delivery relative to pregnant women with lower levels of the oncofetal fibronectin indicating molecule. For example, an elevated amount of an oncofetal fibronectin indicating molecule in the sample from a pregnant woman at or near a 24 week, 35 week, 37 week, 39 week, or beyond full-term pregnancy indicates a higher likelihood of imminent delivery relative to pregnant women at or near a 24 week, 35 week, 37 week, 39 week, or beyond full-term pregnancy with lower levels of the oncofetal fibronectin indicating molecule. In another example, a sample from a pregnant woman with an elevated amount of an oncofetal fibronectin indicating molecule indicates a higher likelihood of delivery within a particular time period relative to pregnant women with lower levels of the oncofetal fibronectin indicating molecule. For example, an elevated amount of an oncofetal fibronectin indicating molecule in the sample from a pregnant woman at or near a 24 week, 35 week, 37 week, 39 week, or beyond full-term pregnancy indicates a higher likelihood of delivery within a particular time period relative to pregnant women at or near a 24 week, 35 week, 37 week, 39 week, or beyond full-term pregnancy with lower levels of the oncofetal fibronectin indicating molecule. Exemplary higher likelihoods of delivery can be at least 5%, 10%, 15%, 20%, 30%, 40%, 50%, 60%, 70%, 80%, 90%, 100% (e.g., 2-fold), 3-fold, 4-fold, 5-fold, 6-fold, 7-fold, 8-fold, 9-fold, 10-fold, 12-fold, 15-fold, 20-fold, 25-fold, 30-fold, 35-fold, 40-fold, 45-fold, or 50-fold higher likelihood of delivery. Exemplary higher likelihoods of delivery for particular time periods include at least 2-fold, 5-fold, 10-fold, 15-fold, 20-fold higher, 30-fold, or 40-fold higher likelihood of delivery within two weeks or about two weeks; at least 50%, 75%, 2-fold, 5-fold, 10-fold, or 15-fold higher likelihood of delivery within six weeks or about six weeks; at least 10%, 15%, 20%, 30%, 40%, 50%, 60%, 70%, 80%, 90%, 100% or 3-fold higher likelihood of delivery within three months or about three months.

Similarly, the degree of likelihood of maintaining pregnancy can be indicated according to the amount of an oncofetal fibronectin indicating molecule present in the sample of a subject. For example, a sample from a pregnant woman with a lower amount of an oncofetal fibronectin indicating molecule indicates a higher likelihood of maintaining pregnancy relative to pregnant women with elevated levels of the oncofetal fibronectin indicating molecule. For example, a lower amount of an oncofetal fibronectin indicating molecule in the sample from a pregnant woman at or near a 24 week, 35 week, 37 week, 39 week, or beyond full-term pregnancy indicates a higher likelihood of maintaining pregnancy relative to pregnant women at or near a 24 week, 35 week, 37 week, 39 week, or beyond full-term pregnancy with elevated levels of the oncofetal fibronectin indicating molecule. In another example, a sample from a pregnant woman with a lower amount of an oncofetal fibronectin indicating molecule indicates a higher likelihood of maintaining pregnancy for a particular time period relative to pregnant women with elevated levels of the oncofetal fibronectin indicating molecule. For example, a lower amount of an oncofetal fibronectin indicating molecule in the sample from a pregnant woman at or near a 24 week, 35 week, 37 week, 39 week, or beyond full-term pregnancy indicates a higher likelihood of maintaining pregnancy for a particular time period relative to pregnant women at or near a 24 week, 35 week, 37 week, 39 week, or beyond full-term pregnancy with elevated levels of the oncofetal fibronectin indicating molecule. Exemplary higher likelihoods of maintaining pregnancy can be at least 1%, 2%, 3%, 4%, 5%, 7%, 10%, 15%, 20%, 25%, 30%, 35%, 40%, 45%, 50%, 55%, 60%, 65%, 70%, 75%, 80%, 85%, 90%, 95%, 100%, 110%, 120%, 130%, 150%, 175%, or 200% higher likelihood of maintaining pregnancy. Exemplary likelihoods of maintaining pregnancy for particular time periods include at least 1%, 2%, 3%, 5%, 7%, 10%, 15%, 20%, 25%, 30%, 40%, or 50% higher likelihood of maintaining pregnancy for at least two weeks or about two weeks; at least 2%, 5%, 10%, 15%, 20%, 25%, 30%, 40%, 50%, 60%, or 75% higher likelihood of maintaining pregnancy for at least six weeks or about six weeks; at least 10%, 15%, 20%, 30%, 40%, 50%, 60%, 70%, 80%, 90%, or 100% higher likelihood of delivery maintaining pregnancy for at least three months or about three months.

In such examples, a threshold level can be defined, where an oncofetal fibronectin indicating molecule amount in a sample that is equal to or above the threshold level indicates an increased likelihood that the subject will soon deliver and an oncofetal fibronectin indicating molecule amount in a sample that is below the threshold level indicates an increased likelihood that the subject will not soon deliver.

For use in conjunction with delivery date and pregnancy maintenance prediction methods herein, a subject is considered positive for oncofetal fibronectin when the presence of an oncofetal fibronectin indicating molecule in a sample is equal to or above one or more threshold levels. As one skilled in the art will recognize, a threshold level can vary according to the type of sample measured and the selected stringency of the test. In one example, a threshold level for a cervicovaginal sample assayed using a test strip can be 50 ng/mL. In another example, a threshold level for a cervicovaginal sample assayed using a test strip can be 150 ng/mL.

In another embodiment, multi-tiered thresholds can be applied to the oncofetal fibronectin indicating molecule measurement, where multi-tiered thresholds include two or more threshold levels, where each larger threshold level indicates a further increased likelihood of imminent delivery or an increased likelihood of delivery within a particular time period, or each lower threshold level indicates a further increased likelihood of maintaining pregnancy or an increased likelihood of maintaining pregnancy for a particular time period. An exemplary multi-tiered threshold is a two-tiered threshold where the lower threshold is 50 ng/mL and the higher threshold is 150 ng/mL for buffer-treated samples. An exemplary multi-tiered threshold is a two-tiered threshold where the lower threshold is 500 ng/mL and the higher threshold is 1500 ng/mL for untreated samples.

As provided herein, particular threshold levels can be identified with particular likelihoods of delivery or likelihoods of maintaining pregnancy, which can be likelihoods of delivery or maintaining pregnancy within a particular time period. For example, an oncofetal fibronectin indicating molecule, such as oncofetal fibronectin protein, concentration in a buffer-treated cervicovaginal swab sample of 150 ng/ml or more (or 1500 ng/ml untreated swab sample or more) or about 150 ng/ml or more (or about 1500 ng/ml untreated swab sample or more) can indicate the likelihood of delivery within a defined amount of time. For example, an oncofetal fibronectin indicating molecule, such as oncofetal fibronectin protein, concentration in a buffer-treated cervicovaginal swab sample of 150 ng/ml or more (or 1500 ng/ml untreated swab sample or more) or about 150 ng/ml or more (or about 1500 ng/ml untreated swab sample or more) can indicate a 5% likelihood of imminent or pre-term delivery within a week or about a week. In another example, an oncofetal fibronectin indicating molecule, such as oncofetal fibronectin protein, concentration in a buffer-treated cervicovaginal swab sample of 150 ng/ml or more (or 1500 ng/ml untreated swab sample or more) or about 150 ng/ml or more (or about 1500 ng/ml untreated swab sample or more) can indicate a 10% likelihood of delivery within two weeks or about two weeks. In another example, an oncofetal fibronectin indicating molecule, such as oncofetal fibronectin protein, concentration in a buffer-treated cervicovaginal swab sample of 150 ng/ml or more (or 1500 ng/ml untreated swab sample or more) or about 150 ng/ml or more (or about 1500 ng/ml untreated swab sample or more) can indicate a 20% likelihood of delivery within 4 weeks or about 4 weeks. In another example, an oncofetal fibronectin indicating molecule, such as oncofetal fibronectin protein, concentration in a buffer-treated cervicovaginal swab sample of 150 ng/ml or more (or 1500 ng/ml untreated swab sample or more) or about 150 ng/ml or more (or about 1500 ng/ml untreated swab sample or more) can indicate a 25% likelihood of delivery within 6 weeks or about 6 weeks. In another example, an oncofetal fibronectin indicating molecule, such as oncofetal fibronectin protein, concentration in a buffer-treated cervicovaginal swab sample of 150 ng/ml or more (or 1500 ng/ml untreated swab sample or more) or about 150 ng/ml or more (or about 1500 ng/ml untreated swab sample or more) can indicate a 30% likelihood of delivery within 8 weeks or about 8 weeks. In another example, an oncofetal fibronectin indicating molecule, such as oncofetal fibronectin protein, concentration in a buffer-treated cervicovaginal swab sample of 150 ng/ml or more (or 1500 ng/ml untreated swab sample or more) or about 150 ng/ml or more (or about 1500 ng/ml untreated swab sample or more) can indicate a 40% likelihood of delivery within 8 weeks or about 8 weeks.

In another example, a woman can be tested for the presence of an oncofetal fibronectin indicating molecule at 24 weeks or about 24 weeks into her pregnancy and a woman having an oncofetal fibronectin indicating molecule, such as oncofetal fibronectin protein, concentration in a buffer-treated cervicovaginal swab sample of 150 ng/ml or more (or 1500 ng/ml untreated swab sample or more) or about 150 ng/ml or more (or about 1500 ng/ml untreated swab sample or more) can indicate a higher risk of imminent or pre-term delivery. For example, a woman at 24 weeks or about 24 weeks in her pregnancy and having an oncofetal fibronectin indicating molecule, such as oncofetal fibronectin protein, concentration in a buffer-treated cervicovaginal swab sample of 150 ng/ml or more (or 1500 ng/ml untreated swab sample or more) or about 150 ng/ml or more (or about 1500 ng/ml untreated swab sample or more) can have a 5% or about a 5% likelihood of delivery within a week or about a week. In another example, a woman at 24 weeks or about 24 weeks in her pregnancy and having an oncofetal fibronectin indicating molecule, such as oncofetal fibronectin protein, concentration in a buffer-treated cervicovaginal swab sample of 150 ng/ml or more (or 1500 ng/ml untreated swab sample or more) or about 150 ng/ml or more (or about 1500 ng/ml untreated swab sample or more) can have a 10% or about a 10% likelihood of delivery within two weeks or about two weeks. In another example, a woman at 24 weeks or about 24 weeks in her pregnancy and having an oncofetal fibronectin indicating molecule, such as oncofetal fibronectin protein, concentration in a buffer-treated cervicovaginal swab sample of 150 ng/ml or more (or 1500 ng/ml untreated swab sample or more) or about 150 ng/ml or more (or about 1500 ng/ml untreated swab sample or more) can have a 20% or about a 20% likelihood of delivery within four weeks about four weeks. In another example, a woman at 24 weeks or about 24 weeks in her pregnancy and having an oncofetal fibronectin indicating molecule, such as oncofetal fibronectin protein, concentration in a buffer-treated cervicovaginal swab sample of 150 ng/ml or more (or 1500 ng/ml untreated swab sample or more) or about 150 ng/ml or more (or about 1500 ng/ml untreated swab sample or more) can have a 25% or about a 25% likelihood of delivery within six weeks or about six weeks. In another example, a woman at 24 weeks or about 24 weeks in her pregnancy and having an oncofetal fibronectin indicating molecule, such as oncofetal fibronectin protein, concentration in a buffer-treated cervicovaginal swab sample of 150 ng/ml or more (or 1500 ng/ml untreated swab sample or more) or about 150 ng/ml or more (or about 1500 ng/ml untreated swab sample or more) can have a 30% or about a 30% likelihood of delivery within eight weeks or about eight weeks. In another example, a woman at 24 weeks or about 24 weeks in her pregnancy and having an oncofetal fibronectin indicating molecule, such as oncofetal fibronectin protein, concentration in a buffer-treated cervicovaginal swab sample of 150 ng/ml or more (or 1500 ng/ml untreated swab sample or more) or about 150 ng/ml or more (or about 1500 ng/ml untreated swab sample or more) can have a 40% or about a 40% likelihood of delivery within twelve weeks or about twelve weeks.

In other examples, an oncofetal fibronectin indicating molecule, such as oncofetal fibronectin protein, concentration in buffer-treated cervicovaginal swab sample of 200 ng/ml or more (or 2000 ng/ml untreated swab sample or more) or about 200 ng/ml or more (or about 2000 ng/ml untreated swab sample or more) can indicate the likelihood of delivery within a defined amount of time. For example, an oncofetal fibronectin indicating molecule, such as oncofetal fibronectin protein, concentration in buffer-treated cervicovaginal swab sample of 200 ng/ml or more (or 2000 ng/ml untreated swab sample or more) or about 200 ng/ml or more (or about 2000 ng/ml untreated swab sample or more) can indicate a 5% likelihood of imminent or pre-term delivery within a week or about a week. In another example, an oncofetal fibronectin indicating molecule, such as oncofetal fibronectin protein, concentration in a buffer-treated cervicovaginal swab sample of 200 ng/ml or more (or 2000 ng/ml untreated swab sample or more) or about 200 ng/ml or more (or about 2000 ng/ml untreated swab sample or more) can indicate a 10% likelihood of delivery within two weeks or about two weeks. In another example, an oncofetal fibronectin indicating molecule, such as oncofetal fibronectin protein, concentration in a buffer-treated cervicovaginal swab sample of 200 ng/ml or more (or 2000 ng/ml untreated swab sample or more) or about 200 ng/ml or more (or about 2000 ng/ml untreated swab sample or more) can indicate a 20% likelihood of delivery within 4 weeks or about 4 weeks. In another example, an oncofetal fibronectin indicating molecule, such as oncofetal fibronectin protein, concentration in a buffer-treated cervicovaginal swab sample of 200 ng/ml or more (or 2000 ng/ml untreated swab sample or more) or about 200 ng/ml or more (or about 2000 ng/ml untreated swab sample or more) can indicate a 25% likelihood of delivery within 6 weeks or about 6 weeks. In another example, an oncofetal fibronectin indicating molecule, such as oncofetal fibronectin protein, concentration in a buffer-treated cervicovaginal swab sample of 200 ng/ml or more (or 2000 ng/ml untreated swab sample or more) or about 200 ng/ml or more (or about 2000 ng/ml untreated swab sample or more) can indicate a 30% likelihood of delivery within 8 weeks or about 8 weeks. In another example, an oncofetal fibronectin indicating molecule, such as oncofetal fibronectin protein, concentration in a buffer-treated cervicovaginal swab sample of 200 ng/ml or more (or 2000 ng/ml untreated swab sample or more) or about 200 ng/ml or more (or about 2000 ng/ml untreated swab sample or more) can indicate a 40% likelihood of delivery within 8 weeks or about 8 weeks.

In one example, a woman can be tested for the presence of oncofetal fibronectin indicating molecule at 24 weeks or about 24 weeks into her pregnancy and a woman having an oncofetal fibronectin indicating molecule, such as oncofetal fibronectin protein, concentration in a buffer-treated cervicovaginal swab sample of 200 ng/ml or more (or 2000 ng/ml untreated swab sample or more) or about 200 ng/ml or more (or about 2000 ng/ml untreated swab sample or more) can have a higher risk of imminent or pre-term delivery. For example, a woman at 24 weeks or about 24 weeks in her pregnancy and having an oncofetal fibronectin indicating molecule, such as oncofetal fibronectin protein, concentration in a buffer-treated cervicovaginal swab sample of about 200 ng/ml or more (or about 2000 ng/ml untreated swab sample or more) can have a 5% or about a 5% likelihood of delivery within a week or about a week. For example, a woman at 24 weeks or about 24 weeks in her pregnancy and having an oncofetal fibronectin indicating molecule, such as oncofetal fibronectin protein, concentration in a buffer-treated cervicovaginal swab sample of about 200 ng/ml or more (or about 2000 ng/ml untreated swab sample or more) can have a 10% or about a 10% likelihood of delivery within two weeks or about two weeks. For example, a woman at 24 weeks or about 24 weeks in her pregnancy and having an oncofetal fibronectin indicating molecule, such as oncofetal fibronectin protein, concentration in a buffer-treated cervicovaginal swab sample of about 200 ng/ml or more (or about 2000 ng/ml untreated swab sample or more) can have a 20% or about a 20% likelihood of delivery within four weeks or about four weeks. For example, a woman at 24 weeks or about 24 weeks in her pregnancy and having an oncofetal fibronectin indicating molecule, such as oncofetal fibronectin protein, concentration in a buffer-treated cervicovaginal swab sample of about 200 ng/ml or more (or about 2000 ng/ml untreated swab sample or more) can have a 25% or about a 25% likelihood of delivery within six weeks or about six weeks. For example, a woman at 24 weeks or about 24 weeks in her pregnancy and having an oncofetal fibronectin indicating molecule, such as oncofetal fibronectin protein, concentration in a buffer-treated cervicovaginal swab sample of about 200 ng/ml or more (or about 2000 ng/ml untreated swab sample or more) can have a 30% or about a 30% likelihood of delivery within eight weeks or about eight weeks. For example, a woman at 24 weeks or about 24 weeks in her pregnancy and having an oncofetal fibronectin indicating molecule, such as oncofetal fibronectin protein, concentration in a buffer-treated cervicovaginal swab sample of about 200 ng/ml or more (or about 2000 ng/ml untreated swab sample or more) can have a 40% or about a 40% likelihood of delivery within twelve weeks or about twelve weeks.

In other examples, an oncofetal fibronectin indicating molecule, such as oncofetal fibronectin protein, concentration in buffer-treated cervicovaginal swab sample less than 150 ng/ml (or 1500 ng/ml untreated swab sample) or about 150 ng/ml (or about 1500 ng/ml untreated swab sample) can indicate the likelihood of maintaining pregnancy for a defined amount of time. For example, an oncofetal fibronectin indicating molecule, such as oncofetal fibronectin protein, concentration in buffer-treated cervicovaginal swab sample of less than 150 ng/ml (or 1500 ng/ml untreated swab sample) or about 150 ng/ml (or about 1500 ng/ml untreated swab sample) can indicate a 99% likelihood of maintaining pregnancy for at least a week or about a week. In another example, an oncofetal fibronectin indicating molecule, such as oncofetal fibronectin protein, concentration in a buffer-treated cervicovaginal swab sample of less than 150 ng/ml (or 1500 ng/ml untreated swab sample) or about 150 ng/ml (or about 1500 ng/ml untreated swab sample) can indicate a 98% likelihood of maintaining pregnancy for at least two weeks or about two weeks. In another example, an oncofetal fibronectin indicating molecule, such as oncofetal fibronectin protein, concentration in a buffer-treated cervicovaginal swab sample of less than 150 ng/ml (or 1500 ng/ml untreated swab sample) or about 150 ng/ml (or about 1500 ng/ml untreated swab sample) can indicate a 97% likelihood of maintaining pregnancy for at least 4 weeks or about 4 weeks. In another example, an oncofetal fibronectin indicating molecule, such as oncofetal fibronectin protein, concentration in a buffer-treated cervicovaginal swab sample of less than 150 ng/ml (or 1500 ng/ml untreated swab sample) or about 150 ng/ml (or about 1500 ng/ml untreated swab sample) can indicate a 95% likelihood of maintaining pregnancy for at least 10 weeks or about 10 weeks.

d. Use With Inducing Delivery

The methods of detecting the presence of an oncofetal fibronectin indicating molecule also can be used in conjunction with inducing delivery in a pregnant woman. As provided herein, an amount of an oncofetal fibronectin indicating molecule detected in the sample from a pregnant woman with increased risk of delivering is elevated over the level for pregnant women with less risk of delivering. Similarly, as provided herein, subjects testing positive for oncofetal fibronectin have an increased risk of delivering after induction, or have a shorter time period between induction and delivery, or require fewer administrations of a parturifacient, or have a decreased likelihood of cesarean delivery, relative to subjects testing negative for oncofetal fibronectin.

In some embodiments, an amount of an oncofetal fibronectin indicating molecule detected in the sample from a pregnant woman with increased risk of delivering is increased compared to a threshold, or when the presence of an oncofetal fibronectin indicating molecule in a sample is equal to or above one or more threshold levels, render the sample positive for oncofetal fibronectin indicating molecule. In another embodiment, a sample is considered negative for oncofetal fibronectin when an amount of an oncofetal fibronectin indicating molecule detected in the sample from a pregnant woman is decreased compared to a threshold As one skilled in the art will recognize, a threshold level can vary according to the type of sample measured and the selected stringency of the test.

Accordingly, by detecting an oncofetal fibronectin indicating molecule in a subject prior to performing an induction method, the likely effect of inducing delivery can be predicted and the likelihood that induction will lead to a prompt delivery can be estimated. For example, by detecting an oncofetal fibronectin indicating molecule in a subject prior to performing an induction method, it is possible to estimate the likely amount of time between administration of a parturifacient or induction procedure and delivery, or to estimate the likely amount of time between oxytocin administration and delivery. Further, by detecting an oncofetal fibronectin indicating molecule in a subject prior to performing an induction method, it is possible to estimate the likelihood of the subject delivering within 24 hours or about 24 hours after induction of delivery, or to estimate the likelihood of the subject delivering within 48 hours or about 48 hours after induction of delivery. Further, by detecting an oncofetal fibronectin indicating molecule in a subject prior to performing an induction method, it is possible to estimate the likelihood that more than a single administration of a parturifacient or induction procedure will be required to induce delivery. Further, by detecting an oncofetal fibronectin indicating molecule in a subject prior to performing an induction method, it is possible to estimate the likelihood that vaginal delivery will be performed and childbirth will not require cesarean section, or, alternatively, to estimate the likelihood that vaginal delivery will not be performed and childbirth will instead be accomplished by cesarean section.

The methods provided herein include a method for determining whether or not to perform a labor induction method, by detecting an oncofetal fibronectin indicating molecule in a sample from a subject and, if the oncofetal fibronectin indicating molecule is present in the sample at a level equal to or above a threshold level, inducing delivery in a subject. Also provided herein is a method of identifying a subject as a good candidate for induction of delivery, the method including detecting an oncofetal fibronectin indicating molecule in a sample from a subject and, if the oncofetal fibronectin indicating molecule is present in the sample at a level equal to or above a threshold level, identifying the subject as a good candidate for induction of delivery. Also provided herein is a method of identifying a subject for whom induction of delivery is likely to be successful, the method including detecting an oncofetal fibronectin indicating molecule in a sample from a subject and, if the oncofetal fibronectin indicating molecule is present in the sample at a level equal to or above a threshold level, identifying the subject as one for whom induction of delivery is likely to be successful. Also provided herein is a method of identifying a subject for whom the time period after initiation of induction or administration of a parturifacient such as a pre-induction agent or oxytocin is likely to be relatively shorter, the method including detecting an oncofetal fibronectin indicating molecule in a sample from a subject and, if the oncofetal fibronectin indicating molecule is present in the sample at a level equal to or above a threshold level, identifying the subject as one for whom the time period after initiation of induction or administration of a parturifacient such as a pre-induction agent or oxytocin is likely to be shorter relative to subjects with oncofetal fibronectin indicating molecule levels below the threshold level. Also provided herein is a method of identifying a subject for whom the time period after initiation of induction is likely to be within 24 hours, the method including detecting an oncofetal fibronectin indicating molecule in a sample from a subject and, if the oncofetal fibronectin indicating molecule is present in the sample at a level equal to or above a threshold level, identifying the subject as one for whom the time period after initiation of induction is likely to be within 24 hours. Also provided herein is a method of identifying a subject for whom the time period after initiation of induction is likely to be within 48 hours, the method including detecting an oncofetal fibronectin indicating molecule in a sample from a subject and, if the oncofetal fibronectin indicating molecule is present in the sample at a level equal to or above a threshold level, identifying the subject as one for whom the time period after initiation of induction is likely to be within 48 hours. Also provided herein is a method of identifying a subject for whom induction of delivery is likely to lead to vaginal delivery, the method including detecting an oncofetal fibronectin indicating molecule in a sample from a subject and, if the oncofetal fibronectin indicating molecule is present in the sample at a level equal to or above a threshold level, identifying the subject as one for whom induction of delivery is likely to lead to vaginal delivery. Also provided herein is a method of identifying a subject for whom the number of induction procedures or administrations of a parturifacient is likely to be relatively fewer, the method including detecting an oncofetal fibronectin indicating molecule in a sample from a subject and, if the oncofetal fibronectin indicating molecule is present in the sample at a level equal to or above a threshold level, identifying the subject as one for whom the number of induction procedures or administrations of a parturifacient is likely to be relatively fewer relative to subjects with oncofetal fibronectin indicating molecule levels below the threshold level.

As provided herein, subjects testing positive for oncofetal fibronectin are more likely to deliver vaginally after induction relative to subjects testing negative for oncofetal fibronectin or to a sample having an amount of oncofetal fibronectin indicating molecule below a threshold. For example, subjects testing positive for oncofetal fibronectin can be at least about 7%, at least about 8%, at least about 9%, at least about 10%, at least about 11%, at least about 12%, at least about 13%, at least about 14%, at least about 15%, at least about 16%, at least about 18%, at least about 20%, at least about 25%, or at least about 30%, more likely to deliver vaginally after induction relative to subjects testing negative for oncofetal fibronectin. Typically, subjects testing positive for oncofetal fibronectin about 3-30%, about 5-25%, about 7-22%, about 8-20%, about 9-18%, about 10-16%, about 11-15%, or about 12-14%, or about 13%, more likely to deliver vaginally after induction relative to subjects testing negative for oncofetal fibronectin.

Analogously, subjects testing negative for oncofetal fibronectin are more likely to require cesarean section after induction relative to subjects testing positive for oncofetal fibronectin or to a sample having an amount of oncofetal fibronectin indicating molecule above a threshold. For example, subjects testing negative for oncofetal fibronectin can be at least about 25%, at least about 26%, at least about 27%, at least about 28%, at least about 29%, at least about 30%, at least about 32%, at least about 34%, at least about 36%, at least about 38%, at least about 40%, at least about 45%, at least about 50%, at least about 55%, or at least about 60%, more likely to require cesarean section after induction relative to subjects testing positive for oncofetal fibronectin. Typically, subjects testing negative for oncofetal fibronectin are about 20-60%, about 21-55%, about 22-50%, about 23-45%, about 24-40%, about 25-38%, about 26-36%, about 27-34%, about 28-32%, or about 29-30%, more likely to require cesarean section after induction relative to subjects testing positive for oncofetal fibronectin.

Also provided herein, subjects testing positive for oncofetal fibronectin are more likely to deliver within 24 hours of induction relative to subjects testing negative for oncofetal fibronectin or to a sample having an amount of oncofetal fibronectin indicating molecule below a threshold. For example, subjects testing positive for oncofetal fibronectin can be at least about 30%, at least about 31%, at least about 32%, at least about 33%, at least about 34%, at least about 35%, at least about 36%, at least about 37%, at least about 38%, at least about 40%, at least about 42%, at least about 44%, at least about 46%, or at least about 50%, more likely to deliver within 24 hours of induction relative to subjects testing negative for oncofetal fibronectin. Typically, subjects testing positive for oncofetal fibronectin are about 20-60%, about 22-55%, about 24-50%, about 26-48%, about 28-46%, about 30-44%, about 32-43%, about 34-42%, about 35-41%, about 36-40%, about 37-39%, or about 38%, more likely to deliver within 24 hours of induction relative to subjects testing negative for oncofetal fibronectin.

Analogously, subjects testing negative for oncofetal fibronectin are more likely to deliver after more than 24 hours after induction relative to subjects testing positive for oncofetal fibronectin or to a sample having an amount of oncofetal fibronectin indicating molecule above a threshold. For example, subjects testing negative for oncofetal fibronectin can be at least about 40%, at least about 41%, at least about 42%, at least about 43%, at least about 44%, at least about 45%, at least about 46%, at least about 48%, at least about 50%, at least about 52%, at least about 55%, at least about 60%, at least about 65%, at least about 75%, or at least about 90%, more likely to deliver after more than 24 hours after induction relative to subjects testing positive for oncofetal fibronectin. Typically, subjects testing negative for oncofetal fibronectin are about 30-90%, about 32-75%, about 34-65%, about 36-60%, about 38-55%, about 39-53%, about 40-51%, about 41-50%, about 42-49%, about 43-48%, about 44-47%, or about 45-46%, more likely to deliver after more than 24 hours after induction relative to subjects testing positive for oncofetal fibronectin.

Also provided herein, subjects testing positive for oncofetal fibronectin are more likely to deliver within 48 hours of induction relative to subjects testing negative for oncofetal fibronectin or to a sample having an amount of oncofetal fibronectin indicating molecule below a threshold. For example, subjects testing positive for oncofetal fibronectin can be at least about 9%, at least about 10%, at least about 11%, at least about 12%, at least about 13%, at least about 14%, at least about 15%, at least about 16%, at least about 17%, at least about 18%, at least about 20%, at least about 22%, at least about 25%, at least about 30%, or at least about 35%, more likely to deliver within 48 hours of induction relative to subjects testing negative for oncofetal fibronectin. Typically, subjects testing positive for oncofetal fibronectin are about 5-35%, about 7-30%, about 8-25%, about 9-22%, about 10-20%, about 11-19%, about 12-18%, about 13-17%, about 14-16%, or about 15%, more likely to deliver within 48 hours of induction relative to subjects testing negative for oncofetal fibronectin.

Analogously, subjects testing negative for oncofetal fibronectin are more likely to deliver after more than 48 hours after induction relative to subjects testing positive for oncofetal fibronectin or to a sample having an amount of oncofetal fibronectin indicating molecule above a threshold. For example, subjects testing negative for oncofetal fibronectin can be at least about 25%, at least about 26%, at least about 27%, at least about 28%, at least about 29%, at least about 30%, at least about 32%, at least about 34%, at least about 36%, at least about 38%, at least about 40%, at least about 45%, at least about 50%, at least about 55%, or at least about 60%, more likely to deliver after more than 48 hours after induction relative to subjects testing positive for oncofetal fibronectin. Typically, subjects testing negative for oncofetal fibronectin are about 20-60%, about 21-55%, about 22-50%, about 23-45%, about 24-40%, about 25-38%, about 26-36%, about 27-34%, about 28-32% or about 29-30%, more likely to deliver after more than 48 hours after induction relative to subjects testing positive for oncofetal fibronectin.

Also provided herein, subjects testing positive for oncofetal fibronectin have a mean time interval between first dose of pre-induction agent and delivery that is shorter than the mean time interval between first dose of parturifacient and delivery for subjects testing negative for oncofetal fibronectin or a sample having an amount of oncofetal fibronectin indicating molecule below a threshold. For example, subjects testing positive for oncofetal fibronectin can have a mean time interval between first dose of pre-induction agent and delivery that is at least about 28%, at least about 29%, at least about 30%, at least about 31%, at least about 32%, at least about 33%, at least about 34%, at least about 35%, at least about 36%, at least about 38%, at least about 40%, at least about 42%, at least about 45%, at least about 50%, at least about 55%, at least about 60%, or at least about 75%, or at least about 6 hours, at least about 6.5 hours, at least about 7 hours, at least about 7.5 hours, at least about 8 hours, at least about 8.5 hours, at least about 9 hours, at least about 9.5 hours, at least about 10 hours, at least about 11 hours, at least about 13 hours, or at least about 15 hours, shorter than the mean time interval between first dose of parturifacient and delivery for subjects testing negative for oncofetal fibronectin. Typically, subjects testing positive for oncofetal fibronectin have a mean time interval between first dose of pre-induction agent and delivery that is 25-75% or about 25-75%, 26-60% or about 26-60%, 27-50% or about 27-50%, 28-45% or about 28-45%, 29-40% or about 29-40%, 30-38% or about 30-38%, 31-36% or about 31-36%, 32-34% or about 32-34%, or 33% or about 33%, or 6-20 hours or about 6-20 hours, 6.5-15 hours or about 6.5-15 hours, 7-14 hours or about 7-14 hours, 7.5-13 hours or about 7.5-13 hours, 8-12 hours or about 8-12 hours, 8.5-11 hours or about 8.5-11 hours, 9-10 hours or about 9-10 hours, or 9.5 or about 9.5 hours, shorter than the mean time interval between first dose of parturifacient and delivery for subjects testing negative for oncofetal fibronectin.

Analogously, subjects testing negative for oncofetal fibronectin have a mean time interval between first dose of pre-induction agent and delivery that is longer than the mean time interval between first dose of parturifacient and delivery for subjects testing positive for oncofetal fibronectin or a sample having an amount of oncofetal fibronectin indicating molecule above a threshold. For example, subjects testing negative for oncofetal fibronectin can have a mean time interval between first dose of pre-induction agent and delivery that is at least 45%, at least 46%, at least 47%, at least 48%, at least 49%, at least 50%, at least 52%, at least 55%, at least 60%, at least 65%, at least 70%, at least 75%, at least 80%, or at least 90%, or at least about 45%, at least about 46%, at least about 47%, at least about 48%, at least about 49%, at least about 50%, at least about 52%, at least about 55%, at least about 60%, at least about 65%, at least about 70%, at least about 75%, at least about 80%, or at least about 90%, or at least 6 hours, at least 6.5 hours, at least 7 hours, at least 7.5 hours, at least 8 hours, at least 8.5 hours, at least 9 hours, at least 9.5 hours, at least 10 hours, at least 11 hours, at least 13 hours, or at least 15 hours, or at least about 6 hours, at least about 6.5 hours, at least about 7 hours, at least about 7.5 hours, at least about 8 hours, at least about 8.5 hours, at least about 9 hours, at least about 9.5 hours, at least about 10 hours, at least about 11 hours, at least about 13 hours, or at least about 15 hours, longer than the mean time interval between first dose of parturifacient and delivery for subjects testing positive for oncofetal fibronectin. Typically, subjects testing negative for oncofetal fibronectin have a mean time interval between first dose of pre-induction agent and delivery that is 30-90% or about 30-90%, 35-80% or about 35-80%, 40-75% or about 40-75%, 42-70% or about 42-70%, 44-65% or about 44-65%, 45-60%, or about 45-60%, 46-58% or about 46-58%, 47-56% or about 47-56%, 48-54% or about 48-54%, 49-52% or about 49-52%, or 50% or about 50%, or 6-20 hours or about 6-20 hours, 6.5-15 hours or about 6.5-15 hours, 7-14 hours or about 7-14 hours, 7.5-13 hours or about 7.5-13 hours, 8-12 hours or about 8-12 hours, 8.5-11 hours or about 8.5-11 hours, 9-10 hours or about 9-10 hours, or 9.5 or about 9.5 hours, longer than the mean time interval between first dose of parturifacient and delivery for subjects testing positive for oncofetal fibronectin.

Also provided herein, subjects testing positive for oncofetal fibronectin have a mean time interval between oxytocin administration and delivery that is shorter than the mean time interval between oxytocin administration and delivery for subjects testing negative for oncofetal fibronectin or a sample having an amount of oncofetal fibronectin indicating molecule below a threshold. For example, subjects testing positive for oncofetal fibronectin can have a mean time interval between oxytocin administration and delivery that is at least 20%, at least 21%, at least 22%, at least 23%, at least 24%, at least 25%, at least 26%, at least 28%, at least 30%, at least 32%, at least 34%, at least 36%, at least 38%, at least 40%, at least 45%, at least 50%, or at least 60%, or at least about 20%, at least about 21%, at least about 22%, at least about 23%, at least about 24%, at least about 25%, at least about 26%, at least about 28%, at least about 30%, at least about 32%, at least about 34%, at least about 36%, at least about 38%, at least about 40%, at least about 45%, at least about 50%, or at least about 60%, or at least 3 hours, at least 3.2 hours, at least 3.4 hours, at least 3.6 hours, at least 3.8 hours, at least 4 hours, at least 4.2 hours, at least 4.4 hours, at least 4.6 hours, at least 4.8 hours, at least 5 hours, at least 5.5 hours, at least 6 hours, at least 6.5 hours, at least 7 hours, or at least 8 hours, or at least about 3 hours, at least about 3.2 hours, at least about 3.4 hours, at least about 3.6 hours, at least about 3.8 hours, at least about 4 hours, at least about 4.2 hours, at least about 4.4 hours, at least about 4.6 hours, at least about 4.8 hours, at least about 5 hours, at least about 5.5 hours, at least about 6 hours, at least about 6.5 hours, at least about 7 hours, or at least about 8 hours, shorter than the mean time interval between oxytocin administration and delivery for subjects testing negative for oncofetal fibronectin. Typically, subjects testing positive for oncofetal fibronectin have a mean time interval between oxytocin administration and delivery that is 15-60% or about 15-60%, 18-50% or about 18-50%, 20-45% or about 20-45%, 21-40% or about 21-40%, 22-35% or about 22-35%, 23-32% or about 23-32%, 24-30% or about 24-30%, 25-28% or about 25-28%, or 26-27% or about 26-27%, or 2-10 hours or about 2-10 hours, 3-8 hours or about 3-8 hours, 3.5-7 hours or about 3.5-7 hours, 3.8-6 hours or about 3.8-6 hours, 4-5 hours or about 4-5 hours, 4.1-4.8 hours or about 4.1-4.8 hours, 4.2-4.6 hours or about 4.2-4.6 hours, or 4.4 hours or about 4.4 hours, shorter than the mean time interval between oxytocin administration and delivery for subjects testing negative for oncofetal fibronectin.

Analogously, subjects testing negative for oncofetal fibronectin have a mean time interval between oxytocin administration and delivery that is longer than the mean time interval between oxytocin administration and delivery for subjects testing positive for oncofetal fibronectin or a sample having an amount of oncofetal fibronectin indicating molecule above a threshold. For example, subjects testing negative for oncofetal fibronectin can have a mean time interval between oxytocin administration and delivery that is at least 30%, at least 31%, at least 32%, at least 33%, at least 34%, at least 35%, at least 36%, at least 37%, at least 38%, at least 40%, at least 42%, at least 45%, at least 50%, at least 55%, at least 60%, or at least 75%, or at least about 30%, at least about 31%, at least about 32%, at least about 33%, at least about 34%, at least about 35%, at least about 36%, at least about 37%, at least about 38%, at least about 40%, at least about 42%, at least about 45%, at least about 50%, at least about 55%, at least about 60%, or at least about 75%, or at least 3 hours, at least 3.2 hours, at least 3.4 hours, at least 3.6 hours, at least 3.8 hours, at least 4 hours, at least 4.2 hours, at least 4.4 hours, at least 4.6 hours, at least 4.8 hours, at least 5 hours, at least 5.5 hours, at least 6 hours, at least 6.5 hours, at least 7 hours, or at least 8 hours, or at least about 3 hours, at least about 3.2 hours, at least about 3.4 hours, at least about 3.6 hours, at least about 3.8 hours, at least about 4 hours, at least about 4.2 hours, at least about 4.4 hours, at least about 4.6 hours; at least about 4.8 hours, at least about 5 hours, at least about 5.5 hours, at least about 6 hours, at least about 6.5 hours, at least about 7 hours, or at least about 8 hours, longer than the mean time interval between oxytocin administration and delivery for subjects testing positive for oncofetal fibronectin. Typically, subjects testing negative for oncofetal fibronectin have a mean time interval between oxytocin administration and delivery that is 20-75% or about 20-75%, 25-60% or about 25-60%, 28-55% or about 28-55%, 30-50% or about 30-50%, 31-45% or about 31-45%, 32-40% or about 32-40%, 33-38% or about 33-38%, 34-36% or about 34-36%, 35% or about 35%, or 2-10 hours or about 2-10 hours, 3-8 hours or about 3-8 hours, 3.5-7 hours or about 3.5-7 hours, 3.8-6 hours or about 3.8-6 hours, 4-5 hours or about 4-5 hours, 4.1-4.8 hours or about 4.1-4.8 hours, 4.2-4.6 hours or about 4.2-4.6 hours, or 4.4 hours or about 4.4 hours, longer than the mean time interval between oxytocin administration and delivery for subjects testing positive for oncofetal fibronectin.

Also provided herein, subjects testing positive for oncofetal fibronectin are likely to receive fewer pre-induction agent administrations relative to subjects testing negative for oncofetal fibronectin or to a sample having an amount of oncofetal fibronectin indicating molecule below a threshold. For example, subjects testing positive for oncofetal fibronectin can be predicted to receive at least 50%, at least 51%, at least 52%, at least 53%, at least 54%, at least 55%, at least 56%, at least 57%, at least 58%, at least 59%, at least 60%, at least 62%, at least 64%, at least 66%, at least 70%, at least 75%, at least 80%, or at least 90%, or at least about 50%, at least about 51%, at least about 52%, at least about 53%, at least about 54%, at least about 55%, at least about 56%, at least about 57%, at least about 58%, at least about 59%, at least about 60%, at least about 62%, at least about 64%, at least about 66%, at least about 70%, at least about 75%, at least about 80%, or at least about 90%, or at least 0.4, at least 0.45, at least 0.5, at least 0.55, at least 0.6, at least 0.65, at least 0.7, at least 0.8, at least 0.9, at least 1.0, or at least 1.1, or at least about 0.4, at least about 0.45, at least about 0.5, at least about 0.55, at least about 0.6, at least about 0.65, at least about 0.7, at least about 0.8, at least about 0.9, at least about 1.0, or at least about 1.1, fewer pre-induction agent administrations relative to subjects testing negative for oncofetal fibronectin. Typically, subjects testing positive for oncofetal fibronectin are predicted to receive 40-90% or about 40-90%, 45-80% or about 45-80%, 48-70% or about 48-70%, 50-68% or about 50-68%, 52-66% or about 52-66%, 54-64% or about 54-64%, 55-62% or about 55-62%, 56-60% or about 56-60%, or 57-58% or about 57-58%, or 0.3-1.1 or about 0.3-1.1, 0.35-1.0 or about 0.35-1.0, 0.4-0.85 or about 0.4-0.85, 0.45-0.75 or about 0.45-0.75, 0.5-0.7 or about 0.5-0.7, 0.52-0.68 or about 0.52-0.68, 0.54-0.66 or about 0.54-0.66, 0.58-0.62 or about 0.58-0.62, or 0.6 or about 0.6, fewer pre-induction agent administrations relative to subjects testing negative for oncofetal fibronectin.

Analogously, subjects testing negative for oncofetal fibronectin are likely to receive more pre-induction agent administrations relative to subjects testing positive for oncofetal fibronectin or to a sample having an amount of oncofetal fibronectin indicating molecule above a threshold. For example, subjects testing negative for oncofetal fibronectin can be likely to receive at least 65%, at least 66%, at least 67%, at least 68%, at least 69%, at least 70%, at least 71%, at least 72%, at least 73%, at least 75%, at least 77%, at least 80%, at least 85%, at least 90%, at least 100%, at least 110%, at least 120%, or at least 130%, or at least about 65%, at least about 66%, at least about 67%, at least about 68%, at least about 69%, at least about 70%, at least about 71%, at least about 72%, at least about 73%, at least about 75%, at least about 77%, at least about 80%, at least about 85%, at least about 90%, at least about 100%, at least about 110%, at least about 120%, or at least about 130%, or at least 0.4, at least 0.45, at least 0.5, at least 0.55, at least 0.6, at least 0.65, at least 0.7, at least 0.8, at least 0.9, at least 1.0, or at least 1.1, or at least about 0.4, at least about 0.45, at least about 0.5, at least about 0.55, at least about 0.6, at least about 0.65, at least about 0.7, at least about 0.8, at least about 0.9, at least about 1.0, or at least about 1.1, more pre-induction agent administrations relative to subjects testing positive for oncofetal fibronectin. Typically, subjects testing negative for oncofetal fibronectin are likely to receive 50-150% or about 50-150%, 55-125% or about 55-125%, 60-110% or about 60-110%, 62-100% or about 62-100%, 64-90% or about 64-90%, 66-85% or about 66-85%, 68-80% or about 68-80%, 70-75% or about 70-75%, 71-73% or about 71-73%, or 72% or about 72%, 0.3-1.1 or about 0.3-1.1, 0.35-1.0 or about 0.35-1.0, 0.4-0.9 or about 0.4-0.9, 0.45-0.75 or about 0.45-0.75, 0.5-0.7 or about 0.5-0.7, 0.52-0.68 or about 0.52-0.68, 0.54-0.66 or about 0.54-0.66, 0.58-0.62 or about 0.58-0.62, or 0.6 or about 0.6, more pre-induction agent administrations relative to subjects testing positive for oncofetal fibronectin.

In one embodiment, for purposes of use in conjunction with induction methods, a subject is considered positive for oncofetal fibronectin when the presence of an oncofetal fibronectin indicating molecule in a sample is equal to or above one or more threshold levels. As one skilled in the art will recognize, a threshold level can vary according to the type of sample measured and the selected stringency of the test. In one example, a threshold level for a buffer-treated cervicovaginal sample assayed using a test strip can be 50 ng/mL. In another example, a threshold level for a buffer-treated cervicovaginal sample assayed using a test strip can be 150 ng/mL.

In another embodiment, multi-tiered thresholds can be applied to the oncofetal fibronectin indicating molecule measurement, where multi-tiered thresholds include two or more threshold levels, where each larger threshold level indicates a further increased likelihood of success of induction, increased likelihood of vaginal delivery upon induction, likely decreased time interval between initiating induction and delivery, likely decreased time interval between administering a pre-induction agent and delivery, likely decreased time interval between administering oxytocin and delivery, increased likelihood of delivering within 24 hours of induction, increased likelihood of delivering within 48 hours of induction and decreased likelihood of more than one administration of pre-induction agent to the subject. An exemplary multi-tiered threshold is a two-tiered threshold where the lower threshold is 50 ng/mL and the higher threshold is 150 ng/mL for buffer-treated samples. An exemplary multi-tiered threshold is a two-tiered threshold where the lower threshold is 500 ng/mL and the higher threshold is 1500 ng/mL for untreated samples.

In accordance with the methods that include multi-tiered thresholds, methods are provided herein for classifying the likely outcome of induction, where the methods include measuring the amount of an oncofetal fibronectin indicating molecule in a sample from a subject and determining which, if any, multi-tiered threshold levels the sample is equal to or greater than and classifying the likely outcome of induction, where each increasing amount in the multi-tiered thresholds classifies the outcome as: increased likelihood of success of induction, increased likelihood of vaginal delivery upon induction, likely decreased time interval between initiating induction and delivery, likely decreased time interval between administering a parturifacient and delivery, likely decreased time interval between administering oxytocin and delivery, increased likelihood of delivering within 24 hours of induction, increased likelihood of delivering within 48 hours of induction and decreased likelihood of more than one administration of pre-induction agent to the subject, or combinations thereof.

In another embodiment, methods for detecting an oncofetal fibronectin indicating molecule in conjunction with induction of labor can be further coupled with one or more additional indicators or markers for induction outcome. Thus, provided herein are methods of determining the success of induction, where the methods include detecting an oncofetal fibronectin indicating molecule in a sample and determining one or more additional indicators or markers of induction outcome, where presence (or level above threshold) of an oncofetal fibronectin indicating molecule and one or more indicators or markers of induction outcome can indicate, relative to absence (or level below threshold) of the oncofetal fibronectin indicating molecule and/or a positive result for one or more additional indicators or markers of induction outcome, an increased likelihood of success of induction, increased likelihood of vaginal delivery upon induction, likely decreased time interval between initiating induction and delivery, likely decreased time interval between administering a parturifacient and delivery, likely decreased time interval between administering oxytocin and delivery, increased likelihood of delivering within 24 hours of induction, increased likelihood of delivering within 48 hours of induction and decreased likelihood of more than one administration of pre-induction agent to the subject, or combinations thereof.

A variety of indicators or markers of induction outcome are provided herein or are otherwise known in the art, and typically include measurements or observations of the pregnant subject or the fetus(es), or medical history of the pregnant subject. Exemplary indicators include, but are not limited to, cervical length, Bishop score, effacement, parity (i.e., previous vaginal delivery by the subject), cervical dilation, gestational age, body mass index (BMI), station, consistency, transvaginal ultrasound, and digital examination. In one example, an indicator is parity. In another example, the indicator is BMI.

i. Induction Methods and Compounds

Induction can be performed by any of a variety of methods known in the art, including administering a parturifacient and performing an induction procedure. A variety of induction procedures are known in the art, including, but not limited to, balloon catheterization such as foley balloon catheterization or Atad balloon catheterization, amniotic membrane stripping, extra-amniotic saline infusion, amniotomy, or nipple stimulation. In addition, a parturifacient can be administered, where the parturifacient can be any of a variety of compounds or compositions known in the art for pre-inducement, cervical ripening, or inducement. Exemplary parturifacients include, but are not limited to, prostaglandins such as PGE1 (misoprostol) and PGE2 (dinoprostone), oxytocic hormnones such as oxytocin and steroids such as RU486 (mifepristone).

The methods provided herein for predicting outcome of induction of a subject or identifying a subject with higher likelihood of successful induction can apply to any of the above induction methods and compounds and combinations thereof. In one example, presence (or level above threshold) of an oncofetal fibronectin indicating molecule in a sample from a subject can indicate a decreased time interval after induction with oxytocin, relative to subjects negative (or level below threshold) for the oncofetal fibronectin indicating molecule.

ii. Post-Induction Measurements

In another embodiment, the success of induction can be monitored by measuring the amount of an oncofetal fibronectin indicating molecule. A pregnant mother can be induced into labor by various methods including administering a parturifacient such as an oxytoxic hormone or a prostaglandin. After induction, the amount of an oncofetal fibronectin indicating molecule can be measured and an amount of an oncofetal fibronectin indicating molecule that is above a threshold level can indicate that the induction was effective and that delivery by the pregnant mother is imminent. Thus, also provided herein is a method for monitoring the effectiveness of induction of a pregnant woman by monitoring the post-induction amount of an oncofetal fibronectin indicating molecule in a pregnant woman. For example, a post-induction measurement of an oncofetal fibronectin indicating molecule that is above a threshold level can indicate that the induction of the pregnant woman is effective and the pregnant woman will soon deliver. Typically imminent delivery or likelihood that a woman will soon deliver, when used in the context of post-induction, refers to an indication that a pregnant woman will deliver within 48 hours or about 48 hours after induction, or within 48 hours or about 48 hours after a positive oncofetal fibronectin measurement. A post-induction measurement of an oncofetal fibronectin indicating molecule that is below a threshold level can indicate that the induction of the pregnant woman is ineffective and the pregnant woman will not soon deliver. In response to a negative post-induction oncofetal fibronectin measurement, a decision can be made whether to administer an additional induction procedure in order to accomplish vaginal delivery by the pregnant woman, or to instead choose to pursue childbirth by cesarean section. Thus, provided herein is a method for determining treatment method after induction of a subject, the method including measuring the amount of an oncofetal fibronectin indicating molecule in a sample from an induced subject and if the amount of the oncofetal fibronectin indicating molecule is at or above a threshold level, determining that additional induction is not required for vaginal delivery.

Also provided herein is a method for determining treatment method after induction of a subject, the method including measuring the amount of an oncofetal fibronectin indicating molecule in a sample from an induced subject and if the amount of the oncofetal fibronectin indicating molecule is below a threshold level, determining to administer one or more additional administrations of induction, or determining to proceed with childbirth by cesarean section.

Post-induction oncofetal fibronectin indicating molecule measurements can be performed on any of the samples and by any of the methods used in pre-induction methods provided herein. Additionally, post-induction oncofetal fibronectin indicating molecule measurements can be used in conjunction with multi-tiered thresholds as provided herein in regard to pre-induction measurements and also can be used in conjunction with one or more additional indicators of induction outcome, as provided herein in regard to pre-induction measurements.

e. Conceptus Indications

Provided herein is a method for selecting a conceptus for implantation. In the method, a conceptus sample, such as from a well or other receptacle containing the conceptus or from the conceptus itself is tested for an oncofetal fibronectin indicating molecule. A conceptus with a sample having an amount greater than a pre-determined level, or an amount greater than the amount for other concepti, or a rate of increase of such amount that is greater than a pre-determined level or compared to other concepti in a group can be identified as favorable for implantation and/or selected for implantation.

The methods, combinations, compositions and kits provided herein can be used for a variety of conceptus indications, where the methods include determining the presence or amount of an oncofetal fibronectin indicating molecule, where the conceptus is identified and/or selected according to the amount of oncofetal fibronectin indicating molecule produced by the conceptus. For example, a conceptus identified as producing oncofetal fibronectin indicating molecule or producing an amount of oncofetal fibronectin indicating molecule at or above a threshold level can be identified as a conceptus with increased competence for or increased likelihood of successfully implanting, relative to a conceptus not producing oncofetal fibronectin indicating molecule or producing an amount of oncofetal fibronectin indicating molecule below a threshold level. In another example, a conceptus identified as producing oncofetal fibronectin indicating molecule or producing an amount of oncofetal fibronectin indicating molecule at or above a threshold level can be identified as a conceptus with increased competence for or increased likelihood of successful subsequent fetal development once transferred, relative to a conceptus not producing oncofetal fibronectin indicating molecule or producing an amount of oncofetal fibronectin indicating molecule below a threshold level. In another example, a conceptus identified as producing oncofetal fibronectin indicating molecule or producing an amount of oncofetal fibronectin indicating molecule at or above a threshold level can be selected for use in implantation. In another example, a conceptus identified as producing oncofetal fibronectin indicating molecule or producing an amount of oncofetal fibronectin indicating molecule at or above a threshold level can be selected for use in a cell culture. In another example, a conceptus identified as producing oncofetal fibronectin indicating molecule or producing an amount of oncofetal fibronectin indicating molecule at or above a threshold level can be selected for use as a stem cell. In another example, a conceptus identified as not producing oncofetal fibronectin indicating molecule or producing an amount of oncofetal fibronectin indicating molecule below a threshold level can be identified as a conceptus with decreased competence for or decreased likelihood of successfully implanting, relative to a conceptus producing oncofetal fibronectin indicating molecule or producing an amount of oncofetal fibronectin indicating molecule at or above a threshold level. In another example, a conceptus identified as not producing oncofetal fibronectin indicating molecule or producing an amount of oncofetal fibronectin indicating molecule below a threshold level can be identified as a conceptus with decreased competence for or decreased likelihood of successful subsequent fetal development once transferred, relative to a conceptus producing oncofetal fibronectin indicating molecule or producing an amount of oncofetal fibronectin indicating molecule at or above a threshold level. In another example, a conceptus identified as not producing oncofetal fibronectin indicating molecule or producing an amount of oncofetal fibronectin indicating molecule below a threshold level can be selected to not use for implantation. In another example, a conceptus identified as not producing oncofetal fibronectin indicating molecule or producing an amount of oncofetal fibronectin indicating molecule below a threshold level can be selected for use in cell culture. In another example, a conceptus identified as not producing oncofetal fibronectin indicating molecule or producing an amount of oncofetal fibronectin indicating molecule below a threshold level can be selected for use as a stem cell.

Following penetration of the ovum by a sperm, fertilization is completed and the male and female pronuclei fuse, forming a zygote. The zygote undergoes rapid cell divisions and begins to develop. Approximately 4-5 days post-fertilization, the cells have developed into a ball of cells known as a morula. Further development at approximately days 5-6, the cells develop into a blastocyst. As the blastocyst develops further, distinct cell layers are formed. The inner cell mass gives rise to the embryo proper (also known as an embryoblast). The outer cell mass, also known as the trophoblast, develops as a layer of epithelium cells surrounding the embryo.

A conceptus attaches to the uterine wall, generally 6 to 7 days post-fertilization. The trophoblast, a layer of epithelial cells at the outer surface of the blastocyst, participates in the attachment of the blastocyst to the endometrial layer of cells in the uterus. Cells at the embryonic pole of the trophoblast layer differentiate to produce syncytioblasts, which begin the process of uterine implantation.

The trophoblast layer is the primary source for subsequent development of extraembryonic membranes including placental tissue, amnion and umbilical cord. The trophoblast cells of the conceptus synthesize and secrete oncofetal fibronectin protein. Oncofetal fibronectin is produced in early stage concepti including early stage embryos, and plays a role in the attachment of the conceptus to the uterine wall and/or vascularization of the attached conceptus. Oncofetal fibronectin is present at placental attachments sites at the placental-uterine junction.

The methods provided herein can be used to measure the presence and or amount of an oncofetal fibronectin indicating molecule produced by a conceptus, at one or more time points, and thereby to identify a conceptus with increased likelihood of successful uterine implantation. Accordingly, as provided herein, a conceptus that produces an oncofetal fibronectin indicating molecule has an increased likelihood of successful uterine implantation relative to a conceptus that does not produce the oncofetal fibronectin indicating molecule. Also, as provided herein, a conceptus that produces higher amounts of an oncofetal fibronectin indicating molecule relative to a conceptus that produces lower amounts of the oncofetal fibronectin indicating molecule, has an increased likelihood of successful uterine implantation. Also, as provided herein, a conceptus that produces an amount of an oncofetal fibronectin indicating molecule at or above a threshold level has an increased likelihood of successful uterine implantation relative to a conceptus that produces an amount of the oncofetal fibronectin indicating molecule below a threshold level. Also, as provided herein, a conceptus that produces a more rapidly increasing amount of an oncofetal fibronectin indicating molecule relative to a conceptus that produces a less rapidly increasing or a decreasing amount of the oncofetal fibronectin indicating molecule, has an increased likelihood of successful uterine implantation.

Similarly, as provided herein, a conceptus that does not produce an oncofetal fibronectin indicating molecule has a decreased likelihood of successful uterine implantation relative to a conceptus that produces the oncofetal fibronectin indicating molecule. Also, as provided herein, a conceptus that produces lower amounts of an oncofetal fibronectin indicating molecule has a decreased likelihood of successful uterine implantation relative to a conceptus that produces higher amounts of the oncofetal fibronectin indicating molecule. Also, as provided herein, a conceptus that produces an amount of an oncofetal fibronectin indicating molecule below a threshold level has a decreased likelihood of successful uterine implantation relative to a conceptus that produces an amount of the oncofetal fibronectin indicating molecule at or above a threshold level. Also, as provided herein, a conceptus that produces a less rapidly increasing or decreasing amount of an oncofetal fibronectin indicating molecule has a decreased likelihood of successful uterine implantation relative to a conceptus that produces a more rapidly increasing amount of the oncofetal fibronectin indicating molecule. The methods provided herein can be used to measure the presence and or amount of an oncofetal fibronectin indicating molecule produced by a conceptus, at one or more time points, and thereby to identify a conceptus with decreased likelihood of successful uterine implantation.

In some cases a conceptus can be categorized as oncofetal fibronectin positive when any oncofetal fibronectin indicating molecule is detected in a conceptus sample. In other cases, a conceptus can be categorized according to the amount of oncofetal fibronectin indicating molecule present in a sample. In other cases, a conceptus can be categorized as oncofetal fibronectin positive when the presence of an oncofetal fibronectin indicating molecule in a conceptus sample is equal to or above one or more threshold levels. In one example, a threshold level of an oncofetal fibronectin indicating molecule such as oncofetal fibronectin protein in conceptus culture medium assayed using a test strip can be 50 ng/mL. In another example, a threshold level of an oncofetal fibronectin indicating molecule such as oncofetal fibronectin protein in conceptus culture medium assayed using a test strip can be 150 ng/mL. Exemplary threshold values for categorizing a conceptus include 50 ng/ml, 150 ng/ml, 200 ng/ml, 300 ng/ml, 500 ng/ml, 750 ng/ml and 1000 ng/ml, or about 50 ng/ml, about 150 ng/ml, about 200 ng/ml, about 300 ng/ml, about 500 ng/ml, about 750 ng/ml and about 1000 ng/ml.

i. Detection of Oncofetal Fibronectin Production by a Conceptus

Any of a variety of methods provided herein or otherwise known in the art for detecting an oncofetal fibronectin indicating molecule in a sample can be used for detecting an oncofetal fibronectin indicating molecule produced by a conceptus, including, but not limited to, dot blot analysis, western blot analysis, northern blot analysis, southern blot analysis, RT-PCR methods, mass spectrometric methods, sandwich assays such as test strip-based sandwich assays and ELISA methods. For example, concepti (e.g., zygotes and embryos) can be placed in culture medium individually.

An oncofetal fibronectin indicating molecule can be detected in any of a variety of conceptus samples. Conceptus samples include conceptus extracts, samples from outside of the conceptus, such as culture medium, cell and tissue extracts, and cells, where one or more cells is removed from a conceptus, leaving the remainder of the conceptus competent for subsequent culture, implantation and/or development. The samples can be analyzed neat, or can be reagent-treated and/or fractionated prior to detection of an oncofetal fibronectin indicating molecule. In one example, an oncofetal fibronectin indicating molecule can be detected in vitro. In vitro detection includes the detection of an oncofetal fibronectin indicating molecule in isolated cells and tissues and cultured cells and tissues, including an oncofetal fibronectin indicating molecule secreted by such cells and tissues. Cells and tissues for detection include, but are not limited to, any and all stages of a conceptus, including zygotes, morulas, blastocysts, embryoblasts, embryo, and placenta, cells and cells layers of a conceptus, including but not limited to, cytotrophoblasts, trophoblasts, syncytiotrophoblasts, hypoblast and epiblast.

In some embodiments, an oncofetal fibronectin indicating molecule produced by a conceptus can be measured by measuring oncofetal fibronectin indicating molecule outside of the conceptus. For example, an oncofetal fibronectin indicating molecule can be present in the culture medium that contains the conceptus. An oncofetal fibronectin indicating molecule in medium that contains the conceptus can include an oncofetal fibronectin indicating molecule secreted by the conceptus. In one example, the presence and/or amount of an oncofetal fibronectin indicating molecule produced and/or secreted by a conceptus can be measured by detecting an oncofetal fibronectin indicating molecule in the culture medium that contains the conceptus. Detection of an oncofetal fibronectin indicating molecule in culture medium can include the comparison to controls including culture medium without any added embryos or zygotes, as will be apparent to one skilled in the art.

In one embodiment, the medium for such oncofetal fibronectin indicating molecule detection methods contains a single conceptus. In such methods, measurement of an oncofetal fibronectin indicating molecule in the medium can indicate the production of the oncofetal fibronectin indicating molecule by the conceptus.

In another embodiment, the medium for such oncofetal fibronectin indicating molecule detection methods contains two or more concepti. As provided herein, presence of an oncofetal fibronectin indicating molecule in culture medium can stimulate production of oncofetal fibronectin in a conceptus. Accordingly, presence of a conceptus in medium containing two or more concepti can indicate that the concepti are stimulated to produce oncofetal fibronectin and, therefore, can be identified as producing oncofetal fibronectin.

In other embodiments, an oncofetal fibronectin indicating molecule produced by a conceptus can be measured by measuring an oncofetal fibronectin indicating molecule present in a cell of a conceptus. For example, the oncofetal fibronectin indicating molecule present in a cell extract can be measured. A cell extract can be collected by removing a portion of cellular fluid such as cytoplasm using, for example, a syringe, or by cell harvesting. Cell harvesting can be performed, for example, by removing one or more cells from a conceptus, while leaving the conceptus sufficiently intact and competent for subsequent development and implantation. Oncofetal fibronectin indicating molecule detection in the removed cell can be performed immediately after removing the cell (e.g., by harvesting the cell), or after culturing the removed cell, where oncofetal fibronectin indicating molecule detection can be performed at one or more time points.

In other embodiments, conceptus extracts can be used for detecting an oncofetal fibronectin indicating molecule. A conceptus can contain one or more cavities, including, but not limited to, the blastoceol. An oncofetal fibronectin indicating molecule can be present in these cavities. A sample of the liquid in a conceptus cavity can be collected using known methods, for example, by extracting with a microsyringe.

Detection includes, but is not limited to, measurement of the presence, amount, rate of production and/or rate of secretion of an oncofetal fibronectin indicating molecule. An amount or rate can be compared to a threshold amount or can be compared to one or more amounts or rates from other concepti. For example, amounts or rates of oncofetal fibronectin indicating molecule production can be compared for two or more concepti, and the concepti can be classified from highest to lowest in amount oncofetal fibronectin indicating molecule produced or rate of increase of oncofetal fibronectin indicating molecule production.

A sample for which an oncofetal fibronectin indicating molecule is to be detected can be collected at any time post-isolation of the gametes and includes detection immediately after fertilization, and times following fertilization up to and including the time of implantation of a conceptus. For example, oncofetal fibronectin indicating molecule detection can be performed immediately following fertilization, and at 1, 2, 3, 4, 5, 6, 7, 8, 16, 24, 30, 36, 40, 48, 60, 72, 84, 96, 108, 120, 132, 144, and 168 hours and at any intermediate times post-fertilization. Detection of an oncofetal fibronectin indicating molecule also can be performed at times prior to transfer to a female including, but not limited to, the day of transfer, and 1 day, 2 days, 3 days, 4 days and 5 days pre-transfer. Oncofetal fibronectin indicating molecule detection can be performed at one or more of any such time points.

ii. Assisted Reproduction Technology Related Uses

The methods, compositions and kits provided herein for detecting an oncofetal fibronectin indicating molecule can be used in Assisted Reproduction Technologies (ART), including as predictive tests and for indicating success of ART. ART includes but is not limited to in vitro fertilization (IVF), zygote intra-fallopian transfer (ZIFT), gamete intra-fallopian transfer (GEFT), blastocyst transfer, in vitro maturation of oocytes coupled with IVF, and frozen embryo transfer (FET); these methods are known in the art. In these procedures gametes (ova and sperm) are collected, manipulated in vitro and then one or more gametes or cells derived from gametes are implanted into the female. One example of ART, in vitro fertilization (IVF), includes the collection of ova and sperm, fertilization of the ova in vitro, culturing the fertilized cells and allowing the fertilized cells to divide and develop in vitro, and then transferring one or more cultured fertilized cells (typically embryos) into the uterus. Another example of ART, zygote intra-fallopian transfer (ZIFT) includes collection of ova and sperm, fertilization of the ova in vitro, and transfer of a zygote (or more than one zygote) into the fallopian tubes. Following transfer of the conceptus (e.g., zygote or embryo) to the female, the conceptus may or may not subsequently attach to the uterine wall, and a conceptus that attaches to the uterine wall can further develop. The ability of the conceptus to successfully implant in the uterine wall plays a key role in the success of these procedures, because if the conceptus does not successfully implant, the development will arrest and the pregnancy will not go to term.

Accordingly, provided herein are methods of performing ART by transferring to a female a conceptus identified using the methods provided herein as having an increased competence for or increased likelihood of successful implantation in the uterus, and/or improved likelihood of successful subsequent fetal development once transferred.

Development of the conceptus in in vitro fertilization and other ART procedures parallels in vivo fertilization in development, with the exception that some of the stages occur in vitro prior to implantation and the remainder are completed post-implantation. In ART procedures, the conceptus is transferred to the uterus generally at approximately 2 to 6 days post-fertilization, usually at approximately 3 to 5 days post-fertilization. The conceptus also can be transferred into the fallopian tubes, generally 1, 2 and/or 3 days post-fertilization. Transfer of conceptus includes transfer of a 2 cell, 2-4 cell, 4 cell, 4-8 cell and greater than 8 cell stage conceptus and can include transfer at the blastocyst stage. Transfer includes transfer of one or more concepti, usually 1-5, 2-5, 3-5 and 2-3 concepti are transferred. In some cases, such as single embryo transfer, only one conceptus is transferred to the female. ART also includes frozen embryo transfer where the embryos, following fertilization and optionally a period of cell culture, are frozen for later use, e.g., implantation into a female at a later time. Such embryos can be stored indefinitely under frozen conditions, such as storage in liquid nitrogen.

iii. Post-Measurement Steps

As provided herein, production of an oncofetal fibronectin indicating molecule can be measured. Oncofetal fibronectin indicating molecule measurements can be used to characterize a conceptus. For example, a conceptus for which an oncofetal fibronectin indicating molecule is present, is at or above a threshold level or has a higher increasing rate of production can be characterized as having an increased competence for or increased likelihood of successful implantation in the uterus, and/or improved likelihood of successful subsequent fetal development once transferred, relative to a conceptus for which the oncofetal fibronectin indicating molecule is absent, is below a threshold level or has a decreasing rate of production.

a. Increasing Oncofetal Fibronectin Production

Also provided herein are methods for increasing production of oncofetal fibronectin in a conceptus. As provided herein, a conceptus that produces oncofetal fibronectin at a sufficiently low level or rate, is not typically selected for implantation. Methods provided herein can be used to select a conceptus producing an oncofetal fibronectin indicating molecule below a threshold level or rate for implantation, and treating the conceptus with one or more methods for increasing production of an oncofetal fibronectin indicating molecule in a conceptus. In one example, a conceptus can be monitored on one or more occasions after such treatment for production of an oncofetal fibronectin indicating molecule, and upon measurement of an amount of rate of production above a threshold level or rate, the conceptus can be as suitable for implantation.

Oncofetal fibronectin synthesis can be increased in amount and/or rate of synthesis by external stimuli. Synthesis of oncofetal fibronectin can increase over time in culture. For example, some isolated human trophoblasts secrete barely detectable oncofetal fibronectin in culture shortly after isolation. The synthesis of oncofetal fibronectin increases over time of culturing in vitro. A variety of constituents of the culture medium can stimulate oncofetal fibronectin production, including but not limited to serum, such as human and other mammalian serum, and transforming growth factors, including TGF-α and TGF-β. Oncofetal fibronectin synthesis also can be stimulated by cell attachment including, but not limited to, incubation of cells with extracellular matrix, synthetic matrices, or plastic.

b. Identify Conceptus Based on Oncofetal Fibronectin Production

In the methods provided herein, detection of an oncofetal fibronectin indicating molecule can be coupled with classification of a conceptus according to the oncofetal fibronectin indicating molecule production by the conceptus. Presence, amount or rate of oncofetal fibronectin indicating molecule production can indicate the competence of a conceptus for implantation, or the likelihood of a conceptus successfully implanting or the likelihood of successful subsequent fetal development once transferred. Accordingly, the methods provided herein can be used to classify a conceptus as having an increased competence for, or increased likelihood of, successful implantation in the uterus, and/or improved likelihood of successful subsequent fetal development once transferred, where a conceptus with the presence of, an increased amount of, or a higher rate of increase of oncofetal fibronectin indicating molecule has an increased competence for, or increased likelihood of, successful implantation in the uterus, and/or improved likelihood of successful subsequent fetal development once transferred, relative to a conceptus with an absence of, a decreased amount of, or a lower rate of increase or a decrease of oncofetal fibronectin indicating molecule. Similarly, methods provided herein can be used to identify a conceptus as suitable for implantation, where a conceptus in which an oncofetal fibronectin indicating molecule is present or is present at or above a threshold level or is increasing in production can be identified as having a sufficiently high rate competence for, or likelihood of, successful implantation in the uterus, and/or likelihood of successful subsequent fetal development once transferred, and therefore as suitable for implantation.

i. Selection of a Conceptus

Detection of an oncofetal fibronectin indicating molecule can be used to predict and to improve conceptus implantation and viability in ART procedures including, but not limited to, in vitro fertilization procedures, zygote intra-fallopian transfer and frozen embryo transfer. As provided herein, the presence, amount, rate of production and/or rate of secretion of an oncofetal fibronectin indicating molecule can be used as an indicator for the ability of a conceptus to implant in the uterus and/or for such implantation to be successfully developed and maintained. A conceptus having an increased competence for or increased likelihood of successful implantation in the uterus, and/or improved likelihood of successful subsequent fetal development once transferred, can be selected for transfer to a female (e.g., transfer to the uterus or fallopian tubes).

In one embodiment, detection of an oncofetal fibronectin indicating molecule is used to select one or more concepti (e.g., embryos and zygotes) for implantation. For example, an ovum can be collected and fertilized in vitro, to form a conceptus. Following fertilization, an oncofetal fibronectin indicating molecule can be detected in one or more samples corresponding to one or more concepti and the presence or amount of oncofetal fibronectin indicating molecule in the samples can be used to select one or more concepti having an increased competence for or increased likelihood of successful implantation in the uterus, and/or improved likelihood of successful subsequent fetal development once transferred.

In yet another embodiment, detection of an oncofetal fibronectin indicating molecule can be used to select a conceptus for frozen storage. In ART procedures, often more concepti are produced in vitro than will be transferred to a female. Concepti that are not transferred can be stored indefinitely in frozen storage such as liquid nitrogen tanks. Concepti can be selected for frozen storage, for example, based on detection of an amount of an oncofetal fibronectin indicating molecule, a threshold level of an oncofetal fibronectin indicating molecule, rate of production and/or secretion of an oncofetal fibronectin indicating molecule, and/or detection coupled with selection in comparison to production of an oncofetal fibronectin indicating molecule by other concepti.

ii. Criteria for Selection

In one aspect of the embodiment, a conceptus with the highest oncofetal fibronectin indicating molecule level and/or concepti (more than one conceptus) with the highest levels of oncofetal fibronectin indicating molecule relative to one or more other concepti are selected for transfer. In another aspect, one or more concepti with the lowest oncofetal fibronectin indicating molecule levels are discarded and/or are not selected for transfer. In yet another aspect, concepti with the lowest oncofetal fibronectin indicating molecule levels are stimulated for oncofetal fibronectin production before transfer.

In another embodiment, a threshold level of detectable oncofetal fibronectin indicating molecule is used to select concepti (e.g., embryos and zygotes) for transfer. In one aspect of the embodiment the presence of an amount equal to or above a threshold level of an oncofetal fibronectin indicating molecule indicates a conceptus to select for transfer. In another aspect of the embodiment, the presence of an amount less than a threshold level is used to discard a conceptus and/or identify conceptus not preferred for transfer. In yet another embodiment, the presence of an amount less than a threshold level is used to select a conceptus for stimulation of oncofetal fibronectin production prior to transfer. In such methods, a positive result can be the presence of any amount of an oncofetal fibronectin indicating molecule equal to or above a threshold level, and a negative result can be any amount of an oncofetal fibronectin indicating molecule below a threshold level.

In another embodiment, the rate of increase of oncofetal fibronectin indicating molecule production is detected and used to select a conceptus for transfer. For example, an oncofetal fibronectin indicating molecule can be detected at two or more time points post-fertilization and a rate of oncofetal fibronectin indicating molecule synthesis and/or oncofetal fibronectin indicating molecule secretion can be determined, based on the change of oncofetal fibronectin indicating molecule levels over time. In one aspect of the embodiment, one or more concepti are chosen that exhibit the highest rate of oncofetal fibronectin indicating molecule production relative to other concepti. In another aspect, one or more concepti are chosen that exhibit a rate equal to or above a chosen threshold rate of oncofetal fibronectin indicating molecule production. In another aspect of the embodiment, concepti that exhibit a lower rate of oncofetal fibronectin indicating molecule relative to other concepti or as compared to a threshold rate are discarded and/or are selected as concepti not for transfer.

c. Other Markers Used in Conjunction With Oncofetal Fibronectin

In any of the embodiments herein, oncofetal fibronectin indicating molecule detection can be coupled with other testing procedures which monitor and/or select criteria in the conceptus and/or female recipient.

i. Conceptus Markers

For example, oncofetal fibronectin indicating molecule detection can be coupled with pre-implantation characterization and/or diagnosis of the conceptus. Such characterization can be based on genetic characteristics, gene expression, and/or morphology of the conceptus. Characterization and/or diagnosis can be performed at any time after fertilization until implantation, and is typically performed between 1 and 7 days after fertilization, for example from 2-3 days after fertilization.

In one example, genetic characterization and/or diagnosis can be conducted. In such procedures, one or more cells, generally a single cell, is removed from the conceptus and tested for the absence and/or presence of genetic markers. In one embodiment, a conceptus can be selected for transfer based on detection of an oncofetal fibronectin indicating molecule and detection of at least one genetic marker. In another example of coupled detection, oncofetal fibronectin (onfFN) detection is coupled with detection of additional implantation competence markers such as additional extracellular matrix proteins. In another example of coupled detection, ofnFN detection is coupled with detection of at least one quality marker including, but not limited to, expression of oxidative stress genes (e.g., MnSOD, CuZnSOD, SOX), apoptosis genes (e.g., Bax), maternal recognition of pregnancy genes (e.g., INF-tau), genes related to communication through gap junctions (e.g., Cx31 and Cx43), and/or differentiation and implantation genes (e.g., LIF and LR-beta). A variety of markers are known in the art, as exemplified in Reese et al., *J. Biol. Chem.*, 276:44137-44145 (2001); and Yoshioka et al., *Biochem. Biophys. Res. Commun.* 272:531-538 (2000).

In another embodiment, oncofetal fibronectin indicating molecule detection can be combined with morphological characterization and/or diagnosis of a conceptus. Morphological features of a conceptus can indicate the likelihood of successful implantation and development to pregnancy of a conceptus. A variety of morphological features characteristic of concepti with an increased likelihood of successful implantation and development to pregnancy are known in the art, and include, but are not limited to, cell number, degree of fragmentation, cell regularity, symmetry, pronuclear morphology, follicle size, follicular fluid volume, multi-nucleation, presence of vacuoles, and granularity.

ii. Maternal Markers

In any of the embodiments herein, oncofetal fibronectin indicating molecule detection can be coupled with other testing procedures which monitor and/or select criteria in the female recipient. For example, a female recipient can be tested for markers correlative with receptivity to successful transfer and subsequent implantation of a conceptus. Such markers can include detection of mucin glycoproteins (e.g., MUC1) and heparin sulfate-binding proteins. Additional markers for use include phenotypes of follicles that can contribute to the competence and viability of the oocyte to participate in successful fertilization and conceptus development, including, but not limited to, expression of 11β-hydroxysteroid dehydrogenase by granulosa cells, adhesion and proliferation of cumulus cells, steroidogenic activity of cumulus and perifollicular vascularity and vascular epithelial growth factors bound to granulosa and cumulus cells.

iv. Cell Culture and Stem Cell Uses

Methods and probes for detection of an oncofetal fibronectin indicating molecule can be used to select cells and tissues for non-implantation uses, including for use in cell culture and as stem cells. In one example, a cell or conceptus not selected for implantation can be selected for use in further in vitro culture as a source of embryonic stem cells. Such cells are useful in the research and treatment of diseases and conditions, including, but not limited to immunological and neurodegenerative diseases such as Parkinson's disease, lupus, diabetes, stroke, rheumatoid arthritis, heart trauma, and in cell replacement therapies and tissue regeneration.

In one embodiment, detection of an oncofetal fibronectin indicating molecule is used to select a conceptus not competent or less competent for transfer to a female. A conceptus further can be selected for use in cell culture or as stem cells, for example, based on their viability in culture. Detection of an oncofetal fibronectin indicating molecule can include any of the detection methods, assays and selections herein, including selections based on detection of an amount, a threshold level, a rate of synthesis and/or a rate of secretion of an oncofetal fibronectin indicating molecule.

2. Indicator of Cancer

As provided herein, the presence or an amount of an oncofetal fibronectin indicating molecule in body tissue or fluid sample can be associated with tumor, cancer, metastasis or neoplasia. An oncofetal fibronectin indicating molecule can serve as a marker for the presence of, the risk of developing, the progression or regression of, the recurrence of, aggressiveness of, or treatment of, tumor, cancer, metastasis or neoplasia in a subject. The methods provided herein can be used to determine the presence or absence, or the amount of an oncofetal fibronectin indicating molecule in a sample, and also can be used to monitor levels of an oncofetal fibronectin indicating molecule in a subject over time. Presence or an elevated amount above a threshold of an oncofetal fibronectin indicating molecule can indicate the presence of, an increased risk of developing, the progression of, the recurrence of, increased aggressiveness of, or ineffectiveness of treatment of, tumor, cancer, metastasis or neoplasia in a subject. Absence or a lower amount below a threshold of an oncofetal fibronectin indicating molecule can indicate the absence of, a decreased risk of developing, the regression of, the lack of recurrence of, decreased aggressiveness of, or effectiveness of treatment of, tumor, cancer, metastasis or neoplasia in a subject.

An oncofetal fibronectin indicating molecule can be used as a biological marker for a variety of cancer (e.g., neoplastic) diseases, including, but not limited to, carcinomas of the lung, breast, ovary, stomach, pancreas, larynx, esophagus, testes, liver, parotid, biliary tract, colon, rectum, cervix, uterus, endometrium, kidney, bladder, prostate, thyroid, pituitary, eye, brain, oral, skin, head and neck cancer, lymphoma, leukemia, squamous cell carcinomas, adenocarcinomas, small cell carcinomas, melanomas, gliomas, sarcomas and neuroblastomas. An oncofetal fibronectin indicating molecule indicating various cancerous (e.g., neoplastic) conditions can be detected in any of a variety of body tissue and fluid samples, including those provided herein or are otherwise known in the art; and any method for collecting a sample can be used that is appropriate for the tissue or organ under examination, as will be understood by one of skill in the art. Any oncofetal fibronectin indicating molecule detection method provided herein or otherwise known in the art can be used to detect the presence or amount of an oncofetal fibronectin indicating molecule in a sample. Provided herein below as non-exclusive examples of cancer-related oncofetal fibronectin indicating molecule detection methods are descriptions of detection of an oncofetal fibronectin indicating molecule in blood, plasma, serum, urine, lavage, sputum, tissue, aspirate, stool, or swab samples that can be used to indicate the presence, risk of, development of, likelihood of recurrence of, progression or regression of, aggressiveness of, or efficacy of treatment of, bladder, breast, cervical, ovarian, prostate, lung, or colorectal cancers.

The methods provided herein can include collecting a sample, measuring for the presence of an oncofetal fibronectin indicating molecule in a sample and/or measuring the amount of an oncofetal fibronectin indicating molecule in the sample, optionally characterizing the oncofetal fibronectin indicating molecule in the sample. Presence of an oncofetal fibronectin indicating molecule, or an amount of oncofetal fibronectin indicating molecule equal to or above one or more thresholds can characterize the sample as oncofetal fibronectin positive, or as falling within a particular group, according to the highest threshold equal to or less than the measured oncofetal fibronectin indicating molecule amount. Absence of an oncofetal fibronectin indicating molecule, or an amount of oncofetal fibronectin indicating molecule below one or more thresholds can characterize the sample as oncofetal fibronectin negative, or as falling within a particular group, according to the lowest threshold greater than the measured oncofetal fibronectin indicating molecule amount.

A sample collected can be taken from any source, as provided herein or otherwise known in the art. Exemplary sources for samples include, but are not limited to, a tissue sample, swab of a region suspected of being cancerous, a lavage sample, a blood sample, a plasma sample, a serum sample, an interstitial fluid sample, a lymph sample, a lymphatic fluid sample, and a urine sample. The methods provided herein for collecting samples permit increased sensitivity, increased ease of use, increased sample quality or combinations thereof, relative to previously used methods. Samples can be stored and/or treated using the methods known in the art or provided herein. Presence of an oncofetal fibronectin indicating molecule in the sample can be determined using the methods provided herein or otherwise known in the art. Exemplary methods include dot blot analysis, western blot analysis, northern blot analysis, southern blot analysis, RT-PCR methods, mass spectrometric methods, sandwich assays such as test strip-based sandwich assays and ELISA methods. The oncofetal fibronectin indicating molecule measurement methods provided herein permit increased sensitivity in oncofetal fibronectin indicating molecule detection and provide additional advantages as well. Accordingly, the methods disclosed herein can be used for early indication of the presence of cancer (e.g., hyperplastic, neoplastic, malignant or metastatic) cells, by, for example being able to detect lower levels of an oncofetal fibronectin indicating molecule in a sample, or by facilitating more frequent testing for cancer.

Detection of an oncofetal fibronectin indicating molecule in a sample can indicate the presence of a solid tumor, a leukemia (i.e., a blood-born cancer), cancer, metastasis, hyperplasia or neoplasia in a subject. Detection of an oncofetal fibronectin indicating molecule in a sample can indicate the stage or severity of a solid tumor, a leukemia, cancer, metastasis, hyperplasia or neoplasia in a subject. As provided herein, an oncofetal fibronectin indicating molecule is present in a variety of cancers (solid and blood-born), tumors, metastases and neoplasias. Thus, an oncofetal fibronectin positive sample can be used to indicate the presence and/or stage of a tumor, cancer, metastasis or neoplasia in a subject, or can be used to indicate the presence of cancer (e.g., neoplastic, malignant or metastatic) cells in a subject. Detection of the presence of an oncofetal fibronectin indicating molecule can indicate the presence and/or stage of a tumor, cancer, metastasis or neoplasia in a subject, or can indicate the presence of cancer (e.g., neoplastic, malignant or metastatic) cells in a subject. In another embodiment, detection of an oncofetal fibronectin indicating molecule at or above one or more threshold levels can indicate the presence and/or stage of a tumor, cancer, metastasis or neoplasia in a subject, or the presence of cancer (e.g., neoplastic, malignant or metastatic) cells in a subject.

Absence or level below a threshold of an oncofetal fibronectin indicating molecule in the sample can indicate the absence of tumor, cancer, metastasis or neoplasia in a subject. As provided herein, since an oncofetal fibronectin indicating molecule is present in body tissues and fluids in numerous cancer (neoplastic) diseases, absence of an oncofetal fibronectin indicating molecule can indicate that the subject is free of a cancer (neoplastic) disease. For example, an oncofetal fibronectin negative sample can be used to indicate absence of a tumor, cancer, metastasis or neoplasia in a subject, or can be used to indicate the absence of cancer (e.g., neoplastic, malignant or metastatic) cells in a subject. The absence or level below a threshold of an oncofetal fibronectin indicating molecule can indicate the absence of tumor, cancer, metastasis or neoplasia in a subject, or can indicate the absence of cancer (e.g., hyperplastic, neoplastic, malignant or metastatic) cells in a subject. Also, an oncofetal fibronectin indicating molecule below one or more threshold levels can indicate the absence of tumor, cancer, metastasis or neoplasia in a subject, or the absence of cancer (e.g., neoplastic, malignant or metastatic) cells in a subject.

In another embodiment, the methods provided herein can be used to indicate an increased risk of a subject developing a tumor, cancer, metastasis or malignant neoplasia. For example, the methods provided herein can be used to indicate an increased risk of an organ, tissue or cell becoming cancerous (neoplastic, malignant or metastatic), relative to a normal population or relative to the individual. An organ, tissue or cell that contains or is adjacent a region containing an oncofetal fibronectin indicating molecule or an amount of an oncofetal fibronectin indicating molecule above normal levels can indicate an increased risk of developing cancer (neoplastic, malignant or metastatic growth) relative to an organ, tissue or cell that does not contain or is not adjacent to a region containing an oncofetal fibronectin indicating molecule or levels of an oncofetal fibronectin indicating molecule above normal. Accordingly, using the methods provided herein, an oncofetal fibronectin positive sample can be used to indicate an increased risk of a subject developing tumor, cancer, metastasis or malignant neoplasia, or to indicate an increased risk of cells, including normal, abnormal, dysplastic or hyperplastic cells, developing into cancer (neoplastic, malignant or metastatic) cells, relative to a subject with an oncofetal fibronectin negative sample or relative to a sample having an amount of oncofetal fibronectin below a threshold. The presence of an oncofetal fibronectin indicating molecule in a sample or an amount of an oncofetal fibronectin indicating molecule in a sample at or above a threshold can indicate an increased risk of an organ, tissue or cell in a subject becoming cancerous (neoplastic, malignant or metastatic), or an increased risk of a normal, abnormal, dysplastic or hyperplastic cell becoming cancerous (neoplastic, malignant or metastatic), relative to a subject with a sample in which an oncofetal fibronectin indicating molecule is absent or below a threshold level. In one aspect, the presence of an oncofetal fibronectin indicating molecule in a sample or an amount of an oncofetal fibronectin indicating molecule in a sample at or above a threshold can indicate an increased risk of an organ, tissue or cell in a subject becoming cancerous (neoplastic, malignant or metastatic), or an increased risk of a normal, abnormal, dysplastic or hyperplastic cell becoming cancerous (neoplastic, malignant or metastatic), relative to a baseline sample of the subject.

In another embodiment, the methods provided herein can be used to indicate a decreased risk of a subject developing a tumor, cancer; metastasis or neoplasia. For example, the methods provided herein can be used to indicate a decreased risk of an organ, tissue or cell becoming cancerous (e.g., neoplastic, malignant or metastatic). An organ, tissue or cell that lacks or is adjacent a region lacking an oncofetal fibronectin indicating molecule or has an amount of an oncofetal fibronectin indicating molecule at or below normal levels can indicate a decreased risk of future development of cancerous (e.g., neoplastic, malignant or metastatic) growth relative to an organ, tissue or cell that does contain or is adjacent to a region containing an oncofetal fibronectin indicating molecule or amounts of an oncofetal fibronectin indicating molecule above normal. Accordingly, using the methods provided herein, an oncofetal fibronectin negative sample can be used to indicate a decreased risk of a subject developing tumor, cancer, metastasis or neoplasia, or to indicate a decreased risk of cells, including normal, abnormal, dysplastic or hyperplastic cells, developing into cancerous (e.g., neoplastic, malignant or metastatic) cells, relative to a subject with an oncofetal fibronectin positive sample or relative to a sample having an amount of oncofetal fibronectin equal to or above a threshold. The presence of an oncofetal fibronectin indicating molecule in a sample or an amount of an oncofetal fibronectin indicating molecule in a sample below a threshold can indicate a decreased risk of an organ, tissue or cell in a subject becoming of cancerous (e.g., neoplastic, malignant or metastatic), or a decreased risk of a normal, abnormal, dysplastic or hyperplastic cell becoming of cancerous (e.g., neoplastic, malignant or metastatic), relative to a subject with a sample in which an oncofetal fibronectin indicating molecule is present or at or above a threshold level, or relative to a baseline sample from the subject.

Further provided herein is a method for indicating the development of cancer by measuring oncofetal fibronectin indicating molecule in a sample, where the presence of an oncofetal fibronectin indicating molecule in a sample or an amount of an oncofetal fibronectin indicating molecule in a sample at or above a threshold can indicate development of an organ, tissue or cell into a cancerous organ, tissue or cell. Standard methods for defining cancerous organs, tissues or cells require histological examination of the morphology of the organ, tissue or cells. As provided herein, measurement of an oncofetal fibronectin indicating molecule can function to indicate that organs, tissues or cells that may not be morphologically defined as cancerous, are developing or have developed into cancerous or pre-cancerous organs, tissues or cells, notwithstanding any morphological classification.

Further provided herein is a method for indicating the development of cancer cells (including normal cells, abnormal cells, dysplastic cells, hyperplastic cells, pre-cancerous neoplastic cells, malignant cells or metastatic cells) into cells that are increasingly primitive, undifferentiated, anaplastic, and/or unregulated in growth. Normal cells can develop into cancerous cells, and the process of this change can take place by normal cells becoming more primitive, undifferentiated, anaplastic, and/or unregulated in growth. The development of normal cells into cancerous cells can include a variety of transitions such as, for example, normal cells developing into abnormal cells, abnormal cells developing into dysplastic cells, dysplastic cells developing into hyperplastic cells, hyperplastic cells developing into neoplastic cells, neoplastic cells developing into malignant cells, and malignant cells developing into metastatic cells. As provided herein, an oncofetal fibronectin positive result indicates that cells are developing or have an increased likelihood of developing into cells that are increasingly primitive, undifferentiated, anaplastic, and/or unregulated in growth. Accordingly, methods are provided herein for indicating that cells are developing into cells that are increasingly primitive, undifferentiated, anaplastic, and/or unregulated in growth, by measuring the oncofetal fibronectin indicating molecule in a sample, where presence, or an amount at or above a threshold indicates that the cells are developing into cells that are increasingly primitive, undifferentiated, anaplastic, and/or unregulated in growth. Also provided herein are methods for indicating that cells have an increased likelihood of developing into cells that are increasingly primitive, undifferentiated, anaplastic, and/or unregulated in growth, by measuring the oncofetal fibronectin indicating molecule in a sample, where presence, or an amount at or above a threshold indicates that the cells have an increased likelihood of developing into cells that are increasingly primitive, undifferentiated, anaplastic, and/or unregulated in growth, relative to a control sample in which an oncofetal fibronectin indicating molecule is absent or is below a threshold. In one example, a sample of abnormal, dysplastic or hyperplastic cells, or a swab of a region containing abnormal, dysplastic or hyperplastic cells, can be examined for the presence and/or amount of an oncofetal fibronectin indicating molecule, where an oncofetal fibronectin positive sample can indicate that the abnormal, dysplastic or hyperplastic cells are developing into cells that are increasingly primitive, undifferentiated, anaplastic, and/or unregulated in growth.

Similarly, absence of an oncofetal fibronectin indicating molecule, or oncofetal fibronectin indicating molecule amounts below a threshold indicate that cells are not developing or have a decreased likelihood of developing into cells that are increasingly primitive, undifferentiated, anaplastic, and/or unregulated in growth. Accordingly, methods are provided herein for indicating that cells are not developing into cells that are increasingly primitive, undifferentiated, anaplastic, and/or unregulated in growth, by measuring an oncofetal fibronectin indicating molecule in a sample, where absence, or an amount below a threshold indicates that the cells are not developing into cells that are increasingly primitive, undifferentiated, anaplastic, and/or unregulated in growth. Also provided herein are methods for indicating that cells have a decreased likelihood of developing into cells that are increasingly primitive, undifferentiated, anaplastic, and/or unregulated in growth, by measuring the oncofetal fibronectin indicating molecule in a sample, where absence, or an amount below a threshold indicates that the cells have a decreased likelihood of developing into cells that are increasingly primitive, undifferentiated, anaplastic, and/or unregulated in growth, relative to a sample in which an oncofetal fibronectin indicating molecule is present or is at or above a threshold. In one example, a sample of abnormal, dysplastic or hyperplastic cells, or a swab of a region containing abnormal, dysplastic or hyperplastic cells, can be examined for the presence and/or amount of an oncofetal fibronectin indicating molecule, where an oncofetal fibronectin negative sample can indicate that the abnormal, dysplastic or hyperplastic cells are not developing into cells that are increasingly primitive, undifferentiated, anaplastic, and/or unregulated in growth.

In another embodiment, the methods provided herein can be used to indicate progression of a tumor, cancer, metastasis or neoplasia in a subject. For example, the methods provided herein can be used to indicate progression of cancer of an organ, tissue or cell. Presence of an oncofetal fibronectin indicating molecule or an amount at or above a threshold can indicate progression of a cancer or metastasis where a cancer or metastasis in a subject continues to be, or is increasingly, malignant or metastatic. Accordingly, using the methods provided herein, an oncofetal fibronectin positive sample can be used to indicate progression of a tumor, cancer, metastasis or neoplasia in a subject, or to indicate progression of cancer cells, in a subject. The presence of an oncofetal fibronectin indicating molecule in a sample or an amount of an oncofetal fibronectin indicating molecule in a sample at or above a threshold can indicate progression of a tumor, cancer, metastasis or neoplasia in a subject, or to indicate progression of cancer cells, in a subject.

In another embodiment, the methods provided herein can be used to indicate regression of a tumor, cancer, metastasis or neoplasia in a subject. For example, the methods provided herein can be used to indicate regression of cancer of an organ, tissue or cell. Absence of an oncofetal fibronectin indicating molecule or an amount below a threshold can indicate regression of a cancer or metastasis, where a cancer or metastasis in a subject ceases to be, or is decreasingly, malignant or metastatic. Accordingly, using the methods provided herein, an oncofetal fibronectin negative sample can be used to indicate regression of a cancer or metastasis in a subject, or to indicate regression of cancer cells, in a subject. The absence of an oncofetal fibronectin indicating molecule in a sample or an amount of an oncofetal fibronectin indicating molecule in a sample below a threshold can indicate regression of a tumor, cancer, metastasis or neoplasia in a subject, or to indicate regression of cancer, in a subject.

In another embodiment, the methods provided herein can be used to distinguish between aggressive and non-aggressive cancer (e.g., a solid tumor or a leukemia). Cancer (solid or leukemia) with rapid growth properties can have different compositions relative to cancer with slow growth properties. For example, aggressive or rapid growth or high grade cancer such as astrocytomas can contain an oncofetal fibronectin indicating molecule or can contain an amount of an oncofetal fibronectin indicating molecule at or above a threshold, while non-aggressive or slow growth or low grade cancer can contain no oncofetal fibronectin indicating molecule, or amounts below a threshold. Accordingly, using the methods provided herein, measurement of an oncofetal fibronectin indicating molecule in a sample can be used to distinguish between an aggressive or rapid growth or high grade cancer and a non-aggressive or slow growth or low grade cancer. The methods can include measuring an oncofetal fibronectin indicating molecule in a sample, where the presence of an oncofetal fibronectin indicating molecule in a sample or an amount of an oncofetal fibronectin indicating molecule in a sample at or above a threshold can indicate an aggressive or rapid growth or high grade cancer; similarly, absence of an oncofetal fibronectin indicating molecule in a sample or an amount of an oncofetal fibronectin indicating molecule in a sample below a threshold can indicate a non-aggressive or slow growth or low grade cancer. The methods provided herein also can be used to distinguish between a aggressive or rapid growth cells, including normal, abnormal, dysplastic, hyperplastic, neoplastic, malignant or metastatic cells and a non-aggressive or slow growth or low grade cell. The methods include measuring an oncofetal fibronectin indicating molecule in a sample, where the presence of an oncofetal fibronectin indicating molecule in a sample or an amount of an oncofetal fibronectin indicating molecule in a sample at or above a threshold can indicate aggressive or rapid growth normal, abnormal, dysplastic, hyperplastic, neoplastic, malignant or metastatic cancer cells; similarly, absence of an oncofetal fibronectin indicating molecule in a sample or an amount of an oncofetal fibronectin indicating molecule in a sample below a threshold can indicate non-aggressive or slow growth normal, abnormal, dysplastic, hyperplastic, neoplastic, malignant or metastatic cancer cells.

Further provided herein is a method for indicating the recurrence or likelihood of recurrence of cancer. Cancer can spontaneously subside or can subside as a result of therapy. A cancer also can recur in a subject. As provided herein, an oncofetal fibronectin positive sample can indicate that cancer has recurred in a subject. An oncofetal fibronectin positive sample also can indicate that cancer has an increased likelihood of recurring in a subject. Also provided herein, an oncofetal fibronectin positive sample can indicate that cancer cells are again present in a subject, or have an increased likelihood of being present again in a subject. The methods include measuring an oncofetal fibronectin indicating molecule in a sample, where the presence of an oncofetal fibronectin indicating molecule in a sample or an amount of an oncofetal fibronectin indicating molecule in a sample at or above a threshold indicates recurrence of cancer) in a subject or recurrence of cancer cells in the subject. The methods also include measuring an oncofetal fibronectin indicating molecule in a sample, where the presence of an oncofetal fibronectin indicating molecule in a sample or an amount of an oncofetal fibronectin indicating molecule in a sample at or above a threshold indicates an increased likelihood of recurrence of cancer in a subject or an increased likelihood of recurrence of cancer cells in the subject, relative to the likelihood of recurrence in a subject with a sample in which an oncofetal fibronectin indicating molecule is absent or is below a threshold, or relative to the likelihood of recurrence in a control sample in which an oncofetal fibronectin indicating molecule is present or is absent or is below a threshold.

Similarly, an oncofetal fibronectin negative sample can indicate that cancer (tumorous, metastatic or neoplastic disease) has not recurred in a subject. An oncofetal fibronectin negative sample also can indicate that the cancer has a decreased likelihood of recurring in a subject. Also provided herein, an oncofetal fibronectin negative sample can indicate that cancer cells are still not present in a subject, or have a decreased likelihood of being present again in a subject. The methods include measuring an oncofetal fibronectin indicating molecule in a sample, where the absence of an oncofetal fibronectin indicating molecule in a sample or an amount of an oncofetal fibronectin indicating molecule in a sample below a threshold indicates a lack of recurrence of cancer in a subject or a lack of recurrence of cancer cells in the subject. The methods also include measuring an oncofetal fibronectin indicating molecule in a sample, where the absence of an oncofetal fibronectin indicating molecule in a sample or an amount of an oncofetal fibronectin indicating molecule in a sample below a threshold indicates a decreased likelihood of recurrence of cancer, in a subject or a decreased likelihood of recurrence of cancer cells in the subject, relative to the likelihood of recurrence in a subject with a sample in which an oncofetal fibronectin indicating molecule is present or is at or above a threshold, or relative to the likelihood of recurrence in a control sample in which an oncofetal fibronectin indicating molecule is present or is at or above a threshold.

In another embodiment, the methods provided herein can be used to determine the success or the likelihood of success of treating a cancer (e.g., a solid tumor, leukemia, metastasis, or neoplastic disease). While some cancers can be successfully treated with therapy such as administration of one or more compounds such as chemotherapeutic compounds, other cancers are less responsive to such compounds or are responsive to different therapies. A cancer in which an oncofetal fibronectin indicating molecule is present or is at or above a threshold level can have a different sensitivity to treatment relative to a cancer in which an oncofetal fibronectin indicating molecule is absent or is below a threshold level. Accordingly, using the methods provided herein, measurement of an oncofetal fibronectin indicating molecule in a sample can be used to predict the success or to indicate the likelihood of success of treating a cancer. The likelihood of success can be a function of the particular therapy. For example a therapy can target neovascularization, or a therapy can target nucleotide synthesis; one skilled in the art can recognize how the presence or amount of an oncofetal fibronectin indicating molecule in sample can affect the likelihood of success of cancer therapy. Presence of an oncofetal fibronectin indicating molecule or an amount of an oncofetal fibronectin indicating molecule in a sample at or above a threshold level can indicate that a particular therapeutic treatment has an increased likelihood of being successful, relative to a sample in which an oncofetal fibronectin indicating molecule is absent or is below a threshold level. In another example, presence of an oncofetal fibronectin indicating molecule or an amount of an oncofetal fibronectin indicating molecule in a sample at or above a threshold level can indicate that a particular therapeutic treatment has a decreased likelihood of being successful, relative to a sample in which an oncofetal fibronectin indicating molecule is absent or is below a threshold level. In another example, absence of an oncofetal fibronectin indicating molecule or an amount of an oncofetal fibronectin indicating molecule in a sample below a threshold level can indicate that a particular therapeutic treatment has a decreased likelihood of being successful, relative to a sample in which an oncofetal fibronectin indicating molecule is present or is at or above a threshold level. In another example, absence of an oncofetal fibronectin indicating molecule or an amount of an oncofetal fibronectin indicating molecule in a sample below a threshold level can indicate that a particular therapeutic treatment has an increased likelihood of being successful, relative to a sample in which an oncofetal fibronectin indicating molecule is present or is at or above a threshold level.

In another embodiment, measurement of an oncofetal fibronectin indicating molecule in a sample can be used to monitor the success of therapeutic treatment of a cancer (e.g., a solid tumor, leukemia, metastasis, or malignant neoplasia). For example, after therapeutic treatment, presence of an oncofetal fibronectin indicating molecule or a level of an oncofetal fibronectin indicating molecule in a sample at or above a threshold level can indicate that a therapeutic treatment being conducted is ineffective. In another example, presence of an oncofetal fibronectin indicating molecule or a level of an oncofetal fibronectin indicating molecule in a sample at or above a threshold level can indicate that a therapeutic treatment being conducted is effective. In another example, absence of an oncofetal fibronectin indicating molecule or a level of an oncofetal fibronectin indicating molecule in a sample below a threshold level can indicate that a therapeutic treatment being conducted is effective. In another example, absence of an oncofetal fibronectin indicating molecule or a level of an oncofetal fibronectin indicating molecule in a sample below a threshold level can indicate that a therapeutic treatment being conducted is ineffective.

In another embodiment, measurement of an oncofetal fibronectin indicating molecule in a sample can be used to select a method of treating a cancer (e.g., a solid tumor, leukemia, metastasis or malignant neoplasia). For example, presence of an oncofetal fibronectin indicating molecule or a level of an oncofetal fibronectin indicating molecule in a sample at or above a threshold level can be used to select a method of treatment that is more effective for cancer associated with oncofetal fibronectin. In another example, absence of an oncofetal fibronectin indicating molecule or a level of an oncofetal fibronectin indicating molecule in a sample below a threshold level can be used to select a method of treatment that is more effective for cancer associated with oncofetal fibronectin.

In some embodiments, detection of an oncofetal fibronectin indicating molecule can be performed in conjunction with detection of one or more additional cancer (i.e., tumor-associated) markers. A variety of detectable cancer markers are known in the art or are provided elsewhere herein, exemplary markers include, but are not limited to, AE1/AE3, BCA-225, Cathepsin D, E-Cadherin, Epidermal Growth Factor Receptor (EGFR), Estrogen receptor (ER), Gross Cystic Disease Fluid Protein 15 (GCDFP-15), HOX-B3, Ki-67, p65, Progesterone Receptor (PR), Retinoblastoma (Rb) and Transglutaminase K (TGK), p21, DCC, NF-1, NF-2, BRCA-3, p16, FHIT, WT-1, MEN-I, MEN-IIa, MEN-IIb, VHL, FCC, MCC, raf, erb, src, fms, jun, trk, ret, gsp, hst, bcr/abl, p53, c-erbB2, c-myc, MUC1, BRCA1, BRCA2, Her-2/neu, bcl-2, bax, PSA, CYFRA 21-1, PTH-RP, CA125, CEA gene family members, pro-gastrin, gastrin G17, gastrin G34, CA 19-9, CA 15-3, CA 27-29, CA 72-4, APC, SCC, HPV subtypes, TK, alphaFP, p62, Kallikrein, ras, vasopressin, gastrin-releasing peptide, annexin I, annexin II, Hu and KOC. Additional cancer markers, occurrence of cancer markers in particular cancers, and occurrence of cancer markers with other cancer markers are known in the art, as exemplified in Rhodes et al., Proc. Natl. Acad. Sci. USA 2004 101: 9309-9314. For example presence of an oncofetal fibronectin indicating molecule and Her-2/neu can indicate that a subject has breast cancer, and presence of an oncofetal fibronectin indicating molecule and PSA can indicate that a subject has prostate cancer. Among the methods provided herein are methods in which the presence and/or level of an oncofetal fibronectin indicating molecule in a sample is measured and the presence and/or level of one or more additional cancer markers is determined. Such methods can serve to further characterize the cancer or identify the cell or tissue source of cancer (dysplastic, neoplastic, malignant or metastatic) cells.

In some instances detection of an oncofetal fibronectin indicating molecule in a sample can have a strong positive predictive value of a present or future cancerous (neoplastic) condition, but a less strong negative predictive value; in such instances, a method for identifying or predicting a present or future cancerous (neoplastic) condition by detecting an oncofetal fibronectin indicating molecule, such as the methods provided herein, can be coupled with use of a second marker with a strong negative predictive value. Agreement of the oncofetal fibronectin indicating molecule measurement and measurement of the second marker can indicate with increased certainty relative to either marker when used alone, the present or future cancer (neoplastic) condition of the subject. For example, presence of oncofetal fibronectin protein in a sample can have a 90% or about a 90% positive predictive value for bladder cancer and absence of bladder tumor antigen in a sample can have a 90% or about a 90% negative predictive value for bladder cancer; when both markers are used in conjunction with each other, results that are either both tests are either positive or negative will be correct for 95% or about 95% of subjects tested.

In other instances detection of an oncofetal fibronectin indicating molecule in a sample can have a strong negative predictive value of a present or future cancerous (neoplastic) condition, but a less strong positive predictive value; in such instances, a method for identifying or predicting a present or future cancerous (neoplastic) condition by detecting an oncofetal fibronectin indicating molecule, such as the methods provided herein, can be coupled with use of a second marker with a strong positive predictive value. Agreement of the oncofetal fibronectin indicating molecule measurement and measurement of the second marker can indicate with increased certainty relative to either marker when used alone, the present or future cancerous (neoplastic) condition of the subject.

In some cases a measurement is considered positive for oncofetal fibronectin when the presence of an oncofetal fibronectin indicating molecule in a sample is equal to or above one or more threshold levels. In some embodiments, the threshold level can vary, for example, as a function of the progression of disease, a subject-specific classification, or the age of the subject. A threshold level that varies as a function of a second factor can be expressed as a threshold curve. In some instances, the rate of change of the amount of an oncofetal fibronectin indicating molecule in a particular sample type from a subject can be used to identify a sample as oncofetal fibronectin positive or negative, or to categorize the sample into two or more populations. The rate of change of the amount of an oncofetal fibronectin indicating molecule in a type of sample can indicate a stable, increasing or decreasing amount of an oncofetal fibronectin indicating molecule in a sample.

In some embodiments, the cancerous (malignant neoplastic, tumorous or metastatic) disease indicating methods provided herein can further include monitoring the presence of an oncofetal fibronectin indicating molecule over time. For example, the same type of sample can be collected from a subject every day, every week, every month or every year, and the oncofetal fibronectin indicating molecule measurements can be compared. In such cases, it is possible to identify an increasing amount of an oncofetal fibronectin indicating molecule in a subject, a decreasing amount of an oncofetal fibronectin indicating molecule in a subject, or a constant level of an oncofetal fibronectin indicating molecule in a subject. As provided herein, an increasing rate of an oncofetal fibronectin indicating molecule, or an increasing rate equal to or greater than a threshold rate, can be considered an oncofetal fibronectin positive measurement for the cancerous disease indicating methods provided herein. Similarly, a decreasing rate of an oncofetal fibronectin indicating molecule, or a decreasing rate equal to or greater than a threshold rate, can be considered an oncofetal fibronectin negative measurement for the cancerous disease indicating methods provided herein. The size of the rate of increase or decrease also can indicate an increasing or decreasing severity or likelihood of the cancerous indication. For example, a greater increasing rate can indicate a more severe neoplastic disease, a higher risk of developing cancer or recurrence of cancer, a faster progression of the cancer, or a more aggressive cancer, or a decreased efficacy of cancer therapy, relative to a smaller increasing rate or a decreasing rate. In another example, a smaller increasing rate can indicate a less severe cancer, a lower risk of developing cancer or recurrence of cancer, a slower progression of the cancer, or a less aggressive cancer, or an increased efficacy of cancer therapy relative to a greater increasing rate. In another example, a decreasing rate can indicate a less severe cancer, a lower risk of developing cancer or recurrence of cancer, a slower progression of the cancer, or a less aggressive cancer, or an increased efficacy of cancer therapy, relative to an increasing rate.

In some instances, multi-tiered thresholds can be applied to the oncofetal fibronectin indicating molecule measurement, where multi-tiered thresholds include two or more threshold levels, where each larger threshold level indicates a separate cancer categorization; for example each larger threshold level can indicate an increased likelihood of having a cancer, an increased risk of a cancer, an increased degree of development of cells into cancer, an increased likelihood of recurrence of a cancer, an increased aggressiveness of a cancer, or an increased likelihood of successful or unsuccessful cancer therapy. In another example, each smaller threshold level indicates a separate cancer categorization; for example each smaller threshold level can indicate a decreased likelihood of having a cancer, a decreased risk of a cancer, a decreased degree of development of cells into cancer cells, a decreased likelihood of recurrence of a cancer), a decreased aggressiveness of a cancer, or a decreased likelihood of successful or unsuccessful cancer therapy. An exemplary multi-tiered threshold is a two-tiered threshold for oncofetal fibronectin protein, where the lower threshold is 50 ng/mL and the higher threshold is 150 ng/mL for buffer-treated samples.

In another embodiment, any detected oncofetal fibronectin indicating molecule can be characterized according to the oncofetal fibronectin domains and/or post-translational modifications present in the oncofetal fibronectin indicating molecule. For example, an oncofetal fibronectin indicating molecule can be characterized as containing one or more of EDA, EDB and IIICS. In another example, the fibronectin or oncofetal fibronectin indicating molecule can be characterized as the EDA portion of an oncofetal fibronectin protein, the EDA-encoding portion of a nucleic acid molecule encoding oncofetal fibronectin, the portion of an autoantibody that binds to EDA of oncofetal fibronectin protein, and the portion of an autoantibody that binds to the EDA-encoding portion of a nucleic acid molecule encoding oncofetal fibronectin. In another example, the fibronectin or oncofetal fibronectin indicating molecule can be characterized as the EDB portion of an oncofetal fibronectin protein, the EDB-encoding portion of a nucleic acid molecule encoding oncofetal fibronectin, the portion of an autoantibody that binds to EDB of oncofetal fibronectin protein, and the portion of an autoantibody that binds to the EDB-encoding portion of a nucleic acid molecule encoding oncofetal fibronectin. In another example, the fibronectin or oncofetal fibronectin indicating molecule can be characterized as the IIICS portion of an oncofetal fibronectin protein, the IIICS-encoding portion of a nucleic acid molecule encoding oncofetal fibronectin, the portion of an autoantibody that binds to IIICS of oncofetal fibronectin protein, and the portion of an autoantibody that binds to the IIICS-encoding portion of a nucleic acid molecule encoding oncofetal fibronectin. In another example, an oncofetal fibronectin indicating molecule can be characterized as containing the IIICS splice variant V64, V89, V95 or V120. In another example, an oncofetal fibronectin protein can be characterized as containing one or more post-translational modifications such as O-glycosylation of threonine 33 of IIICS. In another example, an oncofetal fibronectin protein can be characterized as lacking EDA, EDB or IIICS. In another example, IIICS is identified as lacking amino acids 1-25 of IIICS, or 90-120 of IIICS, or both. Characterization of an oncofetal fibronectin indicating molecule present in a sample can be used, for example, to identify the cell or tissue source of the oncofetal fibronectin indicating molecule.

a. Bladder Cancer

The methods provided herein include use of an oncofetal fibronectin indicating molecule as a marker for bladder cancer. The commonest site of occurrence of bladder cancer is on the trigone and lateral walls of the bladder. The growth can be papillary, sessile, solid or ulcerative. Most bladder cancers are transitional cell carcinoma (TCC). There can be a considerable amount of metaplasia, especially among muscle invasive tumors. Five percent of bladder cancers are pure squamous cell carcinoma, which are usually associated with irritative factors such as chronic indwelling catheters, stones or schistosomiasis infestation. Pure adenocarcinoma of the bladder is rare and metastasis from another primary should be excluded. Carcinoma in situ (CIS) is a flat epithelia lesion which diplays a lack of cellular polarity and has anaplastic features. The lesion can be local or diffuse. When bladder cancer presents as a diffuse lesion, it usually follows an aggressive course.

An oncofetal fibronectin indicating molecule can be present in subjects that have bladder cancer. Oncofetal fibronectin indicating molecule measurements can be used as a marker for bladder cancer in any of the cancer indications provided herein. For example, the oncofetal fibronectin indicating molecule detection methods provided herein can be used for indicating whether or not a subject has cancerous (malignant neoplastic or metastatic) bladder cells. The methods include determining the presence or amount of an oncofetal fibronectin indicating molecule in a sample, and characterizing the sample according to the presence or absence of an oncofetal fibronectin indicating molecule in the sample or according to the amount of an oncofetal fibronectin indicating molecule in the sample, where presence or an amount of an oncofetal fibronectin indicating molecule at or above a threshold level can indicate that a subject has cancerous bladder cells, and absence or an amount of an oncofetal fibronectin indicating molecule below a threshold level can indicate that a subject does not have cancerous bladder cells. The oncofetal fibronectin indicating molecule detection methods provided herein also can be used for determining the risk or lack of risk of bladder cells such as normal, abnormal, dysplastic or hyperplastic bladder cells, becoming cancerous. The oncofetal fibronectin indicating molecule detection methods provided herein also can be used for determining the development or lack of development of bladder cells such as normal, abnormal, dysplastic or hyperplastic bladder cells, into less developed or anaplastic bladder cells. The oncofetal fibronectin indicating molecule detection methods provided herein also can be used for indicating the progression of a bladder tumor, cancer, metastasis or neoplasia. The oncofetal fibronectin indicating molecule detection methods provided herein can be used for distinguishing between aggressive and non-aggressive bladder tumors. The oncofetal fibronectin indicating molecule detection methods provided herein can be used for indicating whether or not a subject has or is likely to have a recurrence of cancerous bladder cells. The oncofetal fibronectin indicating molecule detection methods provided herein can indicate the likely or actual efficacy or lack of efficacy of bladder cancer treatment.

A sample collected for bladder cancer determination can be taken from any source, as provided herein. Exemplary sources for samples include a bladder tissue, a urine sample, a lymphatic sample, a blood sample, a serum sample, a plasma sample and an interstitial fluid sample. For example, the presence of an oncofetal fibronectin indicating molecule can be detected in the urine of subjects with bladder cancer. In one embodiment, detection of any oncofetal fibronectin indicating molecule in a sample can indicate the presence of, risk of, development of, progression of, aggressiveness of, recurrence of, or efficacy in treatment of cancerous bladder cells. In another embodiment, detection of an oncofetal fibronectin indicating molecule at or above a threshold level can indicate the presence of, risk of, development of, progression of, aggressiveness of, recurrence of, or efficacy in treatment of cancerous bladder cells. An exemplary threshold value for oncofetal fibronectin protein in buffer-treated urine sample (diluted from 250 µl to 1000 µl or about 250 µl to about 1000 µl) as an indicator of bladder cancer is 5 ng/ml, 8 ng/ml, 10 ng/ml, 15 ng/ml or 20 ng/ml, or about 5 ng/ml, about 8 ng/ml, about 10 ng/ml, about 15 ng/ml or about 20 ng/ml. All forms of bladder cancer can be indicated using the methods provided herein. Exemplary forms of bladder cancer include transitional cell carcinoma, squamous cell carcinoma and adenocarcinoma.

In one embodiment, characterization of an oncofetal fibronectin indicating molecule in a sample can indicate whether or not the oncofetal fibronectin indicating molecule in the sample was produced by cancerous bladder cells. In some cases, one or more forms of oncofetal fibronectin indicating molecule (varying, e.g., at EDA, EDB, IIICS and/or in post-translational modifications) present in a sample such as urine or bladder tissue are known to be produced by cancerous bladder cells. For example, oncofetal fibronectin protein in urine samples from subjects with bladder cancer contain O-glycosylated threonine 33 in the IIICS region of fibronectin in the urine (Wunderlich et al., *Oncol. Rep.* 8:669-672 (2001)), and fibronectin protein in urine samples from subjects with bladder cancer can contain abnormal glycosylation (Guo et al., *J. Cancer Res. Clin. Oncol.* 127:512-519 (2001)). In other cases, one or more forms of oncofetal fibronectin indicating molecule, although present in a sample such as urine or bladder tissue, are not produced by cancerous bladder cells, but instead are produced by a different tissue or organ source. The methods herein can be used to characterize the oncofetal fibronectin indicating molecule in a sample, and such characterization can indicate whether or not the oncofetal fibronectin indicating molecule observed in the sample is an oncofetal fibronectin indicating molecule form observed in bladder cancer. When a sample contains an oncofetal fibronectin indicating molecule observed in bladder cancer, the presence of the oncofetal fibronectin indicating molecule is consistent with a subject having bladder cancer. When a sample contains an oncofetal fibronectin indicating molecule not observed in bladder cancer, the presence of the oncofetal fibronectin indicating molecule is not consistent with a subject having bladder cancer.

b. Breast Cancer

The methods provided herein include use of an oncofetal fibronectin indicating molecule as a marker for breast cancer. An oncofetal fibronectin indicating molecule can be present in subjects that have breast cancer. Oncofetal fibronectin indicating molecule measurements can be used as a marker for breast cancer in any of the cancer (tumor, metastasis or malignant neoplastic) indications provided herein. For example, the oncofetal fibronectin indicating molecule detection methods provided herein can be used for indicating whether or not a subject has cancerous breast cells. The methods include determining the presence or amount of an oncofetal fibronectin indicating molecule in a sample, and characterizing the sample according to the presence or absence of an oncofetal fibronectin indicating molecule in the sample or according to the amount of an oncofetal fibronectin indicating molecule in the sample, where presence or an amount of an oncofetal fibronectin indicating molecule at or above a threshold level can indicate that a subject has cancerous breast cells, and absence or an amount of an oncofetal fibronectin indicating molecule below a threshold level can indicate that a subject does not have cancerous breast cells. The oncofetal fibronectin indicating molecule detection methods provided herein also can be used for determining the risk or lack of risk of breast cells such as normal, abnormal, dysplastic or hyperplastic breast cells, becoming cancerous. The oncofetal fibronectin indicating molecule detection methods provided herein also can be used for determining the development or lack of development of breast cells such as normal, abnormal, dysplastic or hyperplastic breast cells, into cancerous cells. The oncofetal fibronectin indicating molecule detection methods provided herein can be used for distinguishing between aggressive and non-aggressive breast tumors. The oncofetal fibronectin indicating molecule detection methods provided herein also can be used for indicating the progression of a breast cancer (e.g., tumor or metastasis). The oncofetal fibronectin indicating molecule detection methods provided herein can be used for indicating whether or not a subject has or is likely to have a recurrence of cancerous breast cells. The oncofetal fibronectin indicating molecule detection methods provided herein can indicate the likely or actual efficacy or lack of efficacy of breast cancer treatment.

A sample collected for breast cancer determination can be taken from any source, as provided herein. Exemplary sources for samples include a breast tissue sample, a fine needle aspiration sample, a ductal lavage sample, a blood sample, a serum sample, a plasma sample, a lymph sample or an interstitial fluid sample. For example, the presence of an oncofetal fibronectin indicating molecule can be detected in ductal lavage collected from subjects with breast cancer. In one embodiment, detection of any oncofetal fibronectin indicating molecule in a sample can indicate the presence of, risk of, development of, progression of, aggressiveness of, recurrence of, or efficacy in treatment of cancerous breast cells. In another embodiment, detection of an oncofetal fibronectin indicating molecule at or above a threshold level can indicate the presence of, risk of, development of, progression of, aggressiveness of, recurrence of, or efficacy in treatment of cancerous breast cells. An exemplary threshold value for oncofetal fibronectin protein in a ductal lavage sample (diluted from 250 μl to 1000 μl or about 250 μl to about 1000 μl) as an indicator of breast cancer is 5 ng/ml, 8 ng/ml, 10 ng/ml, 15 ng/ml or 20 ng/ml, or about 5 ng/ml, about 8 ng/ml, about 10 ng/ml, about 15 ng/ml or about 20 ng/ml. All forms of breast cancer can be indicated using the methods provided herein. Exemplary forms of breast cancer include infiltrating ductal carcinoma, invasive ductal carcinoma, other forms of ductal carcinoma, lobular carcinoma, nipple carcinoma and undifferentiated breast carcinoma.

In one embodiment, characterization of an oncofetal fibronectin indicating molecule in a sample can indicate whether or not the oncofetal fibronectin indicating molecule in the sample was produced by cancerous breast cells. In some cases, one or more forms of oncofetal fibronectin indicating molecule (varying, e.g., at EDA, EDB, IIICS and/or in post-translational modifications) present in a sample such as ductal lavage or breast tissue are known to be produced by cancerous breast cells. For example, oncofetal fibronectin protein in breast tissue samples from subjects with invasive ductal carcinoma contained EDB and O-glycosylated threonine 33 in the mcs region of fibronectin in the tissue samples (Kaczmarek et al., *Int. J. Cancer* 59:11-16 (1994)), and cancerous breast tissue samples have also been found to contain EDA+ oncofetal fibronectin (Matsumoto et al., *Jpn. J. Cancer Res.* 90:320-325 (1999)). In other cases, one or more forms of oncofetal fibronectin indicating molecule, although present in a sample such as ductal lavage or breast tissue, are not produced by cancerous breast cells, but instead are produced by a different tissue or organ source. The methods herein can be used to characterize the oncofetal fibronectin indicating molecule in a sample, and such characterization can indicate whether or not the oncofetal fibronectin indicating molecule observed in the sample is an oncofetal fibronectin indicating molecule form observed in breast cancer. When a sample contains an oncofetal fibronectin indicating molecule observed in breast cancer, the presence of the oncofetal fibronectin indicating molecule is consistent with a subject having breast cancer. When a sample contains an oncofetal fibronectin indicating molecule not observed in breast cancer, the presence of the oncofetal fibronectin indicating molecule is not consistent with a subject having breast cancer.

c. Cervical Cancer

The methods provided herein include use of an oncofetal fibronectin indicating molecule as a marker for cervical cancer. An oncofetal fibronectin indicating molecule can be present in subjects that have cervical cancer. Oncofetal fibronectin indicating molecule measurements can be used as a marker for cervical cancer in any of the cancer (tumor, metastasis or malignant neoplastic) indications provided herein. For example, the oncofetal fibronectin indicating molecule detection methods provided herein can be used for indicating whether or not a subject has cancerous (malignant neoplastic or metastatic) cervical cells. The methods include determining the presence or amount of an oncofetal fibronectin indicating molecule in a sample, and characterizing the sample according to the presence or absence of an oncofetal fibronectin indicating molecule in the sample or according to the amount of an oncofetal fibronectin indicating molecule in the sample, where presence or an amount of an oncofetal fibronectin indicating molecule at or above a threshold level can indicate that a subject has cancerous cervical cells, and absence or an amount of an oncofetal fibronectin indicating molecule below a threshold level can indicate that a subject does not have cancerous cervical cells. The oncofetal fibronectin indicating molecule detection methods provided herein also can be used for determining the risk or lack of risk of cervical cells such as normal, abnormal, dysplastic or hyperplastic cervical cells, becoming cancerous. The oncofetal fibronectin indicating molecule detection methods provided herein also can be used for determining the development or lack of development of cervical cells such as normal, abnormal, dysplastic or hyperplastic cervical cells, into cancerous cervical cells. The oncofetal fibronectin indicating molecule detection methods provided herein also can be used for indicating the progression of a cervical cancer. The oncofetal fibronectin indicating molecule detection methods provided herein can be used for distinguishing between aggressive and non-aggressive cervical tumors. The oncofetal fibronectin indicating molecule detection methods provided herein can be used for indicating whether or not a subject has or is likely to have a recurrence of cancerous cervical cells. The oncofetal fibronectin indicating molecule detection methods provided herein can indicate the likely or actual efficacy or lack of efficacy of cervical cancer treatment.

A sample collected for cervical cancer determination can be taken from any source, as provided herein. Exemplary sources for samples include a cervical or vaginal tissue sample, urine, lymph, lymphatic fluid, blood, serum, plasma, interstitial fluid and cervicovaginal fluid. Cervicovaginal fluid can be collected by any of a variety of methods, such as by swab, from any of a variety of cervicovaginal locations. Exemplary cervicovaginal swab samples include a swab of the point of a possible cervicovaginal lesion, the cervical canal, the cervical os, the ectocervix, the transition zone on the cervix between squamous and columnar cells (i.e., the squamocolumnar junction), the vagina, the posterior fornix, the portion of the vagina below the posterior fornix such as the lower third of the vagina, the labia, or combinations thereof. Cervicovaginal samples also can be collected as cervicovaginal fluid leakage from the vagina. In one example, the presence of an oncofetal fibronectin indicating molecule can be detected in a swab of the cervical os in subjects with cervical cancer. Detection of any oncofetal fibronectin indicating molecule in a sample can indicate the presence of, risk of, development of, progression of, aggressiveness of, recurrence of, or efficacy in treatment of cancerous cervical cells. In another embodiment, detection of an oncofetal fibronectin indicating molecule at or above a threshold level can indicate the presence of, risk of, development of, progression of, aggressiveness of, recurrence of, or efficacy in treatment of cancerous cervical cells. An exemplary threshold value for an oncofetal fibronectin indicating molecule, such as oncofetal fibronectin protein, in a cervical os swab buffer-treated sample as an indicator of cervical cancer is 1 ng/ml, 3 ng/ml, 5 ng/ml, 8 ng/ml, 10 ng/ml, 15 ng/ml, 20 ng/ml, or 25 ng/ml, or about 1 ng/ml, about 3 ng/ml, about 5 ng/ml, about 8 ng/ml, about 10 ng/ml, about 15 ng/ml, about 20 ng/ml, or about 25 ng/ml. An exemplary threshold value for an oncofetal fibronectin indicating molecule, such as oncofetal fibronectin protein, in a cervical os swab untreated sample as an indicator of cervical cancer is 5 ng/ml, 10 ng/ml, 20 ng/ml, 30 ng/ml, 40 ng/ml, 50 ng/ml, 60 ng/ml, or 75 ng/ml, or about 5 ng/ml, about 10 ng/ml, about 20 ng/ml, about 30 ng/ml, about 40 ng/ml, about 50 ng/ml, about 60 ng/ml, or about 75 ng/ml. An exemplary threshold value for an oncofetal fibronectin indicating molecule, such as oncofetal fibronectin protein, in a lower vaginal swab buffer-treated sample as an indicator of cervical cancer is 1 ng/ml, 2 ng/ml, 3 ng/ml, 5 ng/ml, 8 ng/ml, 10 ng/ml, 15 ng/ml, or 25 ng/ml, or about 1 ng/ml, about 2 ng/ml, about 3 ng/ml, about 5 ng/ml, about 8 ng/ml, about 10 ng/ml, about 15 ng/ml, or about 25 ng/ml. An exemplary threshold value for an oncofetal fibronectin indicating molecule, such as oncofetal fibronectin protein, in a cervical os swab untreated sample as an indicator of cervical cancer is 2 ng/ml, 5 ng/ml, 10 ng/ml, 15 ng/ml, 20 ng/ml, 30 ng/ml, 40 ng/ml, or 50 ng/ml, or about 2 ng/ml, about 5 ng/ml, about 10 ng/ml, about 15 ng/ml, about 20 ng/ml, about 30 ng/ml, about 40 ng/ml, or about 50 ng/ml. All forms of cervical cancer can be indicated using the methods known in the art or provided herein. Exemplary forms of cervical cancer include squamous cell carcinoma and adenocarcinoma.

In one embodiment, characterization of an oncofetal fibronectin indicating molecule in a sample can indicate whether or not the oncofetal fibronectin indicating molecule in the sample was produced by cancerous cervical cells. In some cases, one or more forms of oncofetal fibronectin indicating molecule (varying, e.g., at EDA, EDB, IIICS and/or in post-translational modifications) present in a sample such as cervicovaginal fluid or cervical tissue are known to be produced by cancerous cervical cells. For example, as provided herein, oncofetal fibronectin protein in cervical os swab samples from subjects with cervical cancer contained O-glycosylated threonine 33 in the IIICS region of fibronectin in the samples. In other cases, one or more forms of oncofetal fibronectin indicating molecule, although present in a sample such as cervicovaginal fluid or cervical tissue, are not produced by cancerous cervical cells, but instead are produced by a different tissue or organ source. The methods herein can be used to characterize the oncofetal fibronectin indicating molecule in a sample, and such characterization can indicate whether or not the oncofetal fibronectin indicating molecule observed in the sample is an oncofetal fibronectin indicating molecule form observed in cervical cancer. When a sample contains an oncofetal fibronectin indicating molecule observed in cervical cancer, the presence of the oncofetal fibronectin indicating molecule is consistent with a subject having cervical cancer. When a sample contains an oncofetal fibronectin indicating molecule not observed in cervical cancer, the presence of the oncofetal fibronectin indicating molecule is not consistent with a subject having cervical cancer.

d. Ovarian Cancer

The methods provided herein include use of an oncofetal fibronectin indicating molecule as a marker for ovarian cancer. An oncofetal fibronectin indicating molecule can be present in subjects that have ovarian cancer. Oncofetal fibronectin indicating molecule measurements can be used as a marker for ovarian cancer in any of the cancer (tumor, metastasis or malignant neoplastic) indications provided herein. For example, the oncofetal fibronectin indicating molecule detection methods provided herein can be used for indicating whether or not a subject has cancerous (malignant neoplastic or metastatic) ovarian cells. The methods include determining the presence or amount of an oncofetal fibronectin indicating molecule in a sample, and characterizing the sample according to the presence or absence of an oncofetal fibronectin indicating molecule in the sample or according to the amount of an oncofetal fibronectin indicating molecule in the sample, where presence or an amount of an oncofetal fibronectin indicating molecule at or above a threshold level can indicate that a subject has cancerous ovarian cells, and absence or an amount of an oncofetal fibronectin indicating molecule below a threshold level can indicate that a subject does not have cancerous ovarian cells. The oncofetal fibronectin indicating molecule detection methods provided herein also can be used for determining the risk or lack of risk of ovarian cells such as normal, abnormal, dysplastic or hyperplastic ovarian cells, becoming cancerous. The oncofetal fibronectin indicating molecule detection methods provided herein also can be used for determining the development or lack of development of ovarian cells such as normal, abnormal, dysplastic or hyperplastic ovarian cells, into cancerous ovarian cells. The oncofetal fibronectin indicating molecule detection methods provided herein also can be used for indicating the progression of an ovarian cancer (tumor, metastasis or malignant neoplasia). The oncofetal fibronectin indicating molecule detection methods provided herein can be used for distinguishing between aggressive and non-aggressive ovarian tumors. The oncofetal fibronectin indicating molecule detection methods provided herein can be used for indicating whether or not a subject has or is likely to have a recurrence of cancerous ovarian cells. The oncofetal fibronectin indicating molecule detection methods provided herein can indicate the likely or actual efficacy or lack of efficacy of ovarian cancer treatment.

A sample collected for ovarian cancer determination can be taken from any source, as provided herein. Exemplary sources for samples include an ovarian tissue sample, ascitic fluid, peritoneal fluid, urine, stool, plasma, blood, serum, lymph, lymphatic fluid and interstitial fluid samples. For example, the presence of an oncofetal fibronectin indicating molecule can be detected in peritoneal fluid collected from subjects with ovarian cancer. Detection of any oncofetal fibronectin indicating molecule in a sample can indicate the presence of, risk of, development of, progression of, aggressiveness of, recurrence of, or efficacy in treatment of cancerous ovarian cells. In another embodiment, detection of an oncofetal fibronectin indicating molecule at or above a threshold level can indicate the presence of, risk of, development of, progression of, aggressiveness of, recurrence of, or efficacy in treatment of cancerous ovarian cells. An exemplary threshold value for an oncofetal fibronectin indicating molecule in a peritoneal sample as an indicator of ovarian cancer is 3 ng/ml, 5 ng/ml, 8 ng/ml, 10 ng/ml, 15 ng/ml, 20 ng/ml, 25 ng/ml, or 30 ng/ml, or about 3 ng/ml, about 5 ng/ml, about 8 ng/ml, about 10 ng/ml, about 15 ng/ml, about 20 ng/ml, about 25 ng/ml, or about 30 ng/ml. All forms of ovarian cancer can be indicated using the methods known in the art or provided herein. Exemplary forms of ovarian cancer include serous cystoma, mucinous cystoma, endometrioid tumor, mesonephroid tumor, dysgerminoma, endodermal sinus tumor, embryonal carcinoma, polyembroma, choriocarcinoma and teratoma.

In one embodiment, characterization of an oncofetal fibronectin indicating molecule in a sample can indicate whether or not the oncofetal fibronectin indicating molecule in the sample was produced by cancerous ovarian cells. In some cases, one or more forms of oncofetal fibronectin indicating molecule (varying, e.g., at EDA, EDB, IIICS and/or in post-translational modifications) present in a sample such as peritoneal fluid or ovarian tissue are known to be produced by cancerous ovarian cells. For example, oncofetal fibronectin protein in peritoneal samples from subjects with ovarian cancer contained O-glycosylated threonine 33 in the IIICS region of fibronectin and at least another portion of the IIICS region of fibronectin in the samples (see, e.g., U.S. Pat. No. 5,523,229; Menzin et al., *Cancer* 82:152-158 (1998)). In other cases, one or more forms of oncofetal fibronectin indicating molecule, although present in a sample such as peritoneal fluid or ovarian tissue, are not produced by cancerous ovarian cells, but instead are produced by a different tissue or organ source. The methods herein can be used to characterize the oncofetal fibronectin indicating molecule in a sample, and such characterization can indicate whether or not the oncofetal fibronectin indicating molecule observed in the sample is an oncofetal fibronectin indicating molecule form observed in ovarian cancer. When a sample contains an oncofetal fibronectin indicating molecule observed in ovarian cancer, the presence of the oncofetal fibronectin indicating molecule is consistent with a subject having ovarian cancer. When a sample contains an oncofetal fibronectin indicating molecule not observed in ovarian cancer, the presence of the oncofetal fibronectin indicating molecule is not consistent with a subject having ovarian cancer.

e. Prostate Cancer

The methods provided herein include use of an oncofetal fibronectin indicating molecule as a marker for prostate cancer. An oncofetal fibronectin indicating molecule can be present in subjects that have prostate cancer. Oncofetal fibronectin indicating molecule measurements can be used as a marker for prostate cancer in any of the cancer (tumor, metastasis or malignant neoplastic) indications provided herein. For example, the oncofetal fibronectin indicating molecule detection methods provided herein can be used for indicating whether or not a subject has cancerous (malignant neoplastic or metastatic) prostate cells. The methods include determining the presence or amount of an oncofetal fibronectin indicating molecule in a sample, and characterizing the sample according to the presence or absence of an oncofetal fibronectin indicating molecule in the sample or according to the amount of an oncofetal fibronectin indicating molecule in the sample, where presence or an amount of an oncofetal fibronectin indicating molecule at or above a threshold level can indicate that a subject has cancerous prostate cells, and absence or an amount of an oncofetal fibronectin indicating molecule below a threshold level can indicate that a subject does not have cancerous prostate cells. The oncofetal fibronectin indicating molecule detection methods provided herein also can be used for determining the risk or lack of risk of prostate cells such as normal, abnormal, dysplastic or hyperplastic prostate cells, becoming cancerous. The oncofetal fibronectin indicating molecule detection methods provided herein also can be used for determining the development or lack of development of prostate cells such as normal, abnormal, dysplastic or hyperplastic prostate cells, into cancerous prostate cells. The oncofetal fibronectin indicating molecule detection methods provided herein also can be used for indicating the progression of a prostate cancer. The oncofetal fibronectin indicating molecule detection methods provided herein can be used for distinguishing between aggressive and non-aggressive prostate tumors. The oncofetal fibronectin indicating molecule detection methods provided herein can be used for indicating whether or not a subject has or is likely to have a recurrence of cancerous prostate cells. The oncofetal fibronectin indicating molecule detection methods provided herein can indicate the likely or actual efficacy or lack of efficacy of prostate cancer treatment.

A sample collected for prostate cancer determination can be taken from any source, as provided herein. Exemplary sources for samples include a prostate tissue sample, semen, urine, stool, plasma, blood, serum, lymph, lymphatic fluid and interstitial fluid samples. For example, the presence of an oncofetal fibronectin indicating molecule can be detected in prostate tissue samples collected from subjects with prostate cancer. Detection of any oncofetal fibronectin indicating molecule in a sample can indicate the presence of, risk of, development of, progression of, aggressiveness of, recurrence of, or efficacy in treatment of cancerous prostate cells. In another embodiment, detection of an oncofetal fibronectin indicating molecule at or above a threshold level can indicate the presence of, risk of, development of, progression of, aggressiveness of, recurrence of, or efficacy in treatment of cancerous prostate cells. An exemplary threshold value for an oncofetal fibronectin indicating molecule in a fine needle aspirate sample as an indicator of prostate cancer is 3 ng/ml, 5 ng/ml, 8 ng/ml, 10 ng/ml, 15 ng/ml, 20 ng/ml, 25 ng/ml, or 30 ng/ml, or about 3 ng/ml, about 5 ng/ml, about 8 ng/ml, about 10 ng/ml, about 15 ng/ml, about 20 ng/ml, about 25 ng/ml, or about 30 ng/ml. All forms of prostate cancer can be indicated using the methods known in the art or provided herein. An exemplary form of prostate cancer includes prostate adenocarcinoma.

In one embodiment, characterization of an oncofetal fibronectin indicating molecule in a sample can indicate whether or not the oncofetal fibronectin indicating molecule in the sample was produced by cancerous prostate cells. In some cases, one or more forms of oncofetal fibronectin indicating molecule (varying, e.g., at EDA, EDB, IIICs and/or in post-translational modifications) present in a sample such as fine needle aspirate or prostate tissue are known to be produced by cancerous prostate cells. For example, an oncofetal fibronectin indicating molecule in tissue samples from subjects with prostate cancer contained the ED-B region of fibronectin in the samples (see, e.g., Albrecht et al., *Histochem. Cell. Biol.* 112:51-61 (1999)). In other cases, one or more forms of oncofetal fibronectin indicating molecule, although present in a sample such as fine needle aspirate or prostate tissue, are not produced by cancerous prostate cells, but instead are produced by a different tissue or organ source. The methods herein can be used to characterize the oncofetal fibronectin indicating molecule in a sample, and such characterization can indicate whether or not the oncofetal fibronectin indicating molecule observed in the sample is an oncofetal fibronectin indicating molecule form observed in prostate cancer. When a sample contains an oncofetal fibronectin indicating molecule observed in prostate cancer, the presence of the oncofetal fibronectin indicating molecule is consistent with a subject having prostate cancer. When a sample contains an oncofetal fibronectin indicating molecule not observed in prostate cancer, the presence of the oncofetal fibronectin indicating molecule is not consistent with a subject having prostate cancer.

f. Lung Cancer

The methods provided herein include use of an oncofetal fibronectin indicating molecule as a marker for lung cancer. An oncofetal fibronectin indicating molecule can be present in subjects that have lung cancer. Oncofetal fibronectin indicating molecule measurements can be used as a marker for lung cancer in any of the cancer (tumor, metastasis or malignant neoplastic) indications provided herein. For example, the oncofetal fibronectin indicating molecule detection methods provided herein can be used for indicating whether or not a subject has cancerous (malignant neoplastic or metastatic) lung cells. The methods include determining the presence or amount of an oncofetal fibronectin indicating molecule in a sample, and characterizing the sample according to the presence or absence of an oncofetal fibronectin indicating molecule in the sample or according to the amount of an oncofetal fibronectin indicating molecule in the sample, where presence or an amount of an oncofetal fibronectin indicating molecule at or above a threshold level can indicate that a subject has cancerous lung cells, and absence or an amount of an oncofetal fibronectin indicating molecule below a threshold level can indicate that a subject does not have cancerous lung cells. The oncofetal fibronectin indicating molecule detection methods provided herein also can be used for determining the risk or lack of risk of lung cells such as normal, abnormal, dysplastic or hyperplastic lung cells, becoming cancerous. The oncofetal fibronectin indicating molecule detection methods provided herein also can be used for determining the development or lack of development of lung cells such as normal, abnormal, dysplastic or hyperplastic lung cells, into cancerous lung cells. The oncofetal fibronectin indicating molecule detection methods provided herein also can be used for indicating the progression of a lung cancer. The oncofetal fibronectin indicating molecule detection methods provided herein can be used for distinguishing between aggressive and non-aggressive lung tumors. The oncofetal fibronectin indicating molecule detection methods provided herein can be used for indicating whether or not a subject has or is likely to have a recurrence of cancerous lung cells. The oncofetal fibronectin indicating molecule detection methods provided herein can indicate the likely or actual efficacy or lack of efficacy of lung cancer treatment.

A sample collected for lung cancer determination can be taken from any source, as provided herein. Exemplary sources for samples include a lung tissue sample, sputum, blood, serum and plasma samples. For example, the presence of an oncofetal fibronectin indicating molecule can be detected in sputum collected from subjects with lung cancer. Detection of any oncofetal fibronectin indicating molecule in a sample can indicate the presence of, risk of, development of, progression of, aggressiveness of, recurrence of, or efficacy in treatment of cancerous lung cells. In another embodiment, detection of an oncofetal fibronectin indicating molecule at or above a threshold level can indicate the presence of, risk of, development of, progression of, aggressiveness of, recurrence of, or efficacy in treatment of cancerous lung cells. An exemplary threshold value for an oncofetal fibronectin indicating molecule in a sputum sample as an indicator of lung cancer is 3 ng/ml, 5 ng/ml, 8 ng/ml, 10 ng/ml, 15 ng/ml, 20 ng/ml, 25 ng/ml, or 30 ng/ml, or about 3 ng/ml, about 5 ng/ml, about 8 ng/ml, about 10 ng/ml, about 15 ng/ml, about 20 ng/ml, about 25 ng/ml, or about 30 ng/ml. All forms of lung cancer can be indicated using the methods known in the art or provided herein. Exemplary forms of lung cancer include small cell carcinoma, adenocarcinoma, squamous cell carcinoma and large cell carcinoma.

In one embodiment, characterization of an oncofetal fibronectin indicating molecule in a sample can indicate whether or not the oncofetal fibronectin indicating molecule in the sample was produced by cancerous lung cells. In some cases, one or more forms of oncofetal fibronectin indicating molecule (varying, e.g., at EDA, EDB, IIICS and/or in post-translational modifications) present in a sample such as sputum or lung tissue are known to be produced by cancerous lung cells. For example, oncofetal fibronectin in tissue samples from subjects with lung cancer contained the EDB region of fibronectin in the samples (Santimaria et al., *Clin Cancer Res* 9:571-579 (2003)). In other cases, one or more forms of oncofetal fibronectin indicating molecule, although present in a sample such as sputum or lung tissue, are not produced by cancerous lung cells, but instead are produced by a different tissue or organ source. The methods herein can be used to characterize the oncofetal fibronectin indicating molecule in a sample, and such characterization can indicate whether or not the oncofetal fibronectin indicating molecule observed in the sample is an oncofetal fibronectin indicating molecule form observed in lung cancer. When a sample contains an oncofetal fibronectin indicating molecule observed in lung cancer, the presence of the oncofetal fibronectin indicating molecule is consistent with a subject having lung cancer. When a sample contains an oncofetal fibronectin indicating molecule not observed in lung cancer, the presence of the oncofetal fibronectin indicating molecule is not consistent with a subject having lung cancer.

g. Colorectal Cancer

The methods provided herein include use of an oncofetal fibronectin indicating molecule as a marker for colorectal cancer. An oncofetal fibronectin indicating molecule can be present in subjects that have colorectal cancer. Oncofetal fibronectin indicating molecule measurements can be used as a marker for colorectal cancer in any of the cancer (tumor, metastasis or malignant neoplastic) indications provided herein. For example, the oncofetal fibronectin indicating molecule detection methods provided herein can be used for indicating whether or not a subject has cancerous (malignant neoplastic or metastatic) colorectal cells. The methods include determining the presence or amount of an oncofetal fibronectin indicating molecule in a sample, and characterizing the sample according to the presence or absence of an oncofetal fibronectin indicating molecule in the sample or according to the amount of an oncofetal fibronectin indicating molecule in the sample, where presence or an amount of an oncofetal fibronectin indicating molecule at or above a threshold level can indicate that a subject has cancerous colorectal cells, and absence or an amount of an oncofetal fibronectin indicating molecule below a threshold level can indicate that a subject does not have cancerous colorectal cells. The oncofetal fibronectin indicating molecule detection methods provided herein also can be used for determining the risk or lack of risk of colorectal cells such as normal, abnormal, dysplastic or hyperplastic colorectal cells, becoming cancerous. The oncofetal fibronectin indicating molecule detection methods provided herein also can be used for determining the development or lack of development of colorectal cells such as normal, abnormal, dysplastic or hyperplastic colorectal cells, into cancerous colorectal cells. The oncofetal fibronectin indicating molecule detection methods provided herein also can be used for indicating the progression of a colorectal cancer. The oncofetal fibronectin indicating molecule detection methods provided herein can be used for distinguishing between aggressive and non-aggressive colorectal tumors. The oncofetal fibronectin indicating molecule detection methods provided herein can be used for indicating whether or not a subject has or is likely to have a recurrence of cancerous colorectal cells. The oncofetal fibronectin indicating molecule detection methods provided herein can indicate the likely or actual efficacy or lack of efficacy of colorectal cancer treatment.

A sample collected for colorectal cancer determination can be taken from any source, as provided herein. Exemplary sources for samples include a colorectal tissue sample, stool, plasma, blood, serum, lymph, lymphatic fluid and interstitial fluid samples. For example, the presence of an oncofetal fibronectin indicating molecule can be detected in stool collected from subjects diagnosed with colorectal cancer. Detection of any oncofetal fibronectin indicating molecule in a sample can indicate the presence of, risk of, development of, progression of, aggressiveness of, recurrence of, or efficacy in treatment of cancerous colorectal cells. In another embodiment, detection of an oncofetal fibronectin indicating molecule at or above a threshold level can indicate the presence of, risk of, development of, progression of, aggressiveness of, recurrence of, or efficacy in treatment of cancerous colorectal cells. An exemplary threshold value for an oncofetal fibronectin indicating molecule in a stool sample as an indicator of colorectal cancer is 3 ng/ml, 5 ng/ml, 8 ng/ml, 10 ng/ml, 15 ng/ml, 20 ng/ml, 25 ng/ml, or 30 ng/ml, or about 3 ng/ml, about 5 ng/ml, about 8 ng/ml, about 10 ng/ml, about 15 ng/ml, about 20 ng/ml, about 25 ng/ml, or about 30 ng/ml. All forms of colorectal cancer can be indicated using the methods known in the art or provided herein. Exemplary forms of colorectal cancer include mucinous (colloid) adenocarcinoma, signet ring adenocarcinoma, scirrhous tumor, carcinoid tumor, squamous cell tumor, leiomyoscarcoma.

In one embodiment, characterization of an oncofetal fibronectin indicating molecule in a sample can indicate whether or not the oncofetal fibronectin indicating molecule in the sample was produced by cancerous colorectal cells. In some cases, one or more forms of oncofetal fibronectin indicating molecule (varying, e.g., at EDA, EDB, IIICS and/or in post-translational modifications) present in a sample such as stool or colorectal tissue are known to be produced by cancerous colorectal cells. For example, an oncofetal fibronectin indicating molecule in tissue samples from subjects with colorectal cancer contained the EDB region of fibronectin (see, e.g., Midulla et al., *Cancer Res.* 60:164-169 (2000)).

In other cases, one or more forms of oncofetal fibronectin indicating molecule, although present in a sample such as stool or colorectal tissue, are not produced by cancerous colorectal cells, but instead are produced by a different tissue or organ source. The methods herein can be used to characterize the oncofetal fibronectin indicating molecule in a sample, and such characterization can indicate whether or not the oncofetal fibronectin indicating molecule observed in the sample is an oncofetal fibronectin indicating molecule form observed in colorectal cancer. When a sample contains an oncofetal fibronectin indicating molecule observed in colorectal cancer, the presence of the oncofetal fibronectin indicating molecule is consistent with a subject having colorectal cancer. When a sample contains an oncofetal fibronectin indicating molecule not observed in colorectal cancer, the presence of the oncofetal fibronectin indicating molecule is not consistent with a subject having colorectal cancer.

h. Additional Cancers

Methods provided herein can be used to provide information regarding any of a variety of additional cancers. A non-limiting group of exemplary cancer types and samples that can be used to detect an oncofetal fibronectin indicating molecule in providing information regarding the respective cancer types include: renal cancers, as indicated using urine, lymph, lymphatic fluid, blood, serum, plasma, interstitial fluid or tissue samples; thyroid cancers, as indicated using tissue such as fine needle aspirate, lymph, lymphatic fluid, blood, serum, plasma and interstitial fluid; skin cancers, as indicated using interstitial fluid, lymph, lymphatic fluid, blood, serum, plasma and tissue samples; oropharyngeal cancer, as indicated using oropharyngeal swab, blood, serum, plasma and tissue samples; lymphomas, as indicated using lymph, blood, serum, plasma and tissue samples such as lymph node samples; and leukemias, as indicated using plasma, blood or serum.

Thus, the oncofetal fibronectin indicating molecule detection methods provided herein can be used for indicating whether or not a subject has cancerous (malignant neoplastic or metastatic) cells of these tissue types. The methods include determining the presence or amount of an oncofetal fibronectin indicating molecule in a sample, and characterizing the sample according to the presence or absence of an oncofetal fibronectin indicating molecule in the sample or according to the amount of an oncofetal fibronectin indicating molecule in the sample, where presence or an amount of an oncofetal fibronectin indicating molecule at or above a threshold level can indicate that a subject has cancerous cells of these tissue types, and absence or an amount of an oncofetal fibronectin indicating molecule below a threshold level can indicate that a subject does not have neoplastic, malignant or metastatic cells of these tissues types. The oncofetal fibronectin indicating molecule detection methods provided herein also can be used for determining the risk or lack of risk of cells such as normal, abnormal, dysplastic or hyperplastic cells of these tissue types, of becoming cancerous. The oncofetal fibronectin indicating molecule detection methods provided herein also can be used for determining the development or lack of development of cells such as normal, abnormal, dysplastic or hyperplastic cells of these tissue types, into cancerous cells of these tissue types. The oncofetal fibronectin indicating molecule detection methods provided herein also can be used for indicating the progression of cancer in these tissue types. The oncofetal fibronectin indicating molecule detection methods provided herein can be used for distinguishing between aggressive and non-aggressive tumors of these tissue types. The oncofetal fibronectin indicating molecule detection methods provided herein can be used for indicating whether or not a subject has or is likely to have a recurrence of neoplastic, malignant or metastatic cells of these tissue types. The oncofetal fibronectin indicating molecule detection methods provided herein can indicate the likely or actual efficacy or lack of efficacy of cancer treatment of these tissue types.

3. Health State Assessment

The presence or absence of an oncofetal fibronectin indicating molecule in a sample can indicate the health state of an individual. The presence of an oncofetal fibronectin indicating molecule in a sample relative to one or more threshold levels can indicate the severity of the health state of an individual. Detection of an oncofetal fibronectin indicating molecule in a body tissue or fluid sample can be an indicator of a variety of health problems or risk therefor. The presence of, or elevated levels of, an oncofetal fibronectin indicating molecule in a cell, tissue and/or fluid sample does not necessarily indicate that the health problem is caused by an oncofetal fibronectin indicating molecule, but that elevated levels of an oncofetal fibronectin indicating molecule are observed in cell, tissue and/or fluid samples. For example, an oncofetal fibronectin indicating molecule can serve as an indicator of cancer, can serve as an indicator of pre-term or imminent delivery and also can serve as an indicator of arthritis (Kriegsman et al., *Rhematol Int.* 24:25-33 (2004)), diabetic retinopathy (Khan et al., Invest. *Opthamol. Vis. Sci.* 45:287-295 (2004)), renal disease, and Dupuytren's contracture (Howard et al., *J. Surg. Res.* 117:232-238 (2004)). Detection of an oncofetal fibronectin indicating molecule in a body tissue or fluid sample at or above one or more thresholds or at a level above a baseline for a particular individual can be an indicator of a variety of health problems or risk therefor. Similarly, its absence or presence below one or more thresholds or at a level below a baseline for a particular individual can be indicative of the absence of any of these variety of diseases and disorders.

Provided herein are methods of screening subjects for the presence of an oncofetal fibronectin indicating molecule in a sample and, if an oncofetal fibronectin indicating molecule is not present in the sample, or is present below a threshold level, concluding that the subject does not have a health problem associated with the presence of an oncofetal fibronectin indicating molecule or with elevated levels of an oncofetal fibronectin indicating molecule. Similarly, provided herein are methods of screening subjects for the presence of an oncofetal fibronectin indicating molecule in a sample and, if an oncofetal fibronectin indicating molecule is present in the sample, or is present at or above a threshold level, determining that the subject has a health problem associated with the presence of an oncofetal fibronectin indicating molecule or with elevated levels of an oncofetal fibronectin indicating molecule.

In one embodiment, a method is provided for indicating that a subject is free of a health problem associated with oncofetal fibronectin, by testing a sample for the presence or absence of an oncofetal fibronectin indicating molecule, where absence (or presence below a threshold) of an oncofetal fibronectin indicating molecule indicates that the subject is free of a health problem associated with oncofetal fibronectin. In another embodiment, a method is provided for screening a subject for a health problem associated with oncofetal fibronectin, by testing a sample from a subject for the presence or absence or an oncofetal fibronectin indicating molecule, wherein presence of an oncofetal fibronectin indicating molecule indicates that the subject has a health problem associated with oncofetal fibronectin.

Similarly, general health, or presence or absence of a health problem associated with oncofetal fibronectin can be indicated by an increased rate of change in an amount of an oncofetal fibronectin indicating molecule; for example, increasing amounts of an oncofetal fibronectin indicating molecule can indicate a health problem associated with oncofetal fibronectin, and decreasing amounts of an oncofetal fibronectin indicating molecule can indicate absence of a health problem associated with oncofetal fibronectin. The amount of an oncofetal fibronectin indicating molecule can be compared to one or more thresholds, where increasing thresholds can indicate increased likelihood or increased severity of a health problem associated with oncofetal fibronectin, and decreasing thresholds can indicate decreased likelihood or decreased severity of a health problem associated with oncofetal fibronectin.

The methods provided herein can be performed in any of a variety of settings or for a variety of purposes, including during a routine physical examination, or as a general diagnostic tool to attempt to determine an unidentified malady or illness of a subject. Baseline levels can be established based on averages in a population or in a particular individual. Deviation from the average or from the baseline in the individual can indicate a change or risk of change in the health status of the individual.

In some embodiments, prior to performing the test for an oncofetal fibronectin indicating molecule, the subject tested is not diagnosed as having a health problem, or is not diagnosed as having a health problem associated with oncofetal fibronectin. In other embodiments, a subject can have an unidentified health problem and testing for an oncofetal fibronectin indicating molecule can be used to as a screen to indicate or diagnose the health problem. Thus, provided herein are methods that include performing routine tests of subjects where the tests include determining the presence or absence and/or amount of an oncofetal fibronectin indicating molecule in subjects' samples and determining the health state of the tested subjects according to the presence or absence (or in comparison to one or more thresholds) and/or amount of oncofetal fibronectin indicating molecule detected.

In one embodiment, detection of an oncofetal fibronectin indicating molecule can be performed in conjunction with one or more additional diagnostic tests, including routine diagnostic tests such as blood pressure, pulse, body weight, health history, family history or sample tests. In another embodiment, if an oncofetal fibronectin indicating molecule is present or is at or above a threshold level, one or more additional diagnostic tests can be conducted to diagnose the health problem of the subject. Such diagnostic tests can be conducted prior to, at the same time as, or subsequent to, testing for an oncofetal fibronectin indicating molecule. In one example, a subject can be identified as having an oncofetal fibronectin indicating molecule present or at or above a threshold level and the subject can then be further tested in one or more subsequent diagnostic tests to identify the health problem of the subject.

In one embodiment, a sample can be tested for the presence or absence (or in comparison to one or more thresholds)

and/or amount of an oncofetal fibronectin indicating molecule and also can be tested for one or more additional properties, including the presence of one or more additional sample components. Collection of samples from a subject and screening the sample for properties such as the presence or absence of a plurality of components such as ions or molecules in the sample or for the level of components such as ions or molecules in the sample is well known in the art. For example, blood sample collection can be used to determine ion content such as sodium ion content, lipid content such as LDL and HDL content and urine samples can be tested for the presence of metabolites or sugar and saliva can be tested for hormones. Any of a variety of samples can be used to measure the presence and/or amount of any of a variety ions or molecules, as is known in the art.

In one example blood can be tested for an oncofetal fibronectin indicating molecule and one or more additional properties. Exemplary properties of blood that are routinely tested include, but are not limited to, red blood cell count, white blood cell count (including count of neutrophils, lymphocytes, T cells, B cells, monocytes, eosinophils and basophils), platelet count, hematocrit, hemoglobin, blood type, Rh factor, glucose, lactose dehydrogenase, creatine phosphokinase, blood urea nitrogen, creatinine, carbon dioxide, sodium, potassium, chloride, calcium, phosphorus, alkaline phosphatase, alanine amino transferase, aspartate amino transferase, albumin, gamma-glutamyl transpeptidase, serum glutamate pyruvate transaminase, total protein, fibrinogen, prothrombin, cholesterol, globulin, bilirubin, high density lipoproteins, low density lipoproteins, very low density lipoproteins, free testosterone, total testosterone, dehydroepiandrosterone, prostate-specific antigen, estradiol, progesterone, homocysteine, C-reactive protein, uric acid, amylase and lipase.

In another example urine can be tested for an oncofetal fibronectin indicating molecule and one or more additional properties. Exemplary properties of urine that are routinely tested include, but are not limited to, color, appearance, specific gravity, pH, total protein, glucose, ketones, hemoglobin, bile, urobilinogen, nitrate, uroglobin, white blood cells, leukocytes, red blood cells, epithelial cells, bacteria, crystals, mucus and casts. In another example saliva can be tested for an oncofetal fibronectin indicating molecule and one or more additional properties. Exemplary properties of saliva that are routinely tested include, but are not limited to, estradiol, testosterone, DHEA-S, cortisol, sodium, potassium, chloride.

In one embodiment, an oncofetal fibronectin indicating molecule is determined as a component of a sample panel. For example, an oncofetal fibronectin indicating molecule can be determined as a component of a blood panel, urine panel or saliva panel.

4. Other Health Problems

An oncofetal fibronectin indicating molecule also can be present in subjects with other health problems such as arthritis, diabetic retinopathy and Dupuytren's contracture. In some embodiments, the presence of an oncofetal fibronectin indicating molecule can indicate the presence of health problems such as arthritis, diabetic retinopathy and Dupuytren's contracture. In other embodiments, the presence of an oncofetal fibronectin indicating molecule can indicate the risk of developing health problems such as arthritis, diabetic retinopathy and Dupuytren's contracture. In yet other embodiments, the presence of an oncofetal fibronectin indicating molecule can indicate the severity of health problems such as arthritis, diabetic retinopathy and Dupuytren's contracture. In addition to the presence of an oncofetal fibronectin indicating molecule indicating presence, risk of developing or severity of such health problems, an amount of an oncofetal fibronectin indicating molecule in a sample can be greater than, equal to, or less than one or more thresholds, where each increasing threshold indicates an increased likelihood of the presence, an increased risk of developing, or increased severity of such health problems, relative to each lower threshold. The rate of increase or decrease of an oncofetal fibronectin indicating molecule in a sample can indicate the degree of likelihood of the presence, the degree of the risk of developing, or the degree of the severity of such health problems, where larger increases represent more likely or more severe health problems relative to smaller increases or decreases.

a. Arthritis

An oncofetal fibronectin indicating molecule can be present in arthritic joints. An oncofetal fibronectin indicating molecule can be present in the synovial fluid, synovial tissue and/or cartilage of individuals with arthritis. An oncofetal fibronectin indicating molecule can be present at higher levels in subjects having rheumatoid arthritis relative to a control sample having an amount of oncofetal fibronectin indicating molecule below a threshold. An oncofetal fibronectin indicating molecule can be present at higher levels in subjects having osteoarthritis relative to a control sample having an amount of oncofetal fibronectin indicating molecule below a threshold. An oncofetal fibronectin indicating molecule can be present at higher levels in subjects with rheumatoid arthritis relative to the levels of oncofetal fibronectin indicating molecule present in subjects with osteoarthritis.

Arthritic subjects can have elevated levels of an oncofetal fibronectin indicating molecule in the affected areas. Thus, in one embodiment, presence of arthritis can be determined by detecting an oncofetal fibronectin indicating molecule in synovial fluid, synovial tissue or cartilage of a subject. Arthritic subjects also can have elevated levels of an oncofetal fibronectin indicating molecule in their bloodstream. Thus, presence of arthritis also can be determined by detecting an oncofetal fibronectin indicating molecule in blood, serum or plasma.

Presence of an oncofetal fibronectin indicating molecule also can be indicative of the risk of a subject developing arthritis. Thus, provided herein are methods for determining the risk of a subject developing arthritis by testing for the presence of an oncofetal fibronectin indicating molecule in a sample, where presence of an oncofetal fibronectin indicating molecule indicates an increased risk of developing arthritis. Presence of an oncofetal fibronectin indicating molecule also can indicate the severity of the arthritis of a subject. Thus, provided herein are methods for determining the severity of arthritis in a subject by testing for the presence of an oncofetal fibronectin indicating molecule in a sample, where presence of an oncofetal fibronectin indicating molecule at or above a threshold indicates an increased severity of arthritis in the subject relative to a sample that is oncofetal fibronectin negative (or below the threshold).

Presence of an oncofetal fibronectin indicating molecule can be measured by determining the presence of EDA+, EDB+ and/or IIICS+ oncofetal fibronectin indicating molecule in a sample. In some embodiments, the presence of EDB in synovial tissue indicates the presence of rheumatoid arthritis in a subject. In other embodiments, presence of a splice variant of IIICS, such as a IIICS splice variant that binds FDC-6, indicates the presence of synovial hyperplasia.

b. Diabetic Retinopathy

An oncofetal fibronectin indicating molecule can be present in diabetic retinopathy. An oncofetal fibronectin indicating molecule can be present in the aqueous humor, vitreous humor, or various tissues of the eye. Subjects with diabetic retinopathy can have elevated levels of EDA+ oncofetal fibronectin indicating molecule relative to subjects without diabetic retinopathy. Subjects with diabetic retinopathy can have elevated levels of EDB+ oncofetal fibronectin indicating molecule relative to subjects without diabetic retinopathy. Subjects with diabetic retinopathy can have elevated levels of IIICS+ oncofetal fibronectin indicating molecule relative to subjects without diabetic retinopathy. Thus, methods for detecting an oncofetal fibronectin indicating molecule associated with diabetic retinopathy can include detecting EDA+, EDB+ and/or IIICS+ oncofetal fibronectin indicating molecule.

In one embodiment, presence of diabetic retinopathy can be determined by detecting an oncofetal fibronectin indicating molecule in the aqueous humor, vitreous humor, or eye tissue sample of a subject. Subjects with diabetic retinopathy also can have elevated levels of an oncofetal fibronectin indicating molecule in their bloodstream. Thus, presence of diabetic retinopathy also can be determined by detecting an oncofetal fibronectin indicating molecule in blood, serum or plasma.

Presence of an oncofetal fibronectin indicating molecule also can be indicative of the risk of a subject developing diabetic retinopathy. Thus, provided herein are methods for determining the risk of a subject developing diabetic retinopathy by testing for the presence of an oncofetal fibronectin indicating molecule in a sample, where presence of an oncofetal fibronectin indicating molecule indicates an increased risk of developing diabetic retinopathy. Presence at or above one or more thresholds of an oncofetal fibronectin indicating molecule also can indicate the severity of the diabetic retinopathy of a subject. Thus, provided herein are methods for determining the severity of diabetic retinopathy in a subject by testing for the presence of an oncofetal fibronectin indicating molecule in a sample, where presence at or above one or more thresholds of an oncofetal fibronectin indicating molecule indicates an increased severity of diabetic retinopathy the subject relative to a sample that is oncofetal fibronectin negative (or below the threshold).

c. Dupuytren's Contracture

An oncofetal fibronectin indicating molecule can be present in Dupuytren's contracture. An oncofetal fibronectin indicating molecule can be present in the blood, serum, plasma or tissue sample of subjects with Dupuytren's contracture. Subjects with Dupuytren's contracture can have elevated levels of IIICS+ oncofetal fibronectin indicating molecule relative to subjects without Dupuytren's contracture. Thus, methods for detecting an oncofetal fibronectin indicating molecule associated with Dupuytren's contracture can include detecting a IIICS+ oncofetal fibronectin indicating molecule.

In one embodiment, presence of Dupuytren's contracture can be determined by detecting an oncofetal fibronectin indicating molecule in tissue samples from an area suspected of having Dupuytren's contracture. Subjects with Dupuytren's contracture also can have elevated levels of an oncofetal fibronectin indicating molecule in their bloodstream. Thus, presence of Dupuytren's contracture also can be determined by detecting an oncofetal fibronectin indicating molecule in blood, serum or plasma.

Presence of an oncofetal fibronectin indicating molecule also can be indicative of the risk of a subject developing Dupuytren's contracture. Thus, provided herein are methods for determining the risk of a subject developing Dupuytren's contracture by testing for the presence of an oncofetal fibronectin indicating molecule in a sample, where presence of an oncofetal fibronectin indicating molecule indicates an increased risk of developing Dupuytren's contracture. Presence of an oncofetal fibronectin indicating molecule at or above one or more thresholds can also indicate the severity of the Dupuytren's contracture of a subject. Thus, provided herein are methods for determining the severity of Dupuytren's contracture in a subject by testing for the presence of an oncofetal fibronectin indicating molecule in a sample, where presence of an oncofetal fibronectin indicating molecule at or above one or more thresholds indicates an increased severity of Dupuytren's contracture in the subject relative to a sample that is oncofetal fibronectin negative (or below the threshold).

E. COLLECTION OF SAMPLES

In accordance with the methods disclosed herein, an oncofetal fibronectin indicating molecule can be detected in any of a variety of types of samples. For example, the sample can include urine, lymph, blood, plasma, serum, saliva, cervical fluid, cervicovaginal fluid, vaginal fluid, breast fluid, breast milk, synovial fluid, semen, seminal fluid, stool, sputum, cerebral spinal fluid, tears, mucus, interstitial fluid, follicular fluid, amniotic fluid, aqueous humor, vitreous humor, peritoneal fluid, ascites, sweat, lymphatic fluid, lung sputum and lavage. In addition, the sample can contain tissues specimens such as a biopsy. When a sample contains solid material, such as a tissue biopsy, the sample can be homogenized in order to bring into solution or otherwise increase the accessibility of sample components for use in the methods provided herein or otherwise known in the art. Exemplary tissue biopsy samples include cervicovaginal tissue and breast tissue biopsy samples.

The sample can be collected by any of a variety of techniques. The particular technique used for a given procedure will depend, at least in part, upon the type of sample to be analyzed. In general, tissue samples can be collected using aspiration (e.g., fine needle aspiration), lavage (e.g., ductal lavage), biopsy, swabbing (using, e.g., a fibrous tipped swab such as a cytobrush, polyester swab, rayon swab or cotton swab), suction, transcutaneous or transdermal extraction and other methods. Liquid samples can be collected by suction, needle-mediated withdrawal, swabbing (using, e.g. a fibrous tipped swab such as a cytobrush, polyester swab, rayon swab or cotton swab) and other methods. When the sample is collected with a cotton swab, the methods provided herein are conducted on the swab itself. As will be recognized by one skilled in the art, depending on the sample, sample collection can be performed by a medical professional, an untrained individual and/or the subject from whom the sample is to be collected. For example, a biopsy or fine needle aspirate sample is likely to be collected by a medical professional. In another example, a urine sample or a vaginal swab sample can be collected by an untrained individual, such as a family member, or by the subject from whom the sample is to be collected. Samples that can be collected by an untrained individual or by the subject from whom the sample is to be collected, can be collected at a site other than a clinical setting, such as the home. For example, a sample can be collected as part of a home testing procedure. Home testing procedures can be performed, for example, using a home testing kit, such as a kit provided herein.

Any of the sample collection techniques provided herein can be used in conjunction with any of the oncofetal fibronectin indicating molecule detection methods provided herein or otherwise known in the art for any of the diagnostic uses or other uses of detection of an oncofetal fibronectin indicating molecule provided herein or otherwise known in the art. The following are exemplary collection methods and sources.

1. Swab and Cervicovaginal Samples

A swab sample can be collected from a subject and tested for the presence of an oncofetal fibronectin indicating molecule. Swab samples can contain body fluids of the subject, cells of the subject, or body fluids and cells. Swab samples can be collected from any of a variety of regions of the subject, including, but not limited to, oral, aural, nasal, anal, urethral, cervicovaginal, ocular, skin, alimentary canal such as esophageal, gastric, intestinal, colon, or any other surface accessible to a swab, or lesions of any of the above.

Swab samples can be collected by a medical professional, an untrained individual such as a family member, or the subject who is providing the sample, according to the sample to be collected and the oncofetal fibronectin indicating molecule test to be performed. For example, a swab of the cervical os to be tested for the presence of an oncofetal fibronectin indicating molecule by mass spectrometry is typically collected by a medical professional, whereas a vaginal and/or labial swab sample to be tested for the presence of an oncofetal fibronectin indicating molecule by a test strip assay can be collected by an untrained individual or by the subject providing the sample and can be used in, for example, a home testing method. Devices that can be used in collecting swab samples can be any swab sample collection device known in the art, including, but not limited to, fibrous tipped swabs such as a cytobrush, polyester swab, rayon swab or cotton swab, configured to facilitate sample collection from the targeted body region. In one embodiment, the swab sample is a cervicovaginal swab sample.

Cervicovaginal samples, including cervicovaginal swab samples, can include samples from any of a variety of cervicovaginal regions and combinations thereof. Cervicovaginal samples can contain cervicovaginal fluid and can optionally contain cells from the cervicovaginal cavity. Cervicovaginal samples such as cervicovaginal fluid can be collected by any of a variety of methods, including cervicovaginal swabbing, or collecting cervicovaginal fluid leakage, for example, using an absorptive collection vehicle such as an absorptive pad. Exemplary cervicovaginal swab samples include, but are not limited to, a swab of the point of a possible cervicovaginal lesion, the cervical canal, the cervical os, the ectocervix, the transition zone on the cervix between squamous and columnar cells (i.e., the squamocolumnar junction), the vagina, the posterior fornix, the portion of the vagina below the posterior fornix such as the lower third of the vagina, the labia, or combinations thereof. In the case of a vaginal swab sample, the sample can be a swab of any portion of the vagina, including the posterior fornix or the portion of the vagina below the posterior fornix, such as, for example, the lower third of the vagina. In the case of a labial swab, the swab can be collected from the labia minora or labia majora and typically includes a swab of the labia minora.

With respect to cervicovaginal samples in general, a tissue or liquid sample to be assayed can be removed in the vicinity of the point of a possible cervicovaginal lesion, the cervical canal, the cervical os, the ectocervix, the transition zone on the cervix between squamous and columnar cells (i.e., the squamocolumnar junction), the vagina, the posterior fornix, the portion of the vagina below the posterior fornix such as the lower third of the vagina, the labia, or combinations thereof. Cervicovaginal samples also can include culdocentesis samples. Cervicovaginal samples can include samples collected by passive collection methods. Passive collection methods include collecting cervicovaginal fluid and, optionally particulate matter such as cells by placing a sample collection vehicle in a position that will contact and typically absorb the fluid and optionally particulate matter. Exemplary passive collection vehicles can include a device for collecting a sample that is inserted into the cervicovaginal cavity (e.g., a tampon-like device that can collect a cervicovaginal sample) and a device for collecting a sample that can collect the sample as it exits the cervicovaginal cavity (e.g., an absorbent pad-like device such as a sanitary napkin-like device). Use of passive collection devices such as modified sanitary napkins, for diagnostic purposes is known in the art, as exemplified in Alary et al., *J. Clin. Microbiol.* 39:2508-2512 (2001).

In some embodiments, as provided herein, the amount of an oncofetal fibronectin indicating molecule in a cervicovaginal swab sample collected from the portion of the vagina below or inferior to the posterior fornix, such as the lower third of the vagina, can be one-third or about one-third the amount of oncofetal fibronectin indicating molecule in a cervicovaginal swab of the posterior fornix collected from the same subject. Accordingly, in methods provided herein in which the level of an oncofetal fibronectin indicating molecule in a sample is compared to a threshold level, the threshold level for a swab of the lower portion of the vagina, such as the lower third of the vagina, can be one-third or about one-third of the threshold level for a swab of the posterior fornix. For example, when the threshold level for a buffer-treated swab of the posterior fornix is 60 ng/ml (or 600 ng/ml for an untreated sample), or about 60 ng/ml (or about 600 ng/ml for an untreated sample), the threshold level of a buffer-treated swab of the lower portion of the vagina such as the lower third of the vagina can be 20 ng/ml (or 200 ng/ml for an untreated sample) or about 20 ng/ml (or about 200 ng/ml for an untreated sample). Similarly, when the threshold level for a buffer-treated swab of the posterior fornix is 50 ng/ml (or 500 ng/ml for an untreated sample) or about 50 ng/ml (or about 500 ng/ml for an untreated sample), 30 ng/ml (or 300 ng/ml for an untreated sample) or about 30 ng/ml (or about 300 ng/ml for an untreated sample), 15 ng/ml (or 150 ng/ml for an untreated sample) or about 15 ng/ml (or about 150 ng/ml for an untreated sample), or 10 ng/ml (or 100 ng/ml for an untreated sample) or about 10 ng/ml (or about 100 ng/ml for an untreated sample), the threshold level of a buffer-treated swab of the lower portion of the vagina such as the lower third of the vagina can respectively be 15-20 ng/ml (or 150-200 ng/ml for an untreated sample) or about 15-20 ng/ml (or about 150-200 ng/ml for an untreated sample), 10 ng/ml (or 100 ng/ml for an untreated sample) or about 10 ng/ml (or about 100 ng/ml for an untreated sample), 5 ng/ml (or 50 ng/ml for an untreated sample) or about 5 ng/ml (or about 50 ng/ml for an untreated sample), or 3-4 ng/ml (or 30-40 ng/ml for an untreated sample) or about 3-4 ng/ml (or about 30-40 ng/ml for an untreated sample).

A cervicovaginal sample generally includes fluid and particulate solids and can contain vaginal or cervical mucus, other vaginal or cervical secretions, cells or cell debris, amniotic fluid, or other fetal or maternal materials.

In some of the methods provided herein, the sample essentially does not contain blood. For example, when the method is an immunoassay such as an ELISA assay or lateral flow, the samples essentially do not contain blood. The sample contains 5% or less, 2% or less, 1% or less, 0.5% or less, or 0.1% or less, or about 5% or less, about 2% or less, about 1% or less, about 0.5% or less, or about 0.1% or less blood. The sample can be removed using any of a variety of techniques including, but not limited to, use of a fibrous tipped swab such as a cytobrush, polyester swab, rayon swab or cotton swab (see, e.g., WO 91/16855, WO 89/10724, U.S. Pat. Nos. 4,759,376, 4,762,133 and 4,700,713), aspirator, suction device, lavage device, needle, or other devices known in the art. In other methods, such as immunoprecipitation, Western blots, dot blots, etc., the assay method is not affected by the presence of blood in the sample. On of ordinary skill in the art can empirically determine whether or not blood would be a contaminant based on the assay method.

Cervicovaginal sample collection can be performed according to the cervicovaginal region to be sampled. For example, a swab of transition zone between squamous and columnar cells of cervix can be performed by a medical professional with the aid of a vaginal speculum. In another example, a vaginal swab, such as a swab of the lower third of the vagina and/or a swab of the labia, can be performed by the subject herself, by an untrained individual such as a family member, or by a medical professional.

In some embodiments directed to vaginal samples, vaginal samples collected at the same location in the vagina can increase the reproducibility of sample collection, and can increase the reliability of the results of oncofetal fibronectin indicating molecule measurements. As provided herein, the concentration of oncofetal fibronectin indicating molecule in the vagina can vary at different locations in the vagina. Accordingly, two or more samples collected from the same location in the vagina have an increased likelihood of containing the same or substantially the same concentration of oncofetal fibronectin indicating molecule relative to two or more samples collected from different locations in the vagina. Thus, provided herein are methods for collecting vaginal samples or methods for determining the presence and/or amount of oncofetal fibronectin indicating molecule in a vaginal sample, where the methods include collecting two or more vaginal samples (from the same or different subjects), where the samples are collected from the same location in the vagina. Two or more samples collected from the same location in the vagina and collected from the same subject on different occasions (e.g., on different days or weeks) can more reliably indicate the change in presence and/or amount of oncofetal fibronectin indicating molecule in the subject over time relative to two or more samples collected from different locations in the vagina of the same subject. Accordingly, the methods provided herein include methods for increasing the reliability of a measured change in presence and/or amount of oncofetal fibronectin indicating molecule in a subject over time by collecting two or more samples from the same location in the vagina of the same subject. Also provided herein, a sample collected from a particular location in the vagina can be compared to one or more thresholds that specifically relate to samples collected at that location; such a sample equal to or greater than such one or more thresholds can more reliably reflect the health condition or likely outcome of the subject relative to samples and threshold that do not relate to a particular location in the vagina. Accordingly, the methods provided herein include methods for increasing the reliability of an indicated health condition or likely health condition outcome by collecting a vaginal sample from the same location in the vagina as the location the location specifically related to by one or more thresholds. Also provided herein, collecting samples from the same location in the vagina can reduce the variability of oncofetal fibronectin indicating molecule amounts present in a sample due to variations in sample collection procedures (e.g., variation between individuals collecting the sample) or sample collection techniques (e.g., improper or careless sample collection techniques). Reduced variability of oncofetal fibronectin indicating molecule amounts due to sample collection can increase the correlation of presence/absence and/or amount of oncofetal fibronectin indicating molecule with a health condition or likely health condition outcome. Accordingly, provided herein are methods of correlating a health condition or health outcome in a subject with presence/absence and/or amount of oncofetal fibronectin indicating molecule in samples by collecting samples from the same location in the vagina of two or more subjects and correlating a health condition or likely health condition outcome with the presence/absence and/or amount of oncofetal fibronectin indicating molecule in the samples. Methods for collecting a vaginal sample from the same location in the vagina are known in the art, and can be accomplished, for example using a swab sample collection device with an over-insertion preventing device attached thereto, where the over-insertion preventing device standardizes the location in the vagina at which the sample is collected.

Following collection, the sample can be transferred to a container for storage and transport to a testing laboratory. The test sample is optionally dispersed in a liquid that preserves biomolecule analytes such as proteins or nucleic acids that can be unstable in the sampled composition. The storage and transfer medium minimizes decline in the protein analyte level during storage and transport. For example, the storage and transfer medium can contain reagents or conditions (e.g., pH, ionic strength or ionic composition) that decrease, inhibit or prevent degradative enzyme activity such as protease or nuclease activity. An exemplary preserving solution for storage and transfer contains of 0.05 M Tris buffer, pH 7.4, 150 mM NaCl, 0.02% $NaN_3$, 1% BSA, 5 mM EDTA, 1 mM phenylmethylsulfonyl fluoride (PMSF), 500 Kallikrein·Units/ml of Aprotinin, and 0.1% Triton X-100, as known in the art and exemplified in U.S. Pat. No. 4,919,889, issued Apr. 24, 1990. The solution can be used, for example, when detecting an oncofetal fibronectin indicating molecule. Calculations to account for any additional dilution of the samples collected using liquids can be performed as part of the interpretation of the assay procedure.

In one embodiment, home and office use devices for immediate processing of the sample can be used. If used, the sample can be placed directly in the device and testing can be performed within minutes of sample collection. In such cases, the need to stabilize the analyte is minimized and any solution that facilitates performing the assay and is not detrimental to analyte stability or user safety can be used. An exemplary solution for home or office use in immediate processing contains of 0.05 M Tris-HCl, pH 7.4; 0.15 M NaCl, 1% BSA and 5 mM EDTA.

In one embodiment, a kit for home testing of a cervicovaginal sample is provided. The kit can contain a sample collection device, such as a swab or a passive sample collection vehicle and optionally a solution for mixing with the sample and typically contains one or more fibronectin or oncofetal fibronectin binding partners and instructions for use and/or interpretation of results.

A variety of diagnostic systems and kits are provided herein and are known in the art, such as those exemplified in U.S. Pat. Nos. 6,394,952 and 6,267,722. Such diagnostic systems and kits can be used to determine the level of an oncofetal fibronectin indicating molecule in the sample, in accordance with the methods provided herein or otherwise known in the art and can be used for any of the diagnostic purposes provided herein or otherwise known in the art.

2. Lavage Samples

An oncofetal fibronectin indicating molecule can be present in or on a variety of regions in a subject's body. Samples of fluids, cells, or other matter from the subject that can contain an oncofetal fibronectin indicating molecule can be gathered from a variety of regions, including cavities and ducts, using lavage methods. Thus, as provided herein, lavage samples can be collected from a subject, where the lavage sample can be tested for any oncofetal fibronectin indicating molecule therein. Any of a variety of body surfaces, cavities and/or ducts can be used for collection of a lavage sample. Exemplary lavage samples include peritoneal, ductal, bronchial, bronchoalveolar, oral, nasal, ear, eye, bladder, colonic, gastric, cervicovaginal lavage samples. Any of a variety of lavage methods and apparatuses known in the art can be used for collecting a lavage sample. Lavage methods generally include contacting a region of the subject's body with a fluid and collecting the fluid. The methods also can include a step of washing or moving the fluid over the region. The methods also can include, but do not require, step of aspirating the fluid or applying a vacuum to collect the fluid.

a. Sample Collection

Lavage samples can be collected using known methods. Generally, a lavage tool is used to probe and/or collect a lavage sample from a region of the subject's body. Once the region of interest is located, a lavage fluid carried in the lavage tool can be contacted with the region. At least a portion of the lavage fluid can then collected to obtain a sample.

In one embodiment, the access tool contains a double lumen catheter. The lavage fluid can be contacted with the region of the subject's body through one of the catheter lumens, and lavage fluid can be removed through the second catheter lumen, and collected. Collection of lavage fluid can further include application of suction to the second catheter lumen to facilitate withdrawal of the lavage fluid from the region of the subject's body and accumulation of the sample in an assayable form. Suction can be applied using any device for creating suction in a lumen. For example, suction can be applied using a syringe or other suction device operatively coupled to the lumen through which lavage fluid will be withdrawn the region of the subject's body. The suction can be applied for a brief period of time or for an extended period of time, according to the procedure intended by one skilled in the art. Introduction of the lavage fluid optionally continues even after the initial portions of the fluid begin to emerge from the second catheter lumen.

The volume of lavage fluid used can be any amount in which an oncofetal fibronectin indicating molecule can be collected, and can vary according to a variety of factors, including, but not limited to, the region of the subject to be contacted, the measurement method, and any sample manipulation methods to be used, as is understood by those of skill in the art. Typically the volume will be at least enough to carry fluid or cells or other components contacted by the fluid that can contain an oncofetal fibronectin indicating molecule and be removed from the subject for oncofetal fibronectin indicating molecule measurement. Typically the volume will not be greater than an amount that can dilute any oncofetal fibronectin indicating molecule in a sample such that the oncofetal fibronectin indicating molecule cannot be detected by the selected oncofetal fibronectin indicating molecule measurement method. Exemplary volumes are at least 0.5 mL or about 0.5 mL, and as much as 25 mL or about 25 mL.

The lavage fluid can be introduced onto the surface of the region, or into a body cavity at a pressure low enough that the lavage method will not disrupt tissues, organs or membranes of the body region, but at a pressure high enough that fluid, cells and/or other material can be separated from the body region and carried by the lavage fluid. For example, the fluid can be introduced at a rate in the range of between 0.1 mL/s and 5 mL/s or about 0.1 mL/s and about 5 mL/s.

b. Lavage Fluid

The lavage fluid can contain any of a variety of components known in the art. The lavage fluid can contain $H_2O$, alcohol, or other liquid compatible with contacting a subject and detecting a oncofetal fibronectin indicating molecule. For example, the sample can be aqueous and contain saline and one or more optional ingredients such as, for example, an anesthetic, an oncotic agent, an osmotic agent, hormone, cytokine, chemokine, an antiseptic agent, an orifice dilating agent, a vasodilator, a vasoconstrictor, a muscle relaxant, a muscle constrictor, an anti-ischemic agent, a beta-blocker, a calcium channel blocker, or a dye or stain. The lavage fluid also can optionally contain one or more gases (e.g., air and/or nitrogen). The presence of gas can serve to increase retrieval of cells and fluid. The gas can be introduced into the lavage fluid by any of a variety of standard methods, including introduction of the gas from a pressurized container.

The anesthetic is any anesthetic agent capable of anesthetizing a region of the subject. The anesthetic can act topically, systemically, locally, or any combination thereof. The anesthetic can include, but is not limited to, the following: lidocaine, prolocaine, prevericaine, or marcaine. The anesthetic also can be a combination or mixture of anesthetic agents.

The oncotic agent includes, but is not limited to, existing commercially available sterile oncotic solutions, such as preparations of high molecular weight hydroxyethyl starch (e.g., Hespan (DuPont)) and low molecular weight hydroxyethyl starch (e.g., Pentaspan (DuPont)). Other polysaccharide derivatives, including hydroxymethyl alpha substituted (1-4) or (1-6) polymers and cyclodextrins, including hydroxypropyl substituted β or γ cyclodextrin, also can be used as oncotic agents.

Osmotic agents are known in the art. Exemplary osmotic agents include, but are not limited to, osmopolymers and osmagents. A variety of oncotic agents are known in the art, as exemplified in U.S. Pat. No. 5,413,572.

The antiseptic agent is any agent that can reduce an opportunity for sepsis at the region of the subject contacted with the lavage fluid. The antiseptic agent can serve a prophylactic purpose in preventing or forestalling sepsis. The antiseptic agent can be, but is not limited to, one or more of the following: a medicinal alcohol (e.g., ethyl alcohol or isopropyl alcohol), a topical antibiotic (e.g., Neosporin or bacteriomycin) and combinations thereof.

The orifice dilating agent is an agent that promotes dilation of an orifice such as a ductal orifice. The orifice dilating agent can include, but is not limited to, one or more of the following: an agent from the red pepper family of plants (genus *Capsicum*, where the agent can be, for example, capsaicin), a hormone capable of prompt or delayed reaction at the orifice (e.g., prolactin or oxytocin) and combinations thereof.

The vasodilator is any agent that encourages vasodilation, or opening of blood vessels to increase blood flow to and within the region contacted. The vasodilator can include, but is not limited to, one or more of the following: a vasodilator typically used in cardiac contexts; any vasodilator that can work at the surface or orifice; and combinations thereof.

The muscle relaxant is any agent that can cause relaxation of muscles in or near the body region to be sampled, such as a sphincter. The muscle relaxant can include, but is not limited to, one or more of the following: a smooth muscle relaxing agent, a calcium channel blocker (e.g., nifedipine), an antispasmodic (e.g., ditropan (oxybutinin), urospas, or terbutyline)) and combinations thereof. For example, the muscle relaxant can include a sphincter relaxer that is effective in relaxing sphincter muscle (e.g., breast duct sphincter muscle). The muscle constricting agent is any agent that can cause constriction of muscles found in or near the body region to be sampled, such as a sphincter.

The lactation stimulating agent is any agent that can stimulate lactation in a lactating woman. For example, an agent, as applied to a nipple surface and breast of a non-lactating woman is believed to act to increase the ductal fluid collectable from the breast duct. The lactation stimulating agent can include, but is not limited to, one or more of the following: oxytocin, prolactin and combinations thereof.

The secretion stimulating agent is any agent that can stimulate secretion of fluids and/or materials from the body region to be sampled. The secretion stimulating agent can include, but is not limited to, one or more of the following: oxytocin, prolactin and combinations thereof.

The anti-ischemic agent is any agent that can prevent or reducing ischemia. The anti-ischemic agent can work in a variety of ways to achieve the anti-ischemic effect and use of the agent is not limited by its mode of action. The anti-ischemic agent can act to increase blood and oxygen flow to the body region to be sampled.

The beta-blocker is any beta-blocker that can act effectively on a body region to be sampled (e.g., a breast) to increase blood and oxygen flow to the body region. The calcium channel blocker is any calcium channel blocker that can act effectively on a body region to be sampled (e.g., a breast) to increase blood and oxygen flow to the body region.

The dye or stain is any agent that can be used to identify a body region contacted by the lavage fluid.

The ductal lavage sample obtained can contain epithelial cells from the body region to be sampled, normally secreted and non-secreted fluids present in the region and proteins, peptides, nucleic acid molecules, antibodies, and other chemical species which can be secreted or otherwise present in the body region to be sampled.

c. Applying a Label with Lavage

Optionally, lavage can be performed in detection and/or therapeutic methods. Identification of an oncofetal fibronectin indicating molecule on body regions and treatment of body regions containing an oncofetal fibronectin indicating molecule can be facilitated by including in the lavage fluid a detectable and/or therapeutic fibronectin or oncofetal fibronectin binding partner conjugate. The surface of the region of the subject's body can be contacted with the lavage fluid, and the conjugate can be detected and/or can have a therapeutic effect on the region to which the conjugate bound. In some embodiments, the body region can be optionally washed with a solution that blocks or unblocks the body region to facilitate or permit specific binding of the binding partner conjugate to an oncofetal fibronectin indicating molecule in the body region. For example, the orifice can become plugged with keratin-containing materials and washing with a keratinolytic solution, such as acetic acid (e.g., 5% to 50% or about 5% to about 50% by weight) admixed in a pharmaceutical delivery vehicle, can expose sufficient oncofetal fibronectin indicating molecule sites to permit binding partner binding. The detectable or therapeutic conjugates can be formulated as liquids (e.g., aqueous solutions) using any of a variety of conventional techniques. For example, a fibronectin or oncofetal fibronectin binding partner conjugate can be in an aqueous solution. A variety of detectable or therapeutic conjugates containing a fibronectin or oncofetal fibronectin binding partner or a fibronectin or oncofetal fibronectin binding partner are provided herein or are known in the art.

d. Ductal Lavage

For exemplary purposes, ductal lavage methods are provided herein. Ductal lavage can be used to collect samples from a duct, or to apply a label to a duct. One skilled in the art will select the ductal lavage method according to the selected an oncofetal fibronectin indicating molecule detection method and guidance provided by the teachings herein.

i. Sample Collection

Samples can be collected from a duct using known methods. Generally, a ductal access tool is used to probe a surface in search of a ductal orifice. Once a ductal orifice is located, a lavage fluid carried in the ductal access tool can be infused into the duct. The lavage fluid can prepare the ductal orifice and duct system for access and fluid and/or can be used for material collection from the duct. In one embodiment, the lavage fluid is introduced into the duct so that it passes substantially throughout the entire ductal network. At least a portion of the lavage fluid can then be collected from the duct to obtain a sample or specimen. In some cases, it can be elected to collect specimens from only a single ductal network. The steps can be repeated in order to identify the presence of an oncofetal fibronectin indicating molecule in two or more ductal networks. For example, between 6 and 9 ducts are typically present in female human breasts, each of which can be sampled individually or at the same time. A variety of ductal lavage techniques are known in the art. Exemplary ductal lavage techniques are described in U.S. Pat. No. 6,168,779 (issued Jan. 2, 2001) and U.S. patent application Nos. 2002/0019017 (published Feb. 14, 2002) and 2002/0037265 (published Mar. 28, 2002).

In one embodiment, the ductal access tool contains a double lumen catheter. The lavage fluid is introduced into the ductal system through one of the catheter lumens. The lavage fluid can be introduced into the ductal system by a syringe operatively connected to the catheter lumen. Once the ductal system is filled with lavage fluid, excess fluid flows outwardly through the second catheter lumen, from which it is collected.

Collection of fluid can further include application of suction to the second catheter lumen to facilitate withdrawal of the lavage fluid from the duct system. Suction can be applied using any device capable of creating suction in a lumen. For example, suction can be applied using a syringe or other suction device operatively coupled to the lumen through which lavage fluid will be withdrawn from the ductal system. The suction can be applied for a brief period of time (e.g., a period of time sufficient to establish flow of the ductal fluid from inside to outside the duct). Alternatively, suction can be applied for an extended period of time (e.g., during a corresponding continuous infusion of lavage fluid).

The ductal system is optionally first accessed with a guide wire, such as a conventional 0.014 in (0.036 cm) guide wire. After the guide wire is inserted past the ductal orifice (e.g., a distance from between 0.25 cm and 2.5 cm or about 0.25 cm and about 2.5 cm past the orifice), the ductal access tool is introduced over the guide wire and into the ductal orifice. After the ductal access tool is in place within the ductal orifice, the guide wire is optionally withdrawn.

When collecting a breast duct sample, for example, external pressure is optionally applied to the breast to facilitate sample collection. The application of external pressure can be manual or mechanical. The pressure is used to more effectively mix fluid, cells and other ductal contents together in the duct. The external pressure can be applied beginning at the base of the breast and working up to the areola and nipple. The pressure can be applied to the breast periodically, continuously, or cyclically during and/or after infusion of lavage fluid.

With respect to breast duct samples, for example, the volume of lavage fluid introduced into the ductal system will typically be at least 5 mL or about 5 mL, more typically between 5 mL and 25 mL or about 5 mL and about 25 mL and often 10 mL or about 10 mL. The lavage fluid is generally introduced into the ductal system at a low pressure (i.e., a pressure which will not rupture the ductal network). For example, the fluid can be introduced at a rate in the range of between 0.1 mL/s and 5 mL/s or about 0.1 mL/s and about 5 mL/s and often between 0.5 mL/s and 1 mL/s or about 0.5 mL/s and about 1 mL/s. In addition, the lavage fluid is generally introduced for a relatively short period of time (e.g., between 1 min and 5 min or about 1 min and about 5 min). Introduction of the lavage fluid optionally continues even after the initial portions of the fluid begin to emerge from the second catheter lumen.

ii. Applying a Label to a Duct

Identification of ductal orifices on the surface is optionally facilitated by first labeling some or all of the ductal orifices. Methods for labeling ductal orifices are known (see, e.g., U.S. Pat. No. 6,168,779). Briefly, a portion of the epithelial lining exposed at the ductal orifice is labeled with a visible or otherwise detectable marker, which allows the treating professional to identify the orifice for each of the ductal networks. Accordingly, one or more tissue markers at the ductal orifice are specifically labeled with a detectable compound that can preferentially bind to the ductal orifice region. In one embodiment, for example, binding of the label to the ductal orifice region is at least 2-fold, generally, 5-, 10-, 50-, 100-, or more fold, or about 2-fold, generally, about 5-, 10-, 50-, 100-, or more fold stronger than binding of the label to other regions. As such, binding of the label to the orifice will provide a discernable indication of the location of the orifice.

In certain embodiments, the surface is optionally washed with a solution capable of unblocking the orifice to facilitate or permit binding of the labeling agent to the tissue marker(s) at the ductal orifice. For example, the orifice can become plugged with keratin-containing materials and washing with a keratinolytic solution, such as acetic acid (e.g., 5% to 50% or about 5% to about 50% by weight) admixed in a pharmaceutical delivery vehicle, will expose sufficient marker sites to permit labeling of the ductal orifices.

The labeling reagents can be formulated as liquids (e.g., aqueous solutions) using any of a variety of conventional techniques. For example, a fibronectin or oncofetal fibronectin binding partner can be in an aqueous solution. The binding partner can be optionally coupled to one member of a signal-producing system capable of generating a detectable visual or other change on the tissue surface. Signal-producing systems include, but are not limited to, fluorescent systems, color-generating systems, luminescent systems, magnetic resonance detection systems, radionuclide systems and ultrasound imaging systems. For example, fluorescent systems that contain a single fluorescent label can be used. Alternatively, other systems that contain two or more components, including enzymes, substrates, catalysts and enhancers, also can be employed. At least one component of the signal-producing system is attached to the binding partner. Alternatively, primary antibodies specific for the tissue marker and labeled secondary antibodies can be employed to indirectly bind to the label to the tissue marker. For example, the primary antibody can be mouse IgG and the labeled secondary antibody can be FITC goat anti-mouse IgG (Zymed).

In particular embodiments, the tissue marker or markers are antigenic or epitopic sites characteristic of the epithelial lining of the breast ducts. The epithelial lining typically extends sufficiently far into the orifice region of the duct to permit successful labeling using generally conventional immunocytochemical labeling reagents and techniques. Exemplary tissue markers include, but are not limited to, antigens and epitopes defined by an oncofetal fibronectin indicating molecule. Other breast epithelial tissue markers include cytokeratins present in the epithelial cytoplasmic lining, such as cytokeratin 8 and cytokeratin 18; and by molecules present in the membrane lining, such as E cadherin and epithelial membrane antigen (EMA), and others described, for example, in Moll et al., *Cell* 30:11-19 (1982); Gown and Vogel, *Am. J. Pathol.*, 1 14:309-321 (1984); and Johnson, *Cancer Metastasis Rev.*, 10:11-22 (1991).

iii. Lavage Fluid

The lavage fluid typically contains saline and one or more optional ingredients such as, for example, an anesthetic, an oncotic agent, an osmotic agent, oxytocin, prolactin, an antiseptic agent, a ductal orifice dilating agent, a vasodilator, a vasoconstrictor, a muscle relaxant, a muscle constrictor, an anti-ischemic agent, a beta-blocker, a calcium channel blocker, a dye or stain to mark the surface excluding ductal orifices, a dye or stain to mark a perimeter of a ductal orifice and a dye or stain to mark a ductal orifice. The lavage fluid also can optionally contain one or more gases (e.g., air and/or nitrogen). It is expected that the presence of gas serves to increase retrieval of cells and fluid. The gas can be introduced into the lavage fluid by any of a variety of standard methods, including introduction of the gas from a pressurized container.

The lactation stimulating agent is any agent capable of stimulating lactation in a lactating woman. The agent, as applied to a nipple surface and breast of a non-lactating woman is believed to act to increase the ductal fluid collectable from the breast duct. The lactation stimulating agent can include, but is not limited to, one or more of the following: oxytocin, prolactin and combinations thereof.

The dye or stain to mark non-ductal orifice regions of the surface is any agent capable of identifying the non-ductal orifice regions on the surface, to the exclusion of the ductal orifices.

The dye or stain to mark the perimeter regions of ductal orifices is any agent capable of identifying a ring or region surrounding one or more ductal orifices.

The dye or stain to mark a ductal orifice is any agent capable of marking a ductal orifice to the exclusion of other regions of the surface. The dye or stain to mark a ductal orifice can include, but is not limited to, one or more keratin ligands having a fluorescent tag. In operation, the keratin ligand binds to a keratin plug at a ductal orifice and the fluorescent tag is observed at the ductal orifice, but not at non-keratinized regions of the surface.

The ductal lavage sample obtained can contain epithelial cells from the lining of the duct, normally secreted and non-secreted fluids present in the ducts and proteins, peptides, nucleic acid molecules, and other chemical species that can be secreted or otherwise released into a duct in response to a disease or other problem to be identified. In connection with breast ducts, material from the terminal ductal lobular unit also can be collected in a lavage procedure, as well as materials residing deep within the ductal passages that access the portion of the breast duct close to the nipple surface, depending upon the depth of penetration of the lavage fluid and the extent to which the fluid that is introduced into the ductal system is retrieved after mixing with fluid and material in the ductal system. The ductal system includes the terminal ductal lobular unit and any tributary ductal passages that connect with or feed into the ductal system leading to the main breast duct that is accessed at the nipple surface.

3. Collection of Urine Samples

Urine can be examined according to the oncofetal fibronectin indicating molecule detection methods known in the art or disclosed herein to screen for the presence of analytes such as an oncofetal fibronectin indicating molecule, which can be used as an indicator for health problems such as overall health, cancer or delivery.

a. Sample Handling

Urine samples can be obtained using any of a variety of techniques known in the art. For example, a sample can be collected by a subject urinating into a sample container, a sample can be collected from a catheter that has been introduced into the bladder, or a sample can be obtained by a urine stream contacting a test device, without the need to be collected into a vessel.

The urine sample can be a pooled collection from a sample container or can be a sample from a urine stream. Either the pooled or the stream samples can contain urine from an entire urination, or only a portion of the urination. Portions of urination can be separated by methods known in the art for different testing purposes, as is known in the art. For example, the first catch of the urination includes the initial portion of the urination. A sample can include the first catch or can exclude the first catch, according to the desired purposes of one skilled in the art.

The urine sample can be collected from a subject at any time. Typically, a sample is collected at least 1 hour or about 1 hour after the most recent urination. A sample can be collected at least 2 hours, 3 hours, 4 hours, 5 hours, 6 hours, or about 2 hours, 3 hours, 4 hours, 5 hours, 6 hours, or more, after the most recent urination. In one example, a sample collected is a first morning void. Samples collected from a catheter can be stored drainage collected from the drainage bag, or can be fresh drainage collected from the catheter as the drainage flows from the bladder. The sample volume can be varied according to the type and number of tests to be performed and can range from as little as 100 microliters or less, to 50 milliliters or more.

The sample can be stored in any of a variety of containers known in the art. Typically, the container will be a plastic (e.g., polypropylene or polyethylene) container capable of forming a fluid-impermeable seal that prevents sample leakage and sample contamination and can optionally be sterile. In some embodiments, the container is formed from a material to which an oncofetal fibronectin indicating molecule does not adhere, such as polypropylene or polyethylene. In other embodiments, the container can be formed from a material to which an oncofetal fibronectin indicating molecule does adhere, such as glass, polycarbonate or polystyrene; in such embodiments, assays for an oncofetal fibronectin indicating molecule can be performed in the container. In one exemplary container, a sample can be stored in a container that permits use of a fraction of a sample without contaminating the remainder of the sample, such as that disclosed in U.S. Pat. No. 5,897,840.

The sample can be stored at room temperature, temperatures below room temperature (such as 4° C.), or can be frozen and stored at temperatures below freezing (such as −20° C. or −70° C.).

Typically, urine samples used in vertical flow assay methods as described herein are tested immediately after collection, within 0.5 hours, within 1 hour, 2 hours, 4 hours, 8 hours or 12 hours after collection, or about 0.5 hours, 1 hour, 2 hours, 4 hours, 8 hours or 12 hours after collection. Generally, urine samples used in other assay methods, including those described herein (e.g., dot blot, lateral flow and western blot), that are stored at room temperature can be tested immediately after collection, within 0.5 hours or about 0.5 hours after collection, within 1 hour, 2 hours, 4 hours, 8 hours or 12 hours, or about 1 hour, 2 hours, 4 hours, 8 hours or 12 hours after collection, or later, such as 1 day after collection. Samples that are stored below room temperature (such as 4° C.) can be tested immediately after collection, within 0.5 hours or about 0.5 hours after collection, within 1 hour, 2 hours, 4 hours, 8 hours or 12 hours, or about 1 hour, 2 hours, 4 hours, 8 hours or 12 hours after collection, or later, such as 1 day after collection, 3 days after collection, 1 week after collection, or more. One of ordinary skill in the art can empirically determine, based on the assay method, whether the urine samples should be tested in a narrower time frame (e.g., within 12 hours after collection).

If a sample is to be frozen, the sample can be frozen by any method known in the art for freezing a liquid. For example, samples can be frozen by placing the sample in a container at −5° C. or less for 1 hour or more. Typically, the sample will be placed in a container, such as a freezer, at a temperature of −20° C., −50° C., −70° C., or less. One skilled in the art will understand that, in order to freeze the sample, the length of time needed for a sample to freeze decreases with a decrease in the temperature of the container in which the sample is placed. After freezing, the sample can be stored at or below a temperature in which the urine sample remains frozen. Typically the storage temperature will be −5° C., −20° C., −50° C., −70° C., or about −5° C., −20° C., −50° C., −70° C., or less. Frozen samples can be stored for 1 week after collection, 2 weeks after collection, 1 month after collection, 2 months after collection, 3 months after collection, 4 months after collection, 5 months after collection, 6 months after collection, or about 1 week after collection, 2 weeks after collection, 1 month after collection, 2 months after collection, 3 months after collection, 4 months after collection, 5 months after collection, 6 months after collection, or more. Frozen samples can be thawed at a variety of temperatures, including room temperature or cooler, such as 4° C. A frozen sample is typically fully thawed prior to analysis of the sample for presence of an oncofetal fibronectin indicating molecule. A frozen sample will usually be subjected to 3 freeze/thaw cycles or less. Typically, a frozen sample is subjected to only one freeze/thaw cycle (i.e., a frozen sample is thawed and tested, not thawed, refrozen, re-thawed and tested).

Typically, a urine sample used in other assay methods as described herein (lateral flow, dot blot, western blot, etc.), can be used b. Sample Condition Modification The urine sample can be used "neat" (i.e., without addition of further reagents) or can have added thereto one or more reagents such as preservatives or compounds that inhibit sample degradation such as protease or nuclease inhibitors as is known in the art (e.g., by dilution with a buffer, such as anti-protease buffer (APB) containing 0.05 M Tris buffer, pH 7.4, 150 mM NaCl, 0.02% NaN$_3$, 1% BSA, 5 mM EDTA, 1 mM phenylmethylsulfonyl fluoride (PMSF), 500 Kallikrein Units/ml of Aprotinin, and 0.1% Triton X-100). Adding one or more reagents can occur by any of a variety of condition modification methods, including, but not limited to, direct mixing of the sample and reagent, dialysis, dilution, filtration and buffer exchange. If the sample conditions are modified, modification can be performed at the time of sample collection, at the time of sample analysis, or any time in between. When a sample is to be frozen, sample condition modification can be performed before freezing the sample, while the sample is being frozen, while thawing the sample, or after the sample is thawed.

Urine samples can vary from subject to subject, or from sample to sample for the same subject. Sample condition modification can address these variations. To address sample variations, sample modification can be conducted using any of a variety of reagents and methods known in the art. Typically, the diluent or liquid for condition exchange (e.g., dialysis) is distilled water or an aqueous solution of one or more compounds. In one example, the diluent or liquid for condition exchange contains APB buffer: 0.05 M Tris buffer, pH 7.4, 150 mM NaCl, 0.02% NaN$_3$, 1% BSA, 5 mM EDTA, 1 mM phenylmethylsulfonyl fluoride (PMSF), 500 Kallikrein Units/ml of Aprotinin, and 0.1% Triton X-100.

i. Ionic Strength

Sample condition modification with a buffer such as APB can result in a change in the ionic strength of the sample, depending on the ionic strength of the unmodified sample and the APB buffer. With increasing amounts of condition modification, the ionic strength of the sample will increasingly approximate the ionic strength of the diluent or liquid exchange buffer.

A sample tested for the presence of an oncofetal fibronectin indicating molecule by contacting the sample with a binding partner specific for an oncofetal fibronectin indicating molecule can yield different test results at different ionic strengths. For example, at low ionic strength, an oncofetal fibronectin indicating molecule can readily bind to a binding partner specific for the oncofetal fibronectin indicating molecule, but other background material such as non-oncofetal fibronectin molecules also can bind to such a binding partner at low ionic strength, thus potentially yielding false positive results. At high ionic strength, non-oncofetal fibronectin molecules will not readily bind to a binding partner specific for an oncofetal fibronectin indicating molecule, but the oncofetal fibronectin indicating molecule also may not strongly bind (detectably bind) to such a binding partner, thus potentially yielding false negative results. A mid-range ionic strength can be selected that permits specific binding between an oncofetal fibronectin indicating molecule and a fibronectin or oncofetal fibronectin binding partner, while at the same time suppresses binding of background material such as non-oncofetal fibronectin molecules to the fibronectin or oncofetal fibronectin binding partner.

Urine samples can vary in ionic strength. In such methods, use of neat samples without sample condition modification can result in either false positive or false negative signals. By modifying the conditions of urine samples with a buffer such as APB, the ionic strength from broadly varying urine samples can be approximated to a mid-range ionic strength determined to permit specific binding partner binding (decreasing false negative results) while suppressing non-specific binding (decreasing false positive results). Thus, modifying the conditions of urine samples with the appropriate buffer can increase the reliability of oncofetal fibronectin indicating molecule detection methods.

A sample can be modified by any of a variety of ratios of sample to modifying substance. When a buffer is added to a sample, the buffer can be added such that a desired ionic strength is achieved without unduly diluting the sample components such as an oncofetal fibronectin indicating molecule. One skilled in the art can determine a desirable dilution ratio, according to the desired ionic strength or range thereof, the ionic strength of the sample, the reagent to be added to the sample and the concentration of sample components. In some embodiments, a minimum amount of reagent is added to arrive at a desired ionic strength or ionic strength range, thus resulting in a minimum amount of sample dilution. In other embodiments, a dilution ratio and reagent that can be used to adjust most or all urine samples to a desired ionic strength or ionic strength range can be selected. Typical dilution ratios include 1:1.5 (volume before dilution:volume after dilution), 1:2, 1:3, 1:4, 1:5, 1:6, 1:7, 1:8, 1:9, 1:10, 1:12, 1:15, 1:20, about 1:1.5, 1:2, 1:3, 1:4, 1:5, 1:6, 1:7, 1:8, 1:9, 1:10, 1:12, 1:15 and 1:20. A typical dilution ratio is 1:4.

In one embodiment, the reagent added to the urine sample is a buffer solution such as a modified APB buffer. Typically, the principal contributor to the ionic strength of a buffer solution can be a salt, including a monovalent salt such as NaCl, KCl, NaBr, KBr and a variety of other salts known in the art. The salt concentrations can be any of a variety of concentrations that achieves the desired ionic strength when added to urine. Exemplary salt concentration ranges can include 50 mM to 350 mM, 100 mM to 250 mM, or 150 mM. Additional exemplary salt concentration ranges can include about 50 mM to about 350 mM, about 100 mM to about 250 mM, or about 150 mM. Such buffer solutions can contain a variety of additional components, including, but not limited to, a buffering compound (e.g., Tris or phosphate), a chelator (e.g., EDTA or EGTA), a protease inhibitor (e.g., PMSF or aprotinin), detergent (e.g., Tween or Triton X-100), other stabilizers (e.g., PEG or BSA), or combinations thereof. In one example, a buffer solution can contain 0.05 M Tris buffer, pH 7.4, 150 mM NaCl, 0.02% NaN$_3$, 1% BSA, 5 mM EDTA, 1 mM phenylmethylsulfonyl fluoride (PMSF), 500 Kallikrein Units/ml of Aprotinin, and 0.1% Triton X-100.

ii. Ionic Strength Testing

Typically, a major ionic component in urine is sodium chloride. The concentrations of either sodium, chloride, or both, or total ionic strength, can be determined using a variety of testing methods known in the art including use of test strips, glass membrane electrodes, conductivity measurement, atomic absorption, laser induced fluorescence or x-ray fluorescence. The results of the ion composition test can either directly measure or approximate the ionic strength of the urine sample. If the ionic strength of the urine sample is higher than a maximum allowable amount, it is possible to use the ionic strength measurement to calculate the minimum amount of dilution necessary to achieve a selected ionic strength in the sample prior to analysis, or the minimum amount of liquid exchange (e.g., dialysis) necessary to achieve a selected ionic strength in the sample prior to analysis. If the ionic strength of the urine sample is lower than a minimum allowable amount, it is possible to use the ionic strength measurement to calculate the minimum amount of salt solution or solid salt to add to the urine to achieve a selected ionic strength in the sample prior to analysis, or the minimum amount of liquid exchange to achieve a selected ionic strength in the sample prior to analysis. As one skilled in the art will recognize, the selected ionic strength for a binding partner to bind to an oncofetal fibronectin indicating molecule can include a range of ionic strengths and can vary based on a variety of factors including the nature of the binding partner. Typically, the selected ionic strength for binding assays ranges from 50μ to 500μ, from 75μ to 400μ, from 100μ to 300μ and will often be 150μ to 250μ. Alternatively, the selected ionic strength for binding assays ranges from about 50μ to about 500μ, from about 75μ to about 400μ, from about 100μ to about 300μ and will often be about 150μ to about 250μ.

iii. Normalization

The concentration of a component of urine can vary from urine sample to urine sample as a function of a variety of factors including condition modification (e.g., dilution or dialysis) of a urine sample and frequency of urination by the subject. One of several methods can be used to estimate a sample variation-independent concentration of an analyte such as an oncofetal fibronectin indicating molecule, in a urine sample, where the estimated concentration is less sensitive to variation between samples. Such a method of estimating sample variation-independent concentrations is termed normalization.

Normalization can be carried out using any of a variety of methods known in the art or provided herein. One method of normalization of a urine sample is to measure the concentrations of the analyte of interest (an oncofetal fibronectin indicating molecule) and a second analyte that typically enters urine at a constant rate. A variety of constantly-entering analytes are known in the art. One example of such an analyte is creatinine, which enters urine at a steady state. The concentration of creatinine can be used to normalize the concentration of an oncofetal fibronectin indicating molecule in urine. A variety of different normalization methods are known in the art, as exemplified in U.S. Pat. Nos. 5,804,452 and 6,436,721.

c. Sample Treatment i. Non-Specific Binding

The urine sample can be contacted with one or more non-specific binding compounds or one or more non-specific binders prior to contacting the urine sample with a molecule that can detect the presence of an oncofetal fibronectin indicating molecule.

Non-specific binding compounds are compounds that bind to at least a portion of background material in a sample without binding more than a small amount (e.g., less than 10%) of oncofetal fibronectin indicating molecule in the sample. Typically, non-specific binding compounds bind to background material more readily than the non-specific binding compounds bind to an oncofetal fibronectin indicating molecule. Non-specific binding compounds that can be used include non-specific binding proteins. Non-specific binding proteins are typically water-soluble proteins including albumins such as bovine serum albumin (BSA), human, rabbit, goat, sheep and horse serum albumins; and other proteins such as ovalbumin, fibrinogen, thrombin, transferrin, glycoproteins, casein, antibodies not specific for an oncofetal fibronectin indicating molecule and other proteins. Non-specific binding proteins also can include water-soluble polyamino acids such as, for example, polymers of one or more amino acids such as lysine, glutamic acid, alanine, histidine, methionine and proline. Exemplary proteins that can be used for a non-specific binding surface include BSA, methylated BSA or antibodies such as mouse anti-MHC-1 antibody (e.g., ATCC No. W632) or mouse IgG. Non-specific binding compounds also can be protein-containing compositions including serum such as fetal calf serum, gelatin and dried milk.

Non-specific binders can include non-specific binding surfaces, which are solid structures that can contain one or more components, where the non-specific binding surface binds to at least a portion of background material in a sample while not binding more than a small amount (e.g., less than 10%) of oncofetal fibronectin indicating molecule in the sample. Typically, non-specific binding surfaces bind to background material more readily than the non-specific binding surfaces bind to an oncofetal fibronectin indicating molecule. Possible solid supports for non-specific binding surfaces include paper and cellulose derivatives, such as cellulose esters and ethers, natural and synthetic polymeric materials, such as latex, vinyl polymers, polypropylene, polyethylene and partially hydrolyzed derivatives, polycondensates, copolymers and inorganic materials. In one embodiment, a non-specific binding surface is a porous or bibulous member capable of transporting a liquid sample along a test strip. Non-specific binding surfaces that can be used include solid supports having immobilized thereon one or more non-specific binding proteins such as, but not limited to, albumin (including bovine serum albumin, or BSA), antibodies not specific for an oncofetal fibronectin indicating molecule and others provided herein or known in the art. Exemplary proteins that can be used for a non-specific binding surface include BSA, methylated BSA or antibodies such as W632 or mouse IgG. In one example, a non-specific binding surface can be a nitrocellulose membrane having methylated BSA immobilized thereon.

ii. Filtration

The urine sample also can be filtered to remove at least a portion of the background materials prior to detecting the presence of an oncofetal fibronectin indicating molecule. Filters that can be used are low protein binding filters that bind to no more than a small amount (less than 10%) of the oncofetal fibronectin indicating molecule present in the urine sample. Typically, filters used in the methods provided herein bind to background material more readily than the non-specific binding compounds bind to an oncofetal fibronectin indicating molecule. Exemplary low protein binding filters include polyester, polyurethane, fiberglass, polyacetate, polyvinylidene fluoride, polycarbonate, nylon, polyethersulfone, polysulfone, cellulose, cellulose acetate, cellulose mixed esters and hydrophilic modifications thereof. An exemplary low protein binding filter is cellulose acetate. The filter pore size can be large enough to permit passage of an oncofetal fibronectin indicating molecule but small enough to prevent passage of at least a portion of the background materials. Filter pore sizes can range from 20 μm to 0.01 μm, 10 μm to 0.02 μm, 5 μm to 0.05 μm, 1 μm to 0.1 μm and from 0.5 μm to 0.2 μm. Exemplary filters have a pore size of 0.2 μm.

4. Interstitial Fluid

Interstitial fluid also can be collected and tested for the presence of an oncofetal fibronectin indicating molecule. Interstitial fluid is the fluid in the spaces between tissue cells and can constitute about 16% of the weight of the body. Interstitial fluid can contain, as one of its components, an oncofetal fibronectin indicating molecule. Normal interstitial fluid either does not contain oncofetal fibronectin, or contains only low amounts of oncofetal fibronectin; therefore, presence of an oncofetal fibronectin indicating molecule in an interstitial fluid sample can indicate presence of a health problem associated with oncofetal fibronectin in the subject. Interstitial fluid can be collected from a variety of locations throughout the body, as is well known in the art. In one embodiment, interstitial fluid can be collected from the tissue or organ under examination, or from tissue adjacent thereto. For example, when a region or organ in or near the alimentary canal is under examination (e.g., large intestine, prostate, stomach, or gall bladder), interstitial fluid can be collected from the epithelium of that region or organ or tissue adjacent to the region or organ (e.g., in order to monitor the prostate, interstitial fluid can be collected from the region of the colon adjacent the prostate). In another embodiment, interstitial fluid can be collected from skin, regardless of whether or not the skin or some distal region or organ is under examination. For example, interstitial fluid in skin can contain an oncofetal fibronectin indicating molecule that indicates neoplasia in the breast or cervix or thyroid. The dermal layer of skin contains collagen fibers, cells and interstitial fluid in the space between the fibers and cells. Interstitial fluid collected from the dermal layer, or from other locations in the body of a subject, can be used to test for the presence of an oncofetal fibronectin indicating molecule in a subject.

Interstitial fluid samples can be collected by a variety of methods known in the art such as, but not limited to, needle aspiration including dermal needle aspiration (see, e.g., U.S. Pat. Nos. 6,702,791, 5,823,973 and 5,582,184), microporation (see, e.g., U.S. Pat. No. 6,508,785), ultrasound extraction (see, e.g., U.S. Pat. No. 6,589,173), transdermal extraction (see, e.g., U.S. Pat. No. 4,595,011), iontophoresis (see, e.g., U.S. Pat. Nos. 6,496,728; 5,989,409; 5,362,307 and 5,279, 543), blister collection such as microblister collection (see, e.g., U.S. Pat. No. 6,334,851), microblade or microneedle array extraction (see, e.g., U.S. Pat. No. 6,562,014), enhanced cell permeation collection (see, e.g., U.S. Pat. No. 6,503,198) and a variety of other methods known in the art.

In one embodiment, an interstitial fluid sample can be collected by penetrating the outer layer, typically the epithelium, of the region or organ from which the interstitial fluid sample is to be collected, with an instrument such as a hypodermic needle, into which interstitial fluid can enter. The vesicle, such as a hypodermic needle, can pass into and/or through the outermost portion of the region or organ, such as the epithelial cells, to a portion of the region or organ in which interstitial fluid is present. The depth of penetration will vary according to the tissue type and location of the region or organ to be examined, as will be known to those skilled in the art. The vesicle that penetrates the region or organ of interest will have an outer dimension that is small enough to pass with relative ease into the tissue or organ while maintaining physical integrity of the vesicle and an inner dimension that is large enough to permit interstitial fluid to pass into the vesicle. For example, needles of a size of 28 to 32 gauge or about 28 to about 32 gauge (360 micron outer diameter to 230 micron outer diameter) can be used; typically, a needle of 29 or 30 gauge is used. Optionally, the vesicle can be operably attached to a negative pressure device, such as a vacuum apparatus or a syringe in which a plunger can be manually or mechanically withdrawn. A variety of apparatuses and methods for collecting interstitial fluid by penetrating the region or organ of interest are known in the art, as exemplified in U.S. Pat. Nos. 6,702,791, 6,624,882, 5,823,973 and 5,582,184.

In one example of collecting interstitial fluid with a vesicle, interstitial fluid can be collected from skin. The vesicle, such as a needle, can pass through the outer layer of the epidermis (known as the stratum corneum) without passing through the dermal layer of the skin. After passing through the stratum corneum, interstitial fluid can enter or be drawn into the vesicle. The depth to which the vesicle, such as a needle, is inserted into the skin will be deep enough to penetrate the stratum corneum, but typically not deep enough to pass through the dermal layer and penetrate the subcutaneous layer. The stratum corneum is typically 10-15 microns or about 10-15 microns thick and the remainder of the epidermis is typically 80 microns or about 80 microns thick. The dermis is about 2,000-3,000 microns thick. As will be appreciated by one skilled in the art, such dimensions will vary somewhat from individual to individual and depending on the body location of the skin from which the sample is to be collected. A vesicle such as a needle, will typically be inserted into the skin at a depth of 50-2,500 microns or about 50-2,500 microns, often 700-1,500 microns or about 700-1,500 microns. The vesicle that penetrates the skin will have an outer dimension that is small enough to pass with relative ease through the stratum corneum with minimal pain while maintaining physical integrity of the vesicle and an inner dimension that is large enough to permit interstitial fluid to pass into the vesicle.

In another embodiment, an interstitial fluid sample can be collected by penetrating into or through the region or organ of interest, such as the epithelium of an organ or the stratum corneum of skin, with a microarray of blades or needles. Such microarrays can be applied to the tissue or organ of interest to provide a path in the tissue or organ, or to provide a vesicle, through which interstitial fluid can pass. For example, a blade microarray can be applied to the skin to provide a path in the stratum corneum through which interstitial fluid can pass. Microblade or microneedle arrays can provide a plurality of locations on the region or organ or interest for collection of interstitial fluid. The depth to which each microblade or microneedle is inserted will be deep enough to penetrate into the region or organ or interest to a region containing interstitial fluid. For example, when an interstitial fluid sample is collected from skin, the depth to which each microblade or microneedle is inserted into the skin will be deep enough to penetrate the stratum corneum, but typically not deep enough to pass through the dermal layer and penetrate the subcutaneous layer. In an exemplary configuration, each microblade or needle can have an outer dimension of 1-50 microns or about 1-50 microns, a length of 50-500 microns or about 50-500 microns and be separated from neighboring microneedles or microblades by 50-1000 microns or about 50-1000 microns. The microblades or microneedles can optionally be operably coupled with an apparatus or compound for increasing interstitial fluid passage through the penetrated tissue. For example, the microneedle or microblade array can be coupled with a negative pressure device, such as a vacuum apparatus. In another example, a microblade array or microneedle array can be coupled with an absorbent pad that can draw interstitial fluid from the subject by capillarity and/or by osmotic pressure. A variety of microblade and microneedle arrays and methods for using such arrays for collecting interstitial fluid are known in the art, as exemplified in U.S. Pat. Nos. 6,663, 612, 6,562,014 and 6,312,612.

In another embodiment, an interstitial fluid sample can be collected by blister formation and harvesting the fluid in the blister. Interstitial fluid can be a major component of a blister. Blisters can be formed by any of a variety of methods known in the art, including suction and heating methods. For example, when a negative pressure of 200 mm Hg or about 200 mm Hg is applied to skin for 1 hour or about 1 hour, a blister will form. The fluid in the suction blister can be collected using any of a variety of methods, such as, but not limited to, aspiration with a hypodermic needle. In another example, heat can be used to form a blister. For example, a laser energy absorbing substance can be placed onto the skin of a subject and exposure of the skin to laser energy can result in blister formation. Placement of the absorbing substance and the amount of laser energy applied can be controlled such that only microblisters form. The fluid in the heat blister can be collected using any of a variety of methods, such as, but not limited to, aspiration with a hypodermic needle. A variety of apparatuses and methods for blister formation and collection of interstitial fluid from the blister are known in the art, as exemplified in U.S. Pat. Nos. 6,409,679, 6,387,059 and 6,334,851.

In another embodiment, an interstitial fluid sample can be collected by ultrasound extraction. Treating a tissue such as skin with ultrasound can permeabilize the tissue and the treated area can remain permeable from 30 minutes or about 30 minutes after treatment up to 10 hours or about 10 hours after treatment. Interstitial fluid can be collected from the treated, permeable area by any of a variety of chemical and/or physical methods, including, but not limited to, applying negative pressure, contacting the area with a surfactant or organic solvent, contacting the area with a composition that creates osmotic pressure, contacting the area with an ultrasound coupling medium and applying electrical current. The interstitial fluid can be collected in a buffer, salve, gel, or other composition that contacts the treated, permeable area. Ultrasound can be applied directly to the region or organ under examination, such as the large intestine, or can be applied to a region adjacent the region or organ under examination, such as the region of the large intestine that is adjacent to the prostate when the prostate is under examination. Ultrasound also can be applied to skin. A variety of apparatuses and methods for collecting interstitial fluid using ultrasound are known in the art, as exemplified in U.S. Pat. Nos. 6,620,123, 6,508,785 and 6,190,315.

In another embodiment, an oncofetal fibronectin indicating molecule in an interstitial fluid sample can be collected by electrical harvesting. In electrical harvesting, a substance such as an oncofetal fibronectin indicating molecule, diffuses through a membrane as a result of applying an electric field. Electrical harvesting can be used to collect substances within intersitial fluid. Electrical harvesting can be performed by conducting electrical current through the tissue to extract the substance into one or more sampling vesicles or into collection compositions (e.g., a buffer, a gel, salve or cream that can absorb components of interstitial fluid). For example, an oncofetal fibronectin indicating molecule sample can be collected by applying electrical energy of sufficient strength and duration to the tissue surface of a subject in order to transport a substance or a metabolite from beneath the tissue surface at a collection site on the surface of the tissue into a defined collection area or into a collection vesicle. These methods include the method known as iontophoresis, which is a method of treatment to drive uncharged non-ionic materials and positive or negative ions out of an organism through tissue. In conventional iontophoresis two electrodes are placed in contact with the tissue. One or both of the electrodes is in a sampling chamber/collection reservoir to collect the substance extracted and a voltage is applied between the two electrodes. The sampling chamber/collection reservoir is provided at the tissue surface to serve as a collector of material transported. Any method known in the art such as iontophoresis that results in collection of components of interstitial fluid by, for example, electrophoresis, electroosmosis, or electroporation, can be used to collect a sample containing an oncofetal fibronectin indicating molecule. The electrical harvesting is typically performed by applying an electrical field to the region or organ under examination, or to a region adjacent thereto. For example, the electrical field can be applied to skin. The electrical field applied to the tissue from which the sample is to be harvested can be any electrical field along which an analyte such as an oncofetal fibronectin indicating molecule can migrate. Exemplary electrical fields include direct current, pulsed direct current and current with alternating polarity such as AC current. A variety of apparatuses and methods for collecting an oncofetal fibronectin indicating molecule from interstitial fluid by electrical harvesting are known in the art, as exemplified in U.S. Pat. Nos. 6,496,728, 6,023,629 and 5,989,409.

In another embodiment, an interstitial fluid sample can be collected using a permeation enhancing compound. A permeation-enhancing compound can serve to increase the permeability of a membrane, cell or tissue and permit interstitial fluid, or selected components thereof such as an oncofetal fibronectin indicating molecule, to pass through the membrane, cell or tissue, to a location at which the interstitial fluid or components can be collected. A permeation enhancing compound typically functions by contacting the surface for which permeation is to be enhanced and causing one or more components of interstitial fluid to pass through the contacted surface. A variety of permeation enhancing compounds are known in the art and include, but are not limited to, aqueous hypertonic solutions, solutions containing organic solvents such as propylene glycol, dimethylsulfoxide or isopropyl alcohol, organic salts such as bile salts including sodium cholate, surfactants such as detergents, including cationic detergents, anionic detergents, non-ionic detergents and zwittergents, organic compounds such as pyrrolidones including N-methyl-pyrrolidone. The permeation compound can be a liquid or a solid, but when the permeation compound is a solid, the solid is typically dissolved in a solvent. The permeation enhancing compounds can be applied directly to the surface of interest, or can be applied in a composition such as a salve, cream, gel, or in an absorbent pad. In one example, the permeation compound can be a component of a transdermal patch that can be affixed to the skin of a subject from which the sample is to be collected. A variety of apparatuses and methods for collecting components of interstitial fluid using permation enhancing compounds are known in the art, as exemplified in U.S. Pat. Nos. 6,503,198, 6,492,180, 5,438,984, 5,139,023, 4,960,467, 4,746,508 and 4,595,011.

In another embodiment, an interstitial fluid sample can be collected by electromagnetic radiation mediated permeation. Electromagnetic irradiation of a membrane, cell or tissue can result in ablation or formation of micropores in the irradiated area. Electromagnetic irradiation can cause ablation or micropore formation by a variety of mechanisms including photochemical, photothermal and photomechanical ablation. Photochemical ablation occurs by dissociation and/or formation of atomic bonds that results in disruption of a membrane or tissue or extracellular matrix. Photothermal ablation occurs by absorption of heat, which can result in denaturation of a membrane or tissue or extracellular matrix, or in water vapor formation within a membrane or tissue or extracellular matrix, which results in pressure formation that causes fracturing of a membrane, tissue or extracellular matrix. Photomechanical ablation occurs by absorption of electromagnetic energy in such a way that mechanical stress is induced onto the absorbing surface, for example, by delivering radiation pulses at time lengths shorter than thermal diffusion time, resulting in mechanical stress caused by compression, expansion and/or recoil of the treated surface. By controlling the variables of electromagnetic irradiation such as the wavelength, intensity, pulse duration, pulse frequency and beam size, one skilled in the art can control the amount and type of energy delivered and the location and area of the irradiated surface. Such control also permits the skilled artisan to select the degree to which ablation or microchannel formation will be accomplished by photochemical, photothermal or photomechanical mechanisms, or combinations thereof. Such control also permits one skilled in the art to determine the size and depth of the micropores or ablations resultant from exposure to electromagnetic radiation. Electromagnetic radiation can be delivered by, for example, one of a variety of lasers which can be selected according to the properties of the particular laser, such as intensity and wavelength, or other considerations such as portability or expense. In addition, one or more electromagnetic energy absorbing compounds such as dyes can be used to aid or further control energy transfer to the surface, as is known in the art. Micropore formation or ablation by magnetic radiation can permit interstitial fluid to pass through the treated region, membrane or tissue. Any of a variety of tissues or organs throughout the body can be treated with electromagnetic radiation to form micropores or ablated tissue. In one example, the stratum corneum of the skin can have formed therein micropores through which interstitial fluid can pass; similarly, the micropores can be formed to pass through the stratum corneum and epidermis and into the dermis. Typically, micropore formation or ablation will be performed such that a sufficient channel is formed to permit interstitial fluid to pass therethrough, without resulting in significant damage to surrounding tissue or discomfort to the subject being treated. Arrays of micropores or ablated tissue also can be readily formed using such methods. Micropore formation or ablation by electromagnetic irradiation can be coupled with any of a variety of methods for harvesting interstitial fluid including, for example, coupling with a negative pressure device such as a vacuum. A variety of apparatuses and methods for collecting interstitial fluid using electromagnetic radiation are known in the art, as exemplified in U.S. Pat. Nos. 6,685,699, 6,508,785 and 6,387,059.

In a similar embodiment, an interstitial fluid sample can be collected by micropore formation as a result of plasma formation or bombardment with microparticles. Plasma, in the present context, refers to any of a variety of charged molecules, atoms or subatomic particles such as electrons. Plasma can be formed on the surface of the target region or organ, such as the surface of skin, by, for example, pulses from an intense laser. The charged particles can be highly reactive and can cause ablation or micropore formation at the surface location of the plasma. A variety of apparatuses and methods for collecting interstitial fluid plasma for micropore formation or ablation are known in the art, as exemplified in U.S. Pat. Nos. 6,387,059 and 5,586,981. Micropores or ablation also can be caused by bombardment with microparticles. Microparticles are solid particles that can range from 0.1 micron in diameter to 100 microns in diameter or about 0.1 micron in diameter to about 100 microns in diameter. Microparticles can be composed of any of a variety of solid compounds or compositions known in the art, ranging from solid water (water ice) or solid carbon dioxide (dry ice) to insoluble compounds such as insoluble inorganic compounds such as aluminum oxide or titanium oxide, to soluble compounds such as sugars, starch or salts, or metals such as gold, platinum or tungsten. Microparticles can form micropores by being accelerated toward the surface of a region or organ under examination. Microparticles can be accelerated toward a surface using any of a variety of methods known in the art including, but not limited to, compressed gas, electric discharge, expansion of a liquid to a gas such as liquid helium expanding to a gas at room temperature, negative pressure acceleration, or momentum transfer by contact with a moving solid surface. The depth and size of the micropores formed can be a function of the size and weight of the microparticles used and the amount of acceleration of the microparticles. Typically, the micropores formed will be sufficiently large to form a channel that permits interstitial fluid to pass therethrough, while not resulting in significant damage to surrounding tissue or discomfort to the subject being treated. For example, the micropores formed by microparticles can range from 10 microns to 1000 microns or about 10 microns to about 1000 microns in diameter. The depth of the micropore can depend on the tissue being sampled; for example, a micropore in skin can be 50 to 2000 microns or about 50 to about 2000 microns in depth. A variety of apparatuses and methods for collecting interstitial fluid using microparticle bombardment are known in the art, as exemplified in U.S. Pat. Nos. 6,706,032 and 6,482,604. Arrays of micropores also can be readily formed using plasma ablation or microparticle bombardment. Micropore formation by plasma or microparticle bombardment can be coupled with any of a variety of methods for harvesting interstitial fluid including, for example, coupling with a negative pressure device such as a vacuum.

The above embodiments can be coupled together in collecting interstitial fluid or components thereof, such as an oncofetal fibronectin indicating molecule. For example, microparticle mediated microporation can be coupled with a permeation enhancing compound in collecting the sample. In another example, different microporation methods can be coupled together, such as, for example, ultrasound and iontophoresis. A large variety of additional combinations of the above methods are known in the art, as described in the patents related to each embodiment and in U.S. Pat. No. 6,692,456. In particular, the methods for enhancing passage of interstitial fluid or components thereof to a collectable region can be coupled with any of a variety of methods for collecting the fluid or components thereof, including applying negative pressure such as a vacuum, applying a liquid, gel, cream, salve, solid support such as a patch, or any other interstitial fluid collection vesicle or compound known in the art.

Methods and apparatuses for collecting interstitial fluid or components thereof, such as an oncofetal fibronectin indicating molecule, can be performed in conjunction with one or more additional steps of sample treatment and/or oncofetal fibronectin indicating molecule detection. In one embodiment, the sample collection device can be coupled with a composition containing a non-specific binding partner. For example, a sample can be collected by coupling a vacuum to a microneedle array and the microneedle array can be in fluid communication with a composition that contains a non-specific binding partner. For example, the microneedle array can be in fluid communication with a buffer containing a non-specific binding partner such as BSA. In another example, the microneedle array can be coupled to a solid support or a gel containing a non-specific binding partner. Any of a variety of formats for the non-specific binding partner, as provided elsewhere herein, can be used with any of the variety of interstitial fluid sampling methods and combinations thereof provided herein.

In another embodiment, the sample collection device can be coupled with a composition containing a fibronectin binding partner or an oncofetal fibronectin binding partner. For example, a sample can be collected by microporation followed by application of a transdermal patch containing a permeation enhancing compound and the transdermal patch can further contain a composition that contains a fibronectin binding partner or an oncofetal fibronectin binding partner. For example, the transdermal patch can contain a buffer containing a colloidal gold fibronectin binding partner conjugate. In another example, the transdermal patch can contain a solid support or containing a fibronectin or oncofetal fibronectin binding partner bound to the solid support. Any of a variety of formats for the fibronectin binding partner or oncofetal fibronectin binding partner, as provided elsewhere herein, can be used with any of the variety of interstitial fluid sampling methods and combinations thereof provided herein.

F. METHODS OF DETECTING ONCOFETAL FIBRONECTIN

Provided herein are methods of detecting an oncofetal fibronectin indicating molecule. Typically, the methods are used to detect an oncofetal fibronectin indicating molecule in a sample, such as a sample from a subject. An oncofetal fibronectin indicating molecule can be, for example, an oncofetal fibronectin protein, a nucleic acid molecule encoding oncofetal fibronectin or a complement thereto, or an autoantibody that specifically binds oncofetal fibronectin protein or a nucleic acid molecule encoding oncofetal fibronectin, or a fragment thereof. Methods of detecting an oncofetal fibronectin indicating molecule in a sample can be used to determine the presence of an oncofetal fibronectin indicating molecule in the sample, can be used to determine the amount or concentration of an oncofetal fibronectin indicating molecule in a sample, can be used to determine whether or not a positive result is a false positive and can be used to determine the regions or composition of an oncofetal fibronectin indicating molecule present in the detected an oncofetal fibronectin indicating molecule.

For example, when the particular type of sample collected from a subject typically does not contain detectable amounts of an oncofetal fibronectin indicating molecule when collected from normal subjects, detecting any amount of an oncofetal fibronectin indicating molecule in such a sample can indicate the presence of a health problem associated with oncofetal fibronectin in the subject. In another example, when the type of sample collected from a subject typically contains a baseline amount of an oncofetal fibronectin indicating molecule when collected from normal subjects, detecting an amount of an oncofetal fibronectin indicating molecule greater than the baseline amount can indicate the presence of a health problem associated with oncofetal fibronectin in the subject.

Assays intended for use in the systems and methods disclosed herein include, but are not limited to: protein detection, including immunoassay or other antigen-binding-based detection; nucleic acid detection, including methods using amplification and non-amplification protocols; any assay that includes colorimetric or spectrometric detection, such as fluorometric and luminescent detection; mass spectrometric analysis; or any assay that includes binding of an oncofetal fibronectin indicating molecule to a fibronectin or oncofetal fibronectin binding partner. Any test that produces a signal, or from which a signal can be generated, or that can be detected by a detector, such as a photodetector, a gamma counter or a mass spectrometer, is intended for use in the methods provided herein. Any wavelength is intended to be included.

Any of the methods for detecting oncofetal fibronectin provided herein can be used in conjunction with any of the sample collection methods provided herein or known in the art, to provide information for any of the indications or other uses of detection of oncofetal fibronectin provided herein or otherwise known in the art.

Binding assays, including competitive binding assays and sandwich assays, are among those that can be used in the methods provided herein. The methods and systems provided herein have broad applicability to a variety of sample types for a variety of different indications, as will be apparent to one skilled in the art. A number of different types of binding assays using a variety of protocols and labels are well known. Binding assays can be performed in a single liquid phase, or a binding partner can be immobilized to a solid support upon which the assay is performed. Sandwich assays can be performed. Competitive assays can be performed. The reaction steps can be performed simultaneously or sequentially, as will be known to those skilled in the art. Threshold assays can be performed, where only analyte levels of above a specified level or rate yield a positive result. Assay formats include, but are not limited to, for example, assays performed in test tubes, on membranes, in wells, in multi-well plates, on microarrays, on chromatographic test strips, as well as dipstick, lateral flow, vertical flow, or migratory format assays.

Assay methods also can include mass measurement, where mass of an oncofetal fibronectin indicating molecule, a fragment thereof, or another compound indicative of the presence of an oncofetal fibronectin indicating molecule can indicate the presence of the oncofetal fibronectin indicating molecule in the sample. An exemplary mass measurement method is mass spectrometry.

The assay methods provided herein also include nucleic acid molecule amplification methods, where a primer can hybridize with a nucleic acid molecule encoding oncofetal fibronectin (e.g., mRNA), and can serve as a substrate for nucleic acid synthesis methods, such as, for example, RT-PCR.

The detection methods provided herein also can include one or more sample manipulation methods. In one example, the sample can have one or more components separated or removed, for example, in a method of increasing the relative amount of oncofetal fibronectin indicating molecule present in the sample. In another example, the sample can be contacted with a fragmentation compound that can fragment oncofetal fibronectin indicating molecule present in the sample.

In one embodiment, detecting an oncofetal fibronectin indicating molecule with two or more different binding partners or with two or more different detection methods can be used to confirm the presence and/or amount of oncofetal fibronectin in the sample. Detecting an oncofetal fibronectin indicating molecule with two or more different binding partners or with two or more different detection methods also can be used to determine the regions present and/or not present in the oncofetal fibronectin indicating molecule. Determination of the regions or composition of an oncofetal fibronectin indicating molecule present in a sample can be used for a variety of purposes, including to identify the cell or tissue type(s) from which an oncofetal fibronectin indicating molecule could have been produced and/or the cell or tissue type(s) from which an oncofetal fibronectin indicating molecule was likely to not have been produced, to indicate or identify the binding or biochemical activity of the oncofetal fibronectin present in the sample (e.g., when EDA is present in oncofetal fibronectin, the oncofetal fibronectin can bind to $\alpha_9\beta_1$ integrin and can have improved cell spreading and migration properties (see, e.g., Manabe et al., *J. Cell. Biol.* 139:295-307 (1997) and Liao et al., *J. Biol. Chem.* 277: 14467-14474 (2002)) and to rule out the possibility of a false positive result for the presence or amount of an oncofetal fibronectin indicating molecule in the sample.

A variety of cell types, tissue types and tumor types are known to contain oncofetal fibronectin proteins that include one or more of EDA, EDB and one of the splice variants of IIICS. In one case, the oncofetal fibronectin protein can be characterized as the EDA portion of an oncofetal fibronectin protein, the EDA-encoding portion of a nucleic acid molecule encoding oncofetal fibronectin, the portion of an autoantibody that binds to EDA of oncofetal fibronectin protein, and the portion of an autoantibody that binds to the EDA-encoding portion of a nucleic acid molecule encoding oncofetal fibronectin. In another example, the fibronectin or oncofetal fibronectin protein can be characterized as the EDB portion of an oncofetal fibronectin protein, the EDB-encoding portion of a nucleic acid molecule encoding oncofetal fibronectin, the portion of an autoantibody that binds to EDB of oncofetal fibronectin protein, and the portion of an autoantibody that binds to the EDB-encoding portion of a nucleic acid molecule encoding oncofetal fibronectin. In another example, the fibronectin or oncofetal fibronectin protein can be characterized as the IIICS portion of an oncofetal fibronectin protein, the IIICS-encoding portion of a nucleic acid molecule encoding oncofetal fibronectin, the portion of an autoantibody that binds to IIICS of oncofetal fibronectin protein, and the portion of an autoantibody that binds to the IIICS-encoding portion of a nucleic acid molecule encoding oncofetal fibronectin. In another example, an oncofetal fibronectin protein can be characterized as containing the IIICS splice variant V64, V89, V95 or V120. In another example, an oncofetal fibronectin protein can be characterized as containing one or more post-translational modifications such as O-glycosylation of threonine 33 of IIICS. A variety of cell types, tissue types and tumor types are known to contain oncofetal fibronectin proteins that do not include one or more of EDA, EDB and one of the splice variants of IIICS. In one case, an oncofetal fibronectin protein can be characterized as lacking EDA, EDB or IIICS. In another example, IIICS is identified as lacking amino acids 1-25 of IIICS, or 90-120 of IIICS, or both. Oncofetal fibronectin variants and their association with various cell types, tissue types and tumor types are exemplified herein and are known in the art. Many samples for which the presence of oncofetal fibronectin can be determined, such as a sample collected from a specific organ or tissue, or from a body fluid sample such as urine, lymph, blood, plasma, serum, saliva, cervical fluid, cervicovaginal fluid, vaginal fluid, breast fluid, breast milk, synovial fluid, semen, seminal fluid, stool, sputum, cerebral spinal fluid, tears, mucus, interstitial fluid, follicular fluid, amniotic fluid, aqueous humor, vitreous humor, peritoneal fluid, ascites, sweat, lymphatic fluid, lung sputum and lavage, can contain components whose sources are two or more cell types, two or more tissue types, or two or more organs. As a result, the cell, tissue or organ source of the oncofetal fibronectin in a sample can be ambiguous. Using the methods provided herein, characterization of the regions or composition of oncofetal fibronectin present in the sample can be used to identify the likely cell source, tissue source or organ source of an oncofetal fibronectin indicating molecule, or can be used to identify the unlikely cell source, tissue source or organ source of an oncofetal fibronectin indicating molecule. Such methods can be used, for example, to identify the type of tumor or neoplastic cell likely present in a subject, or to identify the type of tumor or neoplastic cell unlikely present in a subject.

To illustrate, a sample can contain two or more different oncofetal fibronectin proteins. For example, a sample can contain an oncofetal fibronectin protein that contains EDA and V120 but does not contain EDB, while the same sample also can contain an oncofetal fibronectin that contains EDA, EDB and V120. Such a sample can further be used to identify the likely cell source, tissue source or organ source of the oncofetal fibronectin, or can be used to identify the unlikely cell source, tissue source or organ source of the oncofetal fibronectins. As is known in the art, different cell and tissue types are known to produce two or more different oncofetal fibronectins. The different oncofetal fibronectin indicating molecules present in the sample can be compared to the oncofetal fibronectins known to be produced by one or more cell or tissue types to identify the likely or unlikely cell or tissue source(s) of an oncofetal fibronectin indicating molecule. Similarly, the relative levels of different oncofetal fibronectin indicating molecules present in the sample can be used to identify the likely cell source, tissue source or organ source of an oncofetal fibronectin indicating molecule, or can be used to identify the unlikely cell source, tissue source or organ source of an oncofetal fibronectin indicating molecule. Different cell and tissue types produce known ratios of two or more different oncofetal fibronectins. The relative amount of different oncofetal fibronectin indicating molecules present in the sample can be compared to the relative amount of oncofetal fibronectins known to be produced by one or more cell or tissue types to identify the likely or unlikely cell or tissue source(s) of an oncofetal fibronectin indicating molecule.

In another embodiment, characterizing an oncofetal fibronectin indicating molecule or measuring two or more different oncofetal fibronectin indicating molecules in a sample can be used to indicate the presence of a health problem associated with oncofetal fibronectin. For example, when the type of sample collected from a subject typically does not contain detectable amounts of a particular type of an oncofetal fibronectin indicating molecule when collected from normal subjects, detecting any amount of that particular type of an oncofetal fibronectin indicating molecule in such a sample can indicate the presence of a health problem associated with oncofetal fibronectin in the subject; this can occur even when a sample does typically contain a baseline amount of oncofetal fibronectin, provided that the baseline amount is of a different oncofetal fibronectin. In another example, when the type of sample collected from a subject typically contains a baseline amount of a particular type of oncofetal fibronectin indicating molecule when collected from normal subjects, detecting an amount of that type of oncofetal fibronectin indicating molecule greater than the baseline amount can indicate the presence of a health problem associated with oncofetal fibronectin in the subject. In another example, when the type of sample collected from a subject typically contains a ratio of two or more particular types of oncofetal fibronectin indicating molecules when collected from normal subjects, detecting a ratio of those types of oncofetal fibronectin indicating molecules that is different than the normal ratio can indicate the presence of a health problem associated with oncofetal fibronectin in the subject.

1. Compounds and Compositions in Detecting Oncofetal Fibronectin

Any known assay procedure, including those that can be adapted for use in combination with fibronectin or oncofetal fibronectin binding partners, such as, for example, lateral flow devices, can be used in the systems and methods provided herein. Examples of assay procedures are protein binding assays (e.g., dot blot analysis and Western blot analysis) and nucleic acid molecule hybridization assays (e.g., Northern blot analysis, Southern blot analysis and FISH). These can be practiced with any suitable format, including, for example, immunological methods, such as lateral flow and dip stick formats, mass spectrometry formats and others.

Binding assays, including competitive and non-competitive binding assays, are among those that can be used for determination of the presence or amount of analyte in a subject sample and are exemplified herein. It is understood that binding assays are provided for exemplification and that the methods and systems provided herein have broad applicability to a variety of sample types for a variety of different indications.

A number of different types of binding assays using a variety of protocols and labels are well known. Binding assays can be performed in a single liquid phase, or a binding partner can be immobilized to a solid support upon which the assay is performed. Sandwich assays can be performed. Competitive assays can be performed. The reaction steps can be performed simultaneously or sequentially, as will be known to those skilled in the art. Threshold assays can be performed, where only analyte levels of above a specified level or rate yield a positive result. Assay formats include, but are not limited to, for example, assays performed in test tubes, on membranes, in wells, in multi-well plates, on microarrays, on chromatographic test strips, as well as dipstick, lateral flow, vertical flow, or migratory format assays.

a. Molecules that Indicate the Presence of Oncofetal Fibronectin

Molecules detected in the methods provided herein can indicate the presence of oncofetal fibronectin in a subject. Molecules that can indicate the presence of oncofetal fibronectin in a subject include the oncofetal fibronectin protein, a fragment of the oncofetal fibronectin protein, mRNA encoding oncofetal fibronectin, a fragment of mRNA encoding oncofetal fibronectin, or an amplified nucleic acid molecule complementary to all or a portion of mRNA encoding oncofetal fibronectin (e.g., cDNA). For the detection methods described below, methods for detecting oncofetal fibronectin can apply to any of the oncofetal fibronectin indicating molecules provided herein, whether or not the particular detection method explicitly so indicates, subject to limits clear to one skilled in the art (e.g., use of PCR methods to amplify a molecule that indicates the presence of oncofetal fibronectin is not used to amplify the oncofetal fibronectin protein, protein fragments or autoantibodies).

In addition to the detection of an oncofetal fibronectin protein or nucleic acid molecule, or as an alternative therefor, one or more autoantibodies of oncofetal fibronectin, or antibody fragments thereof, can be detected using the methods provided herein, as will be understood by one skilled in the art. The presence of an autoantibody for oncofetal fibronectin can evidence the presence of oncofetal fibronectin in a subject. Thus, detection of the autoantibody can be used as an indicator of the presence of oncofetal fibronectin in a subject. Any of the protein detection methods described herein in relation to detection of oncofetal fibronectin protein also can be used to detect an autoantibody to oncofetal fibronectin or to a nucleic acid encoding oncofetal fibronectin.

b. Fibronectin Portions Indicative of Oncofetal Fibronectin

The method provided herein can employ detection of a fibronectin region indicative of oncofetal fibronectin, or a fragment thereof. Regions indicative of oncofetal fibronectin include, but are not limited to, EDA, EDB, IIICS, splice variants of IIICS such as V64, V89, V95 and V120 and fragments of IIICS such as CS1, CS2, CS3, CS4, CS5 and CS6. The sequence of nucleotides of nucleic acid encoding human fibronectin EDA, EDB and IIICS regions and oncofetal fibronectins are known in the art and are available in public databases. Exemplary sequences are set forth in SEQ ID NOS: 1-8 and 14-35. The amino acid and nucleic acid molecules for a variety of additional species including rat, mouse, chicken, cow and *Xenopus laevis* also are known and readily available in public databases. Allelic variants and other variants are known and/or can be identified.

Detection of a fibronectin region indicative of oncofetal fibronectin can be performed by a variety of methods known in the art or disclosed herein. For example, a fibronectin region indicative of oncofetal fibronectin can be detected using a protein that binds to an oncofetal fibronectin indicating region of a fibronectin protein. For example, a variety of anti-oncofetal fibronectin antibodies are known in the art, including IST-9, DH1, BC-1, L19, ME4C, H10, A134, C6, FDC-6, 5C10, X18A4, X20C4 and X8E3.

A fibronectin region indicative of oncofetal fibronectin also can bind to an integrin. For example, EDA can bind to $\alpha_4\beta_1$ integrin and $\alpha_9\beta_1$ integrin. The amino acid sequence EDGIHEL of EDA (EDA amino acids 40-46) can bind to $\alpha_4\beta_1$ integrin and $\alpha_9\beta_1$ integrin. IIICS can bind to $\alpha_4\beta_1$ integrin, $\alpha_4\beta_7$ integrin and heparin. The V95 splice variant of IIICS can bind to heparin. CS1 and CS5 can bind to $\alpha_4\beta_1$ integrin and $\alpha_4\beta_7$ integrin. The IIICS amino acid sequence LDV (IIICS amino acids 20-22) can bind to $\alpha_4\beta_1$ integrin and $\alpha_4\beta_7$ integrin. The IIICS amino acid sequence REDV (IIICS amino acids 100-103) can bind to $\alpha_4\beta_1$ integrin and $\alpha_4\beta_7$ integrin.

An oncofetal fibronectin region can be identified by detecting a glycosylation indicative of oncofetal fibronectin. For example, EDB can contain one or more N-linked glycosylation sites. IIICS can contain one or more N-linked glycosylation sites and from 1 to 6 or about 6 O-linked glycosylation sites, particularly IIICS can contain an O-glycosylation at threonine 33 of IIICS.

Detection of a fibronectin region indicative of oncofetal fibronectin can be performed by detecting one or more proteolysis fragments. For example, oncofetal fibronectin can yield trypsin fragments of 235 kDa, 200 kDa, 160 kDa, 120 kDa, 65 kDa and/or 55 kDa. Typically, these six trypsin fragments can bind to the antibody FDC-6. In one example of an oncofetal fibronectin, trypsin fragments from an oncofetal fibronectin can be 200 kDa, 120 kDa or 55 kDa, where each smaller fragment represents a product of further trypsin cleavage of a larger fragment. In another example, trypsin fragments from an oncofetal fibronectin can be 235 kDa, 160 kDa or 65 kDa, where each smaller fragment represents a product of further trypsin cleavage of a larger fragment.

Oncofetal fibronectin can yield cathepsin D fragments of 110 kDa and/or 85 kDa. Typically these two cathepsin D fragments can bind to the antibody FDC-6. Oncofetal fibronectin also can be a fibronectin that yields thermolysin fragments of 120 kDa, 85 kDa and/or 35 kDa. Typically the 120 kDa and 85 kDa can bind to the antibody BC-1 and the 85 kDa fragment represents a product of further thermolysin cleavage of the 120 kDa fragment. Oncofetal fibronectin can be a fibronectin that yields an *Achromobacter* protease I fragment of 14 kDa, where this fragment typically can bind to the antibody FDC-6.

Nucleic acid molecules can indicate the presence of oncofetal fibronectin in a subject. Nucleic acid molecules indicative of the presence of oncofetal fibronectin or complements thereto also can be detected using the methods provided herein or known in the art.

A nucleic acid molecule indicative of the presence of oncofetal fibronectin or of the complement thereof, or of a fragment thereof can be detected herein. A nucleic acid molecule or fragment or complement thereof that can indicate the presence of oncofetal fibronectin indicates the presence of a fibronectin polypeptide region indicative of oncofetal fibronectin. For example, a detection of a nucleic acid molecule or fragment thereof can indicate the presence of a EDA, EDB or IIICS region, including the V0, V64, V89, V95 and V120 splice variants of the IIICS region. See, e.g., SEQ ID Nos. 28-35. Any of a variety of methods for detecting nucleic acid molecules or fragments thereof can be employed to detect a fibronectin polypeptide region indicative of oncofetal fibronectin. For example, a method can be used where the presence of any nucleic acid molecule indicates the presence of oncofetal fibronectin (e.g., where primers are designed to hybridize with the EDA, EDB or IIICS region, presence of any amplified nucleic acid molecules can indicate the presence of oncofetal fibronectin). In another example, presence of a nucleic acid molecule of an expected size can indicate the presence of oncofetal fibronectin (e.g., when a primer is located near EDA, EDB or IIICS encoding regions, small amplified nucleic acid molecules can indicate fibronectin without the EDA, EDB or IIICS encoding regions and large amplified nucleic acid molecules can indicate the presence of oncofetal fibronectin). In another example, presence of a nucleic acid molecule having an expected nucleotide sequence or sequence complementary thereto can indicate the presence of oncofetal fibronectin (e.g., when a Southern blot probe complementary to the EDA, EDB or IIICS encoding regions is used, binding of the probe to a sample band can indicate the presence of oncofetal fibronectin).

c. Autoantibody to Oncofetal Fibronectin or to a Nucleic Acid Molecule Encoding Oncofetal Fibronectin Autoantibodies to oncofetal fibronectin or to a nucleic acid encoding oncofetal fibronectin, can indicate the presence of oncofetal fibronectin in a subject. Autoantibodies can be detected using the methods provided herein or known in the art. Autoantibodies are produced by a subject in response to a subject's own antigen. In the present methods, autoantibodies are produced in response to oncofetal fibronectin or a nucleic acid molecule encoding oncofetal fibronectin. Autoantibodies include endogenous antibodies that specifically bind to oncofetal fibronectin at one or more regions indicative of oncofetal fibronectin, including EDA, EDB, IIICS, splice variants of IIICS such as V64, V89, V95 and V120 and peptide fragments of IIICS such as CS1, CS2, CS3, CS4, CS5 and CS6. Autoantibodies also can bind specifically to oncofetal fibronectin at one or more post-translational modification sites indicative of oncofetal fibronectin, such as one or more N-linked glycosylation sites in EDB or one or more N-linked glycosylation sites or one or more O-linked glycosylation sites in IIICS, particularly the O-glycosylation at threonine 33 of IIICS. Autoantibodies also can bind specifically to nucleic acid molecules encoding oncofetal fibronectin, such as a nucleic acid molecule encoding EDA, EDB, or a splice variant of IIICS such as V64, V89, V95 or V120.

Autoantibodies can be detected in any of a variety of samples, such as a tissue sample or a body fluid sample, including urine, lymph, blood, plasma, serum, saliva, cervical fluid, cervicovaginal fluid, vaginal fluid, breast fluid, breast milk, synovial fluid, semen, seminal fluid, stool, sputum, cerebral spinal fluid, tears, mucus, interstitial fluid, follicular fluid, amniotic fluid, aqueous humor, vitreous humor, peritoneal fluid, ascites, sweat, lymphatic fluid, lung sputum and lavage or purified fractions thereof. Autoantibodies can be detected by any of a variety of methods, including, for example, methods that include binding the autoantibody with a binding partner, such as described herein.

d. Binding Partner

Assays for detection of an oncofetal fibronectin indicating molecule can employ binding partners to aid in or permit detection. Binding partners can be used in a variety of roles in the methods provided herein. For example, binding partners can be used to bind an oncofetal fibronectin indicating molecule to a solid support, to increase the relative purity of an oncofetal fibronectin indicating molecule in a sample, to provide a detectable signal that indicates the presence of an oncofetal fibronectin indicating molecule in a sample, to provide a binding surface to which a detectable label can bind to indicate the presence of an oncofetal fibronectin indicating molecule in a sample, to amplify oncofetal fibronectin encoding nucleic acid molecules or complements thereto, and/or to indicate the presence of a specific domain of an oncofetal fibronectin indicating molecule in a sample.

In one embodiment, a binding partner can specifically bind to a fibronectin indicating molecule; thus, the binding partner can specifically bind to a fibronectin indicating molecule with increased a specificity relative to other molecules present in a sample. In another embodiment, a binding partner can specifically bind to an oncofetal fibronectin indicating molecule; thus, the binding partner can specifically bind to an oncofetal fibronectin indicating molecule with increased a specificity relative to a non-oncofetal fibronectin indicating molecule and/or other molecules present in a sample.

Exemplary binding partners include, but are not limited to, antibodies, antibody fragments, enzymes, metal ions, proteins, peptides, immunoglobulins, nucleic acid molecules, nucleic acid analogs, organic compounds, carbohydrates, lectins, dyes, reducing agents, energy absorbing molecules, affinity capture moieties, photolabile attachment molecules and combinations thereof.

A binding partner can be any of a variety of compounds that specifically bind to fibronectin protein. Examples of compounds that bind to fibronectin protein include integrins such as integrin $\alpha_3\beta_1$, integrin $\alpha_4\beta_1$, integrin $\alpha_4\beta_7$, integrin $\alpha_5\beta_1$, integrin $\alpha_8\beta_1$, integrin $\alpha_9\beta_1$, integrin $\alpha_v\beta_1$, integrin $\alpha_v\beta_3$, integrin $\alpha_v\beta_5$, integrin $\alpha_v\beta_6$ and integrin $\alpha_{IIb}\beta_3$; heparin; fibrin; collagen; gelatin; and antibodies such as IST-4 and 3E3.

A binding partner also can include compounds that bind specifically to oncofetal fibronectin protein. An oncofetal fibronectin binding partner can bind to a portion of oncofetal fibronectin that is not present or is not accessible in non-oncofetal fibronectin. Exemplary portions of oncofetal fibronectin not present in non-oncofetal fibronectin include amino acid regions such as EDA, EDB and V64, V89, V95 and V120 of IIICS. Additional exemplary portions of oncofetal fibronectin not present in non-oncofetal fibronectin include post-translationally modified regions such as O-glycosylated regions. Exemplary portions of oncofetal fibronectin not accessible in non-oncofetal fibronectin include amino acid regions present in oncofetal and non-oncofetal fibronectin, but that are conformationally different, for example, as a result of expression of amino acids not present in non-oncofetal fibronectin or as a result of post-translational modification not present in non-oncofetal fibronectin. Examples of compounds that bind preferentially to oncofetal fibronectin or antibodies therefor include antibodies, but are not limited to BC-1, FDC-6, L19, ME4C, X18A4, 5C10, IST-9 and DH-1.

i. Antibodies

Any antibody, including polyclonal or monoclonal antibodies, or any antigen-binding fragment thereof, include, but are not limited to, a Fab fragment or an scFv, that binds to an oncofetal fibronectin indicating molecule can be employed. For example, a mobile, labeled mouse monoclonal anti-oncofetal fibronectin antibody can be used to bind to oncofetal fibronectin protein in a sample and a polyclonal goat anti-fibronectin antibody immobilized on a test strip can be used to bind to oncofetal fibronectin protein to form a detectable sandwich complex indicating the presence of oncofetal fibronectin. In another example, a mouse monoclonal anti-oncofetal fibronectin antibody immobilized on a test strip can be used to bind to oncofetal fibronectin protein in a sample and a labeled goat polyclonal anti-oncofetal-fibronectin antibody conjugate can be used to bind to oncofetal fibronectin protein to form a detectable sandwich complex indicating the presence of oncofetal fibronectin protein in the sample. In another example, a membrane can be used to non-specifically bind to and immobilize oncofetal fibronectin protein and the immobilized oncofetal fibronectin protein can be exposed to a labeled anti-oncofetal fibronectin antibody conjugate, which can be detected to indicate presence of the oncofetal fibronectin protein in the sample. In another example, immobilized oncofetal fibronectin protein can be exposed to, for example, mouse anti-oncofetal fibronectin antibody and then exposed to a labeled polyclonal goat anti-mouse antibody complex to indicate the presence of oncofetal fibronectin protein in the sample.

Specifically binding antibody fragments for use in the methods described herein can be made from the respective monoclonal or polyclonal antibodies by conventional enzyme or chemical fragmentation procedures or can be made by routine recombinant methods. Various procedures are known (see, e.g., Tijssen, P. *Laboratory Techniques in Biochemistry and Molecular Biology: Practice and Theories* of *Enzyme Immunoassays*, Elsevier, N.Y. (1985)). For example, monoclonal antibody FDC-6 (ATCC Accession Number ATCC HB 9018) can be exposed to a protease such as papain or pepsin, respectively, to form Fab and F(ab)$_2$ fragments, as is known in the art. In addition, the VL and VH of FDC-6 can be joined using recombinant methods using a synthetic linker that permits them to be expressed as a single protein chain in which the VL and VH regions pair to form monovalent molecules (known as single chain Fv (scFv); see e.g., Bird et al., *Science*, 242:423-426 (1988); and Huston et al., *Proc. Natl. Acad. Sci. USA*, 85:5879-5883 (1988)). Bivalent, bispecific antibodies (i.e., diabodies) can be formed in which FDC-6 VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al., *Proc. Natl. Acad Sci. USA* 90:6444-6448 (1993); Poljak, R. J., et al., *Structure* 2:1121-1123 (1994)).

The antibodies can be raised and purified using methods known to those of skill in the art or obtained from publicly available sources. For example, methods for raising and purifying antibodies can be similar to the methods used in raising and purifying monoclonal antibody FDC-6 (deposited at the American Type Culture Collection as accession number ATCC HB 9018; see U.S. Pat. No. 4,894,326; see, also, Matsuura et al., *Proc. Natl. Acad. Sci. USA*, 82:6517-6521 (1985); see, also, U.S. Pat. Nos. 4,919,889; 5,096,830; 5,185,270; 5,223,440; 5,236,846; 5,281,522; 5,468,619 and 5,516,702). Anti-fibronectin antibodies and anti-oncofetal fibronectin antibodies can be formed into conjugates or immobilized on a solid support using methods disclosed herein or known in the art.

a. Antibodies for Oncofetal Fibronectin

In one embodiment, antibodies used herein can specifically bind to oncofetal fibronectin protein. Antibodies used herein can specifically bind an epitope present in oncofetal fibronectin protein. Polyclonal antibodies typically bind to two or more epitopes present in oncofetal fibronectin protein. A monoclonal antibody typically binds a single epitope present in oncofetal fibronectin protein.

In another example, an epitope present in oncofetal fibronectin can include an epitope that can be present in oncofetal fibronectin, such as an epitope that includes EDA, EDB or IIICS domains of oncofetal fibronectin. Antibodies that bind to epitopes present in oncofetal fibronectins include FDC-6 (ATCC Accession Number ATCC HB 9018), IST-9 (Carnemolla et al., *FEBS Lett.* 215:269-273 1987; Accurate Chemical and Scientific Corp., Westbury, N.Y.), DH1 (Vartio et al., *J. Cell Sci.* 88:419-430 1987), BC-1 (Carnemolla et al., *J. Cell Biol.* 108:1139-1148 1989), L19 (U.S. Pat. App. No. 20030176663), ME4C (Giovannoni et al., *Nucleic Acids Res.* 29:e27 (2001); the ME4C scFv nucleic acid and amino acid sequences are provided in SEQ ID NOS: 9 and 10, and are available at GenBank accession no. AJ297960), H10 (U.S. Pat. App. No. 20030176663), A134 (Islami et al., *Eur. J. Obstet. Gynecol. Reprod. Biol.*, 97:40-45 2001), 5C10 (Mandel et al., *APMIS* 100:817-826 1992) and X18A4, X20C4 and X8E3 (U.S. Pat. No. 5,523,229; ATCC accession numbers HB-11587, HB-11589 and HB-11588, respectively).

b. Conjugation of the Antibody to a Label

In one embodiment, an antibody that binds to an analyte of interest can be conjugated to a detectable label. The detectable label used in the antibody conjugate can be any physical or chemical label that can be detected and can be distinguished from other compounds and materials in the assay. For example, an antibody conjugate can be detected on a solid support using a reader, such as a reflectance reader. In one example, a mouse monoclonal anti-onfFN antibody (see, e.g., U.S. Pat. No. 5,281,522), can be conjugated to latex particles containing a blue dye or other spectrometrically detectable label. In an another example, a goat polyclonal antibody to human fibronectin can be conjugated to a colloidal gold label.

Various antibody labels are well known to those of skill in the art. The labels include, but are not limited to enzyme-substrate combinations that produce color upon reaction, colored particles, such as latex particles, quantum dots, colloidal metal or metal or carbon sol labels, fluorescent labels and liposome or polymer sacs, which are detected due to aggregation of the label. In one particular embodiment, the label is a colored latex particle. In an alternative embodiment, colloidal gold is used in the labeled antibody conjugate.

The label can be derivatized for linking to antibodies, such as by attaching functional groups, such as carboxyl groups to the surface of a particle to permit covalent attachment of antibodies. Antibodies can be conjugated to the label using well known coupling methods. Coupling agents such as glutaraldehyde or carbodiimide can be used. The labels can be bonded or coupled to the antibodies by chemical or physical bonding. In an exemplary embodiment, a carbodiimide coupling reagent, 1-ethyl-3-(3-dimethylaminopropyl)carbodiimide (EDAC), is used to link antibodies to latex particles.

ii. Nucleic Acid Molecules

A binding partner also can be a molecule that specifically binds a fibronectin-encoding nucleic acid molecule, a molecule that specifically binds a sequence complementary to a fibronectin-encoding nucleic acid molecule, amplicates thereof, or fragments thereof (the group of which is herein referred to as an oncofetal fibronectin nucleic acid molecule). In one embodiment, at least one binding partner binds specifically to a nucleic acid molecule encoding fibronectin or a complement thereto. In another embodiment, two or more binding partners can bind specifically or preferentially to an oncofetal fibronectin encoding nucleic acid molecule or a complement thereto. Binding partners can include single stranded or double stranded nucleic acid molecules, oligonucleotides, primers, deoxyribonucleic acid molecules (DNA), ribonucleic acid molecules (RNA), nucleic acid homologs such as peptide nucleic acids and hybrids thereof. Binding partners also can include antibodies, antibody fragments, enzymes, metal ions, proteins, peptides, immunoglobulins, carbohydrates, lectins, dyes, reducing agents, energy absorbing molecules, affinity capture moieties, photolabile attachment molecules and combinations thereof.

A binding partner that binds a fibronectin encoding nucleic acid molecule or complement thereto can specifically bind to a fibronectin-encoding nucleic acid molecule or an oncofetal fibronectin-encoding nucleic acid molecule or a complement thereto. A binding partner that binds an oncofetal fibronectin encoding nucleic acid molecule or complement thereto can specifically bind to an oncofetal fibronectin-encoding nucleic acid molecule or a complement thereto. Typically, such a binding partner will be complementary to nucleic acid encoding a fibronectin or oncofetal fibronectin nucleic acid molecule or complement thereof, but not present in other (non-fibronectin-encoding) nucleic acid molecules.

An oncofetal fibronectin binding partner can preferentially bind to an oncofetal fibronectin-encoding nucleic acid molecule or complement thereto relative to binding a non-oncofetal fibronectin-encoding nucleic acid molecule or complement thereto. Typically, such a binding partner will be complementary to a nucleic acid molecule that encodes oncofetal fibronectin or complement thereto. For example, a binding partner that preferentially binds an oncofetal fibronectin-encoding nucleic acid can bind to a nucleic acid sequence encoding the EDA, EDB or IIICS region of oncofetal fibronectin, including, but not limited to, a nucleic acid molecule encoding V120, V95, V89 or V64.

Binding partners used to detect the presence of an oncofetal fibronectin nucleic acid molecule or complement thereto can be conjugated with a moiety useful for binding, isolation, or detection. A moiety can include a bindable moiety such as biotin, nickel, magnetic bead, or other composition or compound used for binding or isolation. For example, a binding partner can be conjugated with a biotin moiety which can be used for binding or isolation when used in conjunction with avidin or streptavidin. Such a moiety also can be a detectable moiety such as a fluorescent compound, a compound containing a radionuclide, a quantum dot, colloidal metal, or any other moiety that can be used for detection by methods including, but not limited to, fluorimetry, absorption, reflection, visible inspection and scintillation. Binding partners also can be immobilized on a solid substrate. Methods for conjugating or immobilizing binding partners such as nucleic acids and nucleic acid analogs are known in the art and can be used in the methods herein.

Binding partners also can serve as nucleotide synthesis primers for amplification of an oncofetal fibronectin encoding nucleic acid molecule or complement thereto. Such binding partners are typically nucleic acid molecules or nucleic acid analogs that contain a 3' hydroxy moiety accessible for phosphodiester bond formation or other nucleotide synthesis steps. Methods for preparing primers for nucleotide synthesis reactions are well known in the art and can be used in the methods herein.

Nucleic acid molecule binding partners can bind to oncofetal fibronectin-encoding nucleic acid molecules or nucleic acid molecules complementary thereto. For example, methods provided herein include nucleic acid molecule synthesis methods in which nucleic acid molecules complementary to oncofetal fibronectin-encoding nucleic acid molecules are formed. Methods for detecting oncofetal fibronectin-encoding nucleic acid molecules are therefore intended to also detect nucleic acid molecules complementary to oncofetal fibronectin-encoding nucleic acid molecules.

In one embodiment, binding partners can be nucleic acid molecules. Typically nucleic acid molecule binding partners are large enough in length to specifically bind to oncofetal fibronectin-encoding nucleic acid molecules or complements thereto, without also specifically binding other non-fibronectin-encoding nucleic acid molecules. In one example, nucleic acid molecule binding partners preferentially bind to oncofetal fibronectin-encoding nucleic acid molecules or complements thereto, without also specifically binding other non-oncofetal fibronectin-encoding nucleic acid molecules or complements thereto. For example, a nucleic acid molecule binding partner can specifically bind to a nucleic acid molecule encoding EDA, EDB or IIICS or complement thereto, or a fragment thereof.

Nucleic acid molecule binding partners can vary in length and can contain extra nucleotides in addition to the oncofetal-fibronectin encoding (or complement thereto) portion of the nucleic acid molecule binding partner (e.g., a transcriptional start site or a chip hybridization sequence). Exemplary lengths of the oncofetal fibronectin-encoding portion (or complement thereto) of a nucleic acid molecule binding partner are at least 5 nucleotides, at least 6 nucleotides, at least 7 nucleotides, at least 8 nucleotides, at least 10 nucleotides, at least 12 nucleotides, at least 15 nucleotides, at least 18 nucleotides, at least 20 nucleotides, at least 25 nucleotides, at least 35 nucleotides, at least 40 nucleotides, at least 50 nucleotides, or at least about 5 nucleotides, at least about 6 nucleotides, at least about 7 nucleotides, at least about 8 nucleotides, at least about 10 nucleotides, at least about 12 nucleotides, at least about 15 nucleotides, at least about 18 nucleotides, at least about 20 nucleotides, at least about 25 nucleotides, at least about 35 nucleotides, at least about 40 nucleotides, at least about 50 nucleotides, or more.

Similarly, the oncofetal fibronectin-encoding nucleic acid molecule or complement thereto need not be bound by the binding partner along the entire length of the oncofetal fibronectin-encoding sequence. In some embodiments; the oncofetal fibronectin-encoding nucleic acid molecule or complement thereto bound by the binding partner is the full length nucleic acid molecule, where the binding partner specifically binds a portion of the oncofetal fibronectin-encoding nucleic acid molecule or complement thereto, without also specifically binding other non-fibronectin-encoding nucleic acid molecules. In one example, a nucleic acid molecule binding partner preferentially binds a portion of an oncofetal fibronectin-encoding nucleic acid molecule or complement thereto, without also specifically binding other non-oncofetal. fibronectin-encoding nucleic acid molecules or complements thereto. For example, a nucleic acid molecule binding partner can specifically bind to the portion of the oncofetal fibronectin-encoding nucleic acid molecule encoding EDA, EDB or IIICS or complements thereto.

In other embodiments, the oncofetal fibronectin-encoding nucleic acid molecule or complement thereto bound by the binding partner is a fragment of the full length nucleic acid molecule, where the binding partner specifically binds the fragment of the oncofetal fibronectin-encoding nucleic acid molecule or complements thereto, without also specifically binding other non-fibronectin-encoding nucleic acid molecules. In one example, a nucleic acid molecule binding partner preferentially binds to a fragment of an oncofetal fibronectin-encoding nucleic acid molecule or complement thereto, without also specifically binding other non-oncofetal fibronectin-encoding nucleic acid molecules or complements thereto. For example, a nucleic acid molecule binding partner can specifically bind to a fragment of the oncofetal fibronectin-encoding nucleic acid molecule encoding at least a portion of EDA, EDB or IIICS or complement thereto. Fragments of an oncofetal fibronectin-encoding nucleic acid molecule or complement thereto can be generated by any of a variety of methods provided herein or otherwise known in the art, including enzymatic, chemical or physical cleavage of nucleic acid molecules and also including nucleic acid synthesis methods such as PCR or RT-PCR, where only a portion of the oncofetal fibronectin-encoding nucleic acid molecule or complement thereto is amplified. In some instances, the fragment will contain only nucleotides encoding EDA, EDB or IIICS or complement thereto, where the fragment can contain the entire splice region or less than the entire splice region or complement thereto. In regard to IIICS, a fragment can contain only nucleotides encoding V120, V95, V89 or V64 or complement thereto; or only the splice regions encoding amino acids 1-25, amino acids 26-89, or amino acids 90-102 or complement thereto. Fragments also can include regions adjacent to any of the aforementioned splice regions or complements thereto. For example, a fragment can contain 10 nucleotides 3' and 10 nucleotides 5' of the EDA splice region or complement thereto. Such fragments can be used, for example, in mass spectrometric detection methods to distinguish between nucleic acid molecules containing an oncofetal fibronectin splice region and nucleic acid molecules lacking the oncofetal fibronectin splice region. For example, a fragment can contain 10 nucleotides 3' and 10 nucleotides 5' of the EDA splice region or complement thereto, and nucleic acid molecules containing an oncofetal fibronectin splice region (110 nucleotide in length) can be distinguished from nucleic acid molecules lacking the oncofetal fibronectin splice region (20 nucleotides in length).

Fragments can vary in length according to any of a variety of factors known to one skilled in the art, including region(s) of oncofetal fibronectin to be detected, detection method and sample. Fragments, such as fragments formed by nucleic acid synthesis reactions, can contain extra nucleotides in addition to the oncofetal fibronectin-encoding portion of the nucleic acid molecule (e.g., a transcriptional start site or a non-oncofetal fibronectin encoding hybridization sequence). Exemplary lengths of the oncofetal fibronectin-encoding portion or complement thereto of a fragment (or complement thereto) are at least 5 nucleotides, at least 6 nucleotides, at least 7 nucleotides, at least 8 nucleotides, at least 10 nucleotides, at least 12 nucleotides, at least 15 nucleotides, at least 18 nucleotides, at least 20 nucleotides, at least 25 nucleotides, at least 35 nucleotides, at least 40 nucleotides, at least 50 nucleotides, or at least about 5 nucleotides, at least about 6 nucleotides, at least about 7 nucleotides, at least about 8 nucleotides, at least about 10 nucleotides, at least about 12 nucleotides, at least about 15 nucleotides, at least about 18 nucleotides, at least about 20 nucleotides, at least about 25 nucleotides, at least about 35 nucleotides, at least about 40 nucleotides, at least about 50 nucleotides, or more.

iii. Binding Partners to Autoantibodies

A binding partner can specifically bind to an autoantibody to oncofetal fibronectin or a nucleic acid molecule encoding oncofetal fibronectin. Such a binding partner can include antibodies, antibody fragments, enzymes, metal ions, proteins, peptides, immunoglobulins, carbohydrates, lectins, dyes, reducing agents, energy absorbing molecules, affinity capture moieties, photolabile attachment molecules and combinations thereof. Binding partners also can include single stranded or double stranded nucleic acids, oligonucleotides, primers, deoxyribonucleic acid molecules (DNA), ribonucleic acid molecules (RNA), nucleic acid homologs such as peptide nucleic acids and hybrids thereof.

A binding partner to an autoantibody also can include oncofetal fibronectin protein or a fragment thereof, or a nucleic acid molecule encoding oncofetal fibronectin or a fragment thereof. The autoantibodies can specifically bind to oncofetal fibronectin protein at one or more regions indicative of oncofetal fibronectin, including EDA, EDB, IIICS, splice variants of IIICS such as V64, V89, V95 and V120 and fragments of IIICS such as CS1, CS2, CS3, CS4, CS5 and CS6. Autoantibodies also can specifically bind to oncofetal fibronectin protein at one or more post-translational modification sites indicative of oncofetal fibronectin, such as one or more N-linked glycosylation sites in EDB or one or more N-linked glycosylation sites or one or more O-linked glycosylation sites in IIICS, particularly the O-glycosylation at threonine 33 of IIICS. Autoantibodies also can specifically bind to nucleic acid molecules encoding oncofetal fibronectin, such as a nucleic acid molecule encoding EDA, EDB, or a splice variant of IIICS such as V64, V89, V95 or V120. Accordingly, a protein or nucleic acid molecule that contains any of the regions indicative of oncofetal fibronectin, post-translation modifications indicative of oncofetal fibronectin, or nucleic acid molecule regions encoding a polypeptide region indicative of oncofetal fibronectin, can be used as a binding partner for an autoantibody in accordance with the methods provided herein. Fragments of a protein or nucleic acid molecule, such as a polypeptide or oligonucleotide, that contains any of the regions indicative of oncofetal fibronectin, post-translation modifications indicative of oncofetal fibronectin, or nucleic acid molecule regions encoding a polypeptide region indicative of oncofetal fibronectin, can be used as a binding partner for an autoantibody. In one example, a fragment such as a peptide or oligonucleotide, contains only a region indicative of oncofetal fibronectin, optionally also containing post-translation modifications indicative of oncofetal fibronectin, or nucleic acid molecule regions encoding a polypeptide region indicative of oncofetal fibronectin. For example, a polypeptide can contain only EDA, EDB, IIICS, splice variants of IIICS such as V64, V89, V95 and V120, peptide fragments of IIICS such as CS1, CS2, CS3, CS4, CS5 and CS6, or fragments thereof, which optionally contain one or more post-translational modification sites indicative of oncofetal fibronectin, such as one or more N-linked glycosylation sites in EDB or one or more N-linked glycosylation sites or one or more O-linked glycosylation sites in IIICS, particularly the O-glycosylation at threonine 33 of IIICS. In another example, an oligonucleotide can contain only nucleotides encoding EDA, EDB, or a splice variant of IIICS such as V64, V89, V95 or V120. Exemplary polypeptide or oligonucleotide fragment sizes can range from 5 to 30 residues, 7 to 20 residues, or 9 to 15 residues, or about 5 to about 30 residues, about 7 to about 20 residues, or about 9 to about 15 residues.

Methods for detecting autoantibodies also can employ antibody binding partners that are not specific for anti-oncofetal fibronectin autoantibodies. For example, antibody binding partners such as anti-human antibodies, including anti-IgG, anti-IgA, anti-IgD, anti-IgE or anti-IgM antibodies, or fragments thereof, can be used in methods for detecting an anti-oncofetal fibronectin autoantibody. Antibody binding partners or fragments thereof can be polyclonal or monoclonal.

Binding partners for autoantibodies used in accordance with the methods provided herein can be used in the same manner as described herein for the use of binding partners for fibronectin or oncofetal fibronectin protein or binding partners for a nucleic acid molecule encoding oncofetal fibronectin. For example, such binding partners can be formed as conjugates or can be immobilized to a solid support. General methods and binding partners for detecting autoantibodies are known in the art and can be used in conjunction with the compounds, compositions and methods provided herein. Such methods and binding partners are exemplified in U.S. Pat. Pub. Nos. 20030232399 and 20040048320 and in WO/03 020115.

iv. Additional Binding Partners

A variety of additional compounds can be used as fibronectin binding partners of oncofetal fibronectin protein or oncofetal fibronectin encoding nucleic acids, including compounds that bind to fibronectin protein such as peptides and non-peptide organic compounds. Compounds that bind to fibronectin protein are known in the art and include, but are not limited to, small peptides such as GGWSHW (SEQ ID NO: 36) and related peptides and variants (e.g., cyclic peptides) thereof, as provided, for example, in U.S. Pat. No. 5,491,130. Also included are compounds that specifically bind to oncofetal fibronectin protein, including, but not limited to, diaryl alkylamines such as 2,2-diphenylethylamine, 2,2-diphenylpropylamine, 3,3-diphenylpropylamine, 2-napthyl, 2-phenylethylamine, 2-napthyl,2-(2,6-dichlorophenyl)ethylamine, 2-phenyl, 2-(4-trifluoromethylphenyl) ethylamine, 2-phenyl, 2-(3,4-methylenedioxybenzyl)ethylamine, 2-phenyl, 2-thienylethylamine, and derivatives thereof, which are known to bind to the EDB domain of oncofetal fibronectin. Such diaryl alkylamines are known in the art, as exemplified in the doctoral thesis of Jörg Scheuermann, submitted to the Swiss Federal Institute of Technology, Zurich, December 2002.

v. Binding Partners That Bind a Region of Oncofetal Fibronectin

As described herein, binding partners can be used to detect the presence of an oncofetal fibronectin indicating molecule. Binding partners also can be used to detect the presence of regions indicative of oncofetal fibronectin. For example, binding partners can be used to detect the presence of EDA, EDB, IIICS and any of the splice variants of IIICS including V0, V64, V89, V95 and V120, in an oncofetal fibronectin indicating molecule. Binding partners can be used to detect one or more regions indicative of oncofetal fibronectin, two or more regions indicative of oncofetal fibronectin, or three or more regions indicative of oncofetal fibronectin.

Binding partners also can be used in the methods herein to detect a post translational modification indicative of oncofetal fibronectin. Post translational modifications include glycosylation such as O-linked and N-linked glycosylation, disulfide bridge formation, proteolysis, lipidylation and other known post translational modifications. Binding partners can be used to detect one or more post translational modifications indicative of oncofetal fibronectin, two or more post translational modifications indicative of oncofetal fibronectin, or three or more post translational modifications indicative of oncofetal fibronectin. Binding partners also can be used to detect combinations of regions indicative of oncofetal fibronectin and post translational modifications indicative of oncofetal fibronectin.

e. Non-Specific Binder

In order to improve detection of an oncofetal fibronectin indicating molecule, background signals can be reduced by, for example, removing, extracting, or decreasing binding of background material from a sample that can non-specifically bind to a binding partner. For example, a urine sample can be contacted with a non specific binder such as a non-specific binding compound or a non-specific binding surface prior to the sample contacting an analyte-specific antibody. For example, when using a lateral flow device, a zone containing a ligand, such as bovine serum albumin (BSA), can be included. This zone can remove background material from a sample solution prior to the sample reaching the zone where presence of an oncofetal fibronectin indicating molecule is to be detected.

Exemplary compounds for reducing non-specific binding include casein, albumin, substituted albumin (e.g., methylated albumin), IgG, antibodies that do not specifically bind to fibronectin or oncofetal fibronectin, and other proteins known to block non-specific protein interactions. In the case of nucleic acid molecule detection, compounds for reducing non-specific binding include salmon sperm DNA, herring sperm DNA, poly(dI-dC)-poly(dI-dC) and other nucleic acid molecules that block non-specific nucleic acid hybridization.

2. Assays for Detecting Oncofetal Fibronectin Complexed with a Binding Partner

A variety of different assay procedures for detecting an oncofetal fibronectin indicating molecule, such as an oncofetal fibronectin protein, a nucleic acid molecule encoding oncofetal fibronectin or complement thereto, an autoantibody to oncofetal fibronectin protein or a nucleic acid molecule encoding oncofetal fibronectin, or a fragment thereof. Typically, assay procedures for detecting the presence of oncofetal fibronectin include, for example, a step of contacting a sample with a fibronectin or oncofetal fibronectin binding partner. Exemplary assay procedures include, but are not limited to, flow cytometry, Western blot analysis, dot blot analysis, Southern blot analysis, Northern blot analysis, sandwich assay, fluorescence polarization, test strip analysis, mass spectrometry and PCR-based methods. Assays can be performed with the oncofetal fibronectin indicating molecule immobilized on a solid support, with a fibronectin or oncofetal fibronectin binding partner immobilized on a solid support, or with no molecules immobilized on a solid support. In embodiments that include a solid support, any solid support provided herein or otherwise known in the art can be used including, but not limited to a microtiter plate, a microarray, a test strip, a mass spectrometry substrate, and a nitrocellulose membrane.

In conducting the assay, a subject sample is obtained. The samples that can be used include any sample provided herein or otherwise known in the art. The samples can contain, for example, fluid and particulate solids and, can be filtered prior to measuring an oncofetal fibronectin indicating molecule, for example, prior to application to an assay test strip. The sample can be removed from the subject using any method known in the art or provided herein, including using a swab having a fibrous tip, an aspirator, suction or lavage device, syringe, or any other known method of removing a bodily sample, including passive methods for collecting urine or saliva. The sample, particularly samples in or attached to an insoluble medium, can be extracted into a buffer solution and optionally filtered. In one embodiment, where oncofetal fibronectin is to be detected in a sample, the sample is obtained from in the vicinity of the point of a possible cervicovaginal lesion, the cervical canal, the cervical os, the ectocervix, the transition zone on the cervix between squamous and columnar cells (i.e., the squamocolumnar junction), the vagina, the posterior fornix, the portion of the vagina below the posterior fornix such as the lower third of the vagina, the labia, or combinations thereof, where the sample can be collected as a swab sample, using, for example, a swab having at its tip a fibrous material such as polyester, rayon, or cotton. When the sample is collected with a cotton swab, the assay methods are conducted on the swab and reagents are added to the swab.

The assay methods provided herein can generally be used for detecting oncofetal fibronectin indicating molecules that are proteins or for detecting oncofetal fibronectin indicating molecules that are nucleic acid molecules. Selection of the reagents and particular methodologies can vary according to the oncofetal fibronectin indicating molecule to be detected, as will be understood by one skilled in the art.

The assay methods provided herein can be used to detect binding of an oncofetal fibronectin indicating molecule and a fibronectin or oncofetal fibronectin binding partner, and also can be used to detect competitive inhibition, where an oncofetal fibronectin indicating molecule in the sample competes with a known amount of oncofetal fibronectin indicating molecule or analog thereof for a predetermined amount of fibronectin or oncofetal fibronectin binding partner. For example, in an assay for oncofetal fibronectin protein, any oncofetal fibronectin protein present in the sample can compete with a known amount of labeled oncofetal fibronectin protein or a labeled analogue thereof for the fibronectin or oncofetal fibronectin binding partner. The amount of labeled fibronectin affixed to the solid phase or remaining in solution can be measured, and the measurement can be used to determine the amount of oncofetal fibronectin indicating molecule in the sample, using methods known in the art.

a. Solution Detection

Presence of an oncofetal fibronectin indicating molecule can be detected in solution. A sample can be contacted with one or more fibronectin or oncofetal fibronectin binding partners and any complex formed between an oncofetal fibronectin indicating molecule and the binding partner can be detected. Detection of the complex can indicate the presence of an oncofetal fibronectin indicating molecule in a sample. Detection of complexes formed in solution are known in the art, such as detection of a signal indicative of complex formation, or detection of a substance with a molecular weight corresponding to complex formation. In some embodiments, detection of competition can be performed, where loss of a signal indicative of a complex can indicate the presence of an oncofetal fibronectin indicating molecule. Solution detection methods can be performed when detecting oncofetal fibronectin proteins or oncofetal fibronectin encoding nucleic acid molecules of complements thereto, as is understood in the art.

i. Signal Indicative of Complex Formation

Complex formation between an oncofetal fibronectin indicating molecule and a fibronectin or oncofetal fibronectin binding partner can result in a signal indicative of complex formation. For example, complex formation can result in a change in a signal, a unique signal, an increasing signal, a decreasing signal, or a combination of signals. The signal indicative of complex formation can be detected by any of a variety methods for detecting signals including, fluorescence polarization, fluorimetry, absorption, scintillation detection and agglutination, and can be configured in any of a number of experimental systems, such as a fluorimeter, flow cytometer, or microscope such as a confocal microscope. Exemplary signals indicative of complex formation can be agglutination of reaction components, a change in fluorescence polarization, a change in the intensity or wavelength of fluorescence, a change in the intensity or wavelength of absorption, a unique signal resulting from energy transfer such as FRET (fluorescence resonance energy transfer), or spatial proximity of two or more signals. Such signals indicative of complex formation can arise from a change resulting from a binding partner complexing with an oncofetal fibronectin indicating molecule (e.g., a conformational change in a binding partner that changes the signal of a detectable moiety), or from two or more binding partners binding to the same oncofetal fibronectin indicating molecule (e.g., a signal resulting from FRET between or among binding partners). Additionally, the above methods can be performed as competition assays, using, for example, a labeled oncofetal fibronectin indicating molecule or analog thereof, where disappearance of a signal as a result of competition from an oncofetal fibronectin indicating molecule in the sample can indicate the presence of the oncofetal fibronectin indicating molecule in the sample.

A variety of methods are known for identifying the presence and/or amount of an analyte in a solution without performing steps of separating the analyte from solution. Exemplified below are particular methods for performing such non-separation assays, however, a variety of additional methods are known in the art, as exemplified in Hussa, "The clinical marker hCG," Praeger Publishers (1987), pp 38-40.

In one embodiment, binding of one binding partner to an oncofetal fibronectin indicating molecule can provide a detectable signal that indicates the presence and/or level of the oncofetal fibronectin indicating molecule in the sample. For example, a binding partner labeled with a fluorescent probe can provide a different fluorescence polarization signal when bound to an oncofetal fibronectin indicating molecule relative to the unbound signal. In another example, a binding partner can be bound by a molecule labeled with a fluorescent probe, where the molecule can be, for example, an oncofetal fibronectin indicating molecule or analog thereof, can provide a different fluorescence polarization signal when bound to oncofetal fibronectin indicating molecule from a sample relative to the signal when sample oncofetal fibronectin indicating molecule is not bound. Fluorescence polarization signals can vary according to the molecular weight of the dye-containing complex; when a fluorescent dye-labeled binding partner binds to an oncofetal fibronectin indicating molecule, the signal can be more polarized relative to the unbound form. Analogously, when a fluorescent dye-labeled oncofetal fibronectin indicating molecule or analog thereof binds to a binding partner, the signal can be more polarized relative to the unbound form, and when an oncofetal fibronectin indicating molecule in a sample displaces the fluorescently labeled oncofetal fibronectin indicating molecule or analog thereof, the signal can be less polarized relative to the bound form. Any of a variety of known dyes can be used in performing such methods, including fluorescein dyes, cyanine dyes, dansyl dyes, and polyazaindacene dyes, such as 4,4-difluoro-4-bora-3a,4a-diaza-s-indacene (BODIPY) dyes (Molecular Probes, Eugene, Oreg.; see, e.g., U.S. Pat. Nos. 6,323,186 and 6,005,113). Fluorescence polarization assays are known in the art and selection of dyes and assay conditions can be determined according to the assay design.

In some fluorescence polarization assays, the fibronectin or oncofetal fibronectin binding partner can be an antibody or an antibody fragment, for example FDC-6 or ME4C, labeled with a fluorescent dye. In embodiments where a larger mass difference between the oncofetal fibronectin indicating molecule and the antibody binding partner is desirable, the antibody binding partner can be an antibody fragment such as, for example, scFv, sc(Fv)$_2$, Fab, Fv, SIP, or another antigen-binding fragment provided herein or otherwise known in the art.

In other fluorescence polarization assays, an oncofetal fibronectin indicating molecule or analog thereof can be attached to a fluorescent dye, and presence of an oncofetal fibronectin indicating molecule in a sample can be determined by competition for binding to a fibronectin or oncofetal fibronectin binding partner. Exemplary analogs of an oncofetal fibronectin indicating molecule include oligopeptides or oligonucleotides containing all or a portion of EDA, EDB or IIICS, where any portion of such a region is selected according to its ability to specifically bind to a fibronectin or oncofetal fibronectin binding partner. For example, an oncofetal fibronectin protein analog can be a hexapeptide of the IIICS region, where the hexapeptide contains the sequence Val-Thr-His-Pro-Gly-Tyr (SEQ ID NO: 39) and having an O-glycosylation at the threonine residue, and can optionally contain a linker, and the analog can be attached to a fluorescent dye, either directly or through a linker, using methods known in the art.

In one embodiment, when two or more binding partners bind to the same oncofetal fibronectin indicating molecule, a first binding partner can transfer energy to a second binding partner to produce a signal that arises only when the first and second binding partners are spatially proximal. For example, a chromophore on a first binding partner can, by fluorescence resonance energy transfer (FRET), transfer a quantum of energy to a proximal fluorophore of a second binding partner, whereupon the fluorophore of the second binding partner fluoresces. Such experiments can be configured such that fluorescence of the fluorophore of the second binding partner can only arise as a result of FRET, which can only arise if the chromophore and fluorophore are spatially close to one another. Detection of fluorescence from the fluorophore of the second binding partner can indicate the two binding partners are spatially proximal, which can indicate the presence of an oncofetal fibronectin indicating molecule. Methods of using FRET are well known in the art, and any of a variety of these methods can be used herein (see, e.g., Gaits et al., *Science STKE* 2003 :PE3).

In another embodiment, spatial proximity of two different signals can indicate the presence of an oncofetal fibronectin indicating molecule in a sample. Binding of two differently labeled binding partners to one oncofetal fibronectin indicating molecule can result in a complex that provides two different signals, for example, fluorescence at two different wavelengths. Detection methods such as flow cytometry or confocal microscopy can be used to examine particular portions of a sample or small volumes of sample at any instant in time. Experimental conditions can be adapted such that the detection of two or more different signals at the same instance can indicate that two differently labeled binding partners are spatially proximate, which occurs when the two or more binding partners are bound to the same molecule, an oncofetal fibronectin indicating molecule. Thus, detection of two or more different signals at the same instance can indicate the presence of an oncofetal fibronectin indicating molecule in a sample.

In another embodiment, a polydentate binding partner, such as a bidentate binding partner can be used in agglutination assays that indicate the presence of an oncofetal fibronectin indicating molecule in a sample. A polydentate binding partner is able to bind two oncofetal fibronectin indicating molecules, which can result in linking together binding partners and oncofetal fibronectin indicating molecules into large complexes. Examples of polydentate binding partners include antibodies, which contain two binding sites and are, therefore, bidentate, and fusion proteins containing two or more regions that bind the same or different regions of oncofetal fibronectin protein (including a bidentate binding partner containing a first region that contains an oncofetal fibronectin binding partner and a second region that contains a fibronectin or oncofetal fibronectin binding partner). Such large complexes can be detected by any of a variety of methods, such as, for example, spectrophotometric detection and visual inspection. An exemplary agglutination assay includes the use of gold sol particles coated with two or more of the same binding partner or two or more different binding partners, and color change by visual or spectrophotometric detection can indicate the presence and/or amount of an oncofetal fibronectin indicating molecule in a sample.

ii. Molecular Weight Corresponding to Complex

When an oncofetal fibronectin indicating molecule and a fibronectin or oncofetal fibronectin binding partner form a complex, the mass of the complex is larger than the masses of the oncofetal fibronectin indicating molecule alone or the binding partner alone. Detection of a mass corresponding to such a complex can indicate the presence of an oncofetal fibronectin indicating molecule in a sample. When a binding partner contains a moiety that can generate a detectable signal, presence of a compound having a molecular weight corresponding to an oncofetal fibronectin indicating molecule-binding partner complex, together with presence of the detectable signal from such a compound, can indicate the presence of an oncofetal fibronectin indicating molecule in a sample.

A variety of methods for determining the mass of a complex are known in the art, including, electrophoretic and chromatographic methods, such as gel electrophoresis (under conditions that do not disrupt the complex) and size exclusion chromatography and mass spectrometry. In one embodiment, a sample can be contacted with a fibronectin or oncofetal fibronectin binding partner conjugated with a fluorescent dye and then loaded onto an analytical gel filtration column. Elution can be monitored in terms of volume and fluorescence, where volume eluted is calibrated to molecular weight. A fluorescence signal at a volume corresponding to a molecular weight of an oncofetal fibronectin indicating molecule-binding partner complex can indicate the presence of an oncofetal fibronectin indicating molecule in a sample.

b. Immobilized Sample

A sample suspected of containing an oncofetal fibronectin indicating molecule can be examined for presence of the oncofetal fibronectin indicating molecule by immobilizing the sample on a solid support and probing the immobilized sample using a fibronectin or oncofetal fibronectin binding partner, where detection of binding of the binding partner to the solid support is indicative of the presence of an oncofetal fibronectin indicating molecule in the sample. Any oncofetal fibronectin indicating molecule, such as an oncofetal fibronectin protein, an oncofetal fibronectin-encoding nucleic acid molecule or a complement thereto, or an autoantibody to oncofetal fibronectin protein or a nucleic acid molecule encoding oncofetal fibronectin, can be immobilized to a solid support in the methods provided herein. A binding partner can be detected directly or indirectly. Direct detection of the binding partner can be performed using a binding partner conjugated to a detectable moiety or conjugated to a bindable moiety. Indirect detection of a fibronectin or an oncofetal fibronectin binding partner can be performed using a binding partner that can bind to the fibronectin or oncofetal fibronectin binding partner and can generate a detectable signal or can be bound by another binding partner. Competition assays using labeled and unlabeled (or differently labeled) binding partners also can be performed.

Solid supports used in the present methods can be any solid support to which, upon contact with a sample, an oncofetal fibronectin indicating molecule can be immobilized. Exemplary solid supports include microplates, microarrays, or membranes such as nitrocellulose, polyvinylidine fluoride (PVDF) or nylon membranes. Methods for immobilizing a sample on solid supports are known in the art and can be used in the methods herein. When sample is immobilized in two or more discrete locations, such as in a dot blot, a microplate or microarray, each sample can be independently treated, where all samples can be differently treated, or some samples can be equally treated while others are differently treated. Exemplary treatments include contacting with different binding partners, including binding partners that bind to different regions of an oncofetal fibronectin indicating molecule such as EDA, EDB and IIICS, contacting under different buffer conditions, and contacting with different concentrations of binding partner. Such methods are known to those skilled in the art.

Detection of a signal also can be used to quantitate the amount of an oncofetal fibronectin indicating molecule present in the sample, using any of a variety of known methods. For example, the intensity of the signal corresponding to an oncofetal fibronectin indicating molecule can be measured using any of a variety of methods known in the art, including, for example, fluorescence or absorption spectrometry, or phosphor imager measurement. In one example, known concentrations of a standard also can be included and the intensity of one or more sample signals can be qualitatively or quantitatively compared to the standards using known methods to provide an estimate or calculation of the amount of an oncofetal fibronectin indicating molecule in the sample. In another example, multiple dilutions of the sample can be detected, and the signal measured at each dilution can be used to estimate the amount of an oncofetal fibronectin indicating molecule using known methods.

i. Dot Blot Analysis

Dot blot assays can be used to detect the presence of an oncofetal fibronectin indicating molecule in a sample. Dot blot can be performed by first preparing a solid support, typically a membrane such as a nitrocellulose membrane or a PVDF membrane, such as by wetting the membrane in a solvent such as methanol or distilled water. In other examples, no preparation of the membrane is required. A sample can then be added to the membrane. In a dot blot, one or more aliquots of sample can be added at discrete loci on a membrane to form one or more "dots" on the membrane. When multiple sample aliquots are used, the aliquots can be identical or different, where the different aliquots can be at different levels of sample dilution or can be aliquots which have been treated with at least one different reagent. For example, different aliquots can be contacted with different non-specific binding compounds or surfaces; or one or more first aliquots can be untreated and one or more second aliquots can be treated, for example, using a non-specific binding compound. Control or reference samples also can be added at one or more discrete loci on the membrane. In one embodiment, samples applied to a membrane can be drawn through the membrane by a suction pump, or other similar device. The oncofetal fibronectin can be immobilized onto the membrane by any known methods, including, for example, drying the membrane or exposing the membrane to ultraviolet radiation. Such a membrane also can be washed to remove any substances that were not immobilized to the membrane. Wash solutions are known in the art and can contain detergent, such as a nonionic detergent such as Tween-20.

Membranes to which sample has been added can be contacted with a fibronectin or oncofetal fibronectin binding partner. In one embodiment, after adding the sample, but prior to adding a fibronectin or oncofetal fibronectin binding partner, the membrane can be washed with a solution that suppresses additional non-specific binding to the membrane. For example, in the case of protein (including autoantibody) detection, a membrane can be washed with a solution containing, for example, BSA or casein, which can bind to all remaining surfaces of the membrane that can non-specifically bind to proteins. In the case of nucleic acid detection, a membrane can be washed with a solution containing, for example, salmon sperm DNA, which can bind to all remaining surfaces of the membrane that can non-specifically bind to nucleic acids. After washing with a solution that suppresses non-specific binding, a fibronectin or oncofetal fibronectin binding partner can be added. The presence of the fibronectin or oncofetal fibronectin binding partner on the membrane can be detected directly or indirectly. In one example, the binding partner can be conjugated to a moiety that can produce a directly detectable signal.

If the fibronectin or oncofetal fibronectin binding partner is not conjugated with a detectable moiety, the fibronectin or oncofetal fibronectin binding partner can be detected indirectly using a binding partner that binds to a fibronectin or oncofetal fibronectin binding partner, where the binding partner that binds to a fibronectin or oncofetal fibronectin binding partner can be conjugated with a moiety that can produce a detectable signal, or can itself be bound by a binding partner. For example, the fibronectin or oncofetal fibronectin binding partner can be a mouse monoclonal anti-oncofetal fibronectin antibody and the binding partner that binds to the mouse monoclonal anti-oncofetal fibronectin antibody can be a horseradish peroxidase-conjugated goat anti-mouse IgG antibody.

Moieties that can produce a detectable signal include radionuclides, fluorescent molecules, quantum dots, colloidal metal and proteins including green fluorescence protein, horseradish peroxidase and chloramphenicol acetyl transferase. Moieties can be detected directly, such as by detecting fluorescence of a fluorescent molecule. Moieties also can be detected indirectly such as by detecting chemiluminescence catalyzed by horseradish peroxidase. Detection of a moiety at a discrete location on the membrane can indicate presence of an oncofetal fibronectin indicating molecule in the sample that was applied to that discrete location. In one embodiment, the amount of an oncofetal fibronectin indicating molecule present in the sample can be quantitated using known methods, for example, using multiple dilutions of a sample at two or more dot loci and detecting binding partner(s) present at each locus.

ii. Western Blot Analysis

Western blot analysis can be used to detect the presence of oncofetal fibronectin protein or autoantibody in a sample. Western blotting is performed by first loading a protein sample in a gel, such as a sodium dodecyl sulfate polyacrylamide gel and electrophoresing the sample, using known methods. One sample can be loaded on each lane of the gel, which can contain a plurality of lanes. In one embodiment, a gel can contain multiple sample aliquots. When multiple sample aliquots are used, the aliquots can be identical or different, where the different aliquots can be at different levels of sample dilution or can be aliquots which have been treated with at least one different reagent. For example, different aliquots can be contacted with different non-specific binding compounds or surfaces; or one or more first aliquots can be untreated and one or more second aliquots can be treated, for example, using a non-specific binding compound. Control or reference samples also can be added to the gel. The gel can then be electrophoresed according to known methods.

The electrophoresed gel can then be placed onto a prepared membrane (as known in the art and described in regard to dot blot analysis) and the protein of the gel can be electroblotted onto the membrane using known methods. The membrane can then be washed, blocked and a fibronectin or oncofetal fibronectin binding partner can be added as described in regard to dot blot analysis. As with dot blot analysis, the fibronectin or oncofetal fibronectin binding partner can be detected directly, for example, using a fibronectin or oncofetal fibronectin binding partner conjugated with a moiety that can produce a detectable signal, or indirectly, for example, using a binding partner conjugate that binds the fibronectin or oncofetal fibronectin binding partner.

Detection of a signal from a moiety in one lane of the membrane can indicate the presence of oncofetal fibronectin protein or autoantibody in the sample loaded in that lane. Further, the location of the signal in the lane can be used to determine the molecular weight of the sample component to which the fibronectin or oncofetal fibronectin binding partner bound. This information can be used, for example, to eliminate false positive signals if a detected signal does not correspond to an expected molecular weight of oncofetal fibronectin protein or autoantibody (or a fragment thereof). This information also can be used, for example, to characterize the type of oncofetal fibronectin protein variant present, for example, to distinguish between a V0, V64, V89, V95 or V120 splice variant. In one embodiment, the amount of oncofetal fibronectin protein or autoantibody present in the sample can be quantitated using known methods.

iii. Southern and Northern Blot Analyses

Southern and Northern blot analysis can be used to detect the presence of a nucleic acid encoding oncofetal fibronectin or complementary thereto in a sample. A nucleic acid encoding oncofetal fibronectin can include mRNA encoding oncofetal fibronectin or amplicates thereof (e.g., cDNA) and fragments thereof. Southern and Northern blot analysis are performed by first loading a DNA (Southern) or RNA (Northern) sample in a gel, such as an agarose gel or polyacrylamide gel, and electrophoresing the sample under denaturing conditions, using known methods. One sample can be loaded on each lane of the gel, which can contain a plurality of lanes. In one embodiment, a gel can contain multiple sample aliquots. When multiple sample aliquots are used, the aliquots can be identical or different, where the different aliquots can be at different levels of sample dilution or can be aliquots which have been treated with at least one different reagent. For example, different aliquots can be contacted with different non-specific binding compounds or surfaces; or one or more first aliquots can be untreated and one or more second aliquots can be treated, for example, using a non-specific binding compound. Control or reference samples also can be added to the gel. The gel can then be electrophoresed according to known methods.

The electrophoresed gel can then be placed onto a prepared membrane (as known in the art or described herein), such as a nylon membrane and the nucleic acid molecules of the gel can be blotted onto the membrane using known methods, including electroblotting, vacuum blotting, semi-dry electroblotting, bidirection transfer and positive pressure, as known in the art.

The membrane can then be washed, blocked and a fibronectin or oncofetal fibronectin binding partner can be added as described above. As with dot blot analysis, the fibronectin or oncofetal fibronectin binding partner can be conjugated with a moiety that can produce a detectable signal, or a binding partner conjugate that binds the fibronectin or oncofetal fibronectin binding partner can be used.

Detection of a signal from a moiety in one lane of the membrane can indicate the presence of an oncofetal fibronectin encoding nucleic acid or complement thereto or fragment thereof in the sample loaded in that lane. Further, the location of the signal in the lane can be used to determine the molecular weight of the sample component to which the fibronectin or oncofetal fibronectin binding partner bound. This information can be used, for example, to eliminate false positive signals if a detected signal does not correspond to an expected molecular weight of an oncofetal fibronectin encoding nucleic acid or complement thereto (or a fragment thereof). This information also can be used, for example, to characterize the oncofetal fibronectin as containing or not containing EDA, EDB and/or the splice variant of IIICS or complement thereto.

Detection of a signal also can be used to quantitate the amount of oncofetal fibronectin encoding nucleic acid molecule or complement thereto present in the sample. For example, the intensity of the band corresponding to oncofetal fibronectin can be measured using any of a variety of methods known in the art, including, for example, phosphor imager measurement. In one example, known concentrations of a standard also can be included in the blot and the intensity of one or more sample bands can be qualitatively or quantitatively compared to the standards using known methods to provide an estimate or calculation of the amount of oncofetal fibronectin encoding nucleic acid molecule or complement thereto present in the sample.

iv. In Situ Analysis

Presence of an oncofetal fibronectin indicating molecule can be determined in situ. An oncofetal fibronectin indicating molecule can be detected in tissue or organ samples, or can be detected in a subject. For example, a fibronectin or oncofetal fibronectin binding partner conjugated to a fluorophore can be applied to a tissue sample and detection of fluorescence on the tissue sample can indicate the presence of an oncofetal fibronectin indicating molecule in the tissue. In another example, a fibronectin or oncofetal fibronectin binding partner conjugated to an imaging agent can be administered to a subject and detection of a localized imaging agent signal in the subject can indicate the presence and location of an oncofetal fibronectin indicating molecule in the subject. In another example, a fibronectin or oncofetal fibronectin binding partner, optionally conjugated to a therapeutic agent can be administered to a subject in treating the subject.

Methods of administering a fibronectin or oncofetal fibronectin binding partner conjugate to a subject for detecting an oncofetal fibronectin indicating molecule in a subject also can be used for treatment of the subject. For example, a detectable fetal fibronectin or oncofetal fibronectin binding partner conjugate, such as a radionuclide-containing conjugate, can be detected by known methods and also can be used for treating the subject. Conjugates that can be used for both detection and therapeutic methods are known in the art.

In one embodiment, anti-fibronectin or anti-oncofetal fibronectin autoantibodies can be used according to the use of the fibronectin or oncofetal fibronectin binding partners. For example, anti-fibronectin or anti-oncofetal fibronectin autoantibodies can be removed from a subject and have conjugated thereto a detectable and/or therapeutic agent, and the autoantibody can then be administered back to the subject, where the autoantibody conjugate can be detectable, therapeutic, or both.

a. Tissue or Organ Samples

Presence of an oncofetal fibronectin indicating molecule can be determined in situ in a tissue or organ sample. A tissue or organ sample includes biological matter removed from a subject, where typically the biological matter contains cells or is solid. An exemplary tissue or organ sample is a biopsy or a paraffin-embedded tissue sample. In one embodiment, a fibronectin or oncofetal fibronectin binding partner conjugate can be applied to a tissue sample and detection of the conjugate bound to the tissue sample can indicate the presence of an oncofetal fibronectin indicating molecule in the tissue. A variety of conjugates useful for such methods are provided herein or known in the art and include conjugates containing fluorescent moieties, radionuclides, chromophores, latex microspheres, quantum dots, colloidal metal, or an enzyme capable of producing a detectable signal such as horseradish peroxidase or luciferase. In another embodiment, a fibronectin or oncofetal fibronectin binding partner can be applied to a tissue sample and detection of the fibronectin or oncofetal fibronectin binding partner bound to the tissue sample can indicate the presence of an oncofetal fibronectin indicating molecule in the tissue. Presence of the fibronectin or oncofetal fibronectin binding partner can be detected using any of a variety of methods, including contacting the tissue or organ sample with a detectable compound that specifically binds a fibronectin or oncofetal fibronectin binding partner, including, but not limited to, an antibody or an oligonucleotide. For example, when the sample is contacted with an anti-oncofetal fibronectin mouse monoclonal antibody, the sample can be subsequently contacted with a goat anti-mouse IgG antibody conjugated to, for example, an enzyme such as luciferase and presence of a luminescent signal can indicate the presence of anti-oncofetal fibronectin mouse monoclonal antibody bound to the sample and thereby indicate the presence of an oncofetal fibronectin indicating molecule in the sample.

Any of a variety of known histochemical methods can be used for determining the presence of an oncofetal fibronectin indicating molecule in a tissue or organ sample, according to the sample to be used, the oncofetal fibronectin indicating molecule to be detected, and the binding partner and binding partner detection method to be used. Generally, such techniques typically include steps of sample preparation or fixation, any post-fixation and/or antigen retrieval steps appropriate according to the sample preparation and an oncofetal fibronectin indicating molecule detection methods, blocking non-specific binding and other false positive blocking steps such as endogenous peroxidase blocking, hybridization with a fibronectin or oncofetal fibronectin binding partner, washing and detection of the fibronectin or oncofetal fibronectin binding partner bound to the sample either directly or indirectly through a secondary compound. Any method known in the art for tissue or organ sample preparation can be used, including, but not limited to, fixing the sample with formaldehyde and embedding the sample in paraffin, fixing the sample in acetone and embedding the sample in paraffin and fixing the sample in paraformaldehyde and flash freezing the sample in liquid nitrogen. An oncofetal fibronectin indicating molecule detection methods can be performed according to any of a variety of well known methods, according to the oncofetal fibronectin indicating molecule to be detected. In one example, when an oncofetal fibronectin protein or fragment thereof, is to be detected, standard immunohistochemical methods employing a fibronectin or oncofetal fibronectin binding partner such as an anti-oncofetal fibronectin antibody such as FDC-6 or BC-1 can be performed. In another example, when an oncofetal fibronectin encoding nucleic acid molecule or fragment thereof, is to be detected, standard nucleotide in situ hybridization methods (e.g., FISH), employing an oligonucleotide complementary to an oncofetal fibronectin encoding nucleic acid molecule can be performed. Various known imaging methods can be used to detect the presence of an oncofetal fibronectin indicating molecule in the sample. In one example, confocal microscopy can be used to detect the presence of an oncofetal fibronectin indicating molecule in the sample.

The fibronectin or oncofetal fibronectin binding partner (e.g., antibody or oligonucleotide probe) can be selected according to the characteristics of the oncofetal fibronectin indicating molecule to be determined. For example, if presence of a IIICS-containing oncofetal fibronectin is to be determined, an antibody such as FDC-6 or X18A4 can be used, or an oligonucleotide probe complementary to at least a portion of the IIICS region can be used. Similar selections of oncofetal fibronectin binding partners can be used to determine the presence of EDA or EDB containing an oncofetal fibronectin indicating molecule in a sample and also to determine the presence of various splice variants of IIICS in an oncofetal fibronectin indicating molecule present in the sample. Oncofetal fibronectin binding partners also can bind oncofetal fibronectin protein or autoantibody, to indicate post-translational modifications of oncofetal fibronectin protein in the subject. Combinations of two or more oncofetal fibronectin binding partners that can, for example, detect the presence of two or more different regions of an oncofetal fibronectin indicating molecule can be used. In one example, multiple oligonucleotides can be used for detecting a nucleic acid molecule encoding oncofetal fibronectin. For example, five oligonucleotide probes can be used to determine the presence of oncofetal fibronectin containing EDA, oncofetal fibronectin containing EDB, oncofetal fibronectin containing the first, 25 amino acid splice region of IIICS, oncofetal fibronectin containing the second, 64 amino acid splice region of IIICS and oncofetal fibronectin containing the third, 31 amino acid splice region of IIICS; alternatively, 10 amplification primers can be used to determine the presence of these 5 regions using standard nucleic acid amplification methods. Oncofetal fibronectin binding partners disclosed herein or known in the art can be used alone or in combinations, for example, of 2 or more oncofetal fibronectin binding partners, 3 or more oncofetal fibronectin binding partners, 4 or more oncofetal fibronectin binding partners, or 5 or more oncofetal fibronectin binding partners. In one embodiment, each different oncofetal fibronectin binding partner is differently detectable; for example, each different oncofetal fibronectin binding partner can contain a fluorescent moiety that fluoresces at peak wavelength different from the other fluorescent moieties.

A variety of methods for detecting an oncofetal fibronectin indicating molecule in a tissue sample are known in the art. For example, antibodies can be used for detecting oncofetal fibronectin protein in a tissue sample. Among antibodies that can be used is FDC-6, which can be used for detecting a variety of cancers (neoplastic diseases) in a subject, including carcinomas of the lung, breast, ovary, stomach, pancreas, larynx, esophagus, testes, liver, parotid, biliary tract, colon, rectum, cervix, uterus, endometrium, kidney, bladder, prostate, thyroid, pituitary, eye, brain, oral, skin, head and neck cancer, lymphoma, leukemia, squamous cell carcinomas, adenocarcinomas, small cell carcinomas, melanomas, gliomas, sarcomas and neuroblastomas. In one example, FDC-6 can be used to detect glycosylated IIICS-containing oncofetal fibronectin protein in cancerous tissue samples such as breast cancer (Kaczmarek et al., *Int. J. Cancer* 59:11-16 (1994)). Other antibodies that bind oncofetal fibronectin protein also can be used. For example, BC-1 can be used to detect the presence of an EDB-containing oncofetal fibronectin protein in cancerous tissue samples such as brain meningiomas and lung carcinoma (Camemolla et al., *J. Cell. Biol.* 108:1139-1148 (1989)), L19 can be used to detect the presence of EDB-containing oncofetal fibronectin protein in tumorous tissue in mice (Borsi et al., *Int. J. Cancer* 102:75-85 (2002)), 5C10 can be used to detect glycosylated IIICS-containing oncofetal fibronectin protein in cancerous tissue samples such as oral squamous cell carcinoma (Lyons et al., *Br. J. Oral Maxillofac. Surg.* 39:471-477 (2001)), X18A4 can be used to detect the presence of IIICS-containing oncofetal fibronectin protein in cancerous tissue samples such as ovarian cancer (Menzin et al., *Cancer* 82:152-158 (1998)) and IST-9 can be used to detect the presence of EDA-containing oncofetal fibronectin protein in cancerous tissue samples such as papillary carcinoma of the thyroid (Scarpino et al., *J. Pathol.* 188:163-167 (1999)). In another example, IST-9 and BC-1 can be used to detect the presence of EDA and EDB in oncofetal fibronectin protein, respectively, in hepatocellular carcinoma (Oyama et al., *Cancer Res.* 53:2005-2011 (1993)). Additional combinations of particular neoplastic diseases and oncofetal fibronectin protein binding partners can be determined empirically.

Nucleic acid probes also can be used for in situ detection of a nucleic acid encoding oncofetal fibronectin. For example, a nucleic acid probe can be used to detect the presence of mRNA encoding IIICS-containing oncofetal fibronectin in cancerous tissue samples such as thyroid papillary and anaplastic carcinoma (Takano et al., *Br. J. Cancer* 78:221-224 (1998)). In another example, a nucleic acid probe can be used to detect the presence of mRNA encoding EDB-containing oncofetal fibronectin in cancerous tissue such as oral squamous cell carcinoma (Kosmehl et al., *Br. J. Cancer* 81:1071-1079 (1999)). Additional combinations of particular neoplastic diseases and oncofetal fibronectin encoding nucleic acid molecule binding partners can be determined empirically.

b. Detection in a Subject

Presence of an oncofetal fibronectin indicating molecule can be determined in vivo in a subject. A variety of tumorous tissues, such as cervical tumor tissue (as provided herein), express oncofetal fibronectin protein. In addition, as provided herein, cells or tissues expressing oncofetal fibronectin or expressing increased amounts of oncofetal fibronectin protein relative to normal cells or tissues can be developing into neoplastic cells or tissues or can have an increased likelihood of developing into neoplastic cells or tissues. Accordingly, by administering to a subject a fibronectin or oncofetal fibronectin binding partner or conjugate thereof, tumorous tissues or tissues with increased likelihood of developing into tumorous tissues can be specifically targeted. In accordance with this embodiment, a fibronectin or oncofetal fibronectin binding partner conjugate can be administered to a subject and detection of the conjugate at a location in the subject can indicate the presence of oncofetal fibronectin expression in that location. For example, tumorous tissue in a subject can be imaged by administering to a subject a fibronectin or oncofetal fibronectin binding partner conjugated to an imaging moiety, whereby the conjugate localizes to an oncofetal fibronectin indicating molecule at or near tumorous tissue and then detecting the localization of the conjugate within the subject to thereby image tumorous tissue in the subject. In another example, tissue developing or likely to develop into tumorous tissue can be imaged by administering to a subject a fibronectin or oncofetal fibronectin binding partner conjugated to an imaging moiety, whereby the conjugate localizes to an oncofetal fibronectin indicating molecule at or near tissue developing into or likely to develop into tumorous tissue and then detecting the localization of the conjugate within the subject to thereby image tissue developing or likely to develop into tumorous tissue in the subject. In such cases, the conjugate can localize to the tumorous or pre-tumorous tissue itself, or to extracellular matrix or vasculature adjacent the tumorous or pre-tumorous tissue. Further, a fibronectin or oncofetal fibronectin binding partner conjugate can be administered to a subject and detection of the conjugate at a location in the subject can indicate the presence of cancerous (tumorous or neoplastic) cells, or cells with increased likelihood of developing into cancerous cells in that location. For example, cancerous (tumorous or neoplastic) cells in a subject can be imaged by administering to a subject a fibronectin or oncofetal fibronectin binding partner conjugated to an imaging moiety, whereby the conjugate localizes to cancerous (tumorous or neoplastic) cells containing an oncofetal fibronectin indicating molecule and then detecting the localization of the conjugate within the subject to thereby image cancerous (tumorous or neoplastic) cells in the subject. In another example, cells developing into or having an increased likelihood of developing into cancerous (tumorous or neoplastic) cells can be imaged by administering to a subject a fibronectin or oncofetal fibronectin binding partner conjugated to an imaging moiety, whereby the conjugate localizes to cells developing into or with increased likelihood of developing into cancerous (tumorous or neoplastic) cells containing an oncofetal fibronectin indicating molecule and then detecting the localization of the conjugate within the subject to thereby image cells developing into or with increased likelihood of developing into cancerous (tumorous or neoplastic) cells in the subject. Methods also are provided herein for detecting an oncofetal fibronectin indicating molecule in a subject, by administering to a subject a fibronectin or oncofetal fibronectin binding partner conjugated to an imaging moiety, whereby the conjugate localizes to regions in the subject containing an oncofetal fibronectin indicating molecule and detecting the localization of the conjugate within the subject, thereby detecting an oncofetal fibronectin indicating molecule in the subject.

A variety of non-invasive imaging methods are known in the art, including magnetic resonance imaging or other resonance methods, ultrasonic imaging, fluorescence imaging, scintography, or tomography methods such as computed tomography, computerized axial tomography, positron emission tomography, single photon emission computed tomography, ultrasound tomography or x-ray tomography. For example, BC-1 labeled with technetium(Tc)-99m can be used to indicate the presence of EDB containing oncofetal fibronectin protein in brain tumors in a subject (Calcagno et al., *Cancer* 80:2484-2489 (1997)) and $^{123}$I-labeled-L19 can be used to indicate the presence of EDB containing oncofetal fibronectin protein in lung cancer or colorectal cancer in a subject (Santimaria et al., *Clin. Cancer Res.* 9:571-579 (2003)). In another example, L19 labeled with the fluorophore Cy5 can be used for in vivo fluorescence indication of the presence of EDB containing oncofetal fibronectin protein in angiogenesis in the eye (U.S. Pat. Pub. No. 20030045681).

Compounds that can be used in the imaging methods provided herein or known in the art typically contain a fibronectin or oncofetal fibronectin binding partner conjugated to an imaging moiety. For example, FDC-6 can be conjugated to $^{18}$F, which can be detected by positron emission tomography. Any of a variety of fibronectin or oncofetal fibronectin binding partners disclosed herein or otherwise known in the art can be used in the treatment methods provided herein, including fibronectin or oncofetal fibronectin binding partner proteins, fibronectin or oncofetal fibronectin binding partner nucleic acid molecules and fibronectin or oncofetal fibronectin binding partner organic molecules. The fibronectin or oncofetal fibronectin binding partner also can be a binding partner that specifically binds the EDA, EDB, IIICS regions of oncofetal fibronectin, or a particular splice variant of IIICS such as V64, V89, V95 or V120, or a particular post-translational modification of oncofetal fibronectin protein such as O-glycosylation of threonine 33 of IIICS, or combinations thereof. Typically the fibronectin or oncofetal fibronectin binding partner will be a binding partner that can be present in a subject for a length of time sufficient to localize to one or more sites where oncofetal fibronectin is present within the subject (e.g., the prostate, lungs, brain, breast, ovary, thyroid, cervix or bladder) and sufficient to be imaged by one or more of the imaging methods provided herein or known in the art. The fibronectin or oncofetal fibronectin binding partner will also typically preferentially bind to an oncofetal fibronectin indicating molecule such that imaging methods can determine the location of an oncofetal fibronectin indicating molecule within the subject. An exemplary oncofetal fibronectin binding partner that can be used for in vivo imaging is an antibody such as FDC-6, BC-1, ME4C or L19. In one embodiment, the anti-oncofetal fibronectin antibody can be a "humanized" or chimeric antibody bearing human constant and/or variable domains, or can be an antibody otherwise derived from a human antibody source or human antibody sequence, such as L19. Methods of deriving antibodies from a human antibody source or human antibody sequence using, for example, phage display or filter selection of antibody-expressing bacteria are known in the art, as exemplified in WO 97/45544 and WO 02/46455. Methods for deriving antibodies from a human antibody sequence using, for example transgenic animals expressing human antibody sequences are known in the art, as exemplified in U.S. Pat. Nos. 6,632,976 and 6,713,610.

The conjugate used for in vivo detection methods typically contains a moiety that permits imaging. A variety of imaging moieties are known in the art, including fluorescent moieties, radionuclides, magnetically detectable isotopes or compounds, sonographic imaging agents, chromophores, latex microspheres, or quantum dots. The moiety can be selected according to the imaging method to be used. For example, a variety of ultrasound imaging agents are known in the art, including, but not limited to, microspheres containing perfluorocarbon such as perfluorocarbon-filled albumin microspheres (see, e.g., U.S. Pat. No. 6,174,287) or phospholipid coated microbubbles filled with perfluorocarbon gas (see, e.g., U.S. Pat. No. 6,146,657) and also including other imaging agents such as simethicone-coated cellulose (see, e.g., U.S. Pat. No. 6,024,939) or galactose and palmitic acid microparticles (see, e.g., U.S. Pat. No. 5,380,411). In another example, a variety of computed tomography imaging agents are known in the art, including, but not limited to, compounds containing $^{131}$I, $^{18}$F, $^{123}$I, $^{201}$Tl, $^{111}$In and Tc-99m. In another example, a variety of magnetic resonance imaging agents are known in the art, including, but not limited to, metal complexes such as iron, manganese or gadolinium-containing complexes, or other compounds containing atoms that are low in natural abundance and have a nuclear magnetic moment, for example, compounds containing $^{13}$C, $^{15}$N, $^{17}$O, $^{19}$F, $^{29}$Si, or $^{31}$P. In another example, any of a variety of luminescent or fluorescent compounds can be used including bioluminescent enzymes (e.g., luciferase), fluorescent proteins (e.g., green fluorescence protein), fluorophores, dyes, latex microspheres and quantum dots. In another example, any of a variety of x-ray contrast agents can be used, including, but not limited to, barium compounds such as barium sulfate and iodinated compounds including ionic compounds such as iodamide, iodipamide and ioglycamic acid and non-ionic iodinated compounds such as metrizamide, iopamidol, iohexyl, iopromide, iobitridol, iomeprol, iopentol, ioversol, ioxilan, iodixanol, iotrolan.

A fibronectin or oncofetal fibronectin binding partner conjugated to a detectable moiety can be administered to a subject in any of a variety of manners known in the art for delivering compounds to a subject, according to a variety of factors known to those skilled in the art, including, but not limited to, the nature of the fibronectin or oncofetal fibronectin binding partner and the detectable moiety, the regions of the subject's body to be imaged, the selected speed of administration and the likelihood of unintended clearance. In one embodiment, the conjugate is administered intravenously to a subject. In another embodiment, the conjugate is administered topically, for example, as a component of a lavage composition, or as a cream, salve or gel. The conjugate also can be administered topically to a variety of additional surfaces including, but not limited to, dermal, oral, aural, nasal, anal, urethral, ocular, breast, cervicovaginal, alimentary canal such as esophageal, gastric, intestinal, or colon surfaces. Exemplary topical applications include contacting the vaginal and uterine cavities with a conjugate, or contacting one or more breast ducts with a conjugate.

The methods provided herein also can include imaging cells or tissues containing a particular an oncofetal fibronectin indicating molecule variant. For example, imaging can be performed using an oncofetal fibronectin binding partner that specifically binds the EDA, EDB, IIICS regions of an oncofetal fibronectin indicating molecule, or a particular splice variant of IIICS such as V64, V89, V95 or V120, or a particular post-translational modification of oncofetal fibronectin protein such as O-glycosylation of threonine 33 of IIICS, or combinations thereof. Accordingly cells or tissues can be specifically imaged according to whether or not the cells or tissues contain an oncofetal fibronectin indicating molecule containing EDA, EDB, or IIICS, or a particular splice variant of IIICS such as V64, V89, V95 or V120, or a particular post-translational modification of oncofetal fibronectin protein such as O-glycosylation of threonine 33 of IIICS, or combinations thereof.

c. Treatment in a Subject

Presence of an oncofetal fibronectin indicating molecule also can be used for in vivo treatment of a subject. A variety of tumorous tissues are known to express, shed and/or secrete oncofetal fibronectin. Accordingly, by administering to a subject a fibronectin or oncofetal fibronectin binding partner or conjugate thereof, cancerous (tumorous) tissues can be specifically targeted. As provided herein, tissues developing into cancerous tissues or with increased risk of developing into cancerous tissues express oncofetal fibronectin. Accordingly, by administering to a subject a fibronectin or oncofetal fibronectin binding partner or conjugate thereof, tissues developing into cancerous tissues or with increased risk of developing into cancerous tissues can be specifically targeted. In accordance with this embodiment, a fibronectin or oncofetal fibronectin binding partner or a fibronectin or oncofetal fibronectin binding partner conjugate can be administered to a subject and the binding partner or conjugate can accumulate in a location in the subject that has an oncofetal fibronectin indicating molecule, such as a location at or near tumorous tissue or tissue developing into neoplastic tissue or with increased risk of developing into cancerous tissue. For example, the conjugate can localize to the tumorous tissue itself, or to extracellular matrix or vasculature adjacent the tumorous tissue. In another example, the conjugate can localize to tissue developing into cancerous tissues or with increased risk of developing into cancerous tissues itself, or to extracellular matrix or vasculature adjacent the tissue developing into cancerous tissues or with increased risk of developing into cancerous tissues. Further, a fibronectin or oncofetal fibronectin binding partner or conjugate thereof can be administered to a subject and the binding partner or conjugate can accumulate in a location in the subject that has cancerous cells. Additionally, a fibronectin or oncofetal fibronectin binding partner or conjugate thereof can be administered to a subject and the binding partner or conjugate can accumulate in a location in the subject that has cells developing into cancerous cells or with increased risk of developing into cancerous cells. The localized binding partner or conjugate can then, directly or indirectly, inhibit cell growth in that location or cause cell death in that location or inhibit development of cells into cancerous cells in that location.

Cell growth can be inhibited by any of a variety of methods, including but not limited to, reducing the amount of neovascularization in a location, or down-regulating cell growth-promoting cellular processes. Cell death can be caused by any of a variety of methods including increasing a subject's immune response, generating apoptosis signal or otherwise initiating apoptosis, or applying a toxin or toxic substance such diphtheria toxin or a radionuclide or chemotherapeutic substance.

A fibronectin or oncofetal fibronectin binding partner alone can cause tumor inhibition or cell death response or a fibronectin or oncofetal fibronectin binding partner conjugate with a moiety that inhibits cell growth or promotes cell death can cause tumor inhibition or cell death response. Any of a variety of fibronectin or oncofetal fibronectin binding partners disclosed herein or otherwise known in the art can be used in the treatment methods provided herein, including fibronectin or oncofetal fibronectin binding partners that are proteins, fibronectin or oncofetal fibronectin binding partners that are nucleic acid molecules and fibronectin or oncofetal fibronectin binding partners that are organic molecules. The oncofetal fibronectin binding partner also can be a binding partner that specifically binds the EDA, EDB, IIICS regions of an oncofetal fibronectin indicating molecule, or a particular splice variant of IIICS such as V64, V89, V95 or V120, or a particular post-translational modification of oncofetal fibronectin protein such as O-glycosylation of threonine 33 of IIICS, or combinations thereof. In one example, the oncofetal fibronectin binding partner can be an anti-oncofetal fibronectin antibody and the anti-oncofetal fibronectin antibody can bind to oncofetal fibronectin protein located at or near the targeted cell or the targeted tissue and elicit an immune response by the subject's immune system which can result in death of at least a portion of the cells in the location to which the fibronectin or oncofetal fibronectin binding partner localizes. In another example, a fibronectin or oncofetal fibronectin binding partner can bind an oncofetal fibronectin indicating molecule and inhibit one or more activities of the oncofetal fibronectin indicating molecule, resulting in inhibition of cell proliferation. For example, a fibronectin or oncofetal fibronectin binding partner that binds an oncofetal fibronectin encoding nucleic acid molecule can inhibit expression of oncofetal fibronectin, resulting in inhibition of cell proliferation. In another example, a fibronectin or oncofetal fibronectin binding partner that binds oncofetal fibronectin protein can alter, inhibit or modulate the binding properties of oncofetal fibronectin, resulting in inhibition of cell proliferation. For present purposes, a fibronectin or oncofetal fibronectin binding partner conjugated to a moiety that does not inhibit cell growth or cause cell death can have the same cell growth inhibitory or cell death causing effect as the fibronectin or oncofetal fibronectin binding partner alone. Typically the fibronectin or oncofetal fibronectin binding partner will be a binding partner that can be present in a subject for a length of time sufficient to localize to one or more sites where oncofetal fibronectin is present within the subject (e.g., the prostate, lungs, brain, breast, ovary, thyroid, colon or rectum, cervix or bladder) and sufficient to inhibit cell growth or cause cell death, for example, by eliciting an immune response in the subject. An exemplary fibronectin or oncofetal fibronectin binding partner that can be used for in vivo treatment is an antibody such as FDC-6, BC-1, ME4C or L19. In one embodiment, the antibody can be a "humanized" or chimeric antibody bearing human constant and/or variable domains, or can be an antibody otherwise derived from a human antibody source or human antibody sequence, such as L19. Methods of deriving antibodies from a human antibody source using, for example, phage display or filter selection of antibody-expressing bacteria are known in the art. Methods for deriving antibodies from a human antibody sequence using, for example transgenic animals expressing human antibody sequences are known in the art.

The fibronectin or oncofetal fibronectin binding partner also can be administered as a conjugate. The conjugate typically contains a therapeutic moiety that inhibits cell growth or promotes cell death, that can be activated to inhibit cell growth or promote cell death, or that can activate a compound to inhibit cell growth or promote cell death. Optionally, the moiety also can have one or more additional properties such as acting as an imaging agent, as described elsewhere herein. A variety of therapeutic moieties are known in the art, including, but not limited to, biological toxins, cytokines, photosensitizing agents, toxins, anticancer antibiotics, chemotherapeutic compounds, radionuclides, binding partners and bioluminescent compounds. For example, a therapeutic moiety can be a biological toxin such as, but not limited to, pseudomonas exotoxin, diphtheria toxin, ricin, cholera toxin, gelonin, shigella toxin, pokeweed anti-viral protein, exotoxin A, abrin toxin or saporin (see, e.g., U.S. Pub. No. 2004/0009551). For example, a therapeutic moiety can be a signaling compound such as a cytokine or growth factor such as an interleukin including interleukin-1, interleukin-2, interleukin-6 and interleukin-12, a tumor necrosis factor such as tumor necrosis factor alpha (TNF-α), an interferon such as interferon gamma (IFN-γ), granulocyte macrophage colony stimulating factor (GM-CSF), angiogenin, or tissue factor (see, e.g., U.S. Pub. No. 20030232010). For example, a therapeutic moiety can be an anticancer antibiotic such as, but not limited to, porfiromycin, doxorubicin, dactinomycin, plicamycin, mitomycin, bleomycin, actinomycin, and daunorubucin (see, e.g., U.S. Pub. No. 20040054014). For example, a therapeutic moiety can be a photosensitizing agent such as, but not limited to, indocyanine green, toluidine blue, aminolevulinic acid, texaphyrins, benzoporphyrins, phenothiazines, phthalocyanines, porphyrins such as sodium porfimer, chlorins such as tetra(m-hydroxyphenyl)chlorin or tin(IV) chlorin e6, purpurins such as tin ethyl etiopurpurin, purpurinimides, bacteriochlorins, pheophorbides, pyropheophorbides and cationic dyes (see, e.g., U.S. Pub. Nos. 20040019032 and 20030114434). For example, a therapeutic moiety can be a high energy radionuclide such as, but not limited to, a compound containing $^{32}$Phosphate, $^{60}$Cobalt, $^{90}$Yttirum, $^{99}$Technicium, $^{103}$Palladium, $^{106}$Ruthenium, $^{111}$Indium, $^{117}$Lutetium, $^{125}$Iodine, $^{131}$Iodine, $^{137}$Cesium, $^{153}$Samarium, $^{186}$Rhenium, $^{188}$Rhenium, $^{192}$Iridium, $^{198}$Gold, $^{211}$Astatine, $^{212}$Bismuth and $^{213}$Bismuth.

A therapeutic moiety can include a variety of other toxins including, but not limited to, any of a large number of chemotherapeutic compounds such as, but not limited to, 5-fluorouridine, calicheamicin and maytansine (see, e.g., U.S. Pub. No. 20020039557). Additional chemotherapeutic compounds include alkylating agents such as thiotepa and cyclosphosphamide; alkyl sulfonates such as busulfan, improsulfan and piposulfan; aziridines such as benzodopa, carboquone, meturedopa and uredopa; ethylenimines and methylamelamines including altretamine, triethylenemelamine, trietylenephosphoramide, triethylenethiophosphaoramide and trimethylolomelamime nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; polysaccharide-K; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; cytosine arabinoside; cyclophosphamide; thiotepa; taxoids, e.g. paclitaxel and doxetaxel; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone and toremifene (Fareston); and antiandrogens such as flutamide, nilutamide, bicalutamide, leuprolide and goserelin; and pharmaceutically acceptable salts, acids or derivatives of any of the above. Such chemotherapeutic compounds that can be used herein include compounds whose toxicities preclude use of the compound in general systemic chemotherapeutic methods.

Therapeutic moieties also can be binding partners such as an antibody or fragment thereof, receptor or fragment thereof or ligand for an antibody or receptor, where such moieties can bind to any of a variety of substances or compounds for inhibiting cell growth or causing cell death. Binding partners can bind, for example, toxins, chemotherapeutic compounds, or compounds containing a radionuclide. Binding partners also can bind, for example, cell surface proteins such as a cell surface protein on a leukocyte or other cell related to an immune response. For example, a binding partner can bind to a lymphocyte such as a B cell, T cell or NK cell; an exemplary binding partner is an IgG that can bind to the Fc receptor of an NK cell. Therapeutic moieties also can activate a compound to inhibit cell growth or promote cell death. For example, a therapeutic moiety can be bioluminescent, such as luciferase and can, upon administration to the subject of an appropriate substrate such as luciferin and a photosensitizing agent, activate the photosensitizing agent in the area of localization of the conjugate to inhibit cell growth or cause cell death in that location.

Therapeutic moieties can be cleavable from the binding partner portion of the conjugate. A variety of cleavable linkages are known in the art including photocleavable linkages, chemically cleavable linkages, thermally cleavable linkages, enzymatically cleavable linkages. For example, the linkage can be through a disulfide bond, by a photocleavable biotin derivative, or protease-sensitive peptides (see, e.g., U.S. Pat. No. 6,416,758). In one embodiment a moiety attached to the binding partner via a cleavable linkage is a moiety that directly inhibits cell growth or causes cell death.

A fibronectin or oncofetal fibronectin binding partner or fibronectin or oncofetal fibronectin binding partner conjugate can be administered to a subject in any of a variety of manners known in the art for delivering compounds to a subject, according a variety of factors known to those skilled in the art, including, but not limited to, the nature of the fibronectin or oncofetal fibronectin binding partner and the nature of the therapeutic moiety in a fibronectin or oncofetal fibronectin binding partner conjugate, the regions of the subject's body to be treated, the selected speed of administration and the likelihood of unintended clearance. In one embodiment, the binding partner or conjugate is administered intravenously to a subject. In another embodiment, the binding partner or conjugate is administered topically, for example, as a component of a lavage composition, or as a cream, salve or gel. The binding partner or conjugate also can be administered topically to a variety of additional surfaces including, but not limited to, dermal, oral, aural, nasal, anal, urethral, ocular, breast, cervicovaginal, alimentary canal such as esophageal, gastric, intestinal, or colon surfaces. Exemplary topical applications include contacting the vaginal and uterine cavities with a binding partner or conjugate, or contacting one or more breast ducts with a binding partner or conjugate.

The methods provided herein also can include treating cells or tissues containing a particular an oncofetal fibronectin indicating molecule variant. For example, treatment methods can be performed using an oncofetal fibronectin binding partner that specifically binds the EDA, EDB, IIICS regions of an oncofetal fibronectin indicating molecule, or a particular splice variant of IIICS such as V64, V89, V95 or V120, or a particular post-translational modification of oncofetal fibronectin protein such as O-glycosylation of threonine 33 of IIICS, or combinations thereof. Accordingly cells or tissues can be specifically treated by containing an oncofetal fibronectin indicating molecule containing EDA, EDB, or IIICS, or a particular splice variant of IIICS such as V64, V89, V95 or V120, or a particular post-translational modification of oncofetal fibronectin protein such as O-glycosylation of threonine 33 of IIICS, or combinations thereof.

The methods provided herein also can include method for inhibiting the recurrence of neoplastic disease in a subject. Such methods can include treating a subject for a neoplastic disease and administering to the subject a fibronectin or oncofetal fibronectin binding partner, whereby recurrence of neoplastic disease is inhibited. Treatment of the subject can be performed by any of a variety of methods known in the art, including chemotherapy, radiation therapy, administration of a bacteria or virus, administration of a tumor-specific compound and combinations thereof, including administration of a fibronectin or oncofetal fibronectin binding partner. In addition to the treatment for neoplastic disease, the subject can have administered thereto a fibronectin or oncofetal fibronectin binding partner which can serve to inhibit recurrence or metastasis of a neoplastic disease. Such administration can be concomitantly, subsequently, or intermittently or mixtures thereof with the treatment of the neoplastic disease.

c. Immobilized Binding Partner

Presence of an oncofetal fibronectin indicating molecule in a sample can be detected by contacting a sample with a solid support, to which a fibronectin binding partner or an oncofetal fibronectin binding partner is immobilized. When an oncofetal fibronectin indicating molecule is present in the sample, complex formation of the immobilized binding partner and oncofetal fibronectin indicating molecule can be detected. Detection of a complex between the immobilized binding partner and oncofetal fibronectin indicating molecule can indicate the presence of the oncofetal fibronectin indicating molecule in a sample. Complex detection can be achieved by any of a variety of methods known in the art. In one example, complex formation between a fibronectin or oncofetal fibronectin binding partner and an oncofetal fibronectin indicating molecule can be detected by detecting the presence of a second binding partner (either fibronectin or oncofetal fibronectin binding partner) in the complex, forming a "sandwich" complex. A binding partner can be detected directly or indirectly. Direct detection of the binding partner can be performed using a binding partner conjugated to a detectable moiety or conjugated to a bindable moiety. Indirect detection of a fibronectin or an oncofetal fibronectin binding partner can be performed using a binding partner that can bind to the fibronectin or oncofetal fibronectin binding partner and can generate a detectable signal or can be bound by another binding partner. In another example, complex formation between an oncofetal fibronectin indicating molecule and a fibronectin or oncofetal fibronectin binding partner can be detected by competition assay. For example, a fibronectin or oncofetal fibronectin binding partner can be contacted with a labeled oncofetal fibronectin indicating molecule or analog thereof, and then contacted with the sample; presence of oncofetal fibronectin indicating molecule in the sample will result in a decrease in the presence of labeled oncofetal fibronectin indicating molecule or analog thereof in complex with the binding partner. Thus, presence of an oncofetal fibronectin indicating molecule can be detected by disappearance of a signal in a competition assay.

A fibronectin binding partner or an oncofetal fibronectin binding partner can be immobilized on a solid support by known methods for use in the methods provided herein. A solid support on which a binding partner can be immobilized can be any of a variety of supports to which the binding partner can bind directly or can be bound via a linker or coating. Exemplary solid supports include microplates, microarrays, or membranes such as nitrocellulose, polyvinylidine fluoride (PVDF) or nylon membranes. For example, a binding partner can be immobilized on an untreated microplate or a treated microplate, including a microplate coated with a compound for binding the binding partner. Methods for immobilizing a sample on solid supports are known in the art and can be used in the methods herein.

A solid support containing a fibronectin or oncofetal fibronectin binding partner immobilized thereon can be subjected to one or more treatment steps prior to contacting the solid support with a sample. Such treatment steps include blocking steps to prohibit the surface of the solid support from non-specifically binding one or more components of a sample. Any of a variety of blocking steps known in the art can be applied to the solid support; also, a step of contacting the solid support with a non-specific binding compound such as a non-specific binding protein for oncofetal fibronectin protein assays, and a non-specific binding nucleic acid molecule for assays of a nucleic acid molecule encoding oncofetal fibronectin or complement thereto.

Prior to contacting the sample to the solid support containing fibronectin or oncofetal fibronectin binding partner, a sample can be treated by one or more steps as provided herein or otherwise known in the art. Exemplary treatment steps include filtering the sample to remove particulate matter, contacting the sample with a non-specific binding compound or surface to reduce background material binding to immobilized binding partner, adding a soluble or mobile fibronectin or oncofetal fibronectin binding partner or conjugate thereof to the sample solution, and addition of one or more buffers or reagents to modify ambient conditions such as pH or ionic strength.

Sample, treated or untreated, can be contacted with the solid support under conditions in which the fibronectin or oncofetal fibronectin binding partner can specifically bind to an oncofetal fibronectin indicating molecule. In one embodiment, the solid support is contacted with a sample under conditions in which background materials do not significantly interfere with the solid support binding oncofetal fibronectin (i.e., 10% or about 10% or less of the binding partners on the solid support bind to background materials or 90% or about 90% or more of an oncofetal fibronectin indicating molecule in the sample is bound by binding partners on the solid support). Exemplary conditions include 0.05 M Tris buffer, pH 7.4, 150 mM NaCl, 0.02% $NaN_3$, 1% BSA, 5 mM EDTA, 1 mM phenylmethylsulfonyl fluoride (PMSF), 500 Kallikrein Units/ml of Aprotinin, and 0.1% Triton X-100. The solid support can optionally be washed to remove any background material that can be non-specifically binding to the solid support.

When a fibronectin or oncofetal fibronectin binding partner is immobilized in two or more discrete locations, such as in a dot blot, a microplate or microarray, each discrete location can be independently treated, where all locations can be differently treated, or some locations can be equally treated while others are differently treated. Exemplary treatments include contacting with different dilutions of sample, contacting with different soluble or mobile binding partners, including binding partners that bind to different regions of an oncofetal fibronectin indicating molecule such as EDA, EDB and IIICS, and contacting under different buffer conditions. Such methods are known to those skilled in the art.

Complex formation of the binding partner and an oncofetal fibronectin indicating molecule can be determined in a number of ways. Complex formation can be determined by use of soluble or mobile fibronectin or oncofetal fibronectin binding partners. The soluble or mobile fibronectin or oncofetal fibronectin binding partners can be detected directly using, for example, a detectable moiety conjugated with the binding partner, or indirectly using binding partners that bind fibronectin or oncofetal fibronectin binding partners. The assay can be quantitative, for example, can be an enzyme-linked immunosorbent assay (ELISA) in which at least a first fibronectin or oncofetal fibronectin binding partner is immobilized to a solid support and at least a second fibronectin or oncofetal fibronectin binding partner is soluble or mobile. An oncofetal fibronectin assay can be based on competitive inhibition, where an oncofetal fibronectin indicating molecule in the sample competes with a known amount of oncofetal fibronectin indicating molecule or analog thereof (typically labeled) for a fibronectin or oncofetal fibronectin binding partner. For example, in an assay for oncofetal fibronectin protein, any oncofetal fibronectin protein present in the sample can compete with a known amount of labeled oncofetal fibronectin protein or a labeled analog thereof for the fibronectin or oncofetal fibronectin binding partner. The amount of labeled oncofetal fibronectin indicating molecule affixed to the solid phase or remaining in solution can be measured, and the measurement can be used to determine the amount of oncofetal fibronectin indicating molecule in the sample, using methods known in the art.

Detection of a signal also can be used to quantitate the amount of an oncofetal fibronectin indicating molecule present in the sample, using any of a variety of known methods. For example, the intensity of the signal corresponding to an oncofetal fibronectin indicating molecule can be measured using any of a variety of methods known in the art, including, for example, fluorescence or absorption spectrometry, or phosphor imager measurement. In one example, known concentrations of a standard also can be included and the intensity of one or more sample signals can be qualitatively or quantitatively compared to the standards using known methods to provide an estimate or calculation of the amount of an oncofetal fibronectin indicating molecule in the sample. In another example, multiple dilutions of the sample can be detected, and the signal measured at each dilution can be used to estimate the amount of an oncofetal fibronectin indicating molecule using known methods.

i. Sandwich Assay

An oncofetal fibronectin indicating molecule can be detected when bound to two or more fibronectin or oncofetal fibronectin binding partners, where such a complex can produce a signal indicative of complex formation. For example, presence of an oncofetal fibronectin indicating molecule bound to an immobilized fibronectin or oncofetal fibronectin binding partner can be detected by detecting presence of a soluble or mobile fibronectin or oncofetal fibronectin binding partner or conjugate thereof, bound to a solid support, as a result of a complex with an oncofetal fibronectin indicating molecule. Detection can be performed immediately after contacting the solid support with a sample or after one or more subsequent steps such as washing steps. In assays in which no label soluble or mobile fibronectin or oncofetal fibronectin binding partner conjugate is added, the solid support can optionally be washed and the solid support can be contacted with one or more additional reagents, such as a binding partner that binds a fibronectin or oncofetal fibronectin binding partner.

In some instances, the mobile or soluble fibronectin or oncofetal fibronectin binding partner will be detected, either directly or indirectly. Direct detection can include, for example, detecting a detectable moiety conjugated to the mobile or soluble fibronectin or oncofetal fibronectin binding partner. Indirect detection can include, for example, detecting a binding partner that binds the mobile or soluble fibronectin or oncofetal fibronectin binding partner. For example, indirect detection of a soluble mouse anti-oncofetal fibronectin antibody can be accomplished by contacting a solid support with a goat anti-mouse IgG antibody conjugated to horseradish peroxidase and measuring light formation upon using the appropriate substrate. In any of the above assays, presence of a detectable signal on the solid support can indicate that the soluble binding partner is bound to an oncofetal fibronectin indicating molecule that is bound to an immobilized binding partner. Thus, presence of a detectable signal on the solid support can indicate the presence of an oncofetal fibronectin indicating molecule in a sample.

The immobilized fibronectin or oncofetal fibronectin binding partner, sample, and soluble or mobile fibronectin or oncofetal fibronectin binding partner can be added to each other in any order, as will be understood by one skilled in the art. For example, a sample can be treated with a soluble or mobile fibronectin or oncofetal fibronectin binding partner prior to contacting the sample with the solid support (which contains immobilized fibronectin or oncofetal fibronectin binding partner), and subsequent steps can include contacting the solid support with the sample that contains the soluble or mobile fibronectin or oncofetal fibronectin binding partner. In another example, a sample can be contacted with a solid support containing immobilized fibronectin or oncofetal fibronectin binding partner prior to contacting the sample with a soluble or mobile fibronectin or oncofetal fibronectin binding partner, and subsequent steps can include contacting the solid support with the soluble or mobile fibronectin or oncofetal fibronectin binding partner. In another example, a solid support containing immobilized fibronectin or oncofetal fibronectin binding partner can be contacted with a soluble or mobile fibronectin or oncofetal fibronectin binding partner prior to either binding partner contacting the sample, and subsequent steps can include contacting the solid support with the sample.

ii. Test Device

A test device can contain an immobilized fibronectin or oncofetal fibronectin binding partner. Any test device that can be used to produce a signal, or from which a signal can be generated, is intended for use as part of the methods, combinations and kits provided herein (e.g., lateral flow formats and vertical flow formats). A test device can contain a test strip and one or more additional components used for determining the presence of an oncofetal fibronectin indicating molecule.

a. Test strip

A test strip can be used in the test device to indicate the presence of an oncofetal fibronectin indicating molecule in a sample. Any test strip that can provide a detectable signal, for example, visually inspectable or reader-adapted test strip can be used in the methods, combinations and kits provided herein. Such test strip devices and methods for use as are known to those skilled in the art can be used in systems described herein (see, e.g., U.S. Pat. Nos. 6,394,952, 6,267, 722, 5,658,801, 5,656,503, 5,656,502, 5,654,162, 5,622,871, 5,591,645, 5,578,577, 5,500,375, 5,270,166, 5,252,459, 5,209,904, 5,149,622, 5,132,097, 5,120,643, 5,073,484, 4,960,691 and 4,956,302).

A test strip generally can accommodate flow of a liquid sample and contains a region containing a fibronectin or oncofetal fibronectin binding partner and/or a fibronectin or oncofetal fibronectin binding partner conjugate immobilized thereto. A test strip also can contain one or more additional regions such as a region for applying the sample, a region for removing particulate or solid or undissolved matter from the sample, a region for removing background material that can non-specifically bind to a fibronectin or oncofetal fibronectin binding partner, a region containing a non-specific binding compound, a region containing a fibronectin or oncofetal fibronectin binding partner or conjugate thereof that is mobilizable upon contact with the sample, a region containing a binding partner that can specifically bind to a fibronectin or oncofetal fibronectin binding partner or conjugate thereof, and combinations thereof.

A test strip can include a membrane system that defines a liquid flow pathway. Exemplary test strips and systems include the Rapid fFN Cassette and the fFN membrane immunoassay. The test strips can be visually inspected, or used in conjunction with a test strip reader, such as the point of care device described in U.S. Pat. Nos. 6,267,722 and 6,394,952.

When a reader is used, one or more measurements can be made by the reader and the one or more measurements can be subjected to further analysis, such as image reconstruction or otherwise classifying an image. Methods for processing of reflectance data and methods of classifying an image are known in the art, as exemplified in U.S. Pat. No. 6,267,722.

The results of the test strip measurement and/or the results from classifying an image can be used alone, or in conjunction with other information input into a decision support system, such as a neural network that can analyze a variety of data or information to guide further testing or treatment of a subject. Such neural nets generally analyze patient data or information, typically patient history or clinical data (see, e.g., U.S. Pat. Nos. 6,678,669 and 6,267,722).

Lateral flow test immunoassay devices are among those that can be employed in the methods herein. In such devices, a membrane system forms a single fluid flow pathway along the test strip. The membrane system includes components that act as a solid support for immunoreactions. For example, porous or bibulous or absorbent materials can be placed on a strip such that they partially overlap, or a single material can be used, in order to conduct liquid along the strip. The membrane materials can be supported on a backing, such as a plastic backing. In an exemplary embodiment, the test strip includes a glass fiber pad, a nitrocellulose strip and an absorbent cellulose paper strip supported on a plastic backing.

Fibronectin or oncofetal fibronectin binding partners and/or conjugates thereof can be immobilized on the solid support. The binding partners or conjugates can be bound to the test strip by adsorption, ionic binding, van der Waals adsorption, electrostatic binding, or by covalent binding, by using a coupling agent, such as glutaraldehyde. For example, the binding partners or conjugates can be applied to the conjugate pad and nitrocellulose strip using standard dispensing methods, such as a syringe pump, air brush, ceramic piston pump or drop-on-demand dispenser. In one embodiment, a volumetric ceramic piston pump dispenser is used to stripe binding partners that bind to the analyte of interest, including a labeled binding partner conjugate, onto a glass fiber conjugate pad and a nitrocellulose strip.

The test strip can be otherwise treated, for example, with sugar to facilitate mobilization of reagents including a fibronectin or oncofetal fibronectin binding partner or conjugate thereof, or with proteins, such as albumins, including bovine (BSA), immunoproteins, other animal proteins, water-soluble polyamino acids, or casein to block non-specific binding sites on the test strip. In one embodiment, a binding partner that can bind to a labeled fibronectin or oncofetal fibronectin binding partner conjugate is immobilized on the test strip; such a binding partner can bind to a labeled fibronectin or oncofetal fibronectin binding partner conjugate that is not complexed with an oncofetal fibronectin indicating molecule and thereby can be used as a control. For example, where the labeled conjugate includes a mouse monoclonal anti-oncofetal fibronectin antibody, a polyclonal goat anti-mouse IgG antibody can be used to bind the conjugate.

In test strips using a defined liquid sample flow pathway, a test strip can contain two or more separate regions, where the sample contacts a first region prior to contacting a second region. Typically, all regions can accommodate a liquid sample such that at least a portion of the liquid sample can pass through the region and, if applicable, interact with a binding partner immobilized thereto. For example, a test strip can contain a region for applying the sample and a region containing immobilized fibronectin or oncofetal fibronectin binding partner, where the sample contacts the sample application region prior to contacting the binding partner region.

A test strip can contain a region for applying the sample. This region can be referred to as the sample application region. This region is the region first contacted by the sample. This region can be formed from any of a variety of substances to form a solid structure capable of accommodating a liquid sample. This region also can be the site for one or more additional regions such as a filter region, non-specific surface region, or other region described herein.

A test strip can contain a region containing a fibronectin or oncofetal fibronectin binding partner or a conjugate thereof, immobilized onto the test strip. This region can be referred to as a fibronectin or oncofetal fibronectin binding region. Typically, the immobilized binding partner or conjugate will be in a region that can accommodate a liquid sample such that the liquid sample can interact with the immobilized binding partner or conjugate. An immobilized fibronectin or oncofetal fibronectin binding partner can react with the sample to specifically bind a fibronectin or oncofetal fibronectin indicating molecule, respectively. Accordingly, this region of the test strip can be a region where an oncofetal fibronectin indicating molecule in a sample forms a complex with one or more fibronectin and/or oncofetal fibronectin binding partners. Exemplary binding partners include polyclonal anti-fibronectin antibodies, monoclonal anti-oncofetal fibronectin antibodies, heparin, collagen, an integrin, fibrin, or a nucleic acid complementary to an oncofetal fibronectin nucleotide sequence. An additional exemplary binding partner is oncofetal fibronectin protein or an oncofetal fibronectin encoding nucleic acid molecule or fragment thereof, which can bind to an autoantibody to oncofetal fibronectin protein or nucleic acid present in the sample.

A test strip also can contain a filter region. A filter region can be a region in which particulate, solid or undissolved matter present in a sample that are greater than a cutoff size are physically blocked from advancing through the test strip. Exemplary matter that can be filtered include cells, mucus, debris, and insoluble matter. Cutoff sizes can be any of a variety of sizes, according to the selected substances to be removed from the sample. For example, a cutoff filter size can be 10 mm, 5 mm, 1 mm, 500 µm, 200 µm, 100 µm, 50 µm, 20 µm, 10 µm, 5 µm, 2 µm, 1 µm, 0.5 µm, 0.2 µm or 0.1 µm, or about 10 mm, 5 mm, 1 mm, 500 µm, 200 µm, 100 µm, 50 µm, 20 µm, 10 µm, 5 µm, 2 µm, 1 µm, 0.5 µm, 0.2 µm or 0.1 µm. Filter regions can be formed from any of a variety of substances used for filtration of particulate matter, including glass (e.g., glass wool), cellulose, nylon, polyether sulfone, polyvinyl chloride, teflon and any other substance having the selected cutoff size and properties. In one embodiment, the filter substance is a low protein binding substance. The filtering region can be located at the region of sample application to the test strip, or can be located downstream of the sample application region. Typically, the filter region is located upstream of a fibronectin or oncofetal fibronectin binding region.

A test strip also can contain a region containing a non-specific binder. This region can be referred to as a non-specific binding region. Non-specific binder can be present on solid structures, where the non-specific binder binds to at least a portion of background material in a sample while not binding more than a small amount (e.g., less than 10%) of an oncofetal fibronectin indicating molecule in the sample. Possible solid supports for non-specific binders include paper and cellulose derivatives, such as cellulose esters and ethers, natural and synthetic polymeric materials, such as latex, vinyl polymers, polypropylene, polyethylene and partially hydrolyzed derivatives, polycondensates, copolymers and inorganic materials. In one embodiment, a non-specific binder is a porous or bibulous member capable of transporting a liquid sample along a test strip. Non-specific binders that can be used include solid supports having immobilized thereon one or more non-specific binding proteins such as albumin (including bovine serum albumin, or BSA), antibodies not specific for an oncofetal fibronectin indicating molecule and other surfaces known in the art or disclosed herein. Exemplary proteins that can be used for a non-specific binder include BSA, methylated BSA or antibodies such as W632 or mouse IgG. In one example, a non-specific binder can be a nitrocellulose membrane having BSA immobilized thereon. A non-specific binder can be at the same region as a sample application region, or downstream of a sample application region. A non-specific binder can be at the same region as a filter region, if present, or upstream or downstream of a filter region, if present. A non-specific binder is typically upstream of a fibronectin or oncofetal fibronectin binding region.

A test strip also can contain a region having immobilized thereto a binding partner that can bind to a fibronectin or oncofetal fibronectin binding partner. This region can be referred to as a control region. Such a region can act as a positive or negative control, according to the design of the test strip. Typically, the immobilization will be in a region that can accommodate a liquid sample such that the liquid sample can interact with the immobilized binding partner that binds to a fibronectin or oncofetal fibronectin binding partner. An immobilized binding partner of a fibronectin or oncofetal fibronectin binding partner can specifically bind to a fibronectin or oncofetal fibronectin binding partner. In one example, the immobilized binding partner of a fibronectin or oncofetal fibronectin binding partner can bind to a fibronectin or oncofetal fibronectin binding partner to which an oncofetal fibronectin indicating molecule is not bound. Exemplary binding partners include polyclonal anti-mouse IgG antibodies or other antibodies that specifically bind to a protein or nucleic acid or other compound that binds to a fibronectin or oncofetal fibronectin indicating molecule, or a nucleic acid molecule complementary to a nucleic acid molecule encoding a fibronectin or oncofetal fibronectin. A control region is typically downstream from a sample application region. A control region can be at the same region as a filter region, if present, or can be downstream of a filter region, if present. A control region can be upstream or downstream of a fibronectin or oncofetal fibronectin binding region, or upstream and downstream (i.e., two or more control regions can be present) of a fibronectin or oncofetal fibronectin binding region. A control region can be at the same region, upstream or downstream of a non-specific binding region (if present), or combinations thereof.

A test strip also can contain a region containing a mobilizable fibronectin or oncofetal fibronectin binding partner or conjugate thereof. Such a region can be termed a mobilization region. A mobilizable fibronectin or oncofetal fibronectin binding partner can specifically bind to a fibronectin or oncofetal fibronectin indicating molecule. Exemplary fibronectin or oncofetal fibronectin binding partners include polyclonal anti-fibronectin antibodies, monoclonal anti-oncofetal fibronectin antibodies, heparin, collagen, an integrin, fibrin, or a nucleic acid molecule complementary to a fibronectin or oncofetal fibronectin encoding nucleotide sequence. An additional exemplary binding partner is oncofetal fibronectin protein or nucleic acid molecule encoding oncofetal fibronectin or fragment thereof, which can bind to an autoantibody to oncofetal fibronectin protein or nucleic acid present in the sample. A mobilizable binding partner or conjugate can be a compound which, upon contact with a liquid sample, is mobilized such that the mobilizable compound can interact with solutes of the liquid sample and the mobilizable compound can migrate along the test strip as the liquid sample migrates along the test strip. For example, a mobilizable fibronectin or oncofetal fibronectin binding partner or conjugate thereof can be a water soluble compound affixed to the surface of the test strip in a non-aqueous format (e.g., in the absence of any solvent, or in a non-aqueous solvent). Accordingly, a mobilizable compound that is a fibronectin or oncofetal fibronectin binding partner can, upon mobilization, bind or react with an oncofetal fibronectin indicating molecule present in the sample. A mobilizable fibronectin or oncofetal fibronectin binding partner or conjugate thereof can be located in the sample application region or downstream of the sample application region. A mobilizable fibronectin or oncofetal fibronectin binding partner or conjugate thereof can be located at the fibronectin or oncofetal fibronectin binding region or upstream of the fibronectin or oncofetal fibronectin binding region. A mobilizable fibronectin or oncofetal fibronectin binding partner or conjugate thereof can be located upstream, at the same region, or downstream of a filter region (if present), or combinations thereof. A mobilizable fibronectin or oncofetal fibronectin binding partner or conjugate thereof can be located upstream, at the same region, or downstream of a non-specific binding region (if present), or combinations thereof. A mobilizable fibronectin or oncofetal fibronectin binding partner or conjugate thereof is typically located upstream of a control region, if present.

The above description of a test strip is meant to exemplify different possible regions that can be present and arrangements of possible regions; the above description is not meant to limit possible test strip combinations to those described above, since a variety of combinations will be apparent to one skilled in the art according to the selected assay configuration. A test strip can contain various combinations of the regions described herein, including two or more of the same type of regions in different locations along the test strip. A test strip also can contain two or more different compositions in the same region (e.g., a non-specific binding region can be at the same location as the filter region).

b. Test Strip Housing

The test strip optionally can be contained within a housing. Such a housing can serve any of a variety of purposes, including facilitating handling of the test strip or for insertion into a reflectance reader. A variety of test strip housings are known in the art, as exemplified in U.S. Pat. No. 6,267,722.

In an exemplary embodiment, the test strip housing includes a symbology, such as a bar code that can be associated with data related to the assay device, subject data and/or test run. For example, information associated with the device, such as lot number, expiration date, analyte and intensity value, or information related to the test run, such as date, calibration data, reflectance value or other such information, can be encoded and associated, such as in a database with a bar code imprinted on the device. Any bar code system that provides the appropriate line thickness and spacing can be used. Code 39 and Code 128 are among the known bar code systems.

In a particular embodiment, Code 39 is used. The bar code is made up of 11 alphanumerics, including 2 alphabetic and 9 numeric characters. The first and last characters are asterisks (*), as is standard in the Code 39 system. The lot number is stored as 1 alpha and 4 numeric codes so that product complaints or questions can be traced to a particular lot number. In the exemplified embodiment, the first character represents the month of production, the second is a digit representing the year of production and the last three are an index value indicating the lot number. Thus, the lot number "A8001" represents the first device in a lot produced in January, 1998. The next two characters ("01") represent the identity of the analyte as 2 numerics (00-99). This permits the use of up to 100 different analytes with the system. The reflectance intensity value (00-99) is stored as the next two numeric characters ("01"). The intensity value sets the reference threshold for which controls and subject samples can be compared. This eliminates the need to run liquid reference samples on a daily basis. Finally, the cassette expiration date is stored as 1 alpha and 1 numeric code to prevent the use of expired devices. In the example given, an expiration code of "A9" represents an expiration date of January, 1999.

c. Analysis with a Test Device

A volume of sample can be delivered to a test strip using any known device for transporting a sample, for example, a standard plastic pipet. In one embodiment, for example, when the sample is liquid, the neat (e.g., undiluted or without added reagents) sample can be applied to the test strip, which can include direct application to the test strip (e.g., contacting the test strip with a urine stream). In another embodiment, any an oncofetal fibronectin indicating molecule present in the sample can bind to a labeled mobilizable fibronectin or oncofetal fibronectin binding partner conjugate (e.g., labeled anti-oncofetal fibronectin antibody conjugate) and the resulting complex migrates along the test strip. Alternatively, the sample can be pre-mixed with a labeled conjugate prior to applying the mixture to the test strip. When the labeled complex encounters a fibronectin or oncofetal fibronectin binding region of the test strip, an immobilized fibronectin or oncofetal fibronectin binding partner (e.g., anti-fibronectin antibody) therein can bind to the complexed an oncofetal fibronectin indicating molecule to form a sandwich complex, thereby resulting in a region in which the label of the mobilizable fibronectin or oncofetal fibronectin binding partner conjugate accumulates and can be detected.

In one embodiment, prior to contacting the fibronectin or oncofetal fibronectin binding region of a test strip, the sample can be contacted with a non-specific binder such as a non-specific binding compound or a non-specific binding surface. For example, a sample can be added to a test strip that is configured to have the sample flow through a non-specific binding region prior to flowing through a fibronectin or oncofetal fibronectin binding region. By first contacting the non-specific binder such as a non-specific binding compound or non-specific binding surface, background materials in the sample, which might otherwise non-specifically bind to a fibronectin or oncofetal fibronectin binding partner or conjugate thereof, instead bind to the non-specific binding compound or surface such that the background materials are at least partially prohibited from binding to a fibronectin or oncofetal fibronectin binding partner or conjugate thereof.

In another embodiment, prior to contacting a non-specific binder such as a non-specific binding compound or a non-specific binding surface, the sample can be contacted with a mobilizable fibronectin or oncofetal fibronectin binding partner or conjugate thereof. For example, a sample can be added to a test strip that is configured to have the sample flow through a mobilization region containing a fibronectin or oncofetal fibronectin binding partner conjugate prior to flowing through a non-specific binding region. By first contacting the mobilizable fibronectin or oncofetal fibronectin binding partner or conjugate, an oncofetal fibronectin indicating molecule that might otherwise attach to the non-specific binder such as the non-specific binding compound or non-specific binding surface, instead bind to the mobilizable fibronectin or oncofetal fibronectin binding partner or conjugate such that a larger amount of an oncofetal fibronectin indicating molecule can be bound to a binding partner.

In another embodiment, prior to contacting a mobilizable fibronectin or oncofetal fibronectin binding partner or conjugate thereof, the sample can be contacted with a non-specific binder such as a non-specific binding compound or a non-specific binding surface. For example, a sample can be added to a test strip that is configured to have the sample flow through a non-specific binding region prior to flowing through a mobilization region containing a fibronectin or oncofetal fibronectin binding partner conjugate. By first contacting the non-specific binder such as a non-specific binding compound or non-specific binding surface, background materials in the sample, which might otherwise non-specifically bind to a fibronectin or oncofetal fibronectin binding partner or conjugate, instead bind to the non-specific binding compound or surface such that the background materials are at least partially prohibited from binding to a fibronectin or oncofetal fibronectin binding partner or conjugate.

As the sample passes through the fibronectin or oncofetal fibronectin binding region, any unbound binding partner continues to migrate into a control zone where it can be captured by an immobilized binding partner that can bind to the fibronectin or oncofetal fibronectin binding partner. For example, a goat anti-mouse IgG antibody can be located in a control region and can bind to a mouse anti-oncofetal fibronectin antibody conjugate. The complex formed between the immobilized binding partner that binds to an fibronectin or oncofetal fibronectin binding partner and the fibronectin or oncofetal fibronectin binding partner can form a detectable signal in this region, such as a colored stripe, that reflects the aggregation of the labeled conjugate. Presence of a detectable signal in this region can indicate that the assay run has completed and also can serve as a positive control.

The results of the assay can be assessed using a reader and associated software. Use of the point of care device described in U.S. Pat. Nos. 6,267,722 and 6,394,952 provides, at the very least, the same clinically relevant information as an onfFN ELISA (an enzyme linked immunosorbent sandwich assay (ELISA); see, e.g., U.S. Pat. No. 5,281,522), but in significantly less time and at the point of care. This oncofetal fibronectin immunoassay allows the user to test a cervicovaginal swab sample in 20 minutes or about 20 minutes. When comparing the 20 minute rapid onfFN test to the data from the onfFN ELISA, a Kappa coefficient of 0.81 was found with a 95% confidence interval [0.75, 0.88] and an overall concordance of at least 94.9%. These data were obtained using a system including an immunoassay test strip in combination with a reflectance reader and data processing software employing data reduction and curve fitting algorithms or neural networks, as known in the art.

iii. Quantitation

Immobilized fibronectin or oncofetal fibronectin binding partner also can be used in a format amenable to quantitation of the amount of oncofetal fibronectin indicating molecule in a sample. For example, a fibronectin or oncofetal fibronectin binding partner can be immobilized on a solid support that can be used in spectrophotometric measurements.

In one example, the amount of oncofetal fibronectin protein in a sample can be quantitated using an enzyme-linked immunosorbent assay (ELISA). An exemplary ELISA method can be performed by coating one or more wells of a reaction vessel such as a microtiter plate or microtiter strip with a fibronectin or oncofetal fibronectin binding partner, and incubating a sample in such wells. The incubated wells can be washed and then reacted with a mobile or soluble fibronectin or oncofetal fibronectin binding partner or conjugate thereof, and then washed again. The amount of mobile or soluble fibronectin or oncofetal fibronectin binding partner bound to the wells can be indirectly or directly measured spectrophotometrically. Methods for preparing ELISA plates and reagents and performing ELISA are known in the art, and can be used for the oncofetal fibronectin indicating molecule detection methods provided herein.

iv. Affinity-Based Isolation of Oncofetal Fibronectin

A fibronectin or oncofetal fibronectin binding partner can be used to specifically isolate an oncofetal fibronectin indicating molecule. A fibronectin or oncofetal fibronectin binding partner can be used to increase the concentration of an oncofetal fibronectin indicating molecule in a sample. A fibronectin or oncofetal fibronectin binding partner can be used to increase the concentration of an oncofetal fibronectin indicating molecule in a sample relative to the concentration of one or more background components of the sample, thereby increasing the purity of the oncofetal fibronectin indicating molecule in the sample. In accordance with other uses provided herein or otherwise known in the art, a fibronectin or oncofetal fibronectin binding partner can be affixed to a solid support and contacted with a sample. Any oncofetal fibronectin indicating molecule present in the sample can bind to the binding partner and one or more subsequent steps (e.g., washing and elution steps) can be used to separate the oncofetal fibronectin indicating molecule from background material and/or decrease the volume in which the oncofetal fibronectin indicating molecule is present.

A fibronectin or oncofetal fibronectin binding partner can be affixed to any solid support as described herein or known in the art. For example, a fibronectin or oncofetal fibronectin can be affixed to beads such as beads used in liquid chromatography, magnetic beads, or any beads that can be isolated by physical methods (e.g., centrifugation). The solid support can be in any form, including, but not limited to, in the form of a liquid chromatographic column or a slurry of beads.

The solid support can be contacted with a sample under conditions in which the fibronectin or oncofetal fibronectin binding partner can specifically bind to an oncofetal fibronectin indicating molecule. In one embodiment, the solid support is contacted with a sample under conditions in which background materials do not significantly interfere with the binding partners on the solid support binding an oncofetal fibronectin indicating molecule (i.e., 10% or about 10% or less of the binding partners on the solid support bind to background materials or 90% or about 90% or more of oncofetal fibronectin indicating molecule in the sample is bound by binding partners on the solid support). Exemplary conditions include standard phosphate-buffered saline (PBS) conditions (e.g., 137 mM NaCl, 2.7 mM KCl, 10 mM phosphate buffer pH 7.4).

In one embodiment, the solid support is washed with a solution that removes background material from the solid support in preference to removal of an oncofetal fibronectin indicating molecule from the solid support. Such conditions will typically remove 50% or about 50% or more background material while removing 10% or about 10% or less oncofetal fibronectin indicating molecule from the solid support. The conditions can be the same as initial conditions for contacting the sample and solid support, or can be different. Exemplary conditions include increased salt or detergent concentrations, or different pH, relative to the initial conditions for contacting the sample and solid support. Methods for determining conditions are known in the art.

An oncofetal fibronectin indicating molecule can be released from the solid support by any of a variety of methods known in the art. For example, an oncofetal fibronectin indicating molecule can be released from the solid support by a change in pH or ionic strength of the ambient buffer. In another example, an oncofetal fibronectin indicating molecule can be released from the solid support by subjecting the oncofetal fibronectin indicating molecule to denaturing conditions including denaturing, salt, pH, urea, detergent or temperature conditions. An exemplary condition for release of an oncofetal fibronectin indicating molecule from the solid support is 100 mM glycine, pH 2.5-3.0.

After release of the oncofetal fibronectin indicating molecule from the solid support, the solution containing the oncofetal fibronectin indicating molecule can be used directly for detection of the oncofetal fibronectin indicating molecule or can be treated prior to detection methods. Exemplary treatment includes adding a concentration solution of APB in order to achieve a final, diluted concentration of 1×APB or 0.05 M Tris buffer, pH 7.4, 150 mM NaCl, 0.02% $NaN_3$, 1% BSA, 5 mM EDTA, 1 mM phenylmethylsulfonyl fluoride (PMSF), 500 Kallikrein Units/ml of Aprotinin, and 0.1% Triton X-100.

Presence of an oncofetal fibronectin indicating molecule can be detected using any of a variety of methods, such as the methods provided herein or detection methods known in the art. For example, an oncofetal fibronectin indicating molecule can be detected by gel electrophoresis, including SDS-PAGE and a band having a molecular weight corresponding to an oncofetal fibronectin indicating molecule can indicate the presence of an oncofetal fibronectin indicating molecule in the sample. An oncofetal fibronectin indicating molecule also can be detected using any of the methods described herein that use a binding partner conjugate to detect the presence of an oncofetal fibronectin indicating molecule, including, but not limited to, sandwich assays and blot analyses.

d. Detection of Regions of Oncofetal Fibronectin

Binding partners can be used to detect the presence of particular regions in an oncofetal fibronectin indicating molecule. Detection of the presence of particular regions in an oncofetal fibronectin indicating molecule can serve a variety of purposes, including identifying the likely cell or tissue or organ source of the oncofetal fibronectin indicating molecule, identifying the unlikely cell or tissue or organ source of the oncofetal fibronectin indicating molecule, or identifying a health problem associated with a particular form of oncofetal fibronectin. In one example, the antibody L19 can be used to detect the presence of EDB in an oncofetal fibronectin protein. Binding partners that bind oncofetal fibronectin proteins or autoantibodies to oncofetal fibronectin proteins also can be used to detect the presence of one or more post translational modifications in an oncofetal fibronectin protein. For example, the antibody FDC-6 can be used to detect the presence of O-glycosylation at threonine 33 of the IIICS region of oncofetal fibronectin protein. Binding partners also can be used to detect a IIICS splice variant (e.g., V0, V64, V89, V95 or V120 splice variants of IIICS) or to detect the presence of one or more splice regions of IIICS (e.g., aa1-25, aa26-89 or aa90-120 splice regions of IIICS).

Detection of particular oncofetal fibronectin regions, IIICS splice regions and post-translational modifications, can serve to characterize the oncofetal fibronectin indicating molecule in the sample. For example, binding partners can be used to characterize an oncofetal fibronectin indicating molecule present in a sample as containing or lacking the EDA, EDB or IIICS regions. Binding partners can be used to characterize oncofetal fibronectin protein present in a sample as containing or lacking one or more particular post-translational modifications, such as O-glycosylation at threonine 33 of IIICS. Binding partners can be used to characterize an oncofetal fibronectin indicating molecule present in a sample as containing or lacking a particular splice variant of IIICS such as V0, V64, V89, V95 or V120.

In using the binding methods disclosed herein to characterize an oncofetal fibronectin indicating molecule, two or more binding partners can be used in the same or different assays performed on a sample. Each binding partner can provide information regarding the composition of the oncofetal fibronectin indicating molecule in a sample. For example, if an oncofetal fibronectin protein binds FDC-6 and IST-9, but not L19, the oncofetal fibronectin protein can be characterized as containing EDA and IIICS and containing an O-glycosylation at threonine 33 of IIICS, but not containing EDB.

Thus, provided herein are methods for characterizing an oncofetal fibronectin indicating molecule in a sample by identifying one or more binding partners to which the oncofetal fibronectin indicating molecule is bound and by identifying any binding partners which are not bound to the oncofetal fibronectin indicating molecule. The bound and unbound binding partners (e.g., a binding profile) can be indicative of a region of oncofetal fibronectin or indicative of a particular oncofetal fibronectin variant. In one embodiment, such methods can be performed by comparing bound and unbound binding partners in an assay of a sample to bound and unbound binding partners in an assay of a reference (e.g., bound and unbound binding partners contacted with a known oncofetal fibronectin indicating molecule) or by comparing a binding profile to a calculated binding profile.

3. Detection of Oncofetal Fibronectin by Mass Spectrometry

Disclosed herein are methods of detecting an oncofetal fibronectin indicating molecule using mass spectrometric formats. Using mass spectrometry, an atom, molecule or molecule fragment, such as a fragment of oncofetal fibronectin protein or oncofetal fibronectin-encoding nucleic acid or complement thereto, can be detected using mass spectrometry. The presence of that atom, molecule or molecule fragment, can indicate the presence of an oncofetal fibronectin indicating molecule in a sample. Oncofetal fibronectin indicating molecules detected using mass spectrometric methods described herein, include, but are not limited to, an oncofetal fibronectin protein, an autoantibody of oncofetal fibronectin protein or nucleic acid encoding oncofetal fibronectin, mRNA encoding oncofetal fibronectin, amplicates of the aforementioned mRNA, and fragments thereof.

A variety of mass spectrometric techniques can be used to perform the oncofetal fibronectin indicating molecule detection methods provided herein. Mass spectrometric techniques generally include desorption and detection methods. Any known desorption method can be used herein, including, for example, ultraviolet (UV) and infrared (IR) Matrix-Assisted Laser Desorption/Ionization (MALDI; see, e.g., published International PCT Application No. WO 99/57318 and U.S. Pat. No. 5,118,937) and electrospray (ES). Selection of the particular desorption method to be used can be made by one skilled in the art according to the selected mass measurement to be performed. Any known detection method can be used herein, including, for example, time-of-flight (TOF), Fourier transform and magnetic sector/magnetic deflection instruments in single or triple quadrupole mode. Selection of the particular detection method to be used can be made by one skilled in the art according to the selected mass measurement to be performed.

In some embodiments, prior to detection by mass spectrometry by the methods disclosed herein, a sample can be manipulated in one or more steps, which can include, for example, isolation of an oncofetal fibronectin indicating molecule, fragmentation of an oncofetal fibronectin indicating molecule and sample conditioning. For example, a sample containing an oncofetal fibronectin indicating molecule can be first treated in a step of isolating an oncofetal fibronectin indicating molecule, then second treated in a step of contacting the sample with a fragmenting compound and third treated in a step of measuring the fragment masses using mass spectrometry.

In one embodiment, the mass spectrometry is used to measure the molecular weights of a sample treated with a protease, such as trypsin or cathepsin D. Measurement of one or more protease fragments within defined mass ranges can indicate the presence of oncofetal fibronectin protein in a sample.

The mass spectrometric methods provided herein can be used to detect both proteins and nucleic acid molecules that indicate the presence of oncofetal fibronectin in a subject. As is understood by one skilled in the art methods for protein detection by mass spectrometry (and sample treatment methods prior to detection) can differ from nucleic acid molecule detection methods. The methods provided herein can be modified by routine methods to detect the appropriate analyte.

a. Sample Manipulation

Prior to mass measurement using mass spectrometry, a sample can be manipulated and/or treated in one or more steps. Exemplary manipulation steps include, but are not limited to, contacting the sample with an ionic surface, contacting the sample with a hydrophobic surface, contacting a sample with a fibronectin or oncofetal fibronectin binding partner and contacting a sample with a fragmentation compound. Such manipulation also can include conditioning, which includes any procedures that improve resolution of a mass spectrum. Such manipulation steps also can include one or more rinsing steps where oncofetal fibronectin is at least partially separated from background material in the sample.

The sample manipulation steps can occur in any reaction vessel and can be performed immediately before mass measurement, or one or more hours or one or more days before mass measurement or concurrent therewith. In one embodiment, at least one sample manipulation step is performed on a mass spectrometry substrate. In another embodiment, two or more sample manipulation steps are performed on a mass spectrometry substrate.

Such manipulation steps include any of a variety of surface-enhanced laser desorption ionization (SELDI) mass spectrometric methods known in the art. For example, a mass spectrometry substrate can be coated with a substance or compound for sample manipulation, such as a reverse phase substance, ion exchange substance, binding partner, metal affinity substance, or other substances or compounds known in the art. A substrate can contain such a substance or compound at separate discrete locations. A substrate can also have combinations of such substances or compounds at the same location or at separate discrete locations. When a substrate contains two or more discrete locations, sample can be applied to each discrete location, and each discrete location can have added thereto the same solution or different solutions. When a particular substance or compound or combination is present at multiple discrete locations, each location can have added thereto different solutions to result in variation in the compounds adhered to each discrete location; for example, discrete locations can be treated with different solutions to form a gradient ranging from lower specificity to higher specificity. These and other SELDI methods are known in the art, as exemplified in U.S. Pat. Nos. 5,719,060, 5,894,063, 6,124,137 and 6,225,047.

i. Contact with Binding Partner

A sample can be contacted with a binding partner, such as an anti-oncofetal fibronectin antibody, or other moiety that binds to a fibronectin or oncofetal fibronectin indicating molecule with greater affinity than to other components in the sample. A binding partner can be used, as disclosed herein, to specifically and/or preferentially bind to an oncofetal fibronectin indicating molecule. For example, by contacting a sample with a binding partner and subsequently detecting the molecular weights of sample components that bind to the binding partner, an oncofetal fibronectin indicating molecule can be more readily detected among the components in the sample. Such a contacting step can achieve a reduction in the number of different masses measured and can resolve and enrich masses corresponding to an oncofetal fibronectin indicating molecule relative to masses of sample components that do not correspond to the oncofetal fibronectin indicating molecule.

For example, a binding partner immobilized on a solid support can be contacted with a sample under conditions in which an oncofetal fibronectin indicating molecule in the sample can bind to the binding partner. After contacting the sample with the solid support, the solid support can optionally be washed. Sample components bound to the solid support can be measured by mass spectrometry by desorbing the sample components using mass spectrometric desorption methods such as MALDI or ES, or sample components can be removed from the solid support using solvent conditions in which an oncofetal fibronectin indicating molecule no longer binds to the fibronectin or oncofetal fibronectin binding partner. Sample components removed from the solid support by solvent conditions optionally can be subjected to one or more subsequent sample manipulation steps prior to mass measurement of the sample components, including one or more fragmentation steps.

When a sample contains an oncofetal fibronectin indicating molecule, a step of contacting the sample with a fibronectin or oncofetal fibronectin binding partner bound to a solid support can be used to increase the relative concentration of the oncofetal fibronectin indicating molecule in the sample, thus facilitating detection of the oncofetal fibronectin indicating molecule using the mass measurement methods provided herein.

ii. Contact with a Fragmentation Compound

A sample can be contacted with a fragmentation compound. A fragmentation compound can be used to fragment an oncofetal fibronectin indicating molecule at specific sites (i.e., specifically fragment an oncofetal fibronectin indicating molecule), or can be used to fragment an oncofetal fibronectin indicating molecule at random sites (i.e., non-specifically fragment an oncofetal fibronectin indicating molecule), where random fragmentation refers to fragmentation where no particular site is more than two-fold more frequently cleaved than any other site, but random fragmentation does not require pure randomness in fragmentation.

A fragmentation compound can be a protein, peptide, oligonucleotide, or other compound that can be used to fragment proteins or nucleic acid molecules. In one embodiment, a fragmentation compound can be a protease or other compound that can be used to fragment an oncofetal fibronectin protein. Exemplary compounds for fragmenting oncofetal fibronectin protein include cathepsin D, trypsin, thermolysin, 2-nitro-5-thiocyanobenzoic acid (for S-cyanylation), *Achromobacter* protease 1, *S. aureus* V8 protease and hydroxylamine. In another embodiment, a fragmentation compound can be nuclease, ribozyme, DNAzyme, or other compound that can be used to fragment an oncofetal fibronectin encoding nucleic acid molecule or complement thereto. Exemplary compounds for fragmenting nucleic acid molecules include restriction endonucleases, hammerhead ribozymes and RNases.

Fragmentation methods can be performed prior to other steps of sample treatment, such as contacting the sample with a fibronectin or oncofetal fibronectin binding partner (e.g., a solid support to which a fibronectin or oncofetal fibronectin binding partner is immobilized), or conditioning the sample. Fragmentation methods can be performed subsequent to other steps of sample treatment. Fragmentation methods can coincide with other steps of sample treatment; for example, fragmentation methods can be performed while sample components are bound to a solid support.

a. Trypsin Proteolysis

In one embodiment, a sample can be treated with trypsin. When digested with trypsin, a human oncofetal fibronectin protein can yield proteolytic fragments that are 235 kDa, 200 kDa, 160 kDa, 120 kDa, 65 kDa and/or 55 kDa in mass. Typically, each of these six trypsin fragments specifically binds to the antibody FDC-6. Thus, measurement of one or more trypsin fragments that are 235 kDa, 200 kDa, 160 kDa, 120 kDa, 65 kDa or 55 kDa in mass and that can specifically bind to FDC-6 can indicate the presence of oncofetal fibronectin protein in a sample.

In an exemplary trypsin digest, trypsin fragments of a human oncofetal fibronectin protein can be 200 kDa, 120 kDa and/or 55 kDa, where each smaller fragment represents a product of further trypsin cleavage of a larger fragment. In another exemplary trypsin digest, trypsin fragments of oncofetal fibronectin protein can be 235 kDa, 160 kDa and/or 65 kDa, where each smaller fragment represents a product of further trypsin cleavage of a larger fragment.

In an exemplary method of oncofetal fibronectin protein detection, a sample can be contacted with a solid surface to which FDC-6 is immobilized, rinsed and then contacted with a dissociation solution that causes oncofetal fibronectin protein to no longer bind to FDC-6. The dissociation solution eluate can then be contacted by trypsin and the trypsin-treated eluate can be analyzed by MALDI-TOF mass spectrometry. A mass spectrum from such a treated sample having one or more measured masses of 235 kDa, 200 kDa, 160 kDa, 120 kDa, 65 kDa or 55 kDa, or about 235 kDa, 200 kDa, 160 kDa, 120 kDa, 65 kDa or 55 kDa can be identified as a sample containing oncofetal fibronectin protein. In another exemplary method, a sample can be contacted with trypsin and then can be contacted with a solid surface to which FDC-6 is immobilized. The solid surface can then be rinsed and then treated under conditions that cause oncofetal fibronectin protein to no longer bind to FDC-6. A mass spectrum from such a treated sample having one or more measured masses of 235 kDa, 200 kDa, 160 kDa, 120 kDa, 65 kDa or 55 kDa, or about 235 kDa, 200 kDa, 160 kDa, 120 kDa, 65 kDa or 55 kDa can be identified as a sample containing oncofetal fibronectin protein. In another exemplary method, a sample can be contacted with a solid surface to which FDC-6 is immobilized and then the solid surface can be contacted with trypsin. The solid surface can then be rinsed and then treated under conditions that cause oncofetal fibronectin protein to no longer bind to FDC-6. A mass spectrum from such a treated sample having one or more measured masses of 235 kDa, 200 kDa, 160 kDa, 120 kDa, 65 kDa or 55 kDa, or about 235 kDa, 200 kDa, 160 kDa, 120 kDa, 65 kDa or 55 kDa can be identified as a sample containing oncofetal fibronectin protein. In one exemplary case, a mass spectrum that identifies a sample as containing oncofetal fibronectin protein will contain all three 200 kDa, 120 kDa and 55 kDa masses. In another exemplary case, a mass spectrum that identifies a sample as containing oncofetal fibronectin protein will contain all three 235 kDa, 160 kDa and 65 kDa masses.

b. Cathepsin D Proteolysis

In another embodiment, a sample can be treated with cathepsin D. When digested with cathepsin D, oncofetal fibronectin protein can yield fragments that are 110 kDa and/or 85 kDa in mass. Typically these two cathepsin D fragments specifically bind to the antibody FDC-6. Thus, measurement of one or more cathepsin D fragments that are 110 kDa or 85 kDa in mass and that can specifically bind to FDC-6 can indicate the presence of oncofetal fibronectin protein in a sample.

In an exemplary method of oncofetal fibronectin protein detection, a sample can be contacted with a solid surface to which FDC-6 is immobilized, rinsed and then contacted with a dissociation solution that causes oncofetal fibronectin protein to no longer bind to FDC-6. The dissociation solution eluate can then be contacted by cathepsin D and the cathepsin D-treated eluate can be analyzed by MALDI-TOF mass spectrometry. A mass spectrum from such a treated sample having one or more measured masses of 110 kDa or 85 kDa, or about 110 kDa or 85 kDa can be identified as a sample containing oncofetal fibronectin protein. In other examples, the sample can be first contacted with cathepsin D and subsequently contacted with a solid support, or the sample can be contacted with a solid support and contacted with cathepsin D prior to eluting the sample from the solid support.

c. Thermolysin Proteolysis

In another embodiment, a sample can be treated with thermolysin. When digested with thermolysin, oncofetal fibronectin protein can yield fragments that are 120 kDa, 85 kDa and/or 35 kDa in mass. Typically the 120 kDa and 85 kDa can bind to the antibody BC-1. Thus, measurement of one or more thermolysin fragments that are 120 kDa or 85 kDa in mass and that can specifically bind to BC-1 can indicate the presence of oncofetal fibronectin protein in a sample. In an exemplary thermolysin digest, the 35 kDa and 85 kDa fragments represent products of further thermolysin cleavage of a larger fragment.

In an exemplary method of oncofetal fibronectin protein detection, a sample can be contacted with a solid surface to which BC-1 is immobilized, rinsed and then contacted with a dissociation solution that causes oncofetal fibronectin protein to no longer bind to BC-1. The dissociation solution eluate can then be contacted by thermolysin and the thermolysin-treated eluate can be analyzed by MALDI-TOF mass spectrometry. A mass spectrum from such a treated sample having one or more measured masses of 120 kDa, 85 kDa or 35 kDa, or about 120 kDa, 85 kDa or 35 kDa can be identified as a sample containing oncofetal fibronectin protein. In other examples, the sample can be first contacted with thermolysin and subsequently contacted with a solid support, or the sample can be contacted with a solid support and contacted with thermolysin prior to eluting the sample from the solid support. In one exemplary case, a mass spectrum that identifies a sample as containing oncofetal fibronectin protein will contain all three 120 kDa, 85 kDa and 35 kDa masses.

d. *Achromobacter* Protease I Proteolysis

In another embodiment, a sample can be treated with *Achromobacter* protease I. When digested with *Achromobacter* protease I, oncofetal fibronectin protein can yield a fragment that is 14 kDa in mass. Typically, this 14 kDa fragment can bind to the antibody FDC-6. Thus, measurement of a *Achromobacter* protease I fragment that is 14 kDa and that can specifically bind to FDC-6 can indicate the presence of oncofetal fibronectin protein in a sample.

In an exemplary method of oncofetal fibronectin protein detection, a sample can be contacted with a solid surface to which FDC-6 is immobilized, rinsed and then contacted with a dissociation solution that causes oncofetal fibronectin protein to no longer bind to FDC-6. The dissociation solution eluate can then be contacted by *Achromobacter* protease I and the *Achromobacter* protease I-treated eluate can be analyzed by MALDI-TOF mass spectrometry. A mass spectrum from such a treated sample having a measured mass of 14 kDa or about 14 kDa can be identified as a sample containing oncofetal fibronectin protein. In other examples, the sample can be first contacted with *Achromobacter* protease I and subsequently contacted with a solid support, or the sample can be contacted with a solid support and contacted with *Achromobacter* protease I prior to eluting the sample from the solid support.

iii. Solid Support

A fibronectin or oncofetal fibronectin binding partner, a fragmentation compound, or both, can be immobilized on one or more solid supports for use in the methods provided herein. A solid support on which a binding partner or fragmentation compound can be immobilized can be any of a variety of supports to which the binding partner or fragmentation compound can bind to directly or can be bound using a linker. For example, a binding partner or fragmentation compound can be immobilized on a membrane such as a nitrocellulose membrane. A binding partner or fragmentation compound also can be immobilized on a microplate, such as a microplate coated with a compound for binding the binding partner. A binding partner or fragmentation compound also can be immobilized on a probe, pipette tip, or a conical, needle-shaped, or similarly shaped structure.

iv. Conditioning

An oncofetal fibronectin indicating molecule or fragment thereof, or an oncofetal fibronectin indicating molecule or fragment thereof bound to a fibronectin or oncofetal fibronectin binding partner, can be optionally "conditioned". Conditioning is performed prior to mass spectrometric analysis and typically subsequent to or simultaneous with, one or more binding partner contacting or fragmentation steps. Conditioning can be performed, for example, in order to decrease the laser energy required for volatilization and/or to minimize unintended fragmentation. Conditioning can be performed before adding the oncofetal fibronectin indicating molecule, or fragment or complex thereof, to a mass spectrometry substrate. Conditioning can be performed while the oncofetal fibronectin indicating molecule, or fragment or complex thereof is bound or immobilized on the substrate. Conditioning can be performed after the oncofetal fibronectin indicating molecule, or fragment or complex thereof dissociates or is otherwise no longer bound to the substrate. Methods for conditioning are known in the art and include use of cation exchange resins and use of acetonitrile solutions.

v. Combinations of Sample Manipulation Steps

Sample manipulation steps that include different permutations of binding partners and fragmentation compounds can be employed. For example, a sample can be first contacted with an immobilized binding partner and then can be released from the solid support and contacted with an immobilized fragmentation compound. In another example, a sample can be first contacted with mobile or soluble fragmentation compound and then contacted with a solid support containing binding partner immobilized thereto. In another example, a sample can be first contacted with a solid support containing binding partner immobilized thereto and, while the sample is still exposed to the solid support, mobile or soluble fragmentation compound can be added to the sample. In another example, sample can first be contacted with a solid support containing binding partner immobilized thereto and then can be released from the solid support and contacted with a soluble or mobile fragmentation compound. In another example, a sample can be contacted with a solid support containing binding partner and fragmentation compound immobilized thereto. In another example, a sample can be first contacted with an immobilized fragmentation compound and then can be released from the solid support and contacted with an immobilized binding partner. Additional combinations also can be performed, as will be clear to one skilled in the art.

The sample manipulation steps prior to mass measurement can be in any order. For example, a sample can first be contacted with a fragmentation compound and then subsequently contacted with a binding partner. In another example, a sample can be first contacted with a binding partner and then subsequently contacted with a fragmentation compound. In another example, a sample can be contacted with a fragmentation compound while the sample is in contact with a binding partner. The binding partner, the fragmentation compound, or both, can be immobilized on a support. Where the fragmentation compound and binding partner are immobilized, they can be immobilized on the same or different solid supports. A solid support containing immobilized binding partner or immobilized fragmentation compound, or both, can serve as a substrate for mass spectrometric analysis.

In one example, a sample is first contacted by a first solid support to which a fibronectin or oncofetal fibronectin binding partner, such as FDC-6, is immobilized, under conditions in which an oncofetal fibronectin indicating molecule can bind to the fibronectin or oncofetal fibronectin binding partner. Exemplary buffer conditions include 1% bovine serum albumin in phosphate-buffered saline (PBS; typically 10 mM phosphate, pH 7.4 , 150 mM NaCl and 3 mM KCl). The contact between the sample and the first solid support can extend for any duration of time that results in binding of sufficient oncofetal fibronectin indicating molecule for carrying out subsequent steps such that one or more measurable fragments can be measured by mass spectrometry. For example, the first solid support can contact the sample for 10 minutes, 30 minutes, 1 hour, 2 hours, 5 hours, 10 hours, 24 hours, or about 10 minutes, 30 minutes, 1 hour, 2 hours, 5 hours, 10 hours, 24 hours, or more. The first solid support can then be separated from the sample and, in some embodiments, subjected to one or more washing steps. For example, the excess sample can be removed by washing the substrate with PBS and 0.05% Tween-20. The first solid support can then be exposed to an analyte release solution which causes bound sample compounds (including an oncofetal fibronectin indicating molecule, if present) to be released from the binding partner on the first solid support. Buffer conditions for releasing an oncofetal fibronectin indicating molecule from the binding partner generally include low pH solutions, high ionic strength solutions, or solutions containing a compound that displaces oncofetal fibronectin from the oncofetal fibronectin binding partner. Exemplary buffer conditions include buffers with a pH at or below 3.0 or about 3.0, buffers containing NaCl concentrations at or above about 1 M, or, buffers containing chaotropic agents such as 4 M NaSCN or 6 M urea. Released sample compounds (including oncofetal fibronectin, if present) can be, directly (e.g., immediately upon release from the solid support) or indirectly (e.g., after storage in a vessel, buffer exchange, freezing, centrifugation, filtration, etc.), added to a second solid support to which has been immobilized a fragmentation compound, such as trypsin. In one embodiment, the second solid support can serve as the substrate used for desorption of analytes to be measured by mass spectrometry. Released sample compounds (including an oncofetal fibronectin indicating molecule, if present) then are exposed to the fragmentation compound under conditions in which the fragmentation compound can cleave an oncofetal fibronectin indicating molecule in at least one site. The incubation of the released sample compounds (including oncofetal fibronectin, if present) and the second solid support can extend for any duration of time that results in fragmentation sufficient for carrying out subsequent steps such that one or more measurable fragments can be measured by mass spectrometry. For example, the second solid support can contact the released compounds for 10 seconds, 20 seconds, 30 seconds, 45 seconds, 1 minute, 2 minutes, 5 minutes, 10 minutes, 30 minutes, 1 hour, 2 hours, 5 hours, 10 hours, 24 hours, or about 10 seconds, 20 seconds, 30 seconds, 45 seconds, 1 minute, 2 minutes, 5 minutes, 10 minutes, 30 minutes, 1 hour, 2 hours, 5 hours, 10 hours, 24 hours, or more.

After fragmentation, the sample compounds (including oncofetal fibronectin fragments, if present) on the second solid support can be transferred to a substrate for desorption in mass spectrometry, or can be directly desorbed from the second solid support. Mass spectrometric methods can then be used to measure the charge to mass ratio of the sample compounds and/or fragments (including oncofetal fibronectin fragments, if present), to detect the molecular weights of the sample compounds (including oncofetal fibronectin fragments, if present). Sample compound and fragment masses can then be used for further determinations of the presence of oncofetal fibronectin in a sample, as described elsewhere herein.

Exemplary binding partners, fragmentation compounds, solid supports to which binding partners or fragmentation compounds are immobilized, substrates for mass spectrometric analysis and methods including fragmentation, specific binding of analyte and mass spectrometric measurement of fragments and systems for carrying out one or more such steps are disclosed herein and known in the art (see, e.g., U.S. Pat. Nos. 6,498,039, 6,316,266, 6,093,541, 6,004,770, 5,955, 729 and 5,719,060; and in U.S. patent application Nos. 20030027216, 20020164818, 20020110904, 20020094566, 20020042075, 20010021535 and 20010019829). Any of a variety of methods of mass spectrometric analysis and analysis of mass spectrometric results known in the art or described herein can be used in conjunction with the above sample manipulation methods.

b. Substrate for Mass Spectrometry

The substrate for mass spectrometry can be any of a variety of materials. In particular, the substrate can be fabricated from virtually any insoluble or solid material that can be used in a particular mass spectrometry format.

MALDI substrates that can be used in the methods provided herein include those that are commercially available. For example, substrates can be metals such as gold, silicon, silver, copper, aluminum, or steel; non-metals such as glass or quartz; and polymers such as hydrocarbon polymers, polysilanes, PTFE, PTE, PE, PFA, perfluoro alkylates and methacrylates, polyethylene, polypropylene, polyamide, polyurethane, polyvinyldifluoride, polyvinylidenefluoride, polysiloxanes optionally substituted with fluoroalkyl groups, perfluorodecyltrichlorosilanes, octadecyltrichlorosilanes, fluoropolymers, silicones, graphite, graphite filed polymers, or polysilanes. MALDI substrates can have any of a variety of shapes including beads, capillaries, flat surfaces (including flat surfaces containing pits such as an array of pits), microarrays, or pins (such as an array of pins). The substrate can be porous or non-porous, contain pits or wells and can have features (e.g., pits, wells, pins, etc.) organized in an array. MALDI substrates also can be coated with a monolayer, thin film, or thick film, using methods known in the art. A variety of compositions, shapes and coatings of substrates are commercially available and known in the art, as exemplified in U.S. Pat. App. No. 20030138823, U.S. Pat. Nos. 5,808,300, 6265,715, 6,287,872 and 6,465,778.

The substrate can be the solid support to which the binding partner is immobilized, the solid support to which the fragmentation compound is immobilized, or the solid support to which the binding partner and the fragmentation compound are immobilized. The substrate also can have neither the binding partner nor the fragmentation compound immobilized thereto.

In some embodiments, the substrate can contain or have immobilized thereto, one or more energy absorbing compounds, such as matrix compounds, which can promote analyte desorption and ionization. For example, energy-absorbing compounds can be attached to a substrate by covalent attachment or physiadsorption, as is known in the art, and exemplified in U.S. Pat. No. 5,894,063. In another example, the substrate can have attached thereto a substance or compound to which an oncofetal fibronectin indicating molecule binds (including, e.g., a hydrophobic substance, ionic substance, or binding partner), where the substance or compound binds to an oncofetal fibronectin indicating molecule via a photolabile attachment or the substance or compound is energy absorbing and can promote analyte desorption and ionization. Such substrates are known in the art, as exemplified in U.S. Pat. No. 6,124,137.

c. Mass Spectrometric Analysis

Mass spectrometry can be used to detect presence of an oncofetal fibronectin indicating molecule. Mass spectrometric detection can be a direct detection of oncofetal fibronectin protein, a nucleic acid molecule encoding oncofetal fibronectin or complement thereto, an autoantibody for oncofetal fibronectin or a nucleic acid molecule encoding oncofetal fibronectin, or a fragment thereof, or can be a detection of a mass marker or other atom or molecule indicating presence of oncofetal fibronectin protein, nucleic acid molecule encoding oncofetal fibronectin or complement thereto, autoantibody therefor, or a fragment thereof. Mass spectrometry can be used following complex formation between a binding partner and oncofetal fibronectin protein, a nucleic acid molecule encoding oncofetal fibronectin or complement thereto, an autoantibody therefor, or a fragment thereof.

A variety of mass spectrometric detection formats are known to those skilled in the art. These include, for example, MALDI-TOF mass spectrometry, electrospray ionization mass spectrometry, inductively coupled plasma mass spectrometry, fast atom bombardment mass spectrometry, fourier transform mass spectrometry, electron impact mass spectrometry, chemical ionization mass spectrometry, ion cyclotron resonance mass spectrometry and combinations thereof, such methods for ionization and detection are known in the art, as exemplified in U.S. Pat. No. 6,657,191. Any known format can be adapted for detection of an oncofetal fibronectin indicating molecule.

i. Formation of Ions in the Gas Phase

In one step of mass spectrometry, gas phase ions are formed from sample material. Formation of gas phase ions of the sample can be accomplished using any of a variety of techniques. For example, a fragment of an oncofetal fibronectin indicating molecule can be desorbed and ionized using ultraviolet Matrix-Assisted Laser Desorption/Ionization, infrared Matrix-Assisted Laser Desorption/Ionization, electrospray, ion cyclotron resonance and/or inductively coupled plasma. In one example, if the sample material is sufficiently volatile, ions can be formed by electron impact (EI) or chemical ionization (CI) of the gas phase sample molecules. For solid samples, ions can be formed by desorption and ionization of sample molecules by bombardment with high energy photons or particles. Secondary ion mass spectrometry (SIMS), for example, uses keV ions to desorb and ionize sample material. In the SIMS process, a large amount of energy is deposited in the analyte molecules. As a result, fragile molecules will be fragmented. This fragmentation is not typically used when information regarding the original composition of the sample, e.g., the molecular weight of sample molecules, will be lost.

In another example, for more labile or fragile molecules, other ionization methods now exist. The plasma desorption (PD) process results in the desorption of larger, more labile species—e.g., insulin and other protein molecules. Lasers can be used in a similar manner to induce desorption of biological or other labile molecules, as exemplified in Van Breeman et al., *Int. J. Mass Spectrom. Ion Phys.* 49:35-50 (1983); Tabet et al., *Anal. Chem.* 56:1662 (1984); Olthoff et al., *Anal. Instrument.* 16:93 (1987). The plasma or laser desorption and ionization of labile molecules relies on the deposition of little or no energy in the analyte molecules of interest. One use of lasers to desorb and ionize labile molecules intact is termed matrix assisted laser desorption ionization (MALDI) (see, e.g., Tanaka et al., *Rapid Commun. Mass Spectrom.* 2:151 (1988) and Karas et al., *Anal. Chem.* 60:2299 (1988)). In an example of the MALDI process, an analyte is dissolved in a solid, organic matrix. Laser light of a wavelength that is absorbed by the solid matrix but not by the analyte is used to excite the sample. The matrix is excited directly by the laser and the excited matrix sublimes into the gas phase carrying with it the analyte molecules. The analyte molecules then are ionized by proton, electron, or cation transfer from the matrix molecules to the analyte molecules. The MALDI process is typically used in conjunction with time-of-flight mass spectrometry (TOF-MS) and can be used to measure the molecular weights of proteins in excess of 100,000 daltons.

In another example, atmospheric pressure ionization (API) methods also can be used. Typically, analyte ions are produced from liquid solution at atmospheric pressure. One such method, is known as electrospray ionization (ESI) (see, e.g., Dole et al., *J. Chem. Phys.* 49:2240 (1968)). In the electrospray technique, analyte is dissolved in a liquid solution and sprayed from a needle. The spray is induced by the application of a potential difference between the needle and a counter electrode. The spray results in the formation of fine, charged droplets of solution containing analyte molecules. In the gas phase, the solvent evaporates leaving behind charged, gas phase, analyte ions. Very large ions can be formed by this method. Ions as large as 1 MDa have been detected by ESI in conjunction with mass spectrometry (ESMS). A variety of electrospray methods are known in the art, as exemplified by Wilm et al., *Int. J. Mass Spectrom. Ion Processes* 136:167 (1994), which teaches use of a small diameter needle in a method termed nano electrospray MS.

In one embodiment, when an oncofetal fibronectin indicating molecule or a fragment thereof is complexed with a fibronectin or oncofetal fibronectin binding partner that is immobilized on the substrate, the oncofetal fibronectin indicating molecule or fragment thereof is desorbed from the substrate. The desorption method can cause the oncofetal fibronectin indicating molecule or fragment thereof to desorb from the substrate without causing the binding partner to desorb from the substrate. In other embodiments, desorption methods can cause the oncofetal fibronectin indicating molecule or fragment thereof and its binding partner to desorb from the substrate.

For desorption methods such as MALDI, the sample is mixed with, or provided with, a matrix material that absorbs the laser light used in the MALDI method, sufficiently for matrix and sample to desorb from the substrate. Many types of matrix materials are known in the art, including, for example, nicotinic acid, 3'-hydroxypicolinic acid, 2,5-dihydroxybenzoic acid, sinapinic acid, succinic acid, glycerol, urea and Tris-HCl, pH 7.3 or about 7.3. The matrix material can be applied simultaneously with the sample by, for example, mixing the matrix material with the sample. Alternatively, the matrix material can be present on a derivatized substrate prior to application of the sample, or introduced after application of the sample.

The gas phase ions of oncofetal fibronectin proteins, nucleic acids, fragments or complexes, then are detected using mass spectrometry.

ii. Detection

Gas phase ions can be detected by any of a variety of mass analyzers, such as a time-of-flight (TOF) mass analyzer. Mass analysis of gas phase ions can be performed using, for example, a magnetic or electrostatic analyzer, or both. Ions passing through a magnetic or electrostatic field will follow a curved path. In a magnetic field the curvature of the path will be indicative of the momentum-to-charge ratio of the ion. In an electrostatic field, the curvature of the path will be indicative of the energy-to-charge ratio of the ion. If magnetic and electrostatic analyzers are used consecutively, then the momentum-to-charge and energy-to-charge ratios of the ions can be detected and the mass of the ion can thereby be determined.

Another exemplary mass analyzer is a time-of-flight (TOF) mass analyzer. Typical TOF instruments take advantage of pulsed ionization as occurs with methods such as laser desorption methods including MALDI. In TOF methods, the ions are accelerated by a potential of 10-30 kV or about 10-30 kV and then allowed to drift down a field free region 1-2 m or about 1-2 m in length. Due to different velocities resulting from differences in mass, the ions arrive at the detector separated in time, permitting the mass to be determined. Reflector TOF mass analyzers also can be used in mass determination.

In another example, quadrupole mass analyzers can be used. In these mass analyzers, ions are accelerated electrically (5-15V) and passed along a long central axis of four rods arranged symmetrically. By applying combined DC and oscillating RF potentials, the ions drift along irregular flight paths along the rod axis. The DC/RF ratio is held constant and the absolute values of DC and RF are varied. Only ions with a particular m/z value have stable trajectories for a given value of DC and RF. If DC is set to 0, then all ions have stable trajectories. Quadrupole mass analyzers also can be used in conjunction with ion traps.

Ion cyclotron resonance (ICR) mass analyzers also can be used. In ICR mass analyzers, a range of rf components are used to excite a sample. By placing the ion trap within a superconducting magnet, the trapped ions undergo cyclotron gyration and are radially confined. The frequency of the cyclotron radiation is inversely proportional to the m/z ratio for an ion and directly proportional to the magnetic field. If an ion is excited at its natural cyclotron frequency, it moves to a higher energy level. The ion clouds then induce an image current at two or more detection electrodes. The resulting signal when subjected to Fourier transform analysis yields an extremely precise measure of ion cyclotron frequencies and hence m/z values and molecular weights.

iii. Use of Mass Spectrometry for Detecting Oncofetal Fibronectin in a Sample

Mass spectrometric methods can be used to detect the presence of an oncofetal fibronectin indicating molecule in a sample by detecting the molecular weight of a molecule, molecule fragment or atom indicative of the presence of an oncofetal fibronectin indicating molecule in a sample. In one embodiment, the molecule, molecule fragment or atom indicative of the presence of an oncofetal fibronectin indicating molecule in a sample includes an oncofetal fibronectin protein fragment, or a fragment of an oncofetal fibronectin encoding nucleic acid molecule or complement thereto. As described further hereinbelow, mass spectrometry can be used to detect the presence of particular regions in an oncofetal fibronectin indicating molecule. For example, a protein or nucleic acid fragment having a particular detected molecular weight can indicate the presence of EDA, EDB or IIICS in an oncofetal fibronectin protein or nucleic acid as described herein. Mass spectrometry also can be used to detect the presence of one or more post translational modifications in an oncofetal fibronectin protein. Measurement of an oncofetal fibronectin protein or nucleic acid fragment can be used to detect the presence of an oncofetal fibronectin protein or nucleic acid molecule in a sample and also to characterize structural elements present in the oncofetal fibronectin protein or nucleic acid molecule. Further in accordance with this embodiment, the method can include detecting the molecular weights of two or more oncofetal fibronectin protein fragments, or fragments of an oncofetal fibronectin encoding nucleic acid molecule or complement thereto; three or more oncofetal fibronectin protein fragments, or fragments of an oncofetal fibronectin encoding nucleic acid molecule or complement thereto; four or more oncofetal fibronectin protein fragments, or fragments of an oncofetal fibronectin encoding nucleic acid molecule or complement thereto; or more.

Mass spectrometry can be used to detect compounds according to their molecular weights. Detected signals can be used in measuring the molecular weights of compounds, and the measured molecular weights can be compared to one or more expected molecular weights, such as the molecular weight of an oncofetal fibronectin indicating molecule or fragment thereof. Detected mass spectrometric signals also can be compared to one or more references, such as reference mass spectra or reference signals of one or more mass spectra. A reference, such as a reference mass spectra or signal, can be a mass spectrum or signal corresponding to an oncofetal fibronectin indicating molecule or fragment thereof, or corresponding to a reference sample that contained an oncofetal fibronectin indicating molecule or fragment thereof. When detected mass spectrometric signals are compared to one or more references, calculation of the molecular weight of any particular peak is optional. For example, the mass spectrum from a sample can be compared to one or more references, where a detected signal that matches a reference signal can be identified as a detected signal indicative of the presence in the sample of an oncofetal fibronectin indicating molecule or fragment thereof.

In another embodiment, the molecule, molecule fragment or atom indicative of the presence of an oncofetal fibronectin indicating molecule in a sample will be detected by mass spectrometry after a binding event between an oncofetal fibronectin indicating molecule and a fibronectin or oncofetal fibronectin binding partner. A molecule, molecule fragment or atom that signals a binding event between an oncofetal fibronectin indicating molecule and a fibronectin or oncofetal fibronectin binding partner can take any of a variety of forms. For example, a signalling molecule, molecule fragment or atom can be an oncofetal fibronectin protein, nucleic acid, autoantibody, or fragment thereof. In another example, a signalling molecule, molecule fragment or atom can be a fibronectin or oncofetal fibronectin binding partner or fragment thereof. In another example, a signalling molecule, molecule fragment or atom can be a detectable moiety bound to an oncofetal fibronectin protein, nucleic acid, autoantibody, binding partner, or fragment thereof. Such a detectable moiety can be any moiety that can be measured by a mass spectrometric method, typically a moiety having a mass or mass to charge ratio in a mass spectrometer that can be resolved from other detected masses or mass to charge ratios in the mass spectrum. Exemplary moieties include, for example, mass labels, as known in the art and described herein.

In one example of detecting a binding event between an oncofetal fibronectin indicating molecule and a fibronectin or oncofetal fibronectin binding partner, a first oncofetal fibronectin binding partner can be fixed on a solid support and an oncofetal fibronectin indicating molecule-containing sample can be applied to the solid support to form a complex between the oncofetal fibronectin indicating molecule and the first oncofetal fibronectin binding partner. Following complex formation, a second fibronectin or oncofetal fibronectin binding partner can be applied to the solid support to form a complex between the oncofetal fibronectin indicating molecule and the first and second oncofetal fibronectin binding partners (i.e., a sandwich complex). The second fibronectin or oncofetal fibronectin binding partner can contain a detectable moiety, such as a photocleavable mass label. The detectible moiety can be measured directly using mass spectrometry, or the signal of the detectible moiety can be enhanced prior to measurement by increasing the number of detectible moieties present when an oncofetal fibronectin indicating molecule-oncofetal fibronectin binding partner complex forms.

a. Direct Measurement

Presence of an oncofetal fibronectin indicating molecule such as oncofetal fibronectin protein, a nucleic acid encoding oncofetal fibronectin or complement thereto, or an oncofetal fibronectin autoantibody, can be determined by directly detecting the oncofetal fibronectin indicating molecule, or a fragment thereof. For example, an oncofetal fibronectin indicating molecule can be detected using mass spectrometry by selectively binding an oncofetal fibronectin indicating molecule with a fibronectin or oncofetal fibronectin binding partner attached to a solid support, then subjecting the oncofetal fibronectin indicating molecule to conditions under which the oncofetal fibronectin indicating molecule or a fragment thereof no longer binds to the fibronectin or oncofetal fibronectin binding partner and then detecting oncofetal fibronectin indicating molecule or a fragment thereof using mass spectrometry. Conditions under which an oncofetal fibronectin indicating molecule or fragment thereof no longer binds to a binding partner can include, for example, low-binding buffer conditions, where a buffer contains substances such as high salt, low pH, surfactants and denaturants; proteolysis; competitive displacement with a mass-distinguishable analog; or ionization or desorption, optionally coupled with fragmentation.

Presence of an oncofetal fibronectin indicating molecule also can be determined by directly detecting an oncofetal fibronectin indicating molecule in complex with a corresponding binding partner. For example, an oncofetal fibronectin indicating molecule/binding partner complex can be detected using mass spectrometry by selectively binding an oncofetal fibronectin indicating molecule with a fibronectin or oncofetal fibronectin binding partner attached to a solid support, then subjecting the complex to conditions under which the fibronectin or oncofetal fibronectin binding partner or a fragment thereof no longer is attached to solid substrate and then detecting oncofetal fibronectin indicating molecule/binding partner or a fragment thereof complex using mass spectrometry. Conditions under which a fibronectin or oncofetal fibronectin binding partner or fragment thereof no longer is attached to a solid substrate are known in the art and include, for example, ionization, desorption, proteolysis, or cleavage of a linker linking the binding partner to the substrate.

In yet another embodiment, presence of an oncofetal fibronectin indicating molecule or fragment thereof can be detected using a cleavable indicator atom or molecule, such as a cleavable mass label. A variety of cleavable mass labels can be selected and attached to a fibronectin or oncofetal fibronectin binding partner via appropriate cleavable linking chemistries. In accordance with the present method, upon binding or after binding of the binding partner to an oncofetal fibronectin indicating molecule or a fragment thereof, the mass label can be released and detected, to thereby indicate the presence of the oncofetal fibronectin indicating molecule or a particular fragmioent thereof.

A variety of mass labels and cleavable linking chemistries are known in the art, as exemplified in patent application Nos. US200301947171, WO 98/31830, WO 98/26095, WO 97/27327 and U.S. Pat. Nos. 5,770,367, 6,558,902. Such mass labels can be detectable by mass spectrometry. Mass labels can include a vast array of different types of compounds including biopolymers and synthetic polymers. In one example of mass labels, biological monomer units can be used, either singly or in polymeric form, including amino acids, non-natural amino acids, nucleic acids, saccharides, carbohydrates, peptide mimics and nucleic acid mimics. Amino acids include those with simple aliphatic side chains (e.g., glycine, alanine, valine, leucine and isoleucine), amino acids with aromatic side chains (e.g., phenylalanine, tryptophan, tyrosine and histidine), amino acids with oxygen and sulfur containing side chains (e.g., serine, threonine, methionine and cysteine), amino acids with side chains containing carboxylic or amide groups (e.g., aspartic acid, glutamic acid, asparagine and glutamine) and amino acids with side chains containing strongly basic groups (e.g., lysine and arginine) and proline. Derivatives of the above described amino acids are monomer units. An amino acid derivative includes any compound that contains within its structure the basic amino acid core of an amino-substituted carboxylic acid, with representative examples including, but not limited to, azaserine, fluoroalanine, GABA, ornithine, norleucine and cycloserine. Polypeptides derived from the above described amino acids also can be used as monomer units. Representative examples include naturally occurring and synthetic polypeptides with molecular weight above 500 Daltons or about 500 Daltons.

Representative examples of saccharides include ribose, arabinose, xylose, glucose, galactose and other sugar derivatives composed of chains from 2-7 carbons. Representative polysaccharides include combinations of the saccharide units listed above linked via a glycosidic bond. Mass labels also can be composed of nucleobase compounds, which include any moiety having within its structure a purine, a pyrimidine, a nucleic acid, nucleoside, nucleotide or derivative of any of these, such as a protected nucleobase, purine analog, pyrimidine analog, folinic acid analog, methyl phosphonate derivatives, phosphotriester derivatives, borano phosphate derivatives or phosphorothioate derivatives.

Mass labels also can include any organic or inorganic polymer that has a defined mass value, remains water soluble during bioassays and is detectable by mass spectrometry. Representative synthetic monomer units that can be used as mass units in polymeric form include polyethylene glycols, polyvinyl phenols, polymethyl methacrylates, polypropylene glycol, polypyroles and derivatives thereof. The polymers can be composed of a single type of monomer unit or combinations of monomer units to create a mixed polymer. The sequence of the polymeric units within any one mass label is not critical; the total mass is the key feature of the label. For nonvolatile mass labels having mass below 500 Da or about 500 Da, usually significant ionic character is required; representative examples include polyethylene glycol oligomers of quaternary ammonium salts (e.g., R—(O—CH2-CH2)n-N(CH3)3+/Cl—) and polyethylene glycol oligomers of carboxylic acids and salts (e.g., R—(O—CH2-CH2)n-CO2-No+). Examples of involatile mass labels typically include small oligomers of polyethylene glycol and small peptides (natural or modified) less than 500 Da or about 500 Da in molecular weight. In these instances, as for all of the cases considered herein, mass analysis is not by electron attachment. Exemplary mass labels include a variety of nonvolatile and involatile organic compounds which are nonpolymeric. Representative examples of nonvolatile organic compounds include heme groups, dyes, organometallic compounds, steroids, fullerenes, retinoids, carotenoids and polyaromatic hydrocarbons.

A variety of cleavable linkers known in the art can be used to link the mass label to the fibronectin or oncofetal fibronectin binding partner. Different linker chemistries will confer cleavability under different specific physical or chemical conditions. Examples of conditions which serve to cleave various designs of linker include acid, base, oxidation, reduction, fluoride, thiol exchange, photolysis, ionization and enzymatic conditions. Examples of cleavable linkers that satisfy the general criteria for linkers listed above will be well known to those in the art and include, for example, those found in the catalog available from Pierce (Rockford, Ill.). Examples include: ethylene glycobis succinimidylsuccinate) (EGS), an amine reactive cross-linking reagent which is cleavable by hydroxylamine (1 M at 37° C. for 3-6 hours); disuccinimidyl tartarate (DST) and sulfo-DST, which are amine reactive cross-linking reagents, cleavable by 0.015 M sodium periodate; bis[2-(succinimidyloxycarbonyloxy)ethyl]sulfone (BSOCOES) and sulfo-BSOCOES, which are amine reactive cross-linking reagents, cleavable by base (pH 11.6); 1,4-di-[3'-(2'-pyridyldithio(propionamido))butane (DPDPB), a pyridyldithiol crosslinker which is cleavable by thiol exchange or reduction; a silyl linking group that can be cleaved by fluoride or under acidic conditions; and a 3-, 4-, 5-, or 6-substituted-2-nitrobenzyloxy or 2-, 3-,5- or 6-substituted-4-nitrobenzyloxy linking group that can be cleaved by a photon source (photolysis).

b. With Signal Enhancement

Upon formation of a complex between an oncofetal fibronectin indicating molecule and a fibronectin or oncofetal fibronectin binding partner, a second fibronectin or oncofetal fibronectin binding partner can be introduced that has attached thereto an amplifiable signalling nucleic acid or an amplifiable signalling nucleic acid attachment site. Amplifiable signalling nucleic acid attachment sites include a moiety such as biotin or poly-histidine, which can bind with specificity to a compound bound to an amplifiable signalling nucleic acid or to an intermediary binding partner that can bind with specificity to a compound bound to an amplifiable signalling nucleic acid, such as avidin to which a biotin-conjugated amplifiable signalling nucleic acid is bound.

Upon binding of the amplifiable signalling nucleic acid to the complex, the signalling nucleic acid can be amplified using methods known in the art. For example, a signalling nucleic acid can be amplified by transcription, PCR, ligase chain reaction, strand displacement amplification, rolling circle amplification, or other amplification reactions known in the art. In one example, the signalling nucleic acid is amplified using PCR.

In one embodiment, labeled anti-oncofetal fibronectin antibody (e.g., a biotinylated anti-oncofetal fibronectin antibody) is bound to a complex of oncofetal fibronectin protein and a fibronectin or oncofetal fibronectin binding partner, resulting in the formation of a sandwich complex. Streptavidin or avidin can then be added to the complex and can bind specifically to the labeled antibody. Biotinylated signalling nucleic acid, such as biotinylated linear DNA can then be added to the complex and can bind specifically to the streptavidin or avidin. The bound signalling nucleic acid can then be amplified in a multi-cycle (e.g., 30 cycles or about 30 cycles) polymerase chain reaction procedure. Generally, for example, each cycle includes a 1 minute denaturation step at 94° C., a 1 minute annealing step at 58° C. and a 1 minute primer extension step at 72° C., or about a 1 minute denaturation step at about 94° C., about a 1 minute annealing step at about 58° C. and about a 1 minute primer extension step at about 72° C. Amplification factors of about $10^6$ can be obtained.

Following amplification of the signalling nucleic acid, the signalling nucleic acid can be detected using mass spectrometry to indicate the presence of an oncofetal fibronectin indicating molecule in the sample.

iv. Detection of Regions of Oncofetal Fibronectin

Mass spectrometry can be used to detect the presence of particular regions in a fibronectin to thereby identify and/or characterize the oncofetal fibronectins and species thereof. Detection of the presence of particular regions in a fibronectin can serve a variety of purposes, including identifying the likely cell or tissue or organ source of the oncofetal fibronectin, identifying the unlikely cell or tissue or organ source of the oncofetal fibronectin, or identifying a health problem associated with a particular form of oncofetal fibronectin. In one example, a fragment having a particular detected molecular weight can indicate the presence of an oncofetal fibronectin indication molecule, such as, but not limited to, EDA, EDB or IIICS in a oncofetal fibronectin protein or oncofetal fibronectin encoding nucleic acid molecule or complement thereto as described herein. Mass spectrometry also can be used to detect the presence of one or more post translational modifications in an oncofetal fibronectin protein. For example, a fragment having a particular detected molecular weight can indicate the presence of O-glycosylation at threonine 33 of the IIICS region of oncofetal fibronectin protein. Mass spectrometry also can be used to detect the presence of one or more splice regions of IIICS. For example, a fragment having a particular detected molecular weight can indicate the presence of the amino acid (aa) 90-120 splice region of an oncofetal fibronectin indicating molecule.

Detection of particular oncofetal fibronectin regions, IIICS splice regions and post-translational modifications, can serve to characterize an oncofetal fibronectin indicating molecule in the sample. For example, mass spectrometry can be used to characterize an oncofetal fibronectin indicating molecule present in a sample as containing or lacking all or part of the EDA, EDB or IIICS regions. Mass spectrometry can be used to characterize oncofetal fibronectin protein present in a sample as containing or lacking one or more particular post-translational modifications, such as O-glycosylation at threonine 33 of IIICS. Mass spectrometry can be used to characterize the oncofetal fibronectin indicating molecule present in a sample as containing or lacking a particular splice variant of IIICS such as V0, V64, V89, V95 or V120.

In using the mass spectrometry methods disclosed herein to characterize an oncofetal fibronectin indicating molecule, it is not necessary to use all detected molecular weights to characterize the oncofetal fibronectin indicating molecule. It also is not necessary to identify the composition of fragments whose mass is measured in order to characterize the oncofetal fibronectin. For example, measurement of one mass and comparison of that mass to one or more reference masses can indicate the presence of V120 of IIICS containing O-glycosylated threonine 33 in oncofetal fibronectin protein. In another example, measurement of two or more masses and comparison of those masses to two or more reference masses can indicate the presence of V120 of IIICS containing O-glycosylated threonine 33 in oncofetal fibronectin protein. In another example, measurement of two or more masses and comparison of those masses to two or more reference masses can indicate the presence of V120 of IIICS and EDB in an oncofetal fibronectin indicating molecule. Thus, provided herein are methods for characterizing an oncofetal fibronectin indicating molecule in a sample by identifying one or more masses indicative of a region of oncofetal fibronectin. In one embodiment, such methods can be performed by comparing one or more masses of a mass spectrum to masses of a reference mass spectrum (e.g., a mass spectrum collected from a known oncofetal fibronectin indicating molecule) or by comparing one or more masses of a mass spectrum to one or more reference masses (calculated or experimentally determined).

In another embodiment, one or more detected molecular weights can be used to distinguish or characterize different oncofetal fibronectin indicating molecules. For example, two oncofetal fibronectin indicating molecules having different compositions can yield different mass patterns when subjected to identical sample treatment and mass spectrometric methods. Accordingly, mass patterns for different oncofetal fibronectin indicating molecules can differ by one or more detected molecular weights and such different masses can be used to distinguish or characterize the different oncofetal fibronectin indicating molecules. A mass pattern can be indicative of a particular oncofetal fibronectin indicating molecule structure (e.g., an oncofetal fibronectin protein where the presence or absence of EDA, EDB and IIICS (and splice variants of IIICS), as well as the presence or absence of one or more post-translational modifications are known; or an oncofetal fibronectin nucleic acid or complement thereto known to encode or not encode a fibronectin protein containing EDA, EDB and IIICS (and splice variants thereof)) or complement thereto. Thus, provided herein are methods for characterizing an oncofetal fibronectin indicating molecule in a sample by identifying one or more masses indicative of a particular oncofetal fibronectin indicating molecule. In one embodiment, such methods can be performed by comparing one or more masses of a mass spectrum to masses of a reference mass spectrum (e.g., a mass spectrum collected from a known oncofetal fibronectin indicating molecule) or by comparing one or more masses of a mass spectrum to one or more reference masses (calculated or experimentally determined).

v. Quantitation of Oncofetal Fibronectin

Mass spectrometry can be used to determine the relative concentrations of components of a sample. Based on such methods, the amount of an oncofetal fibronectin indicating molecule or the amount of different types of oncofetal fibronectin indicating molecules in a sample, can be quantitated. In one example, a sample from a subject can have added thereto a known amount of a reference molecule, prior to mass spectrometric analysis. Comparison of the peak intensity of the reference molecule to the intensity of a peak representative of an oncofetal fibronectin indicating molecule can yield the ratio of oncofetal fibronectin indicating molecule present in the sample relative to the reference molecule; and knowledge of the amount of reference molecule present in the sample can then yield the concentration of the oncofetal fibronectin indicating molecule present in the sample. In one embodiment, a plurality of samples containing different concentrations of the reference molecule relative to the concentration of analytes in the sample, can be used to establish a standard curve against which the oncofetal fibronectin indicating molecule-associated peaks can be compared for determination of the amount of the oncofetal fibronectin indicating molecule present in the sample. Methods for quantitating analytes in a sample using mass spectrometry are known in the art, as exemplified in U.S. Pub. No. 20030027216.

4. Detecting Nucleic Acid Molecules

Presence of oncofetal fibronectin in a subject can be indicated by detection of an oncofetal fibronectin-encoding nucleic acid in a sample. Oncofetal fibronectin-encoding nucleic acids include a nucleic acid molecule encoding oncofetal fibronectin such as transcribed mRNA encoding oncofetal fibronectin. Encompassed within the scope of an oncofetal fibronectin-encoding nucleic acid are truncations, splice variants and fragments of an oncofetal fibronectin encoding nucleic acid. Full-length, truncations, variants and fragments of oncofetal fibronectin encoding nucleic acids can be detected using the methods provided herein. Typically, detection of an oncofetal fibronectin-encoding nucleic acid includes detection of a portion of a nucleic acid containing a sequence of nucleotides unique to oncofetal fibronectin or complement thereto.

a. Detection Methods

Amplified nucleic acid molecules from RT-PCR can be measured by a variety of methods for detecting nucleic acid molecules in a sample, including those provided herein and those known in the art. For example, nucleic acid molecules can be detected using gel electrophoresis, Southern blot analysis, Northern blot analysis, mass spectrometry, dot blot analysis, microarray or chip hybridization methods and other methods provided herein or known in the art.

Oncofetal fibronectin-encoding nucleic acids or complements thereto can be detected directly or can be detected indirectly, for example, oncofetal fibronectin-associated nucleic acids or complements thereto can be detected indirectly by detecting nucleic acid molecules after nucleic acid amplification. A variety of amplification methods are known in the art and include, but are not limited to, PCR, rolling circle amplification, transcription, reverse transcription and reverse transcription PCR.

In accord with methods provided herein, detection of an amplified nucleic acid molecule corresponding to an oncofetal fibronectin-encoding nucleic acid molecule or complement thereto can indicate the presence of oncofetal fibronectin encoding nucleic acid molecule in a sample. Such an amplified nucleic acid molecule can contain all or a portion of the nucleotide sequence of the oncofetal fibronectin-encoding nucleic acid molecule or a complement thereto. For example, an amplified nucleic acid molecule can contain all or a portion of the nucleotide sequence encoding the EDA, EDB or IIICS regions of fibronectin or complement thereto. In one embodiment, an amplified nucleic acid molecule contains a nucleotide sequence encoding an amino acid region not present in non-oncofetal fibronectin protein, such as EDA, EDB or IIICS or complement thereto. In such an example, primers for nucleotide synthesis reactions can be designed to be complementary to a nucleotide sequence encoding an amino acid region not present in non-oncofetal fibronectin protein or complement thereto. Primers also can be designed to form amplified nucleic acid molecules which contain all or a portion of the EDA, EDB or IIICS encoding regions or complements thereto, if present, in the template nucleic acid molecule. Depending on the primer design, detection of the presence of any amplified nucleic acid, detection of an amplified nucleic acid having an expected size, or detection of an amplified nucleic acid containing an expected nucleotide sequence can indicate the presence of oncofetal fibronectin in a subject. For example, when the primers are complementary to regions that encode fibronectin portions occurring in oncofetal fibronectin and non-oncofetal fibronectin or complements thereto, but flanking a region that encodes a fibronectin portion occurring only in oncofetal fibronectin or complement thereto, the size of the fragment can indicate the presence or absence of oncofetal fibronectin in the sample, where a smaller fragment contains nucleotides encoding non-oncofetal fibronectin and therefore is not indicative of oncofetal fibronectin in a sample and a larger fragment contains nucleotides encoding oncofetal fibronectin and therefore is indicative of oncofetal fibronectin in a sample. In another example, when one or more primers are complementary to regions encoding fibronectin portions that occur only in oncofetal fibronectin or complements thereto, presence of any amplicate can indicate the presence of oncofetal fibronectin in the sample.

b. Detection of RNA

In one embodiment, an oncofetal fibronectin-encoding nucleic acid is amplified using reverse transcription PCR (RT-PCR). Generally, reverse transcription PCR contains two types of reactions that can be performed in a single step or in separate steps. In the first type of reaction, RNA from a sample is reverse transcribed to complementary DNA (cDNA). In the second type of reaction, the cDNA is amplified using traditional PCR methods.

i. Reverse Transcription

Reverse transcription can be performed by contacting an RNA-containing sample with reverse transcriptase and primer, where the primer can be complementary to an oncofetal fibronectin-encoding RNA. Prior to contacting the sample with reverse transcriptase, the sample can be treated to remove DNA from the sample, using, for example, physical, chemical or enzymatic methods known in the art. Reverse transcription methods using a primer complementary to oncofetal fibronectin-encoding RNA can selectively yield oncofetal fibronectin-encoding cDNA.

The process of converting mRNA to cDNA typically uses a type of enzyme termed a reverse transcriptase, or a related enzyme with reverse transcriptase activity. A reverse transcriptase is an RNA-dependent DNA polymerase. All known reverse transcriptases require a primer to synthesize a DNA transcript from an RNA template. The reverse transcriptase can be obtained from eukaryotic cells which are infected with retrovirus, or from a number of plasmids which contain either a portion of, or the entire retrovirus genome. In addition, messenger RNA-like RNA which contains the RT gene can be obtained from retroviruses. Examples of sources for RT include Moloney murine leukemia virus (M-MLV); human T-cell leukemia virus type I (HTLV-I); bovine leukemia virus (BLV); Rous Sarcoma Virus (RSV); human immunodeficiency virus (HIV); yeast, including *Saccharomyces, Neurospora, Drosophila;* primates; and rodents. See, for example, Weiss et al., U.S. Pat. No. 4,663,290 (1987); Gerard, G. R., *DNA* 5(4):271-279 (1986); Kotewicz, M. L., et al., *Gene* 35:249-258 (1985); Tanese, N., et al., *Proc. Natl. Acad. Sci. USA* 82(15):4944-4948 (1985); Roth, M. J., et al., *J. Biol. Chem.* 260:9326-9335 (1985); Michel, F., et al., *Nature* 316: 641-643 (1986); Akins, R. A., et al., *Cell* 47:505-516 (1986), *EMBO J.* 4:1267-1275 (1985); and Fawcett, D. F., *Cell* 47:1007-1015 (1986). M-MLV reverse transcriptase substantially lacking in RNase H activity has also been described. See, e.g., U.S. Pat. No. 5,244,797.

ii. cDNA Amplification

The methods also can use one or more DNA polymerases, including thermostable DNA polymerases, for amplifying the reverse-transcribed DNA. DNA polymerases can be isolated from natural or recombinant sources, by techniques that are well-known in the art (See WO 92/06200, U.S. Pat. Nos. 5,455,170 and 5,466,591), from a variety of thermophilic bacteria that are available commercially (for example, from American Type Culture Collection, Rockville, Md.). A variety of sources of thermostable polymerases or the genes thereof for expression in recombinant systems are available, including the thermophilic bacteria *Thermus aquaticus, Thermus thermophilus, Thermococcus litoralis, Pyrococcus furiosus, Pyrococcus woosii* and other species of the *Pyrococcus* genus, *Bacillus sterothermophilus, Sulfolobus acidocaldarius, Thermoplasma acidophilum, Thermus flavus, Thermus ruber, Thermus brockianus, Thermotoga neapolitana, Thermotoga maritima* and other species of the *Thermotoga* genus and *Methanobacterium thermoautotrophicum* and mutants, variants or derivatives thereof. As an alternative to isolation, thermostable DNA polymerases are available commercially from, for example, Life Technologies, Inc. (Rockville, Md.), New England BioLabs (Beverly, Mass.), Finnzymes Oy (Espoo, Finland), Stratagene (La Jolla, Calif.), Boehringer Mannheim Biochemicals (Indianapolis, Ind.) and Perkin Elmer Cetus (Norwalk, Conn.). Exemplary thermostable DNA polymerases for use in the compositions and methods provided herein include, but are not limited to, Taq, Tne, Tma, Tli/VENT™, DEEPVENT™, Pfu, Pwo, Tfi or Tth DNA polymerases, or mutants or derivatives thereof. Taq DNA polymerase is commercially available, for example from Life Technologies, Inc. (Rockville, Md.), or can be isolated from its natural source, the thermophilic bacterium *Thermus aquaticus*, as described previously (U.S. Pat. Nos. 4,889,818 and 4,965,188). Tne DNA polymerase can be isolated from its natural source, the thermophilic bacterium *Thermotoga neapolitana* (See U.S. Pat. No. 5,939,301) and Tma DNA polymerase from its natural source, the thermophilic bacterium *Thermotoga maritima* (See U.S. Pat. No. 5,374,553). Methods for producing mutants and derivatives of thermophilic DNA polymerases, particularly of Tne and Tma polymerases, are disclosed in U.S. Pat. Nos. 5,948,614 and 6,015,668. Tfi, Tli/VENT™ and DEEPVENT™ are available commercially (e.g., from New England BioLabs; Beverly, Mass.), or can be produced as previously described (Bej, A. K. and Mahbubani, M. H., in: *PCR Technology: Current Innovations*, Griffin, H. G. and Griffin, A. M., eds., CRC Press, pp. 219-237 (1994) for Tli/VENT™; Flaman, J. M., et al., *Nucl. Acids Res.* 22 (15):3259-3260 (1994) for DEEPVENT™). Thermostable DNA polymerases can be added to the present compositions at a final concentration in solution of 0.1-200 units per milliliter, 0.1-50 units per milliliter, 0.1-40 units per milliliter, 0.1-36 units per milliliter, 0.1-34 units per milliliter, 0.1-32 units per milliliter, 0.1-30 units per milliliter, or 0.1-20 units per milliliter and most typically at a concentration of 20 units per milliliter, or about 0.1-200 units per milliliter, about 0.1-50 units per milliliter, about 0.1-40 units per milliliter, about 0.1-36 units per milliliter, about 0.1-34 units per milliliter, about 0.1-32 units per milliliter, about 0.1-30 units per milliliter, or about 0.1-20 units per milliliter and most typically at a concentration of about 20 units per milliliter.

In single-step reaction embodiments, the concentration of DNA polymerases can be determined as a ratio of the concentration of the enzymes having reverse transcriptase activity. Thus, compositions can have a unit ratio of the reverse transcriptase enzymes to the DNA polymerase enzymes ranging from 0.2:2 to 500:2, 0.5:2 to 250:2, or greater than 3:2, or about 0.2:2 to about 500:2, about 0.5:2 to about 250:2, or greater than about 3:2.

iii. Additional Components

The compositions used herein include one or more nucleotides (e.g., deoxynucleoside triphosphates (dNTPs)). The nucleotide components of the present compositions serve as the "building blocks" for newly synthesized nucleic acids, being incorporated therein by the action of the reverse transcriptases or DNA polymerases. Examples of nucleotides for use in the present compositions include dUTP, dATP, dTTP, dCTP, dGTP, dITP, 7-deaza-dGTP, α-thio-dATP, α-thio-dTTP, α-thio-dGTP, α-thio-dCTP or derivatives thereof, all of which are available commercially from sources including Life Technologies, Inc. (Rockville, Md.), New England BioLabs (Beverly, Mass.) and Sigma Chemical Company (Saint Louis, Mo.). The dNTPs can be unlabeled, or they can be detectably labeled by coupling them by methods known in the art, such as, for example, with mass labels detectable by mass spectrometry, spectroscopically detectible labels, magnetic beads, radioisotopes (e.g., $^3$H, $^{14}$C, $^{32}$P or $^{35}$S), vitamins (e.g., biotin), fluorescent moieties (e.g., fluorescein, rhodamine, Texas Red, or phycoerythrin), chemiluminescent labels and dioxigenin. Labeled dNTPs also can be obtained commercially, for example from Life Technologies, Inc. (Rockville, Md.) or Sigma Chemical Company (Saint Louis, Mo.). The dNTPs can be added, for example, to give a working concentration of each dNTP of 10-1000 micromolar, 10-500 micromolar, 10-250 micromolar, 10-100 micromolar, or 100 micromolar, or about 10-1000 micromolar, about 10-500 micromolar, about 10-250 micromolar, about 10-100 micromolar, or about 100 micromolar.

In addition to nucleotides, the compositions include one or more primers which facilitate the synthesis of a first DNA molecule complementary to all or a portion of an RNA template (e.g., a single-stranded cDNA molecule). Primers also can be used to synthesize a DNA molecule complementary to all or a portion of the first DNA molecule, thereby forming a double-stranded cDNA molecule. Additionally, these primers can be used in amplifying nucleic acid molecules in accordance with the methods known in the art or provided herein. Such primers include, but are not limited to, target-specific primers (which are typically gene-specific primers such as oncofetal fibronectin-specific primers), oligo(dT) primers, random primers or arbitrary primers. Methods directed to specific detection of oncofetal fibronectin-encoding mRNA in a sample can use primers that bind specifically to oncofetal fibronectin-encoding mRNA and a reverse transcriptase to thereby selectively reverse transcribe oncofetal fibronectin-encoding mRNA to form oncofetal fibronectin-encoding cDNA.

Compositions for performing RT-PCR also can include one or more RNase inhibitors. Since RNA is the substrate of the reverse transcription reaction, fidelity of the RNA in the sample can be important in detecting RNA encoding oncofetal fibronectin. Any of a variety of known RNase inhibitors can be used in the RT-PCR methods provided herein, including, for example, human placental RNase inhibitor.

iv. Nucleic Acid Synthesis Steps

The reverse transcription reaction is performed by adding to an RNA sample reverse transcriptase, primer and all four deoxynucleoside triphosphates under the appropriate reaction conditions. Typically, the reverse transcription reaction is performed under conditions that prevent or reduce degradation of the mRNA, which could result in incomplete cDNA synthesis. Exemplary reverse transcription reaction conditions include 50 mM Tris-HCl (pH 8.3), 75 mM KCl, 3 mM MgCl$_2$, 10 mM dithiothreitol, 0.5 mM each dATP, dGTP and dTTP, 0.5 mM [$^3$H]dCTP (200 cpm/pmol), 50 µg/ml (dT)$_{12-18}$, 20 µg/ml 2.3 kb RNA and 4,000 units/ml RT and incubated at 37° C.

In one embodiment, DNA is removed from a sample prior to the reverse transcription reaction. DNA can be removed from a sample by any of a variety of methods, including physical, chemical and enzymatic methods. For example, DNA can be removed from a sample using a DNase, such as DNase I. DNA also can be removed by extraction using acid phenol:chloroform followed by precipitation of RNA using, for example, 0.5 M ammonium acetate and ethanol. DNA also can be separated from RNA by precipitation methods; for example, RNA can be precipitated from a sample using 7.5 M LiCl while the DNA remains in the supernatant, which can be discarded.

In another embodiment, DNA is not removed prior to reverse transcription. This embodiment can include a step of separating reverse transcribed DNA from other DNA in a sample prior to PCR or other amplification methods. For example, reverse transcribed DNA can be separated based on sequence composition, including a sequence specific to an oncofetal fibronectin-encoding sequence, or a sequence specific to RNA, such as a polyA sequence. In other embodiments, DNA is not removed prior to amplification, but PCR primers are designed to selectively amplify reversed transcribed DNA. Exemplary selective primers include primers that bind with sequence specificity to an oncofetal fibronectin-encoding sequence and primers that bind with sequence specificity to DNA products of reverse transcription, including DNA containing a poly(dT) sequence.

The RNA-DNA hybrid that results from reverse transcription can be subsequently treated, for example, with alkali or RNase H to selectively hydrolyze the RNA to leave cDNA that can be converted to double-stranded form in a second DNA amplification reaction catalyzed by reverse transcriptase or other DNA polymerase. See Old, R. W., et al., *Principals of Gene Manipulation, second edition, Studies in Microbiology*, Vol. 2, University of California Press, p. 26 (1981).

In the "uncoupled" RT-PCR procedure (e.g., two-step RT-PCR), reverse transcription is performed as an independent step using buffer conditions optimal for reverse transcriptase activity, such as 50 mM Tris-HCl (pH 8.3), 50 mM KCl, 10 mM MgCl$_2$, 15 mM dithiothreitol, 0.1 mg/ml actinomycin D, at 37° C. Following cDNA synthesis, the reaction can be diluted to decrease MgCl$_2$ and deoxyribonucleotide triphosphate (dNTP) concentrations to conditions acceptable for Taq DNA Polymerase activity and PCR can be performed according to standard conditions (see, for example, U.S. Pat. Nos. 4,683,195 and 4,683,202).

In "coupled" RT-PCR methods, a common or compromised buffer is used for reverse transcriptase and Taq DNA Polymerase activities. In one version, the annealing of reverse primer is a separate step preceding the addition of enzymes, which then are added to the single reaction vessel. In another version, the reverse transcriptase activity is a component of the thermostable Tth DNA polymerase. Annealing and cDNA synthesis can be performed in the presence of Mn$^{++}$, then PCR can be performed in the presence of Mg$^{++}$ after the removal of Mn by a chelating agent.

A "continuous" method (e.g., one-step RT-PCR) can be used which integrates annealing, reverse transcription and PCR steps into a single continuous reaction that avoids the opening of the reaction tube for component or enzyme addition. Continuous RT-PCR can be performed as a single enzyme system using the reverse transcriptase activity of thermostable Taq DNA Polymerase and Tth polymerase, or as a two-enzyme system using AMV-RT and Taq DNA Polymerase where the initial temperature is 65° C.

U.S. Pat. Pub. No. 20030113712 describes compositions and methods useful for one-step/one-tube RT-PCR, using M-MLV-RT, or its RNase H-deficient derivatives, in combination with one or more DNA polymerases. The methods can be performed in the presence of sulfur-containing molecules or acetate-containing molecules (or combinations of sulfur-containing molecules and acetate-containing molecules) to relieve the inhibition of PCR when using compositions containing two or more enzymes having reverse transcriptase activity.

In the RT-PCR reaction, the reaction mixtures can be incubated at a temperature sufficient to synthesize a DNA molecule complementary to all or a portion of the RNA template. Such conditions will depend on the enzyme used and can range from 20° C. to 75° C., 35° C. to 60° C., or 45° C. to 55° C., or about 20° C. to about 75° C., about 35° C. to about 60° C., or about 45° C. to about 55° C. After the reverse transcription reaction, the reaction can be incubated at a temperature sufficient to amplify the synthesized DNA molecule. In one embodiment, the amplification is accomplished via one or more polymerase chain reactions (PCRs). Conditions for amplification can include thermocycling, such as alternating heating and cooling of the mixture sufficient to amplify the DNA molecule and which can include alternating from a first temperature range of from 90° C. to 100° C., to a second temperature range of from 45° C. to 75° C., 50° C. to 75° C., 55° C. to 75° C., or 65° C. to 75° C., or from a first temperature range from about 90° C. to about 100° C., to a second temperature range of from about 45° C. to about 75° C., about 50° C. to about 75° C., about 55° C. to about 75° C., or about 65° C. to about 75° C. The thermocycling can be performed any number of times, typically from 5 to 80 times or about 5 to about 80 times, greater than 10 times or about 10 times, or greater than 20 times or about 20 times.

U.S. Pat. Pub. No. 20030157550 provides methods for using oligonucleotide-immobilized microplates to which oligonucleotides are securely immobilized and which can be subjected to thermal cycles of PCR (PCR microplates), capturing of mRNA and reverse transcription-polymerase chain reaction (RT-PCR) can be conducted on the same plates. Using PCR microplates such as those made of polypropylene, polyolefin, or polycarbonate, because of their fluorescent characteristics, immobilized oligonucleotide, hybridized mRNA and synthesized cDNA can be quantitated fluorometrically by using nucleic acid stain or with the aid of a protein by producing fluorescence or chemiluminescence. The PCR microplates also can capture mRNA from crude cell lysates without purification of RNA or mRNA.

Also provided herein are kits for carrying out the reverse transcription PCR methods described herein. Such kits can include a carrier being compartmentalized to receive a close confinement therein, one or more containers, such as vials and tubes, each of the containers including one of the separate elements of the method used to prepare cDNA from RNA. For example, there can be provided a containers containing reverse transcriptase having DNA polymerase activity and substantially no RNase H activity, in solution. Further containers can contain buffers, substrates for DNA synthesis such as the deoxynucleoside triphosphate, oligo(dT) primer and control RNA for use as a standard.

v. Detection

Amplified nucleic acid molecules from RT-PCR can be measured by a variety of methods for detecting nucleic acid molecules in a sample such as mass spectrometry or chip hybridization and any of a variety of detection results can indicate the presence or absence of oncofetal fibronectin encoding nucleic acid molecule in a sample, such as the presence or absence of an amplified nucleic acid molecule, or the size of the detected nucleic acid molecule. Presence of RNA encoding oncofetal fibronectin also can be quantitated using a variety of methods such as relative RT-PCR, competitive RT-PCR, comparative RT-PCR and real time RT-PCR.

a. DNA Detection Methods

Amplified nucleic acid molecules from RT-PCR can be measured by a variety of methods for detecting nucleic acid in a sample, including those provided herein or those known in the art. For example, DNA can be detected using gel electrophoresis, Southern blot analysis, mass spectrometry, dot blot analysis and chip hybridization methods.

In accordance with the methods provided herein, detection of a nucleic acid molecule such as an amplified deoxyribonucleic acid molecule corresponding to an oncofetal fibronectin-encoding nucleic acid molecule or complement thereto can indicate the presence of an oncofetal fibronectin encoding nucleic acid molecule in a sample. Such an amplified nucleic acid molecule can contain all or a portion of the nucleic acid molecule (or complement thereof) encoding the oncofetal fibronectin-encoding nucleic acid molecule. For example, an amplified nucleic acid molecule detected using the methods provided herein can contain all or a portion of the nucleic acid molecule encoding the EDA, EDB or IIICS regions of fibronectin or complement thereto. An amplified nucleic acid molecule also can contain a nucleotide sequence encoding an amino acid region not present in a non-oncofetal fibronectin protein or complement thereto. Primers used for reverse transcription or for amplification for nucleotide synthesis reactions can be designed to be complementary to a nucleic acid molecule encoding an amino acid region not present in non-oncofetal fibronectin protein or complement thereto. Primers also can be designed to form amplified nucleic acid molecules which contain all or a portion of the EDA, EDB or IIICS encoding regions or complement thereto, if present, in the template nucleic acid molecule. According to the primer design, detection of the presence of any amplified nucleic acid, detection of an amplified nucleic acid having a particular size, or detection of an amplified nucleic acid containing a particular nucleotide sequence, can indicate the presence of oncofetal fibronectin in a subject.

b. Quantitation

Presence of RNA encoding oncofetal fibronectin can be quantitated using any of a variety of methods known in the art including relative RT-PCR, competitive RT-PCR, comparative RT-PCR and real time RT-PCR. In relative RT-PCR, amplification of the target nucleic acid molecule (i.e., mRNA encoding oncofetal fibronectin) is compared to amplification of a control sequence, such as the sequence of a housekeeping gene such as β-actin mRNA, GAPDH mRNA, or 18S rRNA. This method is performed for two or more samples in order to normalize the signal between samples, thus permitting quantitative calculation of the amount of the target nucleic acid molecule, such as an oncofetal fibronectin encoding nucleic acid molecule or complement thereto.

Competitive RT-PCR can use reverse transcription of a target nucleic acid molecule, followed by simultaneous PCR amplification of a target nucleic acid molecule and a competitive template for the target nucleic acid molecule, where the competitive template is a designed mutant of the target nucleic acid molecule. Exemplary mutants can arise from point mutations, insertions or deletions. The mutants can be detected as different from the wild type sequences; for example, the mutant can have a deletion and thus provide a shorter nucleic acid molecule than the wild type target nucleic acid molecule. Different amounts of competitive mutant template can be used in several samples in order to construct a standard curve used to quantify the amount of target nucleic acid molecule present. An exemplary competitive method is standardized RT-PCR, which uses standardized, competitor templates to allow for comparison between experiments. U.S. Pat. No. 5,876,978, for example, provides a standardized competitive RT-PCR process including reverse transcription of at least a target nucleic acid molecule and a housekeeping gene, followed by simultaneous PCR amplification of a target nucleic acid molecule, a housekeeping gene and competitive templates for each of these nucleic acids. The method simultaneously uses primers for a target nucleic acid molecule, primers for a housekeeping gene and two internal standard competitive templates that include designed mutants of the target nucleic acid molecule and housekeeping gene. Such methods also can be performed in multiplexed format, as described in WO 03/083051.

Another method for quantitating RT-PCR results is comparative RT-PCR. In this method, reverse transcription on two or more target nucleic acid molecule samples is performed using a unique probe for each sample, where the uniqueness is not in the RNA-recognition portion of the probe, resulting in a unique cDNA for every sample. After reverse transcription, the different target nucleic acid molecule sequences are combined and PCR amplification is performed where the different cDNAs compete with each other (as with competitive RT-PCR, described herein or known in the art). The relative amounts of target nucleic acid molecule in each sample can then be compared by determining the relative amount of each unique cDNA that was amplified.

RT-PCR also can be quantitated after every amplification cycle using "real time" RT-PCR. Real time RT-PCR is based on the ability to detect formation of double-stranded DNA. One exemplary method for real time RT-PCR quantitation includes use of probe nucleotides at least partially complementary to the target nucleic acid molecule and having a fluorescent dye and a quenching dye. The probe nucleotide is designed such that when the probe nucleotide does not interact (e.g., hybridize) with the target nucleic acid molecule, the fluorescent dye is quenched and little or no fluorescent signal arises and when the probe nucleotide does interact with the target nucleic acid molecule, the fluorescent dye is no longer quenched and fluorescent signal arises. As the target nucleic acid molecule is amplified, the probe nucleotide interacts with (e.g., hybridizes to) the target nucleic acid molecule, resulting in a fluorescent signal that increases proportionally to the amount of target nucleic acid molecule present. A variety of probe nucleotides are available, including TaqMan probes, molecular beacons and scorpions, as described, for example, in Bustin, *J. Mol. Endocrinology* 29:23-39 (2002) and Thelwell et al., *Nucleic Acids Res.* 28:3752-61 (2000). Real-time quantitation also can be performed using a dye that emits only upon binding to double-stranded DNA, such as SYBR green (exemplary kit made by Qiagen, Inc. (Valencia, Calif.); see, for example, Mouillesseaux et al., *J. Virol. Methods* 111(2):121-127 (2003)). Additional reagents such as peptide nucleic acids (PNAs) or minor groove binding dyes also can be used (see Bustin, *J. Mol. Endocrinology* 29:23-39 (2002)). Results from real time RT-PCR measurements can be compared to a standardized curve describing signal intensity as a function of nucleic acid concentration, or can be compared to the signal intensity of one or more reference nucleic acids. These methods, such as those using a fluorescent dye/fluorescence quencher probe nucleotides, also can be used in multiplexing reactions.

c. Detection of Regions of Oncofetal Fibronectin

Nucleic acid detection methods can be used to detect the presence of particular regions in oncofetal fibronectin. Detection of the presence of particular regions in oncofetal fibronectin can serve a variety of purposes, including identifying the likely cell or tissue or organ source of the oncofetal fibronectin, identifying the unlikely cell or tissue or organ source of the oncofetal fibronectin, or identifying a health problem associated with a particular form of oncofetal fibronectin. In one example, detection of a particular nucleic acid molecule can indicate the presence of EDA, EDB or IIICS (or a particular splice variant thereof) in an oncofetal fibronectin protein. Nucleic acid detection methods also can be used to detect the presence of one or more splice regions of IIICS. For example, detection of a particular nucleic acid molecule can indicate the presence of the amino acid (aa) 90-120 splice region of oncofetal fibronectin.

Detection of particular oncofetal fibronectin regions and IIICS splice regions can serve to characterize the oncofetal fibronectin in the sample. For example, nucleic acid detection methods can be used to characterize oncofetal fibronectin present in a sample as containing or lacking the EDA, EDB or IIICS regions. Nucleic acid detection methods can be used to characterize oncofetal fibronectin present in a sample as containing or lacking a particular splice variant of IIICS such as V0, V64, V89, V95 or V120.

A variety of methods disclosed herein or known in the art can be used to characterize one or more oncofetal fibronectin nucleic acid molecules or complements thereto present in a sample, including but not limited to gel electrophoresis, mass spectrometry, Southern blot analysis, Northern blot analysis, dot blot analysis, mass spectrometry and chip array hybridization. In one embodiment, an oncofetal fibronectin encoding nucleic acid molecule or complement thereto can be characterized according to the molecular weight of the oncofetal fibronectin nucleic acid molecule or fragment thereof. For example, a nucleic acid molecule encoding oncofetal fibronectin containing EDA, EDB and IIICS V120 or complement thereto can have a greater mass than an oncofetal fibronectin encoding only EDB and IIICS V120 or complement thereto; thus, measurement of mass of the nucleic acid molecules can be used to characterize a sample as containing an oncofetal fibronectin nucleic acid molecule encoding EDA, EDB and IIICS V120 or complement thereto, or encoding EDB and IIICS V120 or complement thereto, or both.

In another embodiment, an oncofetal fibronectin encoding nucleic acid molecule or complement thereto can be characterized by hybridization of a sample nucleic acid molecule to a probe oligonucleotide. For example, a nucleic acid molecule encoding oncofetal fibronectin containing EDA, EDB and IIICS V120 can hybridize to oligonucleotide probes complementary to the EDA, EDB and IIICS V120 splice regions, while a nucleic acid molecule encoding oncofetal fibronectin containing EDB and IIICS V120 can hybridize to oligonucleotide probes complementary to the EDB and IIICS V120 splice regions, but not to an oligonucleotide probe complementary to the EDA splice region.

In using the nucleic acid detection methods disclosed herein to characterize an oncofetal fibronectin encoding nucleic acid molecule, one or more nucleic acid molecules such as probes or primers can be used to characterize the oncofetal fibronectin encoding nucleic acid molecule. For example, two or more nucleic acid molecules complementary to different oncofetal fibronectin regions or complements thereto can be used to distinguish or characterize an oncofetal fibronectin encoding nucleic acid molecule or complement thereto. Thus, provided herein are methods for characterizing oncofetal encoding fibronectin or complement thereto in a sample by identifying one or more nucleic acids indicative of a region of oncofetal fibronectin or indicative of a particular oncofetal fibronectin variant. Depending on the oncofetal fibronectin-encoding nucleic acid molecules or complements thereto present in the sample, some, but not all probe or primer nucleic acid molecules can be detected and/or amplified in characterizing the oncofetal fibronectin encoding nucleic acid molecule or complement thereto. For example, when a sample contains an oncofetal fibronectin-encoding nucleic acid molecule containing a nucleotide sequence that encodes EDA but not EDB, probes or primers complementary to both and to an EDA-encoding nucleic acid molecule and an EDB-encoding nucleic acid molecule can be added to the sample, but only the probes or primers complementary to the EDA-encoding nucleic acid molecule will be amplified and/or detected. It is possible, but not necessary, to identify the nucleic acid molecules or nucleotide compositions of the oncofetal fibronectin-encoding nucleic acid molecules or complements thereto of a sample in order to characterize the oncofetal fibronectin encoding nucleic acid molecule or complement thereto. For example, two oncofetal fibronectin-encoding molecules or complements thereto having different nucleotide compositions (e.g., one encodes EDA and EDB while another encodes EDB but not EDA) can yield different bands on a gel or blot when subjected to identical sample treatment and nucleic acid detection methods, thus permitting characterization of one or both oncofetal fibronectin-encoding molecules or complements thereto without determining the nucleotide sequence or composition of the molecules. In one embodiment, such methods can be performed by comparing measurement of one or more nucleic acid molecules of a sample to measurement of nucleic acid molecules of a reference (e.g., a known oncofetal fibronectin molecule) or by comparing one or more nucleic acid molecules to one or more reference nucleic acid molecules (calculated or experimentally determined).

A variety of methods for using oligonucleotides to detect regions of oncofetal fibronectin in a sample are known in the art, including methods for using oligonucleotides to detect regions of oncofetal fibronectin or complements thereto in a tumorous tissue sample. For example, oligonucleotides can be used to detect the presence of mRNA encoding EDA, EDB and V0, V64 and V89 of IIICS in thyroid papillary carcinomas (Takano et al., *J. Endocrinol. Invest.* 22:18-22 (1999). In another example, oligonucleotides can be used to detect the presence of EDA and EDB in hepatocellular carcinoma (Oyama et al., *Cancer Res.* 53:2005-2011 (1993)).

5. Detection of Autoantibodies to Oncofetal Fibronectin

Detection of autoantibodies reactive against oncofetal fibronectin or a nucleic acid molecule encoding oncofetal fibronectin or a fragment thereof can indicate the presence of oncofetal fibronectin in a subject. Detection of autoantibodies reactive against oncofetal fibronectin or a nucleic acid molecule encoding oncofetal fibronectin or a fragment thereof also can indicate a variety of health conditions and/or health problems including overall health, cancer, or pregnancy-related conditions. Additionally, the monitoring of autoantibody levels can be used to stage the progression of the disease, to determine a disease or disorder outcome, to determine the likelihood of success of a particular treatment of the disease or disorder and/or to determine a treatment regimen. The detection of autoantibodies in a sample such as a serum sample from a subject can be accomplished by any of a number of methods. Any of a variety of methods known for detecting antibodies, including those provided herein, can be used to detect autoantibodies to oncofetal fibronectin or a nucleic acid molecule encoding oncofetal fibronectin. Such methods include immunoassays which include, but are not limited to, assay systems using techniques such as Western blots, radioimmunoassays, ELISA (enzyme linked immunosorbent assay), "sandwich" immunoassays, dipstick immunoassays, lateral flow immunoassays, vertical flow immunoassays, immunoprecipitation assays, precipitin reactions, gel diffusion precipitin reactions, immunodiffusion assays, agglutination assays, complement fixation assays, immunoradiometric assays, fluorescent immunoassays, protein A immunoassays, flow cytometry assays and agglutination assays such as latex bead agglutination assays. Methods and compositions for detecting autoantibodies in a sample are known in the art, as exemplified in U.S. Pat. No. 6,788,128, U.S. Pub. Nos. 20030232399 and 20040048320 and WO 03/020115.

An exemplary immunoassay is carried out by contacting a sample such as a serum sample of a subject with oncofetal fibronectin protein or a fragment thereof under conditions in which a specific antigen-antibody binding complex can form and detecting or measuring the amount of any complex. The presence of any anti-oncofetal fibronectin autoantibodies can indicate the presence of oncofetal fibronectin in a subject, or the presence of an oncofetal fibronectin associated disease or disorder in the subject. In another example, the levels of autoantibodies in a sample can be compared to the levels present in an analogous sample from a subject not having the disease or disorder, or to the levels present in a population of subjects not having the disease or disorder. The presence of anti-oncofetal fibronectin autoantibody levels higher than levels in subjects not having the disease or disorder can indicate an oncofetal fibronectin positive result and can indicate the presence of an oncofetal fibronectin associated disease or disorder in the subject.

In another exemplary immunoassay a sample is contacted with an anti-(human antibody) antibody, such as an anti-human IgG antibody, or a fragment thereof under conditions in which a specific antigen-antibody binding complex can form and detecting or measuring the amount of any complex. The presence of any anti-oncofetal fibronectin autoantibodies can indicate the presence of oncofetal fibronectin or the presence of an oncofetal fibronectin associated disease or disorder in the subject. In another example, the levels of autoantibodies in a sample can be compared to the levels present in an analogous sample from a subject not having the disease or disorder, or to the levels present in a population of subjects not having the disease or disorder. The presence of anti-oncofetal fibronectin autoantibody levels higher than levels in subjects not having the disease or disorder can indicate an oncofetal fibronectin positive result and can indicate the presence of an oncofetal fibronectin associated disease or disorder in the subject.

The immunoassays can be performed in a variety of ways. For example, oncofetal fibronectin protein or oncofetal fibronectin encoding nucleic acid molecule, or a fragment thereof, can be immobilized onto a solid support and anti-oncofetal fibronectin antibodies specifically bound thereto can be detected. Oncofetal fibronectin proteins or oncofetal fibronectin encoding nucleic acid molecules used in the assays provided herein can be prepared via recombinant DNA techniques well known in the art. For example, a DNA molecule encoding oncofetal fibronectin or an antigenic fragment thereof can be genetically engineered into an appropriate expression vector for large scale preparation of oncofetal fibronectin protein or nucleic acid. Fusion proteins can be expressed that facilitate labeling, immobilization or detection of oncofetal fibronectin protein. See, for example, the techniques described in Sambrook et al., 1989, Molecular Cloning: A laboratory Manual, Cold Spring Harbor Press, Cold Spring Harbor, N.Y. Alternatively, oncofetal fibronectin protein or nucleic acid can be purified from natural sources, e.g., purified from cells, using purification and separation techniques known in the art. Such purification techniques can include, but are not limited to, molecular sieve chromatography and/or ion exchange chromatography. In one embodiment, microtiter plates can be used as the solid support for oncofetal fibronectin protein or nucleic acid. The surfaces can be prepared in advance and stored. Anti-oncofetal fibronectin antibodies bound to the solid support can be detected by, for example, contacting the solid support with a detectable antibody such as an anti-(human antibody) antibody, such as an anti-human IgE antibody, where the detectable antibody can be linked to a detectable or bindable moiety or can be detected by a specifically binding partner containing a detectable or bindable moiety, such as an anti-human IgE-horseradish peroxidase conjugate.

In another example, an anti-(human antibody) antibody, such as an anti-human IgE antibody or an anti-human IgG antibody, or a fragment thereof, can be immobilized onto a solid support and anti-oncofetal fibronectin antibodies specifically bound thereto can be detected. Anti-(human antibody) antibodies used in the assays provided herein can be prepared via a variety of methods provided herein or otherwise known in the art. In one example, microtiter plates can be used as the solid support for anti-(human antibody) antibodies. The surfaces can be prepared in advance and stored. Anti-oncofetal fibronectin antibodies bound to the solid support can be detected by, for example, contacting the solid support with a binding partner such as oncofetal fibronectin protein or nucleic acid or a fragment thereof, where the binding partner can be linked to a detectable or bindable moiety or can be specifically bound by a compound containing a detectable or bindable moiety, such as an anti-human fibronectin-horseradish peroxidase conjugate.

In another example, anti-oncofetal fibronectin autoantibodies can be detected by contacting a sample with oncofetal fibronectin protein or nucleic acid or a fragment thereof and separating sample components bound to oncofetal fibronectin protein or nucleic acid or fragment thereof from the remainder of the sample components. Such separation methods can be accomplished in any of a variety of ways known in the art, such as, but not limited to, by contacting a sample with oncofetal fibronectin protein or nucleic acid or fragment thereof immobilized to a solid support and then separating the solid support from the sample (e.g., using a washing buffer), or by contacting a sample with oncofetal fibronectin protein or nucleic acid or fragment thereof conjugated to a bindable moiety such as a magnetic bead or biotin and separating the conjugate from the sample (e.g., using a magnet or solid support containing streptavidin to remove the conjugate from the sample). After separating bound sample components from the remainder of the sample, sample components or fragments thereof, can be dissociated from oncofetal fibronectin protein or nucleic acid or fragment thereof and the molecular weights of bound sample components or fragments thereof can be detected. One or more masses indicative of an antibody can indicate the presence of anti-oncofetal fibronectin autoantibodies in the sample. Optionally, prior to measuring masses of sample components, sample components bound to oncofetal fibronectin protein or nucleic acid or fragment thereof can be released from oncofetal fibronectin protein or nucleic acid or fragment thereof and contacted with an anti-(human antibody) antibody under conditions in which human antibodies will specifically bind to the anti-(human antibody) antibody. Sample components or fragments thereof bound to the anti-(human antibody) antibody can be separated from the remainder of the sample components and after such separation, masses of the bound sample components, or fragments thereof, can be measured. As one skilled in the art will recognize, when two binding and separating events are performed prior to mass measurement, the sequential order of the autoantibody binding partner is readily interchangeable (e.g., sample can be bound first to anti-(human antibody) antibody and second to oncofetal fibronectin protein or nucleic acid, or vice versa).

Mass measurement of sample components or fragments thereof can be performed by, for example, mass spectrometry. When mass spectrometry is used to detect the molecular weights of sample components or fragments thereof, antibodies or fragments thereof can be identified by detected molecular weights. Proteolysis of antibodies can yield antibody fragments with known masses. Thus, proteolysis of sample components while bound to an autoantibody binding partner or after release from an autoantibody binding partner, can result in fragments having a mass indicative of an antibody fragment. Mass spectrometry can accurately measure masses to determine whether or not a fragment is present that has a mass indicative of an antibody fragment. Detection of a proteolysis fragment having a mass indicative of an antibody fragment can identify the sample as containing anti-oncofetal fibronectin autoantibodies and can thereby indicate the presence of oncofetal fibronectin in the subject.

Also provided herein are methods for determining the amino acid sequence of one or more autoantibodies that bind to oncofetal fibronectin protein or nucleic acid. Antibodies and antibody fragments measured by mass spectrometry can be further examined to determine all or a portion of the amino acid sequence of the antibody or antibody fragment. A variety of methods of using mass spectrometry to determine the amino acid sequence of proteins or protein fragments are known in the art, including, for example, tandem mass spectrometry measurement methods and computational methods such as SEQUEST® (Thermo Electron Corp., Woburn Mass.). Examples of the variety of known mass spectrometry sequencing methods are provided in U.S. Pat. Nos. 5,538,897, 6,017,693, 6,489,121, 6,670,194 and 6,716,636 and U.S. Pub. No. 20030104483. In an exemplary method, the amino acid sequence of one or more autoantibodies that bind to oncofetal fibronectin protein or nucleic acid can be determined by contacting a sample with an anti-oncofetal fibronectin autoantibody binding partner, separating sample components not bound to the binding partner, optionally releasing bound components and contacting released components with a second anti-oncofetal fibronectin autoantibody binding partner, optionally fragmenting bound components and detecting the molecular weight of bound components or fragments thereof by mass spectrometry, whereby the amino acid sequence of the components or fragments thereof is determined.

Also provided herein are methods for detecting anti-oncofetal fibronectin autoantibodies in conjunction with detection of one or more additional anti-tumor marker autoantibodies. Such detection methods can be carried out according to the same principles as described herein for detection of anti-oncofetal fibronectin autoantibodies, where the additional tumor marker(s) or fragment thereof can be used as an autoantibody binding partner. For example, a sample can be contacted with an anti-(human antibody) antibody immobilized to a solid support and the solid support also can be contacted with oncofetal fibronectin protein or nucleic acid or fragment thereof and one or more additional tumor markers or fragment thereof, where oncofetal fibronectin protein or nucleic acid and each tumor marker can be conjugated to a distinguishably detectable or bindable moiety (e.g., fluorophores of different emission wavelength, or one conjugated to biotin and another conjugated to a magnetic bead), whereby distinguishable signals or separate binding events can independently identify the presence of autoantibodies to oncofetal fibronectin protein or nucleic acid and/or one or more additional tumor markers in the sample. In another example, a sample can be contacted with oncofetal fibronectin protein or nucleic acid or fragment thereof and one or more additional tumor markers immobilized to a solid support, where oncofetal fibronectin protein or nucleic acid and each tumor marker can be immobilized to different regions of the solid support and the solid support also can be contacted with an anti-(human antibody) antibody optionally conjugated to a detectable or bindable moiety, where presence of autoantibody in one or more regions can independently identify the presence of autoantibodies to oncofetal fibronectin protein or nucleic acid and/or one or more additional tumor markers in the sample. Methods and apparatuses for performing such procedures can be performed using, for example microarray chips, whose general use is known in the art.

A variety of additional tumor markers, for which autoantibodies can be detected, are known in the art, including, but not limited to, p53, c-erbB2, c-myc, MUC1, BRCA1, BRCA2, Her-2/neu, bcl-2, bax, PSA, CYFRA 21-1, PTH-RP, CA125, CEA gene family members, pro-gastrin, gastrin G17, gastrin G34, CA 19-9, CA 15-3, CA 27-29, CA 72-4, APC, SCC, HPV subtypes, TK, alphaFP, p62, Kallikrein, ras, vasopressin, gastrin releasing peptide, annexin I, annexin II, Hu and KOC (see, e.g., U.S. Pub. No. 200030232399).

6. Measurement of Other Analytes

In addition to oncofetal fibronectin, analytes can include, but are not limited to: hormones, such as steroidal hormones, including estriol; proteins or peptides, such as human immunodeficiency virus (HIV) antigens, antigens indicative of infectious organisms, such as *Salmonella, E. coli*, yeast or parasitic infections, apolipoprotein(a) and lipoprotein(a), environmental antigens, human chorionic gonadotropin (hCG), E-3-G, interleukins and other cytokines and immunomodulatory proteins, such as IL-6 and interferon, small nuclear ribonuclear particles (snRNP) antigens, insulin-like growth factor binding protein one (IGFBP-1), a marker of hypochlorous acid such as 3-chlorotyrosine, tumor markers, or other indicators of cancer or pregnancy related conditions; nucleic acids encoding one of the above proteins or peptides or complements thereto, methylated nucleic acids, or other nucleic acids associated with cancer or pregnancy related conditions; creatinine, sample specific gravity or other analytes that can be used to normalize oncofetal fibronectin indicating molecule measurements.

a. Normalization

A neat sample can contain any of a wide range of solute concentrations and also can have added thereto one or more reagents including a dilution buffer. Because of the possible variability of solute concentrations in a sample, it may be ambiguous whether or not the amount of oncofetal fibronectin indicating molecule present in the sample indicates an amount above a threshold level. If necessary, in order to determine whether the amount of oncofetal fibronectin indicating molecule is at or above a threshold level, the concentration of solutes in a sample can be normalized. For example, the concentration of components in a urine sample can vary depending on a variety of factors including time between urinating, food and liquid intake by the subject and kidney function of the subject. In such instances, analyte concentrations can be normalized by, for example, comparing the analyte concentration to the concentration of a constantly produced urine component to yield a normalized analyte concentration that is less affected by, or independent of factors that cause solute concentrations to vary.

In one embodiment, one or more components or other characteristics of a sample can be measured in order to normalize the measured amount of the oncofetal fibronectin indicating molecule to the sample. Measured properties and/or components include pH, specific gravity, ionic strength, concentration of a compound produced at a constant rate and concentration of an administered compound that enters into the sample at a constant rate. In the case of urine, components of urine produced by the subject at a constant rate include creatinine, IgA, IgG, albumin, urea, cystatin-C, DTPA (diethylenetriaminepentaacetic acid), EDTA (ethylenediaminetetraacetic acid), iodinated aromatics, metal complexes and organic dyes (see, e.g., Achilefu et al., *Topics in Current Chemistry*, 222:31-72 (2002)). Methods for normalizing urine components using these and other compounds are known in the art, as exemplified in U.S. Pat. No. 6,436,721 for normalizing with creatinine or inulin and in U.S. Pat. No. 6,368,873 for normalizing with IgA, albumin or IgG. Devices for measuring compounds for normalization as well as analytes are known in the art, as exemplified in U.S. Pat. Nos. 5,804,452, 6,368,873 and 6,436,721.

In one example, the concentration of an oncofetal fibronectin indicating molecule in a urine sample can be normalized by comparing the measured concentration of oncofetal fibronectin indicating molecule in the urine sample to the measured concentration of creatinine in the urine sample. In determining the concentration of an oncofetal fibronectin indicating molecule in a sample, the concentration of oncofetal fibronectin indicating molecule and creatinine in the sample can be measured. The concentration of oncofetal fibronectin indicating molecule can be normalized by determining the ratio of the concentration of the oncofetal fibronectin indicating molecule to the concentration of creatinine in the urine sample. This normalized oncofetal fibronectin indicating molecule concentration can be used to more accurately determine the typical concentration of oncofetal fibronectin indicating molecule in the urine of the subject from whom the sample was collected and/or can be compared to a reference ratio that can be used to identify a subject as positive or negative for oncofetal fibronectin. The normalized oncofetal fibronectin indicating molecule concentration also can be used to more accurately determine a threshold above which a subject has a higher likelihood of disease or delivery. This normalized oncofetal fibronectin indicating molecule concentration also increases the ease of manipulating the urine sample (e.g., concentrating and/or diluting) without changing the experimental results.

b. Combination with Other Markers

In one embodiment, detection of an oncofetal fibronectin indicating molecule can be combined with detection of one or more additional markers to determine increased or decreased likelihood of delivery by a pregnant woman, date of delivery of a pregnant woman, efficacy of induction procedures, presence or absence of a neoplastic disease, efficacy of treatment of a neoplastic disease, or tendency of a subject toward neoplastic disease. For example, an oncofetal fibronectin indicating molecule can be detected in combination with salivary estriol, whereby detection of the oncofetal fibronectin indicating molecule and salivary estriol can indicate increased likelihood of delivery by a pregnant woman, date of delivery of a pregnant woman, or efficacy of induction procedures.

In another example, detection of an oncofetal fibronectin indicating molecule can be combined with detection of one or more additional tumor markers to determine presence of neoplastic cells. For example, an oncofetal fibronectin indicating molecule can be detected in combination with interleukin-6 (IL-6), interleukin-2 (IL-2), interleukin-12 (IL-12) and/or N-acetylgalactosaminyltransferase-T3 (GalNAc-T3). When an oncofetal fibronectin indicating molecule is detected in combination with IL-6, for example, detection of the oncofetal fibronectin indicating molecule and IL-6 can indicate the presence of neoplastic cells, such as neoplastic breast cells, neoplastic bladder cells, neoplastic cervical cells or neoplastic ovarian cells. In another example, tumor markers, such as particular expressed genes, antigens or proteins, or variants thereof, that are indicative of a tumor or neoplastic condition, can be detected in conjunction with the oncofetal fibronectin indicating molecule detection methods provided herein, to indicate the presence or absence of tumorous or neoplastic cells in a subject. For example, oncofetal fibronectin indicating molecule detection can be combined with Her/Neu detection methods in breast cancer diagnostic methods.

i. Indicators of Membrane Rupture

In one embodiment, measurement of an oncofetal fibronectin indicating molecule can be accompanied by measurement of an indicator of membrane rupture. Typically, when the oncofetal fibronectin assay is positive, an assay of an indicator of membrane rupture such as insulin-like growth factor binding protein one (IGFBP-1) or a marker of hypochlorous acid such as 3-chlorotyrosine, can be performed on a sample from the subject to determine whether the membranes are intact. The cervicovaginal sample can be the same or different from the sample used to assay for the oncofetal fibronectin indicating molecule. Methods for performing the IGFBP-1 assay are known in the art, as exemplified in international publication No. WO 94/17405; methods for detecting the presence of hypochlorous acid are known in the art, for example, by detecting 3-chlorotyrosine using one of a variety of methods known in the art and exemplified in WO 04/003555. If the membrane rupture indicator assay is negative, the membranes have not ruptured and the subject can be administered a tocolytic agent, as described herein. If, however, the membrane rupture indicator assay is positive, indicating that the membranes have ruptured, the test indicates that delivery cannot be delayed and the tocolytic agent typically is not administered.

a. Insulin-Like Growth Factor Binding Protein

IGFBP-1 is assayed by any quantitative or semi-quantitative procedure that can either determine the amount of IGFBP-1 in the sample or that the amount of IGFBP-1 is at or above a threshold level that indicates rupture of membranes.

Anti-IGFBP-1 antibodies can be produced by a number of methods. Polyclonal antibodies can be induced by administering an immunogenic composition containing human IGFBP-1 to a host animal. Alternatively, amniotic fluid or another source of high levels of IGFBP-1 can be used as the immunogen and antibodies of the selected specificity can be identified.

Preparation of immunogenic compositions of IGFBP-1 can vary depending on the host animal and is well known. For example, IGFBP-1 or an antigenic portion thereof can be conjugated to an immunogenic substance such as KLH or BSA, or provided in an adjuvant or the like. The induced antibodies can be tested to determine whether the composition is IGFBP-1-specific. If a polyclonal antibody composition does not provide sufficient specificity, the antibodies can be purified to enhance specificity by a variety of conventional methods. For example, the composition can be purified to reduce binding to other substances by contacting the composition with IGFBP-1 affixed to a solid substrate. Those antibodies which bind to the substrate are retained. Purification techniques using antigens affixed to a variety of solid substrates such as affinity chromatography materials including Sephadex, Sepharose are well known.

Monoclonal IGFBP-1-specific antibodies also can be prepared by conventional methods. A mouse can be injected with an immunogenic composition containing IGFBP-1 and spleen cells obtained. Those spleen cells can be fused with a fusion partner to prepare hybridomas. Antibodies secreted by the hybridomas can be screened to select a hybridoma where the antibodies react with IGFBP-1 and exhibit substantially no reaction with the other proteins which can be present in a sample. Hybridomas that produce antibodies of selected specificity can be cultured by standard techniques. Hybridoma preparation techniques and culture methods are known in the art.

The assay conditions and reagents can be any of a variety methods and conditions known in the art or disclosed herein. The assay can be heterogeneous or homogeneous, conveniently a sandwich assay. The assay usually employs solid phase-affixed anti-IGFBP-1 antibodies. The antibodies can be polyclonal or monoclonal or antibody fragments or other binding moieties. The solid phase-affixed antibodies are combined with the sample. Binding between the antibodies and sample can be determined in a number of ways. Complex formation can be determined by use of soluble antibodies specific for IGFBP-1. The antibodies can be labeled directly or can be detected using labeled second antibodies specific for the species of the soluble antibodies. Various labels include radionuclides, enzymes, fluorescent compounds, colloidal metals or the like. Conveniently, the assay will be a quantitative enzyme-linked immunosorbent assay (ELISA) in which antibodies specific for IGFBP-1 are used as the solid phase-affixed and enzyme-labeled, soluble antibodies. Alternatively, the assay can be based on competitive inhibition, where IGFBP-1 in the sample competes with a known amount of IGFBP-1 for a predetermined amount of anti-IGFBP-1 antibody. For example, any IGFBP-1 present in the sample can compete with a known amount of the labeled IGFBP-1 or IGFBP-1 analogue for antibody binding sites. The amount of labeled IGFBP-1 affixed to the solid phase or remaining in solution can be determined.

Appropriate dilution of the conjugate can be performed to detect the selected threshold level of IGFBP-1 which is above background values for the assay as a positive sample.

The assay results can be interpreted as follows. IGFBP-1 levels below 20-50 ng/mL can be considered background and are negative. The cutoff of choice for the background level depends upon whether a high sensitivity or high specificity test is to be selected. For example, 24 cervicovaginal secretion specimens that exhibited a positive oncofetal fibronectin test results (>50 ng/mL for buffer-treated swab samples) for impending delivery, and exhibited negative ferning, pooling and nitrazine test results for rupture of membranes were tested for IGFBP-1. One of these specimens demonstrated 42 ng/mL IGFBP-1, and the remainder exhibited less than 20 ng/mL IGFBP-1. If a cut-off of 20 ng/mL were to be used, the demonstrated specificity of the test to rule out rupture would be 97%. On the other hand, if 50 ng/mL were to be used, the rule out specificity of the test would be 100%. In most cases, high rule-out specificity can be used, since subjects with ruptured membranes are in greater danger of infection than those who do not have rupture, so a cutoff can range between 20-50 ng/ml or about 20-50 ng/mL.

Other assays using different reagents can have different cutoff values. For example, IGFBP-1 antibodies which differ in their antigen binding characteristics can produce assay results with different optimal cutoff values. One of skill in the art understands that background values can vary when different reagents are used and will understand how to determine the proper background level for the selected specificity and sensitivity for a selected assay. In addition, different optimal cutoffs can be used for different applications. For example, when using oncofetal fibronectin as a predictor of delivery date, a cutoff for a buffer-treated swab sample of 50 ng/ml or about 50 ng/mL oncofetal fibronectin protein can be used.

The presence of IGFBP-1 in a cervicovaginal secretion sample from a subject who is positive for a marker that indicates increased risk of delivery indicates that the membranes have ruptured. If IGFBP-1 is less than 20-50 ng/mL or undetectable (background for the assay), the membranes remain intact. When IGFBP-1 is positive (>20-50 ng/mL) and the delivery marker (e.g., oncofetal fibronectin) is negative, then amniotic membranes can have ruptured, although most subjects who have ruptured membranes will exhibit positive IGFBP-1 and the delivery marker simultaneously. When IGFBP-1 is negative, the IGFBP-1 test can be repeated, typically daily, until the sample is positive for IGFBP-1.

b. Hypochlorous Acid

Presence of hypochlorous acid can be assayed by any of a variety of known methods, as known in the art, as exemplified in Winterbourn et al., *Free Radic. Biol. Med.* 29:403-409 (2000) and Chapman et al., Arch. Biochem. Biophys. 377:95-100 (2000). A typical method for determining the presence of hypochlorous acid is performed by detecting 3-chlorotyrosine and/or other chlorotyrosines in a sample. Methods for detecting 3-chlorotyrosine and other chlorotyrosines including dichlorotyrosine, are known in the art, as exemplified in WO 04/003555 to Woods et al., Kettle, A J, *Methods Enzymol.* 300:111-120 (1999) and Hazen et al., *J. Clin. Invest.* 99:2075-2081 (1997). Typical methods for detecting chlorotyrosines such as 3-chlorotyrosine include gas chromatography/mass spectrometry methods (see, e.g., Hazen et al., *J. Clin. Invest.* 99:2075-2081 (1997)) and binding partner-based methods such as immunoassays including ELISA (see, e.g., WO 04/003555 to Woods et al.).

In one embodiment, the presence of any indicator of hypochlorous acid can indicate membrane rupture. In other embodiments, the presence of an amount of indicator of hypochlorous acid at or above a threshold level can indicate membrane rupture. Typically, the amount of indicator of hypochlorous acid that can indicate membrane rupture is an amount greater than the average amount, such as mean or median amount, present in pregnant women without membrane rupture. The degree to which a sample can reflect membrane rupture can be determined according to the number of standard deviations above the mean amount present in pregnant women without membrane rupture, according to the diagnosis goal. For example, one standard deviation can be used for an assay that can include false positives which can be selected for further evaluation, or for subjects known to have normal or low estriol values and relatively little variation between samples, or for high risk individuals. Two standard deviations above the mean or three standard deviations above the mean, are typically used.

Anti-chlorotyrosine antibodies can be produced by a number of methods known in the art. Exemplary methods and antigens for raising such antibodies are demonstrated in WO 04/003555. For example, polyclonal antibodies can be induced by administering to a host animal an immunogenic composition containing, for example, 3-(3-chloro-4-hydroxy-benzyl)-6-mercaptomethylpiperazine-2,5-dione linked to a carrier protein, N-acetyl-3-chlorotyrosine linked to a carrier protein, or N-acetyl-3,5-chlorotyrosine linked to a carrier protein.

Preparation of immunogenic compositions can vary depending on the host animal and is well known. For example, a chlorotyrosine-containing compound can be conjugated to an immunogenic substance such as KLH or BSA, or provided in an adjuvant. The induced antibodies can be tested to determine whether the composition is chlorotyrosine-specific. If a polyclonal antibody composition does not provide sufficient specificity, the antibodies can be purified to enhance specificity by a variety of conventional methods. For example, the composition can be purified to reduce binding to other substances by contacting the composition with chlorotyrosine affixed to a solid substrate. Those antibodies which bind to the substrate are retained. Purification techniques using antigens affixed to a variety of solid substrates such as affinity chromatography materials including Sephadex, and Sepharose are well known.

Monoclonal chlorotyrosine-specific antibodies also can be prepared by conventional methods. A mouse can be injected with an immunogenic composition containing chlorotyrosine and spleen cells obtained. Those spleen cells can be fused with a fusion partner to prepare hybridomas. Antibodies secreted by the hybridomas can be screened to select a hybridoma where the antibodies react with chlorotyrosine and exhibit substantially no reaction with the other proteins which can be present in a sample. Hybridomas that produce antibodies of selected specificity can be cultured by standard techniques. Hybridoma preparation techniques and culture methods are known in the art.

The assay conditions and reagents can be any of a variety methods and conditions known in the art or disclosed herein. The assay can be heterogeneous or homogeneous, conveniently a sandwich assay. The assay can employ solid phase-affixed anti-chlorotyrosine antibodies. The antibodies can be polyclonal or monoclonal or antibody fragments or other binding moieties. The solid phase-affixed antibodies are combined with the sample. Binding between the antibodies and sample can be determined in a number of ways. Complex formation can be determined by use of soluble antibodies specific for chlorotyrosine. The antibodies can be labeled directly or can be detected using labeled second antibodies specific for the species of the soluble antibodies. Various labels include radionuclides, enzymes, fluorescers, colloidal metals or the like. Conveniently, the assay will be a quantitative enzyme-linked immunosorbent assay (ELISA) in which antibodies specific for chlorotyrosine are used as the solid phase-affixed and enzyme-labeled, soluble antibodies. Alternatively, the assay can be based on competitive inhibition, where chlorotyrosine in the sample competes with a known amount of chlorotyrosine or compounds containing chlorotyrosine for a predetermined amount of anti-chlorotyrosine antibody and competition can be measured by methods known in the art.

Gas chromatography/Mass spectrometry methods for detecting chlorotyrosine can be performed as known in the art and exemplified in Hazen et al., *J. Clin. Invest.* 99:2075-2081 (1997). Briefly, a sample can be treated in one or more separation steps, including liquid chromatography or gas chromatography steps. The chromatographed sample can then be ionized, by, for example, chemical ionization and the mass and/or mass to charge ratio of the ions measured by mass spectrometry.

ii. Estriol

In addition to, or as an alternative to, the IGFBP-1 assay, the concentration of estriol can be determined in a sample obtained from the subject. There are no limitations on the type of assay used to measure estriol. Any assay for estriol can be employed.

A variety of examples of estriol assays are known in the art, as exemplified in U.S. Pat. No. 5,480,776, issued Jan. 2, 1996. Briefly, the assay can be performed on any sample of body fluid, such as blood (or a blood fraction, especially serum or plasma), urine, cervical or vaginal secretions, sweat, saliva or other fluid. Estriol is sufficiently soluble in water so that it is distributed in fluids throughout the body. For simplicity of sampling and because, unlike in urine, detection is not complicated by the presence of estrogen conjugates, saliva can be used.

Assays are generally directed to detection of free estriol, since conjugated estriol has reduced biological activity. In saliva about 92% of estriol is in the free form, while most estriol in urine is present as a conjugate. As will be clear to those familiar with steroid metabolism, an estriol conjugate is a compound formed by formation of a covalent linkage of a non-steroidal compound to estriol. Linkage is typically through a hydroxyl group of the steroidal ring system. The non-steroidal component can be inorganic (e.g., a sulfate group) or organic (e.g., a glucuronide group).

There are no limitations on the collection and handling of samples as long as consistency is maintained. With some body fluids, such as saliva and plasma, there is little diurnal variation in estriol levels. For other fluids, notably urine, variations occur. In one embodiment variations are eliminated to the extent possible, for example by taking samples at the same time of day. Other techniques can be used to ensure consistency of measurement of analytes in clinical fluids. For example, creatinine can be measured concurrently with estriol in urine to normalize the concentration of estriol. Creatinine is produced at a constant rate in the kidneys and measurement of creatinine concentration allows correction of volume errors in urine samples, as is well known in the art.

Optionally and depending on the source of the fluid being tested, free estriol can be separated from estriol conjugates. Techniques for such separations are known in the art. See, for example, Evan, N. Z. *Med. Lab. Tech.* 33:86 (1979), which describes such separations as well as two radioimmunoassays useful for measuring plasma estriol. These separations are generally difficult and assays that do not require separation, either because of the use of specific antibodies or other binding partners that differentiate between free and conjugated estriol, or because the sample is obtained from a source containing mostly free estriol, such as saliva, can be used.

The concentration of estriol in the fluid assayed is correlated with a standard value to determine when labor is imminent. The standard is usually (1) a predetermined range of estriol concentrations for the same body fluid in normal pregnant humans in the general population, either at the corresponding time in the pregnancy or a specific time relative to normal termination of pregnancy, or (2) a previously measured estriol concentration of the same body fluid of the same pregnant human. A measured higher concentration of estriol relative to the standard value is an indication of potential onset of pre-term labor. The methods herein do not require the measurement of any other substance, such as the progesterone concentration in the body fluid, or require the measurement of total estriol production for a time interval. Optionally, measurements of total estriol for a given time period, such as 24 hours, can be used with urine.

The first general standard set out above, namely a predetermined range of estriol concentrations for the same body fluid in normal pregnant humans in general, is typically obtained by the same assay technique that will be used in the application of the method to an individual being tested, in order to ensure the highest correlation. Sufficient measurements are made in a normal population of pregnant women to produce a statistically significant range of normal values for the value to which a comparison will be made, which typically is at preselected time intervals during normal pregnancy. While comparison to a time immediately prior to normal delivery (38 to 40 weeks) is often used, other time periods can be used. For example, estriol levels during a given week of a individual pregnancy (i.e., that of the subject) can be compared to the normal range of concentrations for the same time period (e.g., the 20th week). Generally, the minimum concentration indicative of possible onset of labor is considered to be at least 1, generally at least 2, typically at least 3 or at least 4, standard deviations above the mean estriol concentration determined just prior to the onset of labor for normal pregnant humans for any given body fluid.

It will be recognized by those familiar with statistics that the number of standard deviations used as an indication of pregnancy complications will be selected with an appropriate diagnosis goal in mind. For example, one standard deviation would encompass 68% or about 68% of normal samples; that is, 32% of normal samples would be expected to fall outside the lower and upper limits set by one standard deviation from the mean (16% would thus be expected to be above the selection limit). Thus, one standard deviation above the normal mean is not used for routine analysis, as it would include too many false positives. One standard deviation is appropriate for an assay that is selected to sweep in for further evaluation all possible candidates who might be predisposed toward pre-term labor, or this limit can be selected for subjects known to have normal or low estriol values and relatively little variation between samples. One standard deviation also can be selected for a subject known to have problems with pre-term labor in order to determine when to more closely monitor the subject under controlled conditions (such as by having a subject admitted to a hospital for constant monitoring). Two standard deviations from the mean would encompass 95% or about 95% of normal samples; three standard deviations, 99% or about 99%; four standard deviations, more than 99%. These levels are more appropriate generally, especially for subjects whose levels of estriol are known to be normal or slightly above normal or to vary from sample to sample as well as for assays with a high coefficient of variation.

It is not necessary to express the lower limit of the indication of labor (upper limit of the normal range) in standard deviations. Any other system that can be used to provide a statistically significant indication of probable onset of labor can be used. For example, the limit can be set to be a concentration that is at least as high as the $95^{th}$ percentile concentration for normal subjects for the same body fluid for a normal pregnancy. In any case, a normal limit from the 38-42 week period, typically 40 weeks or about 40 weeks, can be selected for normal pregnancies. Monitoring the concentration can be initiated at a selected time, such as 20, 21, 22, 23, 24, 25, 26, 27, 28, 29 or 30 weeks or earlier, and continued until delivery.

Because of the many different possible clinical goals, the actual estriol level indicative of probable onset of pre-term labor is best selected by the attending physician after collecting data from several samples during the initial portion of the pregnancy and taking into consideration the time at which the measurement is being made. For example, in a normal pregnancy at week 30, the change expected in the estriol concentration prior to the onset of labor is smaller than 2 standard deviations from the mean concentration of estriol at 30 weeks. Thus, while assays in the first portion of a pregnancy (prior to 30 weeks) can use 3 or 4 standard deviations as an indication of onset of labor, two, one and a half, or even one standard deviation would be more appropriate in the later portion of a pregnancy (e.g., after 30 weeks) depending on the condition of the subject, other clinical indications in the mother known to the attending physician and the health of the fetus. It is the earlier stages of a pregnancy that require greater attention to avoiding pre-term labor, because of the lack of fetal development at these stages and the higher risk of infant death post partum. Pre-term labor is generally considered to be any labor prior to the end of a normal 40-week term of pregnancy.

The methods herein can be used for pregnancies during weeks 20 to 36, when prolonging pregnancy for even a short time is most efficacious in reducing the effects of premature birth. The assay, particularly when used to a detect rate of increase, can be employed in pregnancies terminated by labor and delivery after the end of 40 weeks and measurements can be made during this time period. When employed at weeks 38 and higher, the methods provided herein typically are practiced using the "self-comparison" method discussed elsewhere herein; i.e., by comparing the measurement at a given time with a measurement made earlier with the same subject.

In a similar manner, subject to the same constraints discussed above, an assay concentration of at least 1, generally at least 2, typically at least 3 or at least 4, standard deviations above the mean normal concentration for the same stage of pregnancy also can be used as an indication of an abnormal pregnancy and thus as an indication of possible onset of labor, although the probability is lower if the measured amount does not reach the levels considered normal for weeks 38-42.

Standard values will vary with the specific body fluid whose concentration is being measured and with the specific assay being used (although to a lesser extent). Typical minimum indicative levels of labor onset in an assay that measures unconjugated estriol are as follows for the indicated body fluids (all concentrations are in nM): saliva, at least 3, typically at least 5 or at least 6 or at least 7; serum, 30, at least 35 or at least 45.

As an alternative to comparing estriol concentrations to those present in a normal population, a previously measured estriol concentration of the same body fluid of the same pregnant human can be used as a standard for comparison. In this case, what is being determined is usually the rate of increase in estriol concentration in the fluid being tested. A positive assay (i.e., indication of imminent onset of labor) is considered to be present when the measured concentration exceeds a previously measured estriol concentration made in the same body fluid in the same pregnant human female by 50%, generally 75%, typically 100%, within one week. Again the selection of a particular rate of increase to label as the lower limit of labor onset can be selected by the attending physician for the particular reason selected. For example a screening test that is intended to collect potential problem subjects into the hospital for further observation and study could select the 50% increase as its limit in order to avoid false negative results, while accepting the problems caused by including a relatively large number of false positives. Higher percentage increases as the minimum positive indication are more acceptable for home assays and point of care assays, in the same manner as described above for standard deviations from the normal population mean. Increases in estriol concentration that meet the standards of this paragraph and additionally reach levels previously indicated to be indicative of the onset of labor in normal populations of subjects are particularly likely to indicate imminent onset of labor.

Many assays can be used. For example, in U.S. Pat. No. 5,480,776, an enzyme-label component (here a labeled estriol molecule or derivative thereof) is used in a competitive binding assay for estriol. The assay is a non-instrumented enzyme immunoassay that provides present/not-present or "threshold" (±) analysis results at a preselected cut-off value and thus can be used herein.

In a typical assay using this technique, the enzyme-labeled, competitive binding component contains estriol (or the portion thereof used to generate the antibody used in the assay) bound to the immunogen that is used to produce the antibody of the assay. An enzyme label is bound to this moiety, such as through a bulky linker such as an avidin-biotin complex. The use of such a competitive binding partner allows antibodies to be used without attempting to manipulate affinity of binding of antibody to competitor while still providing the steep competitive binding curve required for a ± analysis.

In a typical such assay, antibody is attached to a solid surface, such as a microtiter plate well, a test tube, or a porous reagent strip (such as cellulose or glass fibers). The antibody-coated solid surface then is contacted simultaneously with a sample and with a competitive binding partner. By providing fewer antibody binding sites than are present in the combined total of analyte and competitive binding partner, only a fraction of the molecules in solution will bind to the solid surface. If there are no analyte molecules present, all of the binding sites will be taken up by the competitive binding partners so that a maximum amount of enzyme is attached to the solid surface. When a substrate for the enzyme is contacted with the solid surface after the sample is washed away, reaction of the enzyme with the substrate provides a detectable signal (usually formation of a color) that indicates to the user the absence of analyte in the sample (a negative result). If analyte is present in the sample, analyte competes for binding sites so that less of the enzyme-label competitor can bind. By using a bulky binding composition, which binds less rapidly to the antibody than does the analyte and by properly selecting the number of binding sites relative to the amount of sample added (which is a standard technique to one of skill in the art), analyte present at a concentration above a preselected minimum level will exclude binding of the competitive binding composition and thus binding of the enzyme to the solid substrate. An example of such a selection process to provide different threshold levels is found in U.S. Pat. No. 5,480,776. Thus, if sufficient analyte is present in the sample, after reaction, no enzyme is present to produce a color change and the reaction mixture stays the same (thus a positive reaction using this reaction scheme).

Other reaction schemes can be used in which the formation of color is indicative of the presence of the analyte. The previous example is merely one of many types of competitive binding assays in which estriol can be measured.

Antibody production for use in an assay for estriol is conventional and is not described here in detail. A brief discussion of general techniques for the production of antibodies specific for steroids follows.

An animal is injected with a composition containing estriol covalently attached to an immunogen, usually a protein, prepared as described above. Multiple injections or the use of an adjuvant will ensure maximum stimulation of the immune system and production of antibodies. If polyclonal antibodies are selected, they can be prepared by simply collecting blood from the immunized animal and separating the antibodies from other blood components by standard techniques. To obtain monoclonal antibodies, the spleen or lymphocytes from the immunized animal are removed and immortalized or used to prepare hybridomas by cell-fusion methods known to those skilled in the art. Antibodies secreted by the immortalized cells are screened to determine the clones that secrete antibodies of the selected specificity. For monoclonal anti-estriol antibodies, the antibodies must bind to estriol. Cells producing antibodies of the selected specificity are selected, cloned and grown to produce the monoclonal antibodies of selected specificity.

Antibody can be attached to a solid surface for use in an assay using known techniques for attaching protein material to solid support materials. The solid support can include plastic surfaces of test tubes or microtiter plates, polymeric beads, dip sticks, or filter materials. The attachment methods include non-specific adsorption of the protein to the support and covalent attachment of the protein, typically through a free amino group, to a chemically reactive group on the solid support, such as an activated carboxyl, hydroxyl, or aldehyde group.

iii. Other Tumor Indicators

Also provided herein are methods for detecting an oncofetal fibronectin indicating molecule in conjunction with detection of one or more additional tumor markers. Such detection methods can be carried out according to the same principles as described herein for detection of an oncofetal fibronectin indicating molecule, including protein detection methods, nucleic acid molecule detection methods and autoantibody detections, such as, but not limited to, mass spectrometric methods, sandwich assays, test strip-based assays and in situ assays.

For example, a sample can be contacted with a solid support having immobilized thereto an anti-oncofetal fibronectin polyclonal antibody and an anti-(tumor marker) polyclonal antibody and the solid support also can be contacted with a monoclonal anti-oncofetal fibronectin antibody or fragment thereof and a monoclonal anti-(tumor marker) antibody or fragment thereof, where the monoclonal antibodies are conjugated to distinguishably detectable or bindable moieties (e.g., fluorophores of different emission wavelength, or one conjugated to biotin and another conjugated to a magnetic bead), whereby distinguishable signals or separate binding events can independently identify the presence of an oncofetal fibronectin indicating molecule and/or one or more additional tumor markers in the sample. A variety of different combinations, such as those discussed for the various methods provided herein, also can be used for detection of an oncofetal fibronectin indicating molecule and one or more additional tumor markers. A variety of additional detectable tumor markers are known in the art, including, but not limited to, AE1/AE3, BCA-225, Cathepsin D, E-Cadherin, Epidermal Growth Factor Receptor (EGFR), Estrogen receptor (ER), Gross Cystic Disease Fluid Protein 15 (GCDFP-15), HOX-B3, Ki-67, p65, Progesterone Receptor (PR), Retinoblastoma (Rb) and Transglutaminase K (TGK), p21, DCC, NF-1, NF-2, BRCA-3, p16, FHIT, WT-1, MEN-I, MEN-IIa, MEN-IIb, VHL, FCC, MCC, raf, erb, src, fms, jun, trk, ret, gsp, hst, bcr/abl, p53, c-erbB2, c-myc, MUC1, BRCA1, BRCA2, Her-2/neu, bcl-2, bax, PSA, CYFRA 21-1, PTH-RP, CA125, CEA gene family members, pro-gastrin, gastrin G17, gastrin G34, CA 19-9, CA 15-3, CA 27-29, CA 72-4, APC, SCC, HPV subtypes, TK, alphaFP, p62, Kallikrein, ras, vasopressin, gastrin releasing peptide, annexin I, annexin II, Hu and KOC. Binding partners for such tumor markers, methods of detecting such tumor markers and tumors correlated with such tumor markers are known in the art, as exemplified in U.S. Pub. Nos. 20030190602 and 20040059519.

G. ANALYSIS OF DETECTION MEASUREMENTS

Oncofetal fibronectin indicating molecule measurements made by any of the methods provided herein or known in the art can be analyzed to provide information about the subject from which the sample was collected, including information about the general health state of the subject, the propensity to childbirth of the subject or information about a tumor or neoplastic disease in the subject.

1. Quantitation

The amount of an oncofetal fibronectin indicating molecule in a sample can be quantitated. Methods provided herein for measurement of oncofetal fibronectin indicating molecules can provide quantitative measurements. For example, mass spectrometry can be used to provide quantitative results about an analyte in a sample by a variety of methods including by use of an internal standard or by labeling components to be measured (see, e.g., Bucknall et al., *J. Am. Soc. Mass Spectrom.*, 13:1015-1027 (2002); Ross et al., *Biotechniques* 2000:620-629; Amexis et al., *Proc. Natl. Acad. Sci. USA* 98:12097-12102 (2001); Griffin et al., *Anal. Chem.* 73:978-986 (2001)). RT-PCR and related methods can yield quantitative results using procedures such as competitive RT-PCR, real time RT-PCR and other methods, as described herein or known in the art. Quantitative binding assays including competitive binding assays also are known in the art and can be used for quantitation of oncofetal fibronectin. A variety of spectroscopic or reflectance measurements can be used to determine the concentration of an oncofetal fibronectin indicating molecule in a sample according to the intensity of the signal that represents the presence of the oncofetal fibronectin indicating molecule. For example, a test strip can be used having a region containing a fibronectin or oncofetal fibronectin binding partner immobilized thereto and the amount of light reflected from the test strip at that region can indicate the amount of oncofetal fibronectin indicating molecule in the sample and the amount of light can be measured by a reflectance reader. Exemplary quantitative methods include ELISA methods for quantitating the level of an oncofetal fibronectin indicating molecule in a cervicovaginal swab sample and use of a lateral flow test strip device and a test strip reader for quantitating the level of an oncofetal fibronectin indicating molecule in a urine sample.

2. Thresholds

Presence of an oncofetal fibronectin indicating molecule in a sample can be an indicator of any of a variety of biological or health conditions, including overall health state, pregnancy or delivery related conditions, pre-cancerous or cancer (e.g., neoplastic disease) conditions in a subject. In some cases a measurement is considered positive for oncofetal fibronectin when any oncofetal fibronectin indicating molecule is detected in a sample. In other cases, a measurement is considered positive for oncofetal fibronectin when the presence of an oncofetal fibronectin indicating molecule in a sample is equal to or above one or more threshold levels. In one example, a threshold level of oncofetal fibronectin protein in a buffer-treated cervicovaginal sample assayed using a test strip can be 50 ng/mL. In another example, a threshold level for oncofetal fibronectin protein in a buffer-treated cervicovaginal sample assayed using a test strip can be 150 ng/mL.

In embodiments that compare the level of oncofetal fibronectin in a sample to a threshold level, the threshold level can be the amount of an oncofetal fibronectin indicating molecule present in an unmodified sample, or the threshold level can be the amount of an oncofetal fibronectin indicating molecule present in a modified sample (e.g., the concentration of an oncofetal fibronectin indicating molecule of a cervicovaginal swab sample after mixture with a buffer solution). Reference herein to the level of an oncofetal fibronectin indicating molecule in a sample or the threshold level of an oncofetal fibronectin indicating molecule typically refers to the level of an oncofetal fibronectin indicating molecule in a modified sample. For example, some oncofetal fibronectin indicating molecule measurements, such as measurement of an oncofetal fibronectin indicating molecule in a cervicovaginal swab sample, are known in the art according to the sample-modified form; thus, oncofetal fibronectin indicating molecule levels and threshold levels for a cervicovaginal swab sample typically refer to the sample modified level.

In some embodiments, the measured amount of an oncofetal fibronectin indicating molecule can be compared to one or more thresholds. Provided herein one or more thresholds is 1, 2, 3, 4, 5, 6, 7, 8, 9, 10 or more thresholds. Typically, an oncofetal fibronectin indicating molecule concentration in the sample equal to or above a threshold level indicates that the sample is oncofetal fibronectin positive. In one embodiment, an oncofetal fibronectin indicating molecule concentration in a buffer-treated cervicovaginal swab sample of 50 ng/ml or more (or 500 ng/ml untreated swab sample or more), or about 50 ng/ml or more (or about 500 ng/ml untreated swab sample or more) indicates that the sample is oncofetal fibronectin positive. Typically, an oncofetal fibronectin indicating molecule concentration in the sample below a threshold level indicates that the sample is oncofetal fibronectin negative. In one embodiment, an oncofetal fibronectin indicating molecule concentration in a buffer-treated cervicovaginal swab sample of less than 50 ng/ml (or less than 500 ng/ml untreated swab sample), or about 50 ng/ml (or less than about 500 ng/ml untreated swab sample) indicates that the sample is oncofetal fibronectin negative.

Different sample types can have different threshold levels. Provided herein, different sample types also can have related threshold levels. For example, the amount of an oncofetal fibronectin indicating molecule in a cervicovaginal swab sample collected from the portion of the vagina below the posterior fornix, such as the lower third of the vagina, can be one-third or about one-third the amount of an oncofetal fibronectin indicating molecule in a cervicovaginal swab of the posterior fornix collected from the same subject. In another example, the amount of an oncofetal fibronectin indicating molecule in a urine sample can be one-tenth or about one-tenth the amount of an oncofetal fibronectin indicating molecule in a cervicovaginal swab of the posterior fornix collected from the same subject.

Exemplary threshold values for buffer-treated samples that can indicate different likelihoods of imminent or pre-term delivery include 50 ng/ml, 150 ng/ml, 200 ng/ml, 300 ng/ml, 500 ng/ml, 750 ng/ml and 1000 ng/ml, or about 50 ng/ml, about 150 ng/ml, about 200 ng/ml, about 300 ng/ml, about 500 ng/ml, about 750 ng/ml and about 1000 ng/ml. Exemplary threshold values for untreated samples that can indicate different likelihoods of imminent or pre-term delivery include 500 ng/ml, 1500 ng/ml, 2000 ng/ml, 3000 ng/ml, 5000 ng/ml, 7500 ng/ml and 10000 ng/ml, or about 500 ng/ml, about 1500 ng/ml, about 2000 ng/ml, about 3000 ng/ml, about 5000 ng/ml, about 7500 ng/ml and about 10000 ng/ml. In some embodiments, the oncofetal fibronectin indicating molecule is oncofetal fibronectin protein.

In one embodiment, where serum or plasma is the sample, a threshold level can be 3 µg/mL to 12 µg/mL, or about 3 µg/mL to about 12 µg/mL of FDC-6 positive oncofetal fibronectin protein. A serum or plasma sample containing more than the threshold level can be indicative of a tumorous or neoplastic disease state in the subject, or indicative of an increased risk of pre-term or imminent delivery, or indicative of some other problem with the health state of the individual. In one example, subjects with preeclampsia exhibited oncofetal fibronectin protein plasma levels ranging from 11.5 µg/mL to 38 µg/mL, while normal subject exhibited oncofetal fibronectin protein levels ranging from 4 µg/mL to 12 µg/mL, as measured by ELISA test using FDC-6 and goat polyclonal anti-human fibronectin as oncofetal fibronectin protein binding partners (Kupferminc et al., *Am. J. Obstet. Gynecol.* 172: 649-652 (1995). Accordingly, detection of FDC-6 reactive oncofetal fibronectin protein levels above 12 µg/mL or about 12 µg/mL in a serum sample can indicate that the subject exhibits oncofetal fibronectin protein levels above the threshold and, therefore, is positive for oncofetal fibronectin; detection of FDC-6 reactive oncofetal fibronectin protein levels in serum between 8 µg/mL and 12 µg/mL or between about 8 µg/mL and about 12 µg/mL can indicate that the subject may or may not be positive for oncofetal fibronectin; and detection of FDC-6 reactive oncofetal fibronectin protein levels in serum below 8 µg/mL or about 8 µg/mL can indicate that the subject is negative for oncofetal fibronectin.

In other cases, multi-tiered thresholds can be applied to the oncofetal fibronectin measurement, where multi-tiered thresholds include two or more threshold levels, where each larger threshold level indicates a separate health state categorization; for example each larger threshold level can indicate a more severe health problem, an increased likelihood of imminent delivery, increased certainty of delivery date, or increased aggressiveness of a cancer. An exemplary multi-tiered threshold is a two-tiered threshold for oncofetal fibronectin protein, where the lower threshold is 50 ng/mL and the higher threshold is 150 ng/mL for buffer-treated samples. A sample can be categorized according to the thresholds below a measured amount of an oncofetal fibronectin indicating molecule in the sample. For example, a pregnant woman at week 24 of her pregnancy having an amount of an oncofetal fibronectin indicating molecule that is higher than a first threshold but not higher than a second threshold, can be categorized as having an increased likelihood of pre-term delivery, whereas a pregnant woman at week 24 of her pregnancy having an amount of an oncofetal fibronectin indicating molecule that is higher than the first and second threshold levels can be categorized as having a higher risk of imminent delivery.

In some instances, one or more threshold levels or one or more threshold curves applied to a measured amount in a subject's sample can be determined according to any of a variety of subject-specific factors. In one example, a subject-specific factor can be the measured amount of one or more samples from a subject.

In another embodiment, the threshold level can vary according to one or more additional factors. Such factors can include, but are not limited to, biological state of the subject, such as the term of pregnancy, the presence of one or more other markers, anatomical factors, previous health history and genetic factors, the progression of disease, or the age of the subject. Factors also can include the change in the biological state of the subject over time, including the rate of increase in oncofetal fibronectin indicating molecule measurements over time. The varying threshold level can be expressed as a threshold curve where the threshold level of an oncofetal fibronectin indicating molecule varies as a function of time (e.g., week of pregnancy term). A threshold level can decrease with increasing time, or a threshold level can increase with increasing time.

In some instances, the rate of change of the amount of an oncofetal fibronectin indicating molecule in a particular sample type (e.g., cervicovaginal swab) from a subject can be used to identify a sample as oncofetal fibronectin positive or negative, or to categorize the sample into two or more populations. The rate of change of the amount of an oncofetal fibronectin indicating molecule in a type of sample can indicate a stable, increasing or decreasing amount of the oncofetal fibronectin indicating molecule in the sample.

3. Identification of Tissue Source

An oncofetal fibronectin indicating molecule can contain any of a variety of different splice regions (e.g., EDA, EDB or IIICS) and oncofetal fibronectin protein can contains post-translational modifications (e.g., O-glycosylation). Thus, a variety of non-identical proteins can be termed oncofetal fibronectin, and a variety of non-identical nucleic acid molecules can encode oncofetal fibronectin. In studies of samples, a variety of different fibronectin proteins containing different combinations of these splice regions and post-translational modifications have been observed. The methods provided herein or known in the art can be used to identify the presence of an oncofetal fibronectin indicating molecule in a sample and also can be used to identify one or more splice regions and/or post-translational modifications present in an oncofetal fibronectin indicating molecule in the sample. Identification of the presence or absence of one or more splice regions and/or post-translational modifications present in an oncofetal fibronectin indicating molecule is referred to herein as characterization of oncofetal fibronectin.

In one embodiment, characterization of oncofetal fibronectin can be used to determine the biological source of the oncofetal fibronectin indicating molecule. For example, characterization of oncofetal fibronectin can be used to identify the tissue source of an oncofetal fibronectin indicating molecule in a sample. For example, oncofetal fibronectin protein containing EDB and IIICS with threonine 33 O-glycosylated (referred to herein as EDB+, FDC-6+ onfFN) has been observed in liver cirrhosis, liver metastases, dilated cardiomyopathy, fibromatosis, rheumatoid arthritis, nodular palmar fibromatosis, pituitary adenoma, breast carcinoma, invasive ductal carcinoma of the breast, oral squamous cell carcinoma, colon carcinoma and renal carcinoma; an oncofetal fibronectin indicating molecule containing EDB (EDB+ onfFN) has been found in extracellular matrix containing newly forming blood vessels, in brain tumor, prostate carcinoma, benign prostatic hyperplasia, stomach adenocarcinoma, kidney clear cell carcinoma, urinary bladder carcinoma, skin carcinoma, skin and ocular melanoma, lung carcinoma and colon carcinoma; an oncofetal fibronectin indicating molecule containing EDB and EDA (EDB+, EDA+ onfFN) has been observed in fibroblasts and macrophages in healing wounds, glomerulonephritis, nodular palmar fibromatosis and thyroid tumor; an oncofetal fibronectin indicating molecule containing EDA (EDA+ onfFN) has been observed in psoriasis and liver tumor; an oncofetal fibronectin indicating molecule containing CS1 (IIICS/CS1+ onfFN) has been observed in liver tumor.

The methods provided herein and known in the art can be used to characterize an oncofetal fibronectin indicating molecule in a sample according to the presence of one or more domains and/or post-translational modifications. After such determination, the characterized an oncofetal fibronectin indicating molecule of the sample can be compared to tissues, tumors and other biological sources known to contain oncofetal fibronectin. A tissue, tumor or other source that is known to contain the same oncofetal fibronectin variant as the characterized oncofetal fibronectin indicating molecule from a sample, can be identified as a potential tissue, tumor or other biological source of the oncofetal fibronectin indicating molecule. For example, if a sample contains EDB+, FDC-6+ onfFN protein, the source of the oncofetal fibronectin protein in the sample can be liver, vascular tissue, pituitary tissue, breast tissue, oral squamous cells, colon or kidney.

Also provided herein are methods for identifying a sample as containing a biological source other than the tissue of the sample. As described above, the methods provided herein can be used to identify the tissue, tumor or other source of an oncofetal fibronectin indicating molecule in a sample. Such methods can be used to identify the oncofetal fibronectin indicating molecule as arising from a biological source other than the tissue of the sample. For example, pancreatic carcinoma typically does not contain EDB+ oncofetal fibronectin protein; thus, if an EDB+ oncofetal fibronectin indicating molecule is identified in a pancreas tissue sample, the sample can be identified as containing a biological material other than pancreatic tissue. In such cases, the biological material other than the tissue of the sample can include, for example metastasized tumor cells. For example, a pancreatic tissue sample containing metastasized liver cells can be a pancreatic tissue sample containing an EDB+ oncofetal fibronectin indicating molecule and thus can be identified using the methods provided herein as a sample containing metastasized tumor cells and not tumorous pancreatic cells or tissue. Thus, methods provided herein that include characterizing an oncofetal fibronectin indicating molecule in a sample can be used in methods for determining the presence of metastasized tumor cells in a sample and methods for distinguishing between a sample containing metastasized tumor cells and non-metastasized tumor cells.

Methods provided herein also can be used to characterize the composition of an oncofetal fibronectin indicating molecule of a particular tissue, tumor or biological source. For example, extracellular matrix containing newly formed or forming vasculature can contain oncofetal fibronectin protein. The methods provided herein can be used to characterize the oncofetal fibronectin protein in the extracellular matrix as containing or not containing EDA, EDB, IIICS (and splice variants thereof) and one or more post translational modifications such as O-glycosylation of threonine 33 of IIICS. The methods provided herein can be used to characterize an oncofetal fibronectin indicating molecule present in any tissue of a subject. Similarly, tissue that is benign, hyperplastic, neoplastic, fetal, male, female, or combinations thereof (e.g., neoplastic male liver tissue, neoplastic female liver tissue), can be used as samples in the methods provided herein and any oncofetal fibronectin indicating molecule present in the sample can be characterized as containing or not containing EDA, EDB, IIICS (and splice variants thereof) and one or more post translational modifications such as O-glycosylation of threonine 33 of IIICS.

H. COMBINATIONS, PROBES, CONJUGATES AND KITS

Combinations and kits containing the combinations also are provided. The combinations include one or more fibronectin or oncofetal fibronectin binding partners; and, optionally, reagents for detecting at least one fibronectin or oncofetal fibronectin binding partner. The combination can include one or more fibronectin or oncofetal fibronectin binding partners immobilized to a solid support, such as a microtiter plate, a microarray, a membrane or a test strip. The combinations also include one or more solutions (e.g., buffer solution) with which the sample can be mixed. The combinations also can include one or more filters for removing particulate or solid or undissolved matter from a liquid sample. The combinations also can include a non-specific binding compound, dry or in solution and/or a solid support containing a non-specific binder. The combinations also can include a structure for immobilizing or manipulating sample components, such as an electrophoresis gel for manipulation of a sample, or a microtiter plate, a microarray, or membrane for immobilizing sample components. When used in connection with pre-term delivery, the combination also optionally contains a tocolytic agent and, optionally, a device for administering the tocolytic agent. When used in connection with inducing delivery, the combination optionally contains an inducing agent and, optionally, a device for administering the inducing agent. The combinations and kits optionally include instructions for collecting the sample and/or performing the assay. Any of a variety of combinations and kits known in the art that can be adapted for use in the methods provided herein, using techniques known to those skilled in the art, are contemplated herein, as exemplified in U.S. Pat. Nos. 5,281,522, 6,394,952, and 6,267,722. The combinations and kits can be used for detection of oncofetal fibronectin in a sample, for determining the amount of an oncofetal fibronectin indicating molecule in a sample and/or for characterizing one or more oncofetal fibronectin indicating molecules in a sample.

The combinations also can include a device or solution for collecting or contacting a sample, such as, but not limited to, a polyester swab, a urine specimen cup, a lavage fluid, a dipstick, a passive sample collection device, or a transdermal patch. Exemplary swabs of the present combinations can include swabs long enough to insert into the vagina, but not long enough to contact the cervix; for example, the length of the swab can be 15 cm or less, 13 cm or less, 12 cm or less, 11 cm or less, 10 cm or less, 9 cm or less, 8 cm or less, 7 cm or less, 6 cm or less, 5 cm or less, 4 cm or less 3 cm or less, or 2 cm or less. Swabs also can be a tissue or pad (e.g., a gauze pad) that can be used to wipe the vaginal vestibule and/or the labia, and/or can be used to wipe portions of the lower third of the vagina. Exemplary passive sample collection devices include absorbent devices, devices that can be inserted into the vagina, such as into the portion of the vagina below the posterior fornix including the lower third of the vagina, devices that contact the labia and/or vaginal orifice, devices that can be located between the labia and/or vaginal orifice and the subject's undergarment. Sample collection devices also can have immobilized thereto one or more fibronectin or oncofetal fibronectin binding partners.

Swabs, passive collection devices, and other sample collection devices that are inserted into the vagina in collecting the sample can optionally have attached thereto an overinsertion preventing device. An overinsertion preventing device can limit the distance into the vagina that the sample collection device can be inserted, and thereby ensure that the sample collection device can be readily withdrawn and/or ensure that the sample does not contact the cervix or other portion of the cervicovaginal cavity that could be damaged by unintended contact with a sample collection device. An overinsertion preventing device also can serve to standardize the location in the vagina at which the sample is collected, by ensuring that the sample is collected no further than a particular distance into the vagina, and, optionally, by demarking the location in the vagina at which some or most of the sample is collected. For example, an overinsertion preventing device that is 5 cm from the polyester tip of a swab can be used to ensure that the polyester tip collects fluid no further than 5 cm into the vagina, and, optionally, that most of the cervicovaginal fluid absorbed by the polyester tip is cervicovaginal fluid located about 5 cm from the vaginal vestibule or vaginal orifice. In one example of an overinsertion device, a long narrow swab, such as a swab with a solid shaft and a polyester tip at one end, can have attached thereto a broad shield that is sufficiently large to not enter the vagina and thereby prevent the swab from being further inserted into the vagina. Any of a variety of overinsertion preventing devices can be used, and typically an overinsertion preventing device portion of a sample collection device is larger than the portion of the sample collection device that is inserted into the vagina. Exemplary overinsertion preventing devices include, but are not limited to, a shield, a handle, or a three-dimensional structure (e.g., a sphere or cube). In some embodiments, an overinsertion preventing device that standardizes the location in the vagina at which the sample is collected can increase the reproducibility of sample collection.

Sample collection devices also can be selected for their ease of use. In some embodiments, the sample collection device can be a device that can be operated by the subject from whom the sample is to be collected or a non-medical professional such as a relative of the subject. Such sample collection device also can be accompanied by instructions for use that instruct the unskilled person on the methods for collecting the sample.

The combinations can include test strips or other devices containing one or more fibronectin or oncofetal fibronectin binding partners, where such devices can be used to detect the presence of an oncofetal fibronectin indicating molecule in a sample or to indicate the amount of an oncofetal fibronectin indicating molecule in a sample. In some embodiments, such a device can be configured to indicate a positive result when the amount of an oncofetal fibronectin indicating molecule is above a defined threshold level. Exemplary threshold levels include 1 ng/ml, 3 ng/ml, 5 ng/ml, 10 ng/ml, 15 ng/ml, 25 ng/ml, 35 ng/ml and 50 ng/ml, or about 1 ng/ml, about 3 ng/ml, about 5 ng/ml, about 10 ng/ml, about 15 ng/ml, about 25 ng/ml, about 35 ng/ml and about 50 ng/ml, for untreated samples, samples before treatment, or undiluted samples. Other exemplary threshold levels include 1 ng/ml, 2 ng/ml, 3 ng/ml, 5 ng/ml, 7 ng/ml, 10 ng/ml, 15 ng/ml and 20 ng/ml, or about 1 ng/ml, about 2 ng/ml, about 3 ng/ml, about 5 ng/ml, about 7 ng/ml, about 10 ng/ml, about 15 ng/ml and about 20 ng/ml, for buffer-treated samples. Methods for configuring devices such as test strips to return a positive result upon the presence of a threshold level of a sample component are known in the art. The test strip can be readable by a machine, such as a test strip reader, or can be configured to be read by an individual and not by a machine.

The combinations can include test strip readers or other devices such as absorbance devices, fluorescence devices, that can be used to determine the amount of an oncofetal fibronectin indicating molecule in a sample. In some embodiments, such a device can be configured to indicate a positive result when the amount of an oncofetal fibronectin indicating molecule is above a defined threshold level. Exemplary threshold levels include 1 ng/ml, 3 ng/ml, 5 ng/ml, 10 ng/ml, 15 ng/ml, 25 ng/ml, 35 ng/ml and 50 ng/ml, or about 1 ng/ml, about 3 ng/ml, about 5 ng/ml, about 10 ng/ml, about 15 ng/ml, about 25 ng/ml, about 35 ng/ml and about 50 ng/ml, for untreated samples or samples before treatment. Other exemplary threshold levels include 1 ng/ml, 2 ng/ml, 3 ng/ml, 5 ng/ml, 7 ng/ml, 10 ng/ml, 15 ng/ml and 20 ng/ml, or about 1 ng/ml, about 2 ng/ml, about 3 ng/ml, about 5 ng/ml, about 7 ng/ml, about 10 ng/ml, about 15 ng/ml and about 20 ng/ml, for buffer-treated samples.

Kits are packaged in combinations that optionally include other reagents or devices. For example, a kit optionally includes one or more devices for obtaining and manipulating a sample from the subject (e.g., a vaginal accessing tool or a ductal accessing tool). A kit also optionally includes one or more devices for transferring or mixing a sample, such as a dropper or pipette. In one embodiment, a kit includes a test strip that contains one or more fibronectin or oncofetal fibronectin binding partners located thereon. A test strip can contain a fibronectin or oncofetal fibronectin binding partner immobilized on the test strip, or mobilizable upon contact with the sample, or can contain an immobilized oncofetal fibronectin binding partner and a mobilizable oncofetal fibronectin binding partner. Optionally, a test strip-containing kit can include a fibronectin or oncofetal fibronectin binding partner in solution or mobile form, with which the sample can be mixed prior to applying the sample to the test strip. One or more of the fibronectin or oncofetal fibronectin binding partners can be conjugated to a moiety for detection of the conjugate. A kit containing a test strip also can include a nonspecific binder such as a non-specific binding compound or a non-specific binding surface, either as a component of a test strip or as a different structure, composition or solution. In one example, a kit contains all necessary components for performing a home test for the presence of an oncofetal fibronectin indicating molecule in a sample, such as, for example, a sample collection device or vesicle, a test strip, instructions for sample collection, use of the test strip and interpretation of the test strip results and optionally one or more compounds, compositions, buffers or solutions for mixing with the sample or for use in conjunction with detection of an oncofetal fibronectin indicating molecule. Typically, a kit that can be used for home testing does not include a swab long enough to contact the cervix when held by an individual.

The combinations provided herein also include a combination that has been contacted by a sample. The combinations can include one or more fibronectin or oncofetal fibronectin binding partners that have been contacted by a sample; and, optionally, reagents for detecting at least one fibronectin or oncofetal fibronectin binding partner, including reagents for detecting fibronectin or oncofetal fibronectin binding partner that have been contacted with a test device and/or fibronectin or oncofetal fibronectin binding partner. The combination can include a solid support, such as a microtiter plate, a microarray, a membrane or a test strip including, for example, a solid support having one or more fibronectin or oncofetal fibronectin binding partners immobilized thereto, where the solid support has been contacted with a sample. The combinations also can include a sample that has been mixed with one or more solutions (e.g., buffer solution). The combinations also can include one or more filters that have been contacted with a liquid sample. The combinations also can include a non-specific binding compound, dry or in solution and/or a solid support containing a non-specific binder that has been contacted by a sample. The combinations also can include a structure having immobilized thereto, or containing, one or more sample components, such as an electrophoresis gel containing sample components, or a microtiter plate, a microarray, or membrane having immobilized thereto sample components. An exemplary combination can be a combination that indicates the presence of an oncofetal fibronectin indicating molecule in the sample, or an amount of an oncofetal fibronectin indicating molecule in the sample, or an amount of an oncofetal fibronectin indicating molecule in the sample at or above a threshold level. Another exemplary combination can be a combination that indicates the absence of an oncofetal fibronectin indicating molecule in the sample, or an amount of an oncofetal fibronectin indicating molecule in the sample below a threshold level.

Also provided herein are kits that contain the combinations provided herein and one or more devices such as a thermal cycler, an apparatus for sample preparation such as a tissue homogenizer, as known in the art or provided herein. A kit also can include the appropriate buffers and solutions for performing the oncofetal fibronectin indicating molecule detection methods described herein.

Also provided herein are systems including one or more fibronectin or oncofetal fibronectin binding partners and one or more devices for detecting the presence of an oncofetal fibronectin indicating molecule in a sample. The binding partners can be mobile in solution, mobilizable on a solid support, or immobilized on a solid support such as a test strip, a mass spectrometry substrate or a DNA array chip. Devices for detecting the presence of an oncofetal fibronectin indicating molecule in a sample can be any of a variety of detection devices including mass spectrometer, absorbance spectrometer, fluorescence spectrometer, reflectance reader, flow cytometer, or electrophoretic gel scanner. In one embodiment, the device for detecting the presence of an oncofetal fibronectin indicating molecule is designed to receive a solid support containing a sample or sample components and, optionally also containing a fibronectin or oncofetal fibronectin binding partner.

The packaging material used in the kit can be one or more physical structures used to house the contents of the kit and can be constructed by well known methods, typically to provide a sterile, contaminant-free environment. The packaging material can have a label which indicates the components of the kit. In addition, the packaging material contains instructions indicating how the materials within the kit are employed to determine the presence of an oncofetal fibronectin indicating molecule, determine the amount of an oncofetal fibronectin indicating molecule, or characterize an oncofetal fibronectin indicating molecule, present in the sample. Instructions typically include a tangible expression describing the reagent concentration or at least one assay method parameter, such as the relative amounts of reagent and sample to be admixed, maintenance time periods for reagent/sample admixtures, temperature, buffer conditions and other parameters. The kit can include one or more containers capable of holding within fixed limits a primer, enzyme or other reactant or buffer solution used in the methods of oncofetal fibronectin indicating molecule determination. For example, a kit can include a glass vial used to contain milligram quantities of a fibronectin or oncofetal fibronectin binding partner. A kit also can include substrates, supports or containers for performing the oncofetal fibronectin indicating molecule determination methods, including vials or tubes, or a mass spectrometry substrate.

Also provided in the kits herein are systems for classifying the sample according to one or more threshold levels. Samples having amounts of oncofetal fibronectin equal to or greater than one or more threshold(s) are considered positive for oncofetal fibronectin. For instance, a sample having equal to or greater than 25 ng/ml is considered positive for oncofetal fibronectin. On the other hand, samples having amounts of oncofetal fibronectin less than one or more threshold(s) are considered negative for oncofetal fibronectin. For instance, a sample having less than 25 ng/ml is considered positive for oncofetal fibronectin.

Probes for detection and/or quantitation of oncofetal fibronectin and indicating molecules thereof also are provided herein. The probes include, for example, a mass spectrometry substrate and a fibronectin or oncofetal fibronectin binding partner immobilized on the mass spectrometry substrate for detecting an oncofetal fibronectin indicating molecule. Mass spectrometry substrates are substances such as, but not limited to, glass, metals, ceramics, Teflon-coated magnetic materials, organic polymers, biopolymers and inorganic polymers. Probes as provided herein can be used to identify oncofetal fibronectin indicating molecules by detecting a particular weight fragment by mass spectrometry.

Conjugates also are provided herein. A conjugate can include, for example, a fibronectin or oncofetal fibronectin binding partner linked directly or indirectly via a linker to a therapeutic agent or an imaging agent or detecting agent. Therapeutic agents include, but are not limited to a cytokine, a photosensitizing agent, a toxin, an anticancer antibiotic, a chemotherapeutic compound, a radionuclide, and a bioluminescent compound or to a detectable moiety such as, for example, a fluorescent moiety, a radionuclide, a magnetically detectable isotope or compound, a sonographic imaging agent, a chromophore, a latex microsphere, or a quantum dot. In certain cases, the therapeutic agent is an angiogenesis inhibitor. In a particular case, a therapeutic agent can be pseudomonas exotoxin, diphtheria toxin, ricin, cholera toxin, gelonin, *shigella* toxin, pokeweed antiviral protein, exotoxin A, abrin toxin, saporin, an interleukin, a tumor necrosis factor, an interferon, granulocyte macrophage colony stimulating factor, angiogenin, tissue factor, porfiromycin, doxorubicin, dactinomycin, plicamycin, mitomycin, bleomycin, actinomycin, daunorubicin, indocyanine green, toluidine blue, aminolevulinic acid, texaphyrin, benzoporphyrin, a phenothiazine, a phthalocyanine, a porphyrin, a chlorin, a purpurin, a purpurinimide, a bacteriochlorin, a pheophorbide, a pyropheophorbide, a cationic dye, $^{32}$Phosphate, $^{60}$Cobalt, $^{90}$Yttirum, $^{99}$Technicium, $^{103}$Palladium, $^{106}$Ruthenium, $^{111}$Indium, $^{117}$Lutetium, $^{125}$Iodine, $^{131}$Iodine, $^{137}$Cesium, $^{153}$Samarium, $^{186}$Rhenium, $^{188}$Rhenium, $^{192}$Iridium, $^{198}$Gold, $^{211}$Astatine, $^{212}$Bismuth, $^{213}$Bismuth, 5-fluorouridine, calicheamicin or maytansine. Therapeutic agents can also be signaling modulators, such as, for example, an inhibitor of MIF (macrophage inhibitory factor), a toll-like receptor agonist, or a stat 3 inhibitor. Binding partners of the conjugates can be antibodies, such as, for example, FDC-6, BC-1, ME4C or L19.

Provided herein is the use of any of the products provided herein for the preparation of a medicament for any of the methods provided herein, including, but not limited to, diagnosis, imaging, and/or treatment of a health disorder characterized by the presence of, or elevated levels of, an oncofetal fibronectin indicating molecule.

The following examples are included for illustrative purposes only and are not intended to limit the scope of the invention.

I. EXAMPLES

Example 1

Polyclonal Anti-Oncofetal Fibronectin Antibody

Oncofetal fibronectin can be purified from amniotic fluid as described by Engvall and Ruoslahti, *Int. J. Cancer,* 20:1-5 (1977).

The anti-(oncofetal fibronectin) antibodies are elicited in rabbits using the immunization techniques and schedules described in the literature, e.g., Stollar, *Meth. Enzymol.,* 70(A):70-85 (1980), immunizing the rabbits with the oncofetal fibronectin antigen. The antiserum is screened in a solid phase assay similar to that used for monoclonal antibodies, such as described by Lange et al., *Clin. Exp. Immunol.* 25(2): 191-198 (1976) and Pisetsky et al., *J. Immun. Meth.* 41(2): 187-200 (1981).

The IgG fraction of the antisera is purified further by affinity chromatography using CNBr-Sepharose 4B (Pharmacia Fine Chemicals) to which has been coupled oncofetal fibronectin. The method used for coupling is that recommended by the gel manufacturer, AFFINITY CHROMATOGRAPHY, *Pharmacia Fine Chemicals*, pp. 15-18.

Briefly, the column is equilibrated with from 2 to 3 volumes of buffer (0.01 M PBS, pH 7.2) and the anti-(oncofetal fibronectin) antibody containing solution then is applied to the column. The absorbency of the eluate is monitored at 280 nm until protein no longer passes from the column. The column then is washed with 0.1 M glycine buffer, pH 2.5, to desorb the immunoaffinity bound anti-(oncofetal fibronectin) antibody. Peak protein fractions are collected, pooled and dialyzed against 0.01 M PBS, pH 7.2, for 24-36 hr at 4° C. with multiple buffer changes.

If a purity of preferentially binding antibodies is to be achieved, the affinity purified IgG can be passed through an adult plasma fibronectin bound affinity column by the procedure described above to remove antibodies that would cross-react with non-oncofetal fibronectin.

Example 2

Monoclonal Anti-Oncofetal Fibronectin Antibody

Using the purified oncofetal fibronectin obtained by the procedure of Example 1, mouse monoclonal antibodies to the oncofetal fibronectin are obtained using standard procedures of Galfre and Milstein, *Meth. Enzymol.,* 73(Pt.B):3-46 (1981); and Matsuura, H. and Hakomori, S. et. al. *Proc. Natl. Acad. Sci. USA,* 82:6517-6521 (1985), using oncofetal fibronectin as the antigen for immunizing the mice. The monoclonal antibodies are screened using a modification of the techniques described in the literature, e.g., Lange et al., *Clin. Exp. Immunol.,* 25(2):191-198 (1976); and Pisetsky et al., *J. Immun. Meth.,* 41(2):187-200 (1981).

Mouse monoclonal antibody is purified from ascites fluid or from hybridoma culture supernatants using Protein-A coupled Sepharose-4B (Pharmacia Fine Chemicals) according to the procedure of Tijsson, *Practice and Theory of Enzyme Immunoassays*, Elsevier Science Publishers, pp. 105-107 (1985).

Example 3

Polyclonal Anti-Oncofetal Fibronectin Antibody-Coated Microtiter Plate

Rabbit anti-(oncofetal fibronectin) prepared and further purified to remove non-oncofetal fibronectin cross-reactivity as described in Example 1 is diluted to 10 µg/mL in 0.05 M carbonate buffer, pH 9.6. 100 µL is dispersed into each well of an IMMULON II microtiter plate (Dynatech). The plate is covered and incubated 4 hr at room temperature or 4° C. overnight. The plate is washed 4 times with Wash Buffer (0.02 M Tris HCl, 0.015 M NaCl, 0.05% TWEEN-20), filling and emptying the wells completely with each use. The plate then is blocked by dispersing into each well 200 µL of a blocking solution (0.01 M PBS, 1% BSA, 0.02% NaN$_3$, pH 7.4) and incubating for 1 hr at room temperature. The wells then are washed 4 times with Wash Buffer, as described above. The plate is now ready for immunoassay of samples.

Example 4

Polyclonal Anti-Human Fibronectin Antibody

Human plasma fibronectin was purified from human plasma as described by Engvall and Ruoslahti, *Int. J. Cancer,* 20:1-5 (1977).

The anti-human plasma fibronectin antibodies were elicited in goats using the immunization techniques and schedules described in the literature, e.g., Stollar, *Meth. Enzymol.,* 70(A):70-85 (1980), immunizing the goats with the human plasma fibronectin antigen. The antiserum was screened in a solid phase assay similar to that used for monoclonal antibodies, e.g., as described by Lange et al., *Clin. Exp. Immunol.,* 25(2):191-198 (1976) and Pisetsky et al., *J. Immun. Meth.,* 41(2):187-200 (1981).

The IgG fraction of the antiserum was purified further by affinity chromatography using CNBr-Sepharose 4B (Pharmacia Fine Chemicals) to which has been coupled human plasma fibronectin according to the method recommended by the manufacturer (AFFINITY CHROMATOGRAPHY, *Pharmacia Fine Chemicals Catalogue,* 1990, pp. 15-18).

Briefly, the column was equilibrated with from 2 to 3 volumes of buffer (0.01 M PBS, pH 7.2) and the anti-human fibronectin antibody-containing solution was then applied to the column. The absorbency of the effluent was monitored at 280 nm until protein no longer passed from the column. The column was then washed with equilibration buffer until a baseline absorbance at 280 nm was obtained.

The immunoaffinity bound anti-human plasma fibronectin antibody was eluted with 0.1 M glycine buffer, pH 2.5. Peak protein fractions were collected, pooled and dialyzed against 0.01 M PBS, pH 7.2, for 24-36 hr at 4° C. with multiple buffer changes. The above procedure was repeated to immunize rabbits with human plasma fibronectin and to purify the resultant polyclonal anti-human fibronectin antibodies.

Example 5

Polyclonal Anti-Fibronectin Antibody-Coated Microtiter Plate

Goat anti-human plasma fibronectin prepared as described in Example 4 is diluted to 10 μg/mL in 0.05 M carbonate buffer, pH 9.6. 100 μL is dispersed into each well of a polystyrene microtiter plate such as supplied by Costar, Nunc, or Dynatech. The plate is covered and incubated 2 to 4 hr at room temperature or 4° C. overnight. The plate is washed 3 to 4 times with Wash Buffer (0.02 M Tris HCl, 0.015 M NaCl, 0.05% TWEEN-20), filling and emptying the wells completely with each use. The plate then is blocked by dispersing into each well 200 μL of a blocking/stabilizing solution (4% sucrose, 1% mannitol, 0.01 M PBS, 1% BSA, 0.02% NaN$_3$, pH 7.4) and incubated for 30 minutes to 2 hrs at room temperature. The wells then are aspirated to dryness, the plate is packaged in an air-tight container with a desiccant pouch and stored at 4° C. until needed.

Example 6

Monoclonal Antibodies from Hybridoma HB 9018

Preparation of the Hybridoma deposited at the American Type Culture Collection and given the accession number ATCC HB 9018 is described U.S. Pat. No. 4,894,326 issued Jan. 16, 1990 to Matsuura et al. The hybridoma was cultured by growth in RPMI 1640 tissue culture medium supplemented with 10% fetal bovine serum. Additionally, the hybridoma was cultured in mice by the injection of the hybrid cells according to the procedure of Mishell and Shiigi, *Selected Methods in Cellular Immunology,* W.H. Freeman & Co, San Francisco, page 368, (1980).

The monoclonal antibody, designated FDC-6, was produced by the hybridoma was prepared for use in an immunoassay by the following procedure. The IgG fraction of the culture supernatant or the ascites was precipitated by ammonium sulfate fractionation. The antibody was redissolved and dialyzed into the appropriate buffer for purification by affinity chromatography on Protein-G Fast Flow (Pharmacia Fine Chemicals) according to the manufacturer's directions.

Example 7

Monoclonal Antibody-Coated Microtiter Plate

Microtiter plates were coated with FDC-6 monoclonal antibody by following the procedure described below.

Monoclonal antibody FDC-6 prepared as described in Example 6 was diluted to 10 μg/mL in phosphate buffer, pH 7.2 and 100 μl/well was dispersed into a polystyrene microtiter plate (Costar). The plates were incubated for 2 hours at room temperature or overnight at 4° C. The contents of the wells were aspirated and the wells washed 3 to 4 times with wash buffer (0.02 M Tris HCl, 0.015 M NaCl and 0.05% TWEEN-20) as described in Example 5. 200 μl/well of blocking/stabilizing solution (4% sucrose, 1% mannitol, 0.5% casein and 0.01 M PBS) was then added to the wells and incubated for 30 minutes to 4 hours at room temperature. The wells were then aspirated to dryness and the plate was packaged in an air-tight container with a desiccant pouch and stored at 4° C. until needed.

The above procedure was repeated using microtiter plates from Nunc and Dynatech and gave equivalent results.

Example 8

Enzyme Labeled Anti-Fibronectin Antibody

Anti-human plasma fibronectin antibody prepared according to Example 4 was conjugated with calf intestine alkaline phosphatase following the one-step glutaraldehyde procedure of Avrameas, *Immunochem.* 6:43 (1969).

Example 9

Oncofetal Fibronectin Assay Kit and Method

An assay kit for oncofetal fibronectin included the following reagents:
1. a microtiter plate coated with affinity-purified murine monoclonal anti-oncofetal fibronectin antibody,
2. calf intestine alkaline phosphatase-conjugated, affinity purified, polyclonal, goat anti-fibronectin antibodies,
3. enzyme substrate,
4. a negative control,
5. a positive control,
6. rinse buffer concentrate (50×), and
7. stopping solution.

The microtiter plate coated with murine monoclonal anti-oncofetal fibronectin antibody and the alkaline phosphatase-conjugated, affinity purified, polyclonal, goat anti-fibronectin antibodies were prepared as described in Examples 7 and 8, respectively. The microtiter plate was packaged as 12 strips of eight wells each in sealed plastic bags containing desiccant and stored at 2° C. to 8° C.

The stock antibody conjugate was appropriately diluted in conjugate diluent (0.05 M Tris Buffer pH 7.2, 2% D-Sorbitol, 2% BSA, 0.1% Sodium Azide, 0.01% Tween-20, 1 mM Magnesium Chloride and 0.1% Zinc Chloride) and 10 mL placed in a polyethylene dropper bottle container.

The enzyme substrate (10 mL in a polyethylene dropper bottle container) was phenolphthalein monophosphate (1 mg/mL) dissolved in 0.4 M aminomethylpropanediol buffer, pH 10 with 0.1 mM magnesium chloride and 0.2% sodium azide.

The positive control (3.4 mL in a polyethylene dropper bottle container) was amniotic fluid containing oncofetal fibronectin diluted to a concentration of oncofetal fibronectin of 50 ng/mL in sample diluent solution (0.05 M Tris buffer pH 7.4, 1% bovine serum albumin (BSA), 0.15 M sodium chloride, 0.02% Sodium Azide, 5 mM ethylenediamine tetraacetic acid (EDTA), 1 mM phenylmethylsulfonyl fluoride (PMSF), 500 Kallikrein Units/mL of Aprotinin and 0.1% Triton X-100). This sample diluent solution is described in U.S. Pat. No. 4,919,889 to Jones et al., issued Apr. 24, 1990.

The negative control (2.5 mL in a polyethylene dropper bottle container) was the sample diluent solution used for the positive control without oncofetal fibronectin.

The rinse buffer (20 mL in a polyethylene dropper bottle container) was a 50× concentrate containing 1.0 M Tris buffer pH 7.4, 4.0 M sodium chloride, 2.5% Tween-20 and 1% sodium azide. The rinse buffer was diluted with distilled or deionized water to a final concentration of 0.02 M Tris, 0.08 M sodium chloride, 0.05% Tween-20 and 0.02% sodium azide for use in the assay. The stopping solution (10 mL in a polyethylene dropper bottle container) contained 50 mM EDTA and 50 mM sodium phosphate.

In addition, 5 µm pore size polyethylene sample filters (Porex Technologies, Fairburn, Ga.), a microtiter strip holder, a microtiter plate cover, storage tubes, and an instruction sheet. All of the dropper bottles in the kit were polyethylene bottles designed to dispense approximately 50 µL drops of the reagent. All of the assay steps performed following sample collection used the reagents and materials in the kit. All samples, positive and negative controls were tested at the same time using kit reagents from the same kit.

The assay was performed as follows. All samples were collected in the vicinity of the posterior fornix or cervical os using polyester swabs. Swab samples were immersed in 1.0 mL of sample diluent in a collection vial. The sample diluent solution is described above. The swabs were removed from the solution leaving as much liquid as possible in the collection tube. All samples and control reagents were pre-warmed to 37° C. for 20 minutes in an incubator or 10 minutes in a 37° C. water bath prior to the assay, either before or after filtration. A sample filter was snapped in place on each sample tube and the filter pushed to the bottom until the entire sample is filtered. For samples of which filtering were not effective, samples were centrifuged at 550×g at room temperature for 5 minutes and test supernatant used in assay. The 8-well strips were snapped into place in a strip holder. The holder had the alphanumeric indications of the 12 columns and eight rows of standard microtiter plates. Duplicate 100 µL aliquots of each sample and the pre-warmed positive and negative controls were placed in separate wells of the microtiter strip and incubated for 1 hour at room temperature, covered.

Following incubation, samples and controls were aspirated from the wells. Wells were washed three times with diluted wash buffer (1×), being sure wells were completely filled each time. Following washing, 100 µL of enzyme-antibody conjugate was added to each well and incubated for 30 minutes at room temperature, covered. The wells were aspirated and washed as described above. Following washing, 100 µL of enzyme substrate was added to each well and incubated for 30 minutes at room temperature, covered. After the 30 minute incubation, 50 µL of stopping solution was added to each well.

Plates were gently agitated by hand or with an orbital shaker to mix the well contents. The frame of strips was placed in an ELISA plate reader. The absorbance of each well at 550 nm was determined. The average absorbance of the duplicate wells for each sample and control was calculated. If the absorbance of the subject sample was less than the absorbance of the positive control, the sample was negative, indicating an undetectable level of oncofetal fibronectin in the sample. If the sample absorbance is greater than or equal to the absorbance of the positive control, the sample was positive, indicating that oncofetal fibronectin was present in the sample. In any assay if the average absorbance of the positive control was not at least 0.02 absorbance units greater than the average absorbance of the negative control, the results were discarded and the assay procedure was repeated.

Example 10

Pre-Term Labor Sandwich Immunoassay

The procedure of Example 9 was repeated with test samples obtained during weeks 20-36 of pregnancy. Studies were conducted at three perinatal referral clinics in the United States. Women were evaluated for admission to the hospital for either suspected pre-term rupture of membranes or suspected pre-term labor with intact membranes.

Confirmation of rupture of membranes was made by visual examination of the vagina for gross pooling of amniotic fluid, microscopic examination of dried vaginal secretions for ferning, presence of alkaline vaginal secretions using nitrazine paper and ultrasound diagnosis of oligohydramnios. Rupture of membranes was defined by the presence of any two of these four diagnostic criteria. One hundred-seventeen women with intact amniotic membranes pregnant between 23 weeks and 36 weeks, 6 days of gestation based on last known menstrual period and expected date of confinement confirmed by first trimester pelvic examination and ultrasonography <28 weeks gestation are subsequently described. Women were determined by the attending physician to be at risk of pre-term labor and subsequent delivery based on medical history and clinical examination including recording of uterine contractions and examination of the cervix. Since the clinical definition of pre-term labor is sometimes difficult to establish, data establishing the clinical utility of oncofetal fibronectin were analyzed using pre-term delivery as the outcome variable.

To assess the potential for cervicovaginal contamination by maternal plasma fibronectin, maternal blood specimens were obtained from 52 women with apparently healthy pregnancies during second or third trimester. Amniotic fluid specimens were obtained from 92 subjects undergoing amniocentesis for genetic diagnosis in early second trimester and 8 subjects undergoing amniocentesis for evaluation of fetal lung maturity prior to elective repeat, cesarean section in third trimester.

The assay results indicated that the concentration of oncofetal fibronectin in amniotic fluid in second trimester was 87.1±4.8 µg/mL (n=92) and 27.1±17.3 µg/mL (n=8) in third trimester.

The concentration of oncofetal fibronectin in maternal plasma in the second trimester was 1.48±0.11 µg/mL (n=20) and 3.19±0.30 µg/mL (n=32) in the third trimester.

For the 117 subjects with suspected pre-term labor and intact amniotic membranes, 49 of 59 (sensitivity=83.1%) women delivering prematurely (PTD) had oncofetal fibronectin in their cervicovaginal secretions compared to 11 of 58 women (specificity=81.0%) delivering at term (TD) (p<0.01). Similarly, those subjects with oncofetal fibronectin in their cervicovaginal secretions were far more likely to deliver prematurely (positive predictive value=81.7%) than those women not expressing cervicovaginal oncofetal fibronectin (negative predictive value=82.5%).

The presence of cervicovaginal oncofetal fibronectin was a sensitive and specific predictor of the risk of pre-term delivery in these women with suspected pre-term labor. The presence of oncofetal fibronectin in these subjects was strongly associated with risk of pre-term delivery with a logistic regression odds ratio of 3.79 (95% CI:2.33, 6.15; p<0.01).

To evaluate for potential confounding by oncofetal fibronectin of maternal origin, the data were analyzed after exclusion of 31 samples contaminated with blood. As shown below, similar proportions of subjects had oncofetal fibronectin in their cervicovaginal secretions and delivered prematurely. Furthermore, inclusion of the presence or absence of vaginal bloody show into the stepwise logistic regression model gave an odds ratio of 1.70 (95% CI: 0.91, 3.18; p=0.1) demonstrating that bloody show was not an independent predictor of pre-term delivery after oncofetal fibronectin was introduced into the model. It was clear, however, from univariate analysis that detection of oncofetal fibronectin in cervicovaginal secretions contaminated with blood is an indicator of imminent delivery.

The utility of oncofetal fibronectin for identifying women at risk of PTD was maintained even when women in pre-term contractions with intact membranes with cervical dilation exceeding 2 cm were eliminated from the analysis. The logistic regression odds ratio of 3.18 (95% CI: 1.8, 5.6, p<0.01) confirmed the predictive value of oncofetal fibronectin in this clinically discrete population.

Example 11

Oncofetal Fibronectin Assay Kit and Method

An assay kit for oncofetal fibronectin included the following components. This kit was designed to be used to perform a rapid, bedside assay.
1. an assay device having a plastic housing and containing:
   (a) a porous nylon membrane to which is bound a monoclonal anti-oncofetal fibronectin antibody;
   (b) a flow control membrane system; and
   (c) an absorbent layer
2. a colloidal gold-labeled goat anti-fibronectin antibody conjugate in a protein matrix
3. conjugate reconstitution buffer
4. a wash solution
5. a sterile, polyester sample collection swab The membrane device was prepared by the following procedure. Approximately 2 µL of the murine monoclonal antibody FDC-6 prepared as described in Example 6 is applied to a membrane surface (1.2 µm nylon, Biodyne-A, Pall) in a pH 6, 0.01 M phosphate buffered saline (PBS), 0.1 M citrate buffer containing 0.5 mg/mL BSA. A procedural control containing human plasma fibronectin purified as described in Example 4 in the same buffer also is applied to a discrete region of the membrane. After the membrane has air dried, a blocking reagent of PBS-buffered, 0.5% nonfat dry milk is added to the membrane. The excess blocking reagent is removed after at least about 20 minutes.

The membrane-holding device (Target Device, V-Tech, Pomona, Calif.) is assembled with a second porous layer (0.45 µm low protein-binding nylon, LoProdyne, Pall) beneath the antibody-bearing membrane (in the direction of sample application) for controlling the flow of sample solution from the assay membrane to the absorbent layer. The two porous membranes then are placed over an absorbent porous polyethylene layer having a capacity of greater than 1.5 mL (Chromex, Brooklyn, N.Y.) and enclosed in the device. The device is packaged individually in a sealed plastic bag containing desiccant.

The colloidal gold is prepared by the reduction of 0.01% tetrachloroauric acid with 0.16% sodium citrate in a manner which produces approximately 30 nm particles. Briefly, the two solutions are heated separately to 90° C. The reducing solution is added to the gold solution while vigorously stirring. The combined solution is boiled (100° C.) for at least 10 minutes.

Affinity purified goat anti-fibronectin antibody (prepared as described in Example 4) was bound to the colloidal gold by adsorption. Briefly, the colloidal gold solution prepared above was combined with the antibody (5-10 µg/mL) in water. Following conjugation, the conjugate solution was stabilized by the addition of 5% BSA and 5% polyvinylpyrrolidine (final concentration).

The stock conjugate was concentrated approximately 10- to 12-fold by ultrafiltration using a hollow fiber filter. The concentrated conjugate was diluted to an appropriate level in 15 mM Tris, 2% BSA, 0.1% Tween 20, 0.2% polyethylene glycol, 8% polyvinylpyrrolidine and 0.04% thimerosal. An appropriate concentration was determined by using a range of dilutions in a sample assay procedure as described below and determining the dilution which produces the best result.

The selected conjugate dilution is placed in polyethylene sample collection tubes and lyophilized. The tubes are fitted with 2 µm pore size polyethylene sample filters (Porex Technologies, Fairburn, Ga.) during the lyophilization process. The lyophilized conjugate is individually packaged in a foil pouch with desiccant.

The conjugate reconstitution buffer is 100 mM sodium acetate. This buffer is packaged as a unit dose in a 1 mL disposable tube.

The wash solution is water packaged as a unit dose in a disposable tube.

The kit additionally contains an individually packaged sterile polyester swab and a procedural summary card.

The assay was performed as follows:
1. Before collecting the sample, remove the plastic tube containing gold conjugate from the foil pouch, remove the dropper tip and add the entire contents of the tube containing the conjugate reconstitution buffer.
2. Collect the sample with the swab provided. During a sterile speculum examination, insert the swab into the posterior fornix of the vagina, twirl for approximately 10 seconds to absorb fluid. Immediately proceed to perform the test. Place the swab in the gold conjugate solution and mix rapidly with an up and down motion for 10 to 15 seconds.
3. Remove as much liquid as possible from the swab by rolling the tip on the inside of the tube. Dispose of the swab in a manner consistent with handling potentially infectious materials.

4. Replace the dropper tip on the plastic tube and immediately dispense the entire volume of diluted filtered sample onto the surface of the membrane device.
5. After the sample liquid has been absorbed into the membrane surface, add a few drops of wash solution and observe the results.
6. A negative result is indicated by a red color in the procedural control area of the membrane only. A positive result is indicated by a pink or red spot in the test zone of the membrane as well as in the control zone.

Example 12

Detection of Oncofetal Fibronectin in Cervicovaginal Samples as a Marker for Cervical Cancer Swab samples of the cervical os of 15 subjects diagnosed with cervical cancer were collected. Specifically, a polyester swab (Adeza Specimen Collection Kit, Adeza Biomedial, Inc., Sunnyvale, Calif.) was used to swab either a cervical lesion at the cervical os, or the transition zone at the cervical os and some transition zone swabs also included a swab of the ectocervix. To extract material from each swab into a buffer, each swab was placed into separate vessels containing 1 ml antiprotease buffer (APB) containing 0.05 M Tris buffer, pH 7.4, 150 mM NaCl, 0.02% $NaN_3$, 1% BSA, 5 mM EDTA, 1 mM phenylmethylsulfonyl fluoride (PMSF), 500 Kallikrein Units/ml of Aprotinin, and 0.1% Triton X-100.

Lateral flow was performed for each sample by adding 200 μl of each swab-released APB sample to a test strip containing an absorbent pad which draws the liquid sample to the test strip. The sample first flowed through a mobilization region containing a conjugate of FDC-6 conjugated to blue microspheres (Adeza Biomedical, Inc.). The conjugate was mobilized by the flow of the sample. The sample and conjugate then flowed through a fibronectin or oncofetal fibronectin binding region containing goat polyclonal anti-fibronectin antibodies, such as those described in Example 4 (also referred to herein as A120 antibodies) non-diffusibly bound to the test strip. Finally, the sample flowed through a control region containing goat polyclonal anti-mouse IgG antibody (which selectively binds the FDC-6 blue latex microsphere conjugate) non-diffusibly bound to the test strip. The test strip was then placed in a reader device which measured light reflectance in the detection and control regions.

Of samples from subjects having cervical cancer, 100% had detectable levels of oncofetal fibronectin in this test (15 out of 15 samples). Similar results were obtained from ELISA assays (see Example 9) of these samples.

Example 13

Detection of Oncofetal Fibronectin in Urine Samples as a Marker for Bladder Cancer Urine samples were collected from 44 bladder cancer subjects. Among these, 23 subjects were diagnosed with T1 stage bladder cancer, 7 subjects were diagnosed with T2 stage bladder cancer, 6 subjects were diagnosed with T3 stage bladder cancer, 2 subjects were diagnosed with T4 stage bladder cancer and 6 subjects had an unknown stage bladder cancer. Control samples from 41 subjects free of bladder cancer also were collected. The samples were frozen and stored at −80° C. Before testing, the samples were thawed. Samples were tested neat (i.e., without adding buffer or reagents) or were diluted, as provided below.

Testing was performed by three different methods: dot blot analysis, dipstick/lateral flow and vertical flow.

A. Dot Blot

For this analysis, 49 urine samples were tested: 29 urine samples from subjects with bladder cancer and 20 urine samples from control subjects (positive and negative). Blot assays were performed by incubating the mouse monoclonal anti-oncofetal fibronectin FDC-6 antibody and a horseradish peroxidase-conjugated anti-mouse IgG antibody with a nitrocellulose membrane to which thawed frozen urine samples were applied. Briefly, frozen urine samples were thawed and were added to a nitrocellulose membrane by applying 5 μl of each sample to a discrete position on the nitrocellulose membrane. Liquid samples applied to the nitrocellulose membrane were air dried. Non-specific protein binding was blocked by incubating the nitrocellulose membrane in a solution containing 20 mM Tris-HCl, 150 mM NaCl, pH 7.5, 0.05% Tween 20 and 5% BSA (BSA/TBS-T), for 1 hour, after which the BSA/TBS-T solution was removed. Next, primary antibody solution containing 6 μg/ml FDC-6 in BSA/TBS-T was incubated with the nitrocellulose membrane for 30 minutes. The nitrocellulose membrane was then rinsed three times in a solution containing 20 mM Tris-HCl, 150 mM NaCl, pH 7.5 and 0.05% Tween 20 (TBS-T). Next, secondary antibody solution containing anti-mouse IgG conjugated with horseradish peroxidase (Jackson Immunologicals, West Grove, Pa.) in BSA/TBS-T was incubated for 30 minutes, followed by three rinses with TBS-T, followed by two rinses in a solution containing a solution containing 20 mM Tris-HCl and 150 mM NaCl, pH 7.5 (TBS). The nitrocellulose membrane was then briefly incubated with equal amounts of enzyme chemiluminescence solutions 1 and 2 (Amersham ECL Western Blotting Detection Reagents, Cat. No. RPN2109; Amersham Biosciences Corp., Piscataway, N.J.); the excess liquid was removed and the nitrocellulose membrane was wrapped in plastic wrap, placed in a film cassette and exposed to film for 1 minute. The film was developed and scanned for exposure to chemiluminescence. Confirmation that the signals were indicative of oncofetal fibronectin was performed by Western blot analysis.

Of samples from subjects having bladder cancer, 79% were positive for oncofetal fibronectin in this test (23 out of 29 samples). Of samples from subjects not having bladder cancer, 90% were negative for oncofetal fibronectin in this test (18 out of 20 samples). Thus, presence of oncofetal fibronectin had a 92% positive predictive value for the presence of bladder cancer and absence of oncofetal fibronectin had a negative predictive value of 75% for the absence of bladder cancer. Determination of being positive for oncofetal fibronectin was made according to the presence of any signal above background.

B. Dipstick/Lateral Flow

For this analysis, 59 urine samples were tested: 35 urine samples from subjects with bladder cancer and 24 urine samples from control (positive and negative) subjects. Lateral flow was performed by adding 100 μl of urine sample to 300 μl of APB (0.05 M Tris buffer, pH 7.4, 150 mM NaCl, 0.02% $NaN_3$, 1% BSA, 5 mM EDTA, 1 mM phenylmethylsulfonyl fluoride (PMSF), 500 Kallikrein Units/ml of Aprotinin and 0.1% Triton X-100), and then by applying 200 μl of this diluted urine sample mixture to a test strip containing an absorbent pad which draws the sample to the test strip. The sample first flowed through a mobilization region containing a conjugate of FDC-6 conjugated to blue microspheres (Adeza Biomedical, Inc.) diffusably bound to the test strip. The conjugate was mobilized by the flow of the sample. Next, the sample and conjugate flowed through a non-specific binding trap region containing methylated BSA attached to the test strip. The sample and conjugate then flowed through a region containing goat polyclonal anti-fibronectin antibodies, such as those described in Example 4 (also referred to herein as A120 antibodies), non-diffusably bound to the test strip. Finally, the sample and conjugate flowed through a control region containing goat polyclonal anti-mouse IgG antibody (which selectively binds the FDC-6 conjugate) non-diffusably bound to the test strip. The test strip was then visually inspected for the presence or absence of blue color in the detection and control regions.

Of samples from subjects having bladder cancer, 66% were positive for oncofetal fibronectin in this test (23 out of 35 samples). Of samples from subjects not having bladder cancer, 88% were negative for oncofetal fibronectin in this test (21 out of 24 samples). Thus, presence of oncofetal fibronectin had a 89% positive predictive value for the presence of bladder cancer and absence of oncofetal fibronectin had a negative predictive value of 64% for the absence of bladder cancer. Determination of being positive for oncofetal fibronectin was made according to the presence of any signal above background.

C. Vertical Flow

Vertical flow analysis was used to examine 43 urine samples of subjects with bladder cancer and 42 urine samples from control subjects. Vertical flow was performed by dissolving a lyophilized polyclonal goat anti-human fibronectin antibody/colloidal gold conjugate in a reconstitution buffer containing 100 mM NaOAC and 3 mM $NaN_3$. Six drops (about 150-300 µl) of urine sample was added to 1 ml of the reconstituted conjugate solution. The sample mixture was added to the surface of a membrane containing beneath the membrane an absorbent pad which draws the liquid sample through the membrane. In the center of the test strip is a fibronectin or oncofetal fibronectin binding region containing FDC-6 (ATCC HB-9018) non-diffusably bound to the test strip. Separate from and encircling the FDC-6 region is a ring-shaped control region containing fibronectin that can specifically bind to the polyclonal goat anti-human fibronectin antibody/colloidal gold conjugate. After the sample passed through the membrane, presence of a ring along the periphery detected by visual inspection indicated that the test was complete and that the anti-fibronectin/colloidal gold conjugate migrated along the test strip. Presence of a pink or purple spot within the ring detected by visual inspection indicated that the test was positive for oncofetal fibronectin.

Of samples from subjects having bladder cancer, 54% were positive for oncofetal fibronectin in this test (23 out of 43 samples). Of samples from subjects not having bladder cancer, 67% were positive for oncofetal fibronectin in this test (28 out of 42 samples). Thus, presence of oncofetal fibronectin had a 62% positive predictive value for the presence of bladder cancer and absence of oncofetal fibronectin had a negative predictive value of 58% for the absence of bladder cancer. Determination of being positive for oncofetal fibronectin was made according to the presence of any signal above background.

D. BTA Stat

For this analysis, 68 urine samples were tested: 26 urine samples from subjects with bladder cancer and 42 urine samples from control (positive and negative) subjects. Blot assays were performed by adding 5 drops of urine to a BTA-stat test strip (Polymedco, Inc., Cortlandt Manor, N.Y.). The BTA-stat test strip contains a mobilizable anti-BTA antibody conjugated to a detectable moiety and the mixture migrates to a region containing an antibody that binds to BTA, which region, when sufficient BTA is present, form a visible line that indicates that the sample is positive for BTA.

Of samples from subjects having bladder cancer, 65% were positive for BTA in this test (17 out of 26 samples). Of samples from subjects not having bladder cancer, 21% were positive for BTA in this test (9 out of 42 samples) and 79% were negative for BTA in this test (33 out of 42 samples). Thus, presence of BTA had a 65% positive predictive value for the presence of bladder cancer and absence of BTA had a negative predictive value of 79% for the absence of bladder cancer.

E. OnfFN and BTA-Stat in Combination

Samples for which BTA analysis and onfFN measurements were performed were compared relative to the cancerous state of the subject; 48 urine samples were tested: 23 urine samples from subjects with bladder cancer and 25 urine samples from control (positive and negative) subjects.

All 15 subjects that provided samples positive for BTA and onfFN had bladder cancer. For subjects that provided samples negative for BTA and onfFN, 91% did not have bladder cancer (20 of 22). For subjects that provided samples negative for BTA and positive for onfFN, 71% had bladder cancer (5 of 7). For subjects that provided samples positive for BTA and negative for onfFN, 25% had bladder cancer (1 of 4).

F. Immunoprecipitation and Western Blot

For this analysis, urine samples were tested. Immunoprecipitation was performed by incubating the mouse monoclonal anti-oncofetal fibronectin A120 antibody (0.5-1.0 ng/well) or antibody A137 (2.5-5.0 ng/well) diluted 1:10 with APB buffer. 30 µl A137 coated beads was added to 800 µl of sample. Acid from the precipitation samples was neutralized by washing with PBS. An internal standard was set: (25 µg/ml in APB=2 ng/well): <50% of 25 ng/ml in APB as negative (−); 50-60% of 25 ng/ml in APB as positive (+); 60-70% of 25 ng/ml in APB as positive (++); 70-80% of 25 ng/ml in APB as positive (+++); and 80-100% of 25 ng/ml in APB as positive (++++). Western blots were performed as described above.

G. Combined Results

Abbreviations are as follows: BC=bladder cancer, PC=prostate cancer; BPH=benign prostate hyperplasia, KC=kidney cancer, hydronephrosis (HN), vasectomy (VS) and incontinence (IN)=symptomatic urinary condition controls, stages and grades are as described above, pos=positive, and neg=negative.

TABLE 2

Urinary oncofetal fibronectin levels as an indication of bladder cancer

| Subject | Condition | Grade | Stage | Dot blot | Lateral flow | BTAStat | Vertical Flow | IP/WB |
|---|---|---|---|---|---|---|---|---|
| 1 | BC | 3 | T3A | 3 | 4 | Pos | | ++++ |
| 2 | BC | 2 | T1A | | | Pos | | |
| 3 | BC | 3 | T1B | 3 | | Pos | | ++++ |
| 4 | BC | 1 | T1A | | | Neg | | |
| 5 | BC | 3 | T1B | 1 | 0 | Pos | 1 | |

TABLE 2-continued

Urinary oncofetal fibronectin levels as an indication of bladder cancer

| Subject | Condition | Grade | Stage | Dot blot | Lateral flow | BTAStat | Vertical Flow | IP/WB |
|---|---|---|---|---|---|---|---|---|
| 6 | BC | 3 | T3AN1 | 0.5 | 0 | Pos | 1 | − |
| 7 | BC | 3 | T2B | 0 | 1 | Neg | 1 | |
| 8 | BC | 3 | T2B | 2 | 0 | Neg | 1 | ++++ |
| 9 | BC | 3 | T3A | 1 | 2 | Pos | 0 | ++++ |
| 10 | BC | 3 | T2 | | | Pos | | |
| 11 | BC | 3 | T1B | 1 | 3 | Pos | 0 | ++++ |
| 12 | BC | 3 | T1B | | | Neg | | |
| 13 | BC | 2 | T1B | 1 | 0.5 | Pos | 1 | − |
| 14 | BC | 3 | T2B | 2 | 1 | Pos | 1 | ++++ |
| 15 | BC | 1 | T1A | 0 | 0 | Neg | 0 | |
| 16 | BC | 1 | T1A | 1 | 1 | Pos | 0 | ++++ |
| 17 | BC | 1 | T1A | 0 | 0.5 | Pos | 0 | − |
| 18 | BC | 3 | | 3 | 2 | Pos | | |
| 19 | BC | 3 | T4 | 3 | 3 | Pos | 1 | ++++ |
| 20 | BC | 3 | | | | Pos | | |
| 21 | BC | | None | 0.5 | 0 | Neg | 1 | − |
| 22 | BC | 2 | T1 | 3 | 1 | Pos | 1 | ++++ |
| 23 | BC | 1 | T1A | | 0 | Pos | | +++ |
| 24 | BC | 2 | T1 | 3 | 3 | Pos | 0 | ++++ |
| 25 | BC | 1 | T1 | 0 | 0 | Neg | 1 | − |
| 26 | BC | | None | 3 | 3 | | | ++++ |
| 27 | BC | 2 | T1 | 0.5 | 0 | Neg | 0 | − |
| 28 | BC | 3 | T1 | 1 | 1 | Neg | 0 | − |
| 29 | BC | 1 | T1 | | | | | ++ |
| 30 | BC | | None | 3 | 3 | | | ++++ |
| 31 | BC | | None | 0 | 0.5 | | | − |
| 32 | BC | 1 | T1 | 0 | 0 | | | 1 |
| 33 | BC | 3 | T1 | 3 | 1 | | | ++++ |
| 34 | BC | 3 | T3 | 0.5 | 0 | | | ++++ |
| 35 | BC | 3 | T2 | 3 | 2 | | | ++++ |
| 36 | BC | 3 | T2 | 3 | 2 | | | ++++ |
| 37 | BC | 1 | T1 | | | | | − |
| 38 | BC | 3 | T4 | | 0 | | | |
| 39 | BC | 3 | T2 | | 0 | | | − |
| 40 | BC | 3 | T3 | | 1 | | | |
| 41 | BC | 2 | T1 | | 1 | | | |
| 42 | BC | 2 | T1 | | | | | + |
| 43 | BC | 3 | T3 | | 0 | | | |
| 44 | BC | 3 | T1 | | 1 | | | ++++ |
| 45 | PC | | | | | Neg | | |
| 46 | PC | | | | 0 | Neg | | ++++ |
| 47 | PC | | | | | Pos | | ++++ |
| 48 | PC | | | | | Neg | | − |
| 49 | PC | | | 0 | 0 | Neg | | − |
| 50 | BPH | | | 0 | 0 | Neg | | |
| 51 | BPH | | | | 0 | Neg | | +++ |
| 52 | BPH | | | | 0 | Neg | | − |
| 53 | BPH | | | | 0 | Neg | | |
| 54 | BPH | | | | 0 | Neg | | − |
| 55 | BPH | | | | 0 | Pos | | ++++ |
| 56 | BPH | | | 0 | 0 | Neg | | − |
| 57 | BPH | | | | | Pos | | ++++ |
| 58 | BPH | | | | | Neg | | − |
| 59 | BPH | | | 0 | | Neg | | |
| 60 | BPH | | | | | Neg | | − |
| 61 | KC | | | 0 | 0 | Neg | | − |
| 62 | KC | | | 0 | 0 | Neg | 1 | |
| 63 | HN | | | | | Neg | | − |
| 64 | VS | | | | | Pos | | − |
| 65 | IN | | | 0 | 0 | Pos | 0 | − |
| 66 | Control | | | 3 | 0.5 | Pos | | |
| 67 | Control | | | 0 | 0 | Neg | | |
| 68 | Control | | | 0 | 0 | Neg | | − |
| 69 | Control | | | 0 | 0 | Neg | | − |
| 70 | Control | | | 0 | 0.5 | Neg | | |
| 71 | Control | | | 0 | 0 | Neg | | |
| 72 | Control | | | 3 | 3 | Neg | | − |
| 73 | Control | | | | | Neg | | − |
| 74 | Control | | | | | Neg | | |
| 75 | Control | | | | | Neg | | |
| 76 | Control | | | 0 | 0 | Neg | 0 | − |
| 77 | Control | | | | | Neg | | − |
| 78 | Control | | | | | Neg | | − |
| 79 | Control | | | | | Pos | | − |
| 80 | Control | | | 0 | 0 | Neg | | − |

TABLE 2-continued

Urinary oncofetal fibronectin levels as an indication of bladder cancer

| Subject | Condition | Grade | Stage | Dot blot | Lateral flow | BTAStat | Vertical Flow | IP/WB |
|---|---|---|---|---|---|---|---|---|
| 81 | Control | | | 0 | 0 | Neg | | – |
| 82 | Control | | | 0 | | Neg | 0 | – |
| 83 | Control | | | 0 | 0 | Pos | 1 | – |
| 84 | Control | | | 0 | 0 | Neg | 0 | – |
| 85 | Control | | | | | Neg | | |

Samples for which onfFN measurements were performed were compared relative to the cancerous state of the subject; 85 urine samples were tested: 44 urine samples from subjects with bladder cancer, 5 urine samples from subjects with prostate cancer, 11 urine samples from subjects with benign prostate hyperplasia, 2 urine samples from subjects with kidney cancer, 2 urine samples from symptomatic controls and 20 urine samples from control subjects.

Of samples from subjects having bladder cancer tested by lateral flow, 71% were positive for onfFN in this test (22 out of 31 samples). Of negative control samples from subjects not having bladder cancer tested by lateral flow, 94% were negative for onfFN in this test (15 out of 16 samples).

Of samples from subjects having bladder cancer as confirmed by immunoprecipitation and western blot, 65% were positive for onfFN in this test (20 out of 31 samples). Of negative control samples from subjects not having bladder cancer as determined by immunoprecipitation and western blot, 100% were negative for onfFN in this test (16 out of 16 samples). When a threshold of >50% of 25 ng/ml of onfFN was set for a positive outcome, 59% of stage T1 bladder cancer subjects were positive for onfFN in this test (10 out of 17 samples), 83% of stage T2 bladder cancer subjects were positive for onfFN in this test (5 out of 6 samples), 75% of stage T3 bladder cancer subjects were positive for onfFN in this test (3 out of 4 samples), 100% of stage T4 bladder cancer subjects were positive for onfFN in this test (1 out of 1 samples), 30% of benign prostate hyperplasia subjects were positive for onfFN in this test (3 out of 10 samples), 50% of prostate subjects were positive for onfFN in this test (2 out of 4 samples), 100% of subjects having symptomatic conditions (i.e., negative controls) were negative for onfFN in this test (10 out of 10 samples) and 100% of negative control subjects were negative for onfFN in this test (3 out of 3 samples).

Using immunoprecipitation and western blot analysis of the urine samples, it was possible to differentiate between invasive and non-invasive bladder cancer. Samples were tested for onfFN as described above, and a threshold of >50% of 25 ng/ml of onfFN was set for a positive outcome. Of the patients who had non-invasive bladder cancer, 54% tested at or above threshold, 80% of the patients identified as having invasive bladder cancer tested positive. In contrast, 100% of negative controls that had a level of onfFN less than 25 ng/ml (16 out of 16 samples).

Example 14

Treatment of Urine Samples to Detect Oncofetal Fibronectin Indicating the Presence of Bladder Cancer Urine samples were diluted 4-fold with antiprotease buffer (APB) containing 0.05 M Tris buffer, pH 7.4, 0.02% NaN$_3$, 1% BSA, 5 mM EDTA, 1 mM phenylmethylsulfonyl fluoride (PMSF), 500 Kallikrein Units/ml of Aprotinin, 150 mM NaCl and 0.1% Triton X-100.

Lateral flow was performed by adding 100 µl of urine sample to 300 µl of APB (0.05 M Tris buffer, pH 7.4, 150 mM NaCl, 0.02% NaN$_3$, 1% BSA, 5 mM EDTA, 1 mM phenylmethylsulfonyl fluoride (PMSF), 500 Kallikrein Units/ml of Aprotinin and 0.1% Triton X-100), and then by applying 200 µl of this diluted urine sample mixture to a test strip containing an absorbent pad which draws the sample to the test strip. The sample first flowed through a mobilization region containing a conjugate of FDC-6 conjugated to blue microspheres (Adeza Biomedical, Inc.) diffusibly bound to the test strip. The conjugate was mobilized by the flow of the sample. Next, the sample and conjugate flowed through a non-specific binding trap region containing methylated BSA attached to the test strip. The sample and conjugate then flowed through a region containing goat polyclonal anti-fibronectin antibodies, such as those described in Example 4 (also referred to herein as A120 antibodies) non-diffusibly bound to the test strip. Finally, the sample and conjugate flowed through a control region containing goat polyclonal anti-mouse IgG antibody (which selectively binds the FDC-6 conjugate) non-diffusibly bound to the test strip. The test strip was then visually inspected for the presence or absence of blue color in the detection and control regions. Variations of the lateral flow method were performed using BSA, W632 (anti-MHC Class I) and mouse IgG in the non-specific binding trap region upstream of the mobilization region.

Example 15

Immunoassay Test Strip

Figure 2:
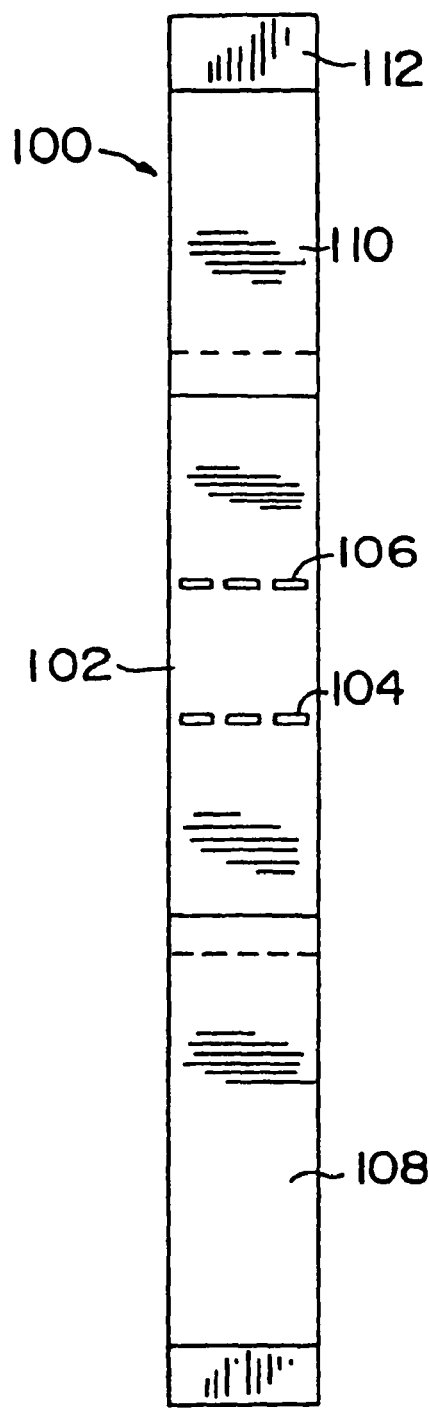
FIG. 2 depicts an overhead view of an exemplary test strip for oncofetal fibronectin indicating molecule detection.
Figure 3:
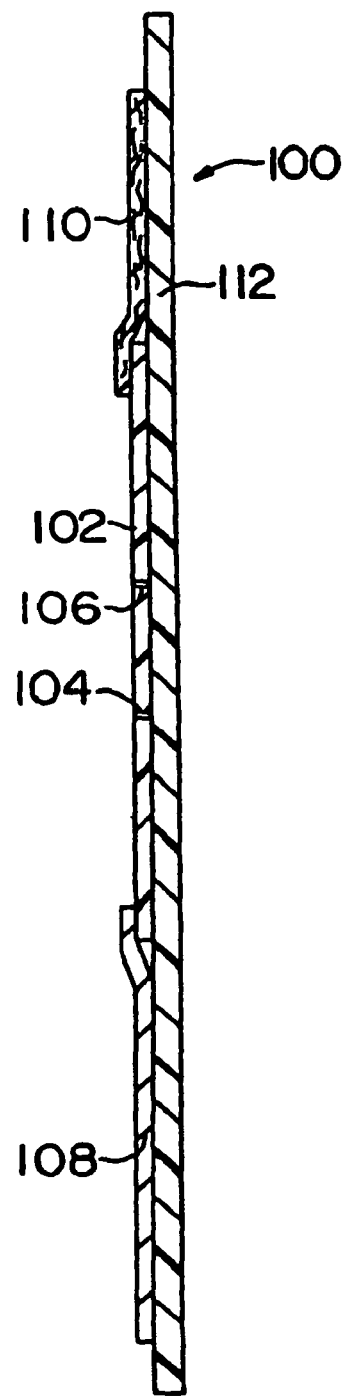
FIG. 3 depicts a side view of an exemplary test strip for oncofetal fibronectin indicating molecule detection.

The test strip 100 of FIGS. 2 and 3 includes a membrane system including three components: a porous or bibulous member 102; a conjugate pad 108; and an absorbent pad 110. The membrane system can be mounted on a substrate or backing 112, with the conjugate pad 108 and the absorbent pad 110 slightly overlapping the porous or bibulous member 102, which is interposed thereinbetween. As can be seen, the conjugate pad 108 overlaps the porous or bibulous member 102 so that a fluid sample placed onto the conjugate pad 108 is communicated from the conjugate pad 108 to the porous or bibulous member 102. Similarly, the absorbent pad 110 overlaps with the porous or bibulous member 102 so that fluid samples introduced into the porous or bibulous member 102 from the conjugate pad 108 can then be transmitted to the absorbent pad 110. Thus, the conjugate pad 108, the absorbent pad 110 and the porous or bibulous member 102 are all in fluid communication with one another, making any fluid sample placed on the conjugate pad 108 able to propagate through the conjugate pad 108 to the porous or bibulous member 110 and then to the absorbent pad 110.

The membrane system includes a conjugate pad 108, which serves as a sample application component and which includes an antibody to the analyte, which is conjugated to a detectable label. The conjugate pad is in fluid communication with the porous or bibulous member 102. The labeled antibody conjugate is diffusively bound to the conjugate pad and becomes mobile upon application of the liquid sample and moves along the test strip. The conjugate pad is made of a porous material, such as glass fiber. The conjugate pad also can act as a prefilter for the sample. The conjugate pad also can contain a non-specific binder such as a non-specific binding surface or a non-specific binding compound immobilized thereto.

The porous or bibulous member 102 is capable of transporting a liquid sample along the test strip and serves as the solid support upon which the immunoreactions occur. Antibodies which react with the target analyte and/or label are immobilized on the solid support. Possible solid supports include paper and cellulose derivatives, such as cellulose esters and ethers, natural and synthetic polymeric materials, such as vinyl polymers and partially hydrolyzed derivatives, polycondensates, copolymers and inorganic materials. An exemplary solid support is a nitrocellulose membrane.

The porous or bibulous member 102 contains at least two distinct zones, an analyte binding zone 104 and a control zone 106, at which different antibodies are immobilized. The analyte zone contains an immobilized analyte binding partner such as an antibody that binds the analyte of interest, whereas the control zone contains an immobilized antibody or other component, such as an antigen, that binds labeled antibody conjugate which has not bound to analyte.

In addition, the porous member can contain a non-specific binder. A non-specific binder can be located along any portion of the conjugate pad 108 or any portion of the porous or bibulous member 102 located between the analyte binding zone 104 and the conjugate pad 108.

The membrane system also can include an absorbent strip 112, which also is in fluid communication with the porous or bibulous member and which serves to draw liquid continuously through the device. The absorbent strip can be made of a material such as cellulose paper or other material known to those of skill in the art.

Figure 4:
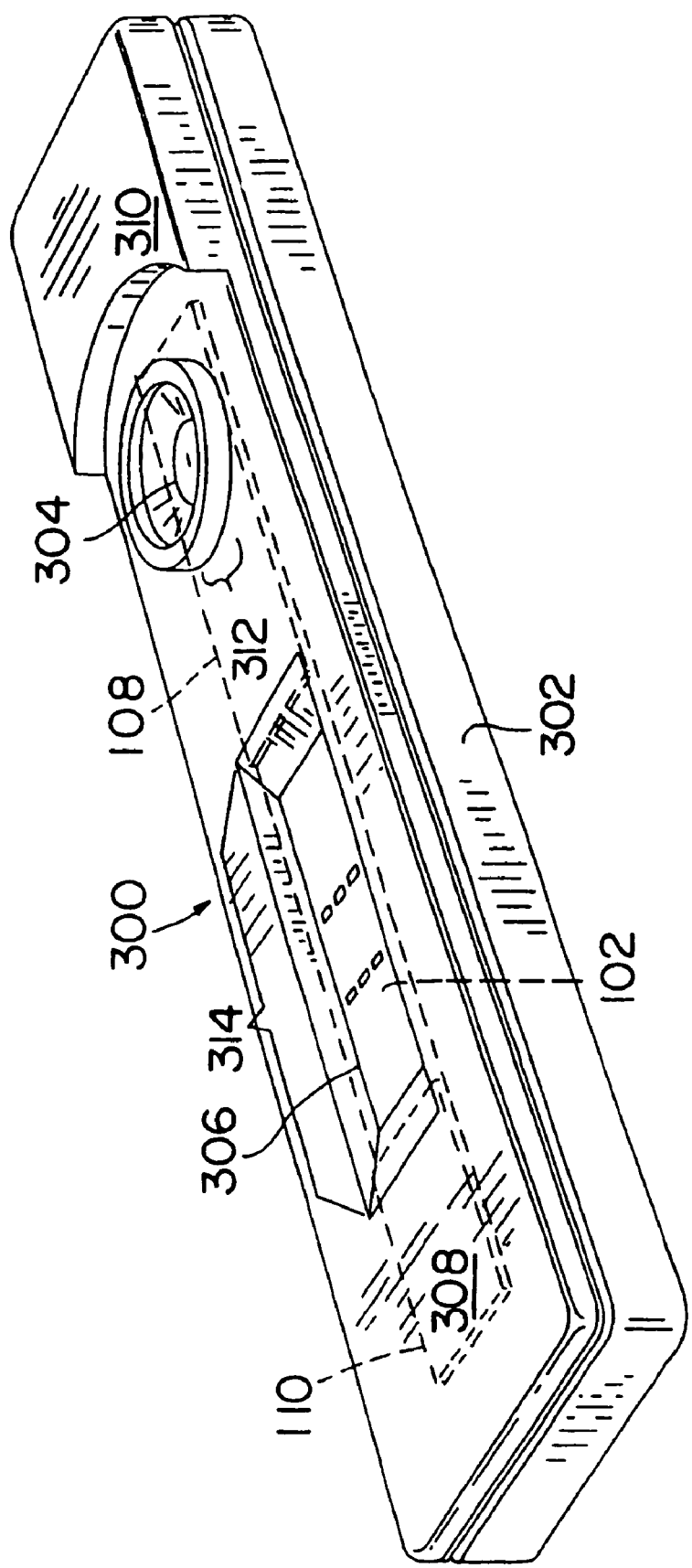
FIG. 4 depicts an exemplary test strip holder for oncofetal fibronectin indicating molecule detection.

Referring to FIG. 4, which depicts an exemplary immunoassay device, including a test strip and housing assembly 300, the housing 302 generally surrounds the test strip 100 (FIGS. 2 and 3) and includes an opening through which test sample is applied 304, as well as an aperture above the detection and control zones 306 that permits measurement of the amount of label by the reader, which is correlated with the amount of analyte in the test sample. The housing 302 includes at its upper surface 308 a fattened end 310, used for gripping the housing 302 and an application window 304 (or sample window) through which a sample is applied to a conjugate pad 108 of an immunoassay test strip within the housing 302. The housing 302 also includes a test window 314 through which the test result of the immunoassay is viewed. In accordance with the embodiments shown, no window material is mounted within the test window 314 (or the sample window 312). Thus, an optical path from outside the housing 302 through the test window 314 to the immunoassay test strip is unobscured by any material. Other alternative embodiments can include an optically transparent material (transparent at wavelengths emitted by light emitted from devices described herein).

Example 16

Oncofetal Fibronectin as an Indicator of Induction Outcome

A. Experimental Design

A.1 Objectives

A multicenter clinical trial was conducted to prospectively evaluate the utility of the onfFN test and outcomes associated with induction of labor in pregnant women with a gestational age of ≧36 0/7 and <42 0/7 weeks. For the purposes of this investigation, favorable outcomes of induction of labor include a reduced rate of cesarean section, an increased rate of vaginal delivery within 24 and 48 hours, a shortened time to delivery following administration of cervical ripening agents, a reduction in the number of cervical ripening agent administrations and a reduction in time interval from oxytocin initiation until delivery.

This study compared:
1. The rate of vaginal delivery within 24 hours and 48 hours of start of induction (including cervical ripening agent administration) in women testing onfFN positive versus onfFN negative.
2. The time interval from first dose of cervical ripening agent to delivery in women testing onfFN positive versus onfFN negative.
3. The number of cervical ripening agent administrations in women testing onfFN positive versus onfFN negative.
4. The time interval from oxytocin initiation to delivery in women testing onfFN positive versus onfFN negative.
5. The rate of cesarean section in nulliparous women with unfavorable cervices and intact amniotic membranes testing onfFN positive versus onfFN negative.

A.2 Study Design

The study was conducted prospectively and clinicians managing patients were blinded to results of the onfFN test. Patient management was not based on the clinician's knowledge of the onfFN test result. Enrolled women were followed from the time the informed consent was signed through delivery. The sample size used was estimated to provide 80-90% power to test each of the above-listed five clinical outcomes. Each outcome was tested at the 2-sided 5% significance level. Nine hundred and one women were considered enrolled. Of these 901 enrolled women, onfFN test results were not available for 26 women due to incorrect specimen handling. Therefore, 875 women were enrolled and deemed evaluable for the safety and effectiveness data analysis.

A.3 Subjects

Women scheduled for an induction of labor were pre-screened for inclusion in the study. Initial chart review determined if the woman was at least 18 years of age, nulliparous and with a singleton pregnancy in cephalic presentation with a gestational age between 36 0/7 and 42 0/7 weeks. An onfFN test specimen was obtained, as well as confirmation that amniotic fluid leakage had not occurred. Specimens for onfFN testing were collected from the posterior fornix of the vagina using the Adeza Biomedical Specimen Collection Kit (Sunnyvale, Calif.) before the clinician performed any other part of the pelvic exam. Testing was performed on the Rapid onfFN for the TLiIQ™ System (Adeza Biomedical, Sunnyvale, Calif.).

A.4 Data Collection and Analysis

Statistical analyses were performed using ANOVA for comparison of three or more groups. The 2-sample t-test was used to compare the means of continuous variables. The Fisher's Exact test, Chi-square Test or Wilcoxon 2-sample rank test was used to compare groups for discrete variables, as appropriate. The univariate and multivariate association of dichotomous or polychotomous variables to clinical outcome variables of interest was evaluated using logistic or general linear regression modeling methods, as appropriate. All tests were two-tailed and a p-value of less than 0.05 was required for statistical significance. Statistical evaluations were performed using the Statistical Analysis System (SAS Institute, Cary, N.C.).

B. Results

Of the 875 study women, 371 (42.4%) tested onfFN positive and 504 (57.6%) tested onfFN negative. The outcomes of induction for this population is presented below.

B.1 The Rate of Cesarean Section in Women Testing onfFN Positive Versus onfFN Negative There was a difference in cesarean section rate in women testing onfFN positive and onfFN negative. In women testing onfFN negative, 187 delivered by cesarean section and 317 did not, resulting in an observed rate of cesarean section of 0.371. In women testing onfFN positive, 107 delivered by cesarean section and 264 did not, resulting in an observed rate of cesarean section of 0.288. The rate difference of 0.083 (standard error=0.032) was statistically significant with a p-value of 0.011 (Fisher's Exact test). Thus the cesarean section rate of women testing onfFN negative was greater than the cesarean section rate for women testing onfFN positive.

The ratio of the rates is another way to quantify the difference in cesarean section rates between women testing onfFN negative and women testing onfFN positive. The rate ratio (0.371/0.288) of 1.29 indicates that women testing onfFN negative prior to induction of labor were 29% [95% CI 6%, 57%] more likely to be delivered by cesarean section than women testing onfFN positive.

B.2 The Rate of Vaginal Delivery Within 24 and 48 Hours of Start of Induction in Women Testing onfFN Positive versus onfFN Negative There was a difference in rate of vaginal delivery within 24 hours of initiation of cervical ripening agents or oxytocin among women testing onfFN positive and onfFN negative. In women testing onfFN positive, 229 delivered vaginally within 24 hours of initiating cervical ripening or oxytocin and 138 did not, resulting in an observed rate of vaginal delivery within 24 hours from initiation of cervical ripening or oxytocin in women testing onfFN positive of 0.624. In women testing onfFN negative, 225 delivered vaginally within 24 hours of initiating cervical ripening or oxytocin and 274 did not, resulting in an observed rate of vaginal delivery within 24 hours from initiation of cervical ripening or oxytocin in women testing onfFN negative of 0.451. Nine women were omitted either because they did not receive cervical ripening or oxytocin, or data were missing for them. The rate difference of 0.173 (standard error=0.034) was statistically significant with a p-value<0.0001 (Fisher's Exact test). Thus, the rate of vaginal delivery within 24 hours from initiation of cervical ripening or oxytocin in women testing onfFN positive was greater than the rate of vaginal delivery within 24 hours from initiation of cervical ripening or oxytocin in women testing onfFN negative.

The ratio of the rates of vaginal delivery within 24 hours from initiation of cervical ripening or oxytocin in women testing onfFN positive versus women testing onfFN negative (0.624/0.451) was 1.38. Thus, when results are expressed as a ratio of rates, women testing onfFN positive prior to induction of labor were 38% [95% CI 22%, 57%] more likely to have a vaginal delivery within 24 hours from initiation of cervical ripening or oxytocin than women testing onfFN negative.

In women testing onfFN positive, 253 delivered vaginally within 48 hours of initiating cervical ripening or oxytocin and 114 did not, resulting in an observed rate of vaginal delivery within 48 hours from initiation of cervical ripening or oxytocin in women testing onfFN positive of 0.689. In women testing onfFN negative, 299 delivered vaginally within 48 hours of initiating cervical ripening or oxytocin and 200 did not, resulting in an observed rate of vaginal delivery within 48 hours from initiation of cervical ripening or oxytocin in women testing onfFN negative of 0.599. Nine women were omitted either because they did not receive cervical ripening or oxytocin, or data were missing for them. The rate difference of 0.090 (standard error=0.033) was statistically significant with a p-value=0.007 (Fisher's Exact test). Thus, the rate of vaginal delivery within 48 hours from initiation of cervical ripening or oxytocin in women testing onfFN positive was greater than the rate of vaginal delivery within 48 hours from initiation of cervical ripening or oxytocin in women testing onfFN negative.

The ratio of the rates of vaginal delivery within 48 hours from initiation of cervical ripening or oxytocin in women testing onfFN positive versus women testing onfFN negative (0.689/0.599) was 1.15. Thus, when results are expressed as a ratio of rates, women testing onfFN positive prior to induction of labor were 15% [95% CI 4%, 27%] more likely to have a vaginal delivery within 48 hours from initiation of cervical ripening or oxytocin than women testing onfFN negative.

B.3 The Time Interval from First Dose of Cervical Ripening Agent or Oxytocin to Delivery in Women Testing onfFN Positive Versus onfFN Negative The mean observed time from the first administration of a cervical ripening agent or oxytocin to delivery was 9.6 hours longer in women testing onfFN negative (28.7 hours) than for women testing onfFN positive (19.1 hours). The standard error of this difference was 1.92 and the 2-sample t-test p-value was <0.0001. Thus the mean number of hours from initiation of cervical ripening or oxytocin to delivery was fewer among women testing onfFN positive than among women testing onfFN negative.

B.4 The Number of Cervical Ripening Agent Administrations in Women Testing onfFN Positive Versus onfFN Negative The mean observed number of cervical ripening agent administrations was 0.60 greater in women testing onfFN negative (1.43) than for women testing onfFN positive (0.83). The standard error of this difference was 0.08 and the 2-sample t-test p-value was <0.0001. Thus, the mean number of cervical ripening administrations was fewer among women testing onfFN positive than among women testing onfFN negative.

B.5 The Time Interval from Oxytocin Initiation to Delivery in Women Testing onfFN Positive Versus onfFN Negative The mean observed time from oxytocin administration to delivery was 4.4 hours longer in women testing onfFN negative (16.8 hours) than for women testing onfFN positive (12.4 hours). The standard error of this difference was 1.07 and the 2-sample t-test p-value was <0.0001. Thus, the mean number of hours from oxytocin initiation to delivery was fewer among women testing onfFN positive than among women testing onfFN negative.

C. Summary of Association of onfFN Test Results with Outcome

The association of the onfFN test with induction of labor outcomes for differences in rates (cesarean section and vaginal delivery within 24 and 48 hours) and for differences in means (time interval from first dose of cervical ripening agent, number of cervical ripening agent administrations and time interval from oxytocin initiation to delivery) is shown in Tables 3 and 4, respectively. Compared to women testing onfFN negative, those testing onfFN positive are less likely to deliver by cesarean section and are more unlikely to have a vaginal delivery within 24 hours, a shortened time to delivery, a reduction in the number of cervical ripening agent administrations and a shortened time from oxytocin initiation until delivery.

TABLE 3

|  | Rate Difference | Standard Error | p-value |
|---|---|---|---|
| Cesarean Section | 0.083 | 0.032 | 0.011 |
| Vaginal Delivery < 24 Hours | 0.173 | 0.035 | <0.0001 |
| Vaginal Delivery > 48 Hours | 0.090 | 0.033 | 0.007 |

TABLE 4

|  | Mean Difference | Standard Error | p-value |
|---|---|---|---|
| Intverval From Cervical Ripening agent or Oxytocin to Delivery (hours) | 9.6 | 1.92 | <0.0001 |
| Number of Cervical Ripening Agent Administrations | 0.603 | 0.085 | <0.0001 |
| Interval from Oxytocin Initiation to Delivery (hours) | 4.4 | 1.07 | <0.0001 |

Example 17

Differential Outcomes at Different Levels of Oncofetal Fibronectin

Cervicovaginal swab samples collected from women in their 24th week of pregnancy were measured for concentrations of oncofetal fibronectin. The pregnant women were then followed and their date of delivery recorded. The pregnant women were pooled into three populations: (a) women with oncofetal fibronectin measurements below 60 ng/ml, (b) women with oncofetal fibronectin measurements between 60 ng/ml and 150 ng/ml and (c) women with oncofetal fibronectin measurements equal to or above 150 ng/ml. The percent of women from each population that remained undelivered was then plotted against the date of delivery (after the 24th week).

Each of the three populations showed different delivery outcomes. The lowest oncofetal fibronectin group had the highest percent undelivered throughout the remainder of the pregnancy term and the highest oncofetal fibronectin group had the lowest percent undelivered throughout the remainder of the pregnancy term. The intermediate group remained similar in outcome to the lowest oncofetal fibronectin group until about week 30 and then showed a delivery rate of about 5% per week for the following 6 weeks (30th week through 36th week). At the 36th week, about 65% of this population remained undelivered. The highest oncofetal fibronectin group showed a delivery rate of about 5% per week for the first four weeks (24th week through 28th week) and about 5% per two weeks for the following eight weeks (28th week through 36th week). Less than 60% of this population remained undelivered at the 36th week.

Example 18

Oncofetal Fibronectin Measurements in Swab Samples Collected from the Lower Third of the Vagina Cervicovaginal swab samples were collected from 259 pregnant subjects in two formats. The first cervicovaginal swab sample format was a swab of the posterior fornix. The second cervicovaginal swab sample format was a swab of the lower third of the vagina.

All samples were applied to a test strip using the lateral flow method described in Example 12, and the concentration of oncofetal fibronectin in the sample was determined according to reflectance intensity measured with a TLiIQ™ reflectance reader. Cervicovaginal swab samples of the posterior fornix were categorized as oncofetal fibronectin positive when the reflectance signal indicated an oncofetal fibronectin concentration of 50 ng/ml or more (for the lot of test strips used, the corresponding reflectance signal indicating 50 ng/ml was 0.315). Cervicovaginal swab samples of the lower third of the vagina were categorized as oncofetal fibronectin positive when the reflectance signal was 0.1 or greater. Since the reflectance signal for this test strip is a linear function of oncofetal fibronectin at these conditions, cervicovaginal swab samples of the lower third of the vagina were categorized as oncofetal fibronectin positive when the amount of oncofetal fibronectin was measured to be 16 ng/ml or more.

Of the two sets of 259 samples, 239 sets of samples were in agreement. Specifically, of 239 sets of samples, for 205 sets both were negative and for 34 sets both were positive. Of the 20 sets of samples that differed, only 3 samples were negative in the lower third of the vagina while being positive in the posterior fornix. The remaining 17 samples were posterior fornix negative and lower third positive. Thus, a positive measurement of the posterior fornix is accompanied by a positive measurement of the lower third of the vagina in 91.9% of the measurements and a negative measurement of the posterior fornix is accompanied by a negative measurement of the lower third of the vagina in 92.3% of the measurements. A positive measurement of the lower third of the vagina is accompanied by a positive measurement for the posterior fornix in 66.7% of the measurements and a negative measurement of the lower third of the vagina is accompanied by a negative measurement for the posterior fornix in 98.6% of the measurements.

Since modifications will be apparent to those of skill in this art, it is intended that this invention be limited only by the scope of the appended claims.

What is claimed is:

1. A method for classifying the level of oncofetal fibronectin in a sample, comprising: measuring the amount of an oncofetal fibronectin indicating molecule in a sample; comparing the amount of oncofetal fibronectin indicating molecule in a sample to two or more threshold levels derived from the source of the oncofetal fibronectin; and classifying the amount of oncofetal fibronectin indicating molecule in a sample according to the highest threshold level that is less than or equal to amount of oncofetal fibronectin indicating molecule in the sample, whereby classification of oncofetal fibronectin indicating molecule in the sample according to the highest threshold identifies an indication of the presence of cancerous cells, an increased risk of developing cancer or recurrence of cancer.

* * * * *

SEQUENCE LISTING

<160> NUMBER OF SEQ ID NOS: 39

<210> SEQ ID NO 1
<211> LENGTH: 7388
<212> TYPE: DNA
<213> ORGANISM: Homo Sapiens
<220> FEATURE:

<223> OTHER INFORMATION: Fibronectin

<400> SEQUENCE: 1

```
gcccgcgccg gctgtgctgc acaggggag gagagggaac cccaggcgcg agcgggaaga     60
ggggacctgc agccacaact tctctggtcc tctgcatccc ttctgtccct ccacccgtcc    120
ccttccccac cctctggccc ccagcctcct ccctatggcc actgtgtcac agacagtggt    180
gtggtctact ctgtggggat gcagtggctg aagacacaag gaaataagca aatgctttgc    240
acgtgcctgg gcaacggagt cagctgccaa gagacagctg taacccagac ttacggtggc    300
aactcaaatg gagagccatg tgtcttacca ttcacctaca atggcaggac gttctactcc    360
tgcaccacag aagggcgaca ggacggacat ctttggtgca gcacaacttc gaattatgag    420
caggaccaga aatactcttt ctgcacagac cacactgttt tggttcagac tcgaggagga    480
aattccaatg gtgccttgtg ccacttcccc ttcctataca caaccacaa ttacactgat    540
tgcacttctg agggcagaag agacaacatg aagtggtgtg ggaccacaca gaactatgat    600
gccgaccaga agtttgggtt ctgccccatg gctgcccacg aggaaatctg cacaaccaat    660
gaaggggtca tgtaccgcat tggagatcag tgggataagc agcatgacat gggtcacatg    720
atgaggtgca cgtgtgttgg gaatggtcgt ggggaatgga catgcattgc ctactcgcag    780
cttcgagatc agtgcattgt tgatgacatc acttacaatg tgaacgacac attccacaag    840
cgtcatgaag agggcacat gctgaactgt acatgcttcg gtcagggtcg gggcaggtgg    900
aagtgtgatc ccgtcgacca atgccaggat tcagagactg gacgttttta tcaaattgga    960
gattcatggg agaagtatgt gcatggtgtc agataccagt gctactgcta tggccgtggc    1020
attggggagt ggcattgcca acctttacag acctatccaa gctcaagtgg tcctgtcgaa    1080
gtatttatca ctgagactcc gagtcagccc aactcccacc ccatccagtg gaatgcacca    1140
cagccatctc acatttccaa gtacattctc aggtggagac ctaaaaattc tgtaggccgt    1200
tggaaggaag ctaccatacc aggccactta aactcctaca ccatcaaagg cctgaagcct    1260
ggtgtggtat acgagggcca gctcatcagc atccagcagt acggccacca agaagtgact    1320
cgctttgact tcaccaccac cagcaccagc acacctgtga ccagcaacac cgtgacagga    1380
gagacgactc cctttctcc tcttgtggcc acttctgaat ctgtgaccga atcacagcc    1440
agtagctttg tggtctcctg ggtctcagct tccgacaccg tgtcgggatt ccgggtggaa    1500
tatgagctga gtgaggaggg agatgagcca cagtacctgg atcttccaag cacagccact    1560
tctgtgaaca tccctgacct gcttcctggc cgaaaataca ttgtaaatgt ctatcagata    1620
tctgaggatg gggagcagag tttgatcctg tctacttcac aaacaacagc gcctgatgcc    1680
ccacctgacc cgactgtgga ccaagttgat gacacctcaa ttgttgttcg ctggagcaga    1740
ccccaggctc ccatcacagg gtacagaata gtctattcgc catcagtaga aggtagcagc    1800
acagaactca accttcctga aactgcaaac tccgtcaccc tcagtgactt gcaacctggt    1860
gttcagtata acatcactat ctatgctgtg gaagaaaatc aagaaagtac acctgttgtc    1920
attcaacaag aaaccactgg caccccacgc tcagatacag tgccctctcc cagggacctg    1980
cagtttgtgg aagtgacaga cgtgaaggtc accatcatgt ggacaccgcc tgagagtgca    2040
gtgaccggct accgtgtgga tgtgatcccc gtcaacctgc ctggcgagca cgggcagagg    2100
ctgcccatca gcaggaacac ctttgcagaa gtcaccgggc tgtcccctgg ggtcacctat    2160
tacttcaaag tctttgcagt gagccatggg agggagagca gcctctgac tgctcaacag    2220
acaaccaaac tggatgctcc cactaacctc cagtttgtca atgaaactga ttctactgtc    2280
```

```
ctggtgagat ggactccacc tcgggcccag ataacaggat accgactgac cgtgggcctt    2340
acccgaagag gacagcccag gcagtacaat gtgggtccct ctgtctccaa gtacccactg    2400
aggaatctgc agcctgcatc tgagtacacc gtatccctcg tggccataaa gggcaaccaa    2460
gagagcccca aagccactgg agtctttacc acactgcagc ctgggagctc tattccacct    2520
tacaacaccg aggtgactga gaccaccatt gtgatcacat ggacgcctgc tccaagaatt    2580
ggttttaagc tgggtgtacg accaagccag ggaggagagg caccacgaga agtgacttca    2640
gactcaggaa gcatcgttgt gtccggcttg actccaggag tagaatacgt ctacaccatc    2700
caagtcctga gagatggaca ggaaagagat gcgccaattg taaacaaagt ggtgacacca    2760
ttgtctccac caacaaactt gcatctggag gcaaaccctg acactggagt gctcacagtc    2820
tcctgggaga ggagcaccac cccagacatt actggttata gaattaccac aaccccctaca   2880 aacggccagc agggaaattc tttggaagaa gtggtccatg ctgatcagag ctcctgcact    2940
tttgataacc tgagtcccgg cctggagtac aatgtcagtg tttacactgt caaggatgac    3000
aaggaaagtg tccctatctc tgataccatc atcccagagg tgccccaact cactgaccta    3060
agctttgttg atataaccga ttcaagcatc ggcctgaggt ggaccccgct aaactcttcc    3120
accattattg ggtaccgcat cacagtagtt gcggcaggag aaggtatccc tattttttgaa    3180 gattttgtgg actcctcagt aggatactac acagtcacag ggctggagcc gggcattgac    3240
tatgatatca gcgttatcac tctcattaat ggcggcgaga gtgcccctac tacactgaca    3300
caacaaacgg ctgttcctcc tcccactgac ctgcgattca ccaacattgg tccagacacc    3360
atgcgtgtca cctgggctcc accaccatcc attgatttaa ccaacttcct ggtgcgttac    3420
tcacctgtga aaaatgagga agatgttgca gagttgtcaa tttctccttc agacaatgca    3480
gtggtcttaa caaatctcct gcctggtaca gaatatgtag tgagtgtctc cagtgtctac    3540
gaacaacatg agagcacacc tcttagagga agacagaaaa caggtcttga ttccccaact    3600
ggcattgact tttctgatat tactgccaac tcttttactg tgcactggat tgctcctcga    3660
gccaccatca ctggctacag gatccgccat catcccgagc acttcagtgg gagacctcga    3720
gaagatcggg tgccccactc tcggaattcc atcaccctca ccaacctcac tccaggcaca    3780
gagtatgtgg tcagcatcgt tgctcttaat ggcagagagg aaagtcccctt attgattggc    3840 caacaatcaa cagtttctga tgttccgagg gacctgaaag ttgttgctgc gaccccccacc   3900 agcctactga tcagctggga tgctcctgct gtcacagtga gatattacag gatcacttac    3960
ggagaaacag gaggaaatag ccctgtccag gagttcactg tgcctgggag caagtctaca    4020
gctaccatca gcggccttaa acctggagtt gattatacca tcactgtgca tgctgtcact    4080
ggccgtggag acagccccgc aagcagcaag ccaatttcca ttaattaccg aacagaaatt    4140
gacaaaccat cccagatgca agtgaccgat gttcaggaca acagcattag tgtcaagtgg    4200
ctgccttcaa gttcccctgt tactggttac agagtaacca ccactcccaa aaatggacca    4260
ggaccaacaa aaactaaaac tgcaggtcca gatcaaacag aaatgactat tgaaggcttg    4320
cagcccacag tggagtacgt ggttagtgtc tatgctcaga atccaagcgg agagagtcag    4380
cctctggttc agactgcagt aaccaacatt gatcgcccta aaggactggc attcactgat    4440
gtggatgtcg attccatcaa aattgcttgg gaaagcccac aggggcaagt tccaggtac      4500 agggtgaccct actcgagccc tgaggatgga atccatgagc tattccctgc acctgatggt    4560
gaagaagaca ctgcagagct gcaaggcctc agaccgggtt ctgagtacac agtcagtgtg    4620
gttgccttgc acgatgatat ggagagccag cccctgattg gaacccagtc cacagctatt    4680
```

```
cctgcaccaa ctgacctgaa gttcactcag gtcacaccca caagcctgag cgcccagtgg    4740
acaccaccca atgttcagct cactggatat cgagtgcggg tgaccccccaa ggagaagacc   4800 ggaccaatga aagaaatcaa ccttgctcct gacagctcat ccgtggttgt atcaggactt    4860
atggtggcca ccaaatatga agtgagtgtc tatgctctta aggacacttt gacaagcaga    4920
ccagctcagg gtgttgtcac cactctggag aatgtcggcc caccaagaag ggctcgtgtg    4980
acagatgcta ctgagaccac catcaccatt agctggagaa ccaagactga gacgatcact    5040
ggcttccaag ttgatgccgt tccagccaat ggccagactc caatccagag aaccatcaag    5100
ccagatgtca gaagctacac catcacaggt ttacaaccag gcactgacta caagatctac    5160
ctgtacacct tgaatgacaa tgctcggagc tcccctgtgg tcatcgacgc ctccactgcc    5220
attgatgcac catccaacct gcgtttcctg gccaccacac ccaattcctt gctggtatca    5280
tggcagccgc cacgtgccag gattaccggc tacatcatca gtatgagaaa gcctgggtct    5340
cctcccagag aagtggtccc tcggcccgc cctggtgtca cagaggctac tattactggc    5400
ctggaaccgg gaaccgaata caattttat gtcattgccc tgaagaataa tcagaagagc    5460
gagcccctga ttgaaggaa aaagacagac gagcttcccc aactggtaac ccttccacac    5520
cccaatcttc atggaccaga gatcttggat gttccttcca cagttcaaaa gaccccttc    5580 gtcacccacc ctgggtatga cactggaaat ggtattcagc ttcctggcac ttctggtcag    5640
caacccagtg ttgggcaaca atgatctttt gaggaacatg gttttaggcg gaccacaccg    5700
cccacaacgg ccacccccat aaggcatagg ccaagaccat acccgccgaa tgtaggtgag    5760
gaaatccaaa ttggtcacat tcccagggaa gatgtagact atcacctgta cccacacggt    5820
ccgggactca atccaaatgc ctctacacaa gaagctctct ctcagacaac catctcatgg    5880
gccccattcc aggacacttc tgagtacatc atttcatgtc atcctgttgg cactgatgaa    5940
gaacccttac agttcagggt tcctggaact tctaccagtg ccactctgac aggcctcacc    6000
agaggtgcca cctacaacat catagtggag gcactgaaag accagcagag gcataaggtt    6060
cgggaagagg ttgttaccgt gggcaactct gtcaacgaag gcttgaacca acctacggat    6120
gactcgtgct ttgacccta cacagtttcc cattatgccg ttggagatga gtgggaacga    6180
atgtctgaat caggctttaa actgttgtgc cagtgcttag gctttggaag tggtcatttc    6240
agatgtgatt catctagatg gtgccatgac aatggtgtga actacaagat ggagagaag    6300 tgggaccgtc agggagaaaa tggccagatg atgagctgca catgtcttgg aacggaaaa    6360 ggagaattca gtgtgacccc tcatgaggca acgtgttatg atgatgggaa gacataccac    6420
gtaggagaac agtggcagaa ggaatatctc ggtgccattt gctcctgcac atgctttgga    6480
ggccagcggg gctggcgctg tgacaactgc cgcagacctg ggggtgaacc cactcccgaa    6540
ggcactactg gccagtccta caaccagtat tctcagagat accatcagag aacaaacact    6600
aatgttaatt gcccaattga gtgcttcatg cctttagatg tacaggctga cagagaagat    6660
tcccgagagt aaatcatctt tccaatccag aggaacaagc atgtctctct gccaagatcc    6720
atctaaactg gagtgatgtt agcagaccca gcttagagtt cttctttctt tcttaagccc    6780
tttgctctgg aggaagttct ccagcttcag ctcaactcac agcttctcca agcatcaccc    6840
tgggagtttc ctgagggttt tctcataaat gagggctgca cattgcctgt tctgcttcga    6900
agtattcaat accgctcagt attttaaatg aagtgattct aagatttggt ttgggatcaa    6960
taggaaagca tatgcagcca accaagatgc aaatgttttg aaatgatatg accaaaattt    7020
taagtaggaa agtcacccaa acacttctgc tttcacttaa gtgtctggcc cgcaatactg    7080
```

-continued

```
taggaacaag catgatcttg ttactgtgat attttaaata tccacagtac tcactttttc    7140
caaatgatcc tagtaattgc ctagaaatat ctttctctta cctgttattt atcaattttt    7200
cccagtattt ttatacggaa aaaattgtat tgaaaacact tagtatgcag ttgataagag    7260
gaatttggta taattatggt gggtgattat tttttatact gtatgtgcca aagctttact    7320
actgtggaaa gacaactgtt ttaataaaag atttacattc cacaacttga aaaaaaaaa    7380 aaaaaaaa                                                             7388
```

```
<210> SEQ ID NO 2
<211> LENGTH: 2223
<212> TYPE: PRT
<213> ORGANISM: Homo Sapiens

<400> SEQUENCE: 2

Ala Arg Ala Gly Cys Ala Ala Gln Gly Glu Arg Glu Pro Gln Ala
 1               5                  10                  15

Arg Ala Gly Arg Gly Asp Leu Gln Pro Gln Leu Leu Trp Ser Ser Ala
                20                  25                  30

Ser Leu Leu Ser Leu His Pro Ser Pro Ser Pro Ser Gly Pro Gln
         35                  40                  45

Pro Pro Pro Tyr Gly His Cys Val Thr Asp Ser Gly Val Val Tyr Ser
 50                  55                  60

Val Gly Met Gln Trp Leu Lys Thr Gln Gly Asn Lys Gln Met Leu Cys
 65                  70                  75                  80

Thr Cys Leu Gly Asn Gly Val Ser Cys Gln Glu Thr Ala Val Thr Gln
                 85                  90                  95

Thr Tyr Gly Gly Asn Ser Asn Gly Glu Pro Cys Val Leu Pro Phe Thr
             100                 105                 110

Tyr Asn Gly Arg Thr Phe Tyr Ser Cys Thr Thr Glu Gly Arg Gln Asp
         115                 120                 125

Gly His Leu Trp Cys Ser Thr Thr Ser Asn Tyr Glu Asp Gln Lys
         130                 135                 140

Tyr Ser Phe Cys Thr Asp His Thr Val Leu Val Gln Thr Arg Gly Gly
145                 150                 155                 160

Asn Ser Asn Gly Ala Leu Cys His Phe Pro Phe Leu Tyr Asn Asn His
                165                 170                 175

Asn Tyr Thr Asp Cys Thr Ser Glu Gly Arg Arg Asp Asn Met Lys Trp
            180                 185                 190

Cys Gly Thr Thr Gln Asn Tyr Asp Ala Asp Gln Lys Phe Gly Phe Cys
        195                 200                 205

Pro Met Ala Ala His Glu Glu Ile Cys Thr Thr Asn Glu Gly Val Met
    210                 215                 220

Tyr Arg Ile Gly Asp Gln Trp Asp Lys Gln His Asp Met Gly His Met
225                 230                 235                 240

Met Arg Cys Thr Cys Val Gly Asn Gly Arg Gly Glu Trp Thr Cys Ile
                245                 250                 255

Ala Tyr Ser Gln Leu Arg Asp Gln Cys Ile Val Asp Asp Ile Thr Tyr
            260                 265                 270

Asn Val Asn Asp Thr Phe His Lys Arg His Glu Glu Gly His Met Leu
        275                 280                 285

Asn Cys Thr Cys Phe Gly Gln Gly Arg Gly Arg Trp Lys Cys Asp Pro
    290                 295                 300

Val Asp Gln Cys Gln Asp Ser Glu Thr Gly Thr Phe Tyr Gln Ile Gly
305                 310                 315                 320
```

-continued

Asp Ser Trp Glu Lys Tyr Val His Gly Val Arg Tyr Gln Cys Tyr Cys
            325                 330                 335

Tyr Gly Arg Gly Ile Gly Glu Trp His Cys Gln Pro Leu Gln Thr Tyr
            340                 345                 350

Pro Ser Ser Ser Gly Pro Val Glu Val Phe Ile Thr Glu Thr Pro Ser
            355                 360                 365

Gln Pro Asn Ser His Pro Ile Gln Trp Asn Ala Pro Gln Pro Ser His
        370                 375                 380

Ile Ser Lys Tyr Ile Leu Arg Trp Arg Pro Lys Asn Ser Val Gly Arg
385                 390                 395                 400

Trp Lys Glu Ala Thr Ile Pro Gly His Leu Asn Ser Tyr Thr Ile Lys
            405                 410                 415

Gly Leu Lys Pro Gly Val Val Tyr Glu Gly Gln Leu Ile Ser Ile Gln
            420                 425                 430

Gln Tyr Gly His Gln Glu Val Thr Arg Phe Asp Phe Thr Thr Thr Ser
        435                 440                 445

Thr Ser Thr Pro Val Thr Ser Asn Thr Val Thr Gly Glu Thr Thr Pro
    450                 455                 460

Phe Ser Pro Leu Val Ala Thr Ser Glu Ser Val Thr Glu Ile Thr Ala
465                 470                 475                 480

Ser Ser Phe Val Val Ser Trp Val Ser Ala Ser Asp Thr Val Ser Gly
            485                 490                 495

Phe Arg Val Glu Tyr Glu Leu Ser Glu Glu Gly Asp Glu Pro Gln Tyr
            500                 505                 510

Leu Asp Leu Pro Ser Thr Ala Thr Ser Val Asn Ile Pro Asp Leu Leu
        515                 520                 525

Pro Gly Arg Lys Tyr Ile Val Asn Val Tyr Gln Ile Ser Glu Asp Gly
    530                 535                 540

Glu Gln Ser Leu Ile Leu Ser Thr Ser Gln Thr Thr Ala Pro Asp Ala
545                 550                 555                 560

Pro Pro Asp Pro Thr Val Asp Gln Val Asp Asp Thr Ser Ile Val Val
            565                 570                 575

Arg Trp Ser Arg Pro Gln Ala Pro Ile Thr Gly Tyr Arg Ile Val Tyr
            580                 585                 590

Ser Pro Ser Val Glu Gly Ser Ser Thr Glu Leu Asn Leu Pro Glu Thr
        595                 600                 605

Ala Asn Ser Val Thr Leu Ser Asp Leu Gln Pro Gly Val Gln Tyr Asn
    610                 615                 620

Ile Thr Ile Tyr Ala Val Glu Glu Asn Gln Glu Ser Thr Pro Val Val
625                 630                 635                 640

Ile Gln Gln Glu Thr Thr Gly Thr Pro Arg Ser Asp Thr Val Pro Ser
            645                 650                 655

Pro Arg Asp Leu Gln Phe Val Glu Val Thr Asp Val Lys Val Thr Ile
            660                 665                 670

Met Trp Thr Pro Pro Glu Ser Ala Val Thr Gly Tyr Arg Val Asp Val
        675                 680                 685

Ile Pro Val Asn Leu Pro Gly Glu His Gly Gln Arg Leu Pro Ile Ser
    690                 695                 700

Arg Asn Thr Phe Ala Glu Val Thr Gly Leu Ser Pro Gly Val Thr Tyr
705                 710                 715                 720

Tyr Phe Lys Val Phe Ala Val Ser His Gly Arg Glu Ser Lys Pro Leu
            725                 730                 735

Thr Ala Gln Gln Thr Thr Lys Leu Asp Ala Pro Thr Asn Leu Gln Phe
            740                 745                 750

```
Val Asn Glu Thr Asp Ser Thr Val Leu Val Arg Trp Thr Pro Arg
        755                 760                 765

Ala Gln Ile Thr Gly Tyr Arg Leu Thr Val Gly Leu Thr Arg Arg Gly
        770                 775                 780

Gln Pro Arg Gln Tyr Asn Val Gly Pro Ser Ser Lys Tyr Pro Leu
785                 790                 795                 800

Arg Asn Leu Gln Pro Ala Ser Glu Tyr Thr Val Ser Leu Val Ala Ile
                805                 810                 815

Lys Gly Asn Gln Glu Ser Pro Lys Ala Thr Gly Val Phe Thr Thr Leu
            820                 825                 830

Gln Pro Gly Ser Ser Ile Pro Pro Tyr Asn Thr Glu Val Thr Glu Thr
            835                 840                 845

Thr Ile Val Ile Thr Trp Thr Pro Ala Pro Arg Ile Gly Phe Lys Leu
        850                 855                 860

Gly Val Arg Pro Ser Gln Gly Gly Glu Ala Pro Arg Glu Val Thr Ser
865                 870                 875                 880

Asp Ser Gly Ser Ile Val Val Ser Gly Leu Thr Pro Gly Val Glu Tyr
                885                 890                 895

Val Tyr Thr Ile Gln Val Leu Arg Asp Gly Gln Glu Arg Asp Ala Pro
                900                 905                 910

Ile Val Asn Lys Val Val Thr Pro Leu Ser Pro Pro Thr Asn Leu His
            915                 920                 925

Leu Glu Ala Asn Pro Asp Thr Gly Val Leu Thr Val Ser Trp Glu Arg
        930                 935                 940

Ser Thr Thr Pro Asp Ile Thr Gly Tyr Arg Ile Thr Thr Thr Pro Thr
945                 950                 955                 960

Asn Gly Gln Gln Gly Asn Ser Leu Glu Glu Val Val His Ala Asp Gln
                965                 970                 975

Ser Ser Cys Thr Phe Asp Asn Leu Ser Pro Gly Leu Glu Tyr Asn Val
                980                 985                 990

Ser Val Tyr Thr Val Lys Asp Asp Lys Glu Ser Val Pro Ile Ser Asp
            995                 1000                1005

Thr Ile Ile Pro Glu Val Pro Gln Leu Thr Asp Leu Ser Phe Val Asp
        1010                1015                1020

Ile Thr Asp Ser Ser Ile Gly Leu Arg Trp Thr Pro Leu Asn Ser Ser
1025                1030                1035                1040

Thr Ile Ile Gly Tyr Arg Ile Thr Val Val Ala Ala Gly Glu Gly Ile
            1045                1050                1055

Pro Ile Phe Glu Asp Phe Val Asp Ser Ser Val Gly Tyr Tyr Thr Val
        1060                1065                1070

Thr Gly Leu Glu Pro Gly Ile Asp Tyr Asp Ile Ser Val Ile Thr Leu
        1075                1080                1085

Ile Asn Gly Gly Glu Ser Ala Pro Thr Thr Leu Thr Gln Gln Thr Ala
        1090                1095                1100

Val Pro Pro Pro Thr Asp Leu Arg Phe Thr Asn Ile Gly Pro Asp Thr
1105                1110                1115                1120

Met Arg Val Thr Trp Ala Pro Pro Ser Ile Asp Leu Thr Asn Phe
                1125                1130                1135

Leu Val Arg Tyr Ser Pro Val Lys Asn Glu Glu Asp Val Ala Glu Leu
            1140                1145                1150

Ser Ile Ser Pro Ser Asp Asn Ala Val Val Leu Thr Asn Leu Leu Pro
            1155                1160                1165

Gly Thr Glu Tyr Val Val Ser Val Ser Ser Val Tyr Glu Gln His Glu
```

1170              1175              1180
Ser Thr Pro Leu Arg Gly Arg Gln Lys Thr Gly Leu Asp Ser Pro Thr
1185              1190              1195              1200

Gly Ile Asp Phe Ser Asp Ile Thr Ala Asn Ser Phe Thr Val His Trp
              1205              1210              1215

Ile Ala Pro Arg Ala Thr Ile Thr Gly Tyr Arg Ile Arg His His Pro
              1220              1225              1230

Glu His Phe Ser Gly Arg Pro Arg Glu Asp Arg Val Pro His Ser Arg
              1235              1240              1245

Asn Ser Ile Thr Leu Thr Asn Leu Thr Pro Gly Thr Glu Tyr Val Val
              1250              1255              1260

Ser Ile Val Ala Leu Asn Gly Arg Glu Glu Ser Pro Leu Leu Ile Gly
1265              1270              1275              1280

Gln Gln Ser Thr Val Ser Asp Val Pro Arg Asp Leu Glu Val Val Ala
              1285              1290              1295

Ala Thr Pro Thr Ser Leu Leu Ile Ser Trp Asp Ala Pro Ala Val Thr
              1300              1305              1310

Val Arg Tyr Tyr Arg Ile Thr Tyr Gly Glu Thr Gly Gly Asn Ser Pro
              1315              1320              1325

Val Gln Glu Phe Thr Val Pro Gly Ser Lys Ser Thr Ala Thr Ile Ser
              1330              1335              1340

Gly Leu Lys Pro Gly Val Asp Tyr Thr Ile Thr Val His Ala Val Thr
1345              1350              1355              1360

Gly Arg Gly Asp Ser Pro Ala Ser Ser Lys Pro Ile Ser Ile Asn Tyr
              1365              1370              1375

Arg Thr Glu Ile Asp Lys Pro Ser Gln Met Gln Val Thr Asp Val Gln
              1380              1385              1390

Asp Asn Ser Ile Ser Val Lys Trp Leu Pro Ser Ser Ser Pro Val Thr
              1395              1400              1405

Gly Tyr Arg Val Thr Thr Thr Pro Lys Asn Gly Pro Gly Pro Thr Lys
              1410              1415              1420

Thr Lys Thr Ala Gly Pro Asp Gln Thr Glu Met Thr Ile Glu Gly Leu
1425              1430              1435              1440

Gln Pro Thr Val Glu Tyr Val Val Ser Val Tyr Ala Gln Asn Pro Ser
              1445              1450              1455

Gly Glu Ser Gln Pro Leu Val Gln Thr Ala Val Thr Asn Ile Asp Arg
              1460              1465              1470

Pro Lys Gly Leu Ala Phe Thr Asp Val Asp Val Asp Ser Ile Lys Ile
              1475              1480              1485

Ala Trp Glu Ser Pro Gln Gly Gln Val Ser Arg Tyr Arg Val Thr Tyr
              1490              1495              1500

Ser Ser Pro Glu Asp Gly Ile His Glu Leu Phe Pro Ala Pro Asp Gly
1505              1510              1515              1520

Glu Glu Asp Thr Ala Glu Leu Gln Gly Leu Arg Pro Gly Ser Glu Tyr
              1525              1530              1535

Thr Val Ser Val Val Ala Leu His Asp Asp Met Glu Ser Gln Pro Leu
              1540              1545              1550

Ile Gly Thr Gln Ser Thr Ala Ile Pro Ala Pro Thr Asp Leu Lys Phe
              1555              1560              1565

Thr Gln Val Thr Pro Thr Ser Leu Ser Ala Gln Trp Thr Pro Pro Asn
              1570              1575              1580

Val Gln Leu Thr Gly Tyr Arg Val Arg Val Thr Pro Lys Glu Lys Thr
1585              1590              1595              1600

```
Gly Pro Met Lys Glu Ile Asn Leu Ala Pro Asp Ser Ser Val Val
            1605                1610                1615

Val Ser Gly Leu Met Val Ala Thr Lys Tyr Glu Val Ser Val Tyr Ala
            1620                1625                1630

Leu Lys Asp Thr Leu Thr Ser Arg Pro Ala Gln Gly Val Val Thr Thr
            1635                1640                1645

Leu Glu Asn Val Gly Pro Pro Arg Arg Ala Arg Val Thr Asp Ala Thr
            1650                1655                1660

Glu Thr Thr Ile Thr Ile Ser Trp Arg Thr Lys Thr Glu Thr Ile Thr
1665                1670                1675                1680

Gly Phe Gln Val Asp Ala Val Pro Ala Asn Gly Gln Thr Pro Ile Gln
            1685                1690                1695

Arg Thr Ile Lys Pro Asp Val Arg Ser Tyr Thr Ile Thr Gly Leu Gln
            1700                1705                1710

Pro Gly Thr Asp Tyr Lys Ile Tyr Leu Tyr Thr Leu Asn Asp Asn Ala
            1715                1720                1725

Arg Ser Ser Pro Val Val Ile Asp Ala Ser Thr Ala Ile Asp Ala Pro
            1730                1735                1740

Ser Asn Leu Arg Phe Leu Ala Thr Thr Pro Asn Ser Leu Leu Val Ser
1745                1750                1755                1760

Trp Gln Pro Pro Arg Ala Arg Ile Thr Gly Tyr Ile Ile Lys Tyr Glu
            1765                1770                1775

Lys Pro Gly Ser Pro Pro Arg Glu Val Val Pro Arg Pro Arg Pro Gly
            1780                1785                1790

Val Thr Glu Ala Thr Ile Thr Gly Leu Glu Pro Gly Thr Glu Tyr Thr
            1795                1800                1805

Ile Tyr Val Ile Ala Leu Lys Asn Asn Gln Lys Ser Glu Pro Leu Ile
            1810                1815                1820

Gly Arg Lys Lys Thr Asp Glu Leu Pro Gln Leu Val Thr Leu Pro His
1825                1830                1835                1840

Pro Asn Leu His Gly Pro Glu Ile Leu Asp Val Pro Ser Thr Val Gln
            1845                1850                1855

Lys Thr Pro Phe Val Thr His Pro Gly Tyr Asp Thr Gly Asn Gly Ile
            1860                1865                1870

Gln Leu Pro Gly Thr Ser Gly Gln Gln Pro Ser Val Gly Gln Gln Met
            1875                1880                1885

Ile Phe Glu Glu His Gly Phe Arg Arg Thr Thr Pro Pro Thr Thr Ala
            1890                1895                1900

Thr Pro Ile Arg His Arg Pro Arg Pro Tyr Pro Pro Asn Val Gly Glu
1905                1910                1915                1920

Glu Ile Gln Ile Gly His Ile Pro Arg Glu Asp Val Asp Tyr His Leu
            1925                1930                1935

Tyr Pro His Gly Pro Gly Leu Asn Pro Asn Ala Ser Thr Gln Glu Ala
            1940                1945                1950

Leu Ser Gln Thr Thr Ile Ser Trp Ala Pro Phe Gln Asp Thr Ser Glu
            1955                1960                1965

Tyr Ile Ile Ser Cys His Pro Val Gly Thr Asp Glu Glu Pro Leu Gln
            1970                1975                1980

Phe Arg Val Pro Gly Thr Ser Thr Ser Ala Thr Leu Thr Gly Leu Thr
1985                1990                1995                2000

Arg Gly Ala Thr Tyr Asn Ile Ile Val Glu Ala Leu Lys Asp Gln Gln
            2005                2010                2015

Arg His Lys Val Arg Glu Glu Val Val Thr Val Gly Asn Ser Val Asn
            2020                2025                2030
```

-continued

```
Glu Gly Leu Asn Gln Pro Thr Asp Asp Ser Cys Phe Asp Pro Tyr Thr
        2035                2040                2045
Val Ser His Tyr Ala Val Gly Asp Glu Trp Glu Arg Met Ser Glu Ser
        2050                2055                2060
Gly Phe Lys Leu Leu Cys Gln Cys Leu Gly Phe Gly Ser Gly His Phe
2065                2070                2075                2080
Arg Cys Asp Ser Ser Arg Trp Cys His Asp Asn Gly Val Asn Tyr Lys
                2085                2090                2095
Ile Gly Glu Lys Trp Asp Arg Gln Gly Glu Asn Gly Gln Met Met Ser
                2100                2105                2110
Cys Thr Cys Leu Gly Asn Gly Lys Gly Glu Phe Lys Cys Asp Pro His
                2115                2120                2125
Glu Ala Thr Cys Tyr Asp Asp Gly Lys Thr Tyr His Val Gly Glu Gln
                2130                2135                2140
Trp Gln Lys Glu Tyr Leu Gly Ala Ile Cys Ser Cys Thr Cys Phe Gly
2145                2150                2155                2160
Gly Gln Arg Gly Trp Arg Cys Asp Asn Cys Arg Arg Pro Gly Gly Glu
                2165                2170                2175
Pro Thr Pro Glu Gly Thr Thr Gly Gln Ser Tyr Asn Gln Tyr Ser Gln
                2180                2185                2190
Arg Tyr His Gln Arg Thr Asn Thr Asn Val Asn Cys Pro Ile Glu Cys
                2195                2200                2205
Phe Met Pro Leu Asp Val Gln Ala Asp Arg Glu Asp Ser Arg Glu
                2210                2215                2220

<210> SEQ ID NO 3
<211> LENGTH: 3185
<212> TYPE: DNA
<213> ORGANISM: Homo Sapiens
<220> FEATURE:
<223> OTHER INFORMATION: Fibronectin ED-A region
<300> PUBLICATION INFORMATION:
<308> DATABASE ACCESSION NUMBER: GenBank X07718
<309> DATABASE ENTRY DATE: 2005-04-18

<400> SEQUENCE: 3
atcaaacaga aatgactatt gaaggcttgc agcccacagt ggagtatgtg gttagtgtct      60
atgctcagaa tccaagcgga gagagtcagc ctctggttca gactgcagta accagtacgt     120
aaccactgct tggtttccat tttcaaagtc aaattttgtt cttgggtgtc tgaatgccca     180
cgacatgtct tttgcaatta cacatagggaa aagtgaactt gttggttagt ttatgtcttg     240
agctgagccc tttacgaaca tcttttttcc ttctcagtgc caagcgagga atttacagag     300
aaagaagttg tgaaaccacc atagttagtt gctgtgcttt gaatttcttt ttgctcaaat     360
ggcctcagcg aaatcttatt tgcctatagc aaatctacaa aaaattttcc tagaccgtct     420
tttctacaac tggatggtaa agttgattga agtgtgcctc atgtagcttt atgtttgggg     480
catttgaagg gctatggctg gaccagagtg taatataaat gcttaataga gaggggaaaa     540
gaagagtgta agaaccatta tagggctggg ctcacgcctg taatcccagc attttgggag     600
gctgaggcgg atcacgaggt caggagttcg agaccagcct gaccaacatg gtgaaacccc     660
atctctacta aaaatacaaa aattagccag tcgcggtggc acgtgcctgt aatcccagct     720
actcacggag gctgaggcag aagaatcact tggacccagg aggcagaagt tgcagtgagc     780
caagatcatg cctctgcacc ccagcctagg tgatagagtg agactccatc tcaaaaaaaa     840
acaaaacaaa acaattataa caatttgaat ctgaaccata tgcaaatcag ctttaccact     900
```

```
tccaaggtat aagaaaatcc aggtctatga gactaacatc acattgtaaa aatcaaatcg      960
tggtagaata cctttaaatt aatataaata catccccatt gtggggacat tttgcagggt     1020
atctgcttat ctcacataca ccatgtttta ataagtgatg caacattgca tattttctaa     1080
accaagaaaa attaagcaag tgtttaagtg attttccctt tgatagtggg ttaattggac     1140
ttcatcaaag aaaatggtat ctgcaaaact gctttgcatg ttataaaaat gcttatttca     1200
caacttgctt tcacataacc tcttaccatt aatttgccta acagacattg atcgccctaa     1260
aggactggca ttcactgatg tggatgtcga ttccatcaaa attgcttggg aaagcccaca     1320
ggggcaagtt tccaggtaca gggtgaccta ctcgagccct gaggatggaa tccatgagct     1380
attccctgca cctgatggtg aagaagacac tgcagagctg caaggcctca gaccgggttc     1440
tgagtacaca gtcagtgtgg ttgccttgca cgatgatatg gagagccagc ccctgattgg     1500
aacccagtcc acaggtatat ggttaattgc acacaggtgc catgggagca gcggctttat     1560
gcctactgaa tgaattatgc ttcactgggc tattgattcc cgtgtaaggg tgaaaaagaa     1620
ttattaggaa agatcctctt taaagaggaa tggtaagaaa caataaaaact taggtgatat     1680
ttaaggaaac aagtctgatt aaagaaatt ttggagtatc ctggcttata cacaagacca     1740
taaagcaaga catttgaaga ggatactaaa gttgtggatt atttcctaag ctctgactcc     1800
ctgtgattac cctcactatg tataaagaaa agaagtttgg cattacagag cttacttata     1860
aaaaggaacc caaactcggg catttcatag cagcatgatt ctgagcacac gtgggtaaga     1920
cctttcttct ctggttagat atcatatgct ggtgtataat tagcttaaat gattgtgatt     1980
tagacaccta ggaaataatc aataagggcaa ttgctttcca taatacttta tcttcttgtg     2040
ctttatttct gaagcagagt agaatgctaa agatgtatcc tagtgacagc ataaacccta     2100
gaggtgacag tctgtattat tgcttttcgc ttctcttttc tgcttctgtt gggagccagt     2160
tttcttctta cgccgcatta cagagagaac gtcaaattta gcaagccata tctgccatag     2220
gtccaaataa agagacaata aaaattattc tctcttttt ggatggaata ctgcgtgaaa     2280
tggttatcca tacaaagata ctttatgtag aatagaaaaa ggaggccggg tgcagtggct     2340
cacacatgta atcctagtgc tttgggaggc taagccggga gcactgattg aggccaggag     2400
ttcatgatca gcctgggcaa tgaagtgaga ccccgtctct acaaaaaat atgaaaaaat     2460
tagcgaggtg tggtgacaca tgcctgtagt cccagctact caagaggctg aggtagagga     2520
tcacttgagc ctacgagttc aaggctgcag tgagctatga taactccact gcactgctgc     2580
ctggatgaca cagagagacc gtttctaaat taattaatta acaattttaa gaagaaaaa      2640
gggccattgc ttatttttcc atacaaaagt aaaataaatc ataatggcca ataagccaat     2700
gtaacttttt tttttaaggg aaagcaaaac ttgtaaaacc taaaatctct tagagttttg     2760
gcatttaccc aaatgttttc agtgattctg agaattggtg gatataaaac acatttctca     2820
gcaaacactt tcttcatttt gcatcccttaa ctgtactttc ttgtactgaa tctttgcttg     2880
accagggaac ccacctagcc caacaagaac aatccattct acttcttgga actacgttta     2940
ttttcctttt cccccatttc ctataagata acctctaacc aatgacaatc tcgacagcta     3000
ttcctgcacc aactgacctg aagttcactc aggtcacacc cacaagcctg agcgcccagt     3060
ggacaccacc caatgttcag ctcactggat atcgagtgcg ggtgacccccc aaggagaaga     3120
ccggaccaat gaaagaagtc aaccttgctc ctgacagctc atccgtggtt gtatcaggac     3180
ttatc                                                                3185

<210> SEQ ID NO 4
```

```
<211> LENGTH: 190
<212> TYPE: PRT
<213> ORGANISM: Homo Sapiens
<300> PUBLICATION INFORMATION:
<308> DATABASE ACCESSION NUMBER: GenBank X07718
<309> DATABASE ENTRY DATE: 2005-04-18

<400> SEQUENCE: 4
```

Gln Thr Glu Met Thr Ile Glu Gly Leu Gln Pro Thr Val Glu Tyr Val
 1               5                  10                  15

Val Ser Val Tyr Ala Gln Asn Pro Ser Gly Glu Ser Gln Pro Leu Val
             20                  25                  30

Gln Thr Ala Val Thr Asn Ile Asp Arg Pro Lys Gly Leu Ala Phe Thr
         35                  40                  45

Asp Val Asp Val Asp Ser Ile Lys Ile Ala Trp Glu Ser Pro Gln Gly
     50                  55                  60

Gln Val Ser Arg Tyr Arg Val Thr Tyr Ser Ser Pro Glu Asp Gly Ile
 65                  70                  75                  80

His Glu Leu Phe Pro Ala Pro Asp Gly Glu Glu Asp Thr Ala Glu Leu
                 85                  90                  95

Gln Gly Leu Arg Pro Gly Ser Glu Tyr Thr Val Ser Val Val Ala Leu
            100                 105                 110

His Asp Asp Met Glu Ser Gln Pro Leu Ile Gly Thr Gln Ser Thr Ala
        115                 120                 125

Ile Pro Ala Pro Thr Asp Leu Lys Phe Thr Gln Val Thr Pro Thr Ser
    130                 135                 140

Leu Ser Ala Gln Trp Thr Pro Pro Asn Val Gln Leu Thr Gly Tyr Arg
145                 150                 155                 160

Val Arg Val Thr Pro Lys Glu Lys Thr Gly Pro Met Lys Glu Val Asn
                165                 170                 175

Leu Ala Pro Asp Ser Ser Ser Val Val Val Ser Gly Leu Ile
            180                 185                 190

```
<210> SEQ ID NO 5
<211> LENGTH: 2823
<212> TYPE: DNA
<213> ORGANISM: Homo Sapiens
<220> FEATURE:
<223> OTHER INFORMATION: Fibronectin ED-B region
<300> PUBLICATION INFORMATION:
<308> DATABASE ACCESSION NUMBER: GenBank X07717
<309> DATABASE ENTRY DATE: 2005-04-18

<400> SEQUENCE: 5
ctgcactttt gataacctga gtcccggcct ggagtacaat gtcagtgttt acactgtcaa      60
ggatgacaag gaaagtgtcc ctatctctga taccatcatc ccaggtaata gaaataagc     120 tgctatcctg agagtgacat tccaataaga gtggggatta gcatcttaat ccccagatgc    180
ttaagggtgt caactatatt tgggatttaa ttccgatctc ccagctgcac tttccaaaac    240
caagaagtca agcagcgat ttggacaaaa tgcttgctgt taacactgct ttactgtctg     300
tgcttcactg ggatgctgtg tgttgcagcg agtatgtaat ggagtggcag ccatggcttt    360
aactctgtat tgtctgctca catggaagta tgactaaaac actgtcacgt gtctgtactc    420
agtactgata ggctcaaagt aatatggtaa atgcatccca tcagtacatt tctgcccgat    480
tttacaatcc atatcaattt ccaacagctg cctatttcat cttgcagttt caaatccttc    540
tttttgaaaa ttggatttta aaaaaagtt aagtaaagt cacaccttca gggttgttct      600
ttcttgtggc cttgaaagac aacattgcaa aggcctgtcc taaggatagg cttgtttgtc    660
```

```
cattgggtta taacataatg aaagcattgg acagatcgtg tcccccttg gactcttcag    720 tagaatgctt ttactaacgc taattacatg ttttgattat gaatgaacct aaaatagtgg    780
caatggcctt aacctaggcc tgtctttcct cagcctgaat gtgcttttga atggcacatt    840
tcacaccata cattcataat gcattagcgt tatggccatg atgttgtcat gagttttgta    900
tgggagaaaa aaaatcaatt tatcacccat ttattatttt ttccggttgt tcatgcaagc    960 ttatttctcta ctaaacagt tttggaatta ttaaaagcat tgctgatact tacttcagat   1020
attatgtcta ggctctaaga atggtttcga catcctaaac agccatatga tttttaggaa   1080
tctgaacagt tcaaattgta cccttaagg atgttttcaa aatgtaaaaa atatatatat   1140
atatatatat tccctaaaag aatattcctg tttattcttc tagggaagca aactgttcat   1200
gatgcttagg aagtcttttc agagaattta aaacagattg catattacca tcattgcttt   1260
aacattccac caattttact actagtaacc tgatatacac tgctttattt tttcctcttt   1320
ttttccctct attttccttt tgcctccccc tccctttgct ttgtaactca atagaggtgc   1380
cccaactcac tgacctaagc tttgttgata taaccgattc aagcatcggc ctgaggtgga   1440
ccccgctaaa ctcttccacc attattgggt accgcatcac agtagttgcg gcaggagaag   1500
gtatccctat ttttgaagat tttgtggact cctcagtagg atactacaca gtcacagggc   1560
tggagccggg cattgactat gatatcagcg ttatcactct cattaatggc ggcgagagtg   1620
cccctactac actgacacaa caaacggtg aattttgaaa acttctgcgt ttgagacata   1680
gatggtgttg catgctgcca ccagttactc cggttaaata tggatgtttc atgggggaag   1740
tcagcaattg gccaaagatt cagataggtg gaattggggg gataaggaat caaatgcatc   1800
tgctaaactg attggagaaa aacacatgca atatcttcag tacactctca tttaaaccac   1860
aagtagatat aaagcctaga gaaatacaga tgtctgctct gttaaatata aaatagcaaa   1920
tgttcattca atttgaagac ctagaatttt tcttcttaaa taccaaacac gaataccaaa   1980
ttgcgtaagt accaattgat aagaatatat caccaaaatg taccatcatg ctcttccttc   2040 tacccttga taaactctac catgctcctt ctttgtagct aaaaacccat caaaatttag   2100
ggtagagtgg atgggcattg ttttgaggta ggagaaaagt aaacttggga ccattctagg   2160
ttttgttgct gtcactaggt aaagaaacac ctctttaacc acagtctggg gacaagcatg   2220
caacatttta aaggttctct gctgtgcatg ggaaaagaaa catgctgaga accaatttgc   2280
atgaacatgt tcacttgtaa gtagaattca ctgaatggaa ctgtagctct agatatctca   2340 catggggga agtttaggac cctccttgtct ttttgtctgt gtgcatgtat ttctttgtaa   2400
agtactgcta tgtttctctt tgctgtgtgg caacttaagc ctcttcggcc tgggataaaa   2460
taatctgcag tggtattaat aatgtacata aagtcaacat atttgaaagt agattaaaat   2520
cttttttaaa tatatcaatg atggcaaaaa ggttaaaggg ggcctaacag tactgtgtgt   2580
agtgttttat ttttaacagt agtacactat aacttaaaat agacttagat tagactgttt   2640
gcatgattat gattctgttt cctttatgca tgaaatattg attttacctt tccagctact   2700
tcgttagctt taattttaaa atacattaac tgagtcttcc ttcttgttcg aaaccagctg   2760
ttcctcctcc cactgacctg cgattcacca acattggtcc agacaccatg cgtgtcacct   2820
ggg                                                                 2823
```

<210> SEQ ID NO 6
<211> LENGTH: 147
<212> TYPE: PRT
<213> ORGANISM: Homo Sapiens
<300> PUBLICATION INFORMATION:

-continued

<308> DATABASE ACCESSION NUMBER: GenBank X07717
<309> DATABASE ENTRY DATE: 2004-04-18

<400> SEQUENCE: 6

Cys Thr Phe Asp Asn Leu Ser Pro Gly Leu Glu Tyr Asn Val Ser Val
1               5                   10                  15

Tyr Thr Val Lys Asp Asp Lys Glu Ser Val Pro Ile Ser Asp Thr Ile
            20                  25                  30

Ile Pro Glu Val Pro Gln Leu Thr Asp Leu Ser Phe Val Asp Ile Thr
        35                  40                  45

Asp Ser Ser Ile Gly Leu Arg Trp Thr Pro Leu Asn Ser Ser Thr Ile
    50                  55                  60

Ile Gly Tyr Arg Ile Thr Val Val Ala Ala Gly Glu Gly Ile Pro Ile
65                  70                  75                  80

Phe Glu Asp Phe Val Asp Ser Ser Val Gly Tyr Tyr Thr Val Thr Gly
                85                  90                  95

Leu Glu Pro Gly Ile Asp Tyr Asp Ile Ser Val Ile Thr Leu Ile Asn
            100                 105                 110

Gly Gly Glu Ser Ala Pro Thr Thr Leu Thr Gln Gln Thr Ala Val Pro
        115                 120                 125

Pro Pro Thr Asp Leu Arg Phe Thr Asn Ile Gly Pro Asp Thr Met Arg
    130                 135                 140

Val Thr Trp
145

<210> SEQ ID NO 7
<211> LENGTH: 360
<212> TYPE: DNA
<213> ORGANISM: Homo Sapiens

<400> SEQUENCE: 7
gacgagcttc cccaactggt aacccttcca cacccccaatc ttcatggacc agagatcttg     60
gatgttcctt ccacagttca aaagacccct ttcgtcaccc accctgggta tgacactgga    120
aatggtattc agcttcctgg cacttctggt cagcaaccca gtgttgggca acaaatgatc    180
tttgaggaac atggttttag gcggaccaca ccgcccacaa cggccacccc cataaggcat    240
aggccaagac cataccccgcc gaatgtaggt gaggaaatcc aaattggtca cattcccagg    300
gaagatgtag actatcacct gtacccacac ggtccgggac tcaatccaaa tgcctctaca    360

<210> SEQ ID NO 8
<211> LENGTH: 120
<212> TYPE: PRT
<213> ORGANISM: Homo Sapiens

<400> SEQUENCE: 8

Asp Glu Leu Pro Gln Leu Val Thr Leu Pro His Pro Asn Leu His Gly
1               5                   10                  15

Pro Glu Ile Leu Asp Val Pro Ser Thr Val Gln Lys Thr Pro Phe Val
            20                  25                  30

Thr His Pro Gly Tyr Asp Thr Gly Asn Gly Ile Gln Leu Pro Gly Thr
        35                  40                  45

Ser Gly Gln Gln Pro Ser Val Gly Gln Gln Met Ile Phe Glu Glu His
    50                  55                  60

Gly Phe Arg Arg Thr Thr Pro Thr Thr Ala Thr Pro Ile Arg His
65                  70                  75                  80

Arg Pro Arg Pro Tyr Pro Pro Asn Val Gly Glu Glu Ile Gln Ile Gly
                85                  90                  95

His Ile Pro Arg Glu Asp Val Asp Tyr His Leu Tyr Pro His Gly Pro
                100                 105                 110

Gly Leu Asn Pro Asn Ala Ser Thr
        115                 120

<210> SEQ ID NO 9
<211> LENGTH: 714
<212> TYPE: DNA
<213> ORGANISM: Artificial Sequence
<220> FEATURE:
<223> OTHER INFORMATION: ME4C
<300> PUBLICATION INFORMATION:
<308> DATABASE ACCESSION NUMBER: GenBank AJ297960
<309> DATABASE ENTRY DATE: 2001-03-01

<400> SEQUENCE: 9
gaggtgcagc tgttggagtc tgggggaggc ttggtacagc ctggggggtc cctgagactc    60
tcctgtgcag cctctggatt cacctttagc agttttttcga tgagctgggt ccgccaggct   120
ccagggaagg ggctggagtg ggtctcatct attagtggta gttcgggtac acatactac    180 gcagactccg tgaagggccg gttcaccatc tccagagaca attccaagaa cacgctgtat   240
ctgcaaatga acagcctgag agccgaggac acggccgtat attactgtgc gaaacagaag   300
agtgcgccgt ttgactactg gggccaggga accctggtca ccgtctcgag tggcgatggg   360
tccagtggcg gtagcggggg cgcgtcgtct tctgagctga ctcaggaccc tgctgtgtct   420
gtggccttgg acagacagt caggatcaca tgccaaggag acagcctcag aagctattat    480
gcaagctggt accagcagaa gccaggacag gcccctgtac ttgtcatcta tggtaaaaac   540
aaccggccct cagggatccc agaccgattc tctggctcca gctcaggaaa cacagcttcc   600
ttgaccatca ctggggctca gcggaagat gaggctgact attactgtaa ctcctctgcg    660
cccgttagta atagggtggt attcggcgga gggaccaagc tgaccgtcct aggc          714

<210> SEQ ID NO 10
<211> LENGTH: 238
<212> TYPE: PRT
<213> ORGANISM: Artificial Sequence
<220> FEATURE:
<223> OTHER INFORMATION: ME4C anti-(ED-B) scFv recombinant antibody
<300> PUBLICATION INFORMATION:
<308> DATABASE ACCESSION NUMBER: GenBank CAC33765
<309> DATABASE ENTRY DATE: 2000-03-01

<400> SEQUENCE: 10

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ser Ser Ile Ser Gly Ser Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gln Lys Ser Ala Pro Phe Asp Tyr Trp Gly Gln Gly Thr Leu
            100                 105                 110

Val Thr Val Ser Ser Gly Asp Gly Ser Ser Gly Gly Ser Gly Gly Ala
        115                 120                 125

```
Ser Ser Ser Glu Leu Thr Gln Asp Pro Ala Val Ser Val Ala Leu Gly
    130                 135                 140

Gln Thr Val Arg Ile Thr Cys Gln Gly Asp Ser Leu Arg Ser Tyr Tyr
145                 150                 155                 160

Ala Ser Trp Tyr Gln Gln Lys Pro Gly Gln Ala Pro Val Leu Val Ile
                165                 170                 175

Tyr Gly Lys Asn Asn Arg Pro Ser Gly Ile Pro Asp Arg Phe Ser Gly
            180                 185                 190

Ser Ser Ser Gly Asn Thr Ala Ser Leu Thr Ile Thr Gly Ala Gln Ala
        195                 200                 205

Glu Asp Glu Ala Asp Tyr Tyr Cys Asn Ser Ser Ala Pro Val Ser Asn
    210                 215                 220

Arg Val Val Phe Gly Gly Gly Thr Lys Leu Thr Val Leu Gly
225                 230                 235

<210> SEQ ID NO 11
<211> LENGTH: 1975
<212> TYPE: DNA
<213> ORGANISM: Homo Sapiens
<220> FEATURE:
<223> OTHER INFORMATION: GalNC-T3 gene, 3' UTR
<300> PUBLICATION INFORMATION:
<308> DATABASE ACCESSION NUMBER: GenBank Y10345
<309> DATABASE ENTRY DATE: 2000-10-27

<400> SEQUENCE: 11
taagtgttcc ttaaaattaa gttgaaaaag gaaatattct ttctcataaa actgtgacta      60
ggcatacact gtagtttttg aaaattatgc aaaagcagct aaatgtaact tattccaagt     120 gcattttct tatttatatc tttatgtagc actactacag aaattctgca agtttctgtt     180
tcaaagcaca ataactagta ataccaaaga ctatttcaaa atgtccagat gtaggggaag     240
agatgtttac agtatgatga aaataatttt ccaagtaaag tgatgtttgt gtgttttgta     300
cacttaggga tatatatata tagctacatt cacacactca caattaaaaa tatttcccct     360
agttttttgg ggggatagga agaaagattt gttactgtat ttttttaact acataaaaat     420
agatcaataa atgtcagcat tggcctctgt gtacaaacca agagctttta cagatccaga     480
atttattagt ttaaaatgca ggtgaacttt tttttgcgtt tggtttactt gtctgtcaaa     540
tgtttcctta acatgaaac tgaataagga gaagagtatt tttaacactt aaatttcttg     600 gcaaattta aaacattttt tagtctgtaa tacactccac ttgaagcact taagtcttcc     660
ttaaatgact tttcttaagt aatgatactg tgtgttttcc caaagcactt ttaaaaaaat     720
ttttataaat tactatctgt tgaaaaggtg tccttttcct ttcttctagt attttttttc     780
ttaccaaaat tcactaatct tgaatgtttg tgatattaaa tttcaaatgc agaatacttg     840
actcatttaa agctaaattt tgttactgat tcaattataa ttgtaatgga ttttttgactt    900 tgtaatggat tctttcatc aaaaagcctt attattttt atctatgtgg aaaacacaat       960
aaaaaatcct caaacactat tgtaatcattt ggttaagtgc ttattcctct tttgggtaaa  1020
atctgtaatt gataataggt ggggggaaaat gaattttgta tgctgaattt ctaagcgcct  1080
attgtttgta aaaccatcag atatttctta tggcacaaaa atgaggaat agcaaaattc    1140 ctgtgttcaa tatttagaaa attttgtatt aatttctgat aaagttcctt aagcatctga  1200
tagaatgatg ttttaaaaaa atttgacgct tgcttaggag atttaccact ttttttttttt  1260 gttttcgtc atttatatt tagatctcct gtattcttgt tcccgaagta aaatacgatc    1320
ggtttcatat tttaaatctg gcagagcctc agctgtacga aaaagagcat atactggtta  1380
```

```
ttgaccctat cttctcattg tttgtttgta agtttgaatt tgtattaaaa agcctgcatt    1440
ctgagctgga catggtggct cagcttctaa tcccagcact ttggtaggca aggtgggag     1500 gatcatttga gctcaggagt tccagaccag cctgggcaac atagcaaaat ctcatctcta    1560
caaaaagtaa aaattaaaaa atgaaattaa aaataaaatt acctaggtgt ggtggcacgc    1620
atctgtagtt ccagctatac aggaaggtga ggcagaagca ttgcttgagc ttgggagatc    1680
gaggctacag tgagctatga ttacaccact gcacttcagt ctgtgtgact gagcaagact    1740
ctttcaaaaa aaaaaaaaag cctacattct ccagttgatt atttccaact aatgtgtatt    1800
atgtgcctaa ttttctatca gaagttgtat taagcccgtt ttcacactgc tgttaaagac    1860
atacctgaga ctgggtaatt tataaagaaa aataggttca atggaccccac aggtccgcgt   1920 ggctggggaa gcttcacaat catggcggaa ggtgaaagca tgtcttacgt ggaag         1975
```

<210> SEQ ID NO 12
<211> LENGTH: 1902
<212> TYPE: DNA
<213> ORGANISM: Homo Sapiens
<220> FEATURE:
<223> OTHER INFORMATION: UDP-GalNAc:polypeptide N-acteylgalatosaminyl
      transferase
<300> PUBLICATION INFORMATION:
<308> DATABASE ACCESSION NUMBER: GenBank X92689
<309> DATABASE ENTRY DATE: 2000-01-07

<400> SEQUENCE: 12

```
atggctcacc taaagcgact agtaaaatta cacattaaaa gacattacca taaaagttc     60 tggaagcttg gtgcagtaat ttttttcttt ataatagttt tggttttaat gcaaagagaa    120
gtaagtgttc aatattccaa agaggaatca aggatggaaa ggaacatgaa aaacaaaaac    180
aagatgttgg atttaatgct agaagctgta acaatatta aggatgccat gccaaaaatg     240
caaataggag caccctgtcag gcaaaacatt gatgctggtg agagaccttg tttgcaagga   300
tattatacag cagcagaatt gaagcctgtc cttgaccgtc cacctcagga ttcaaatgca    360
cctggtgctt ctggtaaagc attcaagaca accaatttaa gtgttgaaga gcaaaaggaa    420
aaggaacgtg gggaagctaa acactgcttt aatgctttcg caagtgacag gatttctttg    480
caccgagatc ttggaccaga cactcgacct cctgaatgta ttgaacaaaa atttaagcgc    540
tgccctcccc tgcccaccac cagtgtcata atagtttttc ataatgaagc gtggtccacg    600
ttgcttagaa ctgtccacag tgtgctctat tcttcacctg caatactgct gaaggaaatc    660
attttggtgg atgatgctag tgtagatgag tacttacatg ataaactaga tgaatatgta    720
aaacaatttt ctatagtaaa aatagtcaga caaagagaaa gaaaggtct gatcactgct     780 cggttgctag gagcaacagt cgcaacagct gaaacgctca catttttaga tgctcactgt    840
gagtgtttct atggttggct agaacctctg ttggccagaa tagctgagaa ctacacggct    900
gtcgtaagtc cagatattgc atccatagat ctgaacacgt tgaattcaa caaaccttct    960 ccttatggaa gtaaccataa ccgtggaaat tttgactgga gtctttcatt tggctgggag   1020
tcgcttcctg atcatgagaa gcaaagaagg aaagatgaaa cctacccaat taaaacaccc    1080
acttttgcag gaggactttt ttccatatca aaagaatatt ttgagtatat ggaagctat    1140 gatgaagaaa tggaaatctg ggaggtgaa aatatagaaa tgtctttcag agtatggcaa    1200
tgtggtgggc agttggagat tatgccttgc tctgttgttg gacatgtttt tcgcagcaaa    1260
agccctcata gctttccaaa aggcactcag gtgattgcta gaaaccaagt tcgccttgca    1320
gaagtctgga tggatgaata caaggaaata ttttataggg gaaatacaga tgcagcaaaa    1380
```

-continued

```
attgttaaac aaaaagcatt tggtgatctt tcaaaaagat ttgaaataaa acaccgtctt    1440
cggtgtaaaa attttacatg gtatctgaac aacatttatc cagaggtgta tgtgccagac    1500
cttaatcctg ttatatctgg atacattaaa agcgttggtc agcctctatg tctggatgtt    1560
ggagaaaaca atcaaggagg caaccatta attatgtata catgtcatgg acttggggga    1620
aaccagtact ttgaatactc tgctcaacat gaaattcggc acaacatcca gaaggaatta    1680
tgtcttcatg ctgctcaagg tctcgttcag ctgaaggcat gtacctacaa aggtcacaag    1740
acagttgtca ctggagagca gatatgggag atccagaagg atcaacttct atacaatcca    1800
ttcttaaaaa tgtgcctttc agcaaatgga gagcatccaa gtttagtgtc atgcaaccca    1860
tcagatccac tccaaaaatg gatacttagc caaaatgatt aa                       1902
```

<210> SEQ ID NO 13
<211> LENGTH: 633
<212> TYPE: PRT
<213> ORGANISM: Homo Sapiens
<300> PUBLICATION INFORMATION:
<308> DATABASE ACCESSION NUMBER: GenBank CAA63371
<309> DATABASE ENTRY DATE: 2001-01-07

<400> SEQUENCE: 13

```
Met Ala His Leu Lys Arg Leu Val Lys Leu His Ile Lys Arg His Tyr
 1               5                   10                  15

His Lys Lys Phe Trp Lys Leu Gly Ala Val Ile Phe Phe Ile Ile
            20                  25                  30

Val Leu Val Leu Met Gln Arg Glu Val Ser Val Gln Tyr Ser Lys Glu
        35                  40                  45

Glu Ser Arg Met Glu Arg Asn Met Lys Asn Lys Asn Lys Met Leu Asp
    50                  55                  60

Leu Met Leu Glu Ala Val Asn Asn Ile Lys Asp Ala Met Pro Lys Met
65                  70                  75                  80

Gln Ile Gly Ala Pro Val Arg Gln Asn Ile Asp Ala Gly Glu Arg Pro
                85                  90                  95

Cys Leu Gln Gly Tyr Tyr Thr Ala Ala Glu Leu Lys Pro Val Leu Asp
            100                 105                 110

Arg Pro Pro Gln Asp Ser Asn Ala Pro Gly Ala Ser Gly Lys Ala Phe
        115                 120                 125

Lys Thr Thr Asn Leu Ser Val Glu Glu Gln Lys Glu Lys Glu Arg Gly
    130                 135                 140

Glu Ala Lys His Cys Phe Asn Ala Phe Ala Ser Asp Arg Ile Ser Leu
145                 150                 155                 160

His Arg Asp Leu Gly Pro Asp Thr Arg Pro Glu Cys Ile Glu Gln
                165                 170                 175

Lys Phe Lys Arg Cys Pro Pro Leu Pro Thr Thr Ser Val Ile Ile Val
            180                 185                 190

Phe His Asn Glu Ala Trp Ser Thr Leu Leu Arg Thr Val His Ser Val
        195                 200                 205

Leu Tyr Ser Ser Pro Ala Ile Leu Leu Lys Glu Ile Ile Leu Val Asp
    210                 215                 220

Asp Ala Ser Val Asp Glu Tyr Leu His Asp Lys Leu Asp Glu Tyr Val
225                 230                 235                 240

Lys Gln Phe Ser Ile Val Lys Ile Val Arg Gln Arg Glu Arg Lys Gly
                245                 250                 255

Leu Ile Thr Ala Arg Leu Leu Gly Ala Thr Val Ala Thr Ala Glu Thr
            260                 265                 270
```

```
Leu Thr Phe Leu Asp Ala His Cys Glu Cys Phe Tyr Gly Trp Leu Glu
            275                 280                 285
Pro Leu Leu Ala Arg Ile Ala Glu Asn Tyr Thr Ala Val Val Ser Pro
        290                 295                 300
Asp Ile Ala Ser Ile Asp Leu Asn Thr Phe Glu Phe Asn Lys Pro Ser
305                 310                 315                 320
Pro Tyr Gly Ser Asn His Asn Arg Gly Asn Phe Asp Trp Ser Leu Ser
                325                 330                 335
Phe Gly Trp Glu Ser Leu Pro Asp His Glu Lys Gln Arg Arg Lys Asp
            340                 345                 350
Glu Thr Tyr Pro Ile Lys Thr Pro Thr Phe Ala Gly Gly Leu Phe Ser
        355                 360                 365
Ile Ser Lys Glu Tyr Phe Glu Tyr Ile Gly Ser Tyr Asp Glu Glu Met
370                 375                 380
Glu Ile Trp Gly Gly Glu Asn Ile Glu Met Ser Phe Arg Val Trp Gln
385                 390                 395                 400
Cys Gly Gly Gln Leu Glu Ile Met Pro Cys Ser Val Val Gly His Val
                405                 410                 415
Phe Arg Ser Lys Ser Pro His Ser Phe Pro Lys Gly Thr Gln Val Ile
            420                 425                 430
Ala Arg Asn Gln Val Arg Leu Ala Glu Val Trp Met Asp Glu Tyr Lys
        435                 440                 445
Glu Ile Phe Tyr Arg Arg Asn Thr Asp Ala Ala Lys Ile Val Lys Gln
450                 455                 460
Lys Ala Phe Gly Asp Leu Ser Lys Arg Phe Glu Ile Lys His Arg Leu
465                 470                 475                 480
Arg Cys Lys Asn Phe Thr Trp Tyr Leu Asn Asn Ile Tyr Pro Glu Val
                485                 490                 495
Tyr Val Pro Asp Leu Asn Pro Val Ile Ser Gly Tyr Ile Lys Ser Val
            500                 505                 510
Gly Gln Pro Leu Cys Leu Asp Val Gly Glu Asn Asn Gln Gly Gly Lys
        515                 520                 525
Pro Leu Ile Met Tyr Thr Cys His Gly Leu Gly Gly Asn Gln Tyr Phe
530                 535                 540
Glu Tyr Ser Ala Gln His Glu Ile Arg His Asn Ile Gln Lys Glu Leu
545                 550                 555                 560
Cys Leu His Ala Ala Gln Gly Leu Val Gln Leu Lys Ala Cys Thr Tyr
                565                 570                 575
Lys Gly His Lys Thr Val Val Thr Gly Glu Gln Ile Trp Glu Ile Gln
            580                 585                 590
Lys Asp Gln Leu Leu Tyr Asn Pro Phe Leu Lys Met Cys Leu Ser Ala
        595                 600                 605
Asn Gly Glu His Pro Ser Leu Val Ser Cys Asn Pro Ser Asp Pro Leu
610                 615                 620
Gln Lys Trp Ile Leu Ser Gln Asn Asp
625                 630

<210> SEQ ID NO 14
<211> LENGTH: 8815
<212> TYPE: DNA
<213> ORGANISM: Homo Sapiens
<220> FEATURE:
<223> OTHER INFORMATION: Oncofetal Fibronectin variant 1
<300> PUBLICATION INFORMATION:
<308> DATABASE ACCESSION NUMBER: GenBank NM 212482
<309> DATABASE ENTRY DATE: 2005-06-10
```

<400> SEQUENCE: 14

```
gcccgcgccg gctgtgctgc acaggggag gagagggaac cccaggcgcg agcgggaaga      60
ggggacctgc agccacaact tctctggtcc tctgcatccc ttctgtccct ccacccgtcc    120
ccttccccac cctctggccc ccaccttctt ggaggcgaca accccggga ggcattagaa     180
gggattttc ccgcaggttg cgaagggaag caaacttggt ggcaacttgc ctcccgtgc      240
gggcgtctct cccccaccgt ctcaacatgc ttaggggtcc ggggcccggg ctgctgctgc    300
tggccgtcca gtgcctgggg acagcggtgc cctccacggg agcctcgaag agcaagaggc    360
aggctcagca aatggttcag ccccagtccc cggtggctgt cagtcaaagc aagcccggtt    420
gttatgacaa tggaaaacac tatcagataa atcaacagtg ggagcggacc tacctaggca    480
atgcgttggt ttgtacttgt tatggaggaa gccgaggttt taactgcgag agtaaacctg    540
aagctgaaga gacttgcttt gacaagtaca ctgggaacac ttaccgagtg ggtgacactt    600
atgagcgtcc taaagactcc atgatctggg actgtacctg catcggggct gggcgaggga    660
gaataagctg taccatcgca aaccgctgcc atgaagggg tcagtcctac aagattggtg     720
acacctggag gagaccacat gagactggtg gttacatgtt agagtgtgtg tgtcttggta    780
atggaaaagg agaatggacc tgcaagccca tagctgagaa gtgttttgat catgctgctg    840
ggacttccta tgtggtcgga gaaacgtggg agaagcccta ccaaggctgg atgatggtag    900
attgtacttg cctgggagaa ggcagcggac gcatcacttg cacttctaga aatagatgca    960
acgatcagga cacaaggaca tcctatagaa ttggagacac ctggagcaag aaggataatc    1020
gaggaaacct gctccagtgc atctgcacag gcaacggccg aggagagtgg aagtgtgaga    1080
ggcacacctc tgtgcagacc acatcgacg gatctggccc cttcaccgat gttcgtgcag     1140
ctgtttacca accgcagcct caccccagc ctcctcccta tggccactgt gtcacagaca     1200
gtggtgtggt ctactctgtg gggatgcagt ggctgaagac acaaggaaat aagcaaatgc    1260
tttgcacgtg cctgggcaac ggagtcagct gccaagagac agctgtaacc cagacttacg    1320
gtggcaactc aaatggagag ccatgtgtct taccattcac ctacaatggc aggacgttct    1380
actcctgcac cacagaaggg cgacaggacg gacatctttg gtgcagcaca acttcgaatt    1440
atgagcagga ccagaaatac tctttctgca gagaccacac tgttttggtt cagactcgag    1500
gaggaaattc caatggtgcc ttgtgccact tccccttcct atacaacaac cacaattaca    1560
ctgattgcac ttctgagggc agaagagaca acatgaagtg gtgtgggacc acacagaact    1620
atgatgccga ccagaagttt gggttctgcc ccatggctgc ccacgaggaa atctgcacaa    1680
ccaatgaagg ggtcatgtac cgcattggag atcagtggga taagcagcat gacatgggtc    1740
acatgatgag gtgcacgtgt gttgggaatg gtcgtgggga atggacatgc attgcctact    1800
cgcagcttcg agatcagtgc attgttgatg acatcactta caatgtgaac gacacattcc    1860
acaagcgtca tgaagagggg cacatgctga actgtacatg cttcggtcag ggtcggggca    1920
ggtggaagtg tgatcccgtc gaccaatgcc aggattcaga gactgggacg ttttatcaaa    1980
ttggagattc atgggagaag tatgtgcatg gtgtcagata ccagtgctac tgctatggcc    2040
gtggcattgg ggagtggcat tgccaacctt tacagaccta tccaagctca agtggtcctg    2100
tcgaagtatt tatcactgag actccgagtc agcccaactc ccacccatc cagtggaatg     2160
caccacagcc atctcacatt tccaagtaca ttctcaggtg agacctaaa aattctgtag     2220
gccgttggaa ggaagctacc ataccaggcc acttaaactc ctacaccatc aaaggcctga    2280
agcctggtgt ggtatacgag ggccagctca tcagcatcca gcagtacggc caccaagaag    2340
```

```
tgactcgctt tgacttcacc accaccagca ccagcacacc tgtgaccagc aacaccgtga    2400
caggagagac gactcccttt tctcctcttg tggccacttc tgaatctgtg accgaaatca    2460
cagccagtag ctttgtggtc tcctgggtct cagcttccga caccgtgtcg ggattccggg    2520
tggaatatga gctgagtgag gagggagatg agccacagta cctggatctt ccaagcacag    2580
ccacttctgt gaacatccct gacctgcttc tggccgaaa atacattgta aatgtctatc     2640
agatatctga ggatggggag cagagtttga tcctgtctac ttcacaaaca acagcgcctg    2700
atgcccctcc tgacccgact gtggaccaag ttgatgacac ctcaattgtt gttcgctgga    2760
gcagacccca ggctcccatc acagggtaca gaatagtcta ttcgccatca gtagaaggta    2820
gcagcacaga actcaacctt cctgaaactg caaactccgt caccctcagt gacttgcaac    2880
ctggtgttca gtataacatc actatctatg ctgtggaaga aaatcaagaa agtacacctg    2940
ttgtcattca acaagaaacc actggcaccc cacgctcaga tacagtgccc tctcccaggg    3000
acctgcagtt tgtggaagtg acagacgtga aggtcaccat catgtggaca ccgcctgaga    3060
gtgcagtgac cggctaccgt gtggatgtga tccccgtcaa cctgcctggc gagcacgggc    3120
agaggctgcc catcagcagg aacacctttg cagaagtcac cgggctgtcc cctggggtca    3180
cctattactt caaagtcttt gcagtgagcc atgggaggga gagcaagcct ctgactgctc    3240
aacagacaac caaactggat gctcccacta acctccagtt tgtcaatgaa actgattcta    3300
ctgtcctggt gagatggact ccacctcggg cccagataac aggataccga ctgaccgtgg    3360
gccttacccg aagaggacag cccaggcagt acaatgtggg tccctctgtc tccaagtacc    3420
cactgaggaa tctgcagcct gcatctgagt acaccgtatc cctcgtggcc ataaagggca    3480
accaagagag ccccaaagcc actggagtct ttaccacact gcagcctggg agctctattc    3540
caccttacaa caccgaggtg actgagacca ccattgtgat cacatggacg cctgctccaa    3600
gaattggttt taagctgggt gtacgaccaa gccaggagg agaggcacca cgagaagtga     3660
cttcagactc aggaagcatc gttgtgtccg gcttgactcc aggagtagaa tacgtctaca    3720
ccatccaagt cctgagagat ggacaggaaa gagatgcgcc aattgtaaac aaagtggtga    3780
caccattgtc tccaccaaca aacttgcatc tggaggcaaa ccctgacact ggagtgctca    3840
cagtctcctg ggagaggagc accaccccag acattactgg ttatagaatt accaacaccc    3900
ctacaaacgg ccagcaggga aattctttgg aagaagtggt ccatgctgat cagagctcct    3960 gcactttga taacctgagt cccggcctgg agtacaatgt cagtgtttac actgtcaagg     4020
atgacaagga aagtgtccct atctctgata ccatcatccc agaggtgccc caactcactg    4080
acctaagctt tgttgatata accgattcaa gcatcggcct gaggtggacc ccgctaaact    4140
cttccaccat tattgggtac cgcatcacag tagttgcggc aggagaaggt atccctattt    4200
ttgaagattt tgtggactcc tcagtaggat actacacagt cacagggctg gagccgggca    4260
ttgactatga tatcagcgtt atcactctca ttaatggcgg cgagagtgcc cctactacac    4320
tgacacaaca aacggctgtt cctcctccca ctgacctgcg attcaccaac attggtccag    4380
acaccatgcg tgtcacctgg gctccacccc catccattga tttaaccaac ttcctggtgc    4440
gttactcacc tgtgaaaaat gaggaagatg ttgcagagtt gtcaatttct ccttcagaca    4500
atgcagtggt cttaacaaat ctcctgcctg gtacagaata tgtagtgagt gtctccagtg    4560
tctacgaaca acatgagagc acacctctta gaggaagaca gaaaacaggt cttgattccc    4620
caactggcat tgacttttct gatattactg ccaactcttt tactgtgcac tggattgctc    4680
ctcgagccac catcactggc tacaggatcc gccatcatcc cgagcacttc agtgggagac    4740
```

```
ctcgagaaga tcgggtgccc cactctcgga attccatcac cctcaccaac ctcactccag    4800
gcacagagta tgtggtcagc atcgttgctc ttaatggcag agaggaaagt cccttattga    4860
ttggccaaca atcaacagtt tctgatgttc cgagggacct ggaagttgtt gctgcgaccc    4920
ccaccagcct actgatcagc tgggatgctc ctgctgtcac agtgagatat tacaggatca    4980
cttacggaga gacaggagga aatagccctg tccaggagtt cactgtgcct gggagcaagt    5040
ctacagctac catcagcggc cttaaacctg gagttgatta ccatcact gtgtatgctg      5100
tcactggccg tggagacagc cccgcaagca gcaagccaat ttccattaat taccgaacag    5160
aaattgacaa accatcccag atgcaagtga ccgatgttca ggacaacagc attagtgtca    5220
agtggctgcc ttcaagttcc cctgttactg gttacagagt aaccaccact cccaaaaatg    5280
gaccaggacc aacaaaaact aaaactgcag gtccagatca aacagaaatg actattgaag    5340
gcttgcagcc cacagtggag tatgtggtta gtgtctatgc tcagaatcca agcggagaga    5400
gtcagcctct ggttcagact gcagtaacca acattgatcg ccctaaagga ctggcattca    5460
ctgatgtgga tgtcgattcc atcaaaattg cttgggaaag cccacagggg caagtttcca    5520
ggtacagggt gacctactcg agccctgagg atggaatcca tgagctattc cctgcacctg    5580
atggtgaaga agacactgca gagctgcaag gcctcagacc gggttctgag tacacagtca    5640
gtgtggttgc cttgcacgat gatatggaga gccagcccct gattgaacc cagtccacag     5700
ctattcctgc accaactgac ctgaagttca ctcaggtcac acccacaagc ctgagcgccc    5760
agtggacacc acccaatgtt cagctcactg gatatcgagt gcgggtgacc cccaaggaga    5820
agaccggacc aatgaaagaa atcaaccttg ctcctgacag ctcatccgtg gttgtatcag    5880
gacttatggt ggccaccaaa tatgaagtga gtgtctatgc tcttaaggac actttgacaa    5940
gcagaccagc tcagggagtt gtcaccactc tggagaatgt cagcccacca agaagggctc    6000
gtgtgacaga tgctactgag accaccatca ccattagctg gagaaccaag actgagacga    6060
tcactggctt ccaagttgat gccgttccag ccaatggcca gactccaatc cagagaacca    6120
tcaagccaga tgtcagaagc tacaccatca caggtttaca accaggcact gactacaaga    6180
tctacctgta caccttgaat gacaatgctc ggagctcccc tgtggtcatc gacgcctcca    6240
ctgccattga tgcaccatcc aacctgcgtt tcctggccac cacacccaat tccttgctgg    6300
tatcatggca gccgccacgt gccaggatta ccggctacat catcaagtat gagaagcctg    6360
ggtctcctcc cagagaagtg gtccctcggc ccgccctgg tgtcacagag gctactatta    6420
ctggcctgga accgggaacc gaatatacaa tttatgtcat tgccctgaag aataatcaga    6480
agagcgagcc cctgattgga aggaaaaaga cagacgagct tccccaactg gtaacccttc    6540
cacacccaa tcttcatgga ccagagatct tggatgttcc ttccacagtt caaaagaccc    6600
ctttcgtcac ccacccctgg gtatgacactg gaaatggtat tcagcttcct ggcacttctg    6660
gtcagcaacc cagtgttggg caacaaatga tctttgagga acatggtttt aggcggacca    6720
caccgcccac aacggccacc cccataaggc ataggccaag accataccg ccgaatgtag     6780
gtgaggaaat ccaaattggt cacatcccca gggaagatgt agactatcac ctgtacccac    6840
acggtccggg actcaatcca aatgcctcta caggacaaga agctctctct cagacaacca    6900
tctcatgggc cccattccag gacacttctg agtacatcat ttcatgtcat cctgttggca    6960
ctgatgaaga acccttacag ttcagggttc ctggaacttc taccagtgcc actctgacag    7020
gcctcaccag aggtgccacc tacaacatca tagtggaggc actgaaagac cagcagaggc    7080
ataaggttcg ggaagaggtt gttaccgtgg gcaactctgt caacgaaggc ttgaaccaac    7140
```

| | | | | | | | | |
|---|---|---|---|---|---|---|---|---|
| ctacggatga | ctcgtgcttt | gaccccctaca | cagtttccca | ttatgccgtt | ggagatgagt | 7200 |
| gggaacgaat | gtctgaatca | ggctttaaac | tgttgtgcca | gtgcttaggc | tttggaagtg | 7260 |
| gtcatttcag | atgtgattca | tctagatggt | gccatgacaa | tggtgtgaac | tacaagattg | 7320 |
| gagagaagtg | ggaccgtcag | ggagaaaatg | gccagatgat | gagctgcaca | tgtcttggga | 7380 |
| acggaaaagg | agaattcaag | tgtgaccctc | atgaggcaac | gtgttatgat | gatgggaaga | 7440 |
| cataccacgt | aggagaacag | tggcagaagg | aatatctcgg | tgccatttgc | tcctgcacat | 7500 |
| gctttggagg | ccagcggggc | tggcgctgtg | acaactgccg | cagacctggg | ggtgaaccca | 7560 |
| gtcccgaagg | cactactggc | cagtcctaca | accagtattc | tcagagatac | catcagagaa | 7620 |
| caaacactaa | tgttaattgc | ccaattgagt | gcttcatgcc | tttagatgta | caggctgaca | 7680 |
| gagaagattc | ccgagagtaa | atcatctttc | caatccagag | gaacaagcat | gtctctctgc | 7740 |
| caagatccat | ctaaactgga | gtgatgttag | cagacccagc | ttagagttct | tctttctttc | 7800 |
| ttaagccctt | tgctctggag | gaagttctcc | agcttcagct | caactcacag | cttctccaag | 7860 |
| catcaccctg | ggagtttcct | gagggttttc | tcataaatga | gggctgcaca | ttgcctgttc | 7920 |
| tgcttcgaag | tattcaatac | cgctcagtat | tttaaatgaa | gtgattctaa | gatttggttt | 7980 |
| gggatcaata | ggaaagcata | tgcagccaac | caagatgcaa | atgttttgaa | atgatatgac | 8040 |
| caaaatttta | gtaggaaag | tcacccaaac | acttctgctt | tcacttaagt | gtctggcccg | 8100 |
| caatactgta | ggaacaagca | tgatcttgtt | actgtgatat | tttaaatatc | cacagtactc | 8160 |
| acttttccca | aatgatccta | gtaattgcct | agaaatatct | ttctcttacc | tgttatttat | 8220 |
| caattttttcc | cagtattttt | atacggaaaa | aattgtattg | aaaacactta | gtatgcagtt | 8280 |
| gataagagga | atttggtata | attatggtgg | gtgattattt | tttatactgt | atgtgccaaa | 8340 |
| gctttactac | tgtggaaaga | caactgtttt | aataaaagat | ttacattcca | caacttgaag | 8400 |
| ttcatctatt | tgatataaga | caccttcggg | ggaaataatt | cctgtgaata | ttcttttttca | 8460 |
| attcagcaaa | catttgaaaa | tctatgatgt | gcaagtctaa | ttgttgattt | cagtacaaga | 8520 |
| ttttctaaat | cagttgctac | aaaaactgat | tggttttttgt | cacttcatct | cttcactaat | 8580 |
| ggagatagct | ttacactttc | tgctttaata | gatttaagtg | gaccccaata | tttattaaaa | 8640 |
| ttgctagttt | accgttcaga | agtataatag | aaataatctt | tagttgctct | tttctaacca | 8700 |
| ttgtaattct | tcccttcttc | cctccacctt | tccttcattg | aataaacctc | tgttcaaaga | 8760 |
| gattgcctgc | aagggaaata | aaaatgacta | agatattaaa | aaaaaaaaaa | aaaaa | 8815 |

<210> SEQ ID NO 15
<211> LENGTH: 2477
<212> TYPE: PRT
<213> ORGANISM: Homo Sapiens
<300> PUBLICATION INFORMATION:
<308> DATABASE ACCESSION NUMBER: GenBank NM 212482
<309> DATABASE ENTRY DATE: 2005-06-10

<400> SEQUENCE: 15

```
Met Leu Arg Gly Pro Gly Pro Gly Leu Leu Leu Leu Ala Val Gln Cys
  1               5                  10                  15

Leu Gly Thr Ala Val Pro Ser Thr Gly Ala Ser Lys Ser Lys Arg Gln
             20                  25                  30

Ala Gln Gln Met Val Gln Pro Gln Ser Pro Val Ala Val Ser Gln Ser
         35                  40                  45

Lys Pro Gly Cys Tyr Asp Asn Gly Lys His Tyr Gln Ile Asn Gln Gln
     50                  55                  60
```

-continued

```
Trp Glu Arg Thr Tyr Leu Gly Asn Ala Leu Val Cys Thr Cys Tyr Gly
 65                  70                  75                  80

Gly Ser Arg Gly Phe Asn Cys Glu Ser Lys Pro Glu Ala Glu Glu Thr
                 85                  90                  95

Cys Phe Asp Lys Tyr Thr Gly Asn Thr Tyr Arg Val Gly Asp Thr Tyr
            100                 105                 110

Glu Arg Pro Lys Asp Ser Met Ile Trp Asp Cys Thr Cys Ile Gly Ala
        115                 120                 125

Gly Arg Gly Arg Ile Ser Cys Thr Ile Ala Asn Arg Cys His Glu Gly
    130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                165                 170                 175

Trp Thr Cys Lys Pro Ile Ala Glu Lys Cys Phe Asp His Ala Ala Gly
            180                 185                 190

Thr Ser Tyr Val Val Gly Glu Thr Trp Glu Lys Pro Tyr Gln Gly Trp
        195                 200                 205

Met Met Val Asp Cys Thr Cys Leu Gly Glu Gly Ser Gly Arg Ile Thr
    210                 215                 220

Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu
                245                 250                 255

Gln Cys Ile Cys Thr Gly Asn Gly Arg Gly Glu Trp Lys Cys Glu Arg
            260                 265                 270

His Thr Ser Val Gln Thr Thr Ser Ser Gly Ser Gly Pro Phe Thr Asp
        275                 280                 285

Val Arg Ala Ala Val Tyr Gln Pro Gln Pro His Pro Gln Pro Pro Pro
    290                 295                 300

Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
                325                 330                 335

Gly Asn Gly Val Ser Cys Gln Glu Thr Ala Val Thr Gln Thr Tyr Gly
            340                 345                 350

Gly Asn Ser Asn Gly Glu Pro Cys Val Leu Pro Phe Thr Tyr Asn Gly
        355                 360                 365

Arg Thr Phe Tyr Ser Cys Thr Thr Glu Gly Arg Gln Asp Gly His Leu
    370                 375                 380

Trp Cys Ser Thr Thr Ser Asn Tyr Glu Gln Asp Gln Lys Tyr Ser Phe
385                 390                 395                 400

Cys Thr Asp His Thr Val Leu Val Gln Thr Arg Gly Gly Asn Ser Asn
                405                 410                 415

Gly Ala Leu Cys His Phe Pro Phe Leu Tyr Asn Asn His Asn Tyr Thr
            420                 425                 430

Asp Cys Thr Ser Glu Gly Arg Arg Asp Asn Met Lys Trp Cys Gly Thr
        435                 440                 445

Thr Gln Asn Tyr Asp Ala Asp Gln Lys Phe Gly Phe Cys Pro Met Ala
    450                 455                 460

Ala His Glu Glu Ile Cys Thr Thr Asn Glu Gly Val Met Tyr Arg Ile
465                 470                 475                 480

Gly Asp Gln Trp Asp Lys Gln His Asp Met Gly His Met Met Arg Cys
                485                 490                 495
```

```
Thr Cys Val Gly Asn Gly Arg Gly Glu Trp Thr Cys Ile Ala Tyr Ser
            500                 505                 510
Gln Leu Arg Asp Gln Cys Ile Val Asp Asp Ile Thr Tyr Asn Val Asn
            515                 520                 525
Asp Thr Phe His Lys Arg His Glu Glu Gly His Met Leu Asn Cys Thr
530             535                 540
Cys Phe Gly Gln Gly Arg Gly Arg Trp Lys Cys Asp Pro Val Asp Gln
545             550                 555                 560
Cys Gln Asp Ser Glu Thr Gly Thr Phe Tyr Gln Ile Gly Asp Ser Trp
            565                 570                 575
Glu Lys Tyr Val His Gly Val Arg Tyr Gln Cys Tyr Cys Tyr Gly Arg
            580                 585                 590
Gly Ile Gly Glu Trp His Cys Gln Pro Leu Gln Thr Tyr Pro Ser Ser
            595                 600                 605
Ser Gly Pro Val Glu Val Phe Ile Thr Glu Thr Pro Ser Gln Pro Asn
            610                 615                 620
Ser His Pro Ile Gln Trp Asn Ala Pro Gln Pro Ser His Ile Ser Lys
625             630                 635                 640
Tyr Ile Leu Arg Trp Arg Pro Lys Asn Ser Val Gly Arg Trp Lys Glu
            645                 650                 655
Ala Thr Ile Pro Gly His Leu Asn Ser Tyr Thr Ile Lys Gly Leu Lys
            660                 665                 670
Pro Gly Val Val Tyr Glu Gly Gln Leu Ile Ser Ile Gln Gln Tyr Gly
            675                 680                 685
His Gln Glu Val Thr Arg Phe Asp Phe Thr Thr Thr Ser Thr Ser Thr
            690                 695                 700
Pro Val Thr Ser Asn Thr Val Thr Gly Glu Thr Thr Pro Phe Ser Pro
705             710                 715                 720
Leu Val Ala Thr Ser Glu Ser Val Thr Glu Ile Thr Ala Ser Ser Phe
            725                 730                 735
Val Val Ser Trp Val Ser Ala Ser Asp Thr Val Ser Gly Phe Arg Val
            740                 745                 750
Glu Tyr Glu Leu Ser Glu Glu Gly Asp Glu Pro Gln Tyr Leu Asp Leu
            755                 760                 765
Pro Ser Thr Ala Thr Ser Val Asn Ile Pro Asp Leu Leu Pro Gly Arg
770             775                 780
Lys Tyr Ile Val Asn Val Tyr Gln Ile Ser Glu Asp Gly Glu Gln Ser
785             790                 795                 800
Leu Ile Leu Ser Thr Ser Gln Thr Thr Ala Pro Asp Ala Pro Pro Asp
            805                 810                 815
Pro Thr Val Asp Gln Val Asp Asp Thr Ser Ile Val Val Arg Trp Ser
            820                 825                 830
Arg Pro Gln Ala Pro Ile Thr Gly Tyr Arg Ile Val Tyr Ser Pro Ser
            835                 840                 845
Val Glu Gly Ser Ser Thr Glu Leu Asn Leu Pro Glu Thr Ala Asn Ser
            850                 855                 860
Val Thr Leu Ser Asp Leu Gln Pro Gly Val Gln Tyr Asn Ile Thr Ile
865             870                 875                 880
Tyr Ala Val Glu Glu Asn Gln Glu Ser Thr Pro Val Val Ile Gln Gln
                            885                 890                 895
Glu Thr Thr Gly Thr Pro Arg Ser Asp Thr Val Pro Ser Pro Arg Asp
            900                 905                 910
Leu Gln Phe Val Glu Val Thr Asp Val Lys Val Thr Ile Met Trp Thr
```

```
                915                 920                 925
Pro Pro Glu Ser Ala Val Thr Gly Tyr Arg Val Asp Val Ile Pro Val
930                 935                 940
Asn Leu Pro Gly Glu His Gly Gln Arg Leu Pro Ile Ser Arg Asn Thr
945                 950                 955                 960
Phe Ala Glu Val Thr Gly Leu Ser Pro Gly Val Thr Tyr Tyr Phe Lys
                965                 970                 975
Val Phe Ala Val Ser His Gly Arg Glu Ser Lys Pro Leu Thr Ala Gln
                980                 985                 990
Gln Thr Thr Lys Leu Asp Ala Pro Thr Asn Leu Gln Phe Val Asn Glu
            995                1000                1005
Thr Asp Ser Thr Val Leu Val Arg Trp Thr Pro Pro Arg Ala Gln Ile
        1010                1015                1020
Thr Gly Tyr Arg Leu Thr Val Gly Leu Thr Arg Arg Gly Gln Pro Arg
1025                1030                1035                1040
Gln Tyr Asn Val Gly Pro Ser Val Ser Lys Tyr Pro Leu Arg Asn Leu
                1045                1050                1055
Gln Pro Ala Ser Glu Tyr Thr Val Ser Leu Val Ala Ile Lys Gly Asn
            1060                1065                1070
Gln Glu Ser Pro Lys Ala Thr Gly Val Phe Thr Thr Leu Gln Pro Gly
        1075                1080                1085
Ser Ser Ile Pro Pro Tyr Asn Thr Glu Val Thr Glu Thr Thr Ile Val
    1090                1095                1100
Ile Thr Trp Thr Pro Ala Pro Arg Ile Gly Phe Lys Leu Gly Val Arg
1105                1110                1115                1120
Pro Ser Gln Gly Gly Glu Ala Pro Arg Glu Val Thr Ser Asp Ser Gly
                1125                1130                1135
Ser Ile Val Val Ser Gly Leu Thr Pro Gly Val Glu Tyr Val Tyr Thr
            1140                1145                1150
Ile Gln Val Leu Arg Asp Gly Gln Glu Arg Asp Ala Pro Ile Val Asn
        1155                1160                1165
Lys Val Val Thr Pro Leu Ser Pro Pro Thr Asn Leu His Leu Glu Ala
    1170                1175                1180
Asn Pro Asp Thr Gly Val Leu Thr Val Ser Trp Glu Arg Ser Thr Thr
1185                1190                1195                1200
Pro Asp Ile Thr Gly Tyr Arg Ile Thr Thr Thr Pro Thr Asn Gly Gln
                1205                1210                1215
Gln Gly Asn Ser Leu Glu Glu Val Val His Ala Asp Gln Ser Ser Cys
            1220                1225                1230
Thr Phe Asp Asn Leu Ser Pro Gly Leu Glu Tyr Asn Val Ser Val Tyr
        1235                1240                1245
Thr Val Lys Asp Asp Lys Glu Ser Val Pro Ile Ser Asp Thr Ile Ile
    1250                1255                1260
Pro Glu Val Pro Gln Leu Thr Asp Leu Ser Phe Val Asp Ile Thr Asp
1265                1270                1275                1280
Ser Ser Ile Gly Leu Arg Trp Thr Pro Leu Asn Ser Ser Thr Ile Ile
                1285                1290                1295
Gly Tyr Arg Ile Thr Val Val Ala Ala Gly Glu Gly Ile Pro Ile Phe
            1300                1305                1310
Glu Asp Phe Val Asp Ser Ser Val Gly Tyr Tyr Thr Val Thr Gly Leu
        1315                1320                1325
Glu Pro Gly Ile Asp Tyr Asp Ile Ser Val Ile Thr Leu Ile Asn Gly
    1330                1335                1340
```

-continued

```
Gly Glu Ser Ala Pro Thr Thr Leu Thr Gln Gln Thr Ala Val Pro Pro
1345                1350                1355                1360

Pro Thr Asp Leu Arg Phe Thr Asn Ile Gly Pro Asp Thr Met Arg Val
                1365                1370                1375

Thr Trp Ala Pro Pro Ser Ile Asp Leu Thr Asn Phe Leu Val Arg
                1380                1385                1390

Tyr Ser Pro Val Lys Asn Glu Glu Asp Val Ala Glu Leu Ser Ile Ser
                1395                1400                1405

Pro Ser Asp Asn Ala Val Val Leu Thr Asn Leu Leu Pro Gly Thr Glu
                1410                1415                1420

Tyr Val Val Ser Val Ser Ser Val Tyr Glu Gln His Glu Ser Thr Pro
1425                1430                1435                1440

Leu Arg Gly Arg Gln Lys Thr Gly Leu Asp Ser Pro Thr Gly Ile Asp
                1445                1450                1455

Phe Ser Asp Ile Thr Ala Asn Ser Phe Thr Val His Trp Ile Ala Pro
                1460                1465                1470

Arg Ala Thr Ile Thr Gly Tyr Arg Ile Arg His His Pro Glu His Phe
                1475                1480                1485

Ser Gly Arg Pro Arg Glu Asp Arg Val Pro His Ser Arg Asn Ser Ile
                1490                1495                1500

Thr Leu Thr Asn Leu Thr Pro Gly Thr Glu Tyr Val Val Ser Ile Val
1505                1510                1515                1520

Ala Leu Asn Gly Arg Glu Glu Ser Pro Leu Leu Ile Gly Gln Gln Ser
                1525                1530                1535

Thr Val Ser Asp Val Pro Arg Asp Leu Glu Val Val Ala Ala Thr Pro
                1540                1545                1550

Thr Ser Leu Leu Ile Ser Trp Asp Ala Pro Ala Val Thr Val Arg Tyr
                1555                1560                1565

Tyr Arg Ile Thr Tyr Gly Glu Thr Gly Gly Asn Ser Pro Val Gln Glu
                1570                1575                1580

Phe Thr Val Pro Gly Ser Lys Ser Thr Ala Thr Ile Ser Gly Leu Lys
1585                1590                1595                1600

Pro Gly Val Asp Tyr Thr Ile Thr Val Tyr Ala Val Thr Gly Arg Gly
                1605                1610                1615

Asp Ser Pro Ala Ser Ser Lys Pro Ile Ser Ile Asn Tyr Arg Thr Glu
                1620                1625                1630

Ile Asp Lys Pro Ser Gln Met Gln Val Thr Asp Val Gln Asp Asn Ser
                1635                1640                1645

Ile Ser Val Lys Trp Leu Pro Ser Ser Ser Pro Val Thr Gly Tyr Arg
                1650                1655                1660

Val Thr Thr Thr Pro Lys Asn Gly Pro Gly Pro Thr Lys Thr Lys Thr
1665                1670                1675                1680

Ala Gly Pro Asp Gln Thr Glu Met Thr Ile Glu Gly Leu Gln Pro Thr
                1685                1690                1695

Val Glu Tyr Val Val Ser Val Tyr Ala Gln Asn Pro Ser Gly Glu Ser
                1700                1705                1710

Gln Pro Leu Val Gln Thr Ala Val Thr Asn Ile Asp Arg Pro Lys Gly
                1715                1720                1725

Leu Ala Phe Thr Asp Val Asp Val Asp Ser Ile Lys Ile Ala Trp Glu
                1730                1735                1740

Ser Pro Gln Gly Gln Val Ser Arg Tyr Arg Val Thr Tyr Ser Ser Pro
1745                1750                1755                1760

Glu Asp Gly Ile His Glu Leu Phe Pro Ala Pro Asp Gly Glu Glu Asp
                1765                1770                1775
```

-continued

Thr Ala Glu Leu Gln Gly Leu Arg Pro Gly Ser Glu Tyr Thr Val Ser
            1780                1785                1790

Val Val Ala Leu His Asp Asp Met Glu Ser Gln Pro Leu Ile Gly Thr
        1795                1800                1805

Gln Ser Thr Ala Ile Pro Ala Pro Thr Asp Leu Lys Phe Thr Gln Val
    1810                1815                1820

Thr Pro Thr Ser Leu Ser Ala Gln Trp Thr Pro Pro Asn Val Gln Leu
1825                1830                1835                1840

Thr Gly Tyr Arg Val Arg Val Thr Pro Lys Glu Lys Thr Gly Pro Met
            1845                1850                1855

Lys Glu Ile Asn Leu Ala Pro Asp Ser Ser Val Val Ser Gly
        1860                1865                1870

Leu Met Val Ala Thr Lys Tyr Glu Val Ser Val Tyr Ala Leu Lys Asp
        1875                1880                1885

Thr Leu Thr Ser Arg Pro Ala Gln Gly Val Val Thr Thr Leu Glu Asn
    1890                1895                1900

Val Ser Pro Pro Arg Arg Ala Arg Val Thr Asp Ala Thr Glu Thr Thr
1905                1910                1915                1920

Ile Thr Ile Ser Trp Arg Thr Lys Thr Glu Thr Ile Thr Gly Phe Gln
            1925                1930                1935

Val Asp Ala Val Pro Ala Asn Gly Gln Thr Pro Ile Gln Arg Thr Ile
        1940                1945                1950

Lys Pro Asp Val Arg Ser Tyr Thr Ile Thr Gly Leu Gln Pro Gly Thr
    1955                1960                1965

Asp Tyr Lys Ile Tyr Leu Tyr Thr Leu Asn Asp Asn Ala Arg Ser Ser
        1970                1975                1980

Pro Val Val Ile Asp Ala Ser Thr Ala Ile Asp Ala Pro Ser Asn Leu
1985                1990                1995                2000

Arg Phe Leu Ala Thr Thr Pro Asn Ser Leu Leu Val Ser Trp Gln Pro
            2005                2010                2015

Pro Arg Ala Arg Ile Thr Gly Tyr Ile Ile Lys Tyr Glu Lys Pro Gly
        2020                2025                2030

Ser Pro Pro Arg Glu Val Val Pro Arg Pro Arg Pro Gly Val Thr Glu
    2035                2040                2045

Ala Thr Ile Thr Gly Leu Glu Pro Gly Thr Glu Tyr Thr Ile Tyr Val
        2050                2055                2060

Ile Ala Leu Lys Asn Asn Gln Lys Ser Glu Pro Leu Ile Gly Arg Lys
2065                2070                2075                2080

Lys Thr Asp Glu Leu Pro Gln Leu Val Thr Leu Pro His Pro Asn Leu
            2085                2090                2095

His Gly Pro Glu Ile Leu Asp Val Pro Ser Thr Val Gln Lys Thr Pro
        2100                2105                2110

Phe Val Thr His Pro Gly Tyr Asp Thr Gly Asn Gly Ile Gln Leu Pro
    2115                2120                2125

Gly Thr Ser Gly Gln Gln Pro Ser Val Gly Gln Gln Met Ile Phe Glu
        2130                2135                2140

Glu His Gly Phe Arg Arg Thr Thr Pro Pro Thr Thr Ala Thr Pro Ile
2145                2150                2155                2160

Arg His Arg Pro Arg Pro Tyr Pro Pro Asn Val Gly Glu Glu Ile Gln
            2165                2170                2175

Ile Gly His Ile Pro Arg Glu Asp Val Asp Tyr His Leu Tyr Pro His
        2180                2185                2190

Gly Pro Gly Leu Asn Pro Asn Ala Ser Thr Gly Gln Glu Ala Leu Ser

```
                     2195                2200                2205
Gln Thr Thr Ile Ser Trp Ala Pro Phe Gln Asp Thr Ser Glu Tyr Ile
    2210                2215                2220

Ile Ser Cys His Pro Val Gly Thr Asp Glu Glu Pro Leu Gln Phe Arg
2225                2230                2235                2240

Val Pro Gly Thr Ser Thr Ser Ala Thr Leu Thr Gly Leu Thr Arg Gly
                2245                2250                2255

Ala Thr Tyr Asn Ile Ile Val Glu Ala Leu Lys Asp Gln Gln Arg His
            2260                2265                2270

Lys Val Arg Glu Glu Val Val Thr Val Gly Asn Ser Val Asn Glu Gly
        2275                2280                2285

Leu Asn Gln Pro Thr Asp Asp Ser Cys Phe Asp Pro Tyr Thr Val Ser
    2290                2295                2300

His Tyr Ala Val Gly Asp Glu Trp Glu Arg Met Ser Glu Ser Gly Phe
2305                2310                2315                2320

Lys Leu Leu Cys Gln Cys Leu Gly Phe Gly Ser Gly His Phe Arg Cys
                2325                2330                2335

Asp Ser Ser Arg Trp Cys His Asp Asn Gly Val Asn Tyr Lys Ile Gly
            2340                2345                2350

Glu Lys Trp Asp Arg Gln Gly Glu Asn Gly Gln Met Met Ser Cys Thr
        2355                2360                2365

Cys Leu Gly Asn Gly Lys Gly Glu Phe Lys Cys Asp Pro His Glu Ala
    2370                2375                2380

Thr Cys Tyr Asp Asp Gly Lys Thr Tyr His Val Gly Glu Gln Trp Gln
2385                2390                2395                2400

Lys Glu Tyr Leu Gly Ala Ile Cys Ser Cys Thr Cys Phe Gly Gly Gln
                2405                2410                2415

Arg Gly Trp Arg Cys Asp Asn Cys Arg Arg Pro Gly Gly Glu Pro Ser
            2420                2425                2430

Pro Glu Gly Thr Thr Gly Gln Ser Tyr Asn Gln Tyr Ser Gln Arg Tyr
        2435                2440                2445

His Gln Arg Thr Asn Thr Asn Val Asn Cys Pro Ile Glu Cys Phe Met
    2450                2455                2460

Pro Leu Asp Val Gln Ala Asp Arg Glu Asp Ser Arg Glu
2465                2470                2475
```

<210> SEQ ID NO 16
<211> LENGTH: 8647
<212> TYPE: DNA
<213> ORGANISM: Homo Sapiens
<220> FEATURE:
<223> OTHER INFORMATION: Oncofetal Fibronectin variant 2
<300> PUBLICATION INFORMATION:
<308> DATABASE ACCESSION NUMBER: GenBank NM 212475
<309> DATABASE ENTRY DATE: 2005-06-10

<400> SEQUENCE: 16

```
gcccgcgccg gctgtgctgc acaggggggag gagagggaac cccaggcgcg agcgggaaga      60
ggggacctgc agccacaact tctctggtcc tctgcatccc ttctgtccct ccacccgtcc     120
ccttccccac cctctggccc ccaccttctt ggaggcgaca accccgggga ggcattagaa     180
gggattttc ccgcaggttg cgaagggaag caaacttggt ggcaacttgc ctcccggtgc      240
gggcgtctct cccccaccgt ctcaacatgc ttaggggtcc ggggcccggg ctgctgctgc     300
tggccgtcca gtgcctgggg acagcggtgc cctccacggg agcctcgaag agcaagaggc     360
aggctcagca aatggttcag ccccagtccc cggtggctgt cagtcaaagc aagcccggtt     420
```

-continued

```
gttatgacaa tggaaaacac tatcagataa atcaacagtg ggagcggacc tacctaggca    480
atgcgttggt ttgtacttgt tatggaggaa gccgaggttt taactgcgag agtaaacctg    540
aagctgaaga gacttgcttt gacaagtaca ctgggaacac ttaccgagtg ggtgacactt    600
atgagcgtcc taaagactcc atgatctggg actgtacctg catcggggct gggcgaggga    660
gaataagctg taccatcgca aaccgctgcc atgaaggggg tcagtcctac aagattggtg    720
acacctggag gagaccacat gagactggtg gttacatgtt agagtgtgtg tgtcttggta    780
atggaaaagg agaatggacc tgcaagccca tagctgagaa gtgttttgat catgctgctg    840
ggacttccta tgtggtcgga gaaacgtggg agaagcccta ccaaggctgg atgatggtag    900
attgtacttg cctgggagaa ggcagcggac gcatcacttg cacttctaga aatagatgca    960
acgatcagga cacaaggaca tcctatagaa ttggagacac ctggagcaag aaggataatc   1020
gaggaaacct gctccagtgc atctgcacag gcaacggccg aggagagtgg aagtgtgaga   1080
ggcacacctc tgtgcagacc acatcgagcg gatctggccc cttcaccgat gttcgtgcag   1140
ctgtttacca accgcagcct cacccccagc ctcctcccta tggccactgt gtcacagaca   1200
gtggtgtggt ctactctgtg gggatgcagt ggctgaagac acaaggaaat aagcaaatgc   1260
tttgcacgtg cctgggcaac ggagtcagct gccaagagac agctgtaacc cagacttacg   1320
gtggcaactc aaatgagag ccatgtgtct taccattcac ctacaatggc aggacgttct   1380
actcctgcac cacagaaggg cgacaggacg gacatctttg gtgcagcaca acttcgaatt   1440
atgagcagga ccagaaatac tctttctgca cagaccacac tgttttggtt cagactcgag   1500
gaggaaattc caatggtgcc ttgtgccact tccccttcct atacaacaac cacaattaca   1560
ctgattgcac ttctgagggc agaagagaca acatgaagtg gtgtgggacc acacagaact   1620
atgatgccga ccagaagttt gggttctgcc ccatggctgc ccacgaggaa atctgcacaa   1680
ccaatgaagg ggtcatgtac cgcattgag atcagtggga taagcagcat gacatgggtc   1740
acatgatgag gtgcacgtgt gttgggaatg gtcgtgggga atggacatgc attgcctact   1800
cgcagcttcg agatcagtgc attgttgatg acatcactta caatgtgaac gacacattcc   1860
acaagcgtca tgaagagggg cacatgctga actgtacatg cttcggtcag ggtcggggca   1920
ggtggaagtg tgatcccgtc gaccaatgcc aggattcaga gactgggacg ttttatcaaa   1980
ttggagattc atgggagaag tatgtgcatg gtgtcagata ccagtgctac tgctatggcc   2040
gtggcattgg ggagtggcat tgccaacctt tacagaccta tccaagctca gtggtcctg   2100 tcgaagtatt tatcactgag actccgagtc agcccaactc ccaccccatc cagtggaatg   2160
caccacagcc atctcacatt tccaagtaca ttctcaggtg gagacctaaa aattctgtag   2220
gccgttggaa ggaagctacc ataccaggcc acttaaactc ctacaccatc aaaggcctga   2280
agcctggtgt ggtatacgag ggccagctca tcagcatcca gcagtacggc caccaagaag   2340
tgactcgctt tgacttcacc accaccagca ccagcacacc tgtgaccagc aacaccgtga   2400
caggagagac gactccctt tctcctcttg tggccacttc tgaatctgtg accgaaatca   2460
cagccagtag ctttgtggtc tcctgggtct cagcttccga caccgtgtcg ggattccggg   2520
tggaatatga gctgagtgag gagggagatg agccacagta cctggatctt ccaagcacag   2580
ccacttctgt gaacatccct gacctgcttc ctggccgaaa atacattgta aatgtctatc   2640
agatatctga ggatgggag cagagtttga tcctgtctac ttcacaaaca acagcgcctg   2700
atgcccctcc tgacccgact gtggaccaag ttgatgacac ctcaattgtt gttcgctgga   2760 gcagaccca ggctcccatc acagggtaca gaatagtcta ttcgccatca gtagaaggta   2820
```

```
gcagcacaga actcaacctt cctgaaactg caaactccgt caccctcagt gacttgcaac    2880
ctggtgttca gtataacatc actatctatg ctgtggaaga aaatcaagaa agtacacctg    2940
ttgtcattca acaagaaacc actggcaccc cacgctcaga tacagtgccc tctcccaggg    3000
acctgcagtt tgtggaagtg acagacgtga aggtcaccat catgtggaca ccgcctgaga    3060
gtgcagtgac cggctaccgt gtggatgtga tccccgtcaa cctgcctggc gagcacgggc    3120
agaggctgcc catcagcagg aacacctttg cagaagtcac cgggctgtcc cctggggtca    3180
cctattactt caaagtcttt gcagtgagcc atgggaggga gagcaagcct ctgactgctc    3240
aacagacaac caaactggat gctcccacta acctccagtt tgtcaatgaa actgattcta    3300
ctgtcctggt gagatggact ccacctcggg cccagataac aggataccga ctgaccgtgg    3360
gccttacccg aagaggacag cccaggcagt acaatgtggg tccctctgtc tccaagtacc    3420
cactgaggaa tctgcagcct gcatctgagt acaccgtatc cctcgtggcc ataaagggca    3480
accaagagag ccccaaagcc actggagtct ttaccacact gcagcctggg agctctattc    3540
caccttacaa caccgaggtg actgagacca ccattgtgat cacatggacg cctgctccaa    3600
gaattggttt taagctgggt gtacgaccaa gccaggagg agaggcacca cgagaagtga    3660
cttcagactc aggaagcatc gttgtgtccg gcttgactcc aggagtagaa tacgtctaca    3720
ccatccaagt cctgagagat ggacaggaaa gagatgcgcc aattgtaaac aaagtggtga    3780
caccattgtc tccaccaaca aacttgcatc tggaggcaaa ccctgacact ggagtgctca    3840
cagtctcctg ggagaggagc accaccccag acattactgg ttatagaatt accacaaccc    3900
ctacaaacgg ccagcaggga aattctttgg aagaagtggt ccatgctgat cagagctcct    3960
gcacttttga taacctgagt cccggcctgg agtacaatgt cagtgtttac actgtcaagg    4020
atgacaagga aagtgtccct atctctgata ccatcatccc agaggtgccc caactcactg    4080
acctaagctt tgttgatata accgattcaa gcatcggcct gaggtggacc ccgctaaact    4140
cttccaccat tattgggtac cgcatcacag tagttgcggc aggagaaggt atccctattt    4200
ttgaagattt tgtggactcc tcagtaggat actacacagt cacagggctg gagccgggca    4260
ttgactatga tatcagcgtt atcactctca ttaatggcgg cgagagtgcc cctactacac    4320
tgacacaaca aacggctgtt cctcctccca ctgacctgcg attcaccaac attggtccag    4380
acaccatgcg tgtcacctgg gctccacccc catccattga tttaaccaac ttcctggtgc    4440
gttactcacc tgtgaaaaat gaggaagatg ttgcagagtt gtcaatttct ccttcagaca    4500
atgcagtggt cttaacaaat ctcctgcctg gtacagaata tgtagtgagt gtctccagtg    4560
tctacgaaca acatgagagc acacctctta gaggaagaca gaaaacaggt cttgattccc    4620
caactggcat tgactttct gatattactg ccaactcttt tactgtgcac tggattgctc    4680
ctcgagccac catcactggc tacaggatcc gccatcatcc cgagcacttc agtgggagac    4740
ctcgagaaga tcgggtgccc cactctcgga attccatcac cctcaccaac ctcactccag    4800
gcacagagta tgtggtcagc atcgttgctc ttaatggcag agaggaaagt cccttattga    4860
ttggccaaca atcaacagtt tctgatgttc cgagggacct ggaagttgtt gctgcgaccc    4920
ccaccagcct actgatcagc tgggatgctc ctgctgtcac agtgagatat acaggatca    4980 cttacgagga gacaggagga aatagccctg tccaggagtt cactgtgcct gggagcaagt    5040
ctacagctac catcagcggc cttaaacctg gagttgatta ccatcacact gtgtatgctg    5100
tcactggccg tggagacagc cccgcaagca gcaagccaat ttccattaat taccgaacag    5160 aaaattgacaa accatcccag atgcaagtga ccgatgttca ggacaacagc attagtgtca    5220
```

```
agtggctgcc ttcaagttcc cctgttactg gttacagagt aaccaccact cccaaaaatg   5280
gaccaggacc aacaaaaact aaaactgcag gtccagatca aacagaaatg actattgaag   5340
gcttgcagcc cacagtggag tatgtggtta gtgtctatgc tcagaatcca agcggagaga   5400
gtcagcctct ggttcagact gcagtaacca acattgatcg ccctaaagga ctggcattca   5460
ctgatgtgga tgtcgattcc atcaaaattg cttgggaaag cccacagggg caagtttcca   5520
ggtacagggt gacctactcg agccctgagg atggaatcca tgagctattc cctgcacctg   5580
atggtgaaga agacactgca gagctgcaag gcctcagacc gggttctgag tacacagtca   5640
gtgtggttgc cttgcacgat gatatggaga gccagcccct gattggaacc cagtccacag   5700
ctattcctgc accaactgac ctgaagttca ctcaggtcac acccacaagc ctgagcgccc   5760
agtggacacc acccaatgtt cagctcactg gatatcgagt gcgggtgacc cccaaggaga   5820
agaccggacc aatgaaagaa atcaaccttg ctcctgacag ctcatccgtg gttgtatcag   5880
gacttatggt ggccaccaaa tatgaagtga gtgtctatgc tcttaaggac actttgacaa   5940
gcagaccagc tcagggagtt gtcaccactc tggagaatgt cagcccacca agaagggctc   6000
gtgtgacaga tgctactgag accaccatca ccattagctg gagaaccaag actgagacga   6060
tcactggctt ccaagttgat gccgttccag ccaatggcca gactccaatc cagagaacca   6120
tcaagccaga tgtcagaagc tacaccatca caggtttaca accaggcact gactacaaga   6180
tctacctgta caccttgaat gacaatgctc ggagctcccc tgtggtcatc gacgcctcca   6240
ctgccattga tgcaccatcc aacctgcgtt tcctggccac cacacccaat tccttgctgg   6300
tatcatggca gccgccacgt gccaggatta ccggctacat catcaagtat gagaagcctg   6360
ggtctcctcc cagagaagtg gtccctcggc ccgcccctgg tgtcacagag ctactatta    6420 ctggcctgga accgggaacc gaatatacaa tttatgtcat tgccctgaag aataatcaga   6480
agagcgagcc cctgattgga aggaaaaaga cagttcaaaa gacccctttc gtcacccacc   6540
ctgggtatga cactggaaat ggtattcagc ttcctggcac ttctggtcag caacccagtg   6600
ttgggcaaca aatgatcttt gaggaacatg gttttaggcg gaccacaccg cccacaacgg   6660 ccaccccat aaggcatagg ccaagaccat acccgccgaa tgtaggacaa gaagctctct   6720
ctcagacaac catctcatgg gccccattcc aggacacttc tgagtacatc atttcatgtc   6780
atcctgttgg cactgatgaa gaaccttac agttcagggt tcctggaact tctaccagtg   6840
ccactctgac aggcctcacc agaggtgcca cctacaacat catagtggag gcactgaaag   6900
accagcagag gcataaggtt cgggaagagg ttgttaccgt gggcaactct gtcaacgaag   6960
gcttgaacca acctacggat gactcgtgct ttgaccccta cacagtttcc cattatgccg   7020
ttggagatga gtgggaacga atgtctgaat caggctttaa actgttgtgc cagtgcttag   7080
gctttggaag tggtcatttc agatgtgatt catctagatg gtgccatgac aatggtgtga   7140
actacaagat tggagagaag tgggaccgtc agggagaaaa tggccagatg atgagctgca   7200
catgtcttgg gaacggaaaa ggagaattca gtgtgaccc tcatgaggca acgtgttatg   7260
atgatgggaa gacataccac gtaggagaac agtggcagaa ggaatatctc ggtgccattt   7320
gctcctgcac atgctttgga ggccagcggg gctggcgctg tgacaactgc cgcagacctg   7380
ggggtgaacc cagtcccgaa ggcactactg gccagtccta caaccagtat tctcagagat   7440
accatcagag aacaaacact aatgttaatt gcccaattga gtgcttcatg cctttagatg   7500
tacaggctga cagagaagat tcccgagagt aaatcatctt tccaatccag aggaacaagc   7560
atgtctctct gccaagatcc atctaaactg gagtgatgtt agcagaccca gcttagagtt   7620
```

```
cttctttctt tcttaagccc tttgctctgg aggaagttct ccagcttcag ctcaactcac    7680
agcttctcca agcatcaccc tgggagtttc ctgagggttt tctcataaat gagggctgca    7740
cattgcctgt tctgcttcga agtattcaat accgctcagt attttaaatg aagtgattct    7800
aagatttggt ttgggatcaa taggaaagca tatgcagcca accaagatgc aaatgttttg    7860
aaatgatatg accaaaattt taagtaggaa agtcacccaa acacttctgc tttcacttaa    7920
gtgtctggcc cgcaatactg taggaacaag catgatcttg ttactgtgat attttaaata    7980
tccacagtac tcacttttc caaatgatcc tagtaattgc ctagaaatat ctttctctta    8040
cctgttattt atcaattttt cccagtattt ttatacggaa aaaattgtat tgaaaacact    8100
tagtatgcag ttgataagag gaatttggta taattatggt gggtgattat tttttatact    8160
gtatgtgcca aagctttact actgtggaaa gacaactgtt ttaataaaag atttacattc    8220
cacaacttga agttcatcta tttgatataa gacaccttcg ggggaaataa ttcctgtgaa    8280
tattcttttt caattcagca aacatttgaa aatctatgat gtgcaagtct aattgttgat    8340
ttcagtacaa gattttctaa atcagttgct acaaaaactg attggttttt gtcacttcat    8400
ctcttcacta atggagatag ctttacactt tctgctttaa tagatttaag tggaccccaa    8460
tatttattaa aattgctagt ttaccgttca gaagtataat agaaataatc tttagttgct    8520
cttttctaac cattgtaatt cttcccttct ccctccacc tttccttcat tgaataaacc    8580
tctgttcaaa gagattgcct gcaagggaaa taaaaatgac taagatatta aaaaaaaaa    8640 aaaaaaa                                                             8647

<210> SEQ ID NO 17
<211> LENGTH: 2421
<212> TYPE: PRT
<213> ORGANISM: Homo Sapiens
<300> PUBLICATION INFORMATION:
<308> DATABASE ACCESSION NUMBER: GenBank NM 212475
<309> DATABASE ENTRY DATE: 2005-06-10

<400> SEQUENCE: 17

Met Leu Arg Gly Pro Gly Pro Gly Leu Leu Leu Leu Ala Val Gln Cys
 1               5                  10                  15

Leu Gly Thr Ala Val Pro Ser Thr Gly Ala Ser Lys Ser Lys Arg Gln
                20                  25                  30

Ala Gln Gln Met Val Gln Pro Gln Ser Pro Val Ala Val Ser Gln Ser
            35                  40                  45

Lys Pro Gly Cys Tyr Asp Asn Gly Lys His Tyr Gln Ile Asn Gln Gln
        50                  55                  60

Trp Glu Arg Thr Tyr Leu Gly Asn Ala Leu Val Cys Thr Cys Tyr Gly
 65                  70                  75                  80

Gly Ser Arg Gly Phe Asn Cys Glu Ser Lys Pro Glu Ala Glu Glu Thr
                85                  90                  95

Cys Phe Asp Lys Tyr Thr Gly Asn Thr Tyr Arg Val Gly Asp Thr Tyr
            100                 105                 110

Glu Arg Pro Lys Asp Ser Met Ile Trp Asp Cys Thr Cys Ile Gly Ala
        115                 120                 125

Gly Arg Gly Arg Ile Ser Cys Thr Ile Ala Asn Arg Cys His Glu Gly
    130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                165                 170                 175
```

-continued

```
Trp Thr Cys Lys Pro Ile Ala Glu Lys Cys Phe Asp His Ala Ala Gly
            180                 185                 190

Thr Ser Tyr Val Val Gly Glu Thr Trp Glu Lys Pro Tyr Gln Gly Trp
            195                 200                 205

Met Met Val Asp Cys Thr Cys Leu Gly Glu Gly Ser Gly Arg Ile Thr
    210                 215                 220

Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu
                245                 250                 255

Gln Cys Ile Cys Thr Gly Asn Gly Arg Gly Glu Trp Lys Cys Glu Arg
                260                 265                 270

His Thr Ser Val Gln Thr Thr Ser Ser Gly Ser Gly Pro Phe Thr Asp
            275                 280                 285

Val Arg Ala Ala Val Tyr Gln Pro Gln Pro His Pro Gln Pro Pro Pro
        290                 295                 300

Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
                325                 330                 335

Gly Asn Gly Val Ser Cys Gln Glu Thr Ala Val Thr Gln Thr Tyr Gly
            340                 345                 350

Gly Asn Ser Asn Gly Glu Pro Cys Val Leu Pro Phe Thr Tyr Asn Gly
        355                 360                 365

Arg Thr Phe Tyr Ser Cys Thr Thr Glu Gly Arg Gln Asp Gly His Leu
    370                 375                 380

Trp Cys Ser Thr Thr Ser Asn Tyr Glu Gln Asp Gln Lys Tyr Ser Phe
385                 390                 395                 400

Cys Thr Asp His Thr Val Leu Val Gln Thr Arg Gly Gly Asn Ser Asn
                405                 410                 415

Gly Ala Leu Cys His Phe Pro Phe Leu Tyr Asn Asn His Asn Tyr Thr
            420                 425                 430

Asp Cys Thr Ser Glu Gly Arg Arg Asp Asn Met Lys Trp Cys Gly Thr
        435                 440                 445

Thr Gln Asn Tyr Asp Ala Asp Gln Lys Phe Gly Phe Cys Pro Met Ala
    450                 455                 460

Ala His Glu Glu Ile Cys Thr Thr Asn Glu Gly Val Met Tyr Arg Ile
465                 470                 475                 480

Gly Asp Gln Trp Asp Lys Gln His Asp Met Gly His Met Met Arg Cys
                485                 490                 495

Thr Cys Val Gly Asn Gly Arg Gly Glu Trp Thr Cys Ile Ala Tyr Ser
            500                 505                 510

Gln Leu Arg Asp Gln Cys Ile Val Asp Asp Ile Thr Tyr Asn Val Asn
        515                 520                 525

Asp Thr Phe His Lys Arg His Glu Glu Gly His Met Leu Asn Cys Thr
    530                 535                 540

Cys Phe Gly Gln Gly Arg Gly Arg Trp Lys Cys Asp Pro Val Asp Gln
545                 550                 555                 560

Cys Gln Asp Ser Glu Thr Gly Thr Phe Tyr Gln Ile Gly Asp Ser Trp
                565                 570                 575

Glu Lys Tyr Val His Gly Val Arg Tyr Gln Cys Tyr Cys Tyr Gly Arg
            580                 585                 590

Gly Ile Gly Glu Trp His Cys Gln Pro Leu Gln Thr Tyr Pro Ser Ser
        595                 600                 605
```

```
Ser Gly Pro Val Glu Val Phe Ile Thr Glu Thr Pro Ser Gln Pro Asn
    610                 615                 620

Ser His Pro Ile Gln Trp Asn Ala Pro Gln Pro Ser His Ile Ser Lys
625                 630                 635                 640

Tyr Ile Leu Arg Trp Arg Pro Lys Asn Ser Val Gly Arg Trp Lys Glu
            645                 650                 655

Ala Thr Ile Pro Gly His Leu Asn Ser Tyr Thr Ile Lys Gly Leu Lys
                660                 665                 670

Pro Gly Val Val Tyr Glu Gly Gln Leu Ile Ser Ile Gln Gln Tyr Gly
            675                 680                 685

His Gln Glu Val Thr Arg Phe Asp Phe Thr Thr Ser Thr Ser Thr
    690                 695                 700

Pro Val Thr Ser Asn Thr Val Thr Gly Glu Thr Thr Pro Phe Ser Pro
705                 710                 715                 720

Leu Val Ala Thr Ser Glu Ser Val Thr Glu Ile Thr Ala Ser Ser Phe
                725                 730                 735

Val Val Ser Trp Val Ser Ala Ser Asp Thr Val Ser Gly Phe Arg Val
            740                 745                 750

Glu Tyr Glu Leu Ser Glu Glu Gly Asp Glu Pro Gln Tyr Leu Asp Leu
                755                 760                 765

Pro Ser Thr Ala Thr Ser Val Asn Ile Pro Asp Leu Leu Pro Gly Arg
    770                 775                 780

Lys Tyr Ile Val Asn Val Tyr Gln Ile Ser Glu Asp Gly Glu Gln Ser
785                 790                 795                 800

Leu Ile Leu Ser Thr Ser Gln Thr Thr Ala Pro Asp Ala Pro Pro Asp
                805                 810                 815

Pro Thr Val Asp Gln Val Asp Asp Thr Ser Ile Val Val Arg Trp Ser
            820                 825                 830

Arg Pro Gln Ala Pro Ile Thr Gly Tyr Arg Ile Val Tyr Ser Pro Ser
                835                 840                 845

Val Glu Gly Ser Ser Thr Glu Leu Asn Leu Pro Glu Thr Ala Asn Ser
850                 855                 860

Val Thr Leu Ser Asp Leu Gln Pro Gly Val Gln Tyr Asn Ile Thr Ile
865                 870                 875                 880

Tyr Ala Val Glu Glu Asn Gln Glu Ser Thr Pro Val Val Ile Gln Gln
                885                 890                 895

Glu Thr Thr Gly Thr Pro Arg Ser Asp Thr Val Pro Ser Pro Arg Asp
            900                 905                 910

Leu Gln Phe Val Glu Val Thr Asp Val Lys Val Thr Ile Met Trp Thr
    915                 920                 925

Pro Pro Glu Ser Ala Val Thr Gly Tyr Arg Val Asp Val Ile Pro Val
    930                 935                 940

Asn Leu Pro Gly Glu His Gly Gln Arg Leu Pro Ile Ser Arg Asn Thr
945                 950                 955                 960

Phe Ala Glu Val Thr Gly Leu Ser Pro Gly Val Thr Tyr Tyr Phe Lys
                965                 970                 975

Val Phe Ala Val Ser His Gly Arg Glu Ser Lys Pro Leu Thr Ala Gln
            980                 985                 990

Gln Thr Thr Lys Leu Asp Ala Pro Thr Asn Leu Gln Phe Val Asn Glu
        995                 1000                1005

Thr Asp Ser Thr Val Leu Val Arg Trp Thr Pro Pro Arg Ala Gln Ile
    1010                1015                1020

Thr Gly Tyr Arg Leu Thr Val Gly Leu Thr Arg Arg Gly Gln Pro Arg
```

-continued

```
            1025                1030                1035                1040
Gln Tyr Asn Val Gly Pro Ser Val Ser Lys Tyr Pro Leu Arg Asn Leu
                    1045                1050                1055
Gln Pro Ala Ser Glu Tyr Thr Val Ser Leu Val Ala Ile Lys Gly Asn
                    1060                1065                1070
Gln Glu Ser Pro Lys Ala Thr Gly Val Phe Thr Thr Leu Gln Pro Gly
                    1075                1080                1085
Ser Ser Ile Pro Pro Tyr Asn Thr Glu Val Thr Glu Thr Thr Ile Val
                    1090                1095                1100
Ile Thr Trp Thr Pro Ala Pro Arg Ile Gly Phe Lys Leu Gly Val Arg
1105                1110                1115                1120
Pro Ser Gln Gly Gly Glu Ala Pro Arg Glu Val Thr Ser Asp Ser Gly
                    1125                1130                1135
Ser Ile Val Val Ser Gly Leu Thr Pro Gly Val Glu Tyr Val Tyr Thr
                    1140                1145                1150
Ile Gln Val Leu Arg Asp Gly Gln Glu Arg Asp Ala Pro Ile Val Asn
                    1155                1160                1165
Lys Val Val Thr Pro Leu Ser Pro Pro Thr Asn Leu His Leu Glu Ala
                    1170                1175                1180
Asn Pro Asp Thr Gly Val Leu Thr Val Ser Trp Glu Arg Ser Thr Thr
1185                1190                1195                1200
Pro Asp Ile Thr Gly Tyr Arg Ile Thr Thr Thr Pro Thr Asn Gly Gln
                    1205                1210                1215
Gln Gly Asn Ser Leu Glu Glu Val Val His Ala Asp Gln Ser Ser Cys
                    1220                1225                1230
Thr Phe Asp Asn Leu Ser Pro Gly Leu Glu Tyr Asn Val Ser Val Tyr
                    1235                1240                1245
Thr Val Lys Asp Asp Lys Glu Ser Val Pro Ile Ser Asp Thr Ile Ile
                    1250                1255                1260
Pro Glu Val Pro Gln Leu Thr Asp Leu Ser Phe Val Asp Ile Thr Asp
1265                1270                1275                1280
Ser Ser Ile Gly Leu Arg Trp Thr Pro Leu Asn Ser Ser Thr Ile Ile
                    1285                1290                1295
Gly Tyr Arg Ile Thr Val Val Ala Ala Gly Glu Gly Ile Pro Ile Phe
                    1300                1305                1310
Glu Asp Phe Val Asp Ser Ser Val Gly Tyr Tyr Thr Val Thr Gly Leu
                    1315                1320                1325
Glu Pro Gly Ile Asp Tyr Asp Ile Ser Val Ile Thr Leu Ile Asn Gly
                    1330                1335                1340
Gly Glu Ser Ala Pro Thr Thr Leu Thr Gln Gln Thr Ala Val Pro Pro
1345                1350                1355                1360
Pro Thr Asp Leu Arg Phe Thr Asn Ile Gly Pro Asp Thr Met Arg Val
                    1365                1370                1375
Thr Trp Ala Pro Pro Ser Ile Asp Leu Thr Asn Phe Leu Val Arg
                    1380                1385                1390
Tyr Ser Pro Val Lys Asn Glu Glu Asp Val Ala Glu Leu Ser Ile Ser
                    1395                1400                1405
Pro Ser Asp Asn Ala Val Val Leu Thr Asn Leu Leu Pro Gly Thr Glu
                    1410                1415                1420
Tyr Val Val Ser Val Ser Ser Val Tyr Glu Gln His Glu Ser Thr Pro
1425                1430                1435                1440
Leu Arg Gly Arg Gln Lys Thr Gly Leu Asp Ser Pro Thr Gly Ile Asp
                    1445                1450                1455
```

-continued

```
Phe Ser Asp Ile Thr Ala Asn Ser Phe Thr Val His Trp Ile Ala Pro
            1460                1465                1470

Arg Ala Thr Ile Thr Gly Tyr Arg Ile Arg His Pro Glu His Phe
        1475                1480                1485

Ser Gly Arg Pro Arg Glu Asp Arg Val Pro His Ser Arg Asn Ser Ile
        1490                1495                1500

Thr Leu Thr Asn Leu Thr Pro Gly Thr Glu Tyr Val Val Ser Ile Val
1505                1510                1515                1520

Ala Leu Asn Gly Arg Glu Glu Ser Pro Leu Leu Ile Gly Gln Gln Ser
            1525                1530                1535

Thr Val Ser Asp Val Pro Arg Asp Leu Glu Val Val Ala Ala Thr Pro
            1540                1545                1550

Thr Ser Leu Leu Ile Ser Trp Asp Ala Pro Ala Val Thr Val Arg Tyr
            1555                1560                1565

Tyr Arg Ile Thr Tyr Gly Glu Thr Gly Gly Asn Ser Pro Val Gln Glu
            1570                1575                1580

Phe Thr Val Pro Gly Ser Lys Ser Thr Ala Thr Ile Ser Gly Leu Lys
1585                1590                1595                1600

Pro Gly Val Asp Tyr Thr Ile Thr Val Tyr Ala Val Thr Gly Arg Gly
            1605                1610                1615

Asp Ser Pro Ala Ser Ser Lys Pro Ile Ser Ile Asn Tyr Arg Thr Glu
            1620                1625                1630

Ile Asp Lys Pro Ser Gln Met Gln Val Thr Asp Val Gln Asp Asn Ser
            1635                1640                1645

Ile Ser Val Lys Trp Leu Pro Ser Ser Pro Val Thr Gly Tyr Arg
            1650                1655                1660

Val Thr Thr Thr Pro Lys Asn Gly Pro Gly Pro Thr Lys Thr Lys Thr
1665                1670                1675                1680

Ala Gly Pro Asp Gln Thr Glu Met Thr Ile Glu Gly Leu Gln Pro Thr
            1685                1690                1695

Val Glu Tyr Val Val Ser Val Tyr Ala Gln Asn Pro Ser Gly Glu Ser
            1700                1705                1710

Gln Pro Leu Val Gln Thr Ala Val Thr Asn Ile Asp Arg Pro Lys Gly
            1715                1720                1725

Leu Ala Phe Thr Asp Val Asp Val Asp Ser Ile Lys Ile Ala Trp Glu
            1730                1735                1740

Ser Pro Gln Gly Gln Val Ser Arg Tyr Arg Val Thr Tyr Ser Ser Pro
1745                1750                1755                1760

Glu Asp Gly Ile His Glu Leu Phe Pro Ala Pro Asp Gly Glu Glu Asp
            1765                1770                1775

Thr Ala Glu Leu Gln Gly Leu Arg Pro Gly Ser Glu Tyr Thr Val Ser
            1780                1785                1790

Val Val Ala Leu His Asp Asp Met Glu Ser Gln Pro Leu Ile Gly Thr
            1795                1800                1805

Gln Ser Thr Ala Ile Pro Ala Pro Thr Asp Leu Lys Phe Thr Gln Val
            1810                1815                1820

Thr Pro Thr Ser Leu Ser Ala Gln Trp Thr Pro Pro Asn Val Gln Leu
1825                1830                1835                1840

Thr Gly Tyr Arg Val Arg Val Thr Pro Lys Glu Lys Thr Gly Pro Met
            1845                1850                1855

Lys Glu Ile Asn Leu Ala Pro Asp Ser Ser Val Val Ser Gly
            1860                1865                1870

Leu Met Val Ala Thr Lys Tyr Glu Val Ser Val Tyr Ala Leu Lys Asp
            1875                1880                1885
```

```
Thr Leu Thr Ser Arg Pro Ala Gln Gly Val Val Thr Thr Leu Glu Asn
    1890                1895                1900

Val Ser Pro Pro Arg Arg Ala Arg Val Thr Asp Ala Thr Glu Thr Thr
1905                1910                1915                1920

Ile Thr Ile Ser Trp Arg Thr Lys Thr Glu Thr Ile Thr Gly Phe Gln
                1925                1930                1935

Val Asp Ala Val Pro Ala Asn Gly Gln Thr Pro Ile Gln Arg Thr Ile
            1940                1945                1950

Lys Pro Asp Val Arg Ser Tyr Thr Ile Thr Gly Leu Gln Pro Gly Thr
        1955                1960                1965

Asp Tyr Lys Ile Tyr Leu Tyr Thr Leu Asn Asp Asn Ala Arg Ser Ser
    1970                1975                1980

Pro Val Val Ile Asp Ala Ser Thr Ala Ile Asp Ala Pro Ser Asn Leu
1985                1990                1995                2000

Arg Phe Leu Ala Thr Thr Pro Asn Ser Leu Leu Val Ser Trp Gln Pro
                2005                2010                2015

Pro Arg Ala Arg Ile Thr Gly Tyr Ile Ile Lys Tyr Glu Lys Pro Gly
            2020                2025                2030

Ser Pro Pro Arg Glu Val Val Pro Arg Pro Arg Pro Gly Val Thr Glu
        2035                2040                2045

Ala Thr Ile Thr Gly Leu Glu Pro Gly Thr Glu Tyr Thr Ile Tyr Val
    2050                2055                2060

Ile Ala Leu Lys Asn Asn Gln Lys Ser Glu Pro Leu Ile Gly Arg Lys
2065                2070                2075                2080

Lys Thr Val Gln Lys Thr Pro Phe Val Thr His Pro Gly Tyr Asp Thr
                2085                2090                2095

Gly Asn Gly Ile Gln Leu Pro Gly Thr Ser Gly Gln Gln Pro Ser Val
            2100                2105                2110

Gly Gln Gln Met Ile Phe Glu Glu His Gly Phe Arg Arg Thr Thr Pro
        2115                2120                2125

Pro Thr Thr Ala Thr Pro Ile Arg His Arg Pro Arg Pro Tyr Pro Pro
    2130                2135                2140

Asn Val Gly Gln Glu Ala Leu Ser Gln Thr Thr Ile Ser Trp Ala Pro
2145                2150                2155                2160

Phe Gln Asp Thr Ser Glu Tyr Ile Ile Ser Cys His Pro Val Gly Thr
                2165                2170                2175

Asp Glu Glu Pro Leu Gln Phe Arg Val Pro Gly Thr Ser Thr Ser Ala
            2180                2185                2190

Thr Leu Thr Gly Leu Thr Arg Gly Ala Thr Tyr Asn Ile Ile Val Glu
        2195                2200                2205

Ala Leu Lys Asp Gln Gln Arg His Lys Val Arg Glu Glu Val Val Thr
    2210                2215                2220

Val Gly Asn Ser Val Asn Glu Gly Leu Asn Gln Pro Thr Asp Asp Ser
2225                2230                2235                2240

Cys Phe Asp Pro Tyr Thr Val Ser His Tyr Ala Val Gly Asp Glu Trp
                2245                2250                2255

Glu Arg Met Ser Glu Ser Gly Phe Lys Leu Leu Cys Gln Cys Leu Gly
            2260                2265                2270

Phe Gly Ser Gly His Phe Arg Cys Asp Ser Ser Arg Trp Cys His Asp
        2275                2280                2285

Asn Gly Val Asn Tyr Lys Ile Gly Glu Lys Trp Asp Arg Gln Gly Glu
    2290                2295                2300

Asn Gly Gln Met Met Ser Cys Thr Cys Leu Gly Asn Gly Lys Gly Glu
```

```
                2305                2310                2315                2320
     Phe Lys Cys Asp Pro His Glu Ala Thr Cys Tyr Asp Asp Gly Lys Thr
                        2325                2330                2335
     Tyr His Val Gly Glu Gln Trp Gln Lys Glu Tyr Leu Gly Ala Ile Cys
                        2340                2345                2350
     Ser Cys Thr Cys Phe Gly Gly Gln Arg Gly Trp Arg Cys Asp Asn Cys
                        2355                2360                2365
     Arg Arg Pro Gly Gly Glu Pro Ser Pro Glu Gly Thr Thr Gly Gln Ser
                        2370                2375                2380
     Tyr Asn Gln Tyr Ser Gln Arg Tyr His Gln Arg Thr Asn Thr Asn Val
     2385                2390                2395                2400
     Asn Cys Pro Ile Glu Cys Phe Met Pro Leu Asp Val Gln Ala Asp Arg
                        2405                2410                2415
     Glu Asp Ser Arg Glu
                 2420

<210> SEQ ID NO 18
<211> LENGTH: 8449
<212> TYPE: DNA
<213> ORGANISM: Homo Sapiens
<220> FEATURE:
<223> OTHER INFORMATION: Oncofetal Fibronectin variant 3
<300> PUBLICATION INFORMATION:
<308> DATABASE ACCESSION NUMBER: GenBank NM 002026
<309> DATABASE ENTRY DATE: 2005-06-10

<400> SEQUENCE: 18
gcccgcgccg gctgtgctgc acaggggag gagagggaac cccaggcgcg agcgggaaga       60
ggggacctgc agccacaact tctctggtcc tctgcatccc ttctgtccct ccacccgtcc     120
ccttccccac cctctggccc ccaccttctt ggaggcgaca accccgggga ggcattagaa     180 gggattttc ccgcaggttg cgaagggaag caaacttggt ggcaacttgc ctcccggtgc      240
gggcgtctct cccccaccgt ctcaacatgc ttaggggtcc ggggcccggg ctgctgctgc     300
tggccgtcca gtgcctgggg acagcggtgc cctccacggg agcctcgaag agcaagaggc     360
aggctcagca aatggttcag ccccagtccc cggtggctgt cagtcaaagc aagcccggtt     420
gttatgacaa tggaaaacac tatcagataa atcaacagtg ggagcggacc tacctaggca     480
atgcgttggt ttgtacttgt tatggaggaa gccgaggttt taactgcgag agtaaacctg     540
aagctgaaga gacttgcttt gacaagtaca ctgggaacac ttaccgagtg ggtgacactt     600
atgagcgtcc taaagactcc atgatctggg actgtacctg catcgggcct gggcgaggga     660
gaataagctg taccatcgca aaccgctgcc atgaagggg tcagtcctac aagattggtg     720
acacctggag gagaccacat gagactggtg gttacatgtt agagtgtgtg tgtcttggta     780
atggaaaagg agaatggacc tgcaagccca tagctgagaa gtgttttgat catgctgctg     840
ggacttccta tgtggtcgga gaaacgtggg agaagcccta ccaaggctgg atgatggtag     900
attgtacttg cctgggagaa ggcagcggac gcatcacttg cacttctaga aatagatgca    960
acgatcagga cacaaggaca tcctataaga ttggagacac tggagcaag aaggataatc    1020 gaggaaacct gctccagtgc atctgcacag gcaacggccg aggagagtgg aagtgtgaga   1080
ggcacacctc tgtgcagacc acatcgacg atctggccc cttcaccgat gttcgtgcag    1140
ctgtttacca accgcagcct caccccagc ctcctcccta tggccactgt gtcacagaca    1200
gtggtgtggt ctactctgtg gggatgcagt ggctgaagac acaaggaaat aagcaaatgc    1260
tttgcacgtg cctgggcaac ggagtcagct gccaagagac agctgtaacc cagacttacg    1320
```

```
gtggcaactc aaatggagag ccatgtgtct taccattcac ctacaatggc aggacgttct  1380
actcctgcac cacagaaggg cgacaggacg gacatctttg gtgcagcaca acttcgaatt  1440
atgagcagga ccagaaatac tctttctgca cagaccacac tgttttggtt cagactcgag  1500
gaggaaattc caatggtgcc ttgtgccact tccccttcct atacaacaac cacaattaca  1560
ctgattgcac ttctgagggc agaagagaca acatgaagtg gtgtgggacc acacagaact  1620
atgatgccga ccagaagttt gggttctgcc ccatggctgc ccacgaggaa atctgcacaa  1680
ccaatgaagg ggtcatgtac cgcattggag atcagtggga taagcagcat gacatgggtc  1740
acatgatgag gtgcacgtgt gttgggaatg gtcgtgggga atggacatgc attgcctact  1800
cgcagcttcg agatcagtgc attgttgatg acatcactta caatgtgaac gacacattcc  1860
acaagcgtca tgaagagggg cacatgctga actgtacatg cttcggtcag ggtcggggca  1920
ggtggaagtg tgatcccgtc gaccaatgcc aggattcaga gactgggacg tttttatcaaa  1980 ttggagattc atgggagaag tatgtgcatg gtgtcagata ccagtgctac tgctatggcc  2040
gtggcattgg ggagtggcat tgccaacctt tacagaccta tccaagctca agtggtcctg  2100
tcgaagtatt tatcactgag actccgagtc agcccaactc ccaccccatc cagtggaatg  2160
caccacagcc atctcacatt tccaagtaca ttctcaggtg gagacctaaa aattctgtag  2220
gccgttggaa ggaagctacc ataccaggcc acttaaactc ctacaccatc aaaggcctga  2280
agcctggtgt ggtatacgag ggccagctca tcagcatcca gcagtacggc caccaagaag  2340
tgactcgctt tgacttcacc accaccagca ccagcacacc tgtgaccagc aacaccgtga  2400
caggagagac gactcccttt tctcctcttg tggccacttc tgaatctgtg accgaaatca  2460
cagccagtag cttttgtggtc tcctgggtct cagcttccga caccgtgtcg ggattccggg  2520
tggaatatga gctgagtgag gagggagatg agccacagta cctggatctt ccaagcacag  2580
ccacttctgt gaacatccct gacctgcttc ctggccgaaa atacattgta aatgtctatc  2640
agatatctga ggatgggggag cagagtttga tcctgtctac ttcacaaaca acagcgcctg  2700
atgcccctcc tgacccgact gtggaccaag ttgatgacac ctcaattgtt gttcgctgga  2760
gcagacccca ggctcccatc acagggtaca gaatagtcta ttcgccatca gtagaaggta  2820
gcagcacaga actcaacctt cctgaaactg caaactccgt caccctcagt gacttgcaac  2880
ctggtgttca gtataacatc actatctatg ctgtggaaga aaatcaagaa agtacacctg  2940
ttgtcattca acaagaaacc actggcaccc cacgctcaga tacagtgccc tctcccaggg  3000
acctgcagtt tgtggaagtg acagacgtga aggtcaccat catgtggaca ccgcctgaga  3060
gtgcagtgac cggctaccgt gtggatgtga tccccgtcaa cctgcctggc gagcacgggc  3120
agaggctgcc catcagcagg aacacctttg cagaagtcac cggctgtcc cctgggtca  3180 cctattactt caaagtcttt gcagtgagcc atggagggga gagcaagcct ctgactgctc  3240
aacagacaac caaactggat gctcccacta acctccagtt tgtcaatgaa actgattcta  3300
ctgtcctggt gagatggact ccacctcggg cccagataac aggataccga ctgaccgtgg  3360
gccttacccg aagaggacag cccaggcagt acaatgtggg tccctctgtc tccaagtacc  3420
cactgaggaa tctgcagcct gcatctgagt acaccgtatc cctcgtggcc ataaagggca  3480
accaagagag cccccaaagcc actggagtct ttaccacact gcagcctggg agctctattc  3540
caccttacaa caccgaggtg actgagacca ccattgtgat cacatggacg cctgctccaa  3600
gaattggttt taagctgggt gtacgaccaa gccaggagg agaggcacca cgagaagtga  3660
cttcagactc aggaagcatc gttgtgtccg gcttgactcc aggagtagaa tacgtctaca  3720
```

```
ccatccaagt cctgagagat ggacaggaaa gagatgcgcc aattgtaaac aaagtggtga   3780
caccattgtc tccaccaaca aacttgcatc tggaggcaaa ccctgacact ggagtgctca   3840
cagtctcctg ggagaggagc accaccccag acattactgg ttatagaatt accacaaccc   3900
ctacaaacgg ccagcaggga aattctttgg aagaagtggt ccatgctgat cagagctcct   3960
gcacttttga taacctgagt cccggcctgg agtacaatgt cagtgtttac actgtcaagg   4020
atgacaagga aagtgtccct atctctgata ccatcatccc agctgttcct cctcccactg   4080
acctgcgatt caccaacatt ggtccagaca ccatgcgtgt cacctgggct ccacccccat   4140
ccattgattt aaccaacttc ctggtgcgtt actcacctgt gaaaaatgag gaagatgttg   4200
cagagttgtc aatttctcct tcagacaatg cagtggtctt aacaaatctc ctgcctggta   4260
cagaatatgt agtgagtgtc tccagtgtct acgaacaaca tgagagcaca cctcttagag   4320
gaagacagaa aacaggtctt gattccccaa ctggcattga cttttctgat attactgcca   4380
actcttttac tgtgcactgg attgctcctc gagccaccat cactggctac aggatccgcc   4440
atcatcccga gcacttcagt gggagacctc gagaagatcg ggtgccccac tctcggaatt   4500
ccatcaccct caccaacctc actccaggca cagagtatgt ggtcagcatc gttgctctta   4560
atggcagaga ggaaagtccc ttattgattg ccaacaatc aacagtttct gatgttccga   4620
gggacctgga agttgttgct gcgaccccca ccagcctact gatcagctgg gatgctcctg   4680
ctgtcacagt gagatattac aggatcactt acggagagac aggaggaaat agccctgtcc   4740
aggagttcac tgtgcctggg agcaagtcta cagctaccat cagcggcctt aaacctggag   4800
ttgattatac catcactgtg tatgctgtca ctggccgtgg agacagcccc gcaagcagca   4860
agccaatttc cattaattac cgaacagaaa ttgacaaacc atcccagatg caagtgaccg   4920
atgttcagga caacagcatt agtgtcaagt ggctgccttc aagttcccct gttactggtt   4980
acagagtaac caccactccc aaaaatggac caggaccaac aaaaaactaaa actgcaggtc   5040
cagatcaaac agaaatgact attgaaggct tgcagcccac agtggagtat gtggttagtg   5100
tctatgctca gaatccaagc ggagagagtc agcctctggt tcagactgca gtaaccaaca   5160
ttgatcgccc taaaggactg gcattcactg atgtggatgt cgattccatc aaaattgctt   5220
gggaaagccc acaggggcaa gtttccaggt acagggtgac ctactcgagc cctgaggatg   5280
gaatccatga gctattccct gcacctgatg gtgaagaaga cactcagagg ctgcaaggcc   5340
tcagaccggg ttctgagtac acagtcagtg tggttgcctt gcacgatgat atggagagcc   5400
agccccctgat tggaacccag tccacagcta ttcctgcacc aactgacctg aagttcactc   5460
aggtcacacc cacaagcctg agcgcccagt ggacaccacc caatgttcag ctcactggat   5520
atcgagtgcg ggtgaccccc aaggagaaga ccggaccaat gaaagaaatc aaccttgctc   5580
ctgacagctc atccgtggtt gtatcaggac ttatggtggc caccaaatat gaagtgagtg   5640
tctatgctct taaggacact ttgacaagca gaccagctca gggagttgtc accactctgg   5700
agaatgtcag cccaccaaga agggctcgtg tgacagatgc tactgagacc accatcacca   5760
ttagctggag aaccaagact gagacgatca ctggcttcca agttgatgcc gttccagcca   5820
atggccagac tccaatccag agaaccatca agccagatgt cagaagctac accatcacag   5880
gtttacaacc aggcactgac tacaagatct acctgtacac cttgaatgac aatgctcgga   5940
gctcccctgt ggtcatcgac gcctccactg ccattgatgc accatccaac ctgcgtttcc   6000
tggccaccac acccaattcc ttgctggtat catggcagcc gccacgtgcc aggattaccg   6060
gctacatcat caagtatgag aagcctgggt ctcctcccag agaagtggtc cctcggcccc   6120
```

```
gccctggtgt cacagaggct actattactg gcctggaacc gggaaccgaa tatacaattt    6180
atgtcattgc cctgaagaat aatcagaaga gcgagcccct gattggaagg aaaaagacag    6240
acgagcttcc ccaactggta acccttccac accccaatct tcatggacca gagatcttgg    6300
atgttccttc cacagttcaa aagacccctt tcgtcaccca ccctgggtat gacactggaa    6360
atggtattca gcttcctggc acttctggtc agcaacccag tgttgggcaa caaatgatct    6420
ttgaggaaca tggttttagg cggaccacac cgcccacaac ggccaccccc ataaggcata    6480
ggccaagacc atacccgccg aatgtaggac aagaagctct ctctcagaca accatctcat    6540 gggcccatt ccaggacact tctgagtaca tcatttcatg tcatcctgtt ggcactgatg    6600 aagaacccctt acagttcagg gttcctggaa cttctaccag tgccactctg acaggcctca    6660
ccagaggtgc cacctacaac atcatagtgg aggcactgaa agaccagcag aggcataagg    6720
ttcgggaaga ggttgttacc gtgggcaact ctgtcaacga aggcttgaac caacctacgg    6780
atgactcgtg cttttgacccc tacacagttt cccattatgc cgttggagat gagtgggaac    6840
gaatgtctga atcaggcttt aaactgttgt gccagtgctt aggctttgga agtggtcatt    6900
tcagatgtga ttcatctaga tggtgccatg acaatggtgt gaactacaag attggagaga    6960
agtgggaccg tcagggagaa aatggccaga tgatgagctg cacatgtctt gggaacggaa    7020
aaggagaatt caagtgtgac cctcatgagg caacgtgtta tgatgatggg aagacatacc    7080
acgtaggaga acagtggcag aaggaatatc tcggtgccat ttgctcctgc acatgctttg    7140
gaggccagcg gggctggcgc tgtgacaact gccgcagacc tgggggtgaa cccagtcccg    7200
aaggcactac tggccagtcc tacaaccagt attctcagag ataccatcag agaacaaaca    7260
ctaatgttaa ttgcccaatt gagtgcttca tgcctttaga tgtacaggct gacagagaag    7320
attcccgaga gtaaatcatc tttccaatcc agaggaacaa gcatgtctct ctgccaagat    7380
ccatctaaac tggagtgatg ttagcagacc cagcttagag ttcttctttc tttcttaagc    7440
cctttgctct ggaggaagtt ctccagcttc agctcaactc acagcttctc caagcatcac    7500
cctgggagtt tcctgagggt tttctcataa atgagggctg cacattgcct gttctgcttc    7560
gaagtattca ataccgctca gtattttaaa tgaagtgatt ctaagatttg gtttgggatc    7620
aataggaaag catatgcagc caaccaagat gcaaatgttt tgaaatgata tgaccaaaat    7680
tttaagtagg aaagtcaccc aaacacttct gctttcactt aagtgtctgg cccgcaatac    7740
tgtaggaaca agcatgatct tgttactgtg atattttaaa tatccacagt actcactttt    7800
tccaaatgat cctagtaatt gcctagaaat atctttctct tacctgttat ttatcaattt    7860
ttcccagtat ttttatacgg aaaaaattgt attgaaaaca cttagtatgc agttgataag    7920
aggaatttgg tataattatg gtgggtgatt attttttata ctgtatgtgc caaagcttta    7980
ctactgtgga aagacaactg ttttaataaa agatttacat tccacaactt gaagttcatc    8040
tatttgatat aagacacctt cggggggaaat aattcctgtg aatattcttt ttcaattcag    8100
caaacatttg aaaatctatg atgtgcaagt ctaattgttg atttcagtac aagatttct    8160 aaatcagttg ctacaaaaac tgattggttt ttgtcacttc atctcttcac taatggagat    8220
agctttacac tttctgcttt aatagattta agtggacccc aatatttatt aaaattgcta    8280
gtttaccgtt cagaagtata atagaaataa tctttagttg ctcttttcta accattgtaa    8340
ttcttccctt cttccctcca cctttccttc attgaataaa cctctgttca aagagattgc    8400
ctgcaaggga aataaaaatg actaagatat taaaaaaaaa aaaaaaaa          8449
```

<210> SEQ ID NO 19

-continued

```
<211> LENGTH: 2355
<212> TYPE: PRT
<213> ORGANISM: Homo Sapiens
<300> PUBLICATION INFORMATION:
<308> DATABASE ACCESSION NUMBER: GenBank NM 002026
<309> DATABASE ENTRY DATE: 2005-06-10

<400> SEQUENCE: 19

Met Leu Arg Gly Pro Gly Pro Gly Leu Leu Leu Leu Ala Val Gln Cys
 1               5                  10                  15

Leu Gly Thr Ala Val Pro Ser Thr Gly Ala Ser Lys Ser Lys Arg Gln
             20                  25                  30

Ala Gln Gln Met Val Gln Pro Gln Ser Pro Val Ala Val Ser Gln Ser
         35                  40                  45

Lys Pro Gly Cys Tyr Asp Asn Gly Lys His Tyr Gln Ile Asn Gln Gln
     50                  55                  60

Trp Glu Arg Thr Tyr Leu Gly Asn Ala Leu Val Cys Thr Cys Tyr Gly
 65                  70                  75                  80

Gly Ser Arg Gly Phe Asn Cys Glu Ser Lys Pro Glu Ala Glu Glu Thr
                 85                  90                  95

Cys Phe Asp Lys Tyr Thr Gly Asn Thr Tyr Arg Val Gly Asp Thr Tyr
            100                 105                 110

Glu Arg Pro Lys Asp Ser Met Ile Trp Asp Cys Thr Cys Ile Gly Ala
        115                 120                 125

Gly Arg Gly Arg Ile Ser Cys Thr Ile Ala Asn Arg Cys His Glu Gly
    130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                165                 170                 175

Trp Thr Cys Lys Pro Ile Ala Glu Lys Cys Phe Asp His Ala Ala Gly
            180                 185                 190

Thr Ser Tyr Val Val Gly Glu Thr Trp Glu Lys Pro Tyr Gln Gly Trp
        195                 200                 205

Met Met Val Asp Cys Thr Cys Leu Gly Glu Gly Ser Gly Arg Ile Thr
    210                 215                 220

Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu
                245                 250                 255

Gln Cys Ile Cys Thr Gly Asn Gly Arg Gly Glu Trp Lys Cys Glu Arg
            260                 265                 270

His Thr Ser Val Gln Thr Thr Ser Ser Gly Ser Gly Pro Phe Thr Asp
        275                 280                 285

Val Arg Ala Ala Val Tyr Gln Pro Gln Pro His Pro Gln Pro Pro Pro
    290                 295                 300

Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
                325                 330                 335

Gly Asn Gly Val Ser Cys Gln Glu Thr Ala Val Thr Gln Thr Tyr Gly
            340                 345                 350

Gly Asn Ser Asn Gly Glu Pro Cys Val Leu Pro Phe Thr Tyr Asn Gly
        355                 360                 365

Arg Thr Phe Tyr Ser Cys Thr Thr Glu Gly Arg Gln Asp Gly His Leu
    370                 375                 380
```

```
Trp Cys Ser Thr Thr Ser Asn Tyr Glu Gln Asp Gln Lys Tyr Ser Phe
385                 390                 395                 400

Cys Thr Asp His Thr Val Leu Val Gln Thr Arg Gly Gly Asn Ser Asn
            405                 410                 415

Gly Ala Leu Cys His Phe Pro Phe Leu Tyr Asn Asn His Asn Tyr Thr
            420                 425                 430

Asp Cys Thr Ser Glu Gly Arg Arg Asp Asn Met Lys Trp Cys Gly Thr
            435                 440                 445

Thr Gln Asn Tyr Asp Ala Asp Gln Lys Phe Gly Phe Cys Pro Met Ala
        450                 455                 460

Ala His Glu Glu Ile Cys Thr Thr Asn Glu Gly Val Met Tyr Arg Ile
465                 470                 475                 480

Gly Asp Gln Trp Asp Lys Gln His Asp Met Gly His Met Met Arg Cys
                485                 490                 495

Thr Cys Val Gly Asn Gly Arg Gly Glu Trp Thr Cys Ile Ala Tyr Ser
            500                 505                 510

Gln Leu Arg Asp Gln Cys Ile Val Asp Asp Ile Thr Tyr Asn Val Asn
            515                 520                 525

Asp Thr Phe His Lys Arg His Glu Glu Gly His Met Leu Asn Cys Thr
            530                 535                 540

Cys Phe Gly Gln Gly Arg Gly Arg Trp Lys Cys Asp Pro Val Asp Gln
545                 550                 555                 560

Cys Gln Asp Ser Glu Thr Gly Thr Phe Tyr Gln Ile Gly Asp Ser Trp
                565                 570                 575

Glu Lys Tyr Val His Gly Val Arg Tyr Gln Cys Tyr Cys Tyr Gly Arg
            580                 585                 590

Gly Ile Gly Glu Trp His Cys Gln Pro Leu Gln Thr Tyr Pro Ser Ser
            595                 600                 605

Ser Gly Pro Val Glu Val Phe Ile Thr Glu Thr Pro Ser Gln Pro Asn
            610                 615                 620

Ser His Pro Ile Gln Trp Asn Ala Pro Gln Pro Ser His Ile Ser Lys
625                 630                 635                 640

Tyr Ile Leu Arg Trp Arg Pro Lys Asn Ser Val Gly Arg Trp Lys Glu
                645                 650                 655

Ala Thr Ile Pro Gly His Leu Asn Ser Tyr Thr Ile Lys Gly Leu Lys
            660                 665                 670

Pro Gly Val Val Tyr Glu Gly Gln Leu Ile Ser Ile Gln Gln Tyr Gly
            675                 680                 685

His Gln Glu Val Thr Arg Phe Asp Phe Thr Thr Thr Ser Thr Ser Thr
690                 695                 700

Pro Val Thr Ser Asn Thr Val Thr Gly Glu Thr Thr Pro Phe Ser Pro
705                 710                 715                 720

Leu Val Ala Thr Ser Glu Ser Val Thr Glu Ile Thr Ala Ser Ser Phe
            725                 730                 735

Val Val Ser Trp Val Ser Ala Ser Asp Thr Val Ser Gly Phe Arg Val
            740                 745                 750

Glu Tyr Glu Leu Ser Glu Glu Gly Asp Glu Pro Gln Tyr Leu Asp Leu
            755                 760                 765

Pro Ser Thr Ala Thr Ser Val Asn Ile Pro Asp Leu Leu Pro Gly Arg
            770                 775                 780

Lys Tyr Ile Val Asn Val Tyr Gln Ile Ser Glu Asp Gly Glu Gln Ser
785                 790                 795                 800

Leu Ile Leu Ser Thr Ser Gln Thr Thr Ala Pro Asp Ala Pro Pro Asp
```

```
                805                 810                 815
Pro Thr Val Asp Gln Val Asp Asp Thr Ser Ile Val Arg Trp Ser
            820                 825                 830

Arg Pro Gln Ala Pro Ile Thr Gly Tyr Arg Ile Val Tyr Ser Pro Ser
            835                 840                 845

Val Glu Gly Ser Ser Thr Glu Leu Asn Leu Pro Glu Thr Ala Asn Ser
            850                 855                 860

Val Thr Leu Ser Asp Leu Gln Pro Gly Val Gln Tyr Asn Ile Thr Ile
865                 870                 875                 880

Tyr Ala Val Glu Glu Asn Gln Glu Ser Thr Pro Val Val Ile Gln Gln
                885                 890                 895

Glu Thr Thr Gly Thr Pro Arg Ser Asp Thr Val Pro Ser Pro Arg Asp
            900                 905                 910

Leu Gln Phe Val Glu Val Thr Asp Val Lys Val Thr Ile Met Trp Thr
            915                 920                 925

Pro Pro Glu Ser Ala Val Thr Gly Tyr Arg Val Asp Val Ile Pro Val
            930                 935                 940

Asn Leu Pro Gly Glu His Gly Gln Arg Leu Pro Ile Ser Arg Asn Thr
945                 950                 955                 960

Phe Ala Glu Val Thr Gly Leu Ser Pro Gly Val Thr Tyr Tyr Phe Lys
                965                 970                 975

Val Phe Ala Val Ser His Gly Arg Glu Ser Lys Pro Leu Thr Ala Gln
            980                 985                 990

Gln Thr Thr Lys Leu Asp Ala Pro Thr Asn Leu Gln Phe Val Asn Glu
            995                 1000                1005

Thr Asp Ser Thr Val Leu Val Arg Trp Thr Pro Pro Arg Ala Gln Ile
    1010                1015                1020

Thr Gly Tyr Arg Leu Thr Val Gly Leu Thr Arg Arg Gly Gln Pro Arg
1025                1030                1035                1040

Gln Tyr Asn Val Gly Pro Ser Val Ser Lys Tyr Pro Leu Arg Asn Leu
            1045                1050                1055

Gln Pro Ala Ser Glu Tyr Thr Val Ser Leu Val Ala Ile Lys Gly Asn
            1060                1065                1070

Gln Glu Ser Pro Lys Ala Thr Gly Val Phe Thr Thr Leu Gln Pro Gly
            1075                1080                1085

Ser Ser Ile Pro Pro Tyr Asn Thr Glu Val Thr Glu Thr Thr Ile Val
            1090                1095                1100

Ile Thr Trp Thr Pro Ala Pro Arg Ile Gly Phe Lys Leu Gly Val Arg
1105                1110                1115                1120

Pro Ser Gln Gly Gly Glu Ala Pro Arg Glu Val Thr Ser Asp Ser Gly
            1125                1130                1135

Ser Ile Val Val Ser Gly Leu Thr Pro Gly Val Glu Tyr Val Tyr Thr
            1140                1145                1150

Ile Gln Val Leu Arg Asp Gly Gln Glu Arg Asp Ala Pro Ile Val Asn
            1155                1160                1165

Lys Val Val Thr Pro Leu Ser Pro Pro Thr Asn Leu His Leu Glu Ala
            1170                1175                1180

Asn Pro Asp Thr Gly Val Leu Thr Val Ser Trp Glu Arg Ser Thr Thr
1185                1190                1195                1200

Pro Asp Ile Thr Gly Tyr Arg Ile Thr Thr Thr Pro Thr Asn Gly Gln
            1205                1210                1215

Gln Gly Asn Ser Leu Glu Glu Val Val His Ala Asp Gln Ser Ser Cys
            1220                1225                1230
```

-continued

```
Thr Phe Asp Asn Leu Ser Pro Gly Leu Glu Tyr Asn Val Ser Val Tyr
    1235                1240                1245
Thr Val Lys Asp Asp Lys Glu Ser Val Pro Ile Ser Asp Thr Ile Ile
    1250                1255                1260
Pro Ala Val Pro Pro Thr Asp Leu Arg Phe Thr Asn Ile Gly Pro
1265                1270                1275                1280
Asp Thr Met Arg Val Thr Trp Ala Pro Pro Ser Ile Asp Leu Thr
                1285                1290                1295
Asn Phe Leu Val Arg Tyr Ser Pro Val Lys Asn Glu Glu Asp Val Ala
                1300                1305                1310
Glu Leu Ser Ile Ser Pro Ser Asp Asn Ala Val Val Leu Thr Asn Leu
    1315                1320                1325
Leu Pro Gly Thr Glu Tyr Val Val Ser Val Ser Ser Val Tyr Glu Gln
                1330                1335                1340
His Glu Ser Thr Pro Leu Arg Gly Arg Gln Lys Thr Gly Leu Asp Ser
1345                1350                1355                1360
Pro Thr Gly Ile Asp Phe Ser Asp Ile Thr Ala Asn Ser Phe Thr Val
                1365                1370                1375
His Trp Ile Ala Pro Arg Ala Thr Ile Thr Gly Tyr Arg Ile Arg His
    1380                1385                1390
His Pro Glu His Phe Ser Gly Arg Pro Arg Glu Asp Arg Val Pro His
                1395                1400                1405
Ser Arg Asn Ser Ile Thr Leu Thr Asn Leu Thr Pro Gly Thr Glu Tyr
                1410                1415                1420
Val Val Ser Ile Val Ala Leu Asn Gly Arg Glu Glu Ser Pro Leu Leu
1425                1430                1435                1440
Ile Gly Gln Gln Ser Thr Val Ser Asp Val Pro Arg Asp Leu Glu Val
                1445                1450                1455
Val Ala Ala Thr Pro Thr Ser Leu Leu Ile Ser Trp Asp Ala Pro Ala
                1460                1465                1470
Val Thr Val Arg Tyr Tyr Arg Ile Thr Tyr Gly Glu Thr Gly Gly Asn
    1475                1480                1485
Ser Pro Val Gln Glu Phe Thr Val Pro Gly Ser Lys Ser Thr Ala Thr
    1490                1495                1500
Ile Ser Gly Leu Lys Pro Gly Val Asp Tyr Thr Ile Thr Val Tyr Ala
1505                1510                1515                1520
Val Thr Gly Arg Gly Asp Ser Pro Ala Ser Ser Lys Pro Ile Ser Ile
                1525                1530                1535
Asn Tyr Arg Thr Glu Ile Asp Lys Pro Ser Gln Met Gln Val Thr Asp
                1540                1545                1550
Val Gln Asp Asn Ser Ile Ser Val Lys Trp Leu Pro Ser Ser Ser Pro
    1555                1560                1565
Val Thr Gly Tyr Arg Val Thr Thr Thr Pro Lys Asn Gly Pro Gly Pro
    1570                1575                1580
Thr Lys Thr Lys Thr Ala Gly Pro Asp Gln Thr Glu Met Thr Ile Glu
1585                1590                1595                1600
Gly Leu Gln Pro Thr Val Glu Tyr Val Val Ser Val Tyr Ala Gln Asn
                1605                1610                1615
Pro Ser Gly Glu Ser Gln Pro Leu Val Gln Thr Ala Val Thr Asn Ile
                1620                1625                1630
Asp Arg Pro Lys Gly Leu Ala Phe Thr Asp Val Asp Val Asp Ser Ile
                1635                1640                1645
Lys Ile Ala Trp Glu Ser Pro Gln Gly Gln Val Ser Arg Tyr Arg Val
    1650                1655                1660
```

```
Thr Tyr Ser Ser Pro Glu Asp Gly Ile His Glu Leu Phe Pro Ala Pro
1665                1670                1675                1680

Asp Gly Glu Glu Asp Thr Ala Glu Leu Gln Gly Leu Arg Pro Gly Ser
            1685                1690                1695

Glu Tyr Thr Val Ser Val Val Ala Leu His Asp Asp Met Glu Ser Gln
        1700                1705                1710

Pro Leu Ile Gly Thr Gln Ser Thr Ala Ile Pro Ala Pro Thr Asp Leu
    1715                1720                1725

Lys Phe Thr Gln Val Thr Pro Thr Ser Leu Ser Ala Gln Trp Thr Pro
1730                1735                1740

Pro Asn Val Gln Leu Thr Gly Tyr Arg Val Arg Val Thr Pro Lys Glu
1745                1750                1755                1760

Lys Thr Gly Pro Met Lys Glu Ile Asn Leu Ala Pro Asp Ser Ser Ser
            1765                1770                1775

Val Val Val Ser Gly Leu Met Val Ala Thr Lys Tyr Glu Val Ser Val
            1780                1785                1790

Tyr Ala Leu Lys Asp Thr Leu Thr Ser Arg Pro Ala Gln Gly Val Val
        1795                1800                1805

Thr Thr Leu Glu Asn Val Ser Pro Pro Arg Arg Ala Arg Val Thr Asp
    1810                1815                1820

Ala Thr Glu Thr Thr Ile Thr Ile Ser Trp Arg Thr Lys Thr Glu Thr
1825                1830                1835                1840

Ile Thr Gly Phe Gln Val Asp Ala Val Pro Ala Asn Gly Gln Thr Pro
            1845                1850                1855

Ile Gln Arg Thr Ile Lys Pro Asp Val Arg Ser Tyr Thr Ile Thr Gly
            1860                1865                1870

Leu Gln Pro Gly Thr Asp Tyr Lys Ile Tyr Leu Tyr Thr Leu Asn Asp
        1875                1880                1885

Asn Ala Arg Ser Ser Pro Val Val Ile Asp Ala Ser Thr Ala Ile Asp
    1890                1895                1900

Ala Pro Ser Asn Leu Arg Phe Leu Ala Thr Thr Pro Asn Ser Leu Leu
1905                1910                1915                1920

Val Ser Trp Gln Pro Pro Arg Ala Arg Ile Thr Gly Tyr Ile Ile Lys
            1925                1930                1935

Tyr Glu Lys Pro Gly Ser Pro Arg Glu Val Val Pro Arg Pro Arg
            1940                1945                1950

Pro Gly Val Thr Glu Ala Thr Ile Thr Gly Leu Glu Pro Gly Thr Glu
        1955                1960                1965

Tyr Thr Ile Tyr Val Ile Ala Leu Lys Asn Asn Gln Lys Ser Glu Pro
    1970                1975                1980

Leu Ile Gly Arg Lys Lys Thr Asp Glu Leu Pro Gln Leu Val Thr Leu
1985                1990                1995                2000

Pro His Pro Asn Leu His Gly Pro Glu Ile Leu Asp Val Pro Ser Thr
            2005                2010                2015

Val Gln Lys Thr Pro Phe Val Thr His Pro Gly Tyr Asp Thr Gly Asn
            2020                2025                2030

Gly Ile Gln Leu Pro Gly Thr Ser Gly Gln Gln Pro Ser Val Gly Gln
        2035                2040                2045

Gln Met Ile Phe Glu Glu His Gly Phe Arg Arg Thr Thr Pro Pro Thr
    2050                2055                2060

Thr Ala Thr Pro Ile Arg His Arg Pro Arg Pro Tyr Pro Pro Asn Val
2065                2070                2075                2080

Gly Gln Glu Ala Leu Ser Gln Thr Thr Ile Ser Trp Ala Pro Phe Gln
```

-continued

```
                        2085                  2090                  2095
Asp Thr Ser Glu Tyr Ile Ile Ser Cys His Pro Val Gly Thr Asp Glu
        2100                  2105                  2110
Glu Pro Leu Gln Phe Arg Val Pro Gly Thr Ser Thr Ser Ala Thr Leu
        2115                  2120                  2125
Thr Gly Leu Thr Arg Gly Ala Thr Tyr Asn Ile Ile Val Glu Ala Leu
        2130                  2135                  2140
Lys Asp Gln Gln Arg His Lys Val Arg Glu Val Val Thr Val Gly
2145                  2150                  2155                  2160
Asn Ser Val Asn Glu Gly Leu Asn Gln Pro Thr Asp Asp Ser Cys Phe
        2165                  2170                  2175
Asp Pro Tyr Thr Val Ser His Tyr Ala Val Gly Asp Glu Trp Glu Arg
        2180                  2185                  2190
Met Ser Glu Ser Gly Phe Lys Leu Leu Cys Gln Cys Leu Gly Phe Gly
        2195                  2200                  2205
Ser Gly His Phe Arg Cys Asp Ser Ser Arg Trp Cys His Asp Asn Gly
        2210                  2215                  2220
Val Asn Tyr Lys Ile Gly Glu Lys Trp Asp Arg Gln Gly Glu Asn Gly
2225                  2230                  2235                  2240
Gln Met Met Ser Cys Thr Cys Leu Gly Asn Gly Lys Gly Glu Phe Lys
        2245                  2250                  2255
Cys Asp Pro His Glu Ala Thr Cys Tyr Asp Asp Gly Lys Thr Tyr His
        2260                  2265                  2270
Val Gly Glu Gln Trp Gln Lys Glu Tyr Leu Gly Ala Ile Cys Ser Cys
        2275                  2280                  2285
Thr Cys Phe Gly Gly Gln Arg Gly Trp Arg Cys Asp Asn Cys Arg Arg
        2290                  2295                  2300
Pro Gly Gly Glu Pro Ser Pro Glu Gly Thr Thr Gly Gln Ser Tyr Asn
2305                  2310                  2315                  2320
Gln Tyr Ser Gln Arg Tyr His Gln Arg Thr Asn Thr Asn Val Asn Cys
        2325                  2330                  2335
Pro Ile Glu Cys Phe Met Pro Leu Asp Val Gln Ala Asp Arg Glu Asp
        2340                  2345                  2350
Ser Arg Glu
        2355

<210> SEQ ID NO 20
<211> LENGTH: 8374
<212> TYPE: DNA
<213> ORGANISM: Homo Sapiens
<220> FEATURE:
<223> OTHER INFORMATION: Oncofetal Fibronectin variant 4
<300> PUBLICATION INFORMATION:
<308> DATABASE ACCESSION NUMBER: GenBank NM 212478
<309> DATABASE ENTRY DATE: 2005-06-10

<400> SEQUENCE: 20
gcccgcgccg gctgtgctgc acaggggag gagagggaac cccaggcgcg agcgggaaga      60
ggggacctgc agccacaact tctctggtcc tctgcatccc ttctgtccct ccacccgtcc    120
ccttccccac cctctggccc ccaccttctt ggaggcgaca accccgggga ggcattagaa    180 gggattttc ccgcaggttg cgaagggaag caaacttggt ggcaacttgc ctcccggtgc    240
gggcgtctct ccccaccgt ctcaacatgc ttagggtcc ggggcccggg ctgctgctgc    300
tggccgtcca gtgcctgggg acagcggtgc cctccacggg agcctcgaag agcaagaggc    360
aggctcagca aatggttcag ccccagtccc cggtggctgt cagtcaaagc aagcccggtt    420
```

```
gttatgacaa tggaaaacac tatcagataa atcaacagtg ggagcggacc tacctaggca    480
atgcgttggt ttgtacttgt tatggaggaa gccgaggttt taactgcgag agtaaacctg    540
aagctgaaga gacttgcttt gacaagtaca ctgggaacac ttaccgagtg ggtgacactt    600
atgagcgtcc taaagactcc atgatctggg actgtacctg catcggggct gggcgaggga    660
gaataagctg taccatcgca aaccgctgcc atgaaggggg tcagtcctac aagattggtg    720
acacctggag gagaccacat gagactggtg gttacatgtt agagtgtgtg tgtcttggta    780
atggaaaagg agaatggacc tgcaagccca tagctgagaa gtgttttgat catgctgctg    840
ggacttccta tgtggtcgga gaaacgtggg agaagcccta ccaaggctgg atgatggtag    900
attgtacttg cctgggagaa ggcagcggac gcatcacttg cacttctaga aatagatgca    960
acgatcagga cacaaggaca tcctatagaa ttggagacac ctggagcaag aaggataatc   1020
gaggaaacct gctccagtgc atctgcacag gcaacggccg aggagagtgg aagtgtgaga   1080
ggcacacctc tgtgcagacc acatcgagcg gatctggccc cttcaccgat gttcgtgcag   1140
ctgtttacca accgcagcct cacccccagc ctcctcccta tggccactgt gtcacagaca   1200
gtggtgtggt ctactctgtg gggatgcagt ggctgaagac acaaggaaat aagcaaatgc   1260
tttgcacgtg cctgggcaac ggagtcagct gccaagagac agctgtaacc cagacttacg   1320
gtggcaactc aaatggagag ccatgtgtct taccattcac ctacaatggc aggacgttct   1380
actcctgcac cacagaaggg cgacaggacg gacatctttg gtgcagcaca acttcgaatt   1440
atgagcagga ccagaaatac tctttctgca cagaccacac tgttttggtt cagactcgag   1500
gaggaaattc caatggtgcc ttgtgccact tccccttcct atacaacaac cacaattaca   1560
ctgattgcac ttctgagggc agaagagaca acatgaagtg gtgtgggacc acacagaact   1620
atgatgccga ccagaagttt gggttctgcc ccatggctgc ccacgaggaa atctgcacaa   1680
ccaatgaagg ggtcatgtac cgcattgag atcagtggga taagcagcat gacatgggtc   1740
acatgatgag gtgcacgtgt gttgggaatg gtcgtgggga atggacatgc attgcctact   1800
cgcagcttcg agatcagtgc attgttgatg acatcactta caatgtgaac gacacattcc   1860
acaagcgtca tgaagagggg cacatgctga actgtacatg cttcggtcag ggtcggggca   1920
ggtggaagtg tgatcccgtc gaccaatgcc aggattcaga gactgggacg ttttatcaaa   1980
ttggagattc atgggagaag tatgtgcatg tgtcagata ccagtgctac tgctatggcc   2040
gtggcattgg ggagtggcat tgccaaccctt tacagaccta ccaagctca agtggtcctg   2100 tcgaagtatt tatcactgag actccgagtc agcccaactc ccacccatc cagtggaatg   2160 caccacagcc atctcacatt tccaagtaca ttctcaggtg gagacctaaa aattctgtag   2220
gccgttggaa ggaagctacc ataccaggcc acttaaactc ctacaccatc aaaggcctga   2280
agcctggtgt ggtatacgag gccagctca tcagcatcca gcagtacggc caccaagaag   2340
tgactcgctt tgacttcacc accaccagca ccagcacacc tgtgaccagc aacaccgtga   2400
caggagagac gactccctttt tctcctcttg tggccacttc tgaatctgtg accgaaatca   2460
cagccagtag ctttgtggtc tcctgggtct cagcttccga caccgtgtcg ggattccggg   2520
tggaatatga gctgagtgag gagggagatg agccacagta cctggatctt ccaagcacag   2580
ccacttctgt gaacatccct gacctgcttc ctggccgaaa atacattgta aatgtctatc   2640
agatatctga ggatgggag cagagtttga tcctgtctac ttcacaaaca acagcgcctg   2700
atgcccctcc tgacccgact gtggaccaag ttgatgacac ctcaattgtt gttcgctgga   2760
gcagacccca ggctcccatc acagggtaca gaatagtcta ttcgccatca gtagaaggta   2820
```

```
gcagcacaga actcaacctt cctgaaactg caaactccgt caccctcagt gacttgcaac   2880
ctggtgttca gtataacatc actatctatg ctgtggaaga aaatcaagaa agtacacctg   2940
ttgtcattca acaagaaacc actggcaccc cacgctcaga tacagtgccc tctcccaggg   3000
acctgcagtt tgtggaagtg acagacgtga aggtcaccat catgtggaca ccgcctgaga   3060
gtgcagtgac cggctaccgt gtggatgtga tccccgtcaa cctgcctggc gagcacgggc   3120
agaggctgcc catcagcagg aacacctttg cagaagtcac cgggctgtcc cctgggctca   3180
cctattactt caaagtcttt gcagtgagcc atgggaggga gagcaagcct ctgactgctc   3240
aacagacaac caaactggat gctcccacta acctccagtt tgtcaatgaa actgattcta   3300
ctgtcctggt gagatggact ccacctcggg cccagataac aggataccga ctgaccgtgg   3360
gccttacccg aagaggacag cccaggcagt acaatgtggg tccctctgtc tccaagtacc   3420
cactgaggaa tctgcagcct gcatctgagt acaccgtatc cctcgtggcc ataaagggca   3480
accaagagag ccccaaagcc actggagtct ttaccacact gcagcctggg agctctattc   3540
caccttacaa caccgaggtg actgagacca ccattgtgat cacatggacg cctgctccaa   3600
gaattggttt taagctgggt gtacgaccaa gccaggagg agaggcacca cgagaagtga   3660
cttcagactc aggaagcatc gttgtgtccg gcttgactcc aggagtagaa tacgtctaca   3720
ccatccaagt cctgagagat ggacaggaaa gagatgcgcc aattgtaaac aaagtggtga   3780
caccattgtc tccaccaaca aacttgcatc tggaggcaaa ccctgacact ggagtgctca   3840
cagtctcctg ggagaggagc accaccccag acattactgg ttatagaatt accacaaccc   3900
ctacaaacgg ccagcaggga aattctttgg aagaagtggt ccatgctgat cagagctcct   3960
gcacttttga taacctgagt cccggcctgg agtacaatgt cagtgtttac actgtcaagg   4020
atgacaagga aagtgtccct atctctgata ccatcatccc agctgttcct cctcccactg   4080
acctgcgatt caccaacatt ggtccagaca ccatgcgtgt cacctgggct ccaccccat   4140
ccattgattt aaccaacttc ctggtgcgtt actcacctgt gaaaaatgag gaagatgttg   4200
cagagttgtc aatttctcct tcagacaatg cagtggtctt aacaaatctc ctgcctggta   4260
cagaatatgt agtgagtgtc tccagtgtct acgaacaaca tgagagcaca cctcttagag   4320
gaagacagaa aacaggtctt gattccccaa ctggcattga cttttctgat attactgcca   4380
actcttttac tgtgcactgg attgctcctc gagccaccat cactggctac aggatccgcc   4440
atcatcccga gcacttcagt gggagacctc gagaagatcg ggtgccccac tctcggaatt   4500
ccatcaccct caccaacctc actccaggca cagagtatgt ggtcagcatc gttgctctta   4560
atggcagaga ggaaagtccc ttattgattg ccaacaatc aacagtttct gatgttccga   4620
gggacctgga agttgttgct gcgacccca ccagcctact gatcagctgg gatgctcctg   4680
ctgtcacagt gagatattac aggatcactt acggagagac aggaggaaat agccctgtcc   4740
aggagttcac tgtgcctggg agcaagtcta cagctaccat cagcggcctt aaacctggag   4800
ttgattatac catcactgtg tatgctgtca ctggccgtgg agacagcccc gcaagcagca   4860
agccaatttc cattaattac cgaacagaaa ttgacaaacc atcccagatg caagtgaccg   4920
atgttcagga caacagcatt agtgtcaagt ggctgccttc aagttcccct gttactggtt   4980
acagagtaac caccactccc aaaaatggac caggaccaac aaaaactaaa actgcaggtc   5040
cagatcaaac agaaatgact attgaaggct tgcagcccac agtggagtat gtggttagtg   5100
tctatgctca gaatccaagc gggagagagtc agcctctggt tcagactgca gtaaccaaca   5160
ttgatcgccc taaaggactg gcattcactg atgtggatgt cgattccatc aaaattgctt   5220
```

```
gggaaagccc acaggggcaa gtttccaggt acagggtgac ctactcgagc cctgaggatg    5280
gaatccatga gctattccct gcacctgatg gtgaagaaga cactgcagag ctgcaaggcc    5340
tcagaccggg ttctgagtac acagtcagtg tggttgcctt gcacgatgat atggagagcc    5400
agcccctgat tggaacccag tccacagcta ttcctgcacc aactgacctg aagttcactc    5460
aggtcacacc cacaagcctg agcgcccagt ggacaccacc caatgttcag ctcactggat    5520
atcgagtgcg ggtgaccccc aaggagaaga ccggaccaat gaaagaaatc aaccttgctc    5580
ctgacagctc atccgtggtt gtatcaggac ttatggtggc caccaaatat gaagtgagtg    5640
tctatgctct taaggacact ttgacaagca gaccagctca gggagttgtc accactctgg    5700
agaatgtcag cccaccaaga agggctcgtg tgacagatgc tactgagacc accatcacca    5760
ttagctggag aaccaagact gagacgatca ctggcttcca agttgatgcc gttccagcca    5820
atggccagac tccaatccag agaaccatca agccagatgt cagaagctac accatcacag    5880
gtttacaacc aggcactgac tacaagatct acctgtacac cttgaatgac aatgctcgga    5940
gctcccctgt ggtcatcgac gcctccactg ccattgatgc accatccaac ctgcgtttcc    6000
tggccaccac acccaattcc ttgctggtat catggcagcc gccacgtgcc aggattaccg    6060
gctacatcat caagtatgag aagcctgggt ctcctcccag agaagtggtc cctcggcccc    6120
gccctggtgt cacagaggct actattactg gcctggaacc gggaaccgaa tatacaattt    6180
atgtcattgc cctgaagaat aatcagaaga gcgagcccct gattggaagg aaaaagacag    6240
ttcaaaagac ccctttcgtc acccaccctg ggtatgacac tggaaatggt attcagcttc    6300
ctggcacttc tggtcagcaa cccagtgttg ggcaacaaat gatctttgag gaacatggtt    6360
ttaggcggac cacaccgccc acaacggcca cccccataag gcataggcca agaccatacc    6420
cgccgaatgt aggacaagaa gctctctctc agacaaccat ctcatgggcc ccattccagg    6480
acacttctga gtacatcatt tcatgtcatc ctgttggcac tgatgaagaa cccttacagt    6540
tcagggttcc tggaacttct accagtgcca ctctgacagg cctcaccaga ggtgccacct    6600
acaacatcat agtggaggca ctgaaagacc agcagaggca taaggttcgg aagaggttg    6660 ttaccgtggg caactctgtc aacgaaggct tgaaccaacc tacggatgac tcgtgctttg    6720 accccctacac agtttcccat tatgccgttg gagatgagtg ggaacgaatg tctgaatcag    6780
gctttaaact gttgtgccag tgcttaggct ttggaagtgg tcatttcaga tgtgattcat    6840
ctagatggtg ccatgacaat ggtgtgaact acaagattgg agagaagtgg gaccgtcagg    6900
gagaaaatgg ccagatgatg agctgcacat gtcttgggaa cggaaaagga gaattcaagt    6960
gtgaccctca tgaggcaacg tgttatgatg atgggaagac ataccacgta ggagaacagt    7020
ggcagaagga atatctcggt gccatttgct cctgcacatg ctttggaggc cagcggggct    7080
ggcgctgtga caactgccgc agacctgggg gtgaacccag tcccgaaggc actactggcc    7140
agtcctacaa ccagtattct cagagatacc atcagagaac aaacactaat gttaattgcc    7200
caattgagtg cttcatgcct ttagatgtac aggctgacag agaagattcc cgagagtaaa    7260
tcatctttcc aatccagagg aacaagcatg tctctctgcc aagatccatc taaactggag    7320
tgatgttagc agacccagct tagagttctt ctttctttct taagccctt gctctggagg    7380 aagttctcca gcttcagctc aactcacagc ttctccaagc atcaccctgg gagtttcctg    7440
agggttttct cataaatgag ggctgcacat tgcctgttct gcttcgaagt attcaatacc    7500
gctcagtatt ttaaatgaag tgattctaag atttggtttg ggatcaatag gaaagcatat    7560
gcagccaacc aagatgcaaa tgttttgaaa tgatatgacc aaaatttta gtaggaaagt    7620
```

-continued

```
cacccaaaca cttctgcttt cacttaagtg tctggcccgc aatactgtag gaacaagcat   7680
gatcttgtta ctgtgatatt ttaaatatcc acagtactca cttttttccaa atgatcctag   7740 taattgccta gaaatatctt tctcttacct gttatttatc aattttttccc agtattttta   7800 tacgaaaaaa attgtattga aaacacttag tatgcagttg ataagaggaa tttggtataa   7860
ttatggtggg tgattatttt ttatactgta tgtgccaaag ctttactact gtggaaagac   7920
aactgtttta ataaaagatt tacattccac aacttgaagt tcatctattt gatataagac   7980
accttcgggg gaaataattc ctgtgaatat tcttttttcaa ttcagcaaac atttgaaaat   8040
ctatgatgtg caagtctaat tgttgatttc agtacaagat tttctaaatc agttgctaca   8100
aaaactgatt ggttttttgtc acttcatctc ttcactaatg gagatagctt tacactttct   8160
gctttaatag atttaagtgg accccaatat ttattaaaat tgctagttta ccgttcagaa   8220
gtataataga aataatctttt agttgctctt ttctaaccat tgtaattctt cccttcttcc   8280
ctccaccttt ccttcattga ataaacctct gttcaaagag attgcctgca agggaaataa   8340
aaatgactaa gatattaaaa aaaaaaaaaa aaaa                                8374
```

<210> SEQ ID NO 21
<211> LENGTH: 2330
<212> TYPE: PRT
<213> ORGANISM: Homo Sapiens
<300> PUBLICATION INFORMATION:
<308> DATABASE ACCESSION NUMBER: GenBank NM 212478
<309> DATABASE ENTRY DATE: 2005-06-10

<400> SEQUENCE: 21

```
Met Leu Arg Gly Pro Gly Pro Gly Leu Leu Leu Leu Ala Val Gln Cys
 1               5                  10                  15

Leu Gly Thr Ala Val Pro Ser Thr Gly Ala Ser Lys Ser Lys Arg Gln
            20                  25                  30

Ala Gln Gln Met Val Gln Pro Gln Ser Pro Val Ala Val Ser Gln Ser
        35                  40                  45

Lys Pro Gly Cys Tyr Asp Asn Gly Lys His Tyr Gln Ile Asn Gln Gln
    50                  55                  60

Trp Glu Arg Thr Tyr Leu Gly Asn Ala Leu Val Cys Thr Cys Tyr Gly
65                  70                  75                  80

Gly Ser Arg Gly Phe Asn Cys Glu Ser Lys Pro Glu Ala Glu Glu Thr
                85                  90                  95

Cys Phe Asp Lys Tyr Thr Gly Asn Thr Tyr Arg Val Gly Asp Thr Tyr
            100                 105                 110

Glu Arg Pro Lys Asp Ser Met Ile Trp Asp Cys Thr Cys Ile Gly Ala
        115                 120                 125

Gly Arg Gly Arg Ile Ser Cys Thr Ile Ala Asn Arg Cys His Glu Gly
    130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                165                 170                 175

Trp Thr Cys Lys Pro Ile Ala Glu Lys Cys Phe Asp His Ala Ala Gly
            180                 185                 190

Thr Ser Tyr Val Val Gly Glu Thr Trp Glu Lys Pro Tyr Gln Gly Trp
        195                 200                 205

Met Met Val Asp Cys Thr Cys Leu Gly Glu Gly Ser Gly Arg Ile Thr
    210                 215                 220

Cys Thr Ser Arg Asn Arg Cys Asn Asp Gln Asp Thr Arg Thr Ser Tyr
```

```
              225                 230                 235                 240
Arg Ile Gly Asp Thr Trp Ser Lys Lys Asp Asn Arg Gly Asn Leu Leu
                    245                 250                 255
Gln Cys Ile Cys Thr Gly Asn Gly Arg Gly Glu Trp Lys Cys Glu Arg
                260                 265                 270
His Thr Ser Val Gln Thr Thr Ser Ser Gly Ser Gly Pro Phe Thr Asp
            275                 280                 285
Val Arg Ala Ala Val Tyr Gln Pro Gln Pro His Pro Gln Pro Pro Pro
        290                 295                 300
Tyr Gly His Cys Val Thr Asp Ser Gly Val Val Tyr Ser Val Gly Met
305                 310                 315                 320
Gln Trp Leu Lys Thr Gln Gly Asn Lys Gln Met Leu Cys Thr Cys Leu
                    325                 330                 335
Gly Asn Gly Val Ser Cys Gln Glu Thr Ala Val Thr Gln Thr Tyr Gly
                340                 345                 350
Gly Asn Ser Asn Gly Glu Pro Cys Val Leu Pro Phe Thr Tyr Asn Gly
            355                 360                 365
Arg Thr Phe Tyr Ser Cys Thr Thr Glu Gly Arg Gln Asp Gly His Leu
        370                 375                 380
Trp Cys Ser Thr Thr Ser Asn Tyr Glu Gln Asp Gln Lys Tyr Ser Phe
385                 390                 395                 400
Cys Thr Asp His Thr Val Leu Val Gln Thr Arg Gly Gly Asn Ser Asn
                    405                 410                 415
Gly Ala Leu Cys His Phe Pro Phe Leu Tyr Asn Asn His Asn Tyr Thr
                420                 425                 430
Asp Cys Thr Ser Glu Gly Arg Arg Asp Asn Met Lys Trp Cys Gly Thr
            435                 440                 445
Thr Gln Asn Tyr Asp Ala Asp Gln Lys Phe Gly Phe Cys Pro Met Ala
        450                 455                 460
Ala His Glu Glu Ile Cys Thr Thr Asn Glu Gly Val Met Tyr Arg Ile
465                 470                 475                 480
Gly Asp Gln Trp Asp Lys Gln His Asp Met Gly His Met Met Arg Cys
                    485                 490                 495
Thr Cys Val Gly Asn Gly Arg Gly Glu Trp Thr Cys Ile Ala Tyr Ser
                500                 505                 510
Gln Leu Arg Asp Gln Cys Ile Val Asp Asp Ile Thr Tyr Asn Val Asn
            515                 520                 525
Asp Thr Phe His Lys Arg His Glu Glu Gly His Met Leu Asn Cys Thr
        530                 535                 540
Cys Phe Gly Gln Gly Arg Gly Arg Trp Lys Cys Asp Pro Val Asp Gln
545                 550                 555                 560
Cys Gln Asp Ser Glu Thr Gly Thr Phe Tyr Gln Ile Gly Asp Ser Trp
                    565                 570                 575
Glu Lys Tyr Val His Gly Val Arg Tyr Gln Cys Tyr Cys Tyr Gly Arg
                580                 585                 590
Gly Ile Gly Glu Trp His Cys Gln Pro Leu Gln Thr Tyr Pro Ser Ser
            595                 600                 605
Ser Gly Pro Val Glu Val Phe Ile Thr Glu Thr Pro Ser Gln Pro Asn
        610                 615                 620
Ser His Pro Ile Gln Trp Asn Ala Pro Gln Pro Ser His Ile Ser Lys
625                 630                 635                 640
Tyr Ile Leu Arg Trp Arg Pro Lys Asn Ser Val Gly Arg Trp Lys Glu
                    645                 650                 655
```

-continued

```
Ala Thr Ile Pro Gly His Leu Asn Ser Tyr Thr Ile Lys Gly Leu Lys
        660                 665                 670

Pro Gly Val Val Tyr Glu Gly Gln Leu Ile Ser Ile Gln Gln Tyr Gly
        675                 680                 685

His Gln Glu Val Thr Arg Phe Asp Phe Thr Thr Ser Thr Ser Thr
    690                 695                 700

Pro Val Thr Ser Asn Thr Val Thr Gly Glu Thr Thr Pro Phe Ser Pro
705                 710                 715                 720

Leu Val Ala Thr Ser Glu Ser Val Thr Glu Ile Thr Ala Ser Ser Phe
                725                 730                 735

Val Val Ser Trp Val Ser Ala Ser Asp Thr Val Ser Gly Phe Arg Val
            740                 745                 750

Glu Tyr Glu Leu Ser Glu Glu Gly Asp Glu Pro Gln Tyr Leu Asp Leu
        755                 760                 765

Pro Ser Thr Ala Thr Ser Val Asn Ile Pro Asp Leu Leu Pro Gly Arg
    770                 775                 780

Lys Tyr Ile Val Asn Val Tyr Gln Ile Ser Glu Asp Gly Glu Gln Ser
785                 790                 795                 800

Leu Ile Leu Ser Thr Ser Gln Thr Thr Ala Pro Asp Ala Pro Pro Asp
                805                 810                 815

Pro Thr Val Asp Gln Val Asp Asp Thr Ser Ile Val Val Arg Trp Ser
            820                 825                 830

Arg Pro Gln Ala Pro Ile Thr Gly Tyr Arg Ile Val Tyr Ser Pro Ser
        835                 840                 845

Val Glu Gly Ser Ser Thr Glu Leu Asn Leu Pro Glu Thr Ala Asn Ser
    850                 855                 860

Val Thr Leu Ser Asp Leu Gln Pro Gly Val Gln Tyr Asn Ile Thr Ile
865                 870                 875                 880

Tyr Ala Val Glu Glu Asn Gln Glu Ser Thr Pro Val Val Ile Gln Gln
                885                 890                 895

Glu Thr Thr Gly Thr Pro Arg Ser Asp Thr Val Pro Ser Pro Arg Asp
            900                 905                 910

Leu Gln Phe Val Glu Val Thr Asp Val Lys Val Thr Ile Met Trp Thr
        915                 920                 925

Pro Pro Glu Ser Ala Val Thr Gly Tyr Arg Val Asp Val Ile Pro Val
    930                 935                 940

Asn Leu Pro Gly Glu His Gly Gln Arg Leu Pro Ile Ser Arg Asn Thr
945                 950                 955                 960

Phe Ala Glu Val Thr Gly Leu Ser Pro Gly Val Thr Tyr Tyr Phe Lys
                965                 970                 975

Val Phe Ala Val Ser His Gly Arg Glu Ser Lys Pro Leu Thr Ala Gln
            980                 985                 990

Gln Thr Thr Lys Leu Asp Ala Pro Thr Asn Leu Gln Phe Val Asn Glu
        995                 1000                1005

Thr Asp Ser Thr Val Leu Val Arg Trp Thr Pro Pro Arg Ala Gln Ile
    1010                1015                1020

Thr Gly Tyr Arg Leu Thr Val Gly Leu Thr Arg Arg Gly Gln Pro Arg
1025                1030                1035                1040

Gln Tyr Asn Val Gly Pro Ser Val Ser Lys Tyr Pro Leu Arg Asn Leu
                1045                1050                1055

Gln Pro Ala Ser Glu Tyr Thr Val Ser Leu Val Ala Ile Lys Gly Asn
            1060                1065                1070

Gln Glu Ser Pro Lys Ala Thr Gly Val Phe Thr Thr Leu Gln Pro Gly
        1075                1080                1085
```

```
Ser Ser Ile Pro Pro Tyr Asn Thr Glu Val Thr Glu Thr Thr Ile Val
    1090                1095                1100

Ile Thr Trp Thr Pro Ala Pro Arg Ile Gly Phe Lys Leu Gly Val Arg
1105            1110                1115                1120

Pro Ser Gln Gly Gly Glu Ala Pro Arg Glu Val Thr Ser Asp Ser Gly
            1125                1130                1135

Ser Ile Val Val Ser Gly Leu Thr Pro Gly Val Glu Tyr Val Tyr Thr
            1140                1145                1150

Ile Gln Val Leu Arg Asp Gly Gln Glu Arg Asp Ala Pro Ile Val Asn
        1155                1160                1165

Lys Val Val Thr Pro Leu Ser Pro Pro Thr Asn Leu His Leu Glu Ala
        1170                1175                1180

Asn Pro Asp Thr Gly Val Leu Thr Val Ser Trp Glu Arg Ser Thr Thr
1185                1190                1195                1200

Pro Asp Ile Thr Gly Tyr Arg Ile Thr Thr Thr Pro Thr Asn Gly Gln
                1205                1210                1215

Gln Gly Asn Ser Leu Glu Glu Val Val His Ala Asp Gln Ser Ser Cys
            1220                1225                1230

Thr Phe Asp Asn Leu Ser Pro Gly Leu Glu Tyr Asn Val Ser Val Tyr
        1235                1240                1245

Thr Val Lys Asp Asp Lys Glu Ser Val Pro Ile Ser Asp Thr Ile Ile
        1250                1255                1260

Pro Ala Val Pro Pro Thr Asp Leu Arg Phe Thr Asn Ile Gly Pro
1265            1270                1275                1280

Asp Thr Met Arg Val Thr Trp Ala Pro Pro Ser Ile Asp Leu Thr
                1285                1290                1295

Asn Phe Leu Val Arg Tyr Ser Pro Val Lys Asn Glu Glu Asp Val Ala
        1300                1305                1310

Glu Leu Ser Ile Ser Pro Ser Asp Asn Ala Val Val Leu Thr Asn Leu
            1315                1320                1325

Leu Pro Gly Thr Glu Tyr Val Val Ser Val Ser Ser Val Tyr Glu Gln
            1330                1335                1340

His Glu Ser Thr Pro Leu Arg Gly Arg Gln Lys Thr Gly Leu Asp Ser
1345                1350                1355                1360

Pro Thr Gly Ile Asp Phe Ser Asp Ile Thr Ala Asn Ser Phe Thr Val
                1365                1370                1375

His Trp Ile Ala Pro Arg Ala Thr Ile Thr Gly Tyr Arg Ile Arg His
            1380                1385                1390

His Pro Glu His Phe Ser Gly Arg Pro Arg Glu Asp Arg Val Pro His
        1395                1400                1405

Ser Arg Asn Ser Ile Thr Leu Thr Asn Leu Thr Pro Gly Thr Glu Tyr
        1410                1415                1420

Val Val Ser Ile Val Ala Leu Asn Gly Arg Glu Glu Ser Pro Leu Leu
1425            1430                1435                1440

Ile Gly Gln Gln Ser Thr Val Ser Asp Val Pro Arg Asp Leu Glu Val
                1445                1450                1455

Val Ala Ala Thr Pro Thr Ser Leu Leu Ile Ser Trp Asp Ala Pro Ala
            1460                1465                1470

Val Thr Val Arg Tyr Tyr Arg Ile Thr Tyr Gly Glu Thr Gly Gly Asn
        1475                1480                1485

Ser Pro Val Gln Glu Phe Thr Val Pro Gly Ser Lys Ser Thr Ala Thr
        1490                1495                1500

Ile Ser Gly Leu Lys Pro Gly Val Asp Tyr Thr Ile Thr Val Tyr Ala
```

```
            1505                1510                1515                1520

Val Thr Gly Arg Gly Asp Ser Pro Ala Ser Ser Lys Pro Ile Ser Ile
                1525                1530                1535

Asn Tyr Arg Thr Glu Ile Asp Lys Pro Ser Gln Met Gln Val Thr Asp
                1540                1545                1550

Val Gln Asp Asn Ser Ile Ser Val Lys Trp Leu Pro Ser Ser Ser Pro
                1555                1560                1565

Val Thr Gly Tyr Arg Val Thr Thr Pro Lys Asn Gly Pro Gly Pro
            1570                1575                1580

Thr Lys Thr Lys Thr Ala Gly Pro Asp Gln Thr Glu Met Thr Ile Glu
1585                1590                1595                1600

Gly Leu Gln Pro Thr Val Glu Tyr Val Val Ser Val Tyr Ala Gln Asn
                1605                1610                1615

Pro Ser Gly Glu Ser Gln Pro Leu Val Gln Thr Ala Val Thr Asn Ile
                1620                1625                1630

Asp Arg Pro Lys Gly Leu Ala Phe Thr Asp Val Asp Val Asp Ser Ile
                1635                1640                1645

Lys Ile Ala Trp Glu Ser Pro Gln Gly Gln Val Ser Arg Tyr Arg Val
                1650                1655                1660

Thr Tyr Ser Ser Pro Glu Asp Gly Ile His Glu Leu Phe Pro Ala Pro
1665                1670                1675                1680

Asp Gly Glu Glu Asp Thr Ala Glu Leu Gln Gly Leu Arg Pro Gly Ser
                1685                1690                1695

Glu Tyr Thr Val Ser Val Val Ala Leu His Asp Asp Met Glu Ser Gln
                1700                1705                1710

Pro Leu Ile Gly Thr Gln Ser Thr Ala Ile Pro Ala Pro Thr Asp Leu
                1715                1720                1725

Lys Phe Thr Gln Val Thr Pro Thr Ser Leu Ser Ala Gln Trp Thr Pro
                1730                1735                1740

Pro Asn Val Gln Leu Thr Gly Tyr Arg Val Arg Val Thr Pro Lys Glu
1745                1750                1755                1760

Lys Thr Gly Pro Met Lys Glu Ile Asn Leu Ala Pro Asp Ser Ser Ser
                1765                1770                1775

Val Val Val Ser Gly Leu Met Val Ala Thr Lys Tyr Glu Val Ser Val
                1780                1785                1790

Tyr Ala Leu Lys Asp Thr Leu Thr Ser Arg Pro Ala Gln Gly Val Val
                1795                1800                1805

Thr Thr Leu Glu Asn Val Ser Pro Pro Arg Arg Ala Arg Val Thr Asp
                1810                1815                1820

Ala Thr Glu Thr Thr Ile Thr Ile Ser Trp Arg Thr Lys Thr Glu Thr
1825                1830                1835                1840

Ile Thr Gly Phe Gln Val Asp Ala Val Pro Ala Asn Gly Gln Thr Pro
                1845                1850                1855

Ile Gln Arg Thr Ile Lys Pro Asp Val Arg Ser Tyr Thr Ile Thr Gly
                1860                1865                1870

Leu Gln Pro Gly Thr Asp Tyr Lys Ile Tyr Leu Tyr Thr Leu Asn Asp
                1875                1880                1885

Asn Ala Arg Ser Ser Pro Val Val Ile Asp Ala Ser Thr Ala Ile Asp
                1890                1895                1900

Ala Pro Ser Asn Leu Arg Phe Leu Ala Thr Thr Pro Asn Ser Leu Leu
1905                1910                1915                1920

Val Ser Trp Gln Pro Pro Arg Ala Arg Ile Thr Gly Tyr Ile Ile Lys
                1925                1930                1935
```

-continued

```
Tyr Glu Lys Pro Gly Ser Pro Pro Arg Glu Val Val Pro Arg Pro Arg
            1940                1945                1950

Pro Gly Val Thr Glu Ala Thr Ile Thr Gly Leu Glu Pro Gly Thr Glu
        1955                1960                1965

Tyr Thr Ile Tyr Val Ile Ala Leu Lys Asn Asn Gln Lys Ser Glu Pro
    1970                1975                1980

Leu Ile Gly Arg Lys Lys Thr Val Gln Lys Thr Pro Phe Val Thr His
1985                1990                1995                2000

Pro Gly Tyr Asp Thr Gly Asn Gly Ile Gln Leu Pro Gly Thr Ser Gly
            2005                2010                2015

Gln Gln Pro Ser Val Gly Gln Gln Met Ile Phe Glu Glu His Gly Phe
        2020                2025                2030

Arg Arg Thr Thr Pro Pro Thr Thr Ala Thr Pro Ile Arg His Arg Pro
        2035                2040                2045

Arg Pro Tyr Pro Pro Asn Val Gly Gln Glu Ala Leu Ser Gln Thr Thr
        2050                2055                2060

Ile Ser Trp Ala Pro Phe Gln Asp Thr Ser Glu Tyr Ile Ile Ser Cys
2065                2070                2075                2080

His Pro Val Gly Thr Asp Glu Glu Pro Leu Gln Phe Arg Val Pro Gly
            2085                2090                2095

Thr Ser Thr Ser Ala Thr Leu Thr Gly Leu Thr Arg Gly Ala Thr Tyr
        2100                2105                2110

Asn Ile Ile Val Glu Ala Leu Lys Asp Gln Gln Arg His Lys Val Arg
        2115                2120                2125

Glu Glu Val Val Thr Val Gly Asn Ser Val Asn Glu Gly Leu Asn Gln
        2130                2135                2140

Pro Thr Asp Asp Ser Cys Phe Asp Pro Tyr Thr Val Ser His Tyr Ala
2145                2150                2155                2160

Val Gly Asp Glu Trp Glu Arg Met Ser Glu Ser Gly Phe Lys Leu Leu
            2165                2170                2175

Cys Gln Cys Leu Gly Phe Gly Ser Gly His Phe Arg Cys Asp Ser Ser
        2180                2185                2190

Arg Trp Cys His Asp Asn Gly Val Asn Tyr Lys Ile Gly Glu Lys Trp
        2195                2200                2205

Asp Arg Gln Gly Glu Asn Gly Gln Met Met Ser Cys Thr Cys Leu Gly
        2210                2215                2220

Asn Gly Lys Gly Glu Phe Lys Cys Asp Pro His Glu Ala Thr Cys Tyr
2225                2230                2235                2240

Asp Asp Gly Lys Thr Tyr His Val Gly Glu Gln Trp Gln Lys Glu Tyr
            2245                2250                2255

Leu Gly Ala Ile Cys Ser Cys Thr Cys Phe Gly Gly Gln Arg Gly Trp
        2260                2265                2270

Arg Cys Asp Asn Cys Arg Arg Pro Gly Gly Glu Pro Ser Pro Glu Gly
        2275                2280                2285

Thr Thr Gly Gln Ser Tyr Asn Gln Tyr Ser Gln Arg Tyr His Gln Arg
        2290                2295                2300

Thr Asn Thr Asn Val Asn Cys Pro Ile Glu Cys Phe Met Pro Leu Asp
2305                2310                2315                2320

Val Gln Ala Asp Arg Glu Asp Ser Arg Glu
            2325                2330

<210> SEQ ID NO 22
<211> LENGTH: 8272
<212> TYPE: DNA
<213> ORGANISM: Homo Sapiens
```

<220> FEATURE:
<223> OTHER INFORMATION: Oncofetal Fibronectin variant 5
<300> PUBLICATION INFORMATION:
<308> DATABASE ACCESSION NUMBER: GenBank NM 212476
<309> DATABASE ENTRY DATE: 2005-06-10

<400> SEQUENCE: 22

```
gcccgcgccg gctgtgctgc acaggggag gagagggaac cccaggcgcg agcgggaaga      60
ggggacctgc agccacaact tctctggtcc tctgcatccc ttctgtccct ccacccgtcc    120
ccttccccac cctctggccc ccaccttctt ggaggcgaca accccgggga ggcattagaa    180
gggattttc ccgcaggttg cgaagggaag caaacttggt ggcaacttgc ctcccgtgc     240
gggcgtctct cccccaccgt ctcaacatgc ttaggggtcc ggggcccggg ctgctgctgc    300
tggccgtcca gtgcctgggg acagcggtgc cctccacggg agcctcgaag agcaagaggc    360
aggctcagca aatggttcag ccccagtccc cggtggctgt cagtcaaagc aagcccggtt    420
gttatgacaa tggaaaacac tatcagataa atcaacagtg ggagcggacc tacctaggca    480
atgcgttggt ttgtacttgt tatggaggaa gccgaggttt aactgcgag agtaaacctg     540
aagctgaaga gcttgcttt gacaagtaca ctgggaacac ttaccgagtg ggtgacactt     600
atgagcgtcc taaagactcc atgatctggg actgtacctg catcgggct gggcgaggga    660
gaataagctg taccatcgca aaccgctgcc atgaaggggg tcagtcctac aagattggtg    720
acacctggag gagaccacat gagactggtg gttacatgtt agagtgtgtg tgtcttggta    780
atggaaaagg agaatggacc tgcaagccca tagctgagaa gtgttttgat catgctgctg    840
ggacttccta tgtggtcgga gaaacgtggg agaagcccta ccaaggctgg atgatggtag    900
attgtacttg cctgggagaa ggcagcgacg catcacttg cacttctaga aatagatgca    960
acgatcagga cacaaggaca tcctatagaa ttggagacac ctggagcaag aaggataatc   1020
gaggaaacct gctccagtgc atctgcacag gcaacggccg aggagagtgg aagtgtgaga   1080
ggcacacctc tgtgcagacc acatcgagcg gatctggccc cttcaccgat gttcgtgcag   1140
ctgtttacca accgcagcct cacccccagc ctcctcccta tggccactgt gtcacagaca   1200
gtggtgtggt ctactctgtg gggatgcagt ggctgaagac acaaggaaat aagcaaatgc   1260
tttgcacgtg cctgggcaac ggagtcagct gccaagagac agctgtaacc cagacttacg   1320
gtggcaactc aaatggagag ccatgtgtct taccattcac ctacaatggc aggacgttct   1380
actcctgcac cacagaaggg cgacaggacg gacatctttg gtgcagcaca cttcgaatt    1440
atgagcagga ccagaaatac tcttttctgca cagaccacac tgttttggtt cagactcgag   1500
gaggaaattc caatggtgcc ttgtgccact tccccttcct atacaacaac cacaattaca   1560
ctgattgcac ttctgagggc agaagagaca acatgaagtg gtgtgggacc acacagaact   1620
atgatgccga ccagaagttt gggttctgcc ccatggctgc ccacgaggaa atctgcacaa   1680
ccaatgaagg ggtcatgtac cgcattgag atcagtggga taagcagcat gacatgggtc   1740
acatgatgag gtgcacgtgt gttgggaatg gtcgtgggga atggacatgc attgcctact   1800
cgcagcttcg agatcagtgc attgttgatg acatcactta caatgtgaac gacacattcc   1860
acaagcgtca tgaagagggg cacatgctga actgtacatg cttcggtcag ggtcggggca   1920
ggtggaagtg tgatcccgtc gaccaatgcc aggattcaga gactgggacg ttttatcaaa   1980
ttggagattc atgggagaag tatgtgcatg gtgtcagata ccagtgctac tgctatggcc   2040
gtggcattgg ggagtggcat tgccaacctt tacagaccta tccaagctca gtggtcctg    2100
tcgaagtatt tatcactgag actccgagtc agcccaactc ccacccatc cagtggaatg    2160
```

```
caccacagcc atctcacatt tccaagtaca ttctcaggtg gagacctaaa aattctgtag      2220
gccgttggaa ggaagctacc ataccaggcc acttaaactc ctacaccatc aaaggcctga      2280
agcctggtgt ggtatacgag ggccagctca tcagcatcca gcagtacggc caccaagaag      2340
tgactcgctt tgacttcacc accaccagca ccagcacacc tgtgaccagc aacaccgtga      2400
caggagagac gactcccttt tctcctcttg tggccacttc tgaatctgtg accgaaatca      2460
cagccagtag ctttgtggtc tcctgggtct cagcttccga caccgtgtcg ggattccggg      2520
tggaatatga gctgagtgag gagggagatg agccacagta cctggatctt ccaagcacag      2580
ccacttctgt gaacatccct gacctgcttc ctggccgaaa atacattgta aatgtctatc      2640
agatatctga ggatggggag cagagtttga tcctgtctac ttcacaaaca acagcgcctg      2700
atgcccctcc tgacccgact gtggaccaag ttgatgacac ctcaattgtt gttcgctgga      2760
gcagacccca ggctcccatc acagggtaca gaatagtcta ttcgccatca gtagaaggta      2820
gcagcacaga actcaacctt cctgaaactg caaactccgt caccctcagt gacttgcaac      2880
ctggtgttca gtataacatc actatctatg ctgtggaaga aaatcaagaa agtacacctg      2940
ttgtcattca acaagaaacc actggcaccc cacgctcaga tacagtgccc tctcccaggg      3000
acctgcagtt tgtggaagtg acagacgtga aggtcaccat catgtggaca ccgcctgaga      3060
gtgcagtgac cggctaccgt gtggatgtga tccccgtcaa cctgcctggc gagcacgggc      3120
agaggctgcc catcagcagg aacacctttg cagaagtcac cgggctgtcc cctggggtca      3180
cctattactt caaagtcttt gcagtgagcc atgggaggga gagcaagcct ctgactgctc      3240
aacagacaac caaactggat gctcccacta acctccagtt tgtcaatgaa actgattcta      3300
ctgtcctggt gagatggact ccacctcggg cccagataac aggataccga ctgaccgtgg      3360
gccttacccg aagaggacag cccaggcagt acaatgtggg tccctctgtc tccaagtacc      3420
cactgaggaa tctgcagcct gcatctgagt acaccgtatc cctcgtggcc ataaagggca      3480
accaagagag ccccaaagcc actggagtct ttaccacact gcagcctggg agctctattc      3540
caccttacaa caccgaggtg actgagacca ccattgtgat cacatggacg cctgctccaa      3600
gaattggttt taagctgggt gtacgaccaa gccaggagg agaggcacca cgagaagtga      3660
cttcagactc aggaagcatc gttgtgtccg gcttgactcc aggagtagaa tacgtctaca      3720
ccatccaagt cctgagagat ggacaggaaa gagatgcgcc aattgtaaac aaagtggtga      3780
caccattgtc tccaccaaca aacttgcatc tggaggcaaa ccctgacact ggagtgctca      3840
cagtctcctg ggagaggagc accaccccag acattactgg ttatagaatt accacaaccc      3900
ctacaaacgg ccagcaggga aattctttgg aagaagtggt ccatgctgat cagagctcct      3960 gcactttga taacctgagt cccggcctgg agtacaatgt cagtgtttac actgtcaagg      4020
atgacaagga aagtgtccct atctctgata ccatcatccc agctgttcct cctcccactg      4080
acctgcgatt taccaacatt ggtccagaca ccatgcgtgt cacctgggct ccaccccat      4140 ccattgattt aaccaacttc ctggtgcgtt actcacctgt gaaaaatgag gaagatgttg      4200
cagagttgtc aatttctcct tcagacaatg cagtggtctt aacaaatctc ctgcctggta      4260
cagaatatgt agtgagtgtc tccagtgtct acgaacaaca tgagagcaca cctcttagag      4320
gaagacagaa aacaggtctt gattcccaa ctggcattga cttttctgat attactgcca      4380
actcttttac tgtgcactgg attgctcctc gagccaccat cactggctac aggatccgcc      4440
atcatcccga gcacttcagt gggagacctc gagaagatcg ggtgcccac tctcggaatt      4500 ccatcaccct caccaacctc actccaggca cagagtatgt ggtcagcatc gttgctctta      4560
```

```
atggcagaga ggaaagtccc ttattgattg gccaacaatc aacagtttct gatgttccga    4620
gggacctgga agttgttgct gcgaccccca ccagcctact gatcagctgg gatgctcctg    4680
ctgtcacagt gagatattac aggatcactt acggagagac aggaggaaat agccctgtcc    4740
aggagttcac tgtgcctggg agcaagtcta cagctaccat cagcggcctt aaacctggag    4800
ttgattatac catcactgtg tatgctgtca ctggccgtgg agacagcccc gcaagcagca    4860
agccaatttc cattaattac cgaacagaaa ttgacaaacc atcccagatg caagtgaccg    4920
atgttcagga caacagcatt agtgtcaagt ggctgccttc aagttcccct gttactggtt    4980
acagagtaac caccactccc aaaaatggac caggaccaac aaaaactaaa actgcaggtc    5040
cagatcaaac agaaatgact attgaaggct tgcagcccac agtggagtat gtggttagtg    5100
tctatgctca gaatccaagc ggagagagtc agcctctggt tcagactgca gtaaccacta    5160
ttcctgcacc aactgacctg aagttcactc aggtcacacc cacaagcctg agcgcccagt    5220
ggacaccacc caatgttcag ctcactggat atcgagtgcg ggtgaccccc aaggagaaga    5280
ccggaccaat gaaagaaatc aaccttgctc ctgacagctc atccgtggtt gtatcaggac    5340
ttatggtggc caccaaatat gaagtgagtg tctatgctct taaggacact ttgacaagca    5400
gaccagctca gggagttgtc accactctgg agaatgtcag cccaccaaga agggctcgtg    5460
tgacagatgc tactgagacc accatcacca ttagctggag aaccaagact gagacgatca    5520
ctggcttcca agttgatgcc gttccagcca atggccagac tccaatccag agaaccatca    5580
agccagatgt cagaagctac accatcacag gtttacaacc aggcactgac tacaagatct    5640
acctgtacac cttgaatgac aatgctcgga gctcccctgt ggtcatcgac gcctccactg    5700
ccattgatgc accatccaac ctgcgtttcc tggccaccac acccaattcc ttgctggtat    5760
catggcagcc gccacgtgcc aggattaccg gctacatcat caagtatgag aagcctgggt    5820
ctcctcccag agaagtggtc cctcggcccc gccctggtgt cacagaggct actattactg    5880
gcctggaacc gggaaccgaa tatacaattt atgtcattgc cctgaagaat aatcagaaga    5940
gcgagcccct gattggaagg aaaaagacag acgagcttcc ccaactggta acccttccac    6000
accccaatct tcatggacca gagatcttgg atgttccttc cacagttcaa aagaccccctt    6060 tcgtcaccca ccctgggtat gacactggaa atggtattca gcttcctggc acttctggtc    6120
agcaacccag tgttgggcaa caaatgatct ttgaggaaca tggttttagg cggaccacac    6180
cgcccacaac ggccaccccc ataaggcata ggccaagacc atacccgccg aatgtaggtg    6240
aggaaatcca aattggtcac atccccaggg aagatgtaga ctatcacctg tacccacacg    6300
gtccgggact caatccaaat gcctctacag gacaagaagc tctctctcag acaaccatct    6360
catgggcccc attccaggac acttctgagt acatcatttc atgtcatcct gttggcactg    6420
atgaagaacc cttacagttc agggttcctg gaacttctac cagtgccact ctgacaggcc    6480
tcaccgagag tgccacctac aacatcatag tggaggcact gaaagaccag cagaggcata    6540
aggttcggga agaggttgtt accgtgggca actctgtcaa cgaaggcttg aaccaaccta    6600
cggatgactg tgctttgac ccctacacag tttcccatta tgccgttgga gatgagtggg    6660
aacgaatgtc tgaatcaggc tttaaactgt tgtgccagtg cttaggcttt ggaagtggtc    6720
atttcagatg tgattcatct agatggtgcc atgacaatgg tgtgaactac aagattggag    6780
agaagtggga ccgtcaggga gaaaatggcc agatgatgag ctgcacatgt cttgggaacg    6840
gaaaaggaga attcaagtgt gaccctcatg aggcaacgtg ttatgatgat gggaagacat    6900
accacgtagg agaacagtgg cagaaggaat atctcggtgc catttgctcc tgcacatgct    6960
```

-continued

```
ttggaggcca gcggggctgg cgctgtgaca actgccgcag acctgggggt gaacccagtc   7020
ccgaaggcac tactggccag tcctacaacc agtattctca gagataccat cagagaacaa   7080
acactaatgt taattgccca attgagtgct tcatgccttt agatgtacag gctgacagag   7140
aagattcccg agagtaaatc atctttccaa tccagaggaa caagcatgtc tctctgccaa   7200
gatccatcta aactggagtg atgttagcag acccagctta gagttcttct ttctttctta   7260 agcccttgc tctggaggaa gttctccagc ttcagctcaa ctcacagctt ctccaagcat   7320
caccctggga gtttcctgag ggttttctca taaatgaggg ctgcacattg cctgttctgc   7380
ttcgaagtat tcaataccgc tcagtatttt aaatgaagtg attctaagat ttggtttggg   7440
atcaatagga aagcatatgc agccaaccaa gatgcaaatg ttttgaaatg atatgaccaa   7500
aattttaagt aggaaagtca cccaaacact tctgctttca cttaagtgtc tggcccgcaa   7560
tactgtagga acaagcatga tcttgttact gtgatatttt aaatatccac agtactcact   7620 tttccaaat gatcctagta attgcctaga aatatctttc tcttacctgt tatttatcaa   7680
tttttcccag tattttttata cggaaaaaat tgtattgaaa acacttagta tgcagttgat   7740
aagaggaatt tggtataatt atggtgggtg attattttt atactgtatg tgccaaagct   7800
ttactactgt ggaaagacaa ctgtttaat aaaagattta cattccacaa cttgaagttc   7860
atctatttga tataagacac cttcggggga ataattcct gtgaatattc tttttcaatt   7920
cagcaaacat ttgaaaatct atgatgtgca agtctaattg ttgatttcag tacaagattt   7980
tctaaatcag ttgctacaaa aactgattgg ttttttgtcac ttcatctctt cactaatgga   8040
gatagcttta cactttctgc tttaatagat ttaagtggac cccaatattt attaaaattg   8100
ctagtttacc gttcagaagt ataatagaaa taatctttag ttgctctttt ctaaccattg   8160
taattcttcc cttcttccct ccaccttcc ttcattgaat aaacctctgt tcaaagagat   8220
tgcctgcaag ggaaataaaa atgactaaga tattaaaaaa aaaaaaaaa aa            8272
```

```
<210> SEQ ID NO 23
<211> LENGTH: 2296
<212> TYPE: PRT
<213> ORGANISM: Homo Sapiens
<300> PUBLICATION INFORMATION:
<308> DATABASE ACCESSION NUMBER: GenBank NM 212476
<309> DATABASE ENTRY DATE: 2005-06-10

<400> SEQUENCE: 23
```

```
Met Leu Arg Gly Pro Gly Pro Gly Leu Leu Leu Leu Ala Val Gln Cys
  1               5                  10                  15

Leu Gly Thr Ala Val Pro Ser Thr Gly Ala Ser Lys Ser Lys Arg Gln
                 20                  25                  30

Ala Gln Gln Met Val Gln Pro Gln Ser Pro Val Ala Val Ser Gln Ser
             35                  40                  45

Lys Pro Gly Cys Tyr Asp Asn Gly Lys His Tyr Gln Ile Asn Gln Gln
         50                  55                  60

Trp Glu Arg Thr Tyr Leu Gly Asn Ala Leu Val Cys Thr Cys Tyr Gly
 65                  70                  75                  80

Gly Ser Arg Gly Phe Asn Cys Glu Ser Lys Pro Glu Ala Glu Glu Thr
                 85                  90                  95

Cys Phe Asp Lys Tyr Thr Gly Asn Thr Tyr Arg Val Gly Asp Thr Tyr
            100                 105                 110

Glu Arg Pro Lys Asp Ser Met Ile Trp Asp Cys Thr Cys Ile Gly Ala
        115                 120                 125

Gly Arg Gly Arg Ile Ser Cys Thr Ile Ala Asn Arg Cys His Glu Gly
```

```
              130                 135                 140
Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                165                 170                 175

Trp Thr Cys Lys Pro Ile Ala Glu Lys Cys Phe Asp His Ala Ala Gly
                180                 185                 190

Thr Ser Tyr Val Val Gly Glu Thr Trp Glu Lys Pro Tyr Gln Gly Trp
                195                 200                 205

Met Met Val Asp Cys Thr Cys Leu Gly Glu Gly Ser Gly Arg Ile Thr
210                 215                 220

Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu
                245                 250                 255

Gln Cys Ile Cys Thr Gly Asn Gly Arg Gly Glu Trp Lys Cys Glu Arg
                260                 265                 270

His Thr Ser Val Gln Thr Thr Ser Ser Gly Ser Gly Pro Phe Thr Asp
                275                 280                 285

Val Arg Ala Ala Val Tyr Gln Pro Gln Pro His Pro Gln Pro Pro Pro
290                 295                 300

Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
                325                 330                 335

Gly Asn Gly Val Ser Cys Gln Glu Thr Ala Val Thr Gln Thr Tyr Gly
                340                 345                 350

Gly Asn Ser Asn Gly Glu Pro Cys Val Leu Pro Phe Thr Tyr Asn Gly
                355                 360                 365

Arg Thr Phe Tyr Ser Cys Thr Thr Glu Gly Arg Gln Asp Gly His Leu
                370                 375                 380

Trp Cys Ser Thr Thr Ser Asn Tyr Glu Gln Asp Gln Lys Tyr Ser Phe
385                 390                 395                 400

Cys Thr Asp His Thr Val Leu Val Gln Thr Arg Gly Gly Asn Ser Asn
                405                 410                 415

Gly Ala Leu Cys His Phe Pro Phe Leu Tyr Asn Asn His Asn Tyr Thr
                420                 425                 430

Asp Cys Thr Ser Glu Gly Arg Arg Asp Asn Met Lys Trp Cys Gly Thr
                435                 440                 445

Thr Gln Asn Tyr Asp Ala Asp Gln Lys Phe Gly Phe Cys Pro Met Ala
                450                 455                 460

Ala His Glu Glu Ile Cys Thr Thr Asn Glu Gly Val Met Tyr Arg Ile
465                 470                 475                 480

Gly Asp Gln Trp Asp Lys Gln His Asp Met Gly His Met Met Arg Cys
                485                 490                 495

Thr Cys Val Gly Asn Gly Arg Gly Glu Trp Thr Cys Ile Ala Tyr Ser
                500                 505                 510

Gln Leu Arg Asp Gln Cys Ile Val Asp Asp Ile Thr Tyr Asn Val Asn
                515                 520                 525

Asp Thr Phe His Lys Arg His Glu Glu Gly His Met Leu Asn Cys Thr
                530                 535                 540

Cys Phe Gly Gln Gly Arg Gly Arg Trp Lys Cys Asp Pro Val Asp Gln
545                 550                 555                 560
```

-continued

```
Cys Gln Asp Ser Glu Thr Gly Thr Phe Tyr Gln Ile Gly Asp Ser Trp
            565                 570                 575
Glu Lys Tyr Val His Gly Val Arg Tyr Gln Cys Tyr Cys Tyr Gly Arg
            580                 585                 590
Gly Ile Gly Glu Trp His Cys Gln Pro Leu Gln Thr Tyr Pro Ser Ser
            595                 600                 605
Ser Gly Pro Val Glu Val Phe Ile Thr Glu Thr Pro Ser Gln Pro Asn
            610                 615                 620
Ser His Pro Ile Gln Trp Asn Ala Pro Gln Pro Ser His Ile Ser Lys
625                 630                 635                 640
Tyr Ile Leu Arg Trp Arg Pro Lys Asn Ser Val Gly Arg Trp Lys Glu
                    645                 650                 655
Ala Thr Ile Pro Gly His Leu Asn Ser Tyr Thr Ile Lys Gly Leu Lys
                    660                 665                 670
Pro Gly Val Val Tyr Glu Gly Gln Leu Ile Ser Ile Gln Gln Tyr Gly
                    675                 680                 685
His Gln Glu Val Thr Arg Phe Asp Phe Thr Thr Thr Ser Thr Ser Thr
            690                 695                 700
Pro Val Thr Ser Asn Thr Val Thr Gly Glu Thr Thr Pro Phe Ser Pro
705                 710                 715                 720
Leu Val Ala Thr Ser Glu Ser Val Thr Glu Ile Thr Ala Ser Ser Phe
                    725                 730                 735
Val Val Ser Trp Val Ser Ala Ser Asp Thr Val Ser Gly Phe Arg Val
                    740                 745                 750
Glu Tyr Glu Leu Ser Glu Glu Gly Asp Glu Pro Gln Tyr Leu Asp Leu
            755                 760                 765
Pro Ser Thr Ala Thr Ser Val Asn Ile Pro Asp Leu Leu Pro Gly Arg
770                 775                 780
Lys Tyr Ile Val Asn Val Tyr Gln Ile Ser Glu Asp Gly Glu Gln Ser
785                 790                 795                 800
Leu Ile Leu Ser Thr Ser Gln Thr Thr Ala Pro Asp Ala Pro Pro Asp
                    805                 810                 815
Pro Thr Val Asp Gln Val Asp Asp Thr Ser Ile Val Val Arg Trp Ser
            820                 825                 830
Arg Pro Gln Ala Pro Ile Thr Gly Tyr Arg Ile Val Tyr Ser Pro Ser
            835                 840                 845
Val Glu Gly Ser Ser Thr Glu Leu Asn Leu Pro Glu Thr Ala Asn Ser
850                 855                 860
Val Thr Leu Ser Asp Leu Gln Pro Gly Val Gln Tyr Asn Ile Thr Ile
865                 870                 875                 880
Tyr Ala Val Glu Glu Asn Gln Glu Ser Thr Pro Val Val Ile Gln Gln
                    885                 890                 895
Glu Thr Thr Gly Thr Pro Arg Ser Asp Thr Val Pro Ser Pro Arg Asp
            900                 905                 910
Leu Gln Phe Val Glu Val Thr Asp Val Lys Val Thr Ile Met Trp Thr
            915                 920                 925
Pro Pro Glu Ser Ala Val Thr Gly Tyr Arg Val Asp Val Ile Pro Val
            930                 935                 940
Asn Leu Pro Gly Glu His Gly Gln Arg Leu Pro Ile Ser Arg Asn Thr
945                 950                 955                 960
Phe Ala Glu Val Thr Gly Leu Ser Pro Gly Val Thr Tyr Tyr Phe Lys
                    965                 970                 975
Val Phe Ala Val Ser His Gly Arg Glu Ser Lys Pro Leu Thr Ala Gln
                    980                 985                 990
```

```
Gln Thr Thr Lys Leu Asp Ala Pro Thr Asn Leu Gln Phe Val Asn Glu
            995                 1000                1005

Thr Asp Ser Thr Val Leu Val Arg Trp Thr Pro Arg Ala Gln Ile
1010                1015                1020

Thr Gly Tyr Arg Leu Thr Val Gly Leu Thr Arg Arg Gly Gln Pro Arg
1025                1030                1035                1040

Gln Tyr Asn Val Gly Pro Ser Val Ser Lys Tyr Pro Leu Arg Asn Leu
            1045                1050                1055

Gln Pro Ala Ser Glu Tyr Thr Val Ser Leu Val Ala Ile Lys Gly Asn
            1060                1065                1070

Gln Glu Ser Pro Lys Ala Thr Gly Val Phe Thr Thr Leu Gln Pro Gly
            1075                1080                1085

Ser Ser Ile Pro Pro Tyr Asn Thr Glu Val Thr Glu Thr Thr Ile Val
            1090                1095                1100

Ile Thr Trp Thr Pro Ala Pro Arg Ile Gly Phe Lys Leu Gly Val Arg
1105                1110                1115                1120

Pro Ser Gln Gly Gly Glu Ala Pro Arg Glu Val Thr Ser Asp Ser Gly
            1125                1130                1135

Ser Ile Val Val Ser Gly Leu Thr Pro Gly Val Glu Tyr Val Tyr Thr
            1140                1145                1150

Ile Gln Val Leu Arg Asp Gly Gln Glu Arg Asp Ala Pro Ile Val Asn
            1155                1160                1165

Lys Val Val Thr Pro Leu Ser Pro Pro Thr Asn Leu His Leu Glu Ala
            1170                1175                1180

Asn Pro Asp Thr Gly Val Leu Thr Val Ser Trp Glu Arg Ser Thr Thr
1185                1190                1195                1200

Pro Asp Ile Thr Gly Tyr Arg Ile Thr Thr Thr Pro Thr Asn Gly Gln
            1205                1210                1215

Gln Gly Asn Ser Leu Glu Glu Val Val His Ala Asp Gln Ser Ser Cys
            1220                1225                1230

Thr Phe Asp Asn Leu Ser Pro Gly Leu Glu Tyr Asn Val Ser Val Tyr
            1235                1240                1245

Thr Val Lys Asp Asp Lys Glu Ser Val Pro Ile Ser Asp Thr Ile Ile
            1250                1255                1260

Pro Ala Val Pro Pro Thr Asp Leu Arg Phe Thr Asn Ile Gly Pro
1265                1270                1275                1280

Asp Thr Met Arg Val Thr Trp Ala Pro Pro Ser Ile Asp Leu Thr
            1285                1290                1295

Asn Phe Leu Val Arg Tyr Ser Pro Val Lys Asn Glu Glu Asp Val Ala
            1300                1305                1310

Glu Leu Ser Ile Ser Pro Ser Asp Asn Ala Val Val Leu Thr Asn Leu
            1315                1320                1325

Leu Pro Gly Thr Glu Tyr Val Val Ser Val Ser Ser Val Tyr Glu Gln
            1330                1335                1340

His Glu Ser Thr Pro Leu Arg Gly Arg Gln Lys Thr Gly Leu Asp Ser
1345                1350                1355                1360

Pro Thr Gly Ile Asp Phe Ser Asp Ile Thr Ala Asn Ser Phe Thr Val
            1365                1370                1375

His Trp Ile Ala Pro Arg Ala Thr Ile Thr Gly Tyr Arg Ile Arg His
            1380                1385                1390

His Pro Glu His Phe Ser Gly Arg Pro Arg Glu Asp Arg Val Pro His
            1395                1400                1405

Ser Arg Asn Ser Ile Thr Leu Thr Asn Leu Thr Pro Gly Thr Glu Tyr
```

```
            1410                1415                1420
Val Val Ser Ile Val Ala Leu Asn Gly Arg Glu Glu Ser Pro Leu Leu
1425                1430                1435                1440

Ile Gly Gln Gln Ser Thr Val Ser Asp Val Pro Arg Asp Leu Glu Val
                1445                1450                1455

Val Ala Ala Thr Pro Thr Ser Leu Leu Ile Ser Trp Asp Ala Pro Ala
                1460                1465                1470

Val Thr Val Arg Tyr Tyr Arg Ile Thr Tyr Gly Glu Thr Gly Gly Asn
                1475                1480                1485

Ser Pro Val Gln Glu Phe Thr Val Pro Gly Ser Lys Ser Thr Ala Thr
                1490                1495                1500

Ile Ser Gly Leu Lys Pro Gly Val Asp Tyr Thr Ile Thr Val Tyr Ala
1505                1510                1515                1520

Val Thr Gly Arg Gly Asp Ser Pro Ala Ser Ser Lys Pro Ile Ser Ile
                1525                1530                1535

Asn Tyr Arg Thr Glu Ile Asp Lys Pro Ser Gln Met Gln Val Thr Asp
                1540                1545                1550

Val Gln Asp Asn Ser Ile Ser Val Lys Trp Leu Pro Ser Ser Ser Pro
                1555                1560                1565

Val Thr Gly Tyr Arg Val Thr Thr Thr Pro Lys Asn Gly Pro Gly Pro
                1570                1575                1580

Thr Lys Thr Lys Thr Ala Gly Pro Asp Gln Thr Glu Met Thr Ile Glu
1585                1590                1595                1600

Gly Leu Gln Pro Thr Val Glu Tyr Val Val Ser Val Tyr Ala Gln Asn
                1605                1610                1615

Pro Ser Gly Glu Ser Gln Pro Leu Val Gln Thr Ala Val Thr Thr Ile
                1620                1625                1630

Pro Ala Pro Thr Asp Leu Lys Phe Thr Gln Val Thr Pro Thr Ser Leu
                1635                1640                1645

Ser Ala Gln Trp Thr Pro Pro Asn Val Gln Leu Thr Gly Tyr Arg Val
                1650                1655                1660

Arg Val Thr Pro Lys Glu Lys Thr Gly Pro Met Lys Glu Ile Asn Leu
1665                1670                1675                1680

Ala Pro Asp Ser Ser Ser Val Val Val Ser Gly Leu Met Val Ala Thr
                1685                1690                1695

Lys Tyr Glu Val Ser Val Tyr Ala Leu Lys Asp Thr Leu Thr Ser Arg
                1700                1705                1710

Pro Ala Gln Gly Val Val Thr Thr Leu Glu Asn Val Ser Pro Pro Arg
                1715                1720                1725

Arg Ala Arg Val Thr Asp Ala Thr Glu Thr Thr Ile Thr Ile Ser Trp
                1730                1735                1740

Arg Thr Lys Thr Glu Thr Ile Thr Gly Phe Gln Val Asp Ala Val Pro
1745                1750                1755                1760

Ala Asn Gly Gln Thr Pro Ile Gln Arg Thr Ile Lys Pro Asp Val Arg
                1765                1770                1775

Ser Tyr Thr Ile Thr Gly Leu Gln Pro Gly Thr Asp Tyr Lys Ile Tyr
                1780                1785                1790

Leu Tyr Thr Leu Asn Asp Asn Ala Arg Ser Ser Pro Val Val Ile Asp
                1795                1800                1805

Ala Ser Thr Ala Ile Asp Ala Pro Ser Asn Leu Arg Phe Leu Ala Thr
                1810                1815                1820

Thr Pro Asn Ser Leu Leu Val Ser Trp Gln Pro Pro Arg Ala Arg Ile
1825                1830                1835                1840
```

-continued

Thr Gly Tyr Ile Ile Lys Tyr Glu Lys Pro Gly Ser Pro Arg Glu
        1845                1850                1855

Val Val Pro Arg Pro Arg Pro Gly Val Thr Glu Ala Thr Ile Thr Gly
    1860                1865                1870

Leu Glu Pro Gly Thr Glu Tyr Thr Ile Tyr Val Ile Ala Leu Lys Asn
        1875                1880                1885

Asn Gln Lys Ser Glu Pro Leu Ile Gly Arg Lys Lys Thr Asp Glu Leu
        1890                1895                1900

Pro Gln Leu Val Thr Leu Pro His Pro Asn Leu His Gly Pro Glu Ile
1905                1910                1915                1920

Leu Asp Val Pro Ser Thr Val Gln Lys Thr Pro Phe Val Thr His Pro
            1925                1930                1935

Gly Tyr Asp Thr Gly Asn Gly Ile Gln Leu Pro Gly Thr Ser Gly Gln
            1940                1945                1950

Gln Pro Ser Val Gly Gln Gln Met Ile Phe Glu Glu His Gly Phe Arg
        1955                1960                1965

Arg Thr Thr Pro Pro Thr Thr Ala Thr Pro Ile Arg His Arg Pro Arg
    1970                1975                1980

Pro Tyr Pro Pro Asn Val Gly Glu Glu Ile Gln Ile Gly His Ile Pro
1985                1990                1995                2000

Arg Glu Asp Val Asp Tyr His Leu Tyr Pro His Gly Pro Gly Leu Asn
            2005                2010                2015

Pro Asn Ala Ser Thr Gly Gln Glu Ala Leu Ser Gln Thr Thr Ile Ser
        2020                2025                2030

Trp Ala Pro Phe Gln Asp Thr Ser Glu Tyr Ile Ile Ser Cys His Pro
        2035                2040                2045

Val Gly Thr Asp Glu Glu Pro Leu Gln Phe Arg Val Pro Gly Thr Ser
    2050                2055                2060

Thr Ser Ala Thr Leu Thr Gly Leu Thr Arg Gly Ala Thr Tyr Asn Ile
2065                2070                2075                2080

Ile Val Glu Ala Leu Lys Asp Gln Gln Arg His Lys Val Arg Glu Glu
            2085                2090                2095

Val Val Thr Val Gly Asn Ser Val Asn Glu Gly Leu Asn Gln Pro Thr
        2100                2105                2110

Asp Asp Ser Cys Phe Asp Pro Tyr Thr Val Ser His Tyr Ala Val Gly
        2115                2120                2125

Asp Glu Trp Glu Arg Met Ser Glu Ser Gly Phe Lys Leu Leu Cys Gln
    2130                2135                2140

Cys Leu Gly Phe Gly Ser Gly His Phe Arg Cys Asp Ser Ser Arg Trp
2145                2150                2155                2160

Cys His Asp Asn Gly Val Asn Tyr Lys Ile Gly Glu Lys Trp Asp Arg
            2165                2170                2175

Gln Gly Glu Asn Gly Gln Met Met Ser Cys Thr Cys Leu Gly Asn Gly
        2180                2185                2190

Lys Gly Glu Phe Lys Cys Asp Pro His Glu Ala Thr Cys Tyr Asp Asp
            2195                2200                2205

Gly Lys Thr Tyr His Val Gly Glu Gln Trp Gln Lys Glu Tyr Leu Gly
        2210                2215                2220

Ala Ile Cys Ser Cys Thr Cys Phe Gly Gly Gln Arg Gly Trp Arg Cys
2225                2230                2235                2240

Asp Asn Cys Arg Arg Pro Gly Gly Glu Pro Ser Pro Glu Gly Thr Thr
            2245                2250                2255

Gly Gln Ser Tyr Asn Gln Tyr Ser Gln Arg Tyr His Gln Arg Thr Asn
        2260                2265                2270

Thr Asn Val Asn Cys Pro Ile Glu Cys Phe Met Pro Leu Asp Val Gln
    2275                2280                2285
Ala Asp Arg Glu Asp Ser Arg Glu
    2290            2295

<210> SEQ ID NO 24
<211> LENGTH: 7912
<212> TYPE: DNA
<213> ORGANISM: Homo Sapiens
<220> FEATURE:
<223> OTHER INFORMATION: Oncofetal Fibronectin variant 6
<300> PUBLICATION INFORMATION:
<308> DATABASE ACCESSION NUMBER: GenBank NM 212474
<309> DATABASE ENTRY DATE: 2005-06-10

<400> SEQUENCE: 24

| | | | | | |
|---|---|---|---|---|---|
| gcccgcgccg | gctgtgctgc | acaggggag | gagagggaac | cccaggcgcg | agcgggaaga | 60 |
| ggggacctgc | agccacaact | tctctggtcc | tctgcatccc | ttctgtccct | ccacccgtcc | 120 |
| ccttccccac | cctctggccc | ccaccttctt | ggaggcgaca | ccccggga | ggcattagaa | 180 |
| gggattttc | ccgcaggttg | cgaagggaag | caaacttggt | ggcaacttgc | ctcccgggtgc | 240 |
| gggcgtctct | cccccaccgt | ctcaacatgc | ttaggggtcc | ggggcccggg | ctgctgctgc | 300 |
| tggccgtcca | gtgcctgggg | acagcggtgc | cctccacggg | agcctcgaag | agcaagaggc | 360 |
| aggctcagca | aatggttcag | ccccagtccc | cggtggctgt | cagtcaaagc | aagcccggtt | 420 |
| gttatgacaa | tggaaaacac | tatcagataa | atcaacagtg | ggagcggacc | tacctaggca | 480 |
| atgcgttggt | ttgtacttgt | tatggaggaa | gccgaggttt | taactgcgag | agtaaacctg | 540 |
| aagctgaaga | gacttgcttt | gacaagtaca | ctgggaacac | ttaccgagtg | ggtgacactt | 600 |
| atgagcgtcc | taaagactcc | atgatctggg | actgtacctg | catcggggct | gggcgaggga | 660 |
| gaataagctg | taccatcgca | aaccgctgcc | atgaagggg | tcagtcctac | aagattggtg | 720 |
| acacctggag | gagaccacat | gagactggtg | gttacatgtt | agagtgtgtg | tgtcttggta | 780 |
| atggaaaagg | agaatggacc | tgcaagccca | tagctgagaa | gtgttttgat | catgctgctg | 840 |
| ggacttccta | tgtggtcgga | gaaacgtggg | agaagcccta | ccaaggctgg | atgatggtag | 900 |
| attgtacttg | cctgggagaa | ggcagcggac | gcatcacttg | cacttctaga | aatagatgca | 960 |
| acgatcagga | cacaaggaca | tcctatagaa | ttggagacac | ctggagcaag | aaggataatc | 1020 |
| gaggaaacct | gctccagtgc | atctgcacag | gcaacggccg | aggagagtgg | aagtgtgaga | 1080 |
| ggcacacctc | tgtgcagacc | acatcgagcg | gatctggccc | cttcaccgat | gttcgtgcag | 1140 |
| ctgtttacca | accgcagcct | caccccagc | ctcctcccta | tggccactgt | gtcacagaca | 1200 |
| gtggtgtggt | ctactctgtg | gggatgcagt | ggctgaagac | acaaggaaat | aagcaaatgc | 1260 |
| tttgcacgtg | cctgggcaac | ggagtcagct | gccaagagac | agctgtaacc | cagacttacg | 1320 |
| gtggcaactc | aaatggagag | ccatgtgtct | taccattcac | ctacaatggc | aggacgttct | 1380 |
| actcctgcac | cacagaaggg | cgacaggacg | gacatctttg | tgtcagcaca | acttcgaatt | 1440 |
| atgagcagga | ccagaaatac | tctttctgca | cagaccacac | tgttttggtt | cagactcgag | 1500 |
| gaggaaattc | caatggtgcc | ttgtgccact | tccccttcct | atacaacaac | cacaattaca | 1560 |
| ctgattgcac | ttctgagggc | agaagagaca | acatgaagtg | gtgtgggacc | acacagaact | 1620 |
| atgatgccga | ccagaagttt | gggttctgcc | ccatggctgc | ccacgaggaa | atctgcacaa | 1680 |
| ccaatgaagg | ggtcatgtac | cgcattgag | atcagtggga | taagcagcat | gacatgggtc | 1740 |
| acatgatgag | gtgcacgtgt | gttgggaatg | gtcgtgggga | atggacatgc | attgcctact | 1800 |

```
cgcagcttcg agatcagtgc attgttgatg acatcactta caatgtgaac gacacattcc   1860
acaagcgtca tgaagagggg cacatgctga actgtacatg cttcggtcag ggtcggggca   1920
ggtggaagtg tgatcccgtc gaccaatgcc aggattcaga gactgggacg ttttatcaaa   1980
ttggagattc atgggagaag tatgtgcatg gtgtcagata ccagtgctac tgctatggcc   2040
gtggcattgg ggagtggcat tgccaacctt tacagaccta tccaagctca agtggtcctg   2100
tcgaagtatt tatcactgag actccgagtc agcccaactc ccaccccatc cagtggaatg   2160
caccacagcc atctcacatt tccaagtaca ttctcaggtg gagacctaaa aattctgtag   2220
gccgttggaa ggaagctacc ataccaggcc acttaaactc ctacaccatc aaaggcctga   2280
agcctggtgt ggtatacgag ggccagctca tcagcatcca gcagtacggc caccaagaag   2340
tgactcgctt tgacttcacc accaccagca ccagcacacc tgtgaccagc aacaccgtga   2400
caggagagac gactcccttt tctcctcttg tggccacttc tgaatctgtg accgaaatca   2460
cagccagtag cttttgtggtc tcctgggtct cagcttccga caccgtgtcg ggattccggg   2520
tggaatatga gctgagtgag gagggagatg agccacagta cctggatctt ccaagcacag   2580
ccacttctgt gaacatccct gacctgcttc tggccgaaaa atacattgta aatgtctatc   2640
agatatctga ggatggggag cagagtttga tcctgtctac ttcacaaaca acagcgcctg   2700
atgcccctcc tgacccgact gtggaccaag ttgatgacac ctcaattgtt gttcgctgga   2760
gcagacccca ggctcccatc acagggtaca gaatagtcta ttcgccatca gtagaaggta   2820
gcagcacaga actcaacctt cctgaaactg caaactccgt caccctcagt gacttgcaac   2880
ctggtgttca gtataacatc actatctatg ctgtggaaga aaatcaagaa agtacacctg   2940
ttgtcattca acaagaaacc actggcaccc cacgctcaga tacagtgccc tctcccaggg   3000
acctgcagtt tgtggaagtg acagacgtga aggtcaccat catgtggaca ccgcctgaga   3060
gtgcagtgac cggctaccgt gtggatgtga tccccgtcaa cctgcctggc gagcacgggc   3120
agaggctgcc catcagcagg aacacctttg cagaagtcac cgggctgtcc cctggggtca   3180
cctattactt caaagtcttt gcagtgagcc atgggaggga gagcaagcct ctgactgctc   3240
aacagacaac caaactggat gctcccacta acctccagtt tgtcaatgaa actgattcta   3300
ctgtcctggt gagatggact ccacctcggg cccagataac aggataccga ctgaccgtgg   3360
gccttacccg aagaggacag cccaggcagt acaatgtggg tccctctgtc tccaagtacc   3420
cactgaggaa tctgcagcct gcatctgagt acaccgtatc cctcgtggcc ataaagggca   3480
accaagagag ccccaaagcc actggagtct ttaccacact gcagcctggg agctctattc   3540
caccttacaa caccgaggtg actgagacca ccattgtgat cacatggacg cctgctccaa   3600
gaattggttt taagctgggt gtacgaccaa gccaggagg agaggcacca cgagaagtga   3660
cttcagactc aggaagcatc gttgtgtccg gcttgactcc aggagtagaa tacgtctaca   3720
ccatccaagt cctgagagat ggacaggaaa gagatgcgcc aattgtaaac aaagtggtga   3780
caccattgtc tccaccaaca aacttgcatc tggaggcaaa ccctgacact ggagtgctca   3840
cagtctcctg ggagagggc accaccccag acattactgg ttatagaatt accacaaccc   3900
ctacaaacgg ccagcaggga aattctttgg aagaagtggt ccatgctgat cagagctcct   3960
gcactttgat aacctgagt cccggcctgg agtacaatgt cagtgtttac actgtcaagg   4020
atgacaagga aagtgtccct atctctgata ccatcatccc agctgttcct cctcccactg   4080
acctgcgatt caccaacatt ggtccagaca ccatgcgtgt cacctgggct ccaccccat   4140 ccattgattt aaccaacttc ctggtgcgtt actcacctgt gaaaaatgag gaagatgttc   4200
```

```
cagagttgtc aatttctcct tcagacaatg cagtggtctt aacaaatctc ctgcctggta    4260
cagaatatgt agtgagtgtc tccagtgtct acgaacaaca tgagagcaca cctcttagag    4320
gaagacagaa aacaggtctt gattccccaa ctggcattga cttttctgat attactgcca    4380
actcttttac tgtgcactgg attgctcctc gagccaccat cactggctac aggatccgcc    4440
atcatcccga gcacttcagt gggagacctc gagaagatcg ggtgccccac tctcggaatt    4500
ccatcaccct caccaacctc actccaggca cagagtatgt ggtcagcatc gttgctctta    4560
atggcagaga ggaaagtccc ttattgattg ccaacaatc aacagtttct gatgttccga     4620
gggacctgga agttgttgct gcgaccccca ccagcctact gatcagctgg gatgctcctg    4680
ctgtcacagt gagatattac aggatcactt acggagagac aggaggaaat agccctgtcc    4740
aggagttcac tgtgcctggg agcaagtcta cagctaccat cagcggcctt aaacctggag    4800
ttgattatac catcactgtg tatgctgtca ctggccgtgg agacagcccc gcaagcagca    4860
agccaatttc cattaattac cgaacagaaa ttgacaaacc atcccagatg caagtgaccg    4920
atgttcagga caacagcatt agtgtcaagt ggctgccttc aagttcccct gttactggtt    4980
acagagtaac caccactccc aaaaatggac caggaccaac aaaaactaaa actgcaggtc    5040
cagatcaaac agaaatgact attgaaggct tgcagcccac agtggagtat gtggttagtg    5100
tctatgctca gaatccaagc ggagagagtc agcctctggt tcagactgca gtaaccacta    5160
ttcctgcacc aactgacctg aagttcactc aggtcacacc cacaagcctg agcgcccagt    5220
ggacaccacc caatgttcag ctcactggat atcgagtgcg ggtgaccccc aaggagaaga    5280
ccggaccaat gaaagaaatc aaccttgctc ctgacagctc atccgtggtt gtatcaggac    5340
ttatggtggc caccaaatat gaagtgagtg tctatgctct taaggacact ttgacaagca    5400
gaccagctca gggagttgtc accactctgg agaatgtcag cccaccaaga agggctcgtg    5460
tgacagatgc tactgagacc accatcacca ttagctggag aaccaagact gagacgatca    5520
ctggcttcca agttgatgcc gttccagcca atggccagc tccaatccag agaaccatca    5580
agccagatgt cagaagctac accatcacag gtttacaacc aggcactgac tacaagatct    5640
acctgtacac cttgaatgac aatgctcgga gctcccctgt ggtcatcgac gcctccactg    5700
ccattgatgc accatccaac ctgcgtttcc tggccaccac acccaattcc ttgctggtat    5760
catggcagcc gccacgtgcc aggattaccg gctacatcat caagtatgag aagcctgggt    5820
ctcctcccag agaagtggtc cctcggcccc gccctggtgt cacagaggct actattactg    5880
gcctggaacc gggaaccgaa tatacaattt atgtcattgc cctgaagaat aatcagaaga    5940
gcgagcccct gattggaagg aaaaagacag acaagaagc tctctctcag acaaccatct    6000
catgggcccc attccaggac acttctgagt acatcatttc atgtcatcct gttggcactg    6060
atgaagaacc cttacagttc agggttcctg gaacttctac cagtgccact ctgacaggcc    6120
tcaccagagg tgccacctac aacatcatag tggaggcact gaaagaccag cagaggcata    6180
aggttcggga agaggttgtt accgtgggca actctgtcaa cgaaggcttg aaccaaccta    6240
cggatgactc gtgctttgac ccctacacag tttcccatta tgccgttgga gatgagtggg    6300
aacgaatgtc tgaatcaggc tttaaactgt tgtgccagtg cttaggcttt ggaagtggtc    6360
atttcagatg tgattcatct agatggtgcc atgacaatgg tgtgaactac aagattggag    6420
agaagtggga ccgtcaggga gaaaatggcc agatgatgag ctgcacatgt cttgggaacg    6480
gaaaaggaga attcaagtgt gaccctcatg aggcaacgtg ttatgatgat gggaagacat    6540
accacgtagg agaacagtgg cagaaggaat atctcggtgc catttgctcc tgcacatgct    6600
```

-continued

```
ttggaggcca gcggggctgg cgctgtgaca actgccgcag acctgggggt gaacccagtc    6660
ccgaaggcac tactggccag tcctacaacc agtattctca gagataccat cagagaacaa    6720
acactaatgt taattgccca attgagtgct tcatgccttt agatgtacag gctgacagag    6780
aagattcccg agagtaaatc atcttttccaa tccagaggaa caagcatgtc tctctgccaa    6840
gatccatcta aactggagtg atgttagcag acccagctta gagttcttct ttctttctta    6900 agcccttttgc tctggaggaa gttctccagc ttcagctcaa ctcacagctt ctccaagcat    6960
caccctggga gtttcctgag ggttttctca taaatgaggg ctgcacattg cctgttctgc    7020
ttcgaagtat tcaataccgc tcagtatttt aaatgaagtg attctaagat ttggtttggg    7080
atcaatagga aagcatatgc agccaaccaa gatgcaaatg ttttgaaatg atatgaccaa    7140
aattttaagt aggaaagtca cccaaacact tctgctttca cttaagtgtc tggcccgcaa    7200
tactgtagga acaagcatga tcttgttact gtgatatttt aaatatccac agtactcact    7260
ttttccaaat gatcctagta attgcctaga aatatctttc tcttacctgt tatttatcaa    7320
tttttcccag tatttttata cggaaaaaat tgtattgaaa acacttagta tgcagttgat    7380
aagaggaatt tggtataatt atggtgggtg attattttt atactgtatg tgccaaagct    7440
ttactactgt ggaaagacaa ctgttttaat aaaagattta cattccacaa cttgaagttc    7500
atctatttga tataagacac cttcggggga ataattcct gtgaatattc tttttcaatt    7560
cagcaaacat ttgaaaatct atgatgtgca agtctaattg ttgatttcag tacaagattt    7620
tctaaatcag ttgctacaaa aactgattgg ttttttgtcac ttcatctctt cactaatgga    7680
gatagcttta cactttctgc tttaatagat ttaagtggac cccaatattt attaaaattg    7740
ctagtttacc gttcagaagt ataatagaaa taatctttag ttgctctttt ctaaccattg    7800
taattcttcc cttcttccct ccacctttcc ttcattgaat aaacctctgt tcaaagagat    7860
tgcctgcaag ggaaataaaa atgactaaga tattaaaaaa aaaaaaaaa aa          7912
```

<210> SEQ ID NO 25
<211> LENGTH: 2176
<212> TYPE: PRT
<213> ORGANISM: Homo Sapiens
<300> PUBLICATION INFORMATION:
<308> DATABASE ACCESSION NUMBER: GenBank NM 212474
<309> DATABASE ENTRY DATE: 2005-06-10

<400> SEQUENCE: 25

```
Met Leu Arg Gly Pro Gly Pro Gly Leu Leu Leu Leu Ala Val Gln Cys
  1               5                  10                  15

Leu Gly Thr Ala Val Pro Ser Thr Gly Ala Ser Lys Ser Lys Arg Gln
             20                  25                  30

Ala Gln Gln Met Val Gln Pro Gln Ser Pro Val Ala Val Ser Gln Ser
         35                  40                  45

Lys Pro Gly Cys Tyr Asp Asn Gly Lys His Tyr Gln Ile Asn Gln Gln
     50                  55                  60

Trp Glu Arg Thr Tyr Leu Gly Asn Ala Leu Val Cys Thr Cys Tyr Gly
 65                  70                  75                  80

Gly Ser Arg Gly Phe Asn Cys Glu Ser Lys Pro Glu Ala Glu Glu Thr
                 85                  90                  95

Cys Phe Asp Lys Tyr Thr Gly Asn Thr Tyr Arg Val Gly Asp Thr Tyr
            100                 105                 110

Glu Arg Pro Lys Asp Ser Met Ile Trp Asp Cys Thr Cys Ile Gly Ala
        115                 120                 125

Gly Arg Gly Arg Ile Ser Cys Thr Ile Ala Asn Arg Cys His Glu Gly
```

```
                130                 135                 140
Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                165                 170                 175

Trp Thr Cys Lys Pro Ile Ala Glu Lys Cys Phe Asp His Ala Ala Gly
                180                 185                 190

Thr Ser Tyr Val Val Gly Glu Thr Trp Glu Lys Pro Tyr Gln Gly Trp
                195                 200                 205

Met Met Val Asp Cys Thr Cys Leu Gly Glu Gly Ser Gly Arg Ile Thr
210                 215                 220

Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu
                245                 250                 255

Gln Cys Ile Cys Thr Gly Asn Gly Arg Gly Glu Trp Lys Cys Glu Arg
                260                 265                 270

His Thr Ser Val Gln Thr Thr Ser Ser Gly Ser Gly Pro Phe Thr Asp
                275                 280                 285

Val Arg Ala Ala Val Tyr Gln Pro Gln Pro His Pro Gln Pro Pro Pro
                290                 295                 300

Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
                325                 330                 335

Gly Asn Gly Val Ser Cys Gln Glu Thr Ala Val Thr Gln Thr Tyr Gly
                340                 345                 350

Gly Asn Ser Asn Gly Glu Pro Cys Val Leu Pro Phe Thr Tyr Asn Gly
                355                 360                 365

Arg Thr Phe Tyr Ser Cys Thr Thr Glu Gly Arg Gln Asp Gly His Leu
                370                 375                 380

Trp Cys Ser Thr Thr Ser Asn Tyr Glu Gln Asp Gln Lys Tyr Ser Phe
385                 390                 395                 400

Cys Thr Asp His Thr Val Leu Val Gln Thr Arg Gly Gly Asn Ser Asn
                405                 410                 415

Gly Ala Leu Cys His Phe Pro Phe Leu Tyr Asn Asn His Asn Tyr Thr
                420                 425                 430

Asp Cys Thr Ser Glu Gly Arg Arg Asp Asn Met Lys Trp Cys Gly Thr
                435                 440                 445

Thr Gln Asn Tyr Asp Ala Asp Gln Lys Phe Gly Phe Cys Pro Met Ala
                450                 455                 460

Ala His Glu Glu Ile Cys Thr Thr Asn Glu Gly Val Met Tyr Arg Ile
465                 470                 475                 480

Gly Asp Gln Trp Asp Lys Gln His Asp Met Gly His Met Met Arg Cys
                485                 490                 495

Thr Cys Val Gly Asn Gly Arg Gly Glu Trp Thr Cys Ile Ala Tyr Ser
                500                 505                 510

Gln Leu Arg Asp Gln Cys Ile Val Asp Asp Ile Thr Tyr Asn Val Asn
                515                 520                 525

Asp Thr Phe His Lys Arg His Glu Glu Gly His Met Leu Asn Cys Thr
                530                 535                 540

Cys Phe Gly Gln Gly Arg Gly Arg Trp Lys Cys Asp Pro Val Asp Gln
545                 550                 555                 560
```

-continued

```
Cys Gln Asp Ser Glu Thr Gly Thr Phe Tyr Gln Ile Gly Asp Ser Trp
                565                 570                 575

Glu Lys Tyr Val His Gly Val Arg Tyr Gln Cys Tyr Cys Tyr Gly Arg
                580                 585                 590

Gly Ile Gly Glu Trp His Cys Gln Pro Leu Gln Thr Tyr Pro Ser Ser
                595                 600                 605

Ser Gly Pro Val Glu Val Phe Ile Thr Glu Thr Pro Ser Gln Pro Asn
                610                 615                 620

Ser His Pro Ile Gln Trp Asn Ala Pro Gln Pro Ser His Ile Ser Lys
625                 630                 635                 640

Tyr Ile Leu Arg Trp Arg Pro Lys Asn Ser Val Gly Arg Trp Lys Glu
                645                 650                 655

Ala Thr Ile Pro Gly His Leu Asn Ser Tyr Thr Ile Lys Gly Leu Lys
                660                 665                 670

Pro Gly Val Val Tyr Glu Gly Gln Leu Ile Ser Ile Gln Gln Tyr Gly
                675                 680                 685

His Gln Glu Val Thr Arg Phe Asp Phe Thr Thr Ser Thr Ser Thr
                690                 695                 700

Pro Val Thr Ser Asn Thr Val Thr Gly Glu Thr Thr Pro Phe Ser Pro
705                 710                 715                 720

Leu Val Ala Thr Ser Glu Ser Val Thr Glu Ile Thr Ala Ser Ser Phe
                725                 730                 735

Val Val Ser Trp Val Ser Ala Ser Asp Thr Val Ser Gly Phe Arg Val
                740                 745                 750

Glu Tyr Glu Leu Ser Glu Glu Gly Asp Glu Pro Gln Tyr Leu Asp Leu
                755                 760                 765

Pro Ser Thr Ala Thr Ser Val Asn Ile Pro Asp Leu Leu Pro Gly Arg
                770                 775                 780

Lys Tyr Ile Val Asn Val Tyr Gln Ile Ser Glu Asp Gly Glu Gln Ser
785                 790                 795                 800

Leu Ile Leu Ser Thr Ser Gln Thr Thr Ala Pro Asp Ala Pro Pro Asp
                805                 810                 815

Pro Thr Val Asp Gln Val Asp Asp Thr Ser Ile Val Val Arg Trp Ser
                820                 825                 830

Arg Pro Gln Ala Pro Ile Thr Gly Tyr Arg Ile Val Tyr Ser Pro Ser
                835                 840                 845

Val Glu Gly Ser Ser Thr Glu Leu Asn Leu Pro Glu Thr Ala Asn Ser
850                 855                 860

Val Thr Leu Ser Asp Leu Gln Pro Gly Val Gln Tyr Asn Ile Thr Ile
865                 870                 875                 880

Tyr Ala Val Glu Glu Asn Gln Glu Ser Thr Pro Val Val Ile Gln Gln
                885                 890                 895

Glu Thr Thr Gly Thr Pro Arg Ser Asp Thr Val Pro Ser Pro Arg Asp
                900                 905                 910

Leu Gln Phe Val Glu Val Thr Asp Val Lys Val Thr Ile Met Trp Thr
                915                 920                 925

Pro Pro Glu Ser Ala Val Thr Gly Tyr Arg Val Asp Val Ile Pro Val
                930                 935                 940

Asn Leu Pro Gly Glu His Gly Gln Arg Leu Pro Ile Ser Arg Asn Thr
945                 950                 955                 960

Phe Ala Glu Val Thr Gly Leu Ser Pro Gly Val Thr Tyr Tyr Phe Lys
                965                 970                 975

Val Phe Ala Val Ser His Gly Arg Glu Ser Lys Pro Leu Thr Ala Gln
                980                 985                 990
```

```
Gln Thr Thr Lys Leu Asp Ala Pro Thr Asn Leu Gln Phe Val Asn Glu
        995                 1000                1005

Thr Asp Ser Thr Val Leu Val Arg Trp Thr Pro Arg Ala Gln Ile
1010                1015                1020

Thr Gly Tyr Arg Leu Thr Val Gly Leu Thr Arg Arg Gly Gln Pro Arg
1025                1030                1035                1040

Gln Tyr Asn Val Gly Pro Ser Val Ser Lys Tyr Pro Leu Arg Asn Leu
        1045                1050                1055

Gln Pro Ala Ser Glu Tyr Thr Val Ser Leu Val Ala Ile Lys Gly Asn
        1060                1065                1070

Gln Glu Ser Pro Lys Ala Thr Gly Val Phe Thr Thr Leu Gln Pro Gly
        1075                1080                1085

Ser Ser Ile Pro Pro Tyr Asn Thr Glu Val Thr Glu Thr Thr Ile Val
        1090                1095                1100

Ile Thr Trp Thr Pro Ala Pro Arg Ile Gly Phe Lys Leu Gly Val Arg
1105                1110                1115                1120

Pro Ser Gln Gly Gly Glu Ala Pro Arg Glu Val Thr Ser Asp Ser Gly
                1125                1130                1135

Ser Ile Val Val Ser Gly Leu Thr Pro Gly Val Glu Tyr Val Tyr Thr
                1140                1145                1150

Ile Gln Val Leu Arg Asp Gly Gln Glu Arg Asp Ala Pro Ile Val Asn
        1155                1160                1165

Lys Val Val Thr Pro Leu Ser Pro Pro Thr Asn Leu His Leu Glu Ala
        1170                1175                1180

Asn Pro Asp Thr Gly Val Leu Thr Val Ser Trp Glu Arg Ser Thr Thr
1185                1190                1195                1200

Pro Asp Ile Thr Gly Tyr Arg Ile Thr Thr Thr Pro Thr Asn Gly Gln
                1205                1210                1215

Gln Gly Asn Ser Leu Glu Glu Val Val His Ala Asp Gln Ser Ser Cys
                1220                1225                1230

Thr Phe Asp Asn Leu Ser Pro Gly Leu Glu Tyr Asn Val Ser Val Tyr
        1235                1240                1245

Thr Val Lys Asp Asp Lys Glu Ser Val Pro Ile Ser Asp Thr Ile Ile
        1250                1255                1260

Pro Ala Val Pro Pro Thr Asp Leu Arg Phe Thr Asn Ile Gly Pro
1265                1270                1275                1280

Asp Thr Met Arg Val Thr Trp Ala Pro Pro Ser Ile Asp Leu Thr
                1285                1290                1295

Asn Phe Leu Val Arg Tyr Ser Pro Val Lys Asn Glu Glu Asp Val Ala
        1300                1305                1310

Glu Leu Ser Ile Ser Pro Ser Asp Asn Ala Val Val Leu Thr Asn Leu
        1315                1320                1325

Leu Pro Gly Thr Glu Tyr Val Val Ser Val Ser Ser Val Tyr Glu Gln
        1330                1335                1340

His Glu Ser Thr Pro Leu Arg Gly Arg Gln Lys Thr Gly Leu Asp Ser
        1345                1350                1355                1360

Pro Thr Gly Ile Asp Phe Ser Asp Ile Thr Ala Asn Ser Phe Thr Val
                1365                1370                1375

His Trp Ile Ala Pro Arg Ala Thr Ile Thr Gly Tyr Arg Ile Arg His
                1380                1385                1390

His Pro Glu His Phe Ser Gly Arg Pro Arg Glu Asp Arg Val Pro His
        1395                1400                1405

Ser Arg Asn Ser Ile Thr Leu Thr Asn Leu Thr Pro Gly Thr Glu Tyr
```

```
                1410                1415                1420
Val Val Ser Ile Val Ala Leu Asn Gly Arg Glu Glu Ser Pro Leu Leu
1425                1430                1435                1440

Ile Gly Gln Gln Ser Thr Val Ser Asp Val Pro Arg Asp Leu Glu Val
                1445                1450                1455

Val Ala Ala Thr Pro Thr Ser Leu Leu Ile Ser Trp Asp Ala Pro Ala
                1460                1465                1470

Val Thr Val Arg Tyr Tyr Arg Ile Thr Tyr Gly Glu Thr Gly Gly Asn
                1475                1480                1485

Ser Pro Val Gln Glu Phe Thr Val Pro Gly Ser Lys Ser Thr Ala Thr
                1490                1495                1500

Ile Ser Gly Leu Lys Pro Gly Val Asp Tyr Thr Ile Thr Val Tyr Ala
1505                1510                1515                1520

Val Thr Gly Arg Gly Asp Ser Pro Ala Ser Ser Lys Pro Ile Ser Ile
                1525                1530                1535

Asn Tyr Arg Thr Glu Ile Asp Lys Pro Ser Gln Met Gln Val Thr Asp
                1540                1545                1550

Val Gln Asp Asn Ser Ile Ser Val Lys Trp Leu Pro Ser Ser Ser Pro
                1555                1560                1565

Val Thr Gly Tyr Arg Val Thr Thr Thr Pro Lys Asn Gly Pro Gly Pro
                1570                1575                1580

Thr Lys Thr Lys Thr Ala Gly Pro Asp Gln Thr Glu Met Thr Ile Glu
1585                1590                1595                1600

Gly Leu Gln Pro Thr Val Glu Tyr Val Val Ser Val Tyr Ala Gln Asn
                1605                1610                1615

Pro Ser Gly Glu Ser Gln Pro Leu Val Gln Thr Ala Val Thr Thr Ile
                1620                1625                1630

Pro Ala Pro Thr Asp Leu Lys Phe Thr Gln Val Thr Pro Thr Ser Leu
                1635                1640                1645

Ser Ala Gln Trp Thr Pro Pro Asn Val Gln Leu Thr Gly Tyr Arg Val
                1650                1655                1660

Arg Val Thr Pro Lys Glu Lys Thr Gly Pro Met Lys Glu Ile Asn Leu
1665                1670                1675                1680

Ala Pro Asp Ser Ser Ser Val Val Val Ser Gly Leu Met Val Ala Thr
                1685                1690                1695

Lys Tyr Glu Val Ser Val Tyr Ala Leu Lys Asp Thr Leu Thr Ser Arg
                1700                1705                1710

Pro Ala Gln Gly Val Val Thr Thr Leu Glu Asn Val Ser Pro Pro Arg
                1715                1720                1725

Arg Ala Arg Val Thr Asp Ala Thr Glu Thr Thr Ile Thr Ile Ser Trp
                1730                1735                1740

Arg Thr Lys Thr Glu Thr Ile Thr Gly Phe Gln Val Asp Ala Val Pro
1745                1750                1755                1760

Ala Asn Gly Gln Thr Pro Ile Gln Arg Thr Ile Lys Pro Asp Val Arg
                1765                1770                1775

Ser Tyr Thr Ile Thr Gly Leu Gln Pro Gly Thr Asp Tyr Lys Ile Tyr
                1780                1785                1790

Leu Tyr Thr Leu Asn Asp Asn Ala Arg Ser Ser Pro Val Val Ile Asp
                1795                1800                1805

Ala Ser Thr Ala Ile Asp Ala Pro Ser Asn Leu Arg Phe Leu Ala Thr
                1810                1815                1820

Thr Pro Asn Ser Leu Leu Val Ser Trp Gln Pro Pro Arg Ala Arg Ile
1825                1830                1835                1840
```

```
Thr Gly Tyr Ile Ile Lys Tyr Glu Lys Pro Gly Ser Pro Pro Arg Glu
            1845                1850                1855
Val Val Pro Arg Pro Arg Pro Gly Val Thr Glu Ala Thr Ile Thr Gly
        1860                1865                1870
Leu Glu Pro Gly Thr Glu Tyr Thr Ile Tyr Val Ile Ala Leu Lys Asn
    1875                1880                1885
Asn Gln Lys Ser Glu Pro Leu Ile Gly Arg Lys Lys Thr Gly Gln Glu
1890                1895                1900
Ala Leu Ser Gln Thr Thr Ile Ser Trp Ala Pro Phe Gln Asp Thr Ser
1905                1910                1915                1920
Glu Tyr Ile Ile Ser Cys His Pro Val Gly Thr Asp Glu Glu Pro Leu
            1925                1930                1935
Gln Phe Arg Val Pro Gly Thr Ser Thr Ser Ala Thr Leu Thr Gly Leu
        1940                1945                1950
Thr Arg Gly Ala Thr Tyr Asn Ile Ile Val Glu Ala Leu Lys Asp Gln
    1955                1960                1965
Gln Arg His Lys Val Arg Glu Glu Val Val Thr Val Gly Asn Ser Val
    1970                1975                1980
Asn Glu Gly Leu Asn Gln Pro Thr Asp Asp Ser Cys Phe Asp Pro Tyr
1985                1990                1995                2000
Thr Val Ser His Tyr Ala Val Gly Asp Glu Trp Glu Arg Met Ser Glu
            2005                2010                2015
Ser Gly Phe Lys Leu Leu Cys Gln Cys Leu Gly Phe Gly Ser Gly His
        2020                2025                2030
Phe Arg Cys Asp Ser Ser Arg Trp Cys His Asp Asn Gly Val Asn Tyr
    2035                2040                2045
Lys Ile Gly Glu Lys Trp Asp Arg Gln Gly Glu Asn Gly Gln Met Met
    2050                2055                2060
Ser Cys Thr Cys Leu Gly Asn Gly Lys Gly Glu Phe Lys Cys Asp Pro
2065                2070                2075                2080
His Glu Ala Thr Cys Tyr Asp Asp Gly Lys Thr Tyr His Val Gly Glu
            2085                2090                2095
Gln Trp Gln Lys Glu Tyr Leu Gly Ala Ile Cys Ser Cys Thr Cys Phe
        2100                2105                2110
Gly Gly Gln Arg Gly Trp Arg Cys Asp Asn Cys Arg Arg Pro Gly Gly
    2115                2120                2125
Glu Pro Ser Pro Glu Gly Thr Thr Gly Gln Ser Tyr Asn Gln Tyr Ser
    2130                2135                2140
Gln Arg Tyr His Gln Arg Thr Asn Thr Asn Val Asn Cys Pro Ile Glu
2145                2150                2155                2160
Cys Phe Met Pro Leu Asp Val Gln Ala Asp Arg Glu Asp Ser Arg Glu
            2165                2170                2175

<210> SEQ ID NO 26
<211> LENGTH: 2402
<212> TYPE: DNA
<213> ORGANISM: Homo Sapiens
<220> FEATURE:
<223> OTHER INFORMATION: Oncofetal Fibronectin variant 7
<300> PUBLICATION INFORMATION:
<308> DATABASE ACCESSION NUMBER: GenBank NM 054034
<309> DATABASE ENTRY DATE: 2005-06-10

<400> SEQUENCE: 26
gcccgcgccg gctgtgctgc acagggggag gagagggaac cccaggcgcg agcgggaaga      60
ggggacctgc agccacaact tctctggtcc tctgcatccc ttctgtccct ccacccgtcc     120
```

```
ccttccccac cctctggccc ccaccttctt ggaggcgaca accccggga ggcattagaa      180
gggattttc ccgcaggttg cgaagggaag caaacttggt ggcaacttgc ctcccggtgc      240
gggcgtctct cccccaccgt ctcaacatgc ttaggggtcc ggggcccggg ctgctgctgc     300
tggccgtcca gtgcctgggg acagcggtgc cctccacggg agcctcgaag agcaagaggc     360
aggctcagca aatggttcag ccccagtccc cggtggctgt cagtcaaagc aagcccggtt     420
gttatgacaa tggaaaacac tatcagataa atcaacagtg ggagcggacc tacctaggca    480
atgcgttggt ttgtacttgt tatggaggaa gccgaggttt taactgcgag agtaaacctg     540
aagctgaaga gacttgcttt gacaagtaca ctgggaacac ttaccgagtg ggtgacactt    600
atgagcgtcc taaagactcc atgatctggg actgtacctg catcggggct gggcgaggga     660
gaataagctg taccatcgca aaccgctgcc atgaagggg tcagtcctac aagattggtg     720
acacctggag gagaccacat gagactggtg gttacatgtt agagtgtgtg tgtcttggta    780
atggaaaagg agaatggacc tgcaagccca tagctgagaa gtgttttgat catgctgctg    840
ggacttccta tgtggtcgga gaaacgtggg agaagcccta ccaaggctgg atgatggtag    900
attgtacttg cctgggagaa ggcagcgac gcatcacttg cacttctaga aatagatgca    960
acgatcagga cacaaggaca tcctatagaa ttggagacac ctggagcaag aaggataatc    1020
gaggaaacct gctccagtgc atctgcacag gcaacggccg aggagagtgg aagtgtgaga   1080
ggcacacctc tgtgcagacc acatcgagcg gatctggccc cttcaccgat gttcgtgcag    1140
ctgtttacca accgcagcct cacccccagc ctcctcccta tggccactgt gtcacagaca    1200
gtggtgtggt ctactctgtg gggatgcagt ggctgaagac acaaggaaat aagcaaatgc    1260
tttgcacgtg cctgggcaac ggagtcagct gccaagagac agctgtaacc cagacttacg    1320
gtggcaactc aaatggagag ccatgtgtct taccattcac ctacaatggc aggacgttct   1380
actcctgcac cacagaaggg cgacaggacg gacatctttg gtgcagcaca acttcgaatt    1440
atgagcagga ccagaaatac tctttctgca cagaccacac tgtttttggtt cagactcgag    1500
gaggaaattc caatggtgcc ttgtgccact tcccttcct atacaacaac cacaattaca    1560
ctgattgcac ttctgagggc agaagagaca acatgaagtg gtgtgggacc acacagaact   1620
atgatgccga ccagaagttt gggttctgcc ccatggctgc ccacgaggaa atctgcacaa    1680
ccaatgaagg ggtcatgtac cgcattggag atcagtggga taagcagcat gacatggggtc    1740
acatgatgag gtgcacgtgt gttgggaatg gtcgtgggga atggacatgc attgcctact   1800
cgcagcttcg agatcagtgc attgttgatg acatcactta caatgtgaac gacacattcc    1860
acaagcgtca tgaagagggg cacatgctga actgtacatg cttcggtcag ggtcggggca    1920
ggtgaagtg tgatcccgtc gaccaatgcc aggattcaga gactgggacg tttatcaaa     1980
ttggagattc atgggagaag tatgtgcatg gtgtcagata ccagtgctac tgctatggcc    2040
gtggcattgg ggagtggcat tgccaacctt tacagaccta tccaagctca gtggtcctg    2100
tcgaagtatt tatcactgag actccgagtc agcccaactc ccacccatc cagtggaatg    2160
caccacagcc atctcacatt tccaagtaca ttctcaggtg gagacctgtg agtatcccac    2220
ccagaaacct tggatactga gtctcctaat cttatcaatt ctgatggttt cttttttcc    2280
cagcttttga gccaacaact ctgattaact attcctatag catttactat atttgtttag    2340
tgaacaaaca atatgtggtc aattaaattg acttgtagac tgaaaaaaaa aaaaaaaaaa    2400
aa                                                                   2402
```

<210> SEQ ID NO 27

```
<211> LENGTH: 657
<212> TYPE: PRT
<213> ORGANISM: Homo Sapiens
<300> PUBLICATION INFORMATION:
<308> DATABASE ACCESSION NUMBER: GenBank NM 054034
<309> DATABASE ENTRY DATE: 2005-06-10

<400> SEQUENCE: 27

Met Leu Arg Gly Pro Gly Pro Gly Leu Leu Leu Leu Ala Val Gln Cys
 1               5                  10                  15

Leu Gly Thr Ala Val Pro Ser Thr Gly Ala Ser Lys Ser Lys Arg Gln
            20                  25                  30

Ala Gln Gln Met Val Gln Pro Gln Ser Pro Val Ala Val Ser Gln Ser
        35                  40                  45

Lys Pro Gly Cys Tyr Asp Asn Gly Lys His Tyr Gln Ile Asn Gln Gln
    50                  55                  60

Trp Glu Arg Thr Tyr Leu Gly Asn Ala Leu Val Cys Thr Cys Tyr Gly
65                  70                  75                  80

Gly Ser Arg Gly Phe Asn Cys Glu Ser Lys Pro Glu Ala Glu Glu Thr
                85                  90                  95

Cys Phe Asp Lys Tyr Thr Gly Asn Thr Tyr Arg Val Gly Asp Thr Tyr
            100                 105                 110

Glu Arg Pro Lys Asp Ser Met Ile Trp Asp Cys Thr Cys Ile Gly Ala
        115                 120                 125

Gly Arg Gly Arg Ile Ser Cys Thr Ile Ala Asn Arg Cys His Glu Gly
    130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                165                 170                 175

Trp Thr Cys Lys Pro Ile Ala Glu Lys Cys Phe Asp His Ala Ala Gly
            180                 185                 190

Thr Ser Tyr Val Val Gly Glu Thr Trp Glu Lys Pro Tyr Gln Gly Trp
        195                 200                 205

Met Met Val Asp Cys Thr Cys Leu Gly Glu Gly Ser Gly Arg Ile Thr
    210                 215                 220

Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu
                245                 250                 255

Gln Cys Ile Cys Thr Gly Asn Gly Arg Gly Glu Trp Lys Cys Glu Arg
            260                 265                 270

His Thr Ser Val Gln Thr Thr Ser Ser Gly Ser Gly Pro Phe Thr Asp
        275                 280                 285

Val Arg Ala Ala Val Tyr Gln Pro Gln Pro His Pro Gln Pro Pro Pro
    290                 295                 300

Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
                325                 330                 335

Gly Asn Gly Val Ser Cys Gln Glu Thr Ala Val Thr Gln Thr Tyr Gly
            340                 345                 350

Gly Asn Ser Asn Gly Glu Pro Cys Val Leu Pro Phe Thr Tyr Asn Gly
        355                 360                 365

Arg Thr Phe Tyr Ser Cys Thr Thr Glu Gly Arg Gln Asp Gly His Leu
    370                 375                 380
```

```
Trp Cys Ser Thr Thr Ser Asn Tyr Glu Gln Asp Gln Lys Tyr Ser Phe
385                 390                 395                 400

Cys Thr Asp His Thr Val Leu Val Gln Thr Arg Gly Gly Asn Ser Asn
            405                 410                 415

Gly Ala Leu Cys His Phe Pro Phe Leu Tyr Asn Asn His Asn Tyr Thr
            420                 425                 430

Asp Cys Thr Ser Glu Gly Arg Arg Asp Asn Met Lys Trp Cys Gly Thr
            435                 440                 445

Thr Gln Asn Tyr Asp Ala Asp Gln Lys Phe Gly Phe Cys Pro Met Ala
            450                 455                 460

Ala His Glu Glu Ile Cys Thr Thr Asn Glu Gly Val Met Tyr Arg Ile
465                 470                 475                 480

Gly Asp Gln Trp Asp Lys Gln His Asp Met Gly His Met Met Arg Cys
            485                 490                 495

Thr Cys Val Gly Asn Gly Arg Gly Glu Trp Thr Cys Ile Ala Tyr Ser
            500                 505                 510

Gln Leu Arg Asp Gln Cys Ile Val Asp Asp Ile Thr Tyr Asn Val Asn
            515                 520                 525

Asp Thr Phe His Lys Arg His Glu Glu Gly His Met Leu Asn Cys Thr
            530                 535                 540

Cys Phe Gly Gln Gly Arg Gly Arg Trp Lys Cys Asp Pro Val Asp Gln
545                 550                 555                 560

Cys Gln Asp Ser Glu Thr Gly Thr Phe Tyr Gln Ile Gly Asp Ser Trp
            565                 570                 575

Glu Lys Tyr Val His Gly Val Arg Tyr Gln Cys Tyr Cys Tyr Gly Arg
            580                 585                 590

Gly Ile Gly Glu Trp His Cys Gln Pro Leu Gln Thr Tyr Pro Ser Ser
            595                 600                 605

Ser Gly Pro Val Glu Val Phe Ile Thr Glu Thr Pro Ser Gln Pro Asn
            610                 615                 620

Ser His Pro Ile Gln Trp Asn Ala Pro Gln Pro Ser His Ile Ser Lys
625                 630                 635                 640

Tyr Ile Leu Arg Trp Arg Pro Val Ser Ile Pro Arg Asn Leu Gly
            645                 650                 655

Tyr

<210> SEQ ID NO 28
<211> LENGTH: 360
<212> TYPE: DNA
<213> ORGANISM: Homo sapiens
<220> FEATURE:
<223> OTHER INFORMATION: Fibronectin IIICS region V120

<400> SEQUENCE: 28
gacgagcttc cccaactggt aaccttcca caccccaatc ttcatggacc agagatcttg      60
gatgttcctt ccacagttca aaagacccct ttcgtcaccc accctgggta tgacactgga     120
aatggtattc agcttcctgg cacttctggt cagcaaccca gtgttgggca acaaatgatc     180
tttgaggaac atggttttag gcggaccaca ccgcccacaa cggccacccc cataaggcat     240
aggccaagac catacccgcc gaatgtaggt gaggaaatcc aaattggtca cattcccagg     300
gaagatgtag actatcacct gtacccacac ggtccgggac tcaatccaaa tgcctctaca     360

<210> SEQ ID NO 29
<211> LENGTH: 120
<212> TYPE: PRT
```

```
<213> ORGANISM: Homo sapiens

<400> SEQUENCE: 29

Asp Glu Leu Pro Gln Leu Val Thr Leu Pro His Pro Asn Leu His Gly
1               5                   10                  15

Pro Glu Ile Leu Asp Val Pro Ser Thr Val Gln Lys Thr Pro Phe Val
            20                  25                  30

Thr His Pro Gly Tyr Asp Thr Gly Asn Gly Ile Gln Leu Pro Gly Thr
        35                  40                  45

Ser Gly Gln Gln Pro Ser Val Gly Gln Gln Met Ile Phe Glu Glu His
    50                  55                  60

Gly Phe Arg Arg Thr Thr Pro Pro Thr Thr Ala Thr Pro Ile Arg His
65                  70                  75                  80

Arg Pro Arg Pro Tyr Pro Pro Asn Val Gly Glu Glu Ile Gln Ile Gly
                85                  90                  95

His Ile Pro Arg Glu Asp Val Asp Tyr His Leu Tyr Pro His Gly Pro
            100                 105                 110

Gly Leu Asn Pro Asn Ala Ser Thr
            115                 120

<210> SEQ ID NO 30
<211> LENGTH: 285
<212> TYPE: DNA
<213> ORGANISM: Homo sapiens
<220> FEATURE:
<223> OTHER INFORMATION: Fibronectin IIICS region V95

<400> SEQUENCE: 30
acagttcaaa agacccctt cgtcacccac cctgggtatg acactggaaa tggtattcag      60
cttcctggca cttctggtca gcaacccagt gttgggcaac aaatgatctt tgaggaacat    120
ggttttaggc ggaccacacc gcccacaacg gccacccca taaggcatag gccaagacca    180
tacccgccga atgtaggtga ggaaatccaa attggtcaca ttcccaggga agatgtagac    240
tatcacctgt acccacacgg tccgggactc aatccaaatg cctct                   285

<210> SEQ ID NO 31
<211> LENGTH: 95
<212> TYPE: PRT
<213> ORGANISM: Homo sapiens

<400> SEQUENCE: 31

Thr Val Gln Lys Thr Pro Phe Val Thr His Pro Gly Tyr Asp Thr Gly
1               5                   10                  15

Asn Gly Ile Gln Leu Pro Gly Thr Ser Gly Gln Gln Pro Ser Val Gly
            20                  25                  30

Gln Gln Met Ile Phe Glu Glu His Gly Phe Arg Arg Thr Thr Pro Pro
        35                  40                  45

Thr Thr Ala Thr Pro Ile Arg His Arg Pro Arg Pro Tyr Pro Pro Asn
    50                  55                  60

Val Gly Glu Glu Ile Gln Ile Gly His Ile Pro Arg Glu Asp Val Asp
65                  70                  75                  80

Tyr His Leu Tyr Pro His Gly Pro Gly Leu Asn Pro Asn Ala Ser
                85                  90                  95

<210> SEQ ID NO 32
<211> LENGTH: 267
<212> TYPE: DNA
<213> ORGANISM: Homo sapiens
<220> FEATURE:
```

<223> OTHER INFORMATION: Fibronectin IIICS region V89

<400> SEQUENCE: 32

```
gacgagcttc cccaactggt aacccttcca caccccaatc ttcatggacc agagatcttg    60
gatgttcctt ccacagttca aagacccct ttcgtcaccc accctgggta tgacactgga   120
aatggtattc agcttcctgg cacttctggt cagcaaccca gtgttgggca acaaatgatc   180
tttgaggaac atggttttag cggaccaca ccgcccacaa cggccacccc cataaggcat   240
aggccaagac catacccgcc gaatgta                                      267
```

<210> SEQ ID NO 33
<211> LENGTH: 89
<212> TYPE: PRT
<213> ORGANISM: Homo sapiens

<400> SEQUENCE: 33

```
Asp Glu Leu Pro Gln Leu Val Thr Leu Pro His Pro Asn Leu His Gly
  1               5                  10                  15
Pro Glu Ile Leu Asp Val Pro Ser Thr Val Gln Lys Thr Pro Phe Val
                 20                  25                  30
Thr His Pro Gly Tyr Asp Thr Gly Asn Gly Ile Gln Leu Pro Gly Thr
             35                  40                  45
Ser Gly Gln Gln Pro Ser Val Gly Gln Gln Met Ile Phe Glu Glu His
         50                  55                  60
Gly Phe Arg Arg Thr Thr Pro Pro Thr Thr Ala Thr Pro Ile Arg His
 65                  70                  75                  80
Arg Pro Arg Pro Tyr Pro Pro Asn Val
                 85
```

<210> SEQ ID NO 34
<211> LENGTH: 192
<212> TYPE: DNA
<213> ORGANISM: Homo sapiens
<220> FEATURE:
<223> OTHER INFORMATION: Fibronectin IIICS region V64

<400> SEQUENCE: 34

```
acagttcaaa agacccctttt cgtcacccac cctgggtatg acactggaaa tggtattcag    60
cttcctggca cttctggtca gcaaccagt gttgggcaac aaatgatctt tgaggaacat   120
ggttttaggc ggaccacacc gcccacaacg ccaccccca taaggcatag ccaagacca   180
tacccgccga at                                                      192
```

<210> SEQ ID NO 35
<211> LENGTH: 64
<212> TYPE: PRT
<213> ORGANISM: Homo sapiens

<400> SEQUENCE: 35

```
Thr Val Gln Lys Thr Pro Phe Val Thr His Pro Gly Tyr Asp Thr Gly
  1               5                  10                  15
Asn Gly Ile Gln Leu Pro Gly Thr Ser Gly Gln Gln Pro Ser Val Gly
                 20                  25                  30
Gln Gln Met Ile Phe Glu Glu His Gly Phe Arg Arg Thr Thr Pro Pro
             35                  40                  45
Thr Thr Ala Thr Pro Ile Arg His Arg Pro Arg Pro Tyr Pro Pro Asn
         50                  55                  60
```

<210> SEQ ID NO 36

```
<211> LENGTH: 6
<212> TYPE: PRT
<213> ORGANISM: Homo sapiens

<400> SEQUENCE: 36

Gly Gly Trp Ser His Trp
 1               5

<210> SEQ ID NO 37
<211> LENGTH: 143947
<212> TYPE: DNA
<213> ORGANISM: Homo sapiens
<220> FEATURE:
<223> OTHER INFORMATION: Fibronectin
<300> PUBLICATION INFORMATION:
<308> DATABASE ACCESSION NUMBER: GenBank AC012462
<309> DATABASE ENTRY DATE: 2005-04-05

<400> SEQUENCE: 37
```

| | | | |
|---|---|---|---|
| gaattctcct tttccgttcc caagacatgt gcagctcatc atctggccat tttctccctg | 60 |
| acggtcccac ttctctccaa tcttgtagtt cacaccattg tcatggcacc atcctgtagg | 120 |
| ggtggggaaa gtcaggacca aaaagttatt tgtatattct gactcacaag acagtaggtg | 180 |
| aactgggacg tgtcacaggg tcttcagaac catgatctgg aaaaatagca agttaaagat | 240 |
| aaaaacccct ataatgggcc atttatttta tttatttatt tacttttttat tttttttttt | 300 |
| tttttttgaga caaagtctttt ctctgtcgcc cagactggag tgaagtggtg caatctcggc | 360 |
| tcactgtaac ctccatctcc tgggttcatg cagttatcct gcctcagcct cctgagtagc | 420 |
| tgggattaca ggcactcccc acagtgctat tttttttttt tttttttttt ttgtattttt | 480 |
| tgtagagatg gggttttacc atgttgggta ggctggtctc aaactcgtga gctcaggtga | 540 |
| tccacccgcc tcagcctcca aaagtgctgg gattacaggt gtgagccacc acacctggcc | 600 |
| aatgggccat ttctttggtt gaattttaaa atattatttt ttatcattta ccattttcta | 660 |
| gggcatttta agacccaatt tattctgcca caatcatgtc atcagaatag tcaaatgaaa | 720 |
| tgactttcat ttgaattctc actattaaga tttaaaattg tggaaaacta agtgggatt | 780 |
| ggagtagact gttaggaata gatcctagat gaaaaatcac ttttggattt gcagaaaccc | 840 |
| tggatacaaa gtagttcaat taaccataaa acaaggatca gctgatctct acacgccacc | 900 |
| acctgtttca tgtacatggg aagagtaaaa atgaacccg ataaaataa acaaaagca | 960 |
| aacaaaatgc taaatcattg gttattatcc acatcaaata agtctggttc tgtggaatat | 1020 |
| ctaaaagtca cagtttttatg cctttaacta ctatacataa gggatgactt tttaacctcc | 1080 |
| agggcttata caacaaaaca cacctcagaa gcttatataa caatatacta ctttttccat | 1140 |
| tttatcaaca attcagcctg ccttaagcta caaagtaaaa taattagaca actgtgtatat | 1200 |
| caaaacaaag attatgtaag ttgagccaaa gagtcacata aatgaacttg acatccccgc | 1260 |
| tcccacaatt gcacctaagt gctcaaacag gtaataaaca tacaaactta aacgtagttc | 1320 |
| gatttcagga gttaaaaacc atctacttga agtcaaatat taaaatttcc agctcctaaa | 1380 |
| cagcatgtga tgttttagt gttttttcatt ttcagatggt caaacatgga agtctatatt | 1440 |
| gaaaacactg gctggctttt acaacttcag tctggattaa atgatttcaa gtatacaagt | 1500 |
| taagtaaaat acttttgaaaa tctcttttac caagtcttat attctaattc cacaggatat | 1560 |
| gatttctgta tgtctatagg aggcttattt ataggcataa cggtcaacac ctataaaaat | 1620 |
| gaaccaattg tcaataatca tcacatctcc taaacacaaa gaataaatga aggtttata | 1680 |
| aattctaatc ctaatctcaa agcataatag atatttccta ggcacatttt aacttaaaaa | 1740 |

```
atttgaaaat taaaacgtat tagaatttga aaatcaaaca tttatcaatt caagttgatt    1800
tttaatgatc taaaagcaga ttatctgttt tttctttcat atttctagca acgttcaagc    1860
tacctgggct atgtgtgtga cgcaaaagtg tgtgcatggg tactatgata tgtgcatgtt    1920
tggtttatgt tgaaggaggc tgttttgag tctaaatgtt cacctctgat ctcattcaac     1980
actgaagatt aaaagagatt tgaggttttt ctgtgtctct aatactctta aatagacctg    2040
gttccaaaag tctttatcca tttgttttca cagaaaattt caaaaatcaa attagcacca    2100
taatcttatg tgtaattaat agttgtattg gcatacaacc cttgaaatga agcaatgtcc    2160
aacaagtaaa atttcccatc atttttctat gatgcaaaat attacttcga gtcaaacagt    2220
attctcttgt ttgcttcatg tttggaagaa cctgtgtctt ccaaacatgc ttccttggca    2280
catgagtgca tgcatggaac ttgaggagac aaacacggaa gtggatggac aaagcaacta    2340
ctcactagat gaatcacatc tgaaatgacc acttccaaag cctaagcact ggcacaacag    2400
tttaaagcct gattcagaca ttcgttccca ctcatctcca acggcataat gggaaactgt    2460
gtagggtca aagcacgagt catccgtagg ttggttcaag ccttcgttga ctatgaagaa     2520
aaggaagaaa aagcaaaaag agacatctta ttaatcgatt tggaccataa gaagaaaatc    2580
gaatgactgt atacaatgac ttaatctaaa acaagaattc caggaggatt aagaggcatt    2640
catctgttct atcaaggcat taactgctct aaaaaaccat ggttagatgt gacacctgtc    2700
acaggcaccc gacaggaagc ccatctttta ttttcccctt gcttctaaga taattgccat    2760
ttctgttgaa actacttcat agaacatgga acagatcttg aggcaattga agctagtgga    2820
gaactttagt gggatgcaaa gactaatgat gcctctccat tggtacctga gtgaccttgg    2880
gccagctatt taataccact ctgccttgct tccctcatct gcaatactag cgtaataata    2940
aaaatatcta tacctcctgg ggaatcttgt gaagattata taaggccatg aattcaaaac    3000
attgaccctt ttccaagact tagaaaatgt tcactaaata aagaataatt attaaaggct    3060
gtcttttgct tataatgcaa aagtcttagc attttaatat accattataa tgtaattttc    3120
acttttatta ttgtaatttt tgcataatag tgcagaaagc ctagattttg gacattgtta    3180
ttatagtggt gagacagctt tatcagtgag gtcaactgtt ccaaataaga aaatgccctt    3240
ggaatataga tgatttagga ataagtaagg gagtctcttc atgttaccta agatcttatc    3300
tctttatgat ttgaaaagc ttattttaaa aaatctatg caaacaaagc atgcttcaaa      3360
ttattcccta aaaattagat aaactaattt gacttaaaat cccactgtgt atttttcttt    3420
ttacagtgca aaactcaaaa gctcaaaagc agtagatatt tgaggtgcct aattttaaa     3480
aggtgtcacc cttaaagaaa atagcgtttt ggagaactgg taagtctgag acgtctcaaa    3540
gctgggagaa cctggttaga atgtagaata ctgctgctgg gaataaggag tttaaaagaa    3600
aaatggaagg aacttaaatt gttactaggg gtttctatac tcaaaagagc caggagttca    3660
aattccatcc taactaaagt taaagagatg gaatctttaa aaaaaaaaaa aaaaaatgac    3720
ttagaaaagc acaaagacct ttttgctctt gaaaattctg ttcacgtggc attctactag    3780
taaaaccaca aaaggcaaag ataagcatta ctgtggatat gtaatacaac aaacacaaaa    3840
taatctcctc ccaacctctc tccagccaaa tgctcaactg cttaattcac aggaatttat    3900
acatgtaaag tagcacagtc ttctatcaga tgagggaagg ggctaaaatt aaacaactgg    3960
ccttaggaat aaaatctgtc acttggcata gacaggactt agcactctct gttggtgtgg    4020
agtagagaac tctcctgttg gaagattggg gattcacggt tttgattatc ccctatctca    4080
tgtgccttgg tgaattttca gctgctgcaa attgagcagc caggtggcac gctattgatt    4140
```

```
taaaaggatt tcccaggtgc tacaaagaag agttaatgat cttttaacct ctatagaagc    4200
ttttaacctg tatagtcaga aaaaaaaatg gaaataacat tggaaaaaaa tggaaataac    4260
attggaataa cattctctgc agacagaaat gcacaatgtt ggtagcattt tatatcagga    4320
gcaaaagcca actgtcccca tgtctgcaga aggggtattt tctttatagg taatcgtttc    4380
agtatttaat cactcaagag gacagcagca tggtgagatg gagagggtct gggaaaagac    4440
atcaggaaac ctgtgcccta tcaactcaga gatactcaga agtaaggact cagagtgttg    4500
tactaaataa tatttgaaat cccttccaga tctataatca tatcaccatt tgagagtctg    4560
tcaattacgt atgcattttg tgaagacaac aggatatggc aggaggtggg ggagagatta    4620
atttaatata aagttgctca tttatttcat gttgatgtgt tgcattaaat cccaaagata    4680
aaaagacaat ggcaacaaag gtacagtcaa cagaaaagcc catctctggt gtacagcaga    4740
ggggagcctg tgtctaaata gtacgtgttt acataccaga gttgcccacg gtaacaacct    4800
cttcccgaac cttatgcctc tgctggtctt tcagtgcctc cactatgacg ttgtaggtgg    4860
cacctctggt gaggcctgtc agagtggcac tggtagaagt tccaggaacc ctgaactgca    4920
attatcggta catccaaagc agagagaaag cattatagtg aggaatgaca cgggctctcc    4980
tcttaccaat aaccctcact gtttaaacaa agcaaaggaa gacaaaaaac aaaaaacaaa    5040
aaaaaaaaaa agagggaggg tatagtggtc ctaaccagct gaggagagaa atggaacaag    5100 gatagggggcc atcgttcctg ccagattttc ctgccaacaa tctacctacg tgctccgtag    5160
ttaacaggag ccctcgacaa tactagagac ggcctgccat tgatcttgct tcagtcgcag    5220
gtctgcataa gccctctgga agccctggcc atgtttgctt cacataaaac ctggacactg    5280
cgctatatgg gagacacggt catgctcctc caggtgacat ctgacccag tgtggagtcc    5340 ttaaaacagt tgggcaaatc ctcaaactca tgtttctaag ctcataaatt tcctacagtg    5400
ttgtcagttt ttaaattctg ccactttcta aagtaacaa cacaataaaa attgatactg    5460
tcagtgggcc gggtgtagtg ggtggctcat gcttgtagtc ccagcacttt gggaggccaa    5520
ggcgggcgga tcacgaggtc aggagatcga gaccatcctg gccaacatcg tgaaaccccg    5580
tctctactaa aaatacaaaa attagctggg tgcggtggca catgcctgta atcccagcta    5640
tttgggaggc tgaggcagga gaattgcttg aacctgggag gcagaggttg cagtgagccg    5700
agatcacgcc actgcactcc agccagggcc atagagcaag actccatctc ggggaaaaaa    5760
aaaaatggat actgtcaaca caaattaaat aatatacgtt ttagagaatc aatcacttat    5820
cagctgctat gcacagcttc gcctgttttt tttttttcttt agatatgttg tagatagtgg    5880
ggttcttcaa ggacaaatcg taaaggtagt gttttagact tctgcacaca aatggaaatt    5940
caggtagaat atctttcttt tctagaatca tctatcttac tcaaaaagga acctcaaatg    6000
tgtgagaata agagaaatag tttcattttc tctatgaaat aaaagctagt gactctctgg    6060
tatgtcctcc aaagtagagc catattggga tttaaaaaaa aaaaaaagca gggcttaaat    6120
gtgccatctt ctaagaggtt ctaaagtgg agccactttt ttttttttt tttttcaag    6180 agacgaggtt tcaccatgtt ggccaggctg gtcttgaact cctaacctca aatgatccac    6240
ctgcctcggc ctcccaaagt gctgggatta caggcgtgag ccatcacacc cggccatgaa    6300 gccactttt attcgagggc tggtcacttc agttacctaa cttattcctt tctgtgctgc    6360
cccatgagaa gtgaagagaa caattaatta cctgtaaggg ttcttcatca gtgccaacag    6420
gatgacatga aatgatgtac tcagaagtgt cctggaatgg ggcccatgag atggttgtct    6480
gagagagagc ttcttgtcct gtagaggcat ttggattgag tcccggaccg tgtgggtaca    6540
```

-continued

```
ggtgatagtc tacatcttcc ctggggatgt gaccaatttg gatttcctca cctacattcg    6600
gcgggtatgg tcttggccta tgccttatgg gggtggccgt tgtgggcggt gtggtccgcc    6660
taaaaccatg ttcctcaaag atcatttgtt gcccaacact gggttgctga ccagaagtgc    6720
caggaagctg aataccattt ccagtgtcat acccagggtg ggtgacgaaa ggggtctttt    6780
gaactgtgga aggaacatcc aagatctctg gtccatgaag attggggtgt ggaagggtta    6840
ccagttgggg aagctcgtct agccgagaga ggttagagcc aaaaaagcaa agcgcattaa    6900
gctccaggaa gtagcagcaa tgataataat cgattcaggc aacaatgact gttcatcaat    6960
ttgataaaag ccaccagaaa atgagcagtt ctgagatcac aaaacacttt ttccagaaag    7020
aaatctttag dattttctc aaaggtttct ttatagttta gaaagaaaaa agtgttagta    7080
tgaatttatc atacacacag ctttaaaccg ctgagccccg tagaagctgc ctctgctcaa    7140
attagaccta atggaactga aatgtgcagt cttttctcttt ctctcttctt tttttaaatt    7200
tgagaagcaa gttgtaggaa gtagaatcca gactaatcat atcagtgtca taagtatgag    7260
aattacagag gtttggctca acagttttc atggtttgaa atggtaaaaa tagataaaac    7320
acacatgttc atttttgaaa ttttcctata tcaggaatac acatttctt gaaattaact    7380 gaaactggat gcaaaagtaa gacattattt agctctaagt tgtagaaacc aaataaagat    7440
aaatgtgaga ggtttctctc cctcctttaa aaaggaaac attttaaaat tcaacgaaag    7500
gtataaaaga agagcaatga tagctcttct tttacatttt aacatcttgt ttgaatttt    7560 aaaaggtgaa taacaaggct ttatattgag tggctgtagt aaagaaaaaa aataaaacca    7620
aactctgcag tgcatgttaa attatttctc ctattaaaga atacaatata tacactatgc    7680
tgttagataa aaaaaatcac aagaaatgca tcaaaacatg gagaaccttt tcatattgca    7740
agattgctca tttgttatta gttttgtcct atctttctcc ttgttacctg caagatactc    7800
ttacctgtct ttttccttcc aatcaggggc tcgctcttct gattattctt cagggcaatg    7860
acataaattg tatattcggt tcccggttcc aggcctgaag ggagaataga accatcacat    7920
tatgtcaatg ggctcagcta gtcaagtgga agtcggtctc accagcagac gctactggga    7980
gcaggcactt cctctccagc tggctgttgg cctcttgaag gtaaaatcga cttcacttt    8040 cctccataaa cacccaaata tcctgcatat aaagtccgca tcgcaaacta attatcttac    8100
tatcatatct gacgcctgaa tagacatttt ttggctaact tttccagggt attcttttt    8160 tttttttttt tttttttttt gagatggagt ctggctctgt cacccaggct ggagtgcagt    8220
ggtgctatct cggctcactg caagctccgc ttcccaggtt cagccattct cctgcctcag    8280
ccacccgagt agctgggact acaggcaccc atcaccacgc ctggctaatt ttgttttgt    8340 attttagta gagatggggt ttcaccgtgt tagccaggat ggtctcgatc tcctgacctt    8400
gtgatctgcc tgcctcggcc tcccaaagtg ctgggattac aggcgtgagc caccgcgcct    8460
ggcctttcca gggtattctt ttaacgtggt cttatttgcc tttttgaatt taagaaaatc    8520
tatcagcatc ataccaccc actggaatat aaatttgaaa gagagtcctg cagattatat    8580
acatgaatct acttaggcct aataaccaag cagtcctcag tggcagatca atgaaaagtg    8640
aaactaaagg caagtgaagg gtaggagaga ttggccagtg tttgtgcagc ctctgtggga    8700
agtgtctagt tcaattcctc tcatgtctgc ttctattttc ctgttcccc caattctaaa    8760 aagccagtgt ctccttctaa tgtctgtatg ttctgtggga attttaaagt ccaggtgata    8820
ctctatacag actgatatgg tttggctctg tgtctgcatc caaatctcat ctggaattgt    8880
aatccccatg tattgaggag aggaggtgat tggatcatgg ggtggttccc ccaggctgtt    8940
```

```
ctcatgatag tgagttctca caagatctga tagttttgta agtatctgga agttcctcct    9000
gtgtgcttct ctctcctgct gccatgtaag acatgcctgc ttttccttcc accatgattg    9060
tacattttct gaggcctccc cagccatgcg gaactgtgag tcaattaaac ctctttatag    9120
cagtatgaaa acagactaat acagatagtt taaatatttc atctcttggg caaaaataat    9180
actagaggct tatagtcttt cccaccaagg tagacaactc ttattcccca ttccaggcat    9240
tcttccaatg tgggtggttg ggactgctct gcctcaagac ctatcctgtg atagtggtca    9300
acaaggtcaa tggcaggtgg tgcactggca agtcctgcaa gattgccata tctatagaga    9360
gctgagtgta atgacagaat cacaatcagc tagtatgctt tgaaaaatat ctttctccag    9420
gactgaattg acaggtatct ggcaaacttg cagcgaaagg aaaacatgag tctagtcatg    9480
ccattagtac agtcttgaaa ttgcattttc cttcactcat gccttttggg atgtattagg    9540
ctctaccact cctacacaga gaatgctttt tgaggttatc aggaacagag tttcgcattc    9600
tcatgacaca gtatcaaaga cgctgtggga gtttgctaag gacttcatgt gtcctaggta    9660
gtaagaagga aaatgacagc atggaagcag caataccagt aatagtagcc tctgtgacac    9720
cagggcgggg ccgagggacc acttctctgg gaggagaccc aggcttctca tacttgatga    9780
tgtagccggt aatcctggca cgtggcggct gccatgatac cagcaaggaa ttgggtgtgg    9840
tggccaggaa acgcaggttg gatggtgcat caatggctga agaaaacaa aattaagtct    9900 ctaagaaggc aaataaccaa gaaaattact cccacacttt tctcccgagc cgttctaaac    9960
acacttaaaa gaatctgaga atactgtaaa ccggaaacaa gattctctgg aatctataat   10020
acaaaaatat acgcctcaca tttgttttt gagttcatga aactgattgc atacaagtca   10080
atggcatttc ctcagtagaa ggtatagtta ccagtggagg cgtcgatgac cacaggggag   10140
ctccgagcat tgtcattcaa ggtgtacagg tagatcttgt agtcagtgcc tggttgtaaa   10200
cctgggattt gagaagagat gattttaac agttcttgct ttttactagg agaattctca   10260
agctagcctg caattttct gggttcttct atcatcccat atttatatag actaccaaag   10320
tggtccacat ttgaacagta aagtagagca tgctatggat gttaactgtt aacaagaaac   10380
atatctcgaa agtgaatcac tgatacagac aaggacactg gtaaagtaaa ttctggaatg   10440
caaaaatgct atgttggaag aggccctctt gcagaatggg ggtcagccac ttattgaggt   10500
tttctcttta ccgtaatcag atggtcaata gttgagcctt ggaatcacaa ttttaaaaag   10560
ctaaaaaaga cctcagatat tgaatattct tcggttacaa ttttggcctt tattaagtgg   10620
tattgtttac ttttatatta actatgcttt ttaatgctaa gatctataca tcactgtttt   10680
ttatttcttt tagttttaaa ccttatgtta caatttttta aataagaaag ggcacaatga   10740
tggaagatca aacttgttga ttgacactta cgcaatttcc atgacaaata ttacacaaaa   10800
tcaggcattc aaaggacaaa actatttctg atcatagcat gaaaataacg ttctaaaact   10860
gggttatgat gataacactg aaaataaatt ttatcagtgt cagtcgtaga acagttaata   10920
agcccgttta cattgtgggt atttgttaac aaatgtggtt agtgcaatga gttccctgac   10980
ctgtgatggt gtagcttctg acatctggct tgatggttct ctggattgga gtctggccat   11040
tggctggaac ggcatcaact tggaagccag tgatcgtctc agtcttggtt ctccagctaa   11100
tggtgatggt ggtctcagta gcatctgtca cacgagccct tcttggtggg ctgacatctg   11160
cacaggagca tagctagaga ttagtgcctg cttggctcat ccatgtaaag ttttggtatt   11220
ttaaaacgtt tccttggtat atatcaaatt catccatttc aagaaatata taactagtaa   11280
tgtgtagatt atctcctttg gcattcagag agaaaggtca actgtaatta gaaaatagga   11340
```

```
aaatatctac ctctcagaca ttttattttg aagagctgaa aagctttata gatactacca    11400
gtggttccca gggctggctt tatagtatct acaaatactt caataaatat taaaattatt    11460
aatgtattat aatgtaaaaa tatgtgtggt aggagttaca ataacatggc cagctaacaa    11520
ttttgtgtgt gtgtgtgtgt atgtgtgtgt gagagagaga gagagtgtgt gtgtgtgtgt    11580
gtgtgtgtgt gtgtctaata ttacggcaag tattttgtat tttctctcaa caggtacaat    11640
gccatccctc ttttataaat gataaaactt tgacactttta cctgactttt gaaaaggcat   11700
acatcaaggt attgatataa cagaagacta gaatctaagc ctgatttggt ccaatggtta    11760
ctgtgctgtg ataaattttg gatatttgtc cctgtccaaa tctctgttga gttgtaatct    11820
ccaatgctgg aggtggggcc tggtgagagg tgtttggatc atgggggcag atcccttgtg    11880
gcttggtgcc ctctttatga cagtgagttc tcaagagact gggtcattta aatgtataag    11940
gtcctccccc cccaactctc tctctctctc ggtcttgctt ttgccacagc catgtgatgt    12000
gcctgctccc ccttggcctt ccaccatgag taagcttccc aaggcctccc tagaagccaa    12060
gaagatacca gcaccatgct tcctgtaaag cctgctggcc tgtgggccaa ttaagcctct    12120
tttctttaga aattacccag tctccggtat ttctttatag taatgcaaga atggcctaat    12180
atgcattgtt aagatatagc agaagccagt ggggtctccc caagcttagc tctatgaaaa    12240
caaattctaa caagtagagc ataaactaga tgtcagtcat agtccataat atcaacatta    12300
taagcttatg aagtgattcc atttttatggg tcagtagacc cctttctgaa ggagtataaa    12360
agatgacagt catgcgtcaa aaaggcaatc aaattgattt tcaaattagg actcattcca    12420
ctgttaacat ataaatctaa aaaattattt attttatttta ttttattttt tttaagagac    12480
agggccttgc tatttgcccg ggtaggtctc aaactcctgg cctcaagtga cgctcccgcc    12540
tcagcttccc aaagtgcttg gattttagac atgagccact gaacccccact gatttaccat    12600
tctttaatttt tgtctatac agaaggtttg tccatatgaa gacattttgt tacttactct    12660
ccagagtggt gacaactccc tgagctggtc tgcttgtcaa agtgtcctta agagcataga    12720
cactcacttc atatttggtg gccacctaga gaaataaggg catggtgagc tttagcaacg    12780
tcctcaactg aaacccaagg agtttcacta cagcattagg taaatgcaat ggttagaaaa    12840
taaaaaataa acaaaccagc aaaacccaca accttgaaaa ttcctagatt aatttcattc    12900
ctacagtgca ggtgataaat gtatttatca attttaaaat gctcttagcg gttaagctta    12960
agtaagccat agattatata cttaaactaa gctggtaaaa aaatgagaa aagtgggtat     13020
tagcgtattt ttcttttta tgatctgaca ggtgtaaatc ataatttttt ccttatcata    13080
gagaggcaaa gagaatgttc cattttgtct ctgaacccctc tttctgtagt ttcccctgaa    13140
attggcctta tgttaagagg tacatcagtc ccctaggttc ctagcagttt tctgcatgta    13200
tgtctggaag gattttaaaa tgttttaatg agggtaggct caaggtagac tggtacaaac     13260
tgtaaaatat tctttaccaa ggtaacagag ctcagaaaat gcataactaa gtcgatttat    13320
gcattcaacc aatggatatg taaattgccc cccacaacct tttaaaataa gcacaataca    13380
tctaaaagag ctgcacaaaa tccaaagcta tttataaaat tctgtcccaa tagtcatctg    13440
gaaaacttag gtcaacataa aggaattccg ttgatataaa attacaataa gattatttga    13500
tgcagaggaa aagaacagtt agatttatta tgatattata ttttcaccac cttagaaact    13560
gtgttagaga tgatctccat ctttattcca atgaacaacg gtcatgtctt accataagtc    13620
ctgatacaac cacggatgag ctgtcaggag caaggttgat ttctttcatt ggtccggtct    13680
tctccttggg ggtcacccgc actcgatatc cagtgagctg aacattgggt ggtgtccact    13740
```

```
gggcgctcag gcttgtgggt gtgacctgag tgaacttcag gtcagttggt gcaggaatag   13800
ctgtcgagat tgtcattggt tagaggttat cttataggaa atgggggaaa aggaaaataa   13860
agtgagttcc aagaagtaga atggattgtt cttgttgggc taggtgggtt ccctggtcaa   13920
gcaaagattc agtacaagaa agtacgtaca gtaagggatg caaaatgaag aaagtgtttg   13980
ctgagaaatg tgttttatat ccaccaattc tcagaatcac tgaaaacatt tgggtaaatg   14040
ccaaaactct aagagatttt aggttttaca agttttgctt tcccttaaaa aaaaaagtta   14100
cattggctta ttggccatta tgatttattt tacttttgta tggaaaaata agcaatggcc   14160 cttttttcttt cttaaaattg ttaattaatt aatttagaaa cggtctctct gtgtcatcca   14220
ggcggcagtg cagtggagtt atcatagctc actgcagcct tgaactcgta ggctcaagtg   14280
atcctctacc tcagcctctt gagtagctgg gactacaggc atgtgtcacc acacctcgct   14340
aattttttca tatttttttg tagagacggg gtctcacttc attgcccagg ctgatcatga   14400
actcctggcc tcaatcagtg ctcccggctt agcctcccaa agcactagga ttacatgtgt   14460
gagccactgc acccggcctc cttttttctat tctacataaa gtatctttgt atggataacc   14520
atttcacgca gtattccatc caaaaaagag agaataatgt ttttattgtc tcttatttg    14580 gaccctatgg cagatatggc tgctaaattt gacgttctct ctgtaatgcg gcgtaagaag   14640
aaaactggct cccaacagaa gcagaaaaga gaagcgaaaa gcaataatac agactgtcac   14700
ctctagggtt tatgctgtca ctaggataca tctttagcat tctactctgc ttcagaaata   14760
aagcacaaga agataaagta ttatggaaag caattgccct attgattatt tcctaggtgt   14820
ctaaatcaca atcatttaag ctaattatac accagcatat gatatctaac cagagaagaa   14880
aggtcttacc cacgtgtgct cagaatcatg ctgctatgaa atgcccgagt ttgggttcct   14940
ttttataagt aagctctgta atgccaaact tcttttcttt atacatagtg agggtaatca   15000
cagggagtca gagcttagga aataatccac aactttagta tcctcttcaa atgtcttgct   15060
ttatggtctt gtgtataagc caggatactc caaaatttct tttaatcaga cttgtttcct   15120
taaatatcac ctaagtttta ttgtttctta ccattcctct ttaaagagga tctttcctaa   15180
taattctttt tcacccttac acgggaatca atagcccagt gaagcataat tcattcagta   15240
gggcataaag ccgctgctcc catgggcacc tggtggtgca attaaccata tacctgtgga   15300
ctgggttcca atcaggggct ggctctccat atcatcgtgc aaggcaacca cactgactgt   15360
gtactcagaa cccggtctga ggccttgcag ctctgcagtg tcttcttcac catcaggtgc   15420
agggaatagc tcatggattc catcctcagg gctcgagtag gtcaccctgt acctggaaac   15480 ttgccctgt gggctttccc aagcaatttt gatggaatcg acatccacat cagtgaatgc   15540
cagtccttta gggcgatcaa tgtctgttag gcaaattaat ggtaagaggt tatgtgaaaa   15600
gcaagttgtg aaataagcat ttttataaca tgcaaagcag ttttgcagat accatttct    15660 ttgatgaagt ccaattaacc cactatcaaa aggaaaaatc acttaaacac ttgcttaatt   15720
tttcttggtt tagaaaatat gcaatgttgc atcacttatt aaaacatagg tgtatgtgag   15780
ataagcagat accctgcaaa atgtcccac aatgggatg tatttatatt aatttaaaga    15840
tattctacca cgatttgatt tttacaatgt gatgttagtc tcatagacct ggattttcta   15900
taccttggaa gtggtaaagc tgatttgcaa tgtcagattc aaattgttat aattgttttg   15960
ttttgttttt ttttgagatg gagtctcact ctatcaccta ggctggggtg cagaggcatg   16020
atcttggctc actgcaactt ctgcctcctg ggtccaagtg attcttctgc ctcagcctcc   16080
tgagtagctg ggattacagg cacgtgccac cgcgactggc taatttttgt attttttagta  16140
```

-continued

```
gagatggggt ttcaccatgt tggtcaggct ggtctcgaac tcctgacctc gtgatccgcc    16200
tgcctcagcc tcccaaaatg ctgggattac aggcgtgagc ccagccctat aatggttctt    16260
acactcttct tttcccctct ctattaagca tttatattac actctggtcc agccatagcc    16320
cttcaaatgc cccaaacata aagctacatg aggcacactt caatcaactt taccatccag    16380
ttgtagaaaa gacggtctag gaaaatttt tgtagatttg ctataggcaa ataagatttc    16440
gctgaggcca tttgagcaaa agaaattcaa agcacagcaa ctaactatgg tggtttcaca    16500
acttctttct ctgtaaattc ctcgcttggc actgagaagg aaaaaagatg ttcgtaaagg    16560
gctcagctca agacataaac taaccaacaa gttcactttc cctatgtgta attgcaaaag    16620
acatgtcgtg ggcattcaga cacccaagaa caaaatttga ctttgaaaat ggaaaccaag    16680
cagtggttac gtactggtta ctgcagtctg aaccagaggc tgactctctc cgcttggatt    16740
ctgagcatag acactaacca catactccac tgtgggctgc aagccttcaa tagtcatttc    16800
tgtttgatct gcaaagggag tgaaaagcaa atgcaacatc cacgtcatcc actataaagt    16860
cctcaagtgg cgtctagagt ttggtagtaa acatatggtg gcctagaatt tttatttgca    16920
gaattgtaac aaaaatatgg agagtcgac tttgatttcc tcttggacaa acctgttcat    16980
tgctaataca aattaccata tgggagtgaa gtcacactca aggataagat ctaaaactta    17040
atatgatgcc cccaacaatt agtgatactg ctctcagaaa aaatgaaaat taacttgact    17100
ctaataaatt gccttaagat cctaatttca caagtattct atttaaaaac aaagacaaca    17160
tagctaaaaa gagctgaaaa agtcagttag gccatttatc tcttcttagt gtgaatgata    17220
aacaaaacca gaagggtgaa tctagtaatt taagatgtcc atatcactaa atagaactat    17280
ccatgtaaaa acagaaatgc acttaagact tctactgtga aagggttga taatgatctt    17340 gagccctgaa ctcatgaatg gggacaatga tgacatagga caaaaaaata catagtactc    17400
acaacaaggt agccatttat ataaaaaaga atattaggtg gtcctacccc atctatcctg    17460
ttgtatatga gatgcagatt actctttttt ttttttttc cctgagatgg agtctctcac    17520
tctgtcaccc aggctggagt gcagtggggc tatcttggct cactgcaacc tctgcctcca    17580
gacttcaagc cattctcctg cctcagcctc ctgagtagct gggattacag gcacaagcca    17640
ccatgcccag ctaattttt tgtattttt agtacagacg gggtttcgcc atattggcca    17700
ggctggtctc gaactcctaa cctcaagtga tctgcccgca tcagcctccc aaagttctgg    17760
gattatagga gtgagccacc gcacctggcc gagatgcaga tgattcttac ctggacctgc    17820
agttttagtt tttgttggtc ctggtccatt ttgggagtg gtggtactc tgtaaccagt    17880 aacaggggaa cttgaaggca gccacttgac actaatgctg ttgtcctgaa catcggtcac    17940
ttgcatctgg gatggtttgt caatttctac aaataaaagc agggagaaac cagtgaagcc    18000
ccagtccttg gagacaagat tggacaagtc ctcctctcta ggtctggtac atattcgaat    18060
gatcgcttac atgagaaagg tatttcttct cgaaagaata cagagagagc ttttagaggg    18120 atgggcagg catctcaata ccatttccta ttttgagat ggttgcttca ttcacaaaga    18180
agctacattc cacaagcagg tgtctcttcc tactttatca actcatccat tctttttccca    18240 caaatactta ctgaacactc tctatgcctg tcgtattgca gacatgcgga atatatcgac    18300
aaaactgact gaacttcctg cccttggggt gcttccttct ttatctggct caaaactctg    18360
ttcgctgcag gtgctagctg caggttgttg ctcattaaaa aggaaaatct attctacaat    18420
tagaaaaata ccttgggaga acattgcaaa acagtatctg aataagtaaa agctggtgtc    18480
accccagagt agaagtttgt acctgttcgg taattaatgg aaattggctt gctgcttgcg    18540
```

```
gggctgtctc cacggccagt gacagcatac acagtgatgg tataatcaac tccaggttta    18600
aggccgctga tggtagctgt agacttgctc ccaggcacag tgaactcctg gacagggcta    18660
tttcctcctg tatgaaaaag ggttagttca gagtgtgagg ggtttagagc tacttgggta    18720
ttactgatta attgaattac cacatttata gcagcatgta aatcacatct tcttgcttat    18780
tcccttttaa agagcgctat cttgaacaga aaggggtatt tatgcatgta gcaaaccttg    18840
gtaagtgtat aaacattgag agaaaattac agttagcgct gttttaacat ttcagcttta    18900
aaatgtcact gagtagtaga gtagcattag aagtgggaga aggtaagccc tcaacccagg    18960
attgcatgca ttgtgtcctt tttaaaactt ttaacagaat acattccttt taaataaaat    19020
ttggaaaata cagaaaagta aagagaagaa aaaataaaaa tcacttattt ccaccactga    19080
taatatgttt gtgaatttac aatccttttta tttcctcagc tctgccgttc ccctctagt     19140 tgtagtatat aaacaacttt ttatttgggt tttagaacaa attatatcat ctatatctta    19200
cgtattttct tggaaaaaac aagggctccg ttgaatggac ttgccaaagt ttctttaatt    19260
ctttgttcac tgttgggctt tcaggttatc cacaacagaa tctgatttaa tcagagtgta    19320
aaatagcatt ttactgctgt acctgtctct ccgtaagtga tcctgtaata tctcactgtg    19380
acagcaggag catcccagct gatcagtagg ctggtggggg tcgcagcaac aacttccagg    19440
tccctcggaa catcagaaac tagaaaaaaa agggaaactt ttcacatccg taattttcaa    19500
acaatattca gatttactgt ttgttcattt tccagataat tgtcttaatg attcttccat    19560
acaatcatgt aaatactacg tgtaattagc agaattttat attatgacga attcaagata    19620
aggggttaca gagcccattc aaattgtgat aaaatgatta tttcaaattt ggggaagagt    19680
ttttttccct caacatttta tttgaaaaaa tttcaaaact acagaaaagt taaaaaaaaa    19740
aaaaaaaaaa aaagtgatac aaggccgggc gtggtggctc acgcctgtaa tcccagcact    19800
ttgggaggcc gaggcgggtg gatcatttga ggtcaggagt tcaaaaccag cctggccaac    19860
atggtaaaat cccatctcta ctaaaaatac aaaaattagc cgggcgtggt ggcgggcacc    19920
tgtagtccca gctacttggg aggctgaggc aagagaattg ctcgagcctg ggaggcagag    19980
gttgcagtga gccaagatcc caccattgca ctccagcctg ggcgacagag caagactcca    20040
tttcaggaag aaaaaaaaaa aaaaaaagt aatacaatga acacctatat acccttccct    20100
taggtatttg tctctggctt gacgacttga gactaaaata cagataacat gatgctactg    20160
ttcccgtaag tacttcagcc tctatctgct aagaacaatg acactattac cctaaaatta    20220
tatttttaaa ggtactttga aacagtgttc agttttccac cttttttttt ttttttttg     20280 agacagagtc tccctctgtc accaggctgg agtgcagtga cacaatcttg gcttactgca    20340
acctccgcct cctgggttca agcaattctc ctgcctcagc ctcctgagta gctgggacta    20400
caggtgcatg ccaccacgcc cagctaattt ttgtattttt agtagagacg aggtttcatc    20460
atgttggcca ggatggtctc gatctcttga cctcgtgatc cacccgcctt ggcctcccaa    20520
agtgctggga ttacaagcgt gagccattgc gcctggccct tttttttttt ttttttttga    20580
gacagggtct tgctctgtca cccaggttgg agtgcaatgg cctgatctca gctcactgca    20640
accttcgcct cccaggttca agattctcc tgcctcagcc tccccagtag ctgggattac     20700
aggtgcatgc caccacacct tgctaatttt tgtatattta gtagagatgg ggtttcacta    20760
tgttggccag gctggtcttg aacttctgac ctcaagtgat ctgcccattt cggcctccca    20820
aagtgctgag attactgacg tgagccaccc cgtccggcca ttttctaca ttttcaacaa     20880 aacttgtgtt attagaaatg cataaatacc caaatcaggt gagaaatttc ttgagaggaa    20940
```

```
aaaaattatc ttctttactg ccaccacgcc cgggcttctt taccatattc taaggaagat    21000
gtttctccac attttctcac ttccctctcc atgtaccatg acaatgatct attttttttt    21060
tttttttttt ttttttttgag agctgatgac agacaacagc aagctacttt acagaatcta    21120
ccaactgggt aggaaagtct tctgagtttc tttgcagaca agaaaagtta cctgttgatt    21180
gttggccaat caataaggga cttcctctc tgccattaag agcaacgatg ctgaccacat    21240
actctgtgcc tggagtgagg ttggtgaggg tgatggaatt ccgagagtgg ggcacccgat    21300
cttctcgagg tctcccactg aagtgctcgg gatgatggcg gatcctgtag ccagtgatgg    21360
tggctcgagg agcaatccag tgcacagtaa aagagttggc agtaatatca gaaagtcaa    21420 tgccagttgg ggaatcaaga cctgtttttc ccacccgggg gaggaagaga aaaaaaaag    21480 aaaagacacc accagtttag gaagtgagga aggtgtaggg gaaattaacg tacatccaac    21540
atttcgttcc tgtctcatca ataccatgat ttgccataaa ccaagagta agatgtactg    21600 attctaagct acatatgaat tttaaaatct taaattgact caattcaaaa tagccagctc    21660
aagcattcat ttttttcttg tgctaagtaa ttcaagcaga ttttaggggt tattacagta    21720
agttctgtgt tcacatttgg agataagtgt tcaagatctt ctgagaattg acattttcaa    21780
attcttcagt gttcaagtat tctgtgtttc tatcctgtaa gtgtatcctt ccaagtaaag    21840
caagatctgc ccactctcaa agtaaatgtt tgactctcag agaagcctcc taagctcaag    21900
aggaaattta tatgtcaaca gagtggtaat gatgccaaac acaaactttt ctgaaactaa    21960
agacattatc ccagacaaat tacaatgctg ataattcctc gtgaattgac agttttgaaa    22020
aatgcatttt tcaaaaatgc acaaaaattc agagtttgtt gcaaattcaa atcacttagt    22080
ctctgggact tccagcaaat ttctgtttca gttacagcat ttactagttc ttttcaataa    22140
gaaaccaaac taagatatca taagtccttt ttggaagcaa gtggactata aataaattaa    22200
tgaatacact aaagtgtacc ttttgaaaga aaaaattaaa agcattcata tttaagtatg    22260
taatatttat gagattcaat tcaacttcct tctagtaaat gcatattta ttaagtaaaa    22320 agaaaatgta aacttgctgg cttagtaaag gaagacaaat agatgacaat gagtgttggg    22380
tcagccatta gacagagctg cctaatgaaa aggaatgtct gctaaatcta aataacaaag    22440
atcttcttag aaaatgtttt ttaaaaggac agacaacaaa tttcttaatt tgttagtgac    22500
tgaaagtcta ggtgattgtt gagtaaggta tcttttagtt tttgagacca gcgataaaat    22560
catactgtga tgacaaaggt acacacacca tgacaacaaa aaatggagat gtattttag    22620 aagtagcatt tcatttgtta tacagaattg ataggcaaaa gctactggat agtcatactg    22680
ccaacaccac tcacctgttt tctgtcttcc tctaagaggt gtgctctcat gttgttcgta    22740
gacactggag acactcacta catattctgt accaggcagg agatctgtag gggcaaatgg    22800
ggcttatttt aaaactctgc tcaaaagcat gagaaactaa agcacgccca ggactatttg    22860
aactgatgaa atatccaaat gtccagtcct atagcctact tacacctaag tgaacactac    22920
agcgaagtgt tcagtgaaca gaccttgaga aggtctgtaa ttagatgata aggaagggtc    22980
accttgcccc atggcctctc gaagccctcc attccacctg tgagtgtgac tcagctggat    23040
ttcgagtggg atgaagttgc tgcaacagct ggatatttct cgcatccacc tgagagtatg    23100
tctctggagg gcacatgata atccttgctg tggtgctgtg gattgccatt tatgcctcac    23160
aacaaccctg gaaggtagtt tgctccttt aaaagcaatt tcttgtcata caacgtactg    23220
catatcttta aagtgatggg ttttacata tgtgtgactt gggagaccat caccgcattc    23280
aagaaatgaa caaacctatc acctctaaaa atttgattta ctacaattat ctccattttg    23340
```

```
taaatgaaaa aacaaaaaac aaaacaaaaa aaaactgagg cacagagaag ttatcttctt    23400
taatttactt gcccaggatc atactgggat tgacccaggc caggactagt ggtcttaata    23460
attaaccttt actggaaaaa agccacactt agaaagcaat cggttctgcc atattaaaat    23520
gagagcagaa tatttttta aaaattaaat atacatccct gagtatcttg ttccattttt    23580
ttttattttt attattttt cttttttgacg aggttttact ctgttgccca ggccggagtg    23640
cagtggtgtg atcttggctc actgaaacct ctgcctcctg ggttcaagtg attctcctgc    23700
ctcagactcc tgagtagctg ggattacagg tgcctgccac catgcctggc taattttttgt   23760 atttttaata gagacggggc ttcaccgtgt taaccaggct tggactggaa atcctgacct    23820
tgtgatccac ccgccttggc ctctcaaagt gctgggatta caggcgtgag ccactgtgcc    23880
cagcttcttc ttccattttg atacacagtc aggcatagct taatggtgga gatacatttt    23940
gataagtgtg tgatttggtg attttattgt gtaagcatca tagagtgtac ctacacaaac    24000
ctagatgggc ttgtaatccc agcactttgg gaggccgagg agggtggatc acttgaggtc    24060
aggagtttga accagcctg gccaacatgg tgaaacccct cgtctactaa aaatacaaaa    24120
aaattagctg ggcgtggtgg ctcacgcctg taatcccagc tactcgggag gctgaggcag    24180
gagaatcact tgagccttgg tggtggaggt tgcagtgagc ccagatcgtg ccactgcact    24240
ccatcctggg caacagaggg agactccgtc tcaaaaacaa aacaaaacaa aacaaaacaa    24300
aaaacctaga tggtagagcc tttgacacac ctaagctata agctatgtgg tctagcctat    24360 tgctccctagg ctatgagcct gtgcagcatg ttactgtact gaacactaga ggcaactgta    24420
atatatggta aatatttgta tatctaaaag atacagagag tgaggtttct aaatttggaa    24480
ctcctactca ctaaaccctc attccccctgc acaccatttg cccttcagcg tttctataaa    24540 gcccccctaca aaagtttgga aaagtgccag aatggaggac cagatgcctg gattccattt    24600
ccaccatact agctggccag tgcaatttta cttaactgct ggggacctcg acggcttcat    24660
gtttatttgt ttgtttattt ttttgagaca gggtctcact ctgtcaccca ggctggagtg    24720
cagtggcacg atcatggctt gctgcagcct caacctcccc aggctcaggt gatcctccta    24780
cctcaacttc ctacatagct gagaccacag gtgtgcacca ccatgcccgg ctaattttttg   24840 tattttttgt agagacttgg tctcactgtg ttgcccaggc tggtctcgaa ctcctgggct    24900
caagcaattg gcccacctca gcctcccaaa gtgctgggat tatacaggcg agagccactg    24960
cactggtttg cttcatcttt aaaagaggat aataatgact ttgctaggag ggagaggggc    25020
taccctgagg tcatctgtag cattaggatt ataataaggt cttagaacac atgattagca    25080
tgtgacaggt ctacggctaa gggacagaca ttgtgatgca ggggcttgta tactgggtga    25140
tgctgtaatt agtgattcca gggtgctcta gaacagaagc aacagccctg gggtggtgga    25200
tatgccaata taaagatatt cttgccctca gccacaaagt aagaaaccaa gattatggtc    25260
acgctgagct gctcttcttt gtgtttcatt atctaaatta tgtttgaaag gtagatgttt    25320
tcagactaat acttggtaat gtacctaaat gtaagctatt ttccccttat gtagaatctt    25380
ttgctgttgt tatatatttg actattacag tgaaaataat aaaaagcact gtttatgtga    25440
aacacagcac catcttgcag cctactgttt tattcttaa caaaagatgt ctattctata    25500
atggttggga ctagaaagag acaatttcca taaattgttg ttatttattt aatgtcagtt    25560 tttttttctaa gctctcagtc ttctgagaaa tccttctaac agattctttt tgaagtacaa    25620
attaaacttc tgactctctt cacaacaaca ttcaatccta gaccaaacaa tcagtcactt    25680
ttctaagtat tcaaatccta aatcaatcaa ctgctgacac ttttttata aaaatgagaa    25740
```

```
taaagcacat atggtgacac tattttcagt tctcattttt ttctctaaag atttagattt    25800
agtcatataa tttctcttga tattcactta tttttacgtg cttatttaga agcagaattt    25860
gtttgaagtc atggaacttt cctgcaggtg ttttccact atgattttt taaagctgta     25920
gatatcaaaa gtatattaag atagcaacaa acattacatc tttcaaaatt aatggagctg   25980
tgcattgaat tcagagttta gtttgtagct tggttgcagc tctcttgctc ttagctcctc   26040
ctacttgaga atttagaatt catttgctat gctctaggtt aatatttatg gaacagatac   26100
attcaactgc ttacttgtta agaccactgc attgtctgaa ggagaaattg acaactctgc   26160
aacatcttcc tcattttca caggtgagta acgcaccagg aagttggtta aatcaatgga    26220
tgggggtgga gcccaggtga cacgcatggt gtctggacca atgttggtga atcgcaggtc   26280
agtgggagga ggaacagctg gtttcgaaca agaaggaaga ctcagttaat gtaattttaa   26340
aattaaagct aacgaagtag ctggaaaggt aaaatcaata tttcatgcat aaaggaaaca   26400
gaatcataat catgcaaaca gtctaatcta agtctatttt aagttatagt gtactactgt   26460
taaaaataaa acactacaca cagtactgtt aggccccctt taacctttt gccatcattg    26520
atatatttaa aaaaattt aatctacttt caaatatgtt gactttatgt acattattaa     26580
taccactgca gattatttta tcccaggccg aagaggctta agttgccaca cagcaaagag   26640
aaacatagca gtactttaca aagaaataca tgcacacaga caaaaagaca agagggtcct   26700
aaacttcccc ccatgtgaga tatctagagc tacagttcca ttcagtgaat tctacttaca   26760
agtgaacatg ttcatgcaaa ttggttctca gcatgtttct tttcccatgc acagcagaga   26820
acctttaaaa tgttgcatgc ttgtccccag actgtggtta aagaggtgtt tctttaccta   26880
gtgacagcaa caaaacctag aatgctccca agtttacttt tctcctacct caaaacaatg   26940
cccatccact ctaccctaaa ttttgatggg ttttagcta caaagaagga gcatggtaga    27000
gtttatcaaa gggtagaagg aagatcatga tggtacattt tggtgatata tttcttataa   27060
ttaattggta cttacgcaat ttggtattcg tgtttggtat ttaagacgaa aaattctagg   27120
tcttcaaatt gaatgaacat ttgctatttt atatttaaca gagcagacat ctgtatttct   27180
ctagctttat atctacttgt ggtttaaatg agagtgtact gaagaatact tgcatgtgtt   27240
tttctccaat cagtttagca gatgcatttg attccttatc cccccaatcc accctatctg   27300
aatctttggc caattgctga cttcccccat gaaacatcca tatttaaccg gagtaactgg   27360
tggcagcatg caacaccatc tatgtctcaa acgcagaagt tttcaaaatt cacccgtttg   27420
ttgtgtcagt gtagtagggg cactctcgcc gccattaatg agagtgataa cgctgatatc   27480
atagtcaatg cccggctcca gccctgtgac tgtgtagtat cctactgagg agtccacaaa   27540
atcttcaaaa ataggggatac cttctcctgc cgcaactact gtgatgcggt acccaataat   27600
ggtggaagag tttagcgggg tccacctcag gccgatgctt gaatcggtta tatcaacaaa   27660
gcttaggtca gtgagttggg gcacctctat tgagttacaa agcaaaggga gggggaggca   27720
aaggaaaat agagggaaaa aaagaggaaa aaataaagca gtgtatatca ggttactagt    27780
agtaaaattg gtggaatgtt aaagcaatga tggtaatatg caatctgttt taaattctct   27840
gaaaagactt cctaagcatc atgaacagtt tgcttcccta gaagaataaa caggaatatt   27900
cttttaggga atatatatat atatatattt tttacatttt gaaacatcc ttaagggta    27960
caatttgaac tgttcagatt cctaaaaatc atatggctgt ttaggatgtc aaaaccattc   28020
ttagagccta gacataatat ctgaagtaag tatcagcaat gctttaata attccaaaac    28080
tgttttagta gaaaataagc ttgcatgaag aaggttaaaa aataataaat gggtgataaa   28140
```

```
ttgattttt  ttctcccata  caaaactcat  gacaacatca  tggccataac  gctaatgcat   28200
tatgaatgta  tggtgtgaaa  tgtgccattc  aaaagcacat  tcaggctgag  gaaagacagg   28260
cctaaggtta  aggccattgc  cactatttta  gttcattcat  aatcaaaaca  tgtaattagc   28320
gttagtaaaa  gcattctact  gaagagtcca  aagggggaca  cgatctgtcc  aatgctttca   28380
ttatgttata  acccaatgga  caaacaagcc  tatccttaga  caggccttg   caatgttgtc   28440
tttcaagcca  caagaaagaa  caccctgaag  gtgtgacttt  tacttctttt  ttttaaaatc   28500
caatttcaa   aagaaggat   ttgaaactgc  aagatgaaaa  actagatgtg  tcaaccaaat   28560
gctgtttcag  tgctcacata  cagggacaaa  actattttat  aggcagctgt  tggaaattga   28620
tatggattgt  aaaatcgggc  agaaatgtac  tgatgggatg  catttaccat  attactttga   28680
gcctatcagt  actgagtaca  gacacgtgac  agtgttttag  tcatacttcc  atgtgagcag   28740
acaatacaga  gttaaagcca  tggctgccac  tccattacat  actcgctgca  acacacagca   28800
tcccagtgaa  gcacagacag  taaagcagtg  ttaacagcaa  gcatttgtcc  aaatcgctgc   28860
tttgacttct  tggttttgga  aagtgcagct  gggagatcgg  aattaaatcc  caaatatagt   28920
tgacacccttaagcatctgg   ggattaagat  gctaatcccc  actcttattg  gaagtgtcac   28980
tctcaggata  gcagcttatt  tttctattac  ctgggatgat  ggtatcagag  ataggacac    29040
tttccttgtc  atccttgaca  gtgtaaacac  tgacattgta  ctccaggccg  ggactcaggt   29100
tatcaaaagt  gcaggagctc  tgatcagcat  ggaccacttc  ttccaaagaa  tttccctgct   29160
ggccgtttgt  aggggttgtg  gtaattctat  aaccagtaat  gtctggagaa  aaaagaaaag   29220
ggaagttatt  gcacagagga  tctgtgagcc  agagcatatt  taactagact  ccaatgatgg   29280
attcacaggg  cggaatgcag  gacttggcat  ttactgagga  ctccactgtc  actgttattc   29340
aatgcttgca  acaatccttt  caggcagtac  taagatcctc  actttattt   tttattttta   29400
tttttggaga  cagtctccct  ctatcaccca  ggctggagtg  cagcggtgtg  atcttggctc   29460
acttcaacct  ccgccaagat  cctcacttta  aggaaatct   tgaaccaggg  gagtgattcc   29520
ccaaagcttt  ctttgtttcc  aaatctcatg  tcctatcac   tgtaccctgc  ttttccttaa   29580
tgaatcattt  gaagacagct  gaggaatatt  cctttctacc  tgcctagtat  agaatcgctc   29640
tccaccttaa  gcacattccc  cagagagctc  tcctaattta  aaaggtctga  aactatggga   29700
tttataggaa  gagaaccaag  aaaggagaaa  aggtgagaaa  caaaagtgct  gatacttatt   29760
ctagaaagag  tattgattgg  gaggttgagg  caggcagatc  acctgaggtt  gggagttcga   29820
gaccagcctg  gccaacacgg  taaaccctg   tctctactaa  aaatctaaaa  aatagctggg   29880
cttggtggcg  catgtctgta  gtcccagcta  cttggggagg  ctgaggcacg  agaatcgctt   29940
gagcccagga  gacggaggtt  gcagtgagtt  gagatgcgc   cactgcactc  caagcctggg   30000
tgacagagtg  agactctgtc  tcaaaaaaa   aaaacaaaac  aaacaaaaaa  agagagtatt   30060
gattgttgaa  gtcttcagga  atcacagaaa  ttgggcagta  aaagagttga  gagggatgag   30120
agacattcaa  ataaaaacag  tgatgactag  agatctgtgg  ggacagatta  aaatgagaaa   30180
gtatattaaa  ctttataaaa  ggcaaggaga  tgacagaata  ttttgccatt  aggaacaggg   30240
taaacactaa  tgtggcaaat  acaaggaaac  ccaactgaat  gagaaataaa  tattgagatc   30300
attcacttg   ctagtggtca  tccatatgtg  tgggctgggc  cattgagacg  agatattaat   30360
gatcctgctg  ctaacaagca  cgaagattgt  caacttaaag  tttcaaattc  agagcaactc   30420
agctggaaat  tgtatagctt  tggcttaaac  aatgttccg   cagataatga  aaactttacc   30480
aaaatcactc  tacttcagag  ggagattaaa  agagatattc  tgagctagtt  tcattctgtg   30540
```

```
tgtttgcata cattaatcag atttagagat gatagcctta gctctgtgcc ccggcaaaga   30600
taagaactat ataatacttt tttttaaaca aaaatttcac aagaatttta cagtaaaatt   30660
agaaatagct aaataataac ctaaacatat cccttaaatt aacaagtata tgaggtaaga   30720
atgcaatcaa cattaattgg aacttttatt tttgtttaag attttctcc ataggtttgt    30780 tgagacttcc atgtggtttt ggcaaaagta atgggtatct aaaatttcct gttattgcta   30840
tagtacgtca tgctgtttga atattgttaa caactatctt tatacatttt agcattttat   30900
aaataatttt caaatatatg tgaacaagga atttagacaa atgcttcatt taaagctcta   30960
aaaatggtca ggaaacccct taatcagaat tttcagtttg catagaatat aattaaaaaa   31020
aaattacatt ccaaatatgt gacattgggt gtgagaagga gtctacaaac ttaagttaca   31080
atcccagttt tgtaacattt aaaatgtgtg actatgagta ggccaatttt ttctaagtct   31140
cagttttctt attctgtaaa atgaaggtat ttctgccttt catcacccct aaatatttgt   31200
ggtgcaaccc atgacaaaac attcataaaa cttcagggaa taataaactt aggctctgta   31260
acaactcaca aagggaaat tacgtaatat gacttcaacc atttgtttgg caatttttaa    31320
tgcactcagc aaaagccacc ttccacagtg cttttcttca gccctacagc tgtgtgagga   31380
tctgtcttgt cccctagac tagtgtaagg ttgttctgct tcctgtgatt gaagtcaacg    31440
tgcattaaag catcctgcag gctgctccat gatgtacatc atgtactgct atagttttta   31500
tggagagcta agcatttgta atttgaatcc cttctttctc tgaaagaaac acagtttcta   31560
aaatctttgt cttgggaagg tatggtgtat acttgccctc tgatccatcc caaacttacc   31620
tggggtggtg ctcctctccc aggagactgt gagcactcca gtgtcagggt ttgcctccag   31680
atgcaagttt gttggtggag acaatgctat gcagaaagaa cattttaaaa gtcaaagctg   31740
acacaaagct cttgacctgt gtaatctttc ctccttccct acctccctct cttccatgct   31800
tcttccctcc ctccctccct cccataaaaa tataggttac attatgaaaa tatgatggac   31860
agcagtaatt ctctgacaaa gacttcttta tgattaatga ttttgcaata ctattgaaat   31920
tattttcatc ttgccagttc ataaatattc ttgacatgga aagaacattt ctgatgccat   31980
aaaatataaa gcatgaattg aacctgctac tccaaattca ggaatagcat taataatata   32040
agtaaggata agatatctcc cctgtgccat tctcataagt aaaaagtgat attgacacta   32100 gctttttcg aaaagtagaa cagttttaaa aactaataga aaagggaaaa aattcttctt    32160
acgtgtcacc actttgttta caattggcgc atctctttcc tgtccatctc tcaggacttg   32220
gatggtgtag acgtattcta ctcctggagt caagccggac acaacgatgc ttcctgagtc   32280
tgaagtcact tctcgtggtg cctctcctcc ctggcttggt cgtacaccca gctagaggaa   32340
ggaatgcaaa gtaaacacca aggacaaata tttccagagg actgttactg ctgtgaggct   32400
atgattatgc tttaaatagt gtaaactctt cagaaactgc acagtgtact tttattggga   32460
aatgatttgg ggactctttt atatacttta gctggaaatt ccccaggtg ggggaggtat    32520 cttccaaact gcattaaggt ggcttgtaat ggaaggttcc agagaaatgt cattacatac   32580
tgttttgctt gataaagaat ctcttgttac aaaccagacg tatacaggga ctgtgggtca   32640
catggtagtt catttctatt tttctgtgtg tgtgctagaa ggaatgtctg agctctccct   32700
ttaacgagtt attcacattc aattaacctt ttagttgcca tttaaaggca ccagcccctg   32760
tagcaactgt attgcaaaaa cacacctttt gaagagatat gtacatagct tcaactgcag   32820
gatgatacat tacaagagaa gaattagaat aactatgccc ataatttaaa atccttttaa   32880
gattctattt caaaaactta ggtaacactg ttatccaata gtgttcaact ctagagagat   32940
```

```
ccttcacaca tcataaggct tctgaaagtc agcatgacat tattaaggga attaaaaggt  33000
atactggcac tcttcagaaa gttcttctat atttgagtag cataatcata aatatggcca  33060
tttacaaact ttatctttgg tgtattttt taaacgatca aggggattga gtcatgattt    33120
ccagcgataa caaatatttc tctcttcaca ctaaatgcca agaatggaa ttcttttaaa    33180 catattcatt tgtattcacc gcttccctaa tatcattact ttaaagaaga tgaatccaga  33240
tatccacagg gaaaccttaa tcttaacttc tattaagaga ttcaccctca gtgctttgaa  33300
cagttggaga tgaaactgat tggatgaaaa tgcgattttt aagtgactct gagtttaact  33360
ggtctcccta aactggcttt tgtgaacttg ttcacactca tttagaacaa cacatcaaat  33420
aaagttttcc catgttttt tgaaatgtaa ttccctgcag gaaaggatag agaaaataag    33480
ataacaataa gcagcagctt cgtgctaatg ttttatcctt tgcaaaacac tttcgcagcc  33540
tccatctacc cttccaacaa ttcagtgagg taggcaggga aggactgtta ggccctgaca  33600
atgtagtcaa agatgtatgg acagaagcag gtgacaaaac ccaggtctcc tgactcctga  33660
gcaccctgtt tccactacat gggaaccaca aggacagctc agggctgtat cacagagatt  33720
aggaacatct gcagtttacc ttaaaaccaa ttcttggagc aggcgtccat gtgatcacaa  33780
tggtggtctc agtcacctcg gtgttgtaag gtggaataga gctcccaggc tgcactgtga  33840
gagagaatca atgcacatat tcaaaactca aactcacaga tgattgcata gcatatagat  33900
aacaagtatt tttatggaga acctcagttt aaccaagcag tggatagagg atgtaacata  33960
ttttttcatt gggtgagaat tgggagagga tcaggcttct caatctttaa tgtgccacac  34020
acatcatctg gggtctggct aaaatgcaga ttctgtttct ggaggtccaa caaaaaacta  34080
gggagtttgc atttctgaca aacacagata ataccaattc tgctggcccg tgaatgatac  34140
ctgagtaaca aggggttaga tgtttgctaa ggtggtcctt tcattgaaat tatataatct  34200
aattcatgtc tttttatgat tgtttgggat tgacttttgat gacaataaat ttccctatat  34260
cgtcagtgta aaatcccttta taaaatgtaa aactggccac cacaaactga ttatcatatt  34320
gtttcttaac cattaattta agaacaatgg taaattatag aaggtgatct aaaaacagct  34380
ttatgctggg cggggatcgg tggctcatga ctgtaatccc agcactttgg gaagccgagg  34440
tgggtggatc acttgaggtc aggagttcga gaccaggctg gcaaacatgg tgaaaccctg  34500
tctctattaa aaatatgaaa aattaactgt catggtggct catgcctgta gtcccagctt  34560
cttgggaggc tgagacacaa gaatcgcttg aaccctggag atagaagttg cagtgagccg  34620
agatcatgcc attgcactcc agcctgggtg acagaatgga actccgtctc aaaaaaagaa  34680 aaaaaaaag ctttacgctg aattattcca caataatggt cagctatttt tggttgcaat     34740
aaaagatgct atataaaagt taaacaaaat ctgccaccat ggatgcactt tgaagtctaa  34800
agatttgtac tttaaatacg tgattattct ttcagaataa tactgcaaaa atttagtatt  34860
ttatcaccag aatcaggaat tataacaaat ttattttgca ttttctagca tcctgacatc  34920
actgttattt ttcttattga aatattact ttggccaggc gcagtggctc atgcctgtaa    34980
tcccagcact ttgggaggct gatgtaggtg aatcacttga ggccaggagt tcaagaccaa  35040
cctggccaac atggtgaaac cttgtctctg ctaaaaatat aaaaattagc caggtgtgat  35100
ggtggatgcc tgtaatccta gctgcttggg aagctgaggc aggagaatca cctgaacctg  35160
ggagatggag gtttcagtga gccaagatca caccactgca ctccagccag ggtgagagag  35220
caaggctcca tctcaaaaaa aaaaaaaaa aaaaaaaga agaaaataa aatttttactt     35280 aaacaatttt tttttgaga tggactcttg ctctgtcacc caggctggag tgcagtggcg  35340
```

```
caatctcatc tcactgtaac ctcagcctcc tgggttcaag tgattctcct gcctcagact    35400
cccaagtagc tgggactaca gttgcccacc accacatcca gctaatttt  gtattttag     35460 taaagatggg gtttcactat gttggccagg ccagtctcga actcctgacc ttaggtgatc    35520
tacccacctc ggcctcccaa agtgctggaa ttacaggcat gagccatcac acctggccaa    35580 aaaaaaaaa  aatcttattt ttaaataaaa gatttgtttt gggttttagc accaaaaata    35640
agaaagaaag aaagagagag agagtgagag agaaagaaag aaaagaaaga aagaaagaaa    35700
gaaagaaaga aagaaagaaa gaaagaaaga aaggaagaaa gaaaggaagg aaaggaaagg    35760
aaaggaagaa aagagagaga gagaaaggaa ggaaggaagg aaagagaaag aaagaaaggg    35820
aaaggaaagg aaagaaaaag aaagaaagag gcatgtatat ataaagttaa gatagagatt    35880
tccaacaacc ttgcaaatct tattataaat gtagaaaggt aagatcgcag aaggccagat    35940
attttgagtt gggtaagttt aagttcaagg gtatcaagtg tgttcatagc tctggtcaca    36000
tgtttgacat ctccacaatt cttcctctct ttacatctca atcaattttt gttcccattg    36060
ggaaaaaacc tctgaatgca tttatactaa attatgaatg gctggcaaga caagaattaa    36120
gtctccagag ttatacaaac agggattaaa aagtgttcag actccagtct caactcaact    36180
ccagtcaatt ttttttttctt tgccatgtgg gaatttagaa tcaacatcgc aattctcgca    36240
tttttttttc agtctggatt ctaaggagcc attttttatt tttattttaa aaatattgtg    36300
tgagaaaaag ccaaatatat gtgtgggcca cttcataatg atagctctaa tggctgaatt    36360
gaggtactac tggtttagtg ggctgtttca tctatgtatg ttattatttt gatggtgttt    36420
ggtggggggt gggggacat  gactgggatg ggtgacccga tgccttttag tacctctgaa    36480
attatacacc acttgactgc tggtgactgt gccaaaatgc catggccagc cctgtgtgac    36540 cattttaat  ggcccacaaa aaacaattca gagaacagtc agtttctttc actgaacatc    36600
tgtgaaaacc acaactttt  ttacaaatta tattcgcctc aactgtcctg ggctttaaga    36660
ctaggtattt tctattgctt gagccagcca cctagagtct tcccaagttt aagatgatgc    36720
tctctgcctg ggaaggccat tatgggaaaa tcaccaaacc acaaacccac aaacgatgtc    36780
aaacaaagga tgtgattcta agtgtgagct atgggtctg  gcaggtcttg ttagggaaga    36840
acagcccagc tgttaaagaa ataaaatttg ccctatcaat ataagactaa gctgaatttt    36900
ccccagaaac agctttttcc cctaactttt ctcacatttg ctcttaagaa tttagcacaa    36960
gttataaaac tcagaaaagt tactcccaga attcagctta gtaagatagt aaaaaactac    37020
agaaatttag taatttcaaa aacatgcaag ccttgtggat gtttacagcc ttagggagtg    37080
cttaaagttc aaatggagtt gtagaatacc ctgcttacat tagtttattt aaatataagc    37140
ttcatttagc tgtttttatt attattcctt tctcaattat ctattcacca aatagttttt    37200
gaaagcatac aatgttccag acactatgtt aacctttatc taataaaatt agttttggct    37260
atcagtactt cagttaaaat cattatattt tatatgaatg tattatgcaa agcataaaat    37320
aatatatcca atatatcagt cttcagaagt acttgaaata tcttggccca ccaccttccc    37380
ttaattattg ttagcatcat taaaaatgct ttttctttta taagcactgt gttcaacaaa    37440
agaaactaca taaaatatgt ctcatgttaa ggaatgaaca agacaactat agaattctac    37500
attttagtaa aagacgacat ctactgaaag ggcgcattca ctgaaatctc cattctaatt    37560
cactgaagga catttataag aaatgaatat ttacaagaaa tataaagaca ttaatttcat    37620
gagagtagat cttagactat cttagaaccg tgtaaaattt tagccaaatt ttcaagtaag    37680
cttatttgca aattaaaagt gaattttact tgcttacgat taactattat ttaggaaaaa    37740
```

```
gccttcatga gccaaacttc atacagtaaa tttaaatgga agtaagtttt tcttaaagta   37800
tgaattctta tggggaaaag tttgtatttt ctttgggaaa tcaattccat agttatttac   37860
aaactaggct tgtatggact ttttgaatgc tttttaacat ccatactttt aaattagtcg   37920
aagagtaaca tttgttgaaa gctcttagaa aattgcaaac tagtccatgg ttagaatata   37980
tgctgaaaaa gtacttatgt taggtgcttc tataattcaa aatgtcgagt tgaaaataac   38040
aaatgatgtt cagctagaaa taaggagtct cataattctc tgtaatgtaa atggaaatgt   38100
atttaatagg aatcggtttg tgaatagagg ttgttattgt gatgtagata tgtgggagat   38160
ttaagaccac ttcctttaaa atgttgagca aaaggataga catgaccaaa aattattgtt   38220 agtattttc tcctctgagg aatttcaaga gtaatttaag aaaagagcga ttccgtctgc    38280
aaaagtactt taatcttctg cagccaacac tcataaagaa atcatttcct tggcttcatg   38340
ttcaattagt tggttcccat tcaatccata gatatttta ttctgcattt atagttacta    38400
ttcaatgccc aaagtaatag aatgtagaca taggtgctaa ttttttcttg cgttaactag   38460
tgtttggtaa attcatttaa tgtaatcgaa tttaattttt ctaataacag actgctttaa   38520
acccatgtta ctcaaagtgc tggccctaga ggaaagagcg agcttggcaa tgtgtgcaaa   38580
ttaacacact gcttccttca tcaagaaaat ctggcttcag aaaaattctc agctgtacta   38640
agcagtgtgc tttgtgattt acgttctggc acaaccgttt ttcttgttgc agactagcag   38700
caaacaatta acgggccagc agccagtcta tggagcacat ttttagtatc actgatttaa   38760
attatgtact aattttttaa tgttttttt gttttgtttt gttttgtttt aaagcatgaa    38820
gaatagagaa tgtaaatata gttaagaaaa ggcacttaat tttcagctta cgtgtggtaa   38880
agactccagt ggctttgggg ctctcttggt tgcccttat ggccacgagg gatacggtgt    38940
actcagatgc aggctgcaga ttcctcagtg ggtacttgga gacagaggga cccacattgt   39000
actgcctggg ctgtcctctt cgggtaaggc ccacggtcag tcggtatcct gttatctggg   39060
cccgaggtgg agtccatctc accaggacag tagaatcagt ttcattgaca aactggaggt   39120
tagtgggagc atccagttct aggaaaaaag atgaaacatg ccaagaaata tttagatcag   39180
taatgatcat aactcaagtc ctgaaacttg attgaatgtc taagtttct ctcctcaagg    39240 ttgtaactat gtgaaagtca aaaccctgga aaaactgagc cagtaagaga ttgagtgcta   39300
cacaaaactt tgccaaaact ctgccagtca tgagaaattg tggaaccatt ttgcttgact   39360
gtgatccttt gggaagtcta attttccagc aagactttcg catcagtctc agaaattata   39420
gttacattaa agcaatggta tttttaaaaa ggcaaaacaa acacttctga agttcacagt   39480
tagctctgag ccaaacagat taaggaaaaa gggatatgcc tcctaaaatg acagcaagaa   39540
gaagctctct atgggtcaaa agcaatattc tgtgaatagc cctttgctag agaaataaaa   39600
gttattttca catggttcag attagacagt aattacagta atgataacgt atcctcagat   39660
tcatggtagg atactggtga gtttgcacta tcagaatcac ataagttgtg gagtttattc   39720
ttgagaataa taaccagcag ttttcccacc gaaatttaaa ttacctttca aatagaggaa   39780
atctttaaga ggcagtcgag tataataatt gagagcatgg gcttcggaca taggtttatag  39840 agccagctct atcccttcct atctctgtga ccctacaagt tgcagaactt ttttaaagcc   39900
tcagtttctt taagtattca atacggatac tagtaagacc ttccggctgg gcacgatggc   39960
tcacgcctgt aatcccagca ctttgggagg ccaaagtggg tggatcactt gaggtcagga   40020
gtttcagacc agcttggcca acacagcgaa acccatttct actaaaaaca caaaaattag   40080
cagggcatgg tggcacacgc ctgtagtccc agctactcgg gaggctgagg caggagaatt   40140
```

```
gcttgaaccc aggtggtaga ggttccagtg agctgagatg gtgccactgt actccagccc    40200
tggcgacaga gcgagactcc atctcaaaaa aataaataaa taaaataata ataataagac    40260
cttccttcct aaggtcaaaa caaagagtaa atatgagaat aatgcttgta aaaactgagc    40320
agataagctg gtggctagta atactagaca cttgacaatt gctattgtta aatgaattct    40380
actctaagtg ttatgatcct gcattttaac tttgatctag atatatttag ttacacgaaa    40440
aatgcactca aattagattc tcttcagttc tcccctctta gtacccttca gctggtacat    40500
gtattttaga aatgggttac cacttagcat ccatggagct tgtctgagtt ttgttttcaa    40560
gtttaatgtg ctttgtgttc actatgcatt cccttgccgg ctgggtattt ccctctctct    40620
aagccataca cctctgagtg aatggtttac tgcactttct cacaggctgc aagtgagggt    40680
ggagaatttg gaggggagat agagatagga gaagacatac tggttgtctg ttgagcagtc    40740
agaggcttgc tctccctccc atggctcact gcaaagactt tgaagtaata ggtgaccccca    40800
ggggacagcc cggtgacttc tgcaaaggtg ttcctgctga tgggcagcct ctgcccgtgc    40860
tcgccaggca ggttgacggg gatcacatcc acacggtagc cggtcactgc actctcaggc    40920
ggtgtccaca tgatggtgac cttcacgtct gtcacttcca caaactgcag gtccctggga    40980
gagggcactg tatctgacag acaagagtca actggtcatt cacattctct gctgaagatt    41040
acttttaaga agccagtttc ttggatatgt taggcagttc attgagcctc tcattcgaga    41100
gttttgctaa gttttgtctc ttaatcagat cacattttca tggtccagtc atagtgctta    41160
aattatgaca tttgaacctt ttatctaaaa taggtaataa gtgagttacc agcatatgaa    41220
gtgtcatatg gtggtggggg gagagggtta taagaaaaga tactaaaaaa ttttttagaa    41280
aaagcctttg aaataactgc agaaaataat gtaacagttt ttgttttact gaatcatttt    41340
ataatactta agaatcaaaa atgaaatgac ccttaagctt ctaggggaaa atttgtagat    41400
ggacgttatg gtgtcagttt ttaatcagaa aggccagtag ccagctttga taagttactt    41460
atgacatttc agctaaatat cagaagttta gggaaaaact aatatataag atttcttgaa    41520
tgagaggact gttgacagag acaaaacaac cctccttcag gaacaatcct gataagataa    41580
cataggaagt gtcttcttaa aaaagttacc tgagcgtggg gtgccagtgg tttcttgttg    41640
aatgacaaca ggtgtacttt cttgattttc ttccacagca tagatagtga tgttatactg    41700
aacaccaggt tgcaagtcac tgagggtgac ggagtttgca gtttcaggaa ggttgagttc    41760
tgtgctgcta ccttctactg atggcgaata gactattctg taccctgcag attcatgagc    41820
aaaagtaaga tgcactgttt tctttgagac agaggcttag aaaacaccata aatcctccct    41880
tttctaatat cccttagcat cttgcttgat tagtgaagag ccagtgatac ttttttgactc   41940
tttgaatatt gccacttctt ctaataatga ctattcagca cgaagataaa ataagaacag    42000
tcatgcgaac ctttttaata ataaatgtca tccttgaaga cctgacatcc ttaataaatg    42060
tcaattagag atgccattag gtgaaaatat tcatgttaag ctgattttc ctctttgagc      42120
tccagacgag ggaagcaatt aatgaaccag cctaagcaga gttgtctagc actgtgtgtg    42180
tcttttggaa acttcagtga tgaggcagtt gaatcaccta atgagctaag acgacagctc    42240
agctttctcc ttaaggataa atcttagagc aacgttttca ggaaattaca cctcttcaac    42300
cctgggaaca cttgctttaa taagccaatg agctggcttt acaggttgtg tgtatgttgt    42360
ggtgtgtgtg tataagggag ttggtgaaat ggtttcaagg ggaaatgtgc catagaaaat    42420
aactccccca ccccgccac acacacacac acacacacac acaaaccct ctcccataaa      42480
ttatattgga gatttaaagt gatatgcagg tccgcagtca gaatctgcgc cctccctgct    42540
```

```
gatgtcatta agattaacat agcagccaaa gagggggacg cttagctgac ctgtgatggg   42600
agcctggggt ctgctccagc gaacaacaat tgaggtgtca tcaacttggt ccacagtcgt   42660
gtcaggaggg gcatcaggcg ctaagaaaga aagaaagtgg ggcaaacagt caggaagtgc   42720
tactacaggc ctgtgtttta cagaaaaaga ttctttaac actatgtagc acacatgtac    42780
ctgttgtttg tgaagtagac aggatcaaac tctgctcccc atcctcagat atctgataga   42840
catttacaat gtattttcgg ccaggaagca ggtcagggat gttcacagaa gtggctgtgc   42900
ttggaagatc tttgaaatga aaagaaaagg taactaatca gagcaaacta gtccctcaaa   42960
tgactctaca gcttataaga aggatatttt aagaattata tattcatagg aaaagcgac    43020 tagaaggtaa tgtgctaata gctaatcagt gattattatt attatttta cacagagtct    43080 tgctgtgttg cccaggctgg agtgcagtgg cacaatttca gctcactgca tcctctacct   43140
ttccggttca agcaattctt ctgcctcggc ctcccgagta gctgggatta caggtgcaca   43200
ccaccacacc cggctatttt ttttgcattt ttattagaga tggaggttca ccatgttggc   43260
caggctgatc tcgaactcct ggcctcaagt gatccaccag cctcagcttc ccgaagtgct   43320
gagattatag gagttagcca ccgcacccac ctaatctgtg attattaatg tactatggga   43380
aaacaccact tcttgtcttt ctcctttctc ctcctcctcc ttcttccttt cattttcca    43440 actttttttc taaagacgta taattttgt aatcgaatgc caatttta aaaatagctc      43500 tctgcagtaa gagtcagggt agtgattatt ggcggaagat gatggggtga gggtagagag   43560 atattcttt ccttgatctg ggtgctggtc ttgtggtgtg ttcactttat aagaattcaa    43620
attcactgaa ctcagtgctt acgatggcac acacttcagt gcgccaatga agtttttaa    43680 aggcccctca ccataacaat ttgaaaagta tgagtgaccg tactgtgctc acattgtcag   43740
ctgcagtcct ggtaattact tccaccaaga acacagcttt gctgtagga acttgtgcac    43800 aggtaggcgc atgatgcagc tggcatcagg gaccaggaac atgtgacagt ggcttggaa    43860 aaacccggcc acttcttaga aagagtcagt ccttcccttc ctcatgccag agggtggttt   43920
gttcagtctg agctgtcaac cagttccaaa ccacagatac cacctgccta gaggccaccc   43980
acccccacaa ggagagtttt ccagcagctg ccctgaacct gtcttgagcg acatattgag   44040
cttacccagg tactgtggct catctcctc ctcactcagc tcatattcca cccggaatcc    44100
cgacacggtg tcggaagctg agacccagga gaccacaaag ctactggctg tgatttcggt   44160
cacagattca gaagtggcca caagaggaga aagggagtc gtctctcctg tcacggtgtt    44220
gcctagagag tcacagaaag gggaaagtca gccttcagtc atctagaaaa tttaccgtcc   44280
tcgtcgccaa catcatttta aaaaacgttg gtgcccctcc tggaagaata tgaattgaga   44340
aggaaagcat tgcctcagga gagcctagct ctaggaacct cggggtagg aggcatgagg    44400 gtggttgtgt acatactggt cacaggtgtg ctggtgctgg tggtggtgaa gtcaaagcga   44460
gtcacttctt ggtggccgta ctgctggatg ctgatgagct ggccctcgta taccacacca   44520
ggcttcaggc ctttgatggt gtaggagttt aagtggcctg gtatggtagc ttccttccaa   44580
cggcctacag aatttttctg aaaatttaaa ttaacacaca cacacacaca cacacgtgtt   44640
tacaaggatg aacatttgaa gatgatgttc agtaatcttc aaagaaaaat gacttaagca   44700
ggacttaggc agctccattc tagaggaaaa tcatggaaaa ctggattccc aatggttata   44760
tcgttagata tagttagata taatgctaac tattgttaac atcaacaaac tgctgcagtt   44820
tacttactga tacccatact ctgtgctgtt tacctacatt ctcccattta gtctccatat   44880
ccttctgatg ataaggcaat ggcattgttg ctcccgtttt acagacggaa aaacagagtg   44940
```

```
atatgtgata tgcccggggt gacatagttg cagacactgg gcaccttcac tttttttttt    45000
tttttttgag acagagtttt gctcttgttg cccaggctag agtgcagtgg ctcaatctca    45060
gctcactgca aactccacct cccaggttta gcgcttctc ctgcctcagc ctcccgagta    45120
gctgggatta gaggcgtgtg ccaccatgcc tggctaattt tatattttta gtagagatgg    45180
ggtttctcca tgttggtcag gctggtctcg aactcccgac ctcaggtgat ccacccgcct    45240
cggactccca aagtgctggg attacaagcg tgagccacca cgcccaccca caccttcact    45300
tttaccaagt taattgtgtt atatcagtaa cataatatga tgaacctaag ctttgcctct    45360
ctcacttatt ttttattcct accacaaaca gatatattcc tctctgaagt acagaaatgc    45420
caatgccata tattttatct tttaactcag tgggatacaa ttcaagtttc ttgtcctgaa    45480
aaaacaaagg cagaatgttg ctttgtgact catcatatac caggttcaac gagtctggtt    45540
ttgtgactca ttcttggata tgagctaccc catcagaagt ggttacccaa ttttggacaa    45600
gactacagaa aaaatgcaat tttggtttat ttaatctttt gcttccagtt tatatttcac    45660
atcctgttca gcttcattaa tatgccatgg gtcacaaaac tcagtgcaat aaaatgtgta    45720
tgaaagaaac acccttcaga aaagatgaga ctctttcaag tgtaaatact ctaaactaat    45780
ataagtcaaa atatattttt tgtgcccagt gatttttaaa aattacccag tcaaccattt    45840
cctcaataat tcaaatactc aagtgtccat ttatatttt ggaataagcg agagtgatcg    45900
tagtactctt cacagtgaaa ttttaactca aatacactgt ggaaaatttt gaaaccagtc    45960
attgcaatta gctcaaattt agtaatcatt tttcaacatg agcttgtttg gttagttatt    46020
acaagaaaat aacagaaaat aaagtctcag gtggcatcca ttagaaaaaa ccctgaattt    46080
ttgtaattgt taaaaatctc aaaaaattca tcactgctgc ttttttgaaga cttttccaatt    46140 caatgtactt tttttttttt tttttgaga tggagtttcg ctcttgttgc ccaggctgga    46200
gtgcagtggc gtgatcctgg ctcactgcaa cctccgcctt ctggtttcaa gcgattctcc    46260
tgcctcagct tcccgagtag ctgggattac aggtatgcgc caccatgccc agctaatttt    46320
tttgtatttt taatagagac ggggtttcac catgttggcc aggatgctct cgatctcttg    46380
acctcgtgat ccgcccacct tggcctccca aagtgctggg attacaggcg tgagccactg    46440
cgcctggccc aaagtacatt ttataccact tttaagtctc ccattgcaat ggtctcacat    46500
aatactttgg atatccttaa ttttaaagta aataaaatta atgatgtaat aagaagatga    46560
gagactagaa gatattggat gcactgatgc tgttgatttc gatcactgga catcaagttc    46620
tgcaaatggc cagattatgg acataggatg aaagaagaaa aagaatgact tttctttttt    46680 ttttttttcat tcaccatttg ttaagcagtg tgccaggtgc tgaagcattc tagactctac    46740
ggagactaca ttgagccaat gagaaagaca cgattcccct ctttaaggga atctgtttcc    46800
attttctatt attctggtct tgcctccatg tagacaacat gcttacacct ctatttgttt    46860
catttgtcaa caataagtca tatttacaga gtctttaata tgagacttga tgatttattt    46920
atatatttat ttatgttgac acagggtctt tctctgtctc ccaggctgga gtgcagtagt    46980
gccatcttgg ctcactgcaa cttccgcctc tcaagctcaa gcgatccttc cgcctcagcc    47040
tcccaagtag ctgggactac aggtgcatgc taccatgccc ggctaatttt tagccactgt    47100
gcccagacaa agttgaggat ttagctcaat aataccaccc tttccttcca gaatcttgga    47160
cattcccagt gtctgacatt tgtatcatta tatttgttct tcttgtgttt atatttgtaa    47220
tttaaagtat tatattaagt atcttttttt tttttttttt ttttacttc atcagcttt    47280 ggtaccatct ctcaattctc tattttgaaa gataaagctg ttatctcctc tcttctccac    47340
```

```
cttccatatc caccattttt catgtaaatg tttactttt attttgtctt gaagttgcaa    47400
ccaagtttcc atgacacatc tatagaccga tcgcatcatg cattagaaat acattctttt    47460
caatgagtct aacatcatga ctgctgggtg gatcaaagtt tccagaatca aggttcaatg    47520
gaattattcc tctttgtttt tataccttaa tattgctgca ttttagtttg cttcgtatag    47580
gaattattgc cttataatac acttgggggt ttttgaaac agaatctcgc tctgttgccc    47640
aggctagggt gcaatggcgc gatcttggct caactccctg caacctttgc ctcctgggtt    47700
caagtgattc tcctacctca gctcctgagg agctgggact acaggcgtgc gcccccaagc    47760
ctggctaatt tttgtatttt tagtagagac ggggtttcgc catgttggcc aagctggtct    47820
cgaactcctg acctcaggta atctgcccgg cttggcctcc caaagtgctg ggattacagg    47880
tgtgagccac tctacccagc cacatttggg tttattatac attcctccac ctgattgtca    47940
tgttgttatt ttaactgcat tatttgcccc tgtgattaat tatccacaag cctactttt    48000
ccatgaagtc ccttttatt cttggagacc tcaatccctg atccctcaat ccatcctca    48060
tctttctgtt ccatctgtat tggctgtcct ctaagccagc tacgcagttg ttgcattgca    48120
aagttttcca cctctatcag gggtctgatt tggaagcact gtttgctgga ccccacaact    48180
tccttcatat ttcactcttg tttttctgga gtgtatctac aaatacccctt aaagaaaagg    48240
atatatggaa gataaactgc ctaaaatctg tctgaaaata ttattttgcc ctcatatttg    48300
attgataacc tggctgagta tagaagactt taaaagtttc tttttatcct tggaactctg    48360
acacatcaaa gatgcgtcta gacgtggttc tttccactaa ttttctgggc acctaggagg    48420
ccctttaaa tctgaaaaat tctgtccctc cactttagaa atttagaaaa agaataattt    48480
taacagctta aattttttcct gaagagttta aatttaaccg cctgggttgg tcaaattttg    48540
tttgtttgtt tctttgtaat tgtagaattc aatagctatg atttaaaatg gacattttt    48600
tctcctgtgt ttaaaacagt gtttctcaaa ttatgagcca tgaactttgg agttaaacag    48660
ggcaggcttg agagagtaag agaaactaaa gctaaattga ccaatatcct ccttatttgg    48720
tttcttcaat ttctagtcac ttctcattag gaaatcacag ggctattgtt taaataaaac    48780
caacttccat cctttatcta aacttccctc ccatcatctc ttttccttct atctaaataa    48840
attcagtggg tcaaaagtaa agttttaaaa atgatcactt aaaaagtgaa tcaaaaaaga    48900
aatatattaa tttggctttt tttttcaaat tatgaaaatg atgccagtaa ttttcctttg    48960
atgaggttgc aagacatata aaaaccttag attctcttcc cacattgggc aagaacaatc    49020
ttaagcatta tcatttctaa gtccttgcaa aaaagatttc tgtaacataa agagctaaat    49080
tcttccaaat accagcccc ccaccgcaaa aaacaaaac ccaaaaccaa accaaaatc    49140
ccctcagtct acaagtcaat ttaattgacc acatattgtt tgttcactaa acaaatatag    49200
taaatgctat aggaatagtt aatcagagtt gttggctcaa aagctgggaa aaaagaaac    49260
catcagaatt gataagatta ggagactcag tatccaaggt ttctgggtgg gatactcaca    49320
ggtctccacc tgagaatgta cttggaaatg tgagatggct gtggtgcatt ccactggatg    49380
gggtgggagt tgggctgact cggagtctca gtgataaata cttcgacagg accacttgag    49440
cctgaaaatg aaaatgtagc atttaattat cttgaatatt cactcacttc aacttaaaac    49500
tgtgtacatg gacagtcatc attataaaca gctttgcttg tcgttaaatg tgagtataat    49560
aaaattatct ggcattaatc ttttaaatat ttacgttgaa aatcaatgca gcaaatccat    49620
ttttagccga taattattat tcttcacatg agaaatgcaa atcatagttg tttatagcaa    49680
ataaaatata ttttaaaaa aaagtctctt ggcttgcttt tattttctct actatcaaag    49740
```

```
taagaattgt gagaaaattg tgaaacgatc ctacaaaaat aatgtaatac agaacacaga   49800
cttcatttac ttattgtatt gagcctcttt taaagcaaat tctaattttg gaaggttttc   49860
atcaagaatg aatctactac ctaagaagga aacaacattc caaaggccat atgagatgat   49920
gtaaaacaaa cacatttcta aatgggggta gaatcttaga caaatagcaa aggtaataat   49980
taaagaccta gttttatttc tcatcagtct aagcagtcta tcagtttgga aaaaacatca   50040
agttttattt ttattcaaga agtttactcc caaatcacac cattgatcca tcaaattatt   50100
aagtgattaa atttattttt tttccaaaat cagttgtcaa cagaaatgac tttatgaagt   50160
gtatactaaa ttcagtattt ctacaccttg atgtatatca ctgttatcaa caaaatttaa   50220
agtatggttt tggttctttt gtttaaaata aaaggaaaat aagggaagta gcatcaattt   50280
ctaagtagtg ttaactccat ttaagataat aatgaaatag ctagaaaatt tatgcttgca   50340
gaacagaaaa ctatctttc ttaaaacact atctttatga tgtcagtcaa tgtttaaatt   50400
actagaaata aaaattgtgt cttatagtaa ccttttcaag aatttctaac tgacactctg   50460
tcaaacagag caaaattttg tatgtgtaat aaagcacttc accagattat taacagattt   50520
aagttttctg aaagcttcta ggaaaaaaaa tacattgatt ttcaaacttt attatctaag   50580
ccattaaatt ctcttggaaa acaaagcttt ctgtagcaga aaaatatat aacttggata   50640 tccatgtaga ttcagaaatt ctaaaacaat atgctcactt ccacaccagt aacaattcaa   50700
agttggttga agattagcaa atactttgaa tcttaattcc atttaatgca catatttcca   50760
agccacatga acaccaaaat tcatgcataa aattatgagt ttttcatttt aaagttgtat   50820
gtatttcaca gaacacacag gatgtttgtt ttaatcaatt ggcataagtc aattccatgc   50880
ctatctttga attacccctt ctgtttatga agatccttac aaatgtaaac catttttaa   50940 agacaactat tcaagaaaaa ttttggagat gtgactattt aacgtacttc catgtaaatc   51000
aggaaagcta ggaatatcat gtccttaatt atttatgata attggcatag ggctatttaa   51060
atattgatcc tttaaataaa tcctactaca atttcctcca taaagagaca cctgatatac   51120
actttattta gtcttgtcaa tcatgatttt gagggggac aagcttatga tggataaatg   51180
tctattaagt tttgaaaaga taacataaat gacctttact gttcacctct aagcctaatc   51240
atatttctat gtccacaagg acacaaggag gaggataaaa atgggcaggg aaaggaaaga   51300 aaagggtac agcagtggtt tttactcaag ccaaagtgga gtacaactac agaggtccct   51360
tttgctttca taagatttcg agcactggtg tgaaattcca cgttttaaaa tctagccctg   51420
tggcatagcc cacctttaaa ggaaatggac tgaacagcat ggaatttagc atgttttgt    51480 tcaggaagta aagagacttt gtgtcagtta tttcttagat caattaaatt cctatattct   51540
agcttatact acgtataatt actctagctt atactatgta tcctttaaag acagaaaagt   51600
taaaaattat gacatctttt acattattta gatttaaact tttgacagtc cttttcgct   51660 actggtagtt ggtataactt tttaaattaa cttaattggc atatactagc tatcgccatt   51720
gtgaaatctt tactccctct cttattcaat atgaataaac taacaataaa atagttgaga   51780
tgataccaaa aaaaggagat agtacaatgt ctacactttt aaaattagtt tcaaataaag   51840
tctaaatgaa taatttccaa tagtagtgtc cttggagaag ttaaacattt atgatttttt   51900
gactcagtcc tttttttctc tatttatttt gctgagatct gtgcttttct agttgcttat   51960
tgacaaacca aatgcctctt atcttttgct agtttgaaca actctaccaa gttctctgta   52020
ggaggaacaa acaaggcagg actcagagac aatctgttgg taatctgctg ttcccttatt   52080
ctcaccacac tcttaaagcc ctacgtgcta ggccacggag caaaccagac atacagataa   52140
```

```
gcaccaaaga gcatatctga ggtcaaattc caatctcttc cctccgaaat cacctctatg   52200
ctcagtggga tcttgctgtt ctccttttta aagagtagga gtaaggtcaa catgtaatac   52260
tccaatactc aaggattcct tcctttccag attttatctc caacatgtcc acctaaatgc   52320
ttccagcaag cagctatgtg gacagcctta tgttgagaga gacgaagatc tctctcaatc   52380
attcagaagg aaatcatttt cagcaaattg caacaccaat aacaatcata aatatagaaa   52440
ccacagagca ttttttttaga agtttctacc attttaagtat catttgcatc atataaacaa  52500
acaaaccatt catatactta tagtacttcc acaatcagat ttaaatatat attaagttac   52560
aaaaaattaa gtgattccta cacctaaatc ctccaagaaa tacaatttag gaggttggtc   52620
aatctgtgct ataagccttc aaaagtgaag tcaccttccc cagcactgac agtgtctgag   52680
ggttgggaaa agcagaatct tccaagttcc tagaaaaggt gcatctgggt gtttagtatt   52740
taggatggaa cattaaaggt aatcagctac aatcttccca tattacagat gaggaaatgg   52800
aggaatgagg cttggctaac actacctttg gccaagttgt tcccatagct tgttctctgt   52860
cacagtgaat ctttatcac agagttaatc ttaatttctg tcgcatgcag attctgacac   52920
cctgaaactc ttttgtttct gaatgtaggc catattttca gtcaaacgtt agtgaagact   52980
ttggagactt tgcacctcag cagttgctca ataactgat gccttttaat tagcctttca    53040
tgttttatta acatgtttta ttataatcac tcagtgaata tttaaatgca attttccccc   53100
caaatgaact aattacacct acagctaggc atgatgtctt tgtgacctgg aaaaacccag   53160
caataaacat ttgagagtgt ttgaactgtg tgggcagaga gttgaccaag ttactcaacc   53220
cttggcccaa catactgtgt tcctggtggc aactgatcaa acaaatgaaa agtttgatgc   53280
aaagggagct tagatgacat gttgaatgaa cacgtacctt atgctgcatt tcatgccatc   53340
tctctatgca gcttctctgt taagaatcat aatataaagc cccaaacctt tactcccagc   53400
ataactcact tggtggtttt tatttccatg tatggatata agatgaaatt agccagagtg   53460
tcttaaccta acagaatatt ttacagagtt aagaagtaaa attataaaca ggcacatttt   53520
catagccttc tctaccttt acttgataga ggaagagaga aaattatttt taatcaaaaa   53580
ttcaattgat tattagataa taacaagaga aaagggtggg aaagagggga gaccccaac    53640
ttaggcatga gagcattaat aatcactgcc ctgttgttat aacccaattg gcagttctca   53700
acttgcagta atagagctac ttacttggat aggtctgtaa aggttggcaa tgccactccc   53760
caatgccacg gccatagcag tagcactggt atctgacacc atgcacatac ttctcccatg   53820
aatctccaat ttgataaaac gtcccagtct ctgaatcctg gcattggtct aaaatacatg   53880
gaaggaaaag ataaacagcc ttgaagactt ataactacga atttaatttc agggtgctag   53940
agcatacatt tagcttaaat agaaatttgc aattgttctt acaaatatat gcagttaaaa   54000
aaatattttg ttcacattct ttaccttaca ggacagtttg tagtaaaaaa aaaaccaaag   54060
tacctattag gaggaatatt tagttttcta aaaggtaata tttctaaata aaaatgtaaa   54120
gatttagatt tcagtgtata ttgataatct acacattaat tttaaatatt agttattatt   54180
tttacccata ttaatataac tggcttaaca tttaaatagc aagaaaaaaa tctgcaataa   54240
tttcattttc cttacttctt caaaatttaa agaaactgtt tgacatttaa atgaatgaac   54300
tagactttac gagtataccct gctgagcagc ttctaagaaa acctctcagg cttctctctc   54360
agttctggta atctcacgtc aaacaaacgg atgttatcag tttgttttct cagtgagcaa   54420
cctgtctctt ttggtaaaga aatagtaatg gatcacctta aactttgtag tgctggtaac   54480
acagctcttt taaggctcag ccttcactat ttgcttagtt ctattttgaa gggcggccaa   54540
```

```
aaaaaaacct agagtgtttt ggtgggtgat atttacaccc tttgctcatg ctgttacaca    54600
gctggtaagg aagtgagttt gagaccagcc tgacccacat ggagaaaccc catctctact    54660
aaagatacaa aattagctgg gcctggtggc gcatgcctgt aatcccagct actcaggagg    54720
ctgaggcagc agaattgctt gaacccagga agcagaggtt gcagtgagcc gagattgtgc    54780
catacactcc agcctgggca acaagagcga aactctctct caaaaaaaca aaacaaaaa     54840 caaaacaaa caaaaaaaaa aggaaagaat acttttaata gcatggatta tctttatgat     54900
tctaaaccca agaataaatt ccattcaatt aaaataagcc taaatttgtc accaaattca    54960
gcaaaaacca gacgactacc aatatcgaga tattttggtc cagtattaga gagaagactt    55020
tgcaaagttc tttgcaagca actgatcaaa gtctggagcc aacttcagtc atgtgatttc    55080
acatagcttt tcttatctga aacttgctaa ccattccccc tgtgcaaact catctaggga    55140
aatagggcta ctcaccgacg ggatcacact tccacctgcc ccgaccctga ccgaagcatg    55200
tacagttcag catgtgcccc tcttcatgac gcttgtggaa tgtgtcgttc acattgtaag    55260
tgatgtcatc aacaatgcac tgatctgttt aggaaacagg tgggtgagtg agaaactttt    55320
taaagttcca ttgatgaaag aaaaaaggta tgcttctcaa agcatacaac tacttccact    55380
taattatcaa caccttccac taaaataact tttctacaag catagaataa catttttttc    55440
aaagtttggt cagtaataca attttttgcca aaaaaatttt tttcttccca aaatgtgtaa    55500
cttttgcaga ggttacagta tgctcaagta aagaatgtgg taaaatacac tttcctgtga    55560
gaagccagta tttgaacaaa tacatgtctt actttctgaa aatttcttgc ttagttgata    55620
atttccttta aatatctgct tgttaggata aataagaaga agattaaaca tatttatcta    55680
acacccagca tgatgtggtg gtctggtctc tggaataggg ggaaggggag agatacttta   55740
gatttgggaa ataaaatgtc aacagtattc acaacgctaa aataaattag gccaactctg    55800
ttgctcactc tttgagagat cctgagaaaa ttacttttttc cttttgggt ctcagctcct    55860 tgatctatat agagtgaggt ctctatgtgt tattaaggtc tctttcagtt ctgcaacacc    55920
acatgtaatt attactcccg gatggtgtta cccactggac accacaaaag gagaacaaat    55980
tcagaccaat atctacgcac tagccacata gattattaat agctcagggt tctcccgaaa    56040
tattactttt catatcaaag aaatggaaaa ctaaaacact tttaaaaagt caatacttcc    56100
tcatattata tagctgggtg caaaggagaa aaactaatct gaacaaggaa agttagtccc    56160
ctatgtattt gtttcctgaa atctggatct gtaaggatct gatttagaa tagcaaggtc     56220 ttcatttctt tacagaaatt atcctatctt ttctagacat gaatccagtg gcatagccta    56280
aagctgaatg gatcaaatgt ttcattctta cttttgaagc catctttttg gctcagccta    56340
agtacttaca tgctaggagt gtttcagaac attagcattg ctatgccgct tgtcttagca    56400
ggctgcctgc taagcctttc aggcttatct taccatgcac agtagactaa tgaatgacgt    56460
ggcattccat atttcttccc ctgcttttgg catagtgcaa gttttcataa aaaaaagtgt    56520 cccttttctgt acctttttgcc atctcaaata tttttgttaa tcagccagca tacctcgaag    56580
ctgcgagtag gcaatgcatg tccattcccc acgaccattc ccaacacacg tgcacctcat    56640
catgtgaccc atgtcatgct gcttatccca ctgatctcca atgcggtaca tgaccccttc    56700
attggttgtg cagatttcct cgtgggctgt ttggaaatgg ataagaaatg cacttgataa    56760
atgatcacca ggtctaaaca tgtatgtgtg caaaaggatc agttcagttt ggtcatccta    56820
agaattctca cttgggaaga agctttgtgt gcatcaaaga catctaagtg ctgtcaggtg    56880
aaggggtaga attttttgagc cctggaggca gaaaacgtag tccaaacgtg tcatagaaaa    56940
```

```
tagttacagg aagggttagg ggatgttaaa ctaagataat atctacacat ccacacaaag   57000
ggttcttgct gttctagaag cctggattta actacagctt cataactttt cccagttcca   57060
gtttattctg gatcaaataa aaactatggg tttggatata gaattacaag caaaagtggg   57120
ttttttcttc taaactcagc atcttctttt gttgaaagaa ataaaagtat aagcaatttc   57180
tttgtctcat agtcacactt gacagtgcct accgcccagg ctcttgtttc tacaactgga   57240
aaattaaagg gaatctatgg ggttcttgaa atctgaaaac aagtaaaagg tattcgtttc   57300
catttgttcg ccatctatac aaactgggga cctttaaaaa aagagtgaga ttccctacct   57360
gttagaaaac attgagtttt agtcactttg gcacttatta ataagtgata gagcttatgc   57420
ccatcaaacc acaaccatgt gtcaatattg tagctctgtg actaaagccg tcatacatat   57480
attaaatgtt gtaagctact cagttgtgtg ctctttacaa agacaaacct gtgcaaattc   57540
atatttccag acttacaaat aagtaattat attttttgaca ttaaatcatg tcaatgaggt   57600
ttaaaaatta tataaataat tatctaatta ttcttcccaa tccttatgta tatgatgtaa   57660
catcacacac acacacacac acacacacac acacaaacac acttcacatg aagttttctg   57720
ttgtctcaaa attgtgttaa tgaatgaaat gggagtaaac tggacactag tctttagtct   57780
ctactcccta aattgttgtc aaacaagaca acccacaagg gcttcatctt accagccatg   57840
gggcagaacc caaacttctg gtcggcatca tagttctgtg tggtcccaca ccacttcatg   57900
ttgtctcttc tgccctcaga agtgcaatca gtgtaattgt ggttgttgta taggaagggg   57960
aagtggcaca aggcaccatt ggaatttcct cctcgagtct gaaccaaaac tgccaggaac   58020
aatacacaac aaagaaggaa aagattaccg ctgagctttc caatgtacac agaattactg   58080
gtctgagaga gccaggtttc tgcagctcat tcacagacag tctatctcag aataaaaaat   58140
gtctgataat atagttctaa gcttcttagc atatttacct tcacaccttc aaaacaggtt   58200
taaatcccac tttcactgtc atttcccccag cacccccccc acaaaagatt aaatgatagc   58260
tttgaataaa acattgtttt aactggaaaa taagctaagg cactaaaaca ttcatccttt   58320
gtattcctca gccctgtggg atcatctact gattccaaaa tacaagtatc tttaatcaca   58380
tcataatccc aatgtgttaa atcaaatgaa ctggaaggct actcccttgg tgtcatttcc   58440
caacagtact ggggaagatg gaagaatcct cagctgttac gtgagcgctg cgatctcttg   58500
agtccaaact gaacaaaagc gatgcttctt gggcgggttc aaaataaatg gctagaatgc   58560
tggcaaataa aactagggca tgaaagtgag tttttctcac ttctgtggct ccccccttggg   58620 acactcacca gtgtggtctg tgcagaaaga gtatttctgg tcctgctcat aattcgaagt   58680
tgtgctgcac caaagatgtc cgtcctgtcg cccttctgtg gtgcaggagt agaacgtcct   58740
gccattgtag gtgaatggta agacacatgg ctctccattt gagttgccac cgtaagtctg   58800
ggttacagct acaatcataa tcaaaagagt gtcagtaaac agagatgctt tatctcccac   58860
cagcagctgc ttatttatgg cttcaatgag atactgagct tgtgccctca aggaagaag   58920 ctatgagtat agatgatcat ctcgttaatt tcagtcaaaa tgcattactc aggaatccat   58980
gtctactgtg gatagaacga cacctgagtt cttctgctga tgtccttcat gaccacttct   59040
gctgccatgc ctcagtttct ctatttgtaa agctatattt atacaggtca attaaggatg   59100
ctgcttaagg atgttgggat aatatttatg actatatcta tgccataaaa ttaatatatg   59160
agactattct gggggagaat tgtgtagcaa ttgttattgc catagtgact accatgtttg   59220
tagtgcagaa tacatatatt aggttattgg aagatgttta catcacaaag ctgctgaaat   59280
ttgagattta gaatataaaa cattgatgat tattcagaaa gtagctctct tgtaacaaca   59340
```

```
ctttagacag ataaatacaa taaaattttt acccatgata tccatgacca gaaagaaaat   59400
acataaatta aaaagattgg aagaaactat ttcaaatgcc aaccctaatt gttatcacag   59460
ggtggtaaga ttacaggctt cttgtttgtt ttattgtttc acattgaaaa tgtattgtcc   59520
ttcaaaaact aaataataaa gtcatcagtc ctattcttca aaaagataat gcatacctgt   59580
ctcttggcag ctgactccgt tgcccaggca cgtgcaaagc atttgcttat ttccttgtgt   59640
cttcagccac tgcatcccca cagagtagac cacaccactg tctgtgacac agtggccata   59700
gggaggaggc tgggggtgag gctgcggttg gtaaacagct gcacgaacat cggtgaaggg   59760
gccagatcct aatggcatga aaagggaatg tcacaaaact gggtgagaga agacaattca   59820
ctactttctg cagtcaggat cttcaggatc tcacagagat cactctgaaa tctatgtcgc   59880
tactggcctg ggactggaaa aaaatgtccc ttattcagca gtagcttttg catttagcct   59940
aggaaataat ccacaagtgt ctaccaagtg gtctccatcc tccagctcag ctgggctac   60000 tgggattata tttcttttg tttgtttgtt ttttggtttt ttgggttgtt tttgagatgg   60060
ggtctcactc tgttgcccag gctggagtgc agtggcgcgg tctcggctca ctgcaacctc   60120
tgcctcctgg gttcaagcta ttctcctgcc tcaacctccc aagtagctgc aattacaggc   60180
acgcaccacc atgcccagct gatttttttt gtatttttta gtagagacgg ggttttgcca   60240
tgttggcaaa ctcctgacct caaactcctg tctcaaactc ctgacctcag gggatccacc   60300
cgcttcggcc tcccaaagtg ctgggattac aggcatgagc cacctcgcct ggccgggatt   60360
atatttctca atcacagaca tcatcctgcc actccataca gcagatacct tcaacacatc   60420
ctcactcttc tgagtaaccg agctcatcag agggtgcctt cagcagctgt cctggatttt   60480
ctggaggtca cctccacctt ccacatttta tttctcctct ggattatttg tgattctatt   60540
gtgttttttc taaaaccaat tgatcctctt aagacagctt tcctttcaga ataacacaac   60600
aggatgtgtt gatcttttct ttttttcttt tttttttttt tttttttttg agacggagtc   60660
tcactctgtc acccaggctg gagtgcagtg gcgcaatctc ggctcactgc aagctctgcc   60720
tcccgggttc acgccattct cctgcctcag cctcccgagt agctgggact acaggcaccc   60780
gccaccacgc ccggctaatt ttttgtattt ttagtagaga cggggtttca ccgtgttagc   60840
caggatggtc tcgatctcct gaccttgtga tccacccgcc ttggcctccc aaagtgctgg   60900
gattacaggc gtgagccacc gcgcccggcc gatcttttct ttcaactttt agatatctgt   60960
tctcttgaag gccagggccc accgcagaac agaatcaggg ctgaggctag accaaaggta   61020
cactgaattc agtgcctccc taagtgctgc tgaacactag aacccaaaga tgttcacaga   61080
caaagaatcc caaggtcaaa cgtactaggg agacatggcg cccatcccct acactctacc   61140
atggagagta tgatgtaaag gaacacacag attctgcaga gcaggttcca tttttgtttaa   61200 cccattgctt ctcaaacttt tttgaacaat ggaatctttt cagtattggc aatattcata   61260
tatagctaac atttattgag tgtttatccc catttaattc ccacctacac ttttaatcta   61320
ttttggtaga ctgacattta aatttttttt tatttttat tttatttat tttttgaga   61380 tggggtctcg ctgtatcacc caggctggag tgcagtggtg cgatctcggg tcactgcaaa   61440
ctccacctcc cgggttcatg ccattctcct gcctcagcct cccgagtagc tgggactaca   61500
ggcgcccgcc acaacgcctg gttaatttt tgtatttta gtagagatgg ggtttcaccg   61560
tgttagccag gatggtcttg atctcctgac ctcgtgatcc gcctgcctcg gcctcccaaa   61620
gtgctgggat tacaggcgtg agccaccgcg cgtggccgat gtttataatt ttttttggcc   61680
agtagcaatt ttattaatga taataaaata actcaaagat attatcaaat ctaatcttgt   61740
```

```
tcaccttcat aagtgctcaa agcaagacaa aaactcatca aaagaagaaa aattagaaca    61800
attaatattt ttaattgaag gatggctgag acactacgta atgatgttgg cacatcatat    61860
agtaaaaagt taatcaaaac atattaaaaa taatgagagg agtgcacgtc cttgttggcc    61920
atatttctct cttcagattt ttatgaaaca tttatgacgt aaaaatcttt ttctcatgcc    61980
aaaaatgatt aaaacttgtt ttttaaaaag aatgcttaga tatcatgtct ttcatggcca    62040
tctctaagtc ctctctgaat ttctaaaatt tcgaatgcca atacatgaag gaataattg     62100
tgtgttactt tatagaatgt aacaaagttt gccagagcat agaaaccaca tataaaggat    62160
ggtttccact acaaaagag ttcaatgtcg ggacagggaa gtatatttca ttcaaaaaca     62220
aacaaacaaa aaatccaaat gcactttttt tgtcctttcc tagcagaaga accaggtagt    62280
catataatta attataactc tcatttcctt tcaaatgaac tttggatatt caaaatacgt    62340
gtgtgtgtgc gtgtgtgcgt gatctatcca tggtaagttt tatgatgcta gcattcttta    62400
aaactcagtt ttatcttttg gagataaatc tggcttttt cccctaagg tttatttgta      62460
tgtcattttt cttttttct gaaaaattta aaacttgaca ttaaaaaaag ttttaacaac     62520
caataatgtg taaattatct taggttatta gctgaaacac tgcaaattat cctcaaatgg   62580
catgtcaaag gaaagatgga tttgcggaaa tatttcttga cctgcttccc catttcccgc    62640
ccctgctcgt cctgtgcctc accgctcgat gtggtctgca cagaggtgtg cctctcacac    62700
ttccactctc ctcggccgtt gcctgtgcag atgcactgga gcaggtttcc tcgattatcc    62760
ttcttgctcc aggtgtctcc aattctatag gatgtccttg tgtcctgatc gttgcatcta    62820
tctgtgtcac aaaggaagca catacataca tcaggtcgag agtcgcaagt ggtcaattca    62880
aacttaaaaa aggaatgcta tctatgcctg gtaatctatt tttggtaata tgttcatatt    62940
cagctctggt gctgcaaggt attacacttc tgaaagatga aattacattt gttacagtgg    63000
aaaggcagct gaatggttta gtctagtttc atctctctgt caaataacat tttcatttat    63060
ctatttattt attgttttca cactgttcct ttgactaact tcattctctg gcattatatt    63120
tcatctttt ccttctcagg ctcttccagg attttctta gtcatcactg tttatggcct     63180
gcctttcaat agggaccttg ctttagaaaa ctaaaaacag gctaagcgcg gtggctcacg    63240
cctgtaatcc tagtacttta ggagggtgga tcacctgcag tcaggagttc aagaccagcc    63300
tgggcaacat ggtgaaaccc ccgtctctac taaaaatacc aaaaaaaatt agccggctgt    63360
ggtggcgggc gcctgtaatc caagctactc gggaagctga ggcaagagaa tcgcttgaac    63420
ccgggaggtg gaggttgcaa tgagctgaga tcacaccatt gcactccagc ctgggcgaca    63480
gggtgagact gtctcaaaaa caaacaaaa caaacaaaa caaaaaaaac aagcaaacaa       63540
aaaaaagctt ataacaatgg ggaggcaagc aggtatcaaa gggtcttcac caatggctac    63600
aaagaagcta taagaaggtg gtagtatctc tttcttcatt tgttatgtaa aaaatgtaga    63660
ggatgcacaa tttctttgac taaaatatta ttttcccttc ccctataccc aaacatctac    63720
agtatttaaa aatcactagc aaaatagccc caaattattc agtgttagcc ctccactgga    63780
agagtgggat caacataaaa tgataatttg taactaaatg accattagtc tatgcgtgca    63840
tttatctggt aaatagatta tttaaattat aatccaaatt tgctctgtgc cacgatgtga    63900
gtatagagga tctgatgtct ttgtgaattg gatattgttg caactcctgg gttagagaaa    63960
aaaaattaat agttgatgta ggttcaaaca aatacacacc cacatccatc taccacaaga    64020
atagaagttt gcatgaaggt ataattactg attagagctt tttcccaaat ccccagcgaa    64080
aagtattatc atcccctgaa cctccatagc actactttca gtatttctgt tgaaatcttt    64140
```

```
aatactgtgt tttgcagatg ataaatatgt ataagacttt ctcatctccc tgaccccta    64200 agtactcttt gaaggctggg ctaatgttca tttcatatct gcaccccctat aataccttga  64260 acaaagtaag tccttataaa attttctgga ataaatgact tctctttgag aaacttttcc   64320
caacttgcta tttaaagagt tctaaataac agataaggtt tgaatcagac atctaatttg   64380
tcttaagcta aaatattgcc acaaagatct tggaagtctg atgatcacag taacatttta   64440
aatgcaaaat atctaataaa ccagcaagtt tctgggaaag cttggtcaa aatggttacc    64500 acttttcatg agagacctat ttttgttagc aaagaatttg aatttggatg atggctatgt   64560
taaaggtagt taaatgggtt cagctagata aataaaacag gttcaaatta tttggatttg   64620
attttaaact tatttacaac accagtagtt aatggctgtt ttacttcaac aaactctcta   64680
gctgttatta gttacaata tcaaaaaagg agccttcaaa cccaaaggca acaattaaga    64740
ccccaagaca atcttagaag gagcagtaaa gacaccagag gccagcttct ttacagcact   64800
aatcaaatgc gttaggtcag agacactatc cctaactcca gagtagataa atcattttaa   64860
tttatgggat aaattctttt taattttatc aatttagcct gtgaatgtgc cctatttaaa   64920
tttcaaacat agaaggaaac ctaaaccttt tgttcaactc tatgtcagtg gcagtgagct   64980
gagattgaac cttatcaaag tgatatgttt ttctattat gtagtcttct ctgaagatgc    65040
ggaataagtt ggttatgaaa gttttcttga cttccagaag ttaccaaagc atgctgatat   65100
actggatgtg ttctgagtaa catagtatta cccttctctc taggaatcca gaaaacaata   65160
cctggcttaa tctttaacat aaagatgtaa aacatacttc tagaagtgca agtgatgcgt   65220
ccgctgcctt ctcccaggca agtacaatct accatcatcc agccttggta gggcttctcc   65280
cacgtttctc cgaccacata ggaagtccca gcagcatgat caaaacactt ctcagctgta   65340
gggaaatttg gaagaaaaac aggaaaaaaa ggttattttg aattgtgcaa gctccctgta   65400
atttaaagtg tagtgtgtaa gcaaaaattc agccacattt ttttaagtg gcactctgtt    65460 cagaaagaat gacacaccca gcatctaagc acacagtaag tagccaaggc aaaagaaagc   65520
tcaagctgag ttggcaggca gaaattccat tctcctaata agtacatgga ctacatattt   65580
tcagcgagcc ccaaacttcc cagcagcatt tccagtagca aggatctatg tatgtatcta   65640
gtctgtggga gactacatat gcaaaattcc aatcttaatt ataaatgacc aattatgaat   65700
tttgagtggc ctaaatacaa tgacaaagaa agctattttt aaatattgga agcaaaaca    65760 atacaaaaca agacaaaaac ctctaaatta gaagacaagt aaacagagta aaatttatag   65820
ccagaaactt tcaggcttgt acttacaaaa ttcaactgag gattgagatc caagaaagct   65880
caacaacttt taatttgaaa agaaatgagc agagtgtgac aagcacacac tatttcatgt   65940
ttcggtccag gacattccat atagaaatgt gtccaaagtg tcattttttt ttcttttaaa   66000
taaattatat cttgacgaag gaggaatctg agatcagcta ttaggtaaaa gaaatgactc   66060
cattctaaat ctttcaattc taccttatgc ttttgaagca aagttaagac ttctatgtgt   66120
agtcagtact ttttgatcta actcctgtaa gaagactatg gattatataa taattcatta   66180
tttcaaacaa aattcccatt tctttattgg ttttcactgg aattcaggtc tatgacctat   66240
gtagatgtga ttctggtcca accccacatt agaactaagc atcccagctc ttgctcagcc   66300
ctaagactca cacacctatg ggcttgcagg tccattctcc ttttccatta ccaagacaca   66360
cacactctaa catgtaacca ccagtctcat gtggtctcct ccaggtgtca ccaatcttgt   66420
aggactgacc cccttcatgg cagcggtctg ttgaagatac aacgaaaatg ttaggagagg   66480
gcagaacaga ttttttttttt tggtctcata ttccacccat ggtaggtact taggttggct   66540
```

```
aaagtagaga cacagacaac agctttccca tcagagacag gggaaacgtt aacaggtctg  66600
gtcacttgga gtcaattcag ttaagtgtct tgcttagaac acaatggaaa accacagaga  66660
aatctggatg gcaaggaaga ggtcatgaat cctgctttcc cagagagatc acaggaaatt  66720
gggtcctaag cagaaaagaa aggctgggag gcttggtctt cactcataca cagcaggcta  66780
agactgagac taattcagtg aaaaggccac atcaggcaca gcactccagc ttttgggagc  66840
atggagagcc tgtattttac cctaggatag aaatgtcatt ttggtggaaa gcaaacagac  66900
atatgcatat aaagtgtgga aatcctggta gttttctaag ttgttaagcc caatggcaca  66960
ttcaaatgct gaactagatt gtaaacacta tggacccttg cctcttgcga tttgcctgtg  67020
aacttggata acccctaaca tgaaatatgg ggaaagttga ttgggcctat tcacacggga  67080
cttgttcttt tgaatagaag tctttaagac gacttatatt taaagaatgg attaaaaaac  67140
ttaaatacta tcttaataga atctattggt aacccagtga atcatactgg aaagagtgcc  67200
ttagctaaac tagagttgag aatcagcccg gttcccaaag ttccttagca aactctattg  67260
ggttaataat tttgtattat ccctaggaat agtgacatct gcttcctggg tataacctac  67320
tggtcaccaa gaaaccagac tgtttctgtg aggtgcaaga ggtctctgca ttgcaaacat  67380
gaagaccaga caacacatgg ctggttcact cttcatgaac accttcccag tcactgcaga  67440
aaagtctcat gatttgtcta gcttgaagat atccaggtga tttaaaatgg gcaactcccc  67500
taagcatgtc ttactgaaat ggaacccaag aggtctcttg gttctactat gtacagaaac  67560
acacacactc ataaatgcac acacactcat aaacgcacac acatcaaaca ctgattccat  67620
ctgtgctcat acccgtcttt aagaaacaca ggaaccagtt gggtgaccac ttaagagtac  67680
ctggtcacca ggggcaaacc tcaaagttcg gaatatccag tcatggataa cagaaaatga  67740
cagtgatggt aacagagaaa ttcatatttg atattttggc atcattttac acaatctctt  67800
ccttacttgc gatggtacag cttattctcc ctcgcccagc cccgatgcag gtacagtccc  67860
agatcatgga gtctttagga cgctcataag tgtcacccac tcggtaagtg ttcccagtgt  67920
acttgtcaaa gcaagtctct tcagctgagg ggaaaaggaa agtccatgtg agcctcactt  67980
aggtacaagc ttttctagtt cactaatccc ctctaaagga aaacccactt ctctattcca  68040
caagtaacat ggtacacctc aaagaataaa atgaagtgag agatacagat ttttatccta  68100
agctctaata aggccatggt ttttgacctt gacatattgt caaattttct gtaaattatt  68160
catattgtag aaaaatctca ggctcttagg aaaaggccat ataaagtact aacttatgac  68220
agagctagat ttgtgaaggg tttcacattc caatctctga ctcagaaagt caaagcaagg  68280
ttcacataaa aagcaaacga ttggccgggc acagtggctc acgcctgtaa tcccagcact  68340
ttgggaggct gaggcgggtg gatcacctga ggtcaggaat tcgagaccac cctgaccaat  68400
acggtgaaac cccgtctcta ctaaaaatat gaaaattagc tgggtgtggt ggcatgtgcc  68460
tgtagtccca gctactcagg aggctgaggc aggagaattg cttgaaccct ggaggcgagg  68520
gttgcagtga gctgagatag tgctactgca ctccagcctg gtgacagagc aagactctgt  68580
ctcaaaaaca aaacaaaaca aaacaaaaca aacaattcga agatccccac ctcccacaag  68640
gccttgacag ttgttaatcc tatgatttcc attttcccct gatcagtgct tctctgacag  68700
agttgctata atttatgaga aaaatatcat tggtcctaaa ggaatgagaa ctttgaagtg  68760
gctaatggtt ttgtgttaac tgccgctgac aaatcatttt acgatgtaag tccccaaagt  68820
gttttctggc tcataaacta acagtttaag atttgagact gctttctaat aaattaaaat  68880
tttataagca atttttttg tcggaggaca cacaaaatct ttcattttc tcatcaaaaa  68940
```

```
ctttgggaga gtaaagcaaa aagaagactc taggaactaa tttgggaaag attcgtttct    69000
ttgttttaaa ggtaaaagca tgtgaaaagc aaatataagc agtttttaaa cttaagagga    69060
aatgacaggt aattctatta gaaaatggt gtatgtattt ttacttacta atgcaaagtt     69120
taacaattac cacttcatgt attaaaagat actaactatg gggcttgttg tcacttacct    69180
tcaggtttac tctcgcagtt aaaacctcgg cttcctccat aacaagtaca aaccaacgca    69240
ttgcctaggt aggtccgctc ccactgttga tttatctgat agtgttttcc attgtcataa    69300
caaccggctg caaataattg aaggaaaacg ttacatttgc atttctcctt ttcccaaaat    69360
tatgaatttt tcttcatgtg aatattgacg tacatatttt ttttccttta actttgctaa    69420
aagttatata caatgatgtc atttccatct ggccaggggt ctacataaaa aagttggaaa    69480
cattttggaa ggcagacaat tgaagtcaca ttttttaaaac atgcaaggaa cttaaatatt   69540
cttttggagt aatagtcaaa aaggacaact ttaagcagct ttctcaaagc aaaaggaggg    69600
tgtgtctttg aaaaacggaa agaattccaa cctctgttct tggtgaagta tcctgagcgg    69660
ccctaaagag gtctgaacca attacatctc ttccaagtta gttagaaaca agacagctat    69720
ttcaataccc ccttttccacc cccatgttga aaatatttga ccaattattt aacagaagga   69780
aataagtagc agtaaggacc acactaatcc cagacggaaa atttatagac atgcatcatt    69840
tttctcttta aaggcaagtt ttggttaatt cctagaagga caatctgaac gtgcagaatt    69900
tattagaaca cgggaaagtc gcagagtcct cgtcctccaa tgcacggtct tatcatccca    69960
ggccctcaga accagcgtgc tcaaaactcg gtccttttgt gtgcacagct ggtttctctc    70020
agtaaagcgc gcacacactc gcacacacgc gcgcgcacaa aacttcagcc ccaactttgg    70080
tcggctttag ggtcccatcc ctgaggcagc ctgtttcagc ccgcggtcag tactcacgct    70140
tgctttgact gacagccacc ggggactggg gctgaaccat ttgctgagcc tgcctcttgc    70200
tcttcgaggc tcccgtggag ggcaccgctg tccccaggca ctggacggcc agcagcagca    70260
gcccgggccc cggaccccta agcatgttga gacggtgggg gagagacgcc cgcaccggga    70320
ggcaagttgc caccaagttt gcttcccttc gcaacctgcg ggaaaaatcc cttctaatgc    70380
ctcccggggg ttgtcgcctc caagaaggtg ggggccagag ggtggggaag gggacgggtg    70440
gagggacaga agggatgcag aggaccagag aagttgtggc tgcaggtccc ctcttcccgc    70500
tcgcgcctgg ggttccctct cctcccctg tgcagcacag ccggcgcggg cgtccgagcg     70560
ccgggagccg gggcttatat gggacggtcc cctcccgccc ctctggaggc ccggggcgcg    70620
ggggaggaga gacccgccgg gctgtccccg ccccgcccca ccccacccgc ccgcccgccc    70680
gccggccgcc gcagccgacc gcgcgccgat tggcccgggc tccgggtgac gtcacggggg    70740 actgtggggtt cgcagcgaac aaaagagatg ctgatggccc gccaggactg gggcaagaca    70800 acttttttc ggtttccttt gcggtcatca aacttttag gggatggggg aagggatggg      70860
aagcggctgg gaggaaaggg agtggctgga cttgtgtgaa gcgaagggt tgcaagacgc      70920 tcccccttcc cttttctttt ttattgggggg tggtggtagt gtttgaggac attgcgtcac    70980
ctctcttcgg ggtggagggg gggaatctct gcttatagga gtgtattttg tgaggaagaa    71040
aacccataaa atatccacga ccttgcagct gttaagaatc cagactttc agtcccaggg     71100 cggggctgcc tttcccccca tcccgctccc tttctttgga ctaaagggta ctgactcggg    71160
actcccttat tttgtcttca cagctccctg ttcggacttc ttcccttctc agcgctgtgc    71220
ctgtctggct ctgagaaagg gccagcgggc gaacgggag caaaggggaa cagagacctt     71280
taatgagctt ctactaagta ccgggagttc cgcggggcgc tttgcagatc ccggggaagt    71340
```

```
tcagagaatg aagttttctt ttgcaaggac aaagtaacag tttactttt  tacacatgca   71400 ggaaagcctt  cctttcctgg  ggatgggacg  cccgtttcca  ctgaaagtga  aatcactgtg   71460
aacaacctga  aaattggaaa  gttggaccag  ctgtggggag  agaaaggtct  tcgtgtcctt   71520
tcccacgttc  accgtgccag  ttacacacaa  agcagagatt  ttttttgcttg aatcattaaa   71580 agccgggtgg  gtggggggca  ccctatgtac  tgtcttgccc  tccttcggcc  ctttctcac    71640 atttatttgc  cattttcttt  ttgctgacaa  gttccattac  agaatgcccc  ctccatcccc   71700
cgccgccaga  ttttttatat  ttcaattgtt  atttactcca  agagtgtgga  aagttctcct   71760
ttaagattcc  cccgccttga  actctaaact  cagagtggaa  agggaatctg  aaaagtctct   71820
catttagcaa  cacatcacat  cagtcctttt  tgtcagataa  acacaggcac  aattgctttt   71880
aaagatcttc  agaaggagga  gtccaccact  tccacagtag  atccagagag  acccgaactg   71940
aatgctttgc  cttctccttg  tgttaggagt  tcagaggttc  catttgctttt aaaacacaag   72000 aagctactaa  taaatatat   ttatttcggc  aaggtaccta  ttttctccaa  aagtttcacc   72060
ttcagtaatt  gccacaggag  taattagaac  tctgtgttct  ataaaatgcc  tgacacatta   72120
aagacacaaa  attagcattt  gttttttattc atgcaaggat  ttaaaaccaa  accaaaacaa   72180
agcaaaacac  ccagcaaata  tcagtttcct  acaaatagtg  taaaaaaacc  tcttgaggaa   72240
tctttgtgac  ccacactcca  aattgaaaga  gtgccatgga  tttccccaaa  tttagaatcc   72300
tgtctgggtt  agaggatttt  tttggaattt  ctcatcactt  gacaaaacag  ttttctctttt  72360 tcaaatataa  aagagctcct  tgtaaaatgc  ttggtaaatt  tctgggaagc  cgagtgtttc   72420
ttccagaggg  aaggatacct  ggaaatccgg  atgtaagcaa  gataaacctg  tagctaaagc   72480
tttcttaaaa  ttcattgatt  ctgggggaag  gaaataagtg  attagaaaag  tatttggtca   72540
accaaaacca  tgatagtttg  atatatttac  tgcactgaaa  atacactaga  atcatatgca   72600
tagtggagct  tgaagtggaa  agcccacctt  acatttttgga agaaactttt  atatttcaat   72660
cccatagata  tctaatttat  ttaaggaaac  aggatatctc  tgtctcataa  gaaaaaaaat   72720
aacatctgac  tgatttttat  aggaatgctt  gggagtttac  tcttttactt  gaaaggtttt   72780
tttttttttt  gcctttttttt ttaaacttta  gaaacagagg  cgtttcttag  ttaagataac   72840
agggcttact  acagtattct  ttaattatca  aggtcccttg  taactctaag  tctgttatct   72900
ctaattggag  agataattaa  atcttaaaga  ccactctgac  tctaattcaa  ccaacgtgtg   72960
tggtgtccag  gatcgttgga  cttccttaag  aattctattt  tatccaggtg  ggttcttcct   73020
cagtaaattg  tattctccta  ttggtaggaa  atactcttgg  atttctttct  ttctttcttt   73080
ttctttcttt  cttctttct   ttctttcttt  cttctttct   ttctttttcc  ttctttcctt   73140
ctttctttct  aaaactgtat  tcagagagag  aaatgtgaca  aaaaaaggga  aatcaataga   73200
gacagaaagt  agattcatgg  gtacccaagt  ttatgggctg  ggaacaggaa  ttaactgtaa   73260
aagggcacag  ggaatcttat  tgaggtgatg  gaaatctgtg  ttctaaaact  acattgcagt   73320
gatgactgta  caatttggta  aaagcttcaa  aattctgggg  attatacaca  aaatgagtga   73380
attttacggt  atgtaaatta  tgcttcaata  agttgttttt  tttcaaaagt  tgatttttaaa  73440 aattagtatt  tgttcttttt  tactcttaac  catctcctga  ttttggtttc  aaagacttgc   73500
tctcaggtag  cagcaacata  cacaaggcgt  cctcatttct  tcattttttct gagaggaagt   73560 ttgccttgaa  tatagtagtg  gatttcttct  acaccagtaa  ctccttctga  aacctactat   73620
ttgtgtgaag  gcatatatgt  ggtagagaca  gaacaaatct  tcatttagga  ctgtgccttg   73680
tttcttcttg  gaattgccat  agtgatagaa  tttttcccaga gcctcaggca  atttaaactt   73740
```

```
tttgtaacaa aaagaagcac atatattttc gggaactagg ggggtgtggg tggcgggggg   73800
caatggtatt gggaaatttt attattccag aaggttaagg aggagcatga gcaattatgg   73860
aaatctgaat taaattgatt tcatttgttt tgaagattag caatggagac atttgattaa   73920
gcacaaaaaa taattgatca gatccagtca tttagaagga ctgaaataaa acaggctag    73980 gtgtggtgat tcattcctgt aatcccagca ctttgggagg ccagtgtgga agggtcactt   74040
aagcccagga gttcaagtcc agcctgggca atatagtgag acactcttaa taataatgat   74100
aataataacc agatatggtg acaggcacct ctcgtcccag ctattcagga gtctgacatg   74160
agtcctgggg gatgactgga gcccagaaga tcgagagatc aaagctgcag ggagctgtga   74220
tcacaccact gcactccaga cccagcctag atgacagagc aagatcctgt ctcaaaaatt   74280
taacatttaa cattgaaatg ttaaatgtta aaggttacat ttaaatatgt cacatttaga   74340
tgttacattt caaatgttac atttaggtgt aacatttaat tgatgggctg ttttttcctga  74400 aacctttggc tttatcctg ttattaattt cttccagttc tgctagagag gaggccattg   74460
actctggaga gctcgaactt tcatttcatc ttcttctata ggtagattag agggagataa   74520
attagggtag tttttttttt ttcttatttt gaatttttt tttttttttg cataaaatg    74580 cttcccttct tccttgaaaa tggccacgtt tacaaaaatg ttactcatta accacaggtg   74640
tgagaagtta aaaataaact tccctgcggg cagccctcgt aagtagaatg tctgaaaagt   74700
ttgtcaagaa ttgacagggt gcctgcaacc agggagaaaa tactggataa gggctttaaa   74760
ttatgccatg aaagctaacc agttttcgct taataggcat tttgtttaca ttttaagtga   74820
ctttattttt taatcagcac ttttttaaaag ccttaatcta tgcttttttgc ttcttaacag  74880 gaatattctt ttctcattag agtgatgtaa ctcccaacag gcatggcaaa ggtgtttaac   74940
ttatccagta aaatgggaac taactactgt gtagctggaa catgtaacca aaactgtctt   75000
ggagaacatt tcatctttcc aagcaaagta gcagcttctt gtaaaaattt taattttgta   75060
tgttatttca tgttgctggc attaaagagt tttttgttgt tgttgaaagg ctgaatttaa   75120
aaaaaaatag aagttttgcc atatttaaat tattttctat ccttttttgca ttaacatact   75180 ttaaacatct catatgcagc taatcacaaa agttagttga gccaaatgct taaaaataac   75240
cacaaacatt atctagtaaa taacaattta tgccaacaat agactatttt gatatgagct   75300
gtcaatattt atgcctacct gtctaattag tgaattaatt agttaaaata aattaagaat   75360
acattcaatc gaattgtaaa gatgccatat acatgttatt gtaaatttat attgaactat   75420
tttctagata agtttgatat attctttcat taagtatgac cattttactg agataaaatg   75480
gacatttaaa atcattacta ttttaaacat taaaaactaa ggcactgctg gccgggcgtg   75540
gtggttcatg cctgtaatcc cagcactttg ggagaccgag gcgggcggat cacgaggtca   75600
ggagatcgag accatcctgg ctaacatggt gaaaccccgt ctctactaaa aaatacaaa   75660 aaaaaaaaaa aaaattagcc aggcatggtg gcaggcgcct gtagtcccag ctactcagga   75720
ggctgaggca ggagaatggc gtgaacccgg gaggcggagc ttgcagtgat ccgagatggc   75780
cccgctgcac tccagcctgg gtgacagagc gagactctgc ctaaaaaaaa aaaaaaaaa   75840 aaaaaaaaa aaagaaaac taaggcactg cttacatgca tgcacattta agtagtcacg   75900
aagtcacaaa gatttcagca cctagataga aataaatagc tacattttat taaacactct   75960
aaaccagatc cagtactaag tgtttcatat gaattttttt catctaacca tcaacaaact   76020
tttaaggtaa gcactatcat cctctcctct tacagatgag gatataaagc ttagaaaaac   76080
aatgtgcaaa aatgctactc attaagcaca gatgtgaaaa ggaaaaagaa aatgccctga   76140
```

```
aggcagctcg catgagtata atgtctgaga agtttgttga taattgacaa agaatgaagt    76200
tttctcaatc acaagccttg tagaaattgt ggcgtcaagt tgtgtcactg tcaataccag    76260
gtgattagtc aagtgattac ataatggtct ccctcagaac caaaggtatg ggcaagacaa    76320
ctggctaaag aattttgtgg gtgacttctt tcacatgaga ttaatttatc aaaagatgtc    76380
acacaggact ctgccaactg acacgctacc agtttccatc tgttgtagcc aaggccattc    76440
ttctgggaac caatttcctt caaacagcct ggctgtgttt cagcattttg aatcaaatgt    76500
ggaagattgt taccatcgac tctccactgg gctggaagtt tgctggggggc agaggctctg    76560 tcttgtttcc tctgtatgcc cagcactagg taccaggcac ccttggataa gtacttggca    76620
aatgtcaaat gaatgaatgg aaggagagaa gggcagatga caaacactct gagattcaca    76680
ttcagtgact atccagccag gcacagtgct aagtgctctg catatgctat tttattttat    76740
cttcaaagct actgccagaa gtagatatca atagtgccat tttactctct gaagctcgga    76800
gctgaaagat ggtcctagag cttatgctgt aagaaaggga cagagctgaa attgaaatca    76860
cggtcctcct gacacaaaat tcttgctctt accgaagaca tacatggctt tccccaaaga    76920
gactttgccc tatatgttaa agaacgttg gaaacactct caggcagtta ctttttatct    76980
tcctctagat cgttctgcct tgcttctggg ccctgggcct gaccctgtga actgcggggc    77040
tgcttcctct gtttgctgga ggacagagga cggagatgag agttgttcct gcccactccc    77100
tccttgttct ggcttcagtg ccagagttct agtggcagct gcctttccct aggacctgca    77160
ttatcaatgg ggcaacagtg ccccaagagg gtaaaagtgg gttcttgggg tagaagggga    77220
gtggttaaaa aatttcaacc ctacctaata aaaattttat tccttagttg tgaatttaac    77280
actttttttt tttttttttt gacagaatct tgctctgtca cccaggctgg agtgcaggga    77340
caagattttg gctcactgca acctctgcct cccgggttca agcgattctc ctgcctcagc    77400
ttcccaagta gctggaacta catacatgag ccaccatgct gggctaattt ttgtattttt    77460
aatagagacg gggtttcatt atgttagcca ggctggtctt gaactcctga cctcaggtga    77520
tccgcccgcc tcggcctccc aaagagctgg gattacaggc atgagccacc atgcctggcc    77580
atgaatttat catattagat agactttaaa tttcatttct ttcctggagg gttgtataag    77640
gtagggcatt aatacataaa agaaaagg agaaacattg ctctaggaca gcagtcctcc    77700
ccaggctttg gtcctccaag gctccagcta tcgctggctc cttccccatg atggcagccg    77760
taggagtgac aaactgccta cattgctagt ccctgggaac ctcagcatcc ctttttat    77820 ccttggtcat gcccacactg gggtaacagt gctttcacaa aattctcccg atggaaatca    77880
ttttaattcc attttctgct aaaaccccgg ggatccagat tcttttttt tcttttttt    77940 aagatggagt ttccctcttg ttccccaggc tggagtgcaa cggcgtgact ggctcactg    78000 caacttccac ctcccgggtt caagcgattc tcctgcctca gccttacagg tatgcgccac    78060
cacgactagc taattttgt attttagta gagatgaggt ttcaccactt taaccaggct    78120
ggtcttgaac acctgacctc aggtgattca cccgcctcgg cctcccaagg tgctgggatt    78180
acaggcatga gccaccatgc ccagcgacga tccagattct aaccatccaa tgatgacatg    78240
agcagtccac cccatagttt taagtcttaa attatagcag aatagactta ggacacacga    78300
attcttttcc aaacttagca actagtatta atcatgctgt gatttctttg tatttcccat    78360
gacttacatg gtcttatttt tttctctcta ctgaatgcat gcgcttttaa cactctatct    78420
ttcccaaagt aaaacgctca gatgatgaa gcaaatgaca tagtcatcat acaatgacgg    78480
agaaaagaaa ccagaatttt atatttaaat ttatgatatt ttagacaggg tctcactttg    78540
```

```
tcgcccagat tgtagtgcag tggcaagatc ttggctcact gcaaactcca cctctcaggc   78600
tcaggcaatc ctcctacctc agcctccgga gtaggtggga ttataggagg tgtacaccac   78660
catgcccggc aaagttttgg tattttttgt agagatgggg ttttgccatg ttgcacagga   78720
tggtctcaaa tttccgggct tgagtgatcc tcctgccttg gcctcccaaa gtgctgggat   78780
tacaggtgtg agccaccacg catggtcatg tcgacgtctt aactgtcttg gaaataattt   78840
gattttgtcc aggtaatttg gttcacgcaa agaagttgag atcggggcac atcagaaaga   78900
gattcatctt ttaaagtgct tcttaaatct acaaatgcaa tatatgtaaa agctaaaggt   78960
ttttatatat ttttcacaca tgtaaaaatg taagttttgc ctttaaattc attttagata   79020
tgaaataatc tagctgagag catgtaaagt cgaggaaagc ttattcagat ccgctctagt   79080
tcagcatgtg gtaaattcct aggtgttcac aatattagtg tacacaaatt ccttctcaag   79140
aaagaaaacc ttggacagac ctggtagact agtatcactt atgccttata gagactttct   79200
gtcaaaacca aacaaaaatc tgtcatatct ttattcatag aataaaatgt gatattaggg   79260
aacacaactg tttctggaat gcattgaaac tgatagtatt ctatagattt ttctacttaa   79320
caattactta ttattactat tattattatt gttgttgttg agactgagtc tcactctatc   79380
acccaggctg gagtgcagtg gcatgatctc agctcactgc agcctgcacc tcccgggctc   79440
aagcaattct cctgcctcag cctccccagt agctgggatt aaaggtgccc accccaacgc   79500
ccagctaatt tttgtatttt tagtagagat gggtttcacc atgttggcca ggctggtctc   79560
gaactcttga cctaaatgat ctgcccgcct tggcctccga aagtgctggg attacaagtg   79620
tgagccactg cacctggcct caacttacat tacttatttt tcaaaaacta gagaatccat   79680
taattttggc ttgtttgaat ttaaaagtga ttataatatt tttgttagtt atatatgagc   79740
agtatttcac tacagctcat cttaaagata tttgataatt tatcttctat ttttacagcg   79800
aaatggtcac attttttgtca gttgacaata aattcttttt ttttttttt ttttttttt   79860 ttttgtagag ttggggtttc gctgtgtttg gccaggctgg tcttgaactc ctggcctcaa   79920
gtgacccacc cggctcagcc tctcaaagtg ctgggattac agatgtgagc caccacacct   79980
ggcagacaat aaattcttga aagattcctg atactttacc aacttacaca ttaagttaat   80040
cttcccattt tctttgtcca attaagtttt aaagcaaaat aatataaata tttatagacc   80100
caaattgtaa acacatttca gttttgaaga acaatataaa gtaaatatac tatggaatta   80160
caattagaaa accaagtttg cactgatatt tttaaaactt ctctgggaa cttagttttt   80220 caacttaagg acacaagtat taaattagaa ggtattttcc ttcactaacg aaaattttg   80280 tttttttaatt atctattctt gtcttcaaa tttaagtttt aatggcggac caattaatgt   80340
tgcttaaagt tacaacttag acaaacagtt aaaatagctt agcaaattgt ggttctggtt   80400
gttctcctat aggtaattaa gagggcaatg actcaagatt taaaaaatta ataacatgt   80460 ccacacaatt ttctctgaaa tgttcccttc agatttttaa aacaggttta ttgagatata   80520
attgccatct cataagcccc acatacctgt atacaatttg acaagtattg acatacttt   80580 gacaattttc tattacgtac attttatctt ttctttttc tttttttttac accaccctc   80640 tccacttatt acatatattt tgactgttgt tttaatattt ccttttagct tatatagcat   80700
taaatccttt tctatcagtc tgagctttgg aaagaaattt tattttttg gaacaagata   80760 tcaaagagta aaattgaaga aaagtttaat ctcaaactca tgggggaaaa gacatcacag   80820
gaaataaatg ctaaaccat ggctttttta tgtgttgaat taaatagtta ttaagttaat   80880
tggtagataa ttatgagatc tattatcatt taatataatt agtatgtaaa taaggtgata   80940
```

```
taaattatgt tctgtgagaa gttgtcactg atggtgattg ttatctctgt gtaaaagtga    81000 gaaaccaac agaaagatga tgattattag tggcaagatt aatgatcatg ggccttttct     81060
aattcttatg gcccaatctg gtattttct tctcctcatt ttgactttac ctatactttt     81120
ttttttttcc acacaggcca gcatattatt atagctcttt caaaaatttt atattgattc    81180
ttttttcccc aacagtactg taaactcttt gattgtaggc actaaattaa ttccttttag    81240
aaagactttt ttttttcttt ctaccatttg aagtttttta agttgtgtgg tggagactgc    81300
tagttgccca cacagatcca ttctcttctt tcacagttag tcccattgta cacagttagg    81360
ctaaatttta cagtctccct tgtagttagg catggcaata gaaatagttc ctcatcagtg    81420
gactgtgaga agaagcgatc tatcccaact ctggttctgt gccttagttt aataacgtca    81480
ctcctccaga ttcccttgtt cattcccact agctgaaata cacaacacag aggacaccca    81540
gcttctaacc atgtagatga tcaaaatgcc ttgggaaaat ttgggacctg aattatcatg    81600
aagagcagac cttgactatt gacatgagcc attcactttg agactgttgc atgagaagta    81660
gacaccctcc tttattgtag aaggccctgt gttactgagc agctttgtta cagcagccca    81720
gctttcatag taaccagtat gatgcactac cttccttaca tgcctagttg ctcagctgct    81780
ctgttcctgc tgactgcatg tgatttgttt actagctttg ccctggtatt tgcaattcta    81840
ctttcgagtt tcctctcttt tcctagcttt ccataaactc cacgcagaat tttagcttct    81900
aagctaaact cccataatat tttaccattt gttttaaat aataaattca agtcttccgt     81960
taaatattct tgagcacctg ctaagagaac tgttatggtt tgaatgatgt ccctcccaaa    82020
ttcagtctgg acccccagtc tttcagaatg taacctgatt tggaaatagg atctttaaag    82080
aggtcatcaa gttaaaacac gtacatcagg gtggatccca atccaatatg actgctgtcc    82140
tataagagag ggaaacagac acacgggcag ggagaatgcc aggaaagatg aagataaaga    82200
tcagggtgag gcatctacaa gccaaggaga aacgaagatt taccgcaaac caccagaagc    82260
tggaggagag gcatggaata gattcttcct cacaaccttc agaaggaacc cacactgctg    82320
acatcttgat tttggacttc tggttttgag aagtgtaaga caatgcattt ctgtggttta    82380
aggcctccat tctatggtac tttgtattac cctagcaaat gaatccaagc acctggagta    82440
ttaatgataa caagagaatg agtgataaat ttaggttcat agatagaact ccagaggcat    82500
gacataatat gcccaaaggc aaatgcctgg ttaactgaag ggctgaattt gttgattctt    82560
gctctttctt acagatgttt ttgtgtcaat cattgtgtgt aggagacgtt gatagataag    82620
atgtaggctc tacttttaag gaatgtaaaa tgtactagtc agttgacaga gataaaaagg    82680 ttgattttg tacactattg gcaagtgtgt cagttggaaa aatgtataca tgtgcacaga     82740
tttttaggag tgaaaattga ggtaatcttt taaaaggaca ttttggcaat atttaaaatg    82800
cacgaaccta agacacagta gactgaacac aagcatttcc tctacaccct cctgaaatca    82860
cacctatagt tcagagatga aaacaattta aacctacaag aataaagaga ataagaaagg    82920
agacagtaga tgagagacaa caacatttg gaaaaggaa cacaggtgga gaagtgatac      82980
ctaaggtcac agaattaatg cctgcaagcc aaaaaaaaa aaagaagctg attgatattc     83040
aagaaacccg gaaagcctca atcatgggag gcatcaggta cctctgaagg gagggcagga    83100
aagtgggact gagaggtgtt tgaaagtatc tgcataaaga ataactggac gcccttgtta    83160
ctcctgcccc tattctaccc agccatggac tgatccactc ctcttgccca gtaggaccc     83220 aggaaatttg ctgtgtagat agattgaacc agaaaaaccc caaactcagt ggcagggagg    83280
gtgatagtgg tgaagcacag ggctaaaaaa aatggagagt taagtgaagg tatacatgct    83340
```

```
tactctccat ttggcagatt gaaaatgttc tctctggact tagtctcttt ggagacaata    83400
atctgtagat ctgacactgg ggagtcctgt agtgaaatag ccagattcta accccatcac    83460
ctacagtgtt gccaatcagt cactaagctc cactcctctg tgcagtttcc aatcagatct    83520
ttagtgtccc gattctaaac atgaatggat gtcaaaggat cagtcaccaa acctttgaga    83580
aaagcctctg acacaaaagg ttaaagtgaa tttatagaat acaaaacaaa agaataagag    83640
gcaatgcaaa aaatagaaga aagtgaaaaa taaaaacaaa ctaaaaccta aaatcatgac    83700
tgtagaaaga gaagatattg tgagaaggaa acaagaatag tgatctatac atgtatgaat    83760
atttagagac caagacccca atcctataag attagcatcc ttattagaag agacaccaga    83820
gacatctccc ccaccctgta cgccttcctg accccaggca agcacagagg aaaaggaatg    83880
taacaggaaa agagcccgca ccagaaacga accctgccag accttgatct tgactaccag    83940
cctccagaac tgtgagaaaa tgaatttcca ttatttaagc cccctaattt gtggtatctg    84000
ttatggcagc ccaaggagac tagcataatg tatcacattt aataaaatta aatgaacact    84060
aaaaacagaa tgcatttgcc ttttgaggca gcaattccaa atttctctct gttctttaag    84120
atatgtaact taacctagga gtcagcaaac ccaggggcca aatccagcct acccttttgtt   84180 tttgtgcagc ctgtgagcta agattgattt ttagaattta tgcagttgaa aaatttaaaa    84240
ataatatttt atgacatgag aatgttatat gagattcaaa tttcagtgtt cataaatgaa    84300
gtttaaaaat atatagccac atctattttt aaaaatgtat catccctggc tacttttctg    84360
ctacagtggc acagttgagc agttgtgaca gggaccatat tgactacaaa actgaaaata    84420
tttactatgt gttcatttag gaaaaagttt gctgactgct ggtgtagacc atctgagtga    84480
aatttccttc cagattctta taatattttc tccaatcttt tatagttgtc gtgcccaaac    84540
tgaattaaca gcaatatttt aaatatctca attttattgc gtcttttccaa agtaattcaa    84600 attggttttc ttaggaattg ctctctttca acattttgat tttaaagata atatggtttg   84660
gatattcacc ccctccaaat ctcatgttga aatgtgatcc ccaattgtat tagtccattg    84720
tcatactgct atgaagaaat acctgagact gagtaattta taaagaaaaa gagatttaat    84780
gactgggaag gcctcacagt catgaaggaa ggcgaaggag cagcaaaggc acattttaca    84840
tggtggcagg caagacagca tgtacagggg aattgctgtt tataaaacca tcagatctca    84900
tgagactcac tcactatcac aagaacagca ccggaaagcc tacctccatg attcaattac    84960
ctcgaacttg gtccctctca tgacacatgg ggataatggg agctacaatt caagatgaga    85020
tttgggtggg gacacagcca aaccatgtca ccaatgttgg aggtgtggtc tagcggaggt    85080
gtttgggtaa tagggcagat ccctcatcag tagcctggtg ccaacctcat ggtaatgagt    85140
gagttctcac tctattagtt cttgggagag ttgattgtta aaaggagtct ggcacttcct    85200
cccttttctc tctttccccc tttctctctc catgtgacat acctgctccc cctgcacctt    85260
ctgccatcag taaaagcttc ctgaggcctc cccagaagcc aagcagatgc tgtatattgc    85320
catgcttgta cagcctgcag aaccatgagc caaataaacc tcttttctta accaattgcc    85380
cagcctcaag tatttctttta tagcaatgca aaacagatga atacaaaagg caaaacagc    85440 ttaattacat aattatcaaa tccattacaa tggcaataaa cagtttggta cccaacaact    85500
gacttctgtt aaacatataa ctcaaattat aagagcacaa gagcagtgac ctgctagggt    85560
ggaatcatga gctttgagta taccttggac atcaccagca cattttatgg agggaaagca    85620
gagcacagtt gggaagtggg ttgcatggaa gttgcgtaag agattttatg ttgtaattag    85680
cctagttatt tcaggtatct gattttttttt ctcgtcccaa ttaaagaata aatctcctaa    85740
```

```
gagcagggat aatattttga tttcttttgt attcttcttt caagcatgga gcaccaagtt    85800
gggcacatga caaatgttga ataaatccct cttgaaaggt tagatgatga agcttctaca    85860
tgccagagat gaccattctt ggggtaagtc agctctcagc cacctagaaa ggttttctca    85920
accgctgatt ttagactctc aatctgtttt gatttgcgat gctgtattct tctttgccat    85980
tctcccaaat gacacgtcag cttttcatgat tcatttttat gttttcttgt ctatcgcctc    86040
aatgttggat ttctgcctaa gcagcaaaat tcaaagaaat ctcttctgtt ggaattgctg    86100
atgtgaaaga agcccatgag gttcaaatga cctcatagtg cataaaacaa tgtgagtgaa    86160 tatgggagt actatttatt gttcaagaca aaaatgagta tgttgtgaaa agcttgctca    86220
gtttatggta agatgaaatt gctgaccgaa gactgcctaa aactcaagtt ctgaaatgtc    86280
attaatatgg acaataaaaa ggaactgtct tagaaagtta attgttacac ataatgtaca    86340
taattcttgc aataactatt ttgattttta gctacccagg agtatgatca agaatctgta    86400
gtagtacaat ctagtttaag ttgccttgtt ggttctaaga gaaaaattct ttggggttga    86460
aaattagccc attttgtaac acatctctgt gtacaattac tgttaaaagt tgaatatgtg    86520
aaatctggtg gcatagtaag cactgataga aattaggtta tttattaatt tattattgat    86580
ttgccttatg attgtagaaa gggtatgtat ttgtataatt taatgactta attactctca    86640
ttgtaaaagc tggataaaat tatatctggt ctattcacat cattagtata ttgcaaagat    86700
gcttgacagt ggcactgatg gctttgggtg gtatgatatt tatcaattat aatttttata    86760
taattgacat tccagttcct gttctgtcag tatatatctg tgtgaacttg attatactta    86820
aatctttgtg cctcagtttc cctatttata aaacaaatat gttgaattag attaattctt    86880
attccttggg ttcaaaaatt acataactgt aaaaagcttt ttgtccatta taattttta    86940 acctcaccta aaaatgccca aatataaaat aatgatatat gtgcacttcc taaacattca    87000
tgtgcacatt ttgcatatac ccagaatatt ggagcacaca tcttcgcaag gaatatagat    87060
ttatatccta aatttgcttt tgtttctaag agaagagatg aagagctcat accttaccac    87120
cagcaagaat aaaagctttg tttctctcct ctgtttaagt aattaaaata tctttgctcc    87180
tttactttat gatttcccat tttgagggtc cctaggggtg agaggagcgc tcattaaaca    87240
actcatctct ttcctgcctg aattccacat agagaactaa ctgatggggg ctaaggtgaa    87300
ggaagtggct cgggaagaga gtgaaggagg cctgcctagt gtacccagag ttagggagtc    87360
tcatctatcc tctgcagtcc ctgctggcca ggagtggccc acacagggca cattgctgtt    87420
ccagtaaagc caactgcacg gacaaacaga ggagcagcag agatcgcagt gagcagcctc    87480
cctacccagg agagaaaagg agagcagagt tgatcaggct ggtctggata ttttccccaa    87540
atttacaaag ccagtgcgtc acttcacttc tccagaggag aaacaaaatg ggaaaattgg    87600
cccagaggag caccaagact gtgcttacgg aaaatcacca ggaaatggga aaatgtgttc    87660
cctctaaacc tagaatcatc gtcactaata gctgtgttct ctataaataa acttttgaaa    87720
attaaaaaag tataaaatgc caagatatgt cgtgtaaaac aatttaatgt aacttttcaa    87780
gtagacttgt ctgtaatgag accactcttg gttttaaatt tgcagatgct ctttgcaaag    87840
aaagtagcat gtgtttaaca tttaccttca gtattaactg tgttaatact accattgctt    87900
attttgacat tttagttttt aacatttata tttggaggaa ttaaaaaacg acttgatttc    87960
aaaggaggta taactcattt tcacaatctg agttcatgtg aatgttttag aagaaatttc    88020
agaaatggct ttgaagttat ctgagaaaat gtttacaatt atgccatttg ggaattacaa    88080
ttctatgtgt tggaattgtt tctatggaga tacaaattgc tgtacaatgt agaatgtagt    88140
```

```
ttgatagaat gagaatgtta gaattttcac agtgcttaaa gactggtaat taaactataa    88200
ctagcaaggt aagaacaaaa taaccacatc ttaagtacag tttgactttc atgactaaag    88260
ataaaaatta cagggaggta ggattttatt tcactataaa gatgaacttc ctaacggtaa    88320
gagctatcta agattgaaat gggctgccat agttaaacaa aaaacataaa attacttggg    88380
gatagtattt gaaggggagt cactcatgct tgtattgtac tgcatgcctt ccaagatctc    88440
ttccaattct aatacttgta ttctataaga gcaacagaat catgcaatga tgaaaacctt    88500
ttcaccaatt ttttcttttg tattagttaa tagacaatac taagagtaca cagcatgcct    88560
ctgcttgcaa taatagaaaa gaaccaagaa catttaaaat gggctattga aggagaccat    88620
ttgaaataaa tttttacaaa ttaaggtgtt aaatcatatc tattttctaa gcagattttt    88680
aaaaaagatc cttgcaggat ctttttttact gctagtattc ctttgttagt tctgaaaaga    88740
gattctgtgc attactctgt aaatagtact gtatattact aaaattttat tggtaaaatt    88800
atttggctga ttctaaagtt tagaagaaaa acactgaaca aaatttccca agaacggac     88860
tgtattaatt tgaaagcaca gtcctgggga gttcccaagt ggatgggttc tagtgacctg    88920
gcaattattc atcaattaac cacagccact tattatctgt atgaatggaa caaagttgat    88980
acacagacct tgaggcaaca atgatcagga tatatggcta gttttcttat tccatctcag    89040
agttacactt cagaaacaaa tttccttaat atttgatatt aagtgtcatg ccctcaatga    89100
caactaggag gagctgtttg gtctcgactc tgcctcagaa ctctttccat gggatcaaac    89160
attgcacctt gtactgaatt aaccttttgt gtcttttgac cacatacgta aaaggtaaat    89220
aaaaatatat gtattttaag ctctgttaaa aaaaaaacac aattgctggc ctcttggata    89280
attaagagtt tataacaatg aagattgctt tgtcctttgt tctcaagatg ccctcatggg    89340
ctgttttaga aggatgacct gttcaatttt cacctcggtc atcatctctg agtcctgttt    89400
ttgcacatgg ggactttcag tgctccttac ctcttctttt agtttgaaaa taagggttt     89460
taaagtctca atctagggtc tgcactgaaa aacgtctttt ctctctagtg gttatgctaa    89520
tgcaagttct ccaatgttac tctgcataac tgaatcacta actctgcatt tcaaagtgcc    89580
aacactggta aacctgaaaa tttattaatg taacaaacat tgtgctggaa acaaaaatat    89640
ggtttctgat ctcaaacatt ttaagatcac attggagaaa agacacgaac tgtaatatct    89700
tcacaattgg taatagcagc agttagaaac aacaggttag gcagtagagg acattttctc    89760
tgtcacagaa ctgagaaatt gtcaacatat atacttttt tggtgtgtgc attttgggga    89820
gtaaagaaca tggggatgag taaaatttat aaacctttat tttttttgcgt cttcctaaaa    89880
tgtcaagtct ttaagaaccc atcagcaaat aatattagct tgatcatcct caaataatgt    89940
tagattgagt caaatgaagt aattatttct gtaggtcaca acagtcaata ttggcaattt    90000
catatggttc acctaatttt aaaaaagtgt gcattagttt tctttttttg agacagagtc    90060
tcactctgtc acccaggctg gagtgcaatg gcacaatctc ggctcactgc aacctctgct    90120
tcctgggttc aagtgattct cctgtttcag ccttccaagt agctgggatt acaggcgcac    90180
accaccatgc tcagctaatt cctgtacttt tagtagagat ggggtttttgc catgttggcc    90240
aggcctctgc caccatgtct ggttaatttt tgtattttttg gtagagacga gggttcacca    90300
tgttggccag gctggtctca aactcctaac ctcaggtgat ccgcccctcct cagcctgcca    90360
aagtgctggg attataggtg tgagccactg catctggcct tgggttagtt ttctggggct    90420
gtagaacaaa tgaccacaaa tctagcccgt taaaacaaca ctcatttatt gtctcacagt    90480
tcagtaggtc agaaatctgg gtgggcttga ctgggttttc tgcttagggt ctcatgaggc    90540
```

```
tgaaatcaag gctgggctcc tatctgaagg ctctggagaa gagtctgcct ccaaactcag    90600
atggattgtt ggcagaattc agttcctggt ggttgttgcc agcggttgtt ttcagaaact    90660
agaagcagct ctccagtcct tgcacgtgtt cccctccatc ttcaggtagc agtggccttg    90720
tgctttgaat ctctctgaca tttcctctgt caccagtctg agaaagctct ttgcttttaa    90780
aaggttcatg tgattagatt aggcccacca gataatctgc ttttaattaa cacaaaaata    90840
actaattaat aaccttaatt acatctgcaa aatcgctttt gccacataac ataacataat    90900
caaaagtgca gtgagaggtt gtgtagtaaa gtggctaagg catgggctt gagaatcaga    90960 ctatctgggt tcaaagtcat gctctatcac taaattaggt gacactggac aaagcttttt    91020
agcttctccg tgcttctgca aaacaagcat catctttaat aacctgcctt gttggttgga    91080
ttttaaaggg atcattctta acaaatattt agcagagtgc ctggcacata atagttgctc    91140
aatgagtaac atttagtatt attattgtag aaaagaaaa tgagaaagaa aaagtgagag    91200
aaaagaaaga agtgaaagaa aattgttgta gacagagtga tcaaggaagg atttataaag    91260
gaggtgaggc ttgagttgga ttaaggttaa ctgaattttt gtaagcatga agaggggcaa    91320
tgtattcatt ctaaattata acaaatttac aataaaagg tttgtatttt gtagaaatga    91380
gaaactgatt acatctgctt atttggacag tgaatggaac cacatattct gcctgttggc    91440
aaacaccaaa tctgtatagt ttatttcct caaaggtaag taatgagaaa attaactgac    91500
aaggcacact ggatcaacag gttactatgc tatatttgat aaataggctt attcctgata    91560
cctcagactt actccaggat tttttttttt tttaatag agtctcgctc tgtcgcccag    91620
gctggagtgc agtggcatga tctgggctca ctgcaacctc tgccttccag gtttaagtgg    91680
ttctactact tcagcctccc agtagctggg attacaggtg cctgctacct cacgtggcta    91740
atttttgtat tttagtaga gacagtgttt tgccatgttg gccagactgg tcttgaactt    91800
ctgacctcaa gtgatctttc cgcctcggct cccaaagtg ctgaaattac agtcatgaac    91860
caccgcgcct ggccaggaat ttggtaagcc atgtttacat atacagtgga ccaggtagga    91920
accctaaata tgcttttcct tggattggtc caaatgcctt ggtcattctc tcccagcata    91980
atccaagcaa agataaacaa tgaccaatga ataaggctca gtagtcaatc ggttgaatgg    92040
gaaagcacca cagccactta gatcataaaa agcccaagtc tgcagccact cagtcagtcc    92100
attctgctag caaattctg tttatatatc ttctctccaa gaaggggctc ttccaaagct    92160
ggccctagat agttcctcag ccgatcggtg aattaatagt caattaacta agtattaggt    92220
tgatgtgaaa gtaatcacgg ttttgccatt gaatatgtta cattgaatat aaaggcaaaa    92280
attgcgatca ctttcatacc aacctaatat tatcacctct ttttctaata tgtgacctg    92340 tgataagaga aaaccccccg atttcctct aaagacccat tcattctcca ctttcagtgc    92400
atgcttttca ggtcctgctg atctcagggt gggatttga ttcaggtccc agtaatcaga    92460
gcactgcagt acctgattac caacagcctt tactatttgt tcatggctgg gcttgcagtc    92520
caaactaggc caatggaaac ccttcctgag aatttttaaa gaattaatta ataatcacac    92580
ttccgtttgg aattgctaaa gtggtagaat gtaggtgtga tgctactggt gattactctg    92640
cctctgtgtg ggaacagcct tcctgagaat gaaggcaccc caaagaaaag tgagctctga    92700 gatgaaggg ctcagctctg aagatgtcat ttgagcatct atacggtgct gcattgtaca    92760
tatcatgctt ctggacttct aagttattga gccaataagt tattatattt tgtttaagca    92820
catttgagtt tgcatttctg tcattgtcaa ccaagagttc taacagtcgg ctcacagagc    92880
ctccgatgta acgttcccac tgtaaacatt cagattgatt aattaatttg aatcccagct    92940
```

```
atagaaccct gatagagaga atctctaccc tctgatccaa tcagacaggc tcacagagca    93000
caaacatacc tgttgtactc tggtgggtgg gtgagggggg atagtgatca tggaagagga    93060
acagagatac ataaccaaag ccatttggtt caaatgtgtg tgacttttat aatcagacaa    93120
taagaatatt tattttgaat aatcacttaa aacaatttaa gtagatttga ataatctatt    93180
aacaaatttt tgcttttttg ttacattcag tggctgccaa gagtttttaa tcactcaagt    93240
gattttagtt aacaattaat aatgaaaatc taagcaacaa aaatgttcac tctaagtcat    93300
ttgacataag agaactagtg ctcagatggt acacggagaa cccatttttc atttccacgc    93360
ttcacaatct cacactcttt tgccaaattc ctacaaccag tccttaatga cctagtctca    93420
gtctcaaagt acctctctcc ctaaggcatc ctgtctcccc agaaacagga atgtattgct    93480
aagtggacct tacagattat ttaggccagc tttcatatga gatgaaaagt ttcaaagaag    93540
tcaataatag tgaaacattt ttttaaaagg ttggggggg gattctaatt ttattgaaat    93600
cccccaaaga acttgatatt acaggtgaca tcagttccag ctcagactgt agctagttga    93660
gtcctctgtt ccacagattt tattcctaag tagatctttg cctttagaag tgagtgtcaa    93720
gcctattcag taatttcaag ctggaagaga ccttgggaat tttctagtcc atatctgtca    93780 ttttatttt attttattt ttttttgagac tgagtcttgc tctgttgccc aggtgggagt    93840
gcagtggtgc tatctcggtt cactgcaacc tctgcctcct gggttcaagg gattctcctg    93900
cctcagcctc ccgagtagct gggattacag gcatgtgcca ccacgcctga ctgattttg    93960 tattttagt agagatgggt tttcactgtg ttggtcaggc tggtcttaac tcctgacctc    94020
tggcgatcca cctaccttgg cttcccaaag tgctgggatt acaggcacga gccactgcac    94080
ccggtccata cccattattt taagaggag gaaactcagg ctcagaaaat atggaccaat    94140
aatcaaagca gggagacacg tacatcccag gaaggaaaaa tggctggaac aaaggcgctg    94200
agtcaagaaa agatatactc agggacaaaa ttttgaaaat gaatttggat gtgactttag    94260
ttgcttaatg ggttgactgt aaacttgaaa ggtaaattat taggtccaaa ttatagaagg    94320
ttttgaatgt taaggtgaag ggttgttgct ttgtttttaa ctttataaac acataaaagt    94380
agggaaagtt gaataatgaa agccatgtgg ttaccaccca ttttctacaa tgatcaactc    94440
atgatcagtt atattccttc tatgactcta cttcctccct ccttctcttc tgtctcccag    94500
attattttga agcaaatctt tgtcataata tagctttata aatatttcaa catatttcaa    94560
gccccaaact aaagacttag agggtttcta agtattctgt agataagaag aagcctttga    94620
atattttcaa cccagggagc aacatgttca gaactgcaga aggctcttcc ggcagttcca    94680
tatgggatgg attggagtag gaagtggcag ggtagtgtaa gcacttgata tgccacattg    94740
tccttgtcac agaagcgttg tttcctattt tccaagttta acgtatgctc tatagtttcc    94800
cttgctggta tttaagggta gaaataattt atagattctt ggccaatgga gatatttccg    94860
ttttagaggt tttgtcattc tgacatttca gtttcacgct ttgtagttct tttatgcatt    94920
gaggtgtatg gcaataatgt aagtgtgaat ttttctattt ctccttatgt attaaatatt    94980 cacctttat tttattatat tgcttaatga ggacattctg tgtactagtt tgatgtttat    95040
ggaagaaaaa caaaagcttc cctagctcta aaaacttgcc ttttaagttc ctcatctcta    95100
taagtagcaa aacataacac ataaattatt caggcaatac aaaatgaaaa taatacatt    95160 tcaattggct atctaagaga ttatttctct gtgcattgag tcttcttta tgtagtcact    95220 gcaaaaccat gaaagattga aatattttct gaatgagaaa tctttcaaca tgaagcagca    95280
cacacagcac tgtgagcaga aactaaaata aaccctgtct ggcctcaagg ttcatgttgc    95340
```

```
atatttagag ttggaaatac tcatttcagg gtacatttt  ctttaaccca gtcatcccag   95400
agtggaacaa caacatagag aatagataag attgtctgtc tggctagctg aacacactgt   95460
ccttcacact gctgagaaat ttgcagagta tggtagaggt ttttagatct tgaaactgta   95520
caaggcactc ttctgctttt aatttatgct ttgaagattt atacaaaata gaaagaccaa   95580
ataactcact ttccatttaa agtgctcacg ttttccatct ggtacattgt tatgaataac   95640
atgtctgcat gacataacag aaaatttttc ataccagtgc gggtctgcca tcaatttata   95700
atcagaaatg tcacatgacg tattgaaaag aaatcagaat tacacacggt tgctgcattt   95760
gccttcttat atttcttacc agaagccctt ttccttcttt tcagctgcct ctgtgaattg   95820
tgtggaatca ttagagaaaa acccaagtag agagctagca attttacaaa actgtaaaaa   95880
agttctttga ataaccataa caatggtata ttttcagtgc ttttcctgtt atcttttgg    95940
ttgcatttt  aaatcaaaac acaaaattga tagatgacag ataataaaaa atttttataa   96000
ccagatctct tctaatgctt gaaatttcag gtgaatcaac agaaagcaat atgagcatga   96060
ttatgctgct ataatgggtc agaccagtac ctcatgctaa ctaaaagtct gtctatgact   96120
gtggcagtca tgtgtatttt ctgaaaaaga attctagctt ctctacagga tttcagactt   96180
agaaagtcag agacctgccc aaagctttcc caaacttcta attaacagag ggccaaggca   96240
gagaacttga gttctcatta ctgatctccc actaatggga tgtgccacct taggtgtatt   96300
gttaatttct gtttacagtg tttcactttc tttatttcca gataagaaaa gattctaatt   96360
acaaaaacaa ttttaaaaga gtctacacat agaagataat aattgctatt atttttactt   96420
atctaaatct agggaatcat gattgccaac aatcactcag caccaacaat ttactgaatg   96480
tttatctgcc tgcattcttc ttgtggctgg aaatgtagca gtgaaccaga ccgagaccct   96540
gatccgctgg gtatatagct gggggagtca gacattcatg aaaatgactt ctagtgccac   96600
agatatttca aaagatgcag taaagagttc tgtgggtctg aatgatatgg tgtgctaacc   96660
aaatatgtga aggtggcgaa ggtctcctag aagaattggt gcaaaacttg agtctcaaag   96720
gatgagctgg gtgaggagtt gggcacagta ttctgggcag tgggaacatc atggacagaa   96780
gcctgaatgc agcggagaga ctgactcact tgtgggcatg aaggagatca gcatgactgg   96840
attggagctc acttcctggt gttttcacct cattgcatgt aagcatcaat ggacctaccc   96900
ctgcttctgg ccatatcaaa cagttcaata gtttggcatc tttgtgatca gcttacagaa   96960
gtgctgtggg ctttgtcaaa ccagttagga agctctagct tactggtcga gagaacttgg   97020
catgagagga tgctgacgag ttagacagag gtctgattgg aagggctgg  gtgctgagcg   97080
ggagttggga aaggaggagt tagtgcaggc aacacattca agatcattga aggttagtga   97140
tatggtttgc ctgtgttctt atgcaaatct catctcaaat tataatcccc ataaaccccg   97200
cgtatcgagg aagaaacttg gtgggaggtg actggatcat ggggccggtt tccctcatgc   97260
agttctcctg aaagtgaata agttcggatg ggatctgatg gttttataag tgtgtgacag   97320
ttcctccttc atgtggtctc tctctctctc acctgctgcg atataagtcg tggctgcttc   97380
tccttctgcc atgattgtaa gtttccggag gcctccagc  catgtggaat tgagtcaatt   97440
aaacctcttt tctttataaa ttacccagtc ttgggaggtt ctttaaagaa gtgtgagaac   97500
agattaatac agtcagagag gccttttctga gcataagttc ttgactatac taagggcaat   97560
tgagagccat ggaaaatgtt taagcaggag aaaagtttgt ctgagaaggg gaggaagaga   97620
ttctgaggtg cctttaagaa atccacttgt aggggccagg cgcggtggct tacgcctgta   97680
atcgcagcac tttgggaggt tgaggcagcg gatcacgagg tcaggagacc gagaccatcc   97740
```

```
tggctaaaac agtgaaaccc cgtctctact aaaaatacaa aaaattagcc gggcatggtg   97800
gcgggtgcct gtagtcccag ctactcggga ggctgaggca ggagaatggc gtgaatacgg   97860
gaggcggagg ttgcagtgag ctgagattgt gccactgcac tccagtctgg gccacagaga   97920
gagactacat ctcaaaaaaa aaaaagaaaa gaaaaagaa atccacttgt agccgctaag    97980
gtctggagct cagagaagag tctgaccccca agcccagttc tccagagtca ttttgattct   98040
aagaaacctt gatattcttt caatacgttc ctttttttt ttttgtccac catagccctg    98100
gttggtttct gttgcttgca atgaaagaac ccttacaaat gcaataatgc agaagtaaca   98160
atgaagatga cactgattca cacaagattt aatttgttac atgagtaaat aaacaaagca   98220
aaatgaacag aatttactat actgcatccc tgctgggagt atgttgagct atctggcctg   98280
gaaggccttt gtgacctgtt gaagaatat acatggattt acttcaggag aaaaataaag    98340
tgttatttta aaaatggatc atgttcattg taattaagaa taaaggttgt aaaaactatg   98400
gattgtggcc gggcttggtg cctcacgcct gtaatcccag cactttggga ggccgaggca   98460
ggtgaatcac ctgaggtcag gagttcaaga ccagcctgac caacatggtg aaaccccatc   98520
tctactaaaa atacaaaaat tggctgggca tggtggtggg cacctgtaat cccagctact   98580
tgggaggctg aggcaggaga attgcttgaa cctgggaggc agaggttgca gtgagccaag   98640
atcacaccac tgcactccag cctgggcaac agagggagac tttgtctcaa agaataataa   98700
taaaaaaaat tgtgggttgt atagaaaaaa attacagtgg aagcattata tgtgaacttc   98760
attggagaaa tatttattat gacatataga gttatatata tgagacataa ggttaaaaag   98820
gtaccttact ttttgtcata cttgtatagt cagtgaaagg ctttttctg tatacattgg    98880
aaaactaatt tttaaattta atatttaaag catggccggg cacggtggct cacacctgta   98940
atcccagcac tttgggaggc cgtgactggt gaatcacaag gtcaggagat caagaccatc   99000
ctggctaaca cagtgaaacc ctgtctctac taaaaataca aaaattagc caggcatggt    99060
ggcaggcgcc tgtggtccca gctactcagg aggctcaggc aggagaatgg cgtgaacccg   99120
ggaggcggag cttgcagtaa gccgagatcg ggccaccgca ctccagcctg ggcgacagag   99180
caagactccg tctcaaaaaa ataaataaat aaataaataa ataaataaaa taaagcagat   99240
agcagttgat atatatgaat tgggcacaaa ttagctagac tatcttccta gggcaaatga   99300
tgtcatttta tttgactcct tttctgtttt agctgagttt tttccagcta ctttaataaa   99360
gaattaatga taaatttttt ctctacttgt attacttcag cagattaatt ttccattttg   99420
tccacgtaga gattaagatg gtagcatccc tatacaaaat cttattaccc atattcactt   99480
ggaaaaatat catgaaaagg ttttactaaa atgaatgagg tgaagccatt cagttttgac   99540
tgtaagtttc agaggtcgtt tcatcaatgc gtaagtagcc taaagacttc actggagttt   99600
tataagaatg caaaagagaa aagcaaacct acgaagacgc ataaaaatta tgaactctgg   99660
gagttatcta atttacacat ggtttctttt cataaattca ggcagaagcg taacctattt   99720
ctcaccccta gttttggaa cttcttcctg ttcctatgct tggttacgtg tggattcggt    99780
ctagacatac catccattaa gcaaccaatt tcacagttaa gtgagttgtc tgtgtttaga   99840
tttcctgttg ccctcttaaa ccctattgtc ttcatctctt gtgatcatca aattatatac   99900
atcatggta tccctatttca gagatatgac ccagtggctc tcatcttagc tctcatctta   99960
gtggcatctc atcttcattc ctggtagaat tcccacccct tgctgttcca catgattttc   100020
ttttgcccta gagcaattgt ctcaatgtac aattgagcct tgataaggaa gtcttcagga   100080
aattctttga tgatgacagg catgtttgta ttcctaccca tgttaatgag acaaacatga   100140
```

```
aatcagtttg aaaaccttaa tgctgttaaa ttttaattaa tgtaattttt cttctgatgc   100200
ctccttcaag gaagcataat taattcttct ctcacatttc tttcagttct cattaacctc   100260
ctccccaaaa gaagtgccac ttttttctaaa atttcaaata tgaactactg aagttattgt   100320
cctaagagat ttttaaatca aatatatatt caagtgtgaa gaaaattaac tctctatcaa   100380
aagctcagaa acaagagata acatgatgta gtcatctacc aagcagcact tctcttattt   100440
gggaaagtaa cattctattc ctcagtcaca cccatccatc tgcccctcc aggtgtctga   100500 caagagcatc tctaaaggta gtggggctgg gaggagctac taacttttc tgaaccaggc   100560 aactaaagtt ataacctcat gccagtggtt tacaactttt ttaacttaca ttttatctaa   100620
ttgagaaaca aattaaaaag ccagatgttt ctgtgactga ggttcaaaaa attagcccat   100680
ccctaaacaa tactggtcaa gtctctttca attgcaagca tccaaaatct cactctaact   100740
ggcctgagca aatgagttaa catgttggct cctataattg aaaagttcac aggcatcaaa   100800
cacagctgga tgcagatgtt taatatgtgt catcagaact tggactcttt ttcaatactc   100860
ctggccctgc cttctccaca ttggcttgtt ttcaggcagg actcctccca tccacaaata   100920
tacagtgata agatgtctag cagcagttcc aggctttat tctcctaatt tagcagaggg   100980
aagaatgcct ctttctccat tgatgcactc tttcagagac tcagtaaaca gcatctgtct   101040
ttgctgcgta gatttggaac cattgagaaa taagaaaata aggagcccaa ataccaccct   101100
tattactgat aaagttggcc ttagatgtca gttggcctca gatggacttc ttaatatgaa   101160
ccatataacc aggcagactt tctactcagt cctggactgg gtctcccaaa ggggcctctg   101220
tgagcaagct ggcctagtga acgtgcccca tttattcttt tcaaatttac caattagata   101280
agtcattctt ccttgaagac tgggaggagg ggttgagaaa ggccagagct gttgcatcta   101340
gcgaagctgg agatgtcatg aatgtggaga agttctgac ctagtatctc ctggctcttt   101400 ttttcttaa ccccctgaat taactattaa acccatgagc agccagaaat gtggctgcct   101460
ccctccaagg acagttttat tccctccttt atagggccac ccccaatagt gaaaaccact   101520
tcattgagga tccctctgga tcttcagtgg tcacccagag ctctgaagtg ggttagagca   101580
aaacaggcat aactcagaga tattgtgggt ttaattctag acgaccctaa taaagccaag   101640
attgcaatat agcaagttgc acaaacttt tggtttctca gtggatacaa aaatgatatt   101700
tctactacac cgtagtcttt taagtgcgca atagcattct gtctaaagaa acaatgtaca   101760
taccttagtt aaaaatgcct tattgcagcc aggcatggtg gctcacgcct gtgatcccag   101820
cactatggga ggcccaggtg ggcggatcac gaggtgagga gttcaagacc agcctgacca   101880
acatggtgaa accccgcctc tactaaaaat acaaaaatta gccaggcacg gtggtgtgca   101940
cctgtaatcc cagctactca ggaggctgac acaggagaat agcttgaacc tgggaggtgg   102000
aggttgcagt gagccgagat cgtggcactg cactccagcc tgggtgacag agggagactc   102060
tgtcccaaaa aacaaacaaa caaaaaacca aaaaaaccca atcttattgt taataaatgc   102120
caatgatgat catctgagcc tttaacatgt tgtaatattt ttgctggtgg agggtcttcc   102180
ctctatgtta atgactgctg actgatcagg gtggtggttg ctgaagtttc ttagaataag   102240
acatcaatga agtttgccac atcaattgac ttttccttc acaaaagttt tctctgtagc   102300
ctgtgatact gtttgaaagc atttacccg cagtagaact tctttcaaaa ttggaataaa   102360
tcccctgaaa ctctaccact gttttatctg ctatgtttat ggaatagtct aatgaagctg   102420 tcattcaac atgttcacag catcttcaca aggtgtagat tccatctcaa gaaaccactt   102480 tcttgttct tccataagaa gcaactcctc atctgttaaa gtttgattaa gagattgcag   102540
```

```
caatccactt acatcttcag gatccacttc taattctagt tccctaacta tttctaccat    102600
atctgcagtg acttccttca ctgaagcttt ggatccctca aagtcatcca tgaaaattag    102660
aataaatttc ttccaaactt ctgttaatgt tgaaaatgtg atctcctccc gtgaatcatg    102720
aatgctctta atggcatctg gaatggtaaa acctttccag gttttcaatg tactttgccc    102780
agatccatca gaggaatcac tatctatggc agctatagcc ttaccaaatg tatttcttta    102840
accataagac ttgagactgg gcgccgtggc tcacgcctgt aatcccagca ctttgggagg    102900
ccgaggtggg cggatcacga ggtcaggaaa tcaagaccat cctggctaac attgtgaaac    102960
cccgtctcta ctaaaaatac aaaaaaatta gccaggcatg gtggctttcg cctgtagtcc    103020
cagctacttg ggaggctgag gcaggagaat cgcttgaacc cgggaggtgg ggttgcggtg    103080
agccgagatc gtgccactgc actccagcct ggagacagag caatactccg tctcaaaaaa    103140
aaaaaaaaaa ccgaaaaaca aaaacaaaa cttgaaagtc aaacttagtc cttgatccat    103200
ttgctgcaga atgaatgctg tgttagcaag catgacagta acattcatct ccttgtacat    103260
cactagagct cttggtgac gaggtgcatt gttaatgagc agtaatattt tgaaaaaaac    103320
aaacaaaaaa aacttttgct ttgagcagta gttctcaaca gtgcacttaa aatagtcagt    103380
aaaccatgcc atgctgtaaa taatgtgct gtcacccagg ccttgttgtc ctacaaccag    103440
agtagattta gcataattct taagggccct aggatttt ca gagtataaat gagcattggc    103500
ttcaacttaa gtaatcaatt gcattagaac ctaacaagag agtcagcctg ccttttgaag    103560
ctttgaagcc aggcattgac ttctcctttc tagctatgaa ggtcctcaat ggcatcttct    103620
tccaatagaa gactgcttca tccacatgga aaatctgtgg tttactgcag caactttttt    103680 ttttttttt ttttttttt tttttttt gtgagacagt ctcactctgt cacctaggct    103740
agagtgcagt ggcaccatct cagctcactg aaacctctgc ctcctgggtt caagcaattc    103800
tcttgcctca gcctcctgag tagctgggac tacaggtgct tgcagccatg cccagctaat    103860
ttttgtagtt ttagtagaga tggggtttcg ctatgttggc caggctggtc tcgaattccc    103920
gatctcaggt gatccgccca cctcggcctc ccaaagtgct gggattacag gtgtgagcca    103980
ccatgcccgg tctactgcag tgactttatc aattatctta ggtatagatt ttttctggat    104040
aattttctac atcagcactt gctgcttcct cttgctcttt tatgtaatga agatggcttc    104100
tttccttaaa ccccatgaac caacctctgt tagcttccaa gttttcttcc acagctgctt    104160
cacctctctc agctttcata gaattgaaga gagttaggac ctactctgga ttaggctttg    104220
gcttgtggga atgttgtagc cagtttgatc tatctagatg gctaaaactt tatatcagca    104280
agaaagcagt tttgccttct tatcattcgt gtgttcactg gagtagcatt tttcatttcc    104340
ttcgagaact tttccattgc ttttacaacc tggataactg gcacaggagg cctagcattc    104400
agcttatctt ggctttttc atgcctttct caccaagctt aatcctttat agcttttgat    104460
ttgaagtggg agatgtgtaa ctctttcttc acttgaacgc ttagaggcca ttgtagggtt    104520
ataaattggc ttgatttcaa tattgttgtg tctcagggaa tgggaaggcc caagaaaaga    104580
gagagagaga gagagaaaga aagaaacaac tggtcagtgg agcagtcaga acacacaaca    104640
tttatcaggt tctcctccat cttgtatggg cacagtttgt gttgctccca aatagttaga    104700
atagtaacat caaagatcac tgatcacaga tcaccataag agatataata ataataaagt    104760
ttaaaatatg agaattgcca aaatgtgaca caaagacaaa aagtgagcac atactgttga    104820
aaaatagtgc caatagattt gttcaatgca gagttgccac aaatctgcaa tttgtaaaaa    104880
atgcagtatc tgtgaagtgc aataaaacaa agcacaataa aacaagttat gggccgggcg    104940
```

```
ccgtggctca cgcctgtaat cccagcactt tgggaggcca aggccgccag atcacctgag 105000
gtcgggagtt caagaccagc ctgaccaaca tggagaaact ccatctctac taaaaataca 105060
aaattagctg ggcatggtgg cacgtgcctg taattccagc tacttgggag gctgaggcag 105120
gagaaccgct tgaacccagg aggcggaggt tgtggtgagt cgagatcatg ccattgcact 105180
ccagcctggg caataagagc aaaactccat ctcaaaaaca aacaaaaaca aaacaaaaca 105240
accgcccccc cccccaaaa aaaaaaaca agttatgcct ggacattaat tcaaccaact 105300
tcaaagccgg tttgtatcaa agactgaata ttcacttcct attctctttc ccatcccacc 105360
tgatgtcctg gatcatccat tatagtcttt cagcggtcaa atgaaatcat aaaaacactc 105420
cactaatgaa atgcatagaa atttcagtca tacattccaa caatttagag atccccccaaa 105480
tgtaaccata acagttttt aatgatcaaa gtcctgggaa gaaattataa agtccataat 105540
aaagctccct tttaaattat aagccacaga tattaaagtc tagagaatat tatattctat 105600
aaataaatgt cacgattctt gtgcacgaaa aggtcaaagt ccaaatgtct gatgttaaag 105660
ttcaaaagcc attctccaaa atgtactatt cagtagctca gtcttattgt gtgaggctgt 105720
gggtatgttg gaagagggaa gcgggtggtt ctttctggac ctcagaaatt atactagttc 105780
cacaccaaat ctctcacttt ctaaagaacc cagagagtta acaggacaca cagatttctg 105840
tagcactggc atcacactcc tcatttttag aaaacaagtt aatacccaac cttctaaagc 105900
agccatcctt agcaaaatta tgtaccaaga actgagtatt ttatgctgcc aaaaagcgtt 105960
acagacatat ggaggtgttt gaagagagga tagtaggtga aaatcttttt ttttttaatct 106020
accaattttt tttttttttt tacaattggg gtctcacagc ctggtacggt ggctcacacc 106080
tgtaatccca gcactttggg atgctgaggt gggtggatca cctgaggtca ggagttcaag 106140
accagcttgg ccaacatggt gaaaccctgt ctctactaaa aatacaaaaa ttagctgggt 106200
gtggtggtat acacctgtaa tcccagtgac ttgggaggct ggggcagaag aatcacttga 106260
acccgggagg cagagattgc agtgagctga gatcgtgcca ttgcactcca gcctgggtga 106320
caagagcaaa actccttctc aaaaaatagt aataataata ataataaat ggggtcttgc 106380
tatgttgtcc aagcttgttg tgaactcctg ggctcaagca atcctcctgc ttcagcctcc 106440
caaaatgctg ggactacagg catgggccac tgtgcctggc ctcccccaat gctagttgcc 106500
tggactccat ggcctataaa cagatattca agtagaagaa gattctcaga aagaaagaag 106560
ttcattctgg cactttgtat ttaccataat ttgggagaaa catccatttc tgcccactct 106620
ctccattcct ggagagtggc atttgagaca ttgctgtctt cttgcgcagt ttgcaaagtg 106680
gcaacaacag ccgcagtcac taagtcttgt ttaagattcc tgttttttctt ctcatactgg 106740
aaaactctta attgctgttt tctcttgatc cctgtttttc tggcactctg gggctgcctt 106800
cagggtaggt tcagcctaat gagatagaat ctacccttc tgggaacagg tatatagatt 106860
cctgaggaac aagaaatctg cctccttaga gaaatactat ttccaattca gagccaaatt 106920
ttgactagat tttcaggcgt ggggttgggg accattgggg ggaaggagtt acggataatt 106980
cttgagcctg tggataaacc ttgcaaattt ttctcccatc actgctctct ccctgaaaaa 107040
gcagagtgga atttgcattt gcgcacacct agcacaccag acttaggccc aaaggaaaca 107100
cattaaatct aaaactcccc agggctctgt agtgcctgag acgagttgc ctggtgattt 107160
aaaagaagac aaatattatt ttgcctatca atgctcaatg gtccttaaag acaccttttc 107220
cctgtcatca attcctggga tgagttgttc ctacttagga aaaggtgttt ccgcttgcag 107280
aattggttct ggatttccca tcagcctagc aagattggaa cttagacctg gtgtacatta 107340
```

```
aattattcag aaattatgtc cttacctaat acaaaaaaaa agcaatcttt aaatttctgg    107400
ccaaatatca atttcctgaa gtcacgtaac tccaaatcta aggatctcaa gtcttctagt    107460
gagaattcca gaatatgttt cttatagatt tgaggaagta aatcatctta gaataactgt    107520
ctcccttcct ccctctctcc ctggtaccac atagtctttt ctccattgca aatagaggaa    107580
atgacaaaat gtgctatgtt ctaattttta tgaaatctgc catgatgtat tttatttatt    107640
atgaccctga gtcccaggtt gggtttatgg tattctactt tctgcctatg caattgacga    107700
gtattatgtt tcctctctct tttggaaagt gatatgtttt ggctgtgtcc ccacccaaat    107760
ctcatcttga attgtagttc ctacaatccc cacgtgttgt ggaagggacc tggtgggagg    107820
taattgaatc atgggggcag gttttttccca tgctgttctc atggtagtga ataagtctca    107880
aaagatctga tggttttata aatgggagtt cctctgaaca agttctcttg cctgatgcca    107940
tgtaagatgt gactttactc cccctcatc ttccaccatg attgtgaggc ctccccagcc    108000
atgtggaact gtgagtcaat taaacctctt tctttataaa ttactcagtc tctggtatat    108060
ttttattagc agcatgagaa tgaactaata cataaagttt gtaagtagcg ctatgtgcta    108120
tgtggtcatt ctgctccaag gctcatgggt ttgtcatgaa ccctgcatgt tacacaatgc    108180
taaagaagca attgtctgca caggtgtctc ttaaattaac ttaagaatat ctatcaagca    108240
cctattttgt gcaaggtggt agggatacaa agaccacagt ctctaattat cttaagcttt    108300
tagtctagtg aatatcttcc ctcttacttt taaggtgcca agtgtcagaa cttgttgctg    108360
tttgttgaat tccaagaggc aatggagaaa atgtaggaat aaactacatt ttcttctaca    108420
tttaagatgt aaagggaaca ttttcttagt agaaaatcct tactttcag aaaataactt    108480 cttaggtaaa gcacatcatt ttaacccttt ttgcagaaaa aaaaaataca atgcttctgg    108540
ttcaaggtgg caatttgagc acatatgttt gaatcctcct ctttcccaaa taaccatgaa    108600
aatgcaggag acactttta gcattgctga accacaaca gggtgacatc cacatgttca    108660
aactgagtgg aattcatgga ggatatatgc agatagaaga agttgagtga tgggcaagac    108720
gaccaatggt tttctgcaca agaagaagcc agtcagagaa gtaggtggaa gcaccttcta    108780
ccccagagag ggagctggag gaaagggtgg gctttggggg ggtctttgag gtgcaaattt    108840
ctgtgacact ggtcatagct cacatagaga gcgattgctg ccacggctct taaattattt    108900
gaactcacac attacgtagc tggtcattcc taggcaaaaa gccagggctt cctttgctga    108960
atcctaacga ggcagttatg ccaggtagga aagggaagtg ctgccccagc tagctagatg    109020
ccgcaacaga ggaggcaagg aattcctcca agagagagg cacactgggg tgtgatggcc    109080
tttggtttga agctggagtt ccttcttact ccccaagttc atgggccacc agcctgagaa    109140
agcagtgaaa atgctttcct ttgtctgttt tcttgttttt gttttatca aagatttgaa    109200 caggtacact tgcaatttct gatgaaagca ttttaaccaa catagataca cctctatctg    109260
tttttgcaag ggtaggtaaa tagaggtgaa tggcaggaca gataagtgag aacccccagc    109320
tgtcaaaagg agaggaccat tatgagaaaa ggtgttcttg tgagacagtg attataaaag    109380
aggactaaaa tgtctaaaag ctcatcttcc aaaattgatt aaataaagtg cctcatcgcc    109440
ataaaatggc agccattaga atgatatgat tagaaacatt tattgcatga aaggattttc    109500
acaatatatt gcaaagctta aaaaaaagag agcaagaaaa caaatgaaat aatagcagaa    109560
tgaatgcatt gtgtgtatgg atgggaggaa ggcgggagtg agggttggca ataataggaa    109620
gatcaatact aaaaaattat acaccaaaat agttaataag gcaaaagtt aatataagtc    109680 tggaatttga tttcaatgat tttataatct ttttgatgat gtattttaa tttttcaca    109740
```

```
caaaatgaac ataaagggat atgttttcct taaagtaaat attgtttctc agaaagctta    109800
cttcccagaa agacactaga ctgaaactat attatggatg cgttcttaac acttaacaaa    109860 gagagggta atttcaattc tatttaaaat attcttcaat gcaggaagaa atggaaagta     109920
taccaattca ttttatgaaa ctatcatatc tctggatatc aaagcctaac aaagggagtt    109980
ggaaaaaaat caagcaggag ccaatttcgg ttgtgaatat gatgcaaatt tttgaaaatg    110040
ataatagaat tgttttagt atttggtaa gtaataatgc tatggccaag tagcgtttca      110100
tctcaaagtg cgaacatatt ttaatactag caagcttatt aacaaaattg ttaagcacat    110160
cagaaagata agctaaggct ctagagatgc ttatatttgt gacacacaaa gcaagagaaa    110220
atggctttca tttcaatctg gcactttgct gcgatggtac attcaacaga gaagagggc     110280 cctgtcacag gtgaccccca acaaggatag ccttgccagt tacaggtggc aggctgggag    110340
gttgccacaa cctagcgagg agaagactga tggctcagaa tgtcgtactc actctctatt    110400
gaagaagttt ggtcctctaa aacgactaaa caaacaaagc aacaacaaca actacaacca    110460
cctaagtttt accccactct cccccttcgga ccctgaaaga cttgtgcagg gatttaaacc    110520
atctctgaca aaatcccta tcaaacagac aatgaagaaa actttaaaaa ataggtcaat     110580
cattttattc ttcagtaatt atataaatag gtaattcatt ttattcttca gtaataaaat    110640
gaattaccta tttatataat tcaataataa attacctatt caagaaaca gaagcaaact     110700 taaaaataa gtagttcatt atatcactga aaattgtgag ggcatttgat ttagatcaag     110760
atgtgaggtc aggaaacgct tcctaggggt gaaaacaagt tatttaaaaa atgtgatgga    110820
agcagtaaat tgcagatgta agaggcagaa ataaaatcgg caaattggaa gacaacttgg    110880
aattctccca gcattaagag aaaaataaaa gaatcaatat gatgagaaga aacaacagac    110940
atgaatgagc gatcctgata gttcagttta tgcatgaaga cttttagaag atgacagaaa    111000
cagatctgag tcagtgaaga tgtgatcttc ttagcaaaag ggctaagaaa atgccaggca    111060
cattaacaaa cacattccat acatagtcat aaacataaaa tttctgaatt tcagagacaa    111120
aggagaatct ttaaatggaa agttaaaggt atcctgacat acagctgcag agacagacac    111180
tgtattgcct cggggagaac tccagccca aaggtgagta ggtgatggag aagaagcaga    111240
gtttgacatg tacaaagcta aagtgagtct ctaaatattt caaatattcc aaatattcct    111300
ctctctgtga aagaaaatag atagtgcttt tccaaaatat gacaaggatc caaagaatt     111360 atgtttcatt accaataaga aggggtgaaa tgaaaagtag ttttttggtac tgtcaataat    111420 aaaaaacaca ttttgatcac taggctatag aaattctctt acacgtctct gtatagataa    111480
aggcattaca aaattttttgt catttggggg gtgattaaag aatatgcaac aaaaaatgta    111540 gaaaatatg tataatattg cagaagtata ccagacaatt aattaatata aatgctatat     111600 ggttttctg gactttctga gttttgtcgt atgttctgat atttgaagat tgtgttggcc     111660
aggtgtggtg gctcgtgcat gtaatcccag gactttggga ggcccaggca agtggatccc    111720
ttgagctcag gagtttgaga ccagactggg caacatggtg aaacctcatc tctttgaaaa    111780
taaaataaaa ataaaatcca aagctcatac tccttctgca cactccattg acacataata    111840 tcttgtatt gggaggggta cccttgaggt tttcaggttc aagggctcag ttgaatatcc     111900
ctcacaaggg cctagtgctc ttagaacttg gaagtttcaa aaacaaaaaa taaaaaaaga    111960
aagaaaatat tttaaaaatt agaaaaaaa gaaattaaaa taaatattta aaaagattgt    112020
atttgttgtt cttctcctt ttaaatgcaa attcatattc atacctaatt ttaaaatcaa     112080
agtattgttt atatacagta aaataagtca ttataattgt tttttttttt cttaaatgta    112140
```

```
acccctaaaa ttgtctaagt ttcaggcatc caaaaccatc ctgtacaaaa cccaggtgcc   112200
ctttctgcat ttctttatcc aaccaagaaa taaatcaaca taaggaagta aaaccttgaa   112260
aaggggatta agaactgaaa ggattctggg tgatatcaca attggaaaat attttaatg    112320 tctacataat tttttttttt tttctgagat ggagtcttgc tctgtctccc aggctggagt   112380
ccagtggcca atctcagctc actgcaagct ctgcctcttg ggttcacgcc attctcctgc   112440
ctcagcctcc agagtagctg gaccacagg cgcccaccac cacgcccggc taatttttg     112500 tagtttagt agagatgggg tttcaccgtg ttagccagga tgatctcgat ctcctgactt    112560
cgtgatccgc ccacctcggc ctcccaaagt gctgggatta cagaagtgag ccactgtgcc   112620
tggcctacat aattgttaat atagttataa aacctagtgt aagtacaaaa agtaatttt    112680 gaaagagaaa aatactataa aaatttatta ttatatatcc gaaatattgg atcattttat   112740
aagatgtggt atggagttgg gggagatatg aagaggacta tatttcccat agtccataag   112800
ctttgtattt agagtctgtt gaggatggta tgtggttttg tcgtttaacc taacattggt   112860
gtaatattct acatgtgata acttgtgtat catgggtatt cacaatcaga atggacattg   112920
gttggaacaa cccacatagc catcctagag catactgaaa caaaacatta tcttagatgt   112980
aaataatcac tggtagaaaa ttgcaattct aaatcattag attttttaaa aaaagcaaat   113040
tctaaaatct tcaattaata tccagttatt cttcagtgag aatgttggat ttgggaatac   113100
aataactatt tagtggatca aaatattcct atcttatcct tgacatcatt aagccaaggc   113160
aaatagagat acagggacac attagctcct atactagatc attagaatac cagtggtcaa   113220
aacataacag ctacaaagct tttggtgcct tcaatgttgg tttcaaagag agcaattgca   113280
gtaaatgtct gtgaactttt gaagggctga tctcactttc ttttctccac tccaggaatg   113340
aaagcaaagc cctttgaaa aaatggtatt catcatctat cagtgccttg actttgttct    113400
tcccattaca ggttcattgg tttaaaaagt atttgctaaa ataggcaaag gccctctttc   113460
cccctcaaaa gcaaataaaa accccaaac ccaaaacaac aataaaattt tctgtgaagt    113520
gctaactaat ttctgcattt gttatataga aaatgttgaa attataattg gaaaagtagt   113580
gaaactcaga cttggaactc tgaaacagtg attcttttcct gtacaaggtg gatattttta   113640
atctttagga cttttaagtt ctatataata ttttttgtt agttgttata gaaaacacaa     113700
ctctagaaat acatcctacc ttcctcttat cctgaaatct caggtcaata cttgatcact   113760
tgtgggttat ggcatagaga tggcattcca attattcatc cgcctgaaca tggcaggagt   113820
attgttccca ccccctttt tttacattac tgtaaactgt tgctactatg tttcaattcg     113880
tttgctggct ataaatgtgt atgtgtgtgt gtatgtgtgt cctatctgtt cctgtataca   113940
aaatttctta gtaactcaag attgtgatac caaggcaaat gtttccagca tcaaaaatga   114000
atatttcatg ggcctgtcat ttttaatttt tattctttg gctttcattt aggaatagtt    114060
tagttcagtt gcttgagtac agttgattga atacagttgc agcaactaat taaaatctgt   114120
tataagttag gggcactta aatctgtgct cttttgtctc cactatgacg cattatttta    114180
agcccagagt ttagaacctg tacaaattcc ctctcagtct gaagctttga tgaatgatga   114240
agaggatgcg gtattactca ctttgaactg aaaaaagtt tgttaaaata taatgttcta    114300 taaaaggtg gcagaaacag attctttctc ttttcttgtt gaaaataggt aaggctcct     114360 tgccattggg tttcctgttt aatggttggg tttttcctgt aaaggtttct ccctgcagga   114420
agtcggagct tcagaggagt gcaaggtcac ggtgtttgtt atcccacctg cctgtctgtc   114480
aagtcgctga ggattggctt tgttcctcta ccaaaggcca cagcccctgc cagggaacct   114540
```

```
cttgtccagc ctgccatctg ggtctattct ttcctccctg tatgtttcca gacctagggc    114600
tggcagcagc tcccttctat tggtaccctc gaggtactgt gcctgccatg tcttcttgct    114660
tcatctaaac cctgcacatt cctttgtaaa aagtggtttt aattaaactc acctcaaatt    114720
ttccagtgta agtgtgcctt ctgttttgtt ttcaggtcct tgggtaaggc agtcatttaa    114780
ataaattagg cattttgggc aatatttatg ataagggaga gagaataggg agccacagag    114840
tcctgcatga cattcctggg caattccttc cctttcaact ccattgattg ccctaattgg    114900
ctcttccttc ttctggcccc cagtttcctc atgtctgact aaagcctttc atttcccttc    114960
tccatgaaat catctctact tcagattaag tccagtactc tagatataat gctctctctc    115020
atctcctgaa cttctcataa acttttttgtc tcctatgcct cattctcttg aacaccgatg    115080
tcaattaatt gttaagtagg aaagcaattt tgacatacta acctatgtta aggcacaaag    115140
gtctactaat gccttaatca tgtgtagcac accatggagt actgacttct gaaaataaaa    115200
atgacttatc ccaggttaca tagcatgaac aaaagagtga ctctctaatg atgaaaatat    115260
cacccgtaaa ggcagggagt gttattagaa agatatattg aagcaacaag cgcaacctaa    115320
agtcacacaa taggagtctg tcagctcaac ttaaaagtaa ggtttgtact gagacctcag    115380
tggtaagttt aatgttcaag actatgccaa aatgagatca tttctcttcc tagtaataag    115440
aacaaaagta gaatggatat tggaaaactt gatacaagaa atgagcacct actataataa    115500
ttatgtctag atgtgagcaa tctccattta gatcttgggt gggtacaact taacgtgtta    115560
aaacttaagt agaaatctga agagtaagga attggacata ctttggataa agttaagacc    115620
ttccgaagga taaggaccat tttcagagcc atgttgcttt ttattcctct gatataaaaa    115680
gtttggggtg tcattaatac ttgtagtcta atttctgatg gtttgcatta ttatgtattt    115740
gacgccatta acgtcagcac tcagatacgc tttacataca atatcttaag agcttctgtt    115800
ggtagtgcca tccaatgtag cccagaaatg aatgaaaaaa tctcactttg tcatatgcac    115860
tttatgcagt ttgattaggg catgcatgta tgttgcatag caggattta ttaaaatact    115920 gcatatcaat tcatttgcat gggggaggcc agtaatgtcc ctccagcatc tacatatgat    115980
ttctagcacc ccaaactaga aatcatttgg ctcagaaata gaacttggag aacagctagg    116040
tttcaacatc agagacagag acctggggat aggagagtgt gaaccagagg gagatttgca    116100
ggagaaaatc ttttagaaag ttcaatcctt tgaaaactct ccctaaacct tccctaaagc    116160
cctcatatac tgaccattga ggtttccatt gaatatttta cactgtttat tttaccattc    116220
accattcatc cagaagatgc ctaccaagca ccagatgcca ctctgggtgc tgcggatgca    116280
ttggtgagaa aaaaatagat aaactacttc taccttgtag ggagtgaggg gcagggaaat    116340
agaccataag caatacatat aataaatcat taggccatat agtgggctag aagatgataa    116400
gtgttggcta aaaagaaata gagctgggta aggggggtcag gaatttggga agttatcatt    116460
tatcaagtga ccttattgag caggtgacat ttgagccaag acttgaagga ggtaagaaaa    116520
tgagccacac agctacctct ttaacactga ccgttaaatc agcctgttaa agcagctctg    116580
cgcctggcgc ggtggctcac gcccgtaatc ccagcacttt gggaggccga ggcaggtgga    116640
ttgcctgagc tcaggagttc gtgaccagcc tgggcaacac ggtgaaaccc cgtctctatt    116700
aaaatacaaa aaattagcca ggtgtggcgg tgtactcttg tagtcccagc tactcggag    116760 gctgaggcag gagaatcact tgaacccagg aggcggaggt tgcagtgagc tgagatcacg    116820
ccattgcact ccagcctggg tgacagagtg agactccatt aaaaaaaaaa aaaaaaaaa    116880 aaaaaagca gctctgtctg gttgaaatag aatgcaaata gcataggtca tttaagattt    116940
```

```
tacagtagtc acattttaaa aagtaaaaag aaataggtaa atttatttta acaaatatt  117000 ttatctaacc tattctattc aaaatatttc agcatgaaat caaaattcta gaaaaaaatt 117060 agattttgc  attttgtttt tcatactaag tcttagacat gtgatgtgta ttttccgatt 117120
acagcacatc tcaatttgga ctagccacat atcacatgct cagtagcaca tatggtcagt 117180
ggataccata ttgggtggta tagccttaaa gagggttgaa aaagtgtcac ttttgaagag 117240
catactcaaa aggagtgagt ggtccctctg ctttcccatc cctccaggct aggcagggg  117300 tgtttgtggg cagtggagag gaggcaatct taatttgggg aaggatgaat ttcctgcaaa 117360
caaagcatta gggagttttc tttctatttt agaccaataa gggtagctat ctcatatcat 117420
cccctttgaa tcagcagtgt gatatgaagg gtcatgttca attctcaggc ctttgtctac 117480
atcttccacc aaagccttcc tctcctttag gaattgtctc actgagagac tggtttggcc 117540
gaattatcca ttcaagatca agcctttatt tgtggtattt tgtatgtttg ttggagatgg 117600
agacgatagc cttaaactag aggttaagaa tgtaaaatag tggctttgaa ggatgcaatt 117660
gtcctgtaga tgccagggtt ctaatattac gaccatttat aagttatcaa gttcagcaag 117720
aatgaggaag aaacaaacca tatattatag ccattttgt  agttcctagc aatcaactat 117780 gaaaacagc  tgttattagt ttttcctttc ccaactagat tataaatcca caaaaatagg 117840
agccatgtat tcatgacatt ctcttttctt ttgtatcctc catagagggt agtgctgagt 117900
tgctatttaa taaatattta tagatcactc caggtgttgg caaaccttt  ctgtaaggac 117960 cagataataa atatttcagt cttgagaac  tatactgttt ctgtcacaac taccctacct 118020
tgctgttgca gcacaaaatc aagcatagat aatatataac tgatgggcat agatgcatgc 118080
caataaaact ttattgatat atacaagttt aaacatcatg caattttac  atgttacaag 118140 gtattgttct gctttgttt  ttttcaattg tttaaaaatg cgaaaaaaca ctgttagctc 118200
agctgtgtga aaacaggcaa tgagctggat taggtctaag agttatcgtg taccaatgcc 118260
tggtttccat tattctcatt ttttgctcag ccatttcgt  ttcttttttt cctgtgcctc 118320
tttattacct aattctctct ccctcctttc tttttgactt tccttcatct cactgctgat 118380
tctcctatat cttccttctt tcccattctt ccttatcttt tcttctttct tcaaccccca 118440
tagccatttt cttctatttg cctaagcact gtcatcttag gtggagcggt ttccagaaac 118500
acagcttcac tttcaggaag aaatagatgg gattaaaata atatttaaaa catggagtcc 118560
taaagttatt atattatgcc ctcccatttc ccttcttctc ctccttctct tctttctatt 118620
tctccatata ccaagtacaa tggtaaaaga ataaaagtga cttacatgtg tatatggaca 118680
gaagtctcat tactaacatg tgcatgtatg agagtgggta atggttatgt cagttgtgct 118740
atttgttttg tgttaacttg tagtaattga gccttttggc tgttcatgct ttcacatttt 118800
tctgcaaaat caggcactta tttgagaaaa ttttcttgac ctgctaacat atttagtttg 118860
gctgaaagta attttatta  tcccaaccac cttttaattg atagctacta attataaata 118920
cgaccttatt caagtctttt tttacaacac tttcacaagc aatttgcctc aaatctatca 118980
ggtttgataa acagtcttta taattcagtt accagggaat ttctgaaagt acagacacac 119040
aaagcaaaaa gcaaacaaaa caacctccac aaaaacaata acaacaaaat cccctttggtt 119100 cttgtcaaca ctgttcagag catgtctcct ttgaaacaag accatttcag caattaaaaa 119160
aaaaatacag cagattttcc cttcttgctt ctttccccct ttttttaaat aaaattgcca 119220
acttaaaaat attataacat tttaccattg tcagcagtta tacagaattt tgctcacaaa 119280
tccaagatgg ttccgccttt ccttattttt ttttaaggac acactgatta ggtattagaa 119340
```

```
tcaatacccc cctgcctttg atagaattct tttttctttt acaagtaatc tctgaattaa 119400
aggttaggca atcgatttct tcagctattt ttaccattgt cttagtcaca gagatctgat 119460
ctaagacaga ccataatttt tccccttaat tcagaatatt cgatagaata tgatagtaca 119520
aatagcataa tctagactga agcaaattgc ttacaaaagg catgaaagct tcataatcat 119580
tctgtcttca aatgaacaca gagtattgat ttgaaatatt gttccagctc ctgtcctctt 119640
gaggagtata ctgacaattc actgaatatt acaaaagcat ctcagttgtg tggattgcag 119700
aaaaatgctg actatgataa catctgtgat ttgttattac aaattgaaag ataataaaat 119760
aattatctct agttgcatag ttactgattt tagcattgca accatattgc acttaatacc 119820
ttgataatgt ttataacatc ccacagatgt gagtgaaaaa tacaaatacc agtattttag 119880
acaagaaagc ataggtattc agcaagtgtt ttgtaataaa atttgtacag tattataaag 119940
ctaatcataa atattaaagt ttagtttaca tactgtttac atttcctcat tgttcatta 120000 acaaaaatta atctgaagac tacaaacata aaaaggttac tgtctataaa acacacaact 120060
ttgccattca gatgtcctaa agtctttcat atactttata tgtagtttta ccaatgttag 120120
agcaagagaa aaagacaacc ttctctttaa atccagaaaa gagcgagaaa atagttttg 120180 tgggcatact caaagaaaca gaggtggtaa ttacggcagc ccactctaag agtgacattt 120240
ctctgtttca gcccactaaa aaaatgtgca aagaaacaag taggccattg tggctgtatt 120300 ttctttttc tttttttttt ttgagacgga gtctcacact gttgctcagg ctggagtgcg 120360
gtggcatatt cttgcaatct ccacctcccg ggttcaagtg attctcctgc ctcaacctcc 120420
tgagtagctg agattacagg tgcacaccac cacgcccagc taattttgt atctttagta 120480 gagacagggt ttcaccatgt tggctaggct ggtctcgaac tcctgacctc aagtgatcca 120540
cccgccttgg catcccaaaa tgctgagatt acaggtgtga gccaccgcgc ccagcctgtg 120600
gctgtatttt ctaaagcttg ttgcaccaat atatatctca ttccacatgc tcttgttaca 120660
gtgttgcatc aacatgcctc cattgagctg tggggtctgt tttctcccct tgaacctggg 120720
tggagctttc taacagcctc aagcaataga acgtgatgaa tatgacatta caggacttat 120780
gagactagga cataaaggga catataattt ctatctggtt cttcttct cactcagggc 120840 acttgcccct ttggagtcag ccaccatgtt atgaggaagt ctgggacaca tgaagaggcc 120900
acatgcactt attctgtcta aaagccctag ctaattgcaa ggctgacagc cagcagcaac 120960 tatcatttt gtgaataaat aagtcttcag atgattccaa atcccagcct ttgagtcacc 121020
ccagctgatg tcaagtagag caaagatgag ctatcctcac cgaactccat ctaaattgct 121080
gattcctgag caaaataaat gtcattgttc taagtctcta aatcttggag tcatttatta 121140
tgtagccata gataacagga atggccttca acaagatagt tctttaacac tgtaaaaatt 121200
atcttgctca tgtaataggg gttccactgg atctccagaa accaatgctg aaccatatca 121260
attcctagca tacttaactc atttccccat ttgttgagta tagagttccc ttttgtgatt 121320
gccttgggaa tggaaacaag agagatcact tcagaacaga aagagaccag ggaattactt 121380
ctctatggtt tttgtgagtc cccagagcta gaaaaaaat taattggctt acactaaaat 121440
gcttaactta gttctgttct tggaggaaca cctttacggc tagcgacatg atagacattg 121500
ccactcttgt gtacttatta tgaaacaaga atgatctatc tccttaattg tagcaaaaat 121560
aacttttgag atgcgggtaa gtaagcagta gggacgggca gagcagtaac taagttgtgt 121620
tcataggtat tgtgcaagtt cttaagtagg ctggaagcac atggttatgg caagtgtgga 121680
gttatttccc cattttttaac tcagcaggat gactcctgtt gttgacctaa gaatcacagg 121740
```

```
atgagaggaa gaaacctgcc aaggcatgtc ggccaactcc tcagagaaat actacagtta   121800
acttagaggt cagtgtcacc atttcagcgt ggcttttta aatgttggca cctttcaaag   121860
attcctgtca acaaaacact taaactttat taacataagt tgtttacagc atctatatgg   121920
aacaactagc tgatgtggct gaaaagttta tatttgggt taattccagg tgttttgagg   121980
actccatgtc aataacatag ttcttccctg gatgagatcc caacaaattc atatggatta   122040
ttgggccaac ataatcttta tagaacagca agaggcttgt atgcagccat gtaatatact   122100
atggtaacat ctgaatcaat tgcagttcag tagacaaaac ttcgagtcaa gcttttatg   122160 caaatattct ttaaaactgc catgatgagg tggccaagac aatataaaat ccatttccta   122220
gaagaagaaa aaggtagaga gtagagtatt taatagtata gactctggag ccagactgtc   122280
tgggttcaaa ttctgtctct gacactggtt tcatgatcct aggtggaggt atgtagtctt   122340
tcttagcctc agttcactca tttacaaaat aaaaatgatg gagttgtagg cagaaagaaa   122400
ttgattcatg cacagagcat acgacagtgc ttgttttgcg gtaagtgctc agtaattgtt   122460
acctattatt attattttgt gagtgaacta tagagtatag tgaataactc aaaaatgtcc   122520
cctctcttcc cattatggag tattttaggg ttctgggcag ttaattattc agcttctttg   122580
gccaggaaaa gatacgctcc aagcacattc tataacatcg acactttctc tagaagtggc   122640
tcagtcgctc taggaatctg ctgtaataac cctaaacacc aacattagat actattcttt   122700
taatttcacc cttggtaagt agagagcaca tcatgaccag tgagtgtgtg gtttcaatgc   122760
tgcatagtga gataatgaga aagccttgca aaagagaaa acaaggcttg tattgtagtt   122820
gtgaaaattg agaaaggagg tgggagactc ctggcttcaa aaggaattca ggctatagat   122880
gatattcttg aagcacttaa tgtttccgag ctagccatca ttattttct cactatgtat   122940 agctcccttc ctataagctt aagaataaat gataggaaat tgtggtttat tctccctgaa   123000
tgcccatcaa agatcgactg gataaagaaa atgtggtaca tatacaccat ggcatactat   123060
gcagccataa aaaagaatga gatcatgtcc tttgcaggaa catgggtgga gctggaggcc   123120
attatactga gcaaactaat gcaggaagag aaaaccaaat accacgttct cacttataag   123180
tgagagctaa gtggtgagaa cacatggaca catagagggg aacgacacac actgggggct   123240
attgcagggt ggaggctgga aggagggaaa cgatcaggaa aaataactaa tgagtactag   123300
atttaatacg gggagaaaat aatttgtgaa caaaccccca cgacacagtt ttacctatat   123360
aacaaacttg cacatgtaca cttgaactaa aaagttaaaa caaacaaac aaaaaatttc   123420 atattttaat tgtatgctgt taatctgtgg aaatacaatt gattttaaa aataaaaacc   123480 ctacactcag aaaaaaatgt ggtttattct caacataaga aagtcatttt gaccgagaag   123540
caaatgacca tgtaacatcc cggaaagtaa tactgtgctg agatcagctc cattgaatgg   123600
tttttccagt aaaatgtgaa gtaacctgac aatggcagac ttttgaggca gaaaacagt   123660 aggaagtgca gagccccaag atagttcagt tttccttaac tttagatcat atccggtgtt   123720
gcacatatgt atctcagttg gctaaaagct gatagcagag atagagaaac ccaagaaggt   123780
gccagtggaa gttctcattc caaaacttcc ctcatcattt ggatgcccac tatattctac   123840
ttttatggga ctgtcaactt tttttttcc ttccttgaaa agacattagt gttttaccat   123900
tatcagcagt tatgagaaac tttgtgaaga cacgattttt cctctctcca tagttctgag   123960 ttttctgtg aattcagcgt ttttatggat gccataatga acagattgtt gaagtatgag   124020
caccttttgt cagtcacttc tcagttttgg tgtcagatcc agtctctgcc cttctcgata   124080
atgggagagc aacacttccc tgtttcccct gcactctgac ttttggatca ctctgaccaa   124140
```

```
tagaaggcac aagtgagaca ctggagggca gaaggagggg agaagacaaa ctaattctct   124200
ctctctgctt tggtcaatat ctctaacaga tgtgtctcct ctgtggctcc agcccccatt   124260
gggcagatgg aaatggttcc actctgcatt gggcttgggc tttagaactt ctgtaacatc   124320
tacttaacac attttctata ttaaggtact tctatggaaa acatagactt atttctgttt   124380
tctgactgga ctctgactga tacacacttg tagaatcttt atgaatatct ctgaaagaaa   124440
acattagaat gctggaaaat tctaagattg tagggtaat agaaattcta aataaataaa   124500
ttctggatca ttgatgatgc tttgggtatc gacaatcatg ccattaatga tcagatatta   124560
ttaggcatag acaagctaat ctttgtgaag accttatcct aggtaaggat agtgagaagt   124620
ttattaactc taaatactac atatggggat ctcttaaggg ctttcttcag agtcttttta   124680
tagtctctat ggagttttaa caaaagcatc agtcacagta tgattagctt agtccttagc   124740
atgcgtaatt tattcaatag taccttagtt gactagaagc taaaatatct cttatatatt   124800
ttttccttaa attaaaaagc ttatttctga cttggagcaa attgctgcaa tagctggatg   124860
tagacagaat gatataggca tttctttctg cagttttagg tttacagaat aattaaccaa   124920
aaagtatata taacttacat ataccccctc actctacccc attccccaca cctcagtttc   124980
ccctagtatt aacatcttgc attagtgtgg tacatttatt agaatagatg agccaatatt   125040
gatacattat tattaagtaa agtctatagt ttacattggg gttcactcta tgtgtgcaca   125100
ttctatgagt tttgacaaat atatgatgat acgtattcaa ttacaatatt atagaaaata   125160
gttccacagc cccccaaaat cccatgctct acctcctcat cccgctgtgt tgaaccctg    125220 acaataatag ctctactgtc tgcaaatttt ttccttttcc agaatgtcat atagttagaa   125280
tcacacagta tgtggccttt ttagattggc ttcttccact tagaaaatatg catttaagtt  125340 tcctccatgt attttcaagt tttgataatg tacttctttt tatcattgaa taccattcag   125400
tgatttggaa taccattgta tggatgtatc acatttgttt actcattaac ctgttgcaag   125460
acatcttgtt tgcttccagg ttttggcaat tatgaataaa gctgttataa gcatttgtat   125520
gcaggttctt gtgtagatgt aagtctttag ctcatttgaa tatataccaa ggaccacatt   125580
gtaagagaac gtttagtttt gtaagaaatt gctaaagtgc cttcaaaagt gactgtatca   125640
tgttgcatga ccactagcaa tgaacgagat tcgtgttgtt ccacatcctg gccagcttcc   125700
ggtgttgtca atgttttgga ttttagccat tctaataggt gtacagtggt accacattgt   125760
tgttttaatc tgtgattccc taatgtgaca tataatgttg agtatcttgt catatacttg   125820
tttgccattt gtatagcttc tctttttgagg tgtctgtcat atcttttacc cacttttttca 125880 agggactgtt tgctttctta ctgttgagtt ttaagagttc ttcatatatt ttgtatatca   125940
aaccattatc agatatgtgt tttgcaaata ttttctccca gtagtctgtg gcttgtcttt   126000
tcattctctt aacaggaaga ctttttagtg taattttcc caatgtctct ggaaattat     126060 taccatcttg ttgaagctag ggtatttcta tggttttgaa tacctgggaa attaattcct   126120
aatgttttga gatagtaact cccctccaag atatttttat gatcagtgga aatgtatttt   126180
atagcccaca acataacttc tagtatcagt tgtgtgtgat cattataatc ttgaagaatt   126240
acgattagtg gtcatagcag tggtatgaaa gggcttggag aaaatatcac tgaatggtct   126300
caatcatact tttagaccat ttctacagtt cacttcccat ttactctgca agcagtaaag   126360
cagtctggct cccagccctc tactcccacc ctttaacctc tctattggaa gtgtcttgag   126420
aaaccaatca gtgacctgtg atgttaactc caatcccttt ttcttgcaaa tctctttact   126480
ataatcttgg cctttgtaac actactttat cctagagaca ggtaggtagg aattttacta   126540
```

```
tctttttttc tgaactttgt aatggcctcc taagttattt cattgcctct ttcttttcca  126600
atatatcctt cacattgtca cagcacagaa ggcaacatgg tacaatgaga agatcacagc  126660
ccttgaagcc aataagacct aggtttacat ctcagctctg ccacataagt gactgaatgc  126720
tgaccctcaa gttcaacatg acatccctta actgtggtaa tttatgactg gagttgtttt  126780
tgaaatcaaa cataataata cctataaagt ggcctgaaca tggtataaag tcatttcaat  126840
ttctgaagaa cgaacccagt tatgaacaca tctctcttcc attagttata caataaattc  126900
cagactcctc agcctggtat gcctggccct gcacaggtga ctgcttcttt tcagtcttag  126960
cttctatgcc atcatacatg ctctgaaaac acagatgggc ttgtttcctt ccacatgtgg  127020
cctcccagct atgcctatgt gtgtgtatat agtgctctca ctgtaatata ttctgtcctc  127080
ctgtcggaat ggcagacttc caatttattc ttcagggccc taatctaata ttacctccca  127140
gtcctttgcc ctcattctaa tagattttga acaacttatg ctattgaagt gatttcctat  127200
ccttgatgat ttggcccttc acatcctgga atttgccaac atgtgaatct gtggctccat  127260
ttctcaagaa gtagataaac tataggacca gctcactttc cttagggct gtttaccctg  127320
cttcaaaag catgatattt cattttaaga acataaactt cagttaaaac tcattgtgat  127380
aattcttggt actggtgaag atgtggtaag ataagcattc catagcactt atgatggaaa  127440
tgcaaatttt agtatctttg gggaatccag tctgtcaata tatatctgag tagatactta  127500
aaatacttat accttttgat ccagtgattt tatttttaaa aataaactta agaaaatat  127560
atttatatat aaacatgttt atcatgtata gtaaaaaaat tgaatggaat ttaataatca  127620
aaacagtttt ttagttacat aaattatatc cataccatag aataataaac agtgattaaa  127680
atgtacatgt ataaagagtt tttaatgaga gaaaaacctt atgatataat attaaataca  127740
aaattcgaat acaaagacag actttcaata tgaccattac tgtattcaat atgtacctag  127800
aaaagagact gaaagaaat atactgaaat gtttgtgatt ctattagtca gggttgacta  127860
cctgcttaat aaacaacctc tgagtctctg tggcttaaca ctaaaggtta atttcttgtt  127920
catgtcacag tacaatgcaa ggttggaagg tggctcttca tgtaattatc tgaggaccta  127980
gactccttcc ttctttaaaa gactgactta ctttatgtat tcactgggca agtgaaggaa  128040
ggaggtttca gaggcatggc ctggaattga gacacatcac ttccatccac ataccactgg  128100
gcagcagagc tcagtcacat gaacccaact aactgcaaaa tattgagaac tatattccca  128160
acagaaagaa aaggaacttg agtattgaca gcactagcat tgtcttcctc atctctaaga  128220
ggaaatctaa taattactgt ttcatttttc tgcattttcc aattattccc cagtactatg  128280
tattacaaga gaaaatgta tatctagaag ccctcaaagt tttaaaagag ggaactcctt  128340
taatttccac cgtgtaaatt tacactgcct aaagtatttc cttggacatt caaaaggtta  128400
aatttggttc aagcaaaagt tgctgttgta agatttcaca acactgcaaa agaaattca  128460
atgcagtatg aacagccttt tgattcagct aatgatatta aaatatgtaa atacatggag  128520
aagcacattg attatcccca cattcatcaa atgttttaa taaaataggg tgttgtaaat  128580
ctaactttaa attatgtttt tagtagaaag agatgagagg tggagatgtc tgagatccac  128640
attggtggac gttaaactct tccctgtagg caccctttct atagtttata gctcccaaat  128700
tgtctttatt gttgatcaca tcagcactct tcttggttgt ggatagagaa taagtagaga  128760
gagaggatgt tggagaccta catggccact ttcttcagcc ctttccttca atgtcctgag  128820
gccagcatat gttctggata gtattaaaaa tcttgttgcc cagactgtca gggtgctggc  128880
aatatttatt tatttatttc cttccttcct tccttccctc cctctctcct tccctctttc  128940
```

```
cttccttcct cacttccttc cttccttcca cccaatcacc tatgcaagag acattgatta    129000
aaaatctaca ctgacccagg aactacacaa tataactcta ttttttgttc tctattttta    129060
tttgttacgt gatgaatgaa agtctttctc gatatgtata ttggagagcc agtatggtga    129120
caaaaattct tcctatttgc tctagaacag ccacactggg gaaagttgca ctaaaaagtt    129180
tgccggttaa aagaatgaaa agatgagcca cagactggga gaaaatattt gcaaaacaca    129240
tatctgataa tggtttgata tacaaaatat ataagaact cttaaaactc aacagtaaga    129300
aagcaaacag tcccgtgaaa aagtgggtaa gagatatgac cagacacccc acaagagaag    129360
ctatacagat ggcaaacaag tatatgacaa gatactcaac attatatgtc acattaggga    129420
atcacagatt aaaacaacaa tgtggtgcca ctgtacacct attagaatgg ctaaaatcca    129480
aaacattgac aacaccaaag gctagccagg atgtggaaca acaggaatct cattcattgc    129540
tggtggggat gcaaaacggt acagtctctt ttgaagacac tttagcaatt tcttataaaa    129600
ctaaacattg ttgatcacat cagcactctt ctgatcctgc tcagactgct gagtggaagt    129660
aacattcttt tgcttattat tttatagtat ttgaggatag acctactctg acagatggtt    129720
gctttccctt ttatgcacac atctgcctca aacctcttat tctcggggct gaaaaaactg    129780
tagcataata gttttttaaa aaatcaagct aaaactagca ggtctaacac aaggtaatta    129840
cttctcaaaa caacacacct tgcaactagg aagtctcaga aagactctaa acagccatag    129900
ccagcccatt accctcaatg tatttgggga taaaagagcc tcagtaaata cagggcgtat    129960
gagccattga ctttgccatc ccatgcctgt caggctggtg gagtattgac agaggagctg    130020
cagccagtga tgttattgtg ctagcagaag aactggtcat gtcctcatgc tgacccaacc    130080
atgatctttc tacacttatt agaatctgct ttcacagtag ttcacaggta tccttcagtc    130140
ccagattgtt aaaggaaaat gtgtctagaa caaaagtcct aaagaagaaa ttgaattaac    130200
aactcatttc attctataat actccagtta aaatgaagaa actctcattt tttttgccct    130260
tctcagttta tcacattgag aaatacagat tgctagtcta taccaaccat gggttattag    130320
catttcacaa tcattaacat ttcattaccc ttttttcttc tcagtacaaa atgtcactgg    130380
aaatatatgt gaaatattta ggaatcttgt ataaaatata taaaagaaca tgaaaaatat    130440
gaacatttaa ggataagagg agcaaagcac ttctcaaaat gtcttgttag tttcctattt    130500
gaattctaaa ctcttggtta gatgcttaag tcaatcctgc ctaactgaat gtgatttcc    130560 acctctccat ccctgcccag tattgcatat ctgctatcta cattcacata tttatgtagt    130620
tggctgtgtc tgcagaacct ggagattctg gacataggat tttattatat gtgtttggga    130680
ttattgaatc acccactcca cattatatta aagtcaagaa cattggattt tctaaattgg    130740
ttttgaaata gataaaattt tctaggtatt tcaatgaccc tctcctttgt ctaggagact    130800
cagggatttg ctcactagtt atgctgatgg ctttattgag tgcacacaag ttaagttatg    130860
cactatatga aaaagttact ttagattcag tccctgacca gcagtctcat agcctttatt    130920
taatactggc acttaaaagc aaacaaaatt aactgcactt ttactgaaat ataattgcta    130980
ttgtataatg gaaaggaaat tatgtttttt tccttttcta tcagcattgc ttggtggtga    131040
taattttgac catgcagtga gagaaataaa agatgcctat tttatgaaag catttttcag    131100
taatacaagt atgtccattt taagtgagaa agtgattttt gggactagaa ttaaccacat    131160
gatatttgag ttgagtatca atgcccacta tttgaggcta ctgctttgtt gcaggaagtc    131220
agggaccccg aatggaggga ccggctgaag ccatggcaga agaatataaa ttgtgaagat    131280
ttcatggaca tttattagat ccccaaatta atactttcat aatttcttac acctgtcttt    131340
```

```
actgtaatct ctgaacataa attgtgaaga tttcacggac acttatcact tccccagtca   131400
ataccctgt  gatttcttat gcctgtcttt actttaatct cttaattccg tcattttcat   131460
aagctgagga ggatgtatgt tgcctcagga ccctgtgatg attgcattaa ctgcacacat   131520
tgtttgtaga gcatgtgtgt ttgaacaata tgaaatctgg gcaccttgaa aaagaacag    131580
gataacagca acgttcaggg aacaagagag ataaccttaa actctgaccg ccggtgagcc   131640
aggcagaaca gagccatatt tctcttcttt caaaagcaaa tgggagaaat atcactgaat   131700
tcttttctc  agcaaggaac atccctgaga aagagaatgc atccctgagg gtgggtctct   131760
aaaatggccc ccatgggtgc agccgtcttt tatggtcgag ctgtagggat gaaataagcc   131820
ccagtttccc atagtgctcc caggcttatt aggacgagga aattcccgcc taataaattt   131880
tggtcagaac ggttgtctgc tctcaaaccc tgtctcctga taagatgtta tcaatgacaa   131940
tgtgtgcccg aaacttcatt agcaatttta atttcgtccc ggtcctgtgg tcctgtgatc   132000
tcgccctgcc tccatttgcc ttgtgatatt ctattacctt gtgaagcacg tgatctctgt   132060
gacccacacc ctattcgtac actccctacc cttttgaaat cactaataaa aacttgctgg   132120
ttttgcatct tgtggggcat cacggaacct accgacatgt catatctccc ctggacgccc   132180
agctttaaaa tttctctctt ttgtactctg tcccttttatt tctcaaaccg gctgatgctt   132240
agggaaaata gcaaagaacg tacgtgaaat atcgggggtg aatttgccc  gatatctggc   132300
tgaatttccc caatactgct tctcagtgag attcaagtta tgtgggagac caatatccaa   132360
tcatttactc caaaaaagtc tctgatctgc tcatagcatc attttctaat aacaatgtga   132420
gagatagatt tataaactgt tcaggaagac taacacgagt ccctgttgga gctgagagac   132480
tgggatagga ataactggca cttttttttt tttttcttt  agcaatgttt taggttaaag    132540
ggcaatatta atcctccttt agaatcaggt gggtcatttg aggtcaggag ttcaagacca   132600
gcctggccaa catgatgaaa ccctgtctct actaaaaata caaaaattag ccaggtgtgg   132660
tggctcacac ctgtagtcct agctatgtag gaggctgagg catgagaatc gctggagcct   132720
gggagtaaga ggctgcagtg agctgaaatc atgccattgc actccagtct gggtgacaaa   132780
gtgagattct gtccaaaaaa aaattatgca ttttcttatt ttctctgtat tctcttgaga   132840
cgacagctcc agtcattaga aaatgtaaac tcagctttcc ttttaccctt tggttaaaaa   132900
aaataaaaaa gtattcacag ttctcttcac aactaggctg gcttactttg gcctgtgttt   132960
ttatttgctc ttttctcccc tatgttgcct tctttgtgcc ctgttttttcc ctttctgctt  133020
cttctgagtc acatgttgac gtaactcagt gtgaagcctg gggtttgaga agatgtggac   133080
gccaagtcca ggtacacaga gattttgtc  tgataacacc acatacactc cgcctgcaga   133140
cttcctacat tggaaacatc gcattttcaa acgccaattt gccaagcagg ttggctgtga   133200
atgtgcctgc cttctgctgc ttgtcgatgt gaggctgact cgctccattc ctctaactct   133260
tgggcttcat tcgtgattta gccacactga taaatatagc ttctttttga agtagagagt   133320
ctagattttt tttctctcag gctttaaaaa aatggattgc tttattccaa actttatttt   133380
tgatgaaata caactcacaa ctcatcttgg aaaaaaagc  tcttcaaatt ttgaactgtt   133440
gaaagtttga gtctgaggtg atatgacatg tttttgatca ttcaataact ttatttcctt   133500
tcttctcgat tgcttcacaa gttggaagtt acatgcacct aataccactg ttcctatttg   133560
atgttctcag atgtgaacag gggtgatgct tcaatcctta attaaatctc ctcttgccca   133620
agctcacttc tacattttta ctaagttctt ttctattcta tttatagttt atgtatgtct   133680
gaattacata gaatgtatga gagggaaaga aacataatag agaaaataaa gagatacaaa   133740
```

```
ggaaagaata aagtgaatga aaagacaatt caaagggggt gagaatctga gcaatgggta    133800
ggaaatttta agaagaaatg gaataggggtt tctacctaag aatatgaaat atttcactag   133860
gtgtagttag acaacttggc ttcttcatg aaacaaaaca taaaactggt atgttttcat     133920
aaagaaatgt tccatatttt aagactgcca aaagatgaca cccacacatg ccggtggaat    133980
ttggtaacat ttaactgtgt gaaaacaaga ggtctcaaag ataatgattc agagtcggca    134040
gagtgtttat ttatctttga tttagaaaag acattgtctg ttatttggct gtagatatgt    134100
cttaaggact cttttaggtg tggtcttgct gaaaccaaga gcttaaggca aaaacagaca    134160 tgcttttcccc tttttgatgt tcatgctgca ccaaaataca cctaacatct atggtctatg   134220
ctgggagacc ctccatgatc acttaacttt aaatagacag atggataaat agatggtact    134280
tgctcttact cagcactggt caaatttta caagaatgta ctttccagct tggagctcca     134340
catcttaaga gaactctaac atttgggaaa gattcagaag agactgtgaa tgttgatgag    134400
agggttggaa aatggaactt ataagaaaga gttaaagaaa ttggaattgc ttttcttgga    134460
gaagagaagt aacctggtaa cagtcttccc attttttgaag ttacataata tacatgatga   134520
ttgccaagtg ttttccttct ctatcaaaga acatcagagg tcaagtgctc acactgcata    134580
tatcacatat aaggaaaact tgttgcttgt ggtggtggta gtgttaaaaa gataaactgg    134640
taaccattgg ctttgtaaaa acttttctgg aattacttaa atattggata gttttttggt    134700
ctcatatttt ctgaggattg gaagataata cttatgtcat agttcttaat gcatcatgat    134760
ttataagtct ataagaacaa aaatgtattt taaagaaata agtgtagata atggcccaag    134820
attcatagaa tctataattt actttccgtt aaataagtga aaccaagaca ggagatgtgg    134880
tttccatagt gacttagga gtaaacattt tagtgtgata ctctgattcc ttaaaaaaac     134940
actgctgcta attgacataa ggaaaggtaa aatcaagtgt gtgtgtgtgt gtgtgtgtgt    135000
gtgtaaaata tacaatagat actatgtata ataatacaat atacaataga tatatgtatg    135060
ctaagttata tggccaccta agaacctcag ttagaatttt atttttttaa aaaagagaaa    135120
aaccccagag ctctttcttt tctttcttt tctctttctt gctttctttc tcttctgtc      135180 tctcttcctt cctcttcctt cctttttct ctgtctttct ttttctttct ctcccttttc     135240
cttccttcct tccttccttt cttttccttct ttctttcttc caactaagtt tattcttcta   135300
gtgatcccca agtagatatg ctgctatgca aaactccttg tgtgaaccaa tatactttaa    135360
atattcctca tgttcccagg ttgtaaaata agctgatcaa ttcaataata aaacaatttg    135420
aatgtctatc tactctatag tcactggtga tgttggttat ttggttacct caatgaagaa    135480
ataaaactca ttgaattctt tgcaaatttt ctactttttg tagtgctagg atcatagaaa    135540
catagtctca tgattcatct gcattttaag ctctaataga acacatcaca ttttaggggg    135600
aaaatcaatt ttcacctaat gttagcaaaa atgagattaa atattgcact tatcaaaaat    135660
agcattatgt gttttccatg atgcagggct atatttatgt tttggttttt aatcatacaa    135720
atgcattgta ttctgttttc agttccactc ttatcactag aagcatttct ttgtgctgag    135780
tagaactaca aatatacaca taattctcta tgagtaggca caaacagctt tgcttttaaa    135840
attttggcag caaatcatct gctatgaaaa catggtttaa taatttctgg tggaaatata    135900
ttaataccac aggctttcag attaagtcat aaaaagaaag gtttagattt ttgtctttca    135960
cattttattt tagaaaaaag acataccaca caggctcaca cctgtaatcc caacactttg    136020
ggaggccaag gcaggtggat cacaaggtca ggaaatcgag actatcctgg ccaacatggt    136080
gaaaccccgt ctgtactaaa aatacaataa ttagctgggc gtggtggcct gcacctgtgg    136140
```

```
tcctagctac ttgggaggct gaagcaggag aatggcgtga acctgggagg cggagcttgc    136200
agtgagccga gattgcacca ctgcactcca gcctcgtgac agagcgagac tccatctcac    136260
aaaaaaaaaa aacaaacaaa aagacataca gtgtttattt aatatagtgg ttttgcttag    136320
atgctcactt ttgaaagtta tttaattggg gggaatgaaa aatgttttaa aactttattg    136380
tggacatttt caaacattca gaaaagcaga taggatggtg taatgaactc ttatcaccca    136440
tcattcaaca tttattaaca ctctgcattc ccactttact taccctacc tctctccctt     136500 aaaacaaaca tacaaacaaa caaacaataa ctttactgga gcttaaatgc acttaaactt    136560
cctttgggaa ttagtgatat ttttgtcagt gtctaaaatg taagcatttt tattagtcaa    136620
tttattcata atttttatact aacatttttgc tacagaatac tgagtatatt aatttcctgt    136680
gactgctgta acaaatgacc acaaacctag ttgcttacac caccaccaac ttattatctt    136740
atagttttgg aggtcagaag tctgaaatgt gtctcagtgg gctaaaatca aggtgtcaac    136800
agcaatgtgt taccttctgg aggctctagg gagaatctct tttcttgcct tttctggctt    136860
gtaaaggctg cctgaatttc atggtctcct ccatcttcaa aaccagcaat tgtcagttaa    136920
gtccttctca catagcatta ctttaactct ccttttctg cctttctttt tctcttataa      136980
agacccttct gattacattg ggcccaactg gaaaatctca tctttaggtc agctaatgag    137040
caacattaat tccatctgta actaccattt acttttgcca agtaacctaa catagtcata    137100
ggttctgagc attaggatac cgacatcttt tggggccatt attttgccta ccacgtaggg    137160 catatttat attgatttgc aaatatacat ttatgtcttt catgtgaaat gtataatata     137220
gatttaacag tcatagagaa atagcaaaga agtattttac catattcttt gggttgagtc    137280
cacatctaat tatgtggcct gattattctt taactcactg ttcaatctga acacacacag    137340
tagtaattat catctcatat ttgggagagt aaagtaaaaa aacagcaata ataacaaaaa    137400
taggccaggt gcagtggctc acacctgtaa tcccagcact tgggaggca tgtggatcac     137460 ctgaggtcag gagtttgaaa ccagacaggc caacatggtg aaccgctgtc tctactaaaa    137520
atacaaaaat tagccaggtg tggtggtgca cacctgtaat cccagctact cgggaggctg    137580
aggcaggaga attgcttgaa cccaggaggc ggaggttgca atgagctgag atggcaccac    137640
tgcactccag cctaggggac agagtgagac tgtctcaaaa aaacaaagca aaacaaaaca    137700
aaacaaaaat gaccacggaa cagatcaatt acagtagaat agtttacgca ggtggaaggg    137760
ccttctgacc aggaatctta acatcacaat ctatacattt atttatccta gagtatgtct    137820
gtagctctgt tacctaggat gcctcagcca actgaaatga taggtacttt ctctccggct    137880
tcacaacttt gtcttccaca gactgcccta ggccccatg ccatgcccag acacttattt     137940
tcccttcatt gtgttcccta atattatggt cagtggggag gcctcttaga tttgccttac    138000
agtgaagagg gatggtgtaa tttcactgtt gccactagcc ataaagttgc agacagagag    138060
gctacagatg tggagcagat gtgcataatg atcatttaaa aaattctttg tatagctctc    138120 ataaaaagt gactgtgata aatgtttgtg tgtttggtgc tcacattcta ttctattatt      138180
taaacagaat cattaacttg tttgtacttt acaatctatt tttatttgca ctaaaaacta    138240
tttattacta cattatttct cttgagcttg ggaggatgac agctttgccc tccctcccaa    138300
tttaggatga attcatttac cttttctcttt ttctgttcta gacggagttg ttccaaagga    138360
tggggaaaca ccttccttga aaggagcata tctcatggag gcagcatcag cattagaacc    138420
aggtgaaatc tgagcccaga cactcgatct agttaatttc tctgagcctt catttcttat    138480
ttgcaaaatg ggactaacaa tataatccat aaagtttctg tgagaaaatg cagggataat    138540
```

```
tatagaaagc aggtagtgct gtatctggtg gattaaaggt ctgttccctt ccctttccta 138600
tggaggaggc catgccacta gaaaaacacc tttagaccca caaacttttg cttttaaata 138660
aaattagttt cctatttgtg ggtatcatga aaattcttag atagacttcc acaaaatttg 138720
gaaagtattg tttaggaaga tctgatttag aatttgggtt atgtggcata tgataagaat 138780
cactttagga gatcctggga agcctcaaag aagtaggcag tcatcataca ggagctgaaa 138840
gtagggttga acaaggggta tgaataaacg tcatttagga gaggcctgtc atattcagta 138900
atatgcccat agatggaaca aaatggaaca ttggtttcca ataggtcctt aaattgaaag 138960
ccataagggt aggtgctttg caaagcaggt atgatttgta tccaaattac ctctcacatg 139020
ggcaccttgt ggatttctct ggacagaagt gcagcaggaa cctactttt aatgaataat 139080 ggttattgag tcattcaaac atcccagaat agccagtggg acctggctgt tctcccttca 139140
agttcttcgc cacctgtaag tcacagagcc acagctgtgg ttcttctgca ggggccacag 139200
agcccttcct ctgcacttgg aaaaaaatgt catgtgctga ctccaagagt gagtcttctg 139260
ggggtacagg agacacagaa acagaaactt ccaagaaaa acacactgac taaaccaaat 139320
gacagagcag aaaacatttt ctgataaggc aaagggtaat aacttggtga gaattacaca 139380
ggtaattaaa tagttgtttc caagggctag gaaaagacag gcatcgtctg tgttggacag 139440
aaggggagtt ttggatttat taacatggat atgagggttt agggttattt gtgtttgtgg 139500
taaagagctc agagaagaag tctttattta ctgcctaaag atttagtaag tcaatttgtt 139560
ccctgccttc tatctcatcc acagacaata tcttcttaaa taggatacta gattgcatgc 139620
atgatgttaa acaaacgtgg agtaggaaaa tcaccttatt gaaatagctc ttgaggtgtc 139680
cttaactcac aagaacattg ggaaattttc agactttctc accaacagag gacataaata 139740
ccaaaggcaa gatgtaaagt tatgcaaacc tctgtggctg gaataaatat tttgtactta 139800
tggaaagtcc actagaagac cacttctgaa ttcagatctg tatcaattaa tggaagaaaa 139860
aaatgggttg gaggagccaa atggggaatg ttacaagacg tattaatgta taatcaaaat 139920
ttagaaatag aggtggttct gaattggaat tggctttaga taaaatacag aacaggaaag 139980
aatgggagtc ctctgttcta gaagggtagg ctggctacaa tcgggtgaat aagacaattt 140040
cataagaaaa cgttttgaaa gaatatgaga ggaaactgca agagcagaag aaagtaataa 140100
actcattgca caagaatttc agaagaacta gggtcaaaaa tacagtcaca atctggcagc 140160
tttcaggagg aggtggggag tagataagga caaagaggtg ggaagggaga tagggccaag 140220
tccaaagtgc ctttcagact ctccctgagt cagcaaacct tgcttctttt tacttttact 140280
ttttctgtgg gctctgaatg gttctttaa tctatattca ggcagagtaa caggcgtgat 140340
gaatttataa tgtaaaaggt cactttggg aggctgaggc gggaggatca cgaagtcagg 140400
agatcgagac catcctggct aacacggtga aaccccgcct ctactaaaga tacaaaaaat 140460
tagccgggcg tggtggcggg cgcctgtagt cccagctact cggaggctg aggcaggaga 140520 atggcgtgaa cccgggaggc ggaggttgca gtgagccgag atcacgccac tgcactccag 140580
cctgggcgac agagtgagac tccgcttcaa aaaaaaaaa aaaaaaaaa agccagaaac 140640 gctcactagg caaaaaaaaa aacttctctt cgagcagcct ggtagggcct ctagctggag 140700
aatattcagt tgtgttaagg catcttagta gagcaccagt ggtatctgga agaaggtgcc 140760
cccaaaagcc tctatccctc atcagcaggt ttacacaatt catcgaacag atttaatagt 140820
tacagattac tctgttaact agattttgag aaaacagtgc agagtgttgg cagagcaaag 140880
agagaaaatc aaattctgga gtgtggaatg tttacccaaa agaaatggca gtagcaggaa 140940
```

```
ctaggagcct gaagggggtg cctttgtgta aaaatgtttt tgatttctga tgcctacagc    141000
tggattttta atgtagctca agtccgacag aatgcaggta ggaaaaagaa agcagcaatg    141060
aattgtttgc ctcttcttta aactctgttt ctgaaaataa aatttgttag tatttttaaac   141120
ttaaaaccct tcatgattat tatatcctta gttcttatgt gtcactgata tactaaaata    141180
ggttgtgaat atgatagaaa gtgagatgaa agagagagag tgtggtaagg ctgtgggtct    141240
gtgaaactcc aaggccagat gctgctcacc ttattatgga acaggtatgt tgattcaagc    141300
acagggtcaa aggaatgggc cagggtgact cttttttggaa taatagtgaa catgtgttac   141360
tcactcatag actcaacctg ctgattaata tatgttatct cttgaatttg agaatgaagt    141420
tgtacaattc ccatttatag ttgtggaagc taaggctcag agatacacag taacttgctg    141480
tgtagccagt tgtggcaaaa aaaaaaaaaa aaaaaaaga atttgtattt atttctgtct     141540
gatcctaaac aggtgttttc caggtatgca cccttcctgc tcacattttg attggttttg    141600
aattcttgtg tattattgac tgtctacttc actaacatca agtataaaac aaaaaatgta    141660
ttgcagccta atgtttagct tctctactct tttatattgc ctatatttcc agttccttag    141720
atttgcaaaa gttatgaagt taaatataaa tcatacctgc aattgcatta gtatattggt    141780
atagtgccct ttcattgagt ttgcaggaag tgagctgtct ttaagaatat ccagttgtag    141840
gaagttcctc ttttttctttt tttgttactc tcaaaaagtc tttggtcttt ccttgtagta   141900
aattactaag cactctagtt tggctgattt ctagattgaa tattaaagaa ttctatgata    141960
aagcaaactt taaaaaatta caaacactga atattttttaa agtcaaagaa taaaatctgc   142020
agaggctgtc cattggatgt gattcagcca catgtgtttt tggtgcagat ttttctccct    142080
ttcagtgaaa atgtctttct attttcttga ctttgatcac tttggtgtca gggtgcttta    142140
tactcagtgg tcatctgtca gccttttcat aagtcagttt cttgcatcca tctggtgaat    142200
ggcaaaagat tttggtttag gcaattgcat gcattactca aaagactgtg gagactttga    142260
gaaggaaaga aggaaaatct tcattgcata cttttaactc ttttttttttt ttaaattaac   142320
ttccccatca gagtgtttga aaaaacattt tgatatggca tgtgaaataa gaacaagagg    142380
aggtgagagg ccttttgatct gtgtgctctc ctgaaatacg catgaccagc tctaggataa    142440
agagggtgag aggcttgtgt tttgcaccca catctctctt tccatcagtt cctcccactc    142500
agctgcgtgc tcttccttgtt gctcagagcc ctacctttttg atctggctgc cagagctgca  142560
tttcttttgg gtaaacgttc cacactccag aatttgattt tctctgtttg ctctgccaac    142620
acataactgc cctgttctcc caaaatctaa ttaatggagt aatctgttaa actattcaat    142680
ctgttcaatg aattgtgtaa acctgctaat gagtgataga ggcttttggg ggctccttct    142740
tccagatacc actggtggtc tactaagatg ccctcacaca actgaatatt ctccagctag    142800
aagcccccac ccaggctgct ggaagagaag ttttttttgc atagtggttg attttggcac    142860
cttttacgtc atacattcct catgcctgtt actctgcctg aatatagatt aaaacaacca    142920
ttcagagccc acagaaaaag tagacaagca actctgaaat tagggtatag ggctggaata    142980
tggaggatac aaaagagtct acattagccc caaatctggc catcacatgg gagaggcagc    143040
tgacacagat atctagaaag caaagcagag gctcataact cctgcagatt tcgggagtgt    143100
agtctggtag cctgacttcc aggaccagtt tattcattta ctcattattt tattctttca    143160
ttcttttcaca tttcttgtac aactattatg ggtcagtcat atgtggttaa atgcgctaac    143220
agttctgtca ttttcctggt tggaaaagta gagtcaattt acaaaaaaga acaaaactag    143280
ggtttctgaa ataaagattt gtaatttgct tttttcatgc aggtgcaaat tatcttaaac    143340
```

```
                                    -continued tgatataaaa aagaagaaac agaaatttta aaatatatgt tttttacaaa tgtgtaccat  143400
ctaattatca gctagaagtc ttattctgtg aagagctaac acaggttcta gtgtaataat  143460
aataatcagc ataacattta ttgagtattt actgtacatg ccaaacaact gtgctgtgtg  143520
tttaacatga atttttgcat ttaatcctta ggaaaaattc tgtgagacag gtttgttatt  143580
accttccttt cccagataag caagcagatc aagaaatgtt gatcgcatag ctggaattta  143640
gagcctgaaa ttgaacccag gcagtctgac tccagagtct gcagtctttt gttgatgtta  143700
cctgtctcta ctccagccac aggtggttca cgacctatga tggttcaact taatgatttt  143760
ttgactttac aatggtacga aagcatttgg tagaaactgt acatcaagta ctcgtataac  143820
cattctgttt ttcactttca gtatagcatt caataaatta cataagatat caacacctt   143880 attatgaaat aggctttgtg ttagatgatt ttgcccaact gtaggctaat aacatagttg  143940
ttctgag                                                           143947

<210> SEQ ID NO 38
<211> LENGTH: 2217
<212> TYPE: PRT
<213> ORGANISM: Homo sapiens
<300> PUBLICATION INFORMATION:
<308> DATABASE ACCESSION NUMBER: GenBank AC012462
<309> DATABASE ENTRY DATE: 2005-04-05

<400> SEQUENCE: 38

Met Leu Arg Gly Pro Gly Pro Gly Leu Leu Leu Leu Ala Val Gln Cys
  1               5                  10                  15

Leu Gly Thr Ala Val Pro Ser Thr Gly Ala Ser Lys Ser Lys Arg Gln
             20                  25                  30

Ala Gln Gln Met Val Gln Pro Gln Ser Pro Val Ala Val Ser Gln Ser
         35                  40                  45

Lys Pro Gly Cys Tyr Asp Asn Gly Lys His Tyr Gln Ile Asn Gln Gln
     50                  55                  60

Trp Glu Arg Thr Tyr Leu Gly Asn Ala Leu Val Cys Thr Cys Tyr Gly
 65                  70                  75                  80

Gly Ser Arg Gly Phe Asn Cys Glu Ser Lys Pro Glu Ala Glu Glu Thr
                 85                  90                  95

Cys Phe Asp Lys Tyr Thr Gly Asn Thr Tyr Arg Val Gly Asp Thr Tyr
            100                 105                 110

Glu Arg Pro Lys Asp Ser Met Ile Trp Asp Cys Thr Cys Ile Gly Ala
        115                 120                 125

Gly Arg Gly Arg Ile Ser Cys Thr Ile Ala Asn Arg Cys His Glu Gly
    130                 135                 140

Gly Gln Ser Tyr Lys Ile Gly Asp Thr Trp Arg Arg Pro His Glu Thr
145                 150                 155                 160

Gly Gly Tyr Met Leu Glu Cys Val Cys Leu Gly Asn Gly Lys Gly Glu
                165                 170                 175

Trp Thr Cys Lys Pro Ile Ala Glu Lys Cys Phe Asp His Ala Ala Gly
            180                 185                 190

Thr Ser Tyr Val Val Gly Glu Thr Trp Glu Lys Pro Tyr Gln Gly Trp
        195                 200                 205

Met Met Val Asp Cys Thr Cys Leu Gly Glu Gly Ser Gly Arg Ile Thr
    210                 215                 220

Cys Thr Ser Arg Asn Arg Cys Asn Asp Gln Asp Thr Arg Thr Ser Tyr
225                 230                 235                 240

Arg Ile Gly Asp Thr Trp Ser Lys Lys Asp Asn Arg Gly Asn Leu Leu
                245                 250                 255
```

```
Gln Cys Ile Cys Thr Gly Asn Gly Arg Gly Glu Trp Lys Cys Glu Arg
            260                 265                 270

His Thr Ser Val Gln Thr Thr Ser Gly Ser Gly Pro Phe Thr Asp
            275                 280                 285

Val Arg Ala Ala Val Tyr Gln Pro Gln Pro His Pro Gln Pro Pro
290                 295                 300

Tyr Gly His Cys Val Thr Asp Ser Gly Val Val Tyr Ser Val Gly Met
305                 310                 315                 320

Gln Trp Leu Lys Thr Gln Gly Asn Lys Gln Met Leu Cys Thr Cys Leu
                325                 330                 335

Gly Asn Gly Val Ser Cys Gln Glu Thr Ala Val Thr Gln Thr Tyr Gly
            340                 345                 350

Gly Asn Ser Asn Gly Glu Pro Cys Val Leu Pro Phe Thr Tyr Asn Gly
            355                 360                 365

Arg Thr Phe Tyr Ser Cys Thr Thr Glu Gly Arg Gln Asp Gly His Leu
    370                 375                 380

Trp Cys Ser Thr Thr Ser Asn Tyr Glu Gln Asp Gln Lys Tyr Ser Phe
385                 390                 395                 400

Cys Thr Asp His Thr Val Leu Val Gln Thr Arg Gly Gly Asn Ser Asn
                405                 410                 415

Gly Ala Leu Cys His Phe Pro Phe Leu Tyr Asn Asn His Asn Tyr Thr
            420                 425                 430

Asp Cys Thr Ser Glu Gly Arg Arg Asp Asn Met Lys Trp Cys Gly Thr
            435                 440                 445

Thr Gln Asn Tyr Asp Ala Asp Gln Lys Phe Gly Phe Cys Pro Met Ala
    450                 455                 460

Ala His Glu Glu Ile Cys Thr Thr Asn Glu Gly Val Met Tyr Arg Ile
465                 470                 475                 480

Gly Asp Gln Trp Asp Lys Gln His Asp Met Gly His Met Met Arg Cys
                485                 490                 495

Thr Cys Val Gly Asn Gly Arg Gly Glu Trp Thr Cys Ile Ala Tyr Ser
            500                 505                 510

Gln Leu Arg Asp Gln Cys Ile Val Asp Asp Ile Thr Tyr Asn Val Asn
    515                 520                 525

Asp Thr Phe His Lys Arg His Glu Glu Gly His Met Leu Asn Cys Thr
    530                 535                 540

Cys Phe Gly Gln Gly Arg Gly Arg Trp Lys Cys Asp Pro Val Asp Gln
545                 550                 555                 560

Cys Gln Asp Ser Glu Thr Gly Thr Phe Tyr Gln Ile Gly Asp Ser Trp
                565                 570                 575

Glu Lys Tyr Val His Gly Val Arg Tyr Gln Cys Tyr Cys Tyr Gly Arg
            580                 585                 590

Gly Ile Gly Glu Trp His Cys Gln Pro Leu Gln Thr Tyr Pro Ser Ser
            595                 600                 605

Ser Gly Pro Val Glu Val Phe Ile Thr Glu Thr Pro Ser Gln Pro Asn
    610                 615                 620

Ser His Pro Ile Gln Trp Asn Ala Pro Gln Pro Ser His Ile Ser Lys
625                 630                 635                 640

Tyr Ile Leu Arg Trp Arg Pro Lys Asn Ser Val Gly Arg Trp Lys Glu
                645                 650                 655

Ala Thr Ile Pro Gly His Leu Asn Ser Tyr Thr Ile Lys Gly Leu Lys
            660                 665                 670

Pro Gly Val Val Tyr Glu Gly Gln Leu Ile Ser Ile Gln Gln Tyr Gly
```

```
                675                 680                 685
His Gln Glu Val Thr Arg Phe Asp Phe Thr Thr Thr Ser Thr Ser Thr
690                     695                 700
Pro Val Thr Ser Asn Thr Val Thr Gly Glu Thr Thr Pro Phe Ser Pro
705                     710                 715                 720
Leu Val Ala Thr Ser Glu Ser Val Thr Glu Ile Thr Ala Ser Ser Phe
                    725                 730                 735
Val Val Ser Trp Val Ser Ala Ser Asp Thr Val Ser Gly Phe Arg Val
                740                 745                 750
Glu Tyr Glu Leu Ser Glu Glu Gly Asp Glu Pro Gln Tyr Leu Asp Leu
            755                 760                 765
Pro Ser Thr Ala Thr Ser Val Asn Ile Pro Asp Leu Leu Pro Gly Arg
        770                 775                 780
Lys Tyr Ile Val Asn Val Tyr Gln Ile Ser Glu Asp Gly Glu Gln Ser
785                 790                 795                 800
Leu Ile Leu Ser Thr Ser Gln Thr Thr Ala Pro Asp Ala Pro Pro Asp
                805                 810                 815
Thr Thr Val Asp Gln Val Asp Asp Thr Ser Ile Val Val Arg Trp Ser
            820                 825                 830
Arg Pro Gln Ala Pro Ile Thr Gly Tyr Arg Ile Val Tyr Ser Pro Ser
        835                 840                 845
Val Glu Gly Ser Ser Thr Glu Leu Asn Leu Pro Glu Thr Ala Asn Ser
    850                 855                 860
Val Thr Leu Ser Asp Leu Gln Pro Gly Val Gln Tyr Asn Ile Thr Ile
865                 870                 875                 880
Tyr Ala Val Glu Glu Asn Gln Glu Ser Thr Pro Val Val Ile Gln Gln
                885                 890                 895
Glu Thr Thr Gly Thr Pro Arg Ser Asp Thr Val Pro Ser Pro Arg Asp
            900                 905                 910
Leu Gln Phe Val Glu Val Thr Asp Val Lys Val Thr Ile Met Trp Thr
        915                 920                 925
Pro Pro Glu Ser Ala Val Thr Gly Tyr Arg Val Asp Val Ile Pro Val
    930                 935                 940
Asn Leu Pro Gly Glu His Gly Gln Arg Leu Pro Ile Ser Arg Asn Thr
945                 950                 955                 960
Phe Ala Glu Val Thr Gly Leu Ser Pro Gly Val Thr Tyr Tyr Phe Lys
                965                 970                 975
Val Phe Ala Val Ser His Gly Arg Glu Ser Lys Pro Leu Thr Ala Gln
            980                 985                 990
Gln Thr Thr Lys Leu Asp Ala Pro Thr Asn Leu Gln Phe Val Asn Glu
        995                 1000                1005
Thr Asp Ser Thr Val Leu Val Arg Trp Thr Pro Pro Arg Ala Gln Ile
    1010                1015                1020
Thr Gly Tyr Arg Leu Thr Val Gly Leu Thr Arg Arg Gly Gln Pro Arg
1025                1030                1035                1040
Gln Tyr Asn Val Gly Pro Ser Val Ser Lys Tyr Pro Leu Arg Asn Leu
                1045                1050                1055
Gln Pro Ala Ser Glu Tyr Thr Val Ser Leu Val Ala Ile Lys Gly Asn
            1060                1065                1070
Gln Glu Ser Pro Lys Ala Thr Gly Val Phe Thr Thr Leu Gln Pro Gly
        1075                1080                1085
Ser Ser Ile Pro Pro Tyr Asn Thr Glu Val Thr Glu Thr Thr Ile Val
    1090                1095                1100
```

-continued

```
Ile Thr Trp Thr Pro Ala Pro Arg Ile Gly Phe Lys Leu Gly Val Arg
1105                1110                1115                1120

Pro Ser Gln Gly Gly Glu Ala Pro Arg Glu Val Thr Ser Asp Ser Gly
            1125                1130                1135

Ser Ile Val Val Ser Gly Leu Thr Pro Gly Val Glu Tyr Val Tyr Thr
            1140                1145                1150

Ile Gln Val Leu Arg Asp Gly Gln Glu Arg Asp Ala Pro Ile Val Asn
            1155                1160                1165

Lys Val Val Thr Pro Leu Ser Pro Pro Thr Asn Leu His Leu Glu Ala
    1170                1175                1180

Asn Pro Asp Thr Gly Val Leu Thr Val Ser Trp Glu Arg Ser Thr Thr
1185                1190                1195                1200

Pro Asp Ile Thr Gly Tyr Arg Ile Thr Thr Thr Pro Thr Asn Gly Gln
            1205                1210                1215

Gln Gly Asn Ser Leu Glu Glu Val Val His Ala Asp Gln Ser Ser Cys
            1220                1225                1230

Thr Phe Asp Asn Leu Ser Pro Gly Leu Glu Tyr Asn Val Ser Val Tyr
            1235                1240                1245

Thr Val Lys Asp Asp Lys Glu Ser Val Pro Ile Ser Asp Thr Ile Ile
    1250                1255                1260

Pro Ala Val Pro Pro Thr Asp Leu Arg Phe Thr Asn Ile Gly Pro
1265                1270                1275                1280

Asp Thr Met Arg Val Thr Trp Ala Pro Pro Pro Ser Ile Asp Leu Thr
            1285                1290                1295

Asn Phe Leu Val Arg Tyr Ser Pro Val Lys Asn Glu Glu Asp Val Ala
            1300                1305                1310

Glu Leu Ser Ile Ser Pro Ser Asp Asn Ala Val Val Leu Thr Asn Leu
            1315                1320                1325

Leu Pro Gly Thr Glu Tyr Val Val Ser Val Ser Ser Val Tyr Glu Gln
            1330                1335                1340

His Glu Ser Thr Pro Leu Arg Gly Arg Gln Lys Thr Gly Leu Asp Ser
1345                1350                1355                1360

Pro Thr Gly Ile Asp Phe Ser Asp Ile Thr Ala Asn Ser Phe Thr Val
            1365                1370                1375

His Trp Ile Ala Pro Arg Ala Thr Ile Thr Gly Tyr Arg Ile Arg His
            1380                1385                1390

His Pro Glu His Phe Ser Gly Arg Pro Arg Glu Asp Arg Val Pro His
            1395                1400                1405

Ser Arg Asn Ser Ile Thr Leu Thr Asn Leu Thr Pro Gly Thr Glu Tyr
            1410                1415                1420

Val Val Ser Ile Val Ala Leu Asn Gly Arg Glu Glu Ser Pro Leu Leu
1425                1430                1435                1440

Ile Gly Gln Gln Ser Thr Val Ser Asp Val Pro Arg Asp Leu Glu Val
            1445                1450                1455

Val Ala Ala Thr Pro Thr Ser Leu Leu Ile Ser Trp Asp Ala Pro Ala
            1460                1465                1470

Val Thr Val Arg Tyr Tyr Arg Ile Thr Tyr Gly Glu Thr Gly Gly Asn
            1475                1480                1485

Ser Pro Val Gln Glu Phe Thr Val Pro Gly Ser Lys Ser Thr Ala Thr
            1490                1495                1500

Ile Ser Gly Leu Lys Pro Gly Val Asp Tyr Thr Ile Thr Val Tyr Ala
1505                1510                1515                1520

Val Thr Gly Arg Gly Asp Ser Pro Ala Ser Ser Lys Pro Ile Ser Ile
            1525                1530                1535
```

Asn Tyr Arg Thr Glu Ile Asp Lys Pro Ser Gln Met Gln Val Thr Asp
            1540                1545                1550

Val Gln Asp Asn Ser Ile Ser Val Lys Trp Leu Pro Ser Ser Ser Pro
        1555                1560                1565

Val Thr Gly Tyr Arg Val Thr Thr Pro Lys Asn Gly Pro Gly Pro
    1570                1575                1580

Thr Lys Thr Lys Thr Ala Gly Pro Asp Gln Thr Glu Met Thr Ile Glu
1585                1590                1595                1600

Gly Leu Gln Pro Thr Val Glu Tyr Val Val Ser Val Tyr Ala Gln Asn
            1605                1610                1615

Pro Ser Gly Glu Ser Gln Pro Leu Val Gln Thr Ala Val Thr Asn Ile
            1620                1625                1630

Asp Arg Pro Lys Gly Leu Ala Phe Thr Asp Val Asp Val Asp Ser Ile
            1635                1640                1645

Lys Ile Ala Trp Glu Ser Pro Gln Gly Gln Val Ser Arg Tyr Arg Val
            1650                1655                1660

Thr Tyr Ser Ser Pro Glu Asp Gly Ile His Glu Leu Phe Pro Ala Pro
1665                1670                1675                1680

Asp Gly Glu Glu Asp Thr Ala Glu Leu Gln Gly Leu Arg Pro Gly Ser
            1685                1690                1695

Glu Tyr Thr Val Ser Val Val Ala Leu His Asp Asp Met Glu Ser Gln
            1700                1705                1710

Pro Leu Ile Gly Thr Gln Ser Thr Ala Ile Pro Ala Pro Thr Asp Leu
            1715                1720                1725

Lys Phe Thr Gln Val Thr Pro Thr Ser Leu Ser Ala Gln Trp Thr Pro
            1730                1735                1740

Pro Asn Val Gln Leu Thr Gly Tyr Arg Val Arg Val Thr Pro Lys Glu
1745                1750                1755                1760

Lys Thr Gly Pro Met Lys Glu Ile Asn Leu Ala Pro Asp Ser Ser Ser
            1765                1770                1775

Val Val Val Ser Gly Leu Met Val Ala Thr Lys Tyr Glu Val Ser Val
            1780                1785                1790

Tyr Ala Leu Lys Asp Thr Leu Thr Ser Arg Pro Ala Gln Gly Val Val
            1795                1800                1805

Thr Thr Leu Glu Asn Val Ser Pro Pro Arg Arg Ala Arg Val Thr Asp
            1810                1815                1820

Ala Thr Glu Thr Thr Ile Thr Ile Ser Trp Arg Thr Lys Thr Glu Thr
1825                1830                1835                1840

Ile Thr Gly Phe Gln Val Asp Ala Val Pro Ala Asn Gly Gln Thr Pro
            1845                1850                1855

Ile Gln Arg Thr Ile Lys Pro Asp Val Arg Ser Tyr Thr Ile Thr Gly
            1860                1865                1870

Leu Gln Pro Gly Thr Asp Tyr Lys Ile Tyr Leu Tyr Thr Leu Asn Asp
            1875                1880                1885

Asn Ala Arg Ser Ser Pro Val Val Ile Asp Ala Ser Thr Ala Ile Asp
            1890                1895                1900

Ala Pro Ser Asn Leu Arg Phe Leu Ala Thr Thr Pro Asn Ser Leu Leu
1905                1910                1915                1920

Val Ser Trp Gln Pro Pro Arg Ala Arg Ile Thr Gly Tyr Ile Ile Lys
            1925                1930                1935

Tyr Glu Lys Pro Gly Ser Pro Pro Arg Glu Val Val Pro Arg Pro Arg
            1940                1945                1950

Pro Gly Val Thr Glu Ala Thr Ile Thr Gly Leu Glu Pro Gly Thr Glu

-continued

```
                   1955               1960                  1965
Tyr Thr Ile Tyr Val Ile Ala Leu Lys Asn Asn Gln Lys Ser Glu Pro
        1970                1975              1980

Leu Ile Gly Arg Lys Lys Thr Asp Glu Leu Pro Gln Leu Val Thr Leu
1985                1990               1995                2000

Pro His Pro Asn Leu His Gly Pro Glu Ile Leu Asp Val Pro Ser Thr
                2005                2010              2015

Val Gln Lys Thr Pro Phe Val Thr His Pro Gly Tyr Asp Thr Gly Asn
                2020                2025              2030

Gly Ile Gln Leu Pro Gly Thr Ser Gly Gln Gln Pro Ser Val Gly Gln
            2035                2040              2045

Gln Met Ile Phe Glu Glu His Gly Phe Arg Arg Thr Thr Pro Pro Thr
        2050                2055              2060

Thr Ala Thr Pro Ile Arg His Arg Pro Arg Pro Tyr Pro Pro Asn Val
2065                2070              2075                2080

Gly Gln Glu Ala Leu Ser Gln Thr Thr Ile Ser Trp Ala Pro Phe Gln
                2085                2090              2095

Asp Thr Ser Glu Tyr Ile Ile Ser Cys His Pro Val Gly Thr Asp Glu
            2100                2105              2110

Glu Pro Leu Gln Phe Arg Val Pro Gly Thr Ser Thr Ser Ala Thr Leu
        2115                2120              2125

Thr Gly Leu Thr Arg Gly Ala Thr Tyr Asn Val Ile Val Glu Ala Leu
    2130                2135              2140

Lys Asp Gln Gln Arg His Lys Val Arg Glu Glu Val Val Thr Val Gly
2145                2150              2155                2160

Asn Ser Val Asn Glu Gly Leu Asn Gln Pro Thr Asp Asp Ser Cys Phe
                2165                2170              2175

Asp Pro Tyr Thr Val Ser His Tyr Ala Val Gly Asp Glu Trp Glu Arg
            2180                2185              2190

Met Ser Glu Ser Gly Phe Lys Leu Leu Cys Gln Cys Leu Gly Phe Gly
        2195                2200              2205

Ser Gly His Phe Arg Cys Asp Ser Ser
    2210                2215

<210> SEQ ID NO 39
<211> LENGTH: 6
<212> TYPE: PRT
<213> ORGANISM: Homo Sapiens

<400> SEQUENCE: 39

Val Thr His Pro Gly Tyr
1               5
```